(12) United States Patent
Eckelman et al.

(10) Patent No.: US 12,365,728 B2
(45) Date of Patent: *Jul. 22, 2025

(54) DLL3 SINGLE DOMAIN ANTIBODIES AND THERAPEUTIC COMPOSITIONS THEREOF

(71) Applicant: Inhibrx Biosciences, Inc., La Jolla, CA (US)

(72) Inventors: Brendan P. Eckelman, La Jolla, CA (US); Michael D. Kaplan, La Jolla, CA (US); Katelyn M. Willis, La Jolla, CA (US); Rajay A. Pandit, La Jolla, CA (US); Angelica N. Sanabria, La Jolla, CA (US); Sydney A. Barnes, La Jolla, CA (US); Margaret E. Haerr, La Jolla, CA (US); John C. Timmer, La Jolla, CA (US)

(73) Assignee: Inhibrx Biosciences, Inc., La Jolla, CA (US)

( * ) Notice: Subject to any disclaimer, the term of this patent is extended or adjusted under 35 U.S.C. 154(b) by 1093 days.

This patent is subject to a terminal disclaimer.

(21) Appl. No.: 17/283,903

(22) PCT Filed: Oct. 9, 2019

(86) PCT No.: PCT/US2019/055436
§ 371 (c)(1),
(2) Date: Apr. 8, 2021

(87) PCT Pub. No.: WO2020/076977
PCT Pub. Date: Apr. 16, 2020

(65) Prior Publication Data
US 2021/0380679 A1  Dec. 9, 2021

Related U.S. Application Data

(60) Provisional application No. 62/832,265, filed on Apr. 10, 2019, provisional application No. 62/877,815, filed on Jul. 23, 2019, provisional application No. 62/744,638, filed on Oct. 11, 2018.

(51) Int. Cl.
| | | |
|---|---|---|
| *C07K 16/28* | (2006.01) |
| *A61K 39/00* | (2006.01) |
| *A61K 40/11* | (2025.01) |
| *A61K 40/42* | (2025.01) |
| *A61P 35/00* | (2006.01) |
| *C07K 16/24* | (2006.01) |

(52) U.S. Cl.
CPC .............. *C07K 16/28* (2013.01); *A61K 40/11* (2025.01); *A61K 40/4202* (2025.01); *A61P 35/00* (2018.01); *C07K 16/249* (2013.01); *C07K 16/2809* (2013.01); *C07K 16/2818* (2013.01); *C07K 16/283* (2013.01); *A61K 2039/505* (2013.01); *A61K 2239/55* (2023.05); *C07K 2317/22* (2013.01); *C07K 2317/24* (2013.01); *C07K 2317/31* (2013.01); *C07K 2317/52* (2013.01); *C07K 2317/56* (2013.01); *C07K 2317/565* (2013.01); *C07K 2317/569* (2013.01); *C07K 2317/624* (2013.01)

(58) Field of Classification Search
CPC ........ C07K 2317/569; C07K 2317/565; C07K 2317/22
See application file for complete search history.

(56) References Cited

U.S. PATENT DOCUMENTS

| | | |
|---|---|---|
| 4,522,811 A | 6/1985 | Eppstein et al. |
| 4,816,567 A | 3/1989 | Cabilly et al. |
| 4,832,959 A | 5/1989 | Engels et al. |
| 5,258,498 A | 11/1993 | Huston et al. |
| 5,500,362 A | 3/1996 | Robinson et al. |
| 5,525,491 A | 6/1996 | Huston et al. |
| 5,731,168 A | 3/1998 | Carter et al. |
| 5,821,337 A | 10/1998 | Carter et al. |
| 5,834,597 A | 11/1998 | Tso et al. |
| 6,054,297 A | 4/2000 | Carter et al. |
| 6,120,762 A | 9/2000 | Johnson et al. |
| 6,132,992 A | 10/2000 | Ledbetter et al. |
| 6,982,321 B2 | 1/2006 | Winter |
| 7,087,409 B2 | 8/2006 | Barbas et al. |

(Continued)

FOREIGN PATENT DOCUMENTS

| | | |
|---|---|---|
| EP | 0 219 781 | 4/1987 |
| EP | 1 391 213 | 2/2004 |

(Continued)

OTHER PUBLICATIONS

U.S. Appl. No. 17/283,902, filed Apr. 8, 2021, by Eckelman et al. (Copy not provided). (Copy not submitted herewith pursuant to the waiver of 37 C.F. R. § 1.98(a)(2)(iii) issued by the Office on Sep. 21, 2004).

(Continued)

*Primary Examiner* — Karen A. Canella
(74) *Attorney, Agent, or Firm* — Wilson Sonsini Goodrich & Rosati

(57) ABSTRACT

Provided herein are binding polypeptides that specifically bind DLL3. More specifically, provided herein are fusion proteins, including multivalent and/or multispecific contracts and chimeric antigen receptors, that bind DLL3. Also provided are pharmaceutical compositions containing the polypeptides, nucleic acid molecules encoding the polypeptides and vectors and cells thereof, and methods of use and uses of the provided DLL3 binding polypeptides for treating diseases and conditions, such as cancer.

32 Claims, 52 Drawing Sheets
Specification includes a Sequence Listing.

(56) References Cited

U.S. PATENT DOCUMENTS

| | | |
|---|---|---|
| 7,183,076 B2 | 2/2007 | Arathoon et al. |
| 7,381,803 B1 | 6/2008 | Weiner et al. |
| 7,527,791 B2 | 5/2009 | Adams et al. |
| 7,635,475 B2 | 12/2009 | Kumagai et al. |
| 7,728,114 B2 | 6/2010 | Mach et al. |
| 7,959,925 B2 | 6/2011 | Weinberg et al. |
| 7,994,289 B2 | 8/2011 | Waldmann et al. |
| 7,998,469 B2 | 8/2011 | Gantier et al. |
| 8,052,964 B2 | 11/2011 | Gantier et al. |
| 9,006,399 B2 | 4/2015 | Liu et al. |
| 9,035,026 B2 | 5/2015 | Hoffmann et al. |
| 9,605,084 B2 | 3/2017 | Moore et al. |
| 9,644,016 B2 | 5/2017 | Stagliano et al. |
| 9,650,446 B2 | 5/2017 | Moore et al. |
| 9,701,750 B2 | 7/2017 | Hoffmann et al. |
| 9,701,759 B2 | 7/2017 | Desjarlais et al. |
| 9,803,021 B2 | 10/2017 | Morrison |
| 10,010,626 B2 | 7/2018 | Chang et al. |
| 10,066,015 B2 | 9/2018 | Zhukovsky et al. |
| 10,087,250 B2 | 10/2018 | Bruenker et al. |
| 10,131,710 B2 | 11/2018 | Moore et al. |
| 10,858,417 B2 | 12/2020 | Moore et al. |
| 11,866,507 B2 | 1/2024 | Eckelman et al. |
| 2006/0270045 A1 | 11/2006 | Cregg et al. |
| 2009/0025106 A1 | 1/2009 | Reini et al. |
| 2011/0274685 A1 | 11/2011 | Keler et al. |
| 2011/0275787 A1 | 11/2011 | Kufer et al. |
| 2012/0149876 A1 | 6/2012 | Von Kreudenstein et al. |
| 2012/0237498 A1 | 9/2012 | Ahrens et al. |
| 2013/0183321 A1 | 7/2013 | Smith et al. |
| 2013/0273054 A1 | 10/2013 | Bossenmaier et al. |
| 2014/0072581 A1 | 3/2014 | Dixit et al. |
| 2014/0154253 A1 | 6/2014 | Ng et al. |
| 2014/0288275 A1 | 9/2014 | Moore et al. |
| 2014/0294823 A1 | 10/2014 | Moore et al. |
| 2014/0322129 A1 | 10/2014 | Leong et al. |
| 2014/0348841 A1 | 11/2014 | Schebye et al. |
| 2014/0363426 A1 | 12/2014 | Moore et al. |
| 2015/0064204 A1 | 3/2015 | Beers et al. |
| 2015/0079088 A1 | 3/2015 | Lowman et al. |
| 2015/0087810 A1 | 3/2015 | Moore et al. |
| 2015/0239991 A1 | 8/2015 | Blein et al. |
| 2015/0307617 A1 | 10/2015 | Du et al. |
| 2015/0307628 A1 | 10/2015 | Kim et al. |
| 2016/0039942 A1 | 2/2016 | Cobbold et al. |
| 2016/0122425 A1 | 5/2016 | Daugherty et al. |
| 2016/0194399 A1 | 7/2016 | Irving et al. |
| 2016/0280795 A1 | 9/2016 | Wang |
| 2016/0289324 A1 | 10/2016 | Moore et al. |
| 2017/0022284 A1 | 1/2017 | Timmer et al. |
| 2017/0081397 A1 | 3/2017 | Stagliano et al. |
| 2017/0198050 A1 | 7/2017 | Eckelman et al. |
| 2017/0204139 A1 | 7/2017 | Moore et al. |
| 2017/0226215 A1 | 8/2017 | Gray et al. |
| 2017/0369563 A1 | 12/2017 | Dubridge et al. |
| 2018/0011883 A1 | 1/2018 | Goldbrenner et al. |
| 2018/0016354 A1 | 1/2018 | Wozniak-Knopp et al. |
| 2018/0194842 A1 | 7/2018 | Mach et al. |
| 2018/0230225 A1 | 8/2018 | Fan et al. |
| 2018/0355038 A1 | 12/2018 | Smith et al. |
| 2019/0010242 A1 | 1/2019 | Eckelman et al. |
| 2019/0218515 A1 | 7/2019 | Ballesteros Nobell et al. |
| 2019/0330366 A1 | 10/2019 | Eckelman et al. |
| 2020/0048350 A1 | 2/2020 | Eckelman et al. |
| 2020/0190193 A1 | 6/2020 | Pandit et al. |
| 2021/0340273 A1 | 11/2021 | Timmer et al. |
| 2023/0295336 A1 | 9/2023 | Eckelman et al. |
| 2024/0101704 A1 | 3/2024 | Eckelman et al. |

FOREIGN PATENT DOCUMENTS

| | | | |
|---|---|---|---|
| EP | | 3502140 | 6/2019 |
| WO | WO-1992/008737 | | 5/1992 |
| WO | WO-1994/004679 | | 3/1994 |
| WO | WO-1998/050431 | | 11/1998 |
| WO | WO-2000/024884 | | 5/2000 |
| WO | WO-2000/041474 | | 7/2000 |
| WO | WO-2002/079249 | | 10/2002 |
| WO | WO-2002/083733 | | 10/2002 |
| WO | WO-2002/086156 | | 10/2002 |
| WO | WO-2002/095067 | | 11/2002 |
| WO | WO-2002/101048 | | 12/2002 |
| WO | WO-2003/000896 | | 3/2003 |
| WO | WO-2003/023032 | | 3/2003 |
| WO | WO-2004/022593 | | 3/2004 |
| WO | WO-2004/022747 | | 3/2004 |
| WO | WO-2004/092219 | | 10/2004 |
| WO | WO-2005/035584 | | 4/2005 |
| WO | WO-2005/040220 | | 5/2005 |
| WO | WO-2005/063816 | | 7/2005 |
| WO | WO-2005/100402 | | 10/2005 |
| WO | WO-2006/029879 | | 3/2006 |
| WO | WO-2007/033230 | | 3/2007 |
| WO | WO-2008/119567 | | 10/2008 |
| WO | WO-2009/018386 | | 2/2009 |
| WO | WO-2009/067800 | | 6/2009 |
| WO | WO-2009/089004 | | 7/2009 |
| WO | WO-2009/124931 | | 10/2009 |
| WO | WO-2010/037836 | | 4/2010 |
| WO | WO-2010/151792 | | 12/2010 |
| WO | WO-2011/056983 | | 5/2011 |
| WO | WO-2011/133886 | | 10/2011 |
| WO | WO-2011/143545 | | 11/2011 |
| WO | WO-2012/025525 | | 3/2012 |
| WO | WO-2012/058768 | | 5/2012 |
| WO | WO-2013/026837 | | 2/2013 |
| WO | WO-2013/101909 | | 7/2013 |
| WO | WO-2013/128194 | | 9/2013 |
| WO | WO-2014/067011 | | 5/2014 |
| WO | WO-2014/099997 | | 6/2014 |
| WO | WO-2014/125273 | | 8/2014 |
| WO | WO-2014/145806 | | 9/2014 |
| WO | WO-2014/194100 | | 12/2014 |
| WO | WO-2015/001085 | | 1/2015 |
| WO | WO-2015/026894 | | 2/2015 |
| WO | WO-2015/168469 | | 11/2015 |
| WO | WO-2015/197598 | | 12/2015 |
| WO | WO-2015/197789 | | 12/2015 |
| WO | WO-2016/020309 | | 2/2016 |
| WO | WO-2016/046778 | | 3/2016 |
| WO | WO-2016/055593 | | 4/2016 |
| WO | WO-2015/095392 | | 6/2016 |
| WO | WO-2016/086189 | | 6/2016 |
| WO | WO-2016/087416 | | 6/2016 |
| WO | WO-2016/105450 | | 6/2016 |
| WO | WO-2016/138038 | | 9/2016 |
| WO | WO-2016138038 A1 * | 9/2016 | ............ A61K 35/17 |
| WO | WO-2016/177762 | | 11/2016 |
| WO | WO-2016/179517 | | 11/2016 |
| WO | WO-2016/180982 | | 11/2016 |
| WO | WO-2016/192613 | | 12/2016 |
| WO | WO-2016/204966 | | 12/2016 |
| WO | WO-2017/015623 | | 1/2017 |
| WO | WO-2017/021349 | | 2/2017 |
| WO | WO-2017/055398 | | 4/2017 |
| WO | WO-2017/060144 | | 4/2017 |
| WO | WO-2017/123650 | | 7/2017 |
| WO | WO-2017/123673 | | 7/2017 |
| WO | WO-2017/134140 | | 8/2017 |
| WO | WO-2017/134440 | | 8/2017 |
| WO | WO-2017/167672 | | 10/2017 |
| WO | WO-2017/172981 | | 10/2017 |
| WO | WO-2018/014260 | | 1/2018 |
| WO | WO-2018/027025 | | 2/2018 |
| WO | WO-2018/068201 | | 4/2018 |
| WO | WO-2018/068695 | | 4/2018 |
| WO | WO-2018/127473 | | 7/2018 |
| WO | WO-2018/185045 | | 10/2018 |
| WO | WO-2018/191438 | | 10/2018 |
| WO | WO-2019/133761 | | 7/2019 |
| WO | WO-2019/200022 | | 10/2019 |
| WO | WO-2020/023553 | | 1/2020 |
| WO | WO-2020/076970 | | 4/2020 |

(56) References Cited

FOREIGN PATENT DOCUMENTS

| WO | WO-2020/076992 | | 4/2020 | |
|---|---|---|---|---|
| WO | WO-2020069028 | A1 * | 4/2020 | ....... A61K 39/39591 |
| WO | WO-2021/155071 | | 8/2021 | |

OTHER PUBLICATIONS

Ackerman et al., "Biologic activity in a fragment of recombinant human interferon alpha," Proc Natl Acad Sci U S A. (1984) 81(4): 1045-1047.
Al-Lazikani et al., "Standard Conformations for the Canonical Structures of Immunoglobulins," J. Mol. Biol. (1997) 273: 927-948.
Alegre et al., "Effect of a single amino acid mutation on the activating and immunosuppressive properties of a "humanized" OKT3 monoclonal antibody," J Immunol (1992) 148(11):3461-3468.
Almagro et al., "Humanization of Antibodies," Frontiers in Bioscience. (2008) 13:1619-1633.
Anasetti et al., "Treatment of acute graft-versus-host disease with a nonmitogenic anti-CD3 monoclonal antibody," Transplantation. (1992) 54(5): 844-51.
Anderson et al., "Fc gamma receptor type III (CD16) is included in the zeta NK receptor complex expressed by human natural killer cells.," Proc Natl Acad Sci USA. (1990) 87(6): 2274-2278.
Arndt et al., "A bispecific diabody that mediates natural killer cell cytotoxicity against xenotransplantated human Hodgkin's tumors," Blood. (1999) 94(8): 2562-2568.
Baca et al., "Antibody Humanization Using Monovalent Phage Display," J. Biol. Chem. (1997) 272(16): 10678-10684.
Bacac et al., "CD20 Tcb (RG6026), a Novel "2:1" T Cell Bispecific Antibody for the Treatment of B Cell Malignancies," Blood (2016) 128:1836.
Behar et al., "Isolation and characterization of anti-FcgammaRIII (CD16) llama single-domain antibodies that activate natural killer cells," Protein Eng Des Sel. (2008) 21(1): 1-10.
Beliveau et al., "Probing the substrate specificities of matriptase, matriptase-2, hepsin and DESC1 with internally quenched fluorescent peptides," FEBS J (2009) 276(8):2213-2226.
Brinkmann et al., "The making of bispecific antibodies," MABS (2017) 9(2):182-212.
Bruggemann et al., "Comparison of the effector functions of human immunoglobulins using a matched set of chimeric antibodies," J Exp Med (1987) 166(5):1351-1361.
Capel et al., "Heterogeneity of Human IgG Fc Receptors," Immunomethods (1994) 4(1): 25-34.
Carter et al., "Bispecific human IgG by design," J Immunol Methods (2001) 248(1-2):7-15.
Carter et al., "Humanization of an Anti-p185HER2 Antibody For Human Cancer Therapy," Proc. Natl. Acad. Sci. USA (1992) 89: 4285-4289.
Chapman et al., "Notch inhibition by the ligand DELTA-LIKE 3 defines the mechanism of abnormal vertebral segmentation in spondylocostal dysostosis," Hum Mol Genet. (2011) 20(5): 905-16.
Chen et al., "Fusion protein linkers: property, design and functionality," Adv Drug Deliv Rev (2013) 65(10):1357-1369.
Clackson et al., "Making Antibody Fragments Using Phage Display Libraries," Nature (1991) 352: 624-628.
Clynes et al., "Fc receptors are required in passive and active immunity to melanoma," Proc Natl Acad Sci USA (1998) 95(2):652-656.
Cragg et al., "Antibody specificity controls in vivo effector mechanisms of anti-CD20 reagents," Blood (2004) 103:2738-2743.
Cragg et al., "Complement-mediated lysis by anti-CD20 mAb correlates with segregation into lipid rafts," Blood (2003) 101(3):1045-1052.
Daeron, "Fc receptor biology," Annu Rev Immunol. (1997) 15: 203-34.

Dall'Acqua et al., "Properties of Human IgG1s Engineered for Enhanced Binding to the Neonatal Fc Receptor (FcRn)*," J Biol Chem (2006) 281(33):23514-23524.
Dall'Acqua et al., "Antibody Humanization by Framework Shuffling," Methods (2005) 36:43-60.
Davis et al., "SEEDbodies: fusion proteins based on strand-exchange engineered domain (SEED) CH3 heterodimers in an Fc analogue platform for asymmetric binders or immunofusions and bispecific antibodies," Protein Eng Des Sel (2010) 23(4):195-202.
De Haas, M. et al. "Fc Gamma receptors of Phagocytes," J. Lab. Clin. Med. (1995) 126:330-341.
Deer et al., "High-Level Expression Of Proteins In Mammalian Cells Using Transcription Regulatory Sequences From The Chinese Hamster EF-1Alpha Gene," Biotechnol. Prog. (2004) 20(3): 880-889.
Deisenhofer, "Crystallographic refinement and atomic models of a human Fc fragment and its complex with fragment B of protein A from *Staphylococcus aureus* at 2.9- and 2.8-.ANG. resolution," Biochemistry (1981) 20(9):2361-2370.
Diaz et al., "Structure of the human type-I interferon gene cluster determined from a YAC clone contig," Genomics. (1994) 22(3): 540-552.
Dotti et al., "Design and development of therapies using chimeric antigen receptor-expressing T cells," Immunol Rev. (2014) 257(1); 35 pages.
Endo et al., "High-Throughput, Genome-Scale Protein Production Method Based On The Wheat Germ Cell-Free Expression System," Biotechnol. Adv. (2003) 21; 695-713.
Gazzano-Santoro et al., "A non-radioactive complement-dependent cytotoxicity assay for anti-CD20 monoclonal antibody," J Immunol Methods (1997) 202(2):163-171.
Ghetie et al,. "FcRn: the MHC Class I-related Receptor That Is More Than An IgG Transporter," Immunol. Today (1997) 18(12): 592-598.
Ghetie et al., "Increasing the Serum Persistence of an IgG Fragment by Random Mutagenesis," Nat Biotech (1997) 15:637-640.
Golovleva et al., "Polymorphism in the interferon-alpha gene family," Am J Hum Genet. (1996) 59(3): 570-8.
Golovleva et al., "Ethnic differences in interferon-alpha allele frequencies," Hum Hered. (1997) 47(4): 185-188.
Golovleva et al., "Novel variants of human IFN-alpha detected in tumor cell lines and biopsy specimens," J Interferon Cytokine Res. (1997) 17(10): 637-645.
Gunasekaran et al., "Enhancing antibody Fc heterodimer formation through electrostatic steering effects: applications to bispecific molecules and monovalent IgG," J Biol Chem (2010) 285(25):19637-19646.
Guyer et al., "Immunoglobulin binding by mouse intestinal epithelial cell receptors," J Immunol. (1976) 117(2): 587-593.
Ha et al., "Immunoglobulin Fc Heterodimer Platform Technology: From Design to Applications in Therapeutic Antibodies and Proteins," Front Immunol (2016) 7:394.
Harwood et al., "ATTACK, a novel bispecific T cell-recruiting antibody with trivalent EGFR binding and monovalent CD3 binding for cancer immunotherapy," Oncoimmunology (2018) 7(1):e1377874.
Hawkins et al., "Phase I evaluation of a synthetic mutant of beta-interferon," Cancer Res. (1985) 45; 5914-20.
Hayward et al., "Lysis of CD3 hybridoma targets by cloned human CD4 lymphocytes," Immunology. (1988) 64(1): 87-92.
Hellstrom et al., "Antitumor effects of L6, an IgG2a antibody that reacts with most human carcinomas," Proc Natl Acad Sci USA (1986) 83(18):7059-7063.
Hellstrom et al., "Strong antitumor activities of IgG3 antibodies to a human melanoma-associated ganglioside," Proc Natl Acad Sci USA (1985) 82(5):1499-1502.
Henry et al., "Stability-Diversity tradeoffs impose fundamental constraints on selection of synthetic human VH/VL single-domain antibodies from in vitro display libraries," Frontiers in Immunology (2017) 8:1-15.
Hernandez-Hoyos et al., "MOR209/ES414, a Novel Bispecific Antibody Targeting PSMA for the Treatment of Metastatic Castration-Resistant Prostate Cancer," Mol Cancer Ther (2016) 15(9):2155-2165.

(56) References Cited

OTHER PUBLICATIONS

Hinman et al. "Preparation and characterization of monoclonal antibody conjugates of the calicheamicins: a novel and potent family of antitumor antibiotics," Cancer Res. (1993) 53(14): 3336-3342.
Hinton et al., "Engineered Human IgG Antibodies with Longer Serum Half-lives in Primates," J. Biol. Chem. (2004) 279(8): 6213-6216.
Holliger et al., "Specific killing of lymphoma cells by cytotoxic T-cells mediated by a bispecific diabody," Protein Engineering Design and Selection (1996) 9(3):299-305.
Honegger et al., "Yet Another Numbering Scheme for Immunoglobulin Variable Domains: An Automatic Modeling and Analysis Tool," J Mol Biol. (2001) 309(3): 657-670.
Hu et al., "Notch3 pathway alterations in ovarian cancer," Cancer Res. (2014) 74(12): 3282-3293.
Husain et al., "Expanding the boundaries of biotherapeutics with bispecific antibodies," Biodrugs (2018) 32(5):441-64.
Hussain et al., "IFN-alpha1a gene is the major variant in the North American population," J Interferon Cytokine Res. (2000) 20(9): 763-768.
Hussain et al., "Interferon-alpha 8b is the only variant of interferon-alpha 8 identified in a large human population," J Interferon Cytokine Res. (1996) 16(7): 523-529.
Hussain et al., "Both variant forms of interferon-alpha4 gene (IFNA4a and IFNA4b) are present in the human population," J Interferon Cytokine Res. (1997) 17(9): 559-566.
Hussain et al., "A new allele of interferon-alpha17 gene encoding IFN-alpha17b is the major variant in human population," J Interferon Cytokine Res. (1998) 18(7): 469-77.
Idusogie et al., "Engineered antibodies with increased activity to recruit complement," J Immunol (2001) 166(4):2571-2575.
Jaitin et al., "Inquiring into the differential action of interferons (IFNs): an IFN-alpha2 mutant with enhanced affinity to IFNAR1 is functionally similar to IFN-beta," Mol Cell Biol. (2006) 26(5): 1888-1897.
Jendeberg et al., "Engineering of Fc(1) and Fc(3) from human immunoglobulin G to analyse subclass specificity for staphylococcal protein A," J Immnuol Methods (1997) 201(1):25-34.
Kabat et al., Sequences of Proteins of Immunological Interest, 5th Edition, U.S. Department of Health and Human Services, (1991) NIH Publication No. 91-3242, p. 689.
Kalie et al., "An interferon alpha2 mutant optimized by phage display for IFNAR1 binding confers specifically enhanced antitumor activities," J Biol Chem. (2007) 282(15): 11602-11611.
Kaneko et al., "Optimizing Therapeutic Antibody Function," Biodrugs (2011) 25(1):1-11.
Kashmiri et al., "SDR grafting—A New Approach to Antibody Humanization," Methods. (2005) 36: 25-34.
Kim et al., "Mutational approaches to improve the biophysical properties of human single-domain antibodies," Biochimica et Biophysica Acta (2014) 1844:1983-2001.
Kim et al., "Localization of the Site of the Murine IgGI Molecule That is Involved in Binding to the Murine Intestinal Fc Receptor," Eur. J. Immunol. (1994) 24:2429-2434.
Kim et al., "Interferon, alpha 17 (IFNA17) Ile184Arg polymorphism and cervical cancer risk," Cancer Lett. (2003) 189(2); 183-188.
Kindt, T.J. et al. (2007). "Antigens And Antibodies," Chapter 4 In Kuby Immunology 6th Ed., W.H. Freeman And Co., p. 91, 14 pages.
Kipriyanov et al., "Bispecific tandem diabody for tumor therapy with improved antigen binding and pharmacokinetics," J Mol Biol (1999) 293(1):41-56.
Kita et al., "Determination of interferon-alpha2 allele composition in the genomic DNA from healthy volunteers and leukemic patients in Japan," J Interferon Cytokine Res. (1997) 17(3); 135-140.
Klimka et al., "Human Anti-CD30 Recombinant Antibodies by Guided Phage Antibody Selection Using Cell Panning," Br. J. Cancer (2000) 83(2):252-260.

Kohler et al., "Continuous Culture of Fused Cells Secreting Antibody of Predefined Specificity," Nature (1975) 256:495-497.
Krause et al., "Signaling by covalent heterodimers of interferon-gamma. Evidence for one-sided signaling in the active tetrameric receptor complex," J Biol Chem. (2000) 275(30); 22995-3004.
Kumar et al., "Molecular cloning and expression of the Fabs of human autoantibodies in *Escherichia coli*," J. Biol. Chem. (2000) 275:35129-36.
Kunnimalaiyaan et al., "Tumor suppressor role of Notch-1 signaling in neuroendocrine tumors," Oncologist. (2007) 12(5): 535-542.
La Rocca et al., "Zymographic detection and clinical correlations of MMP-2 and MMP-9 in breast cancer sera," British Journal of Cancer (2004) 90:1414-1421.
Lazar et al., "Engineered antibody Fc variants with enhanced effector function," Proc Natl Acad Sci USA (2006) 103(11):4005-4010.
Leaver-Fay et al., "Computationally Designed Bispecific Antibodies using Negative State Repertoires," Structure (2016) 24(4):641-651.
Ledbetter et al., "Valency of CD3 binding and internalization of the CD3 cell-surface complex control T cell responses to second signals: distinction between effects on protein kinase C, cytoplasmic free calcium, and proliferation," J Immunol. (1986) 136(11); 3945-3952.
Lefranc et al., "IMGT unique numbering for immunoglobulin and T cell receptor variable domains and Ig superfamily V-like domains," Dev Comp Immunol (2003) 27(1):55-77.
Linge et al., "Transcription of interferon-alpha 2 alleles from virus-induced human leucocytes and lymphoblastoid cells of African origin," Biochim Biophys Acta. (1995) 1264(3):363-8.
Liu et al., "Eradication of Large Colon Tumor Xenografts by Targeted Delivery of Maytansinoids," Proc. Natl. Acad. Sci. USA (1996) 93: 8618-8623.
Lode et al., "Targeted therapy with a novel enediyene antibiotic calicheamicin theta(I)1 effectively suppresses growth and dissemination of liver metastases in a syngeneic model of murine neuroblastoma," Cancer Res. (1998) 58:2925-2928.
Lundell et al., "The carboxyl-terminal region of human interferon gamma is important for biological activity: mutagenic and NMR analysis," Protein Eng. (1991) 4(3): 335-341.
Maccallum et al., "Antibody-antigen interactions: Contact analysis and binding site topography," J. Mol. Biol. (1996) 262, 732-745.
Mandelboim et al., "Human CD16 as a lysis receptor mediating direct natural killer cell cytotoxicity," Proc Natl Acad Sci U S A. (1999) 96(10): 5640-5644.
Mandler et al., "Synthesis and evaluation of antiproliferative activity of a geldanamycin-Herceptin immunoconjugate," Bioorg Med Chem Lett. (2000) 10(10): 1025-1028.
Mandler et al., "Modifications in Synthesis Strategy Improve the Yield and Efficacy of Geldanamycin-Herceptin Immunoconjugates," Bioconjugate Chem. (2002)13:786-791.
Mandler et al., "Immunoconjugates of Geldananlycin and Anti-HER2 Monoclonal Antibodies: Antiproliferative Activity on Human Breast Carcinoma Cell Lines," J. Nat. Cancer Inst. (2000) 92(19): 1573-1581.
Martin et al., "Modeling antibody hypervariable loops: a combined algorithm," Proc Natl Acad Sci U S A. (1989) 86(23): 9268-9272.
Mccafferty et al., "Phage antibodies: filamentous phage displaying antibody variable domains," Nature (1990) 348:552-554.
Mccall et al., "Isolation and characterization of an anti-CD16 single-chain Fv fragment and construction of an anti-HER2/neu/anti-CD16 bispecific scFv that triggers CD16-dependent tumor cytolysis," Mol. Immunol. (1999) 36:433-45.
Merchant et al., "An efficient route to human bispecific IgG," Nat Biotechnol (1998) 16(7):677-681.
Miller, "Protein-protein recognition and the association of immunoglobulin constant domains," JMB (1990) 216(4):965-973.
Moore et al., "A novel bispecific antibody format enables simultaneous bivalent and monovalent co-engagement of distinct target antigens," MAbs (2011) 3(6):546-557.
Moore et al., "Engineered Fc variant antibodies with enhanced ability to recruit complement and mediate effector functions," MAbs (2010) 2(2):181-189.

(56) References Cited

OTHER PUBLICATIONS

Nagorsen et al., "Immunomodulatory therapy of cancer with T cell-engaging BiTE antibody blinatumomab," Exp Cell Res. (2011) 317(9): 1255-60.
Natsume et al., "Engineered Antibodies of IgG1/IgG3 Mixed Isotype with Enhanced Cytotoxic Activities," Cancer Res (2008) 68(10):3863-3872.
Nicolaou et al., "Calicheamicin θ: A Rationally Designed Molecule with Extremely Potent and Selective DNA Cleaving Properties and Apoptosis Inducing Activity," Angew Chem Int Edit (1994) 33(2):183-186.
Nyman et al., "Structural characterisation of N-linked and O-linked oligosaccharides derived from interferon-alpha2b and interferon-alpha14c produced by Sendai-virus-induced human peripheral blood leukocytes," Eur J Biochem. (1998) 253(2): 485-93.
Ohannesian et al., "Carcinoembryonic antigen and other glycoconjugates act as ligands for galectin-3 in human colon carcinoma cells," Cancer Res. (1995) 55(10): 2191-2199.
Osbourn, et al., "From Rodent Regents to Human Therapeutics Using Antibody Guided Selection," Methods. (2005) 36:61-68.
Padlan, "A possible procedure for reducing the immunogenicity of antibody variable domains while preserving their ligand-binding properties," Mol Immunol (1991) 28(4-5):489-498.
Pan et al., "Structural characterization of human interferon gamma. Heterogeneity of the carboxyl terminus," Eur J Biochem. (1987) 166(1): 145-149.
Pan et al., "Site-specific PEGylation of an anti-CEA/CD3 bispecific antibody improves its antitumor efficacy," Int J Nanomedicine. (2018)13: 3189-3201.
Peng et al., "Metastatic melanoma, glioblastoma and high-grade extrapulmonary neuroendocrine carcinomas (NECs) as novel indications for rovalpituzumab tesirine: A delta-like protein 3 (DLL3)-targeted antibody-drug conjugate (ADC)," J. Clin. Oncol. (2016) 34(15) Supp 11611-11611.
Pessano, S. et al., "The T3/T Cell Receptor Complex: Antigenic Distinction Between The Two 20-kd T3 (T3-δ and T3-ε) Subunits," The EMBO Journal (1985) 4(2):337-344.
Pestka et al., The human interferons—from protein purification and sequence to cloning and expression in bacteria: before, between, and beyond, Arch Biochem Biophys. (1983) 221(1): 1-37.
Pestka, vol. 119. Interferons (Part C) (1986) Meth. Enzymol, 199: 3-4.
Petkova et al., "Enhanced half-life of genetically engineered human IgG1 antibodies in a humanized FcRn mouse model: potential application in humorally mediated autoimmune disease," Int Immunol (2006) 18(12):1759-1769.
Pollard et al., "Fixation, processing, and immunochemical reagent effects on preservation of T-lymphocyte surface membrane antigens in paraffin-embedded tissue," J Histochem Cytochem. (1987)35(11): 1329-38.
Portolano et al., "Lack of promiscuity in autoantigen-specific H and L chain combinations as revealed by human H and L chain "roulette"," J. Immunol. (1993) 150:880-887.
Presta et al., "Humanization of an Antibody Directed Against IgE," J. Immunol. (1993) 151(2): 2623-2632.
Queen et al., "A humanized antibody that binds to the interleukin 2 receptor," Proc Natl Acad Sci USA (1989) 86:10029-10033.
Ravetch et al., "Fc receptors," Annu Rev Immunol. (1991) 9:457-92.
Reusch et al., "A Novel Tetravalent Bispecific T and Ab (CD30/CD 16A) Efficiently Recruits NK Cells For The Lysis Of CD30+ Tumor Cells," mAbs (2014) 6(SUPPL 3): 727-738.
Ridgway et al., "'Knobs-into-holes' engineering of antibody CH3 domains for heavy chain heterodimerization," Protein engineering (1996) 9(7):617-621.
Riechmann et al., "Reshaping Human Antibodies for Therapy," Nature (1988) 332: 323-327.
Rodrigues et al., "Engineering a humanized bispecific F(ab')2 fragment for improved binding to T cells," Int J Cancer Suppl. (1992) 7:45-50.
Rosenberg et al., "Use Of Tumor-Infiltrating Lymphocytes And Interleukin-2 In The Immunotherapy Of Patients With Metastatic Melanoma. A Preliminary Report," N Engl J Med. (1988) 319(25): 1676-1680.
Rosok et al., "A Combinatorial Library Strategy for the Rapid Humanization of Anticarcinoma BR96 Fab," J. Biol. Chem. (1996) 271(37): 22611-22618.
Rowland et al., "Drug Localisation And Growth Inhibition Studies of Vindesine-Monoclonal Anti-CEA Conjugates in a Human Tumour Xenograft," Cancer Immunol. Immunother. (1986) 21:183-187.
Rudikoff et al., "Single amino acid substitution altering antigen-binding specificity," Proc Natl Acad Sci USA (1982) 79(6):1979-1983.
Sadelain et al., "The basic principles of chimeric antigen receptor design," Cancer Discov. (2013) 3(4): 388-398.
Sadelain et al., "The promise and potential pitfalls of chimeric antigen receptors," Curr Opin Immunol. (2009) 21(2): 215-23.
Saunders et al., "A DLL3-targeted antibody-drug conjugate eradicates high-grade pulmonary neuroendocrine tumor-initiating cells in vivo," Sci Transl Med. (2015) 7(302): 302ra136.
Seimetz et al., "Development and approval of the trifunctional antibody catumaxomab (anti-EpCAM x anti-CD3) as a targeted cancer immunotherapy," Cancer Treat Rev (2010) 36:458-467.
Serth et al., "O-fucosylation of DLL3 is required for its function during somitogenesis," PLoS One. (2015) 10(4): e0123776.
Shields et al., "High Resolution Mapping of the Binding Site on Human IgG1 for FcγRI, FcγRII, FcγRIII, and FcRn and Design of IgG1 Variants with Improved Binding to the FcγR*," JBC (2001) 276(9):6591-6604.
Sims et al., "A Humanized CD18 Antibody Can Block Function Without Cell Destruction," J. Immunol. (1993) 151(4): 2296-2308.
Sitaraman et al., "High-throughput protein expression using cell-free system," Methods Mol. Biol. (2009) 498: 229-44.
Smith-Gill et al., "Contributions of immunoglobulin heavy and light chains to antibody specificity for lysozyme and two haptens," J. Immunol. (1987) 139:4135-44.
Song et al., "Light chain of natural antibody plays a dominant role in protein antigen binding," Biochem. Biophys. Res. Comm. (2000) 268:390-94.
Spirin, "High-Throughput Cell-Free Systems For Synthesis Of Functionally Active Proteins," Trends Biotechnol. (2004) 22(10): 538-545.
Stavenhagen et al., "Enhancing the potency of therapeutic monoclonal antibodies via Fc optimization," Adv Enzyme Regul (2008) 48:152-164.
Stavenhagen et al., "Fc Optimization of Therapeutic Antibodies Enhances Their Ability to Kill Tumor Cells In vitro and Controls Tumor Expansion In vivo via Low-Affinity Activating Fcγ Receptors," Cancer Res (2007) 67(18):8882-8890.
Streit et al., "Angiogenesis, lymphangiogenesis, and melanoma metastasis," Oncogene (2003) 22(20):3172-3179.
Taylor et al., "Nanocell targeting using engineered bispecific antibodies," Mabs (2015) 7(1):53-65.
Valedkarimi et al., "Antibody-cytokine fusion proteins for improving efficacy and safety of cancer therapy," Biomed Pharmacother. (2017) 95: 731-742.
Van De Winkel et al., "Human IgG Fc receptor heterogeneity: molecular aspects and clinical implications," Immunol Today. (1993) 14(5): 215-21.
Wang, "Lyophilization and development of solid protein pharmaceuticals," Int J Pharm (2000) 203(1-2):1-60.
Ward et al., "Binding activities of a repertoire of single immunoglobulin variable domains secreted from *Escherichia coli*," Nature (1989) 341:544-56.
Wirthmueller et al., "Signal transduction by Fc gamma RIII (CD16) is mediated through the gamma chain," J Exp Med. (1992) 175(5):1381-90.
Yamamoto et al., "Creation of interferon-alpha8 mutants with amino acid substitutions against interferon-alpha receptor-2 binding sites using phage display system and evaluation of their biologic properties," J Interferon Cytokine Res. (2009) 29(3): 161-70.

(56) References Cited

OTHER PUBLICATIONS

Yang et al., "A Common Pathway For T Lymphocyte Activation Involving Both The CD3-Ti Complex And CD2 Sheep Erythrocyte Receptor Determinants," J. Immunol. (1986) 137(4): 1097-1100.

Young et al., "Antibody-Cytokine Fusion Proteins For Treatment Of Cancer: Engineering Cytokines For Improved Efficacy and Safety," Seminars In Oncology. (2014) 41(5):623-636, 19 pages.

Zalevsky et al., "Enhanced antibody half-life improves in vivo activity," Nat Biotechnol (2010) 28(2):157-159.

Asano et al. "Domain order of a bispecific diabody dramatically enhances its antitumor activity beyond structural format conversion: the case of the hEx3 diabody." *Protein Engineering, Design & Selection* 26.5 (2013): 359-367.

Barthelemy et al. "Comprehensive analysis of the factors contributing to the stability and solubility of autonomous human VH domains." *Journal of Biological Chemistry* 283.6 (2008): 3639-3654.

Beiboer et al. "Guided selection of a pan carcinoma specific antibody reveals similar binding characteristics yet structural divergence between the original murine antibody and its human equivalent." *Journal of Molecular Biology* 296.3 (2000): 833-849.

Choi et al. "Predicting antibody complementarity determining region structures without classification." *Molecular BioSystems* 7.12 (2011): 3327-3334.

De Genst et al. "Antibody repertoire development in camelids." *Developmental & Comparative Immunology* 30.1-2 (2006): 187-198.

Driessens et al. "Costimulatory and coinhibitory receptors in anti-tumor immunity." *Immunological reviews* (2009) 229.1: 126-144.

Griffiths et al. "Human anti-self antibodies with high specificity from phage display libraries." *The EMBO journal* 12.2 (1993): 725-734.

Kuo et al., "Engineering a CD123xCD3 bispecific scFv immunofusion for the treatment of leukemia and elimination of leukemia stem cells," Protein Eng Des Sel. (2012) 25(10): 561-9.

Maeda et al., "Engineering of functional chimeric protein G-Vargula luciferase," Anal Biochem. (1997) 249(2):147-52.

Malia et al. "Epitope mapping and structural basis for the recognition of phosphorylated tau by the anti-tau antibody AT8." *Proteins: Structure, Function, and Bioinformatics* 84.4 (2016): 427-434.

Miyazaki, "Studies on Alpaca VHH antibodies for industrial applications," Kagoshima University Repository, Jun. 1, 2015, 102 pages. https://ir.kagoshima-u.ac.jp/records/9025 (Machine translation provided).

Schmiedel et al. "Expression of a bispecific dsFv-dsFv' antibody fragment in *Escherichia coli*." Protein Engineering 13.10 (2000): 725-734.

Weidle et al. "The intriguing options of multispecific antibody formats for treatment of cancer." *Cancer genomics & proteomics* 10.1 (2013): 1-18.

Xing et al., "BiHC, a T-Cell-Engaging Bispecific Recombinant Antibody, Has Potent Cytotoxic Activity Against Her2 Tumor Cells," Transl Oncol (2017) 10(5):780-785.

Zhang et al., "Amplification Ex Vivo and Cytocidal Activity of Leukemia Tumor-Associated Antigen-Specific Cytotoic T Lympohcytes," Chinese Journal of Experimental Hematology, (2015) 23(3); 814-820; (Article in Chinese; English abstract provided).

* cited by examiner

Binding to SHP-77 cells cx4720

Secondary antibody only

Binding to T cells cx4720 antiCD3

Secondary antibody only

Binding to SHP-77 cells cx3715

Secondary antibody only

Binding to T cells cx3715 antiCD3

Secondary antibody only

Binding to SHP-77 cells cx4422

Secondary antibody only

Binding to T cells cx4422 antiCD3

Secondary antibody only

Binding to SHP-77 cells cx3708

Secondary antibody only

Binding to T cells cx3708 antiCD3

Secondary antibody only

Binding to SHP-77 cells cx4052

Secondary antibody only

Binding to T cells cx4052 antiCD3

Secondary antibody only

Binding to SHP-77 cells cx4059

Secondary antibody only

Binding to T cells cx4059 antiCD3

Secondary antibody only

Binding to SHP-77 cells cx4087

Secondary antibody only

Binding to T cells cx4087 antiCD3

Secondary antibody only

Binding to SHP-77 cells cx4088

Secondary antibody only

Binding to T cells cx4088 antiCD3

Secondary antibody only

Binding to SHP-77 cells cx4895

Secondary antibody only

Binding to T cells cx4895 antiCD3

Secondary antibody only

Binding to SHP-77 cells cx3991

Secondary antibody only

Binding to T cells cx3991 antiCD3

Secondary antibody only

Binding to SHP-77 cells cx3711

Secondary antibody only

Binding to T cells cx3711 antiCD3

Secondary antibody only

Binding to SHP-77 cells cx4887

Secondary antibody only

Binding to T cells cx4887 antiCD3

Secondary antibody only

Binding to SHP-77 cells cx4896

Secondary antibody only

Binding to T cells cx4896 antiCD3

Secondary antibody only

Binding to SHP-77 cells

Binding to T cells

Binding to SHP-77 cells cx4888

Secondary antibody only

Binding to T cells (50nM Ab)

cx4888 antiCD3

Secondary antibody only

Binding to SHP-77 cells

Binding to T cells (50nM Ab)

- Knob-VH; Hole-VL
- Knob-VL; Hole-VH

→ Knob-VH; Hole-VL
→ Knob-VL; Hole-VH

DLL3 SINGLE DOMAIN ANTIBODIES AND THERAPEUTIC COMPOSITIONS THEREOF

CROSS-REFERENCE TO RELATED APPLICATIONS

This application is a national stage application under 35 U.S.C. § 371 of International Application No. PCT/US2019/055436, filed on Oct. 9, 2019, which claims priority to U.S. provisional applications 62/744,638, filed Oct. 11, 2018, entitled "DLL3 SINGLE DOMAIN ANTIBODIES AND THERAPEUTIC COMPOSITIONS THEREOF"; 62/832,265, filed Apr. 10, 2019, entitled "DLL3 SINGLE DOMAIN ANTIBODIES AND THERAPEUTIC COMPOSITIONS THEREOF"; and 62/877,815 filed Jul. 23, 2019, entitled "DLL3 SINGLE DOMAIN ANTIBODIES AND THERAPEUTIC COMPOSITIONS THEREOF" the contents of which are incorporated by reference in their entirety for all purposes.

INCORPORATION BY REFERENCE OF SEQUENCE LISTING

The present application is being filed along with a Sequence Listing in electronic format. The Sequence Listing is provided as a file entitled 744952000600SeqList.TXT, created Apr. 1, 2021, which is 441,197 kilobytes in size. The information in the electronic format of the Sequence Listing is incorporated by reference in its entirety.

FIELD

This disclosure generally provides binding polypeptides that specifically bind DLL3. More specifically, the disclosure relates to fusion proteins, including multivalent and/or multispecific constructs and chimeric antigen receptors that bind at least DLL3. The disclosure also provides nucleic acid molecules encoding the polypeptides and vectors and cells thereof, and methods of use and uses of the provided DLL3 binding polypeptides for treating diseases and conditions, such as cancer.

BACKGROUND

Delta-like ligand 3 (DLL3) is an inhibitory Notch pathway ligand that is highly upregulated and aberrantly expressed on the cell surface of tumor and cancer cells, including on the cells of small cell lung cancer (SCLC) and high-grade neuroendocrine tumors. The expression of DLL3 on a variety of cancers in humans, including solid tumors, makes DLL3 a desirable therapeutic target. Improved therapeutic molecules and agents targeting DLL3 are needed. Provided herein are embodiments that meet such needs.

SUMMARY

Provided herein is a DLL3-binding polypeptide construct, comprising at least one heavy chain only variable domain (DLL3 VHH domain) that specifically binds DLL3. In some embodiments the DLL3-binding construct comprises one or more additional binding domains that binds to a target other than DLL3.

Provided herein is a DLL3-binding polypeptide construct, wherein the at least one DLL3 VHH domain comprises a complementarity determining region 1 (CDR1) comprising an amino acid sequence selected from the group consisting of SEQ ID NO: 319, 320, 321, 322, 323, 324, 325, 326, 327, 328, 329, 330, 331, 332, 333, 334, 335 and 456; a complementarity determining region 2 (CDR2) comprising an amino acid sequence selected from the group consisting of SEQ ID NO: 336, 337, 338, 339, 340, 341, 342, 343, 344, 345, 346, 347, 348, 349, 350, 351, 352, 353, 384, 410, and 411; and a complementarity determining region 3 (CDR3) comprising an amino acid sequence selected from the group consisting of SEQ ID NO: 354, 355, 356, 357, 358, 359, 360, 361, 362, 363, 364, 365, 366, 367, 395, and 412-415, and binds DLL3.

Provided herein is a DLL3-binding polypeptide construct, comprising at least one heavy chain only variable domain (DLL3 VHH domain) that specifically binds DLL3 comprising a complementarity determining region 1 (CDR1) comprising an amino acid sequence selected from the group consisting of SEQ ID NO: 319, 320, 321, 322, 323, 324, 325, 326, 327, 328, 329, 330, 331, 332, 333, 334, 335 and 456; a complementarity determining region 2 (CDR2) comprising an amino acid sequence selected from the group consisting of SEQ ID NO: 336, 337, 338, 339, 340, 341, 342, 343, 344, 345, 346, 347, 348, 349, 350, 351, 352, 353, 384, 410, and 411; and a complementarity determining region 3 (CDR3) comprising an amino acid sequence selected from the group consisting of SEQ ID NO: 354, 355, 356, 357, 358, 359, 360, 361, 362, 363, 364, 365, 366, 367, 395, and 412-415, and binds DLL3.

In some of any of the provided embodiments, the at least one DLL3 VHH domain comprises a complementarity determining region 1 (CDR1) comprising an amino acid sequence selected from the group consisting of SEQ ID NO: 319, 320, 321, 322, 323, 324, 325, 326, 327, 328, 329, 330, 331, 332, 333, 334, 335 and 456; a complementarity determining region 2 (CDR2) comprising an amino acid sequence selected from the group consisting of SEQ ID NO: 336, 337, 338, 339, 340, 341, 342, 343, 344, 345, 346, 347, 348, 349, 350, 351, 352 and 353; and a complementarity determining region 3 (CDR3) comprising an amino acid sequence selected from the group consisting of SEQ ID NO: 354, 355, 356, 357, 358, 359, 360, 361, 362, 363, 364, 365, 366 and 367, and binds DLL3.

In some of any of the provided embodiments, the DLL3 is a human DLL3. In some embodiments, the DLL3 has the sequence set forth in SEQ ID NO: 86 or a mature form thereof lacking the signal sequence. In some embodiments, the DLL3 has the sequence set forth in SEQ ID NO: 87 or a mature form thereof lacking the signal sequence.

In some embodiments, the at least one DLL3 VHH domain is humanized. In some embodiments, the DLL3 VHH is a camelid VHH. In some embodiments, the DLL3 VHH is a humanized form of a camelid VHH.

In some of any of the provided embodiments, the one or more additional binding domains binds to an activating receptor on an immune cell. In some embodiments, the immune cell is a T cell. In some of any of the provided embodiments, the activating receptor is CD3 (CD3ε). In some examples, the DLL3-binding polypeptide construct of embodiment is bispecific for DLL3 and CD3. In some embodiments, the immune cell is a Natural Killer (NK) cell.

In some of any of the provided embodiments, the activating receptor is CD16 (CD16a). In some examples, the DLL3-binding polypeptide construct is bispecific for DLL3 and CD16a.

In some of any of the provided embodiments, the one or more additional binding domain binds to a cytokine receptor.

In some of any of the provided embodiments, the one or more additional binding domain comprises an antibody or antigen-binding fragment thereof. In some embodiments, the one or more additional binding domain is monovalent. In some embodiments, the antibody or antigen-binding fragment thereof is an Fv, a disulfide-stabilized Fv (dsFv), scFv, a Fab, a single domain antibody (sdAb), a VNAR, or a VHH. In some embodiments, a single domain antibody (sdAb) is a camelid VHH. In some embodiments, a single domain antibody (sdAb) is a humanized form of a camelid VHH.

In some of any of the provided embodiments, the one or more additional binding domain is a cytokine or is a truncated fragment or variant thereof capable of binding to the cytokine receptor. In some embodiments, the cytokine is an interferon, or is a truncated fragment or variant of an interferon. In some embodiments, the interferon is a type I interferon or a type II interferon, is a truncated fragment or variant of a type I interferon or is a truncated fragment or variant of a type II interferon. In some embodiments, the type I interferon is an IFN-alpha or an IFN-beta or is a truncated fragment or variant thereof; or the type II interferon is an IFN-gamma or is a truncated fragment or variant thereof.

In some of any of the provided embodiments, the polypeptide comprises an immunoglobulin Fc region. In some embodiments, the polypeptide comprises an immunoglobulin Fc region that links the at least one VHH domain and the one or more additional binding domain. In some embodiments, the DLL3-binding polypeptide construct is a dimer. In some embodiments, the Fc region is a homodimeric Fc region.

In some of any of the provided embodiments, the Fc region comprises the sequence of amino acids set forth in any of SEQ ID NOS: 8, 10, 11, 12 or 13, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOS: 8, 10, 11, 12 or 13. In some embodiments, the Fc region is a human IgG1.

In some of any of the provided embodiments, the DLL3-binding polypeptide construct is a dimer. In some embodiments, the Fc region is a homodimeric Fc region.

In some of any of the provided embodiments, the Fc region is a human IgG1.

In some of any of the provided embodiments, the Fc region comprises the sequence of amino acids set forth in SEQ ID NO: 8 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 8.

In some embodiments, the Fc region is a heterodimeric Fc region. In some embodiments, the Fc region exhibits effector function. In some embodiments, the Fc region comprises a polypeptide comprising one or more amino acid modification that reduces effector function and/or reduces binding to an effector molecule selected from an Fc gamma receptor or C1q. In some embodiments, the one or more amino acid modification is deletion of one or more of Glu233, Leu234 or Leu235.

In some of any of the provided embodiments, the Fc region comprises the sequence of amino acids set forth in SEQ ID NO: 9 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 9.

In some of any of the provided embodiments, the at least one DLL3 VHH domain comprises the VHH domain sequence set forth in any of SEQ ID NOS: 244-318 and 455, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOS: 244-318 and 455, and binds DLL3.

In some of any of the provided embodiments, the at least one DLL3 VHH domain comprises the VHH domain sequence set forth in any of SEQ ID NOS: 102, 244-318, 401-409, 416, 455, 476-480-488, and 507-518, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOS: 102, 244-318, 401-409, 416, 455, 476-480-488, and 507-518, and binds DLL3.

In some of any of the provided embodiments, the at least one DLL3 VHH domain comprises the VHH domain sequence set forth in any of SEQ ID NOS: 102, 244-275, 277-300, 302-305, 314, 401, 416, 455, 476-480-488, and 507-518, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOS: 102, 244-275, 277-300, 302-305, 314, 401, 416, 455, 476-480-488, and 507-518, and binds DLL3.

In some of any of the provided embodiments, the at least one DLL3 VHH domain comprises the sequence set forth in (i) SEQ ID NO: 244, (ii) a humanized variant of SEQ ID NO: 244, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 244, and binds DLL3. In some embodiments, the at least one DLL3 VHH domain comprises a CDR1 comprising an amino acid sequence selected from the group consisting of SEQ ID NO: 319, 320, 321, 322, 323, 324, 325 and 326; a CDR2 comprising an amino acid sequence selected from the group consisting of SEQ ID NO: 336, 337 and 338; and a CDR3 comprising an amino acid sequence set forth in SEQ ID NO: 354, and binds DLL3. In some embodiments, the at least one DLL3 VHH domain comprises a CDR1, CDR2 and CDR3 set forth in SEQ ID NOS: 319, 336 and 354, respectively. In some embodiments, the at least one DLL3 VHH domain comprises a CDR1, CDR2 and CDR3 set forth in SEQ ID NOS: 319, 337 and 354, respectively. In some embodiments, the at least one DLL3 VHH domain comprises a CDR1, CDR2 and CDR3 set forth in SEQ ID NOS: 319, 338 and 354, respectively. In some embodiments, the at least one DLL3 VHH domain comprises a CDR1, CDR2 and CDR3 set forth in SEQ ID NOS: 320, 338 and 354, respectively. In some embodiments, the at least one DLL3 VHH domain comprises a CDR1, CDR2 and CDR3 set forth in SEQ ID NOS: 321, 338 and 354, respectively. In some embodiments, the at least one DLL3 VHH domain comprises a CDR1, CDR2 and CDR3 set forth in SEQ ID NOS: 322, 338 and 354, respectively. In some embodiments, the at least one DLL3 VHH domain comprises a CDR1, CDR2 and CDR3 set forth in SEQ ID NOS: 323, 338 and 354, respectively. In some embodiments, the at least one DLL3 VHH domain comprises a CDR1, CDR2 and CDR3 set forth in SEQ ID NOS: 324, 338 and 354, respectively. In some embodiments, the at least one DLL3 VHH domain comprises a CDR1, CDR2 and CDR3 set forth in SEQ ID NOS: 325, 338 and 354, respectively. In some embodiments, the at least one DLL3 VHH domain comprises a CDR1, CDR2 and CDR3 set forth in SEQ ID NOS: 326, 338 and 354, respectively. In some of any of the above embodiments, the at least one DLL3 VHH domain binds DLL3. In some embodiments, the at least one DLL3 VHH domain comprises the sequence of amino acids set forth in any one of SEQ ID NOs: 245-257 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 245-257, and binds DLL3. In some embodiments, the at least one DLL3 VHH domain comprises the sequence of amino acids set forth in any one of SEQ ID NOS: 245-257, and binds DLL3.

In some of any of the provided embodiments, the at least one DLL3 VHH domain comprises the sequence set forth in (i) SEQ ID NO:258, (ii) a humanized variant of SEQ ID NO: 258, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 258, and binds DLL3. In some embodiments, the at least one DLL3 VHH domain comprising a CDR1 comprising an amino acid sequence set forth in SEQ ID NO: 327; a CDR2 comprising an amino acid sequence set forth in SEQ ID NO: 339; and a CDR3 comprising an amino acid sequence set forth in SEQ ID NO: 355, and binds DLL3. In some embodiments, the at least one DLL3 VHH domain comprises a CDR1, CDR2 and CDR3 set forth in SEQ ID NO: 327, 339 and 335, respectively, and binds DLL3. In some embodiments, the at least one DLL3 VHH domain comprises the sequence of amino acids set forth in any one of SEQ ID NOs: 259-263 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 259-263, and binds DLL3. In some embodiments, the at least one DLL3 VHH domain comprises the sequence of amino acids set forth in any one of SEQ ID NOS: 259-263, and binds DLL3.

In some of any of the provided embodiments, the at least one DLL3 VHH domain comprises the sequence set forth in (i) SEQ ID NO: 264 (ii) a humanized variant of SEQ ID NO: 264, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 264, and binds DLL3. In some embodiments, the at least one DLL3 VHH domain comprises a CDR1 comprising an amino acid sequence set forth in SEQ ID NO: 328, 329 or 456; a CDR2 comprising an amino acid sequence set forth in SEQ ID NO: 340; and a CDR3 comprising an amino acid sequence set forth in SEQ ID NO: 356, and binds DLL3. In some embodiments, the at least one DLL3 VHH domain comprises a CDR1, CDR2 and CDR3 set forth in SEQ ID NOS: 328, 340 and 356, respectively. In some embodiments, the at least one DLL3 VHH domain comprises a CDR1, CDR2 and CDR3 set forth in SEQ ID NOS: 329, 340 and 356, respectively. In some embodiments, the at least one DLL3 VHH domain comprises a CDR1, CDR2 and CDR3 set forth in SEQ ID NOS: 456, 340 and 356, respectively. In some of any of the above embodiments, the at least one DLL3 VHH domain binds DLL3. In some embodiments, the at least one DLL3 VHH domain comprises the sequence of amino acids set forth in any one of SEQ ID NOs: 265-274, 416 or 455 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 265-274 or 416 or 455, and binds DLL3. In some embodiments, the at least one DLL3 VHH domain comprises the sequence of amino acids set forth in any one of SEQ ID NOS: 265-274 or 416 or 455, and binds DLL3. In some embodiments, the at least one DLL3 VHH domain comprises the sequence of amino acids set forth in any one of SEQ ID NOs: 265-274, 416, 455, or 476-478 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 265-274, 416, 455, or 476-478, and binds DLL3. In some embodiments, the at least one DLL3 VHH domain comprises the sequence of amino acids set forth in any one of SEQ ID NOS: 265-274, 416, 455, or 476-478, and binds DLL3.

In some of any of the provided embodiments, the at least one DLL3 VHH domain comprises the sequence set forth in (i) SEQ ID NO: 275 (ii) a humanized variant of SEQ ID NO: 275, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 275, and binds DLL3. In some embodiments, the at least one DLL3 VHH domain comprising a CDR1 comprising an amino acid sequence set forth in SEQ ID NO: 320; a CDR2 comprising an amino acid sequence set forth in SEQ ID NO: 341; and a CDR3 comprising an amino acid sequence set forth in SEQ ID NO: 357, and binds DLL3. In some embodiments, the at least one DLL3 VHH domain comprises the sequence of amino acids set forth in any one of SEQ ID NOs: 276-279 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 276-279, and binds DLL3. In some embodiments, the at least one DLL3 VHH domain comprises the sequence of amino acids set forth in any one of SEQ ID NOS: 276-279, and binds DLL3. In some embodiments, the at least one DLL3 VHH domain comprises the sequence of amino acids set forth in any one of SEQ ID NOs: 277-279 and 479 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 277-279 and 479, and binds DLL3. In some embodiments, the at least one DLL3 VHH domain comprises the sequence of amino acids set forth in any one of SEQ ID NOS: 277-279 and 479, and binds DLL3.

In some of any of the provided embodiments, the at least one DLL3 VHH domain comprises the sequence set forth in (i) SEQ ID NO: 280 (ii) a humanized variant of SEQ ID NO: 280, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 280, and binds DLL3. In some embodiments, the at least one DLL3 VHH domain comprising a CDR1 comprising an amino acid sequence set forth in SEQ ID NO: 330; a CDR2 comprising an amino acid sequence set forth in SEQ ID NO: 342; and a CDR3 comprising an amino acid sequence set forth in SEQ ID NO: 358, and binds DLL3. In some embodiments, the at least one DLL3 VHH domain comprises the sequence of amino acids set forth in any one of SEQ ID NOs: 281-286 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 281-286, and binds DLL3. In some embodiments the at least one DLL3 VHH domain comprises the sequence of amino acids set forth in any one of SEQ ID NOS: 281-286, and binds DLL3.

In some of any of the provided embodiments, the at least one DLL3 VHH domain comprises the sequence set forth in (i) SEQ ID NO: 287, (ii) a humanized variant of SEQ ID NO: 287, or (iii) a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 287, and binds DLL3. In some embodiments, the at least one DLL3 VHH domain comprises a CDR1 comprising an amino acid sequence set forth in SEQ ID NO: 320; a CDR2 comprising an amino acid sequence selected from the group consisting of SEQ ID NO: 345, 346 and 347; and a CDR3 comprising an amino acid sequence selected from the group consisting of SEQ ID NO: 359, 360, and 361, and binds DLL3. In some embodiments, the at least one DLL3 VHH domain comprises a CDR1, CDR2 and CDR3 set forth in SEQ ID NOS: 320, 345 and 359, respectively. In some embodiments, the at least one DLL3 VHH domain comprises a CDR1, CDR2 and CDR3 set forth in SEQ ID NOS: 320, 346, and 359, respectively. In some embodiments, the at least one DLL3 VHH domain comprises a CDR1, CDR2 and CDR3 set forth in SEQ ID NOS: 320, 347, and 359, respectively. In some embodiments, the at least one DLL3 VHH domain comprises a CDR1, CDR2 and CDR3 set forth in SEQ ID NOS: 320, 345 and 360, respectively. In some embodiments, the at least one DLL3 VHH domain comprises a CDR1, CDR2 and CDR3 set forth in SEQ ID NOS: 320, 345 and 361, respectively. In some embodiments, the at least one DLL3 VHH domain comprises a CDR1, CDR2 and CDR3 set forth in SEQ ID NOS: 320, 347 and 360, respectively. In some embodiments, any of the above provided DLL3 VHH domains bind DLL3. In some embodiments, the at least one DLL3 VHH domain comprises the sequence of amino acids set forth in any one of SEQ ID NOs: 288-298 or 102 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 288-298 or 102, and binds DLL3. In some embodiments, the at least one DLL3 VHH domain comprises the sequence of amino acids set forth in any one of SEQ ID NOS: 288-298 or 102, and binds DLL3.

In some of any of the provided embodiments, the at least one DLL3 VHH domain comprises the sequence set forth in (i) SEQ ID NO: 299, (ii) a humanized variant of SEQ ID NO: 299, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 299, and binds DLL3. In some embodiments, the at least one DLL3 VHH domain comprises a CDR1 comprising an amino acid sequence set forth in SEQ ID NO: 331; a CDR2 comprising an amino acid sequence selected from the group consisting of SEQ ID NO: 348, 349 and 350; and a CDR3 comprising an amino acid sequence set forth in SEQ ID NO: 356, and binds DLL3. In some embodiments, the at least one DLL3 VHH domain comprises a CDR1, CDR2 and CDR3 set forth in SEQ ID NOS: 331, 348 and 356, respectively. In some embodiments, the at least one DLL3 VHH domain comprises a CDR1, CDR2 and CDR3 set forth in SEQ ID NOS: 331, 349 and 356, respectively. In some embodiments, the at least one DLL3 VHH domain comprises a CDR1, CDR2 and CDR3 set forth in SEQ ID NOS: 331, 350 and 356, respectively. In some embodiments, any of the above provided DLL3 VHH domains bind DLL3. In some embodiments, the at least one DLL3 VHH domain comprises the sequence of amino acids set forth in any one of SEQ ID NOs: 300-305 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 300-305, and binds DLL3. In some embodiments, the at least one DLL3 VHH domain comprises the sequence of amino acids set forth in any one of SEQ ID NOS: 300-305, and binds DLL3. In some embodiments, the at least one DLL3 VHH domain comprises the sequence of amino acids set forth in any one of SEQ ID NOs: 300, 302-305, and 480 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 300, 302-305, and 480, and binds DLL3. In some embodiments, the at least one DLL3 VHH domain comprises the sequence of amino acids set forth in any one of SEQ ID NOS: 300, 302-305, and 480, and binds DLL3.

In some of any of the provided embodiments, the at least one DLL3 VHH domain comprises the sequence set forth in (i) SEQ ID NO: 507, (ii) a humanized variant of SEQ ID NO: 507, or (iii) a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 507, and binds DLL3. the at least one DLL3 VHH domain comprises the sequence set forth in (i) SEQ ID NO: 306, (ii) a humanized variant of SEQ ID NO: 306, or (iii) a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO:306, and binds DLL3. In some embodiments, the at least one DLL3 VHH domain comprises a CDR1 comprising an amino acid sequence set forth in SEQ ID NO: 332; a CDR2 comprising an amino acid sequence selected from the group consisting of SEQ ID NO: 348, 349 and 350; and a CDR3 comprising an amino acid sequence set forth in SEQ ID NO: 362, and binds DLL3. In some embodiments, the at least one DLL3 VHH domain comprises a CDR1, CDR2 and CDR3 set forth in SEQ ID NOS: 332, 348 and 362, respectively. In some embodiments, the at least one DLL3 VHH domain comprises a CDR1, CDR2 and CDR3 set forth in SEQ ID NOS: 332, 349 and 362, respectively. In some embodiments, the at least one DLL3 VHH domain comprises a CDR1, CDR2 and CDR3 set forth in SEQ ID NOS: 332, 350 and 362. In some embodiments, the at least one DLL3 VHH domain comprises the sequence of amino acids set forth in any one of SEQ ID NOs: 300-305 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 307-313, and binds DLL3. In some embodiments, the at least one DLL3 VHH domain comprises the sequence of amino acids set forth in any one of SEQ ID NOS: 307-313, and binds DLL3. In some embodiments, the at least one DLL3 VHH domain comprises the sequence of amino acids set forth in any one of SEQ ID NOs: 508-514 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 508-514, and binds DLL3. In some embodiments, the at least one DLL3 VHH domain comprises the sequence of amino acids set forth in any one of SEQ ID NOS: 508-514, and binds DLL3.

In some of any of the provided embodiments, the at least one DLL3 VHH domain comprises the sequence set forth in (i) SEQ ID NO: 401, (ii) a humanized variant of SEQ ID NO: 401, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 401, and binds DLL3. In some embodiments, the at least one DLL3 VHH domain comprises a CDR1 comprising an amino acid sequence set forth in SEQ ID NO: 320; a CDR2 comprising an amino acid sequence selected from the group consisting of SEQ ID NO: 384, 410 and 411; and a CDR3 comprising an amino acid sequence selected from the group consisting of SEQ ID NO: 395, 412, 413, 414 and 415, and binds DLL3. In some embodiments, the at least one DLL3 VHH domain comprises a CDR1, CDR2 and CDR3 set forth in SEQ ID NOS: 320, 384 and 395, respectively. In some embodiments, the at least one DLL3 VHH domain comprises a CDR1, CDR2 and CDR3 set forth in SEQ ID NOS: 320, 410 and 395, respectively. In some embodiments, the at least one DLL3 VHH domain comprises a CDR1, CDR2 and CDR3 set forth in SEQ ID NOS: 320, 411 and 395, respectively. In some embodiments, the at least one DLL3 VHH domain comprises a CDR1, CDR2 and CDR3 set forth in SEQ ID NOS: 320, 384 and 412, respectively. In some embodiments, the at least one DLL3 VHH domain comprises a CDR1, CDR2 and CDR3 set forth in SEQ ID NOS: 320, 384 and 413, respectively. In some embodiments, the at least one DLL3 VHH domain comprises a CDR1, CDR2 and CDR3 set forth in SEQ ID NOS: 320, 384 and 414, respectively. In some embodiments, the at least one DLL3 VHH domain comprises a CDR1, CDR2 and CDR3 set forth in SEQ ID NOS: 320, 384 and 415, and binds DLL3. In some embodiments, the at least one DLL3 VHH domain comprises the sequence of amino acids set forth in any one of SEQ ID NOs: 402-409 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 402-409, and binds DLL3. In some embodiments, the at least one DLL3 VHH domain comprises the sequence of amino acids set forth in any one of SEQ ID NOS: 402-409, and binds DLL3. In some embodiments, the at least one DLL3 VHH domain comprises the sequence of amino acids set forth in any one of SEQ ID NOs: 481-488 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 481-488, and binds DLL3. In some embodiments, the at least one DLL3 VHH domain comprises the sequence of amino acids set forth in any one of SEQ ID NOS: 481-488, and binds DLL3.

In some of any of the provided embodiments, the at least one DLL3 VHH domain comprises a CDR1, CDR2 and CDR3 set forth in SEQ ID NOS: 333, 351, and 363, respectively. In some of any of the provided embodiments, the at least one DLL3 VHH domain comprises a CDR1, CDR2 and CDR3 set forth in 334, 352 and 364, respectively. In some of any of the provided embodiments, the at least one DLL3 VHH domain comprises a CDR1, CDR2 and CDR3 set forth in 320, 353 and 365, respectively. In some of any of the provided embodiments, the at least one DLL3 VHH domain comprises a CDR1, CDR2 and CDR3 set forth in 334, 339 and 366, respectively. In some of any of the provided embodiments, the at least one DLL3 VHH domain comprises a CDR1, CDR2 and CDR3 set forth in 335, 348 and 367, respectively. In some of any of the provided embodiments, the DLL3 VHH domain binds DDL3. In some embodiments, the at least one DLL3 VHH domain comprises the sequence set forth in (i) SEQ ID NO: 314, 315, 316, 317 or 318 (ii) a humanized variant of SEQ ID NO: 314, 315, 316, 317 or 318, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 314, 315, 316, 317 or 318, and binds DLL3. In some embodiments, the at least one DLL3 VHH domain is set forth in SEQ ID NO: 314, 315, 316, 317 or 318, and binds DLL3. In some embodiments, the at least one DLL3 VHH domain comprises the sequence set forth in (i) SEQ ID NO: 314, 518, 515, 516 or 517 (ii) a humanized variant of SEQ ID NO: 314, 518, 515, 516 or 517, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 314, 518, 515, 516 or 517, and binds DLL3. In some embodiments, the at least one DLL3 VHH domain is set forth in SEQ ID NO: 314, 518, 515, 516 or 517, and binds DLL3.

In some embodiments, a DLL3 VHH domain comprises the VHH domain sequence set forth in SEQ ID NO:244. In some embodiments, a DLL3 VHH domain comprises the VHH domain sequence set forth in SEQ ID NO:251. In some embodiments, a DLL3 VHH domain comprises the VHH domain sequence set forth in SEQ ID NO:264. In some embodiments, a DLL3 VHH domain comprises the VHH domain sequence set forth in SEQ ID NO:268. In some embodiments, a DLL3 VHH domain comprises the VHH domain sequence set forth in SEQ ID NO:275. In some embodiments, a DLL3 VHH domain comprises the VHH domain sequence set forth in SEQ ID NO:287. In some embodiments, a DLL3 VHH domain comprises the VHH domain sequence set forth in SEQ ID NO:299. In some embodiments, a DLL3 VHH domain comprises the VHH domain sequence set forth in SEQ ID NO:507, In some embodiments, a DLL3 VHH domain comprises the VHH domain sequence set forth in SEQ ID NO:314. In some embodiments, a DLL3 VHH domain comprises the VHH domain sequence set forth in SEQ ID NO:518. In some embodiments, a DLL3 VHH domain comprises the VHH domain sequence set forth in SEQ ID NO:515. In some embodiments, a DLL3 VHH domain comprises the VHH domain sequence set forth in SEQ ID NO:516. In some embodiments, a DLL3 VHH domain comprises the VHH domain sequence set forth in SEQ ID NO:517. In some embodiments, a DLL3 VHH domain comprises the VHH domain sequence set forth in SEQ ID NO:455.

In some of any of the provided embodiments, a DLL3 VHH domain may comprise additional amino acids at its N- and/or C-terminal, such as for linkage to another amino acid sequence, such as another polypeptide. In some of any of the provided embodiments, a DLL3 VHH domain may comprise a flexible linker, such as a glycine linker or a linker composed predominately of the amino acids Glycine and Serine, denoted as GS-linkers herein. Such linkers of the present disclosure can be of various lengths, for example, 5, 6, 7, 8, 9, 10, 11, 12, 13, 14, 15, 16, 17, 18, 19, 20 amino acids in length. In some embodiments, the linker comprises an amino acid sequence selected from the group consisting of GGSGGS, i.e., (GGS)$_2$ (SEQ ID NO: 1); GGSGGSGGS, i.e., (GGS)$_3$ (SEQ ID NO: 2); GGSGGSGGSGGS, i.e., (GGS)$_4$ (SEQ ID NO: 3); and GGSGGSGGSGGSGGS, i.e., (GGS)$_5$ (SEQ ID NO: 4), Gly-Gly (GG), GGG, GGGG (SEQ ID NO: 5), GGGGG (SEQ ID NO: 6), and GGGGGG (SEQ ID NO: 7). In some embodiments, the linker is (GGGGS)$_n$, wherein n is 1 to 5 (SEQ ID NO:123); (GGGGGS)$_n$, wherein n is 1 to 4 (SEQ ID NO:124); GGGGS (SEQ ID NO:125); GGGGGS (SEQ ID NO:126); GGGGSGGGGSGGGGS (SEQ ID NO:127); GGGGSGGGSGGGS (SEQ ID NO:128); GGSGGGSGGGGSGGGS (SEQ ID NO:129); or PGGGG (SEQ ID NO:450). In some embodiments, the linker is a GG linker. In some embodiments, the DLL3-binding polypeptide includes a combination of a GS-linker and a Glycine linker. In some embodiments, a DLL3 VHH domain may comprise the additional linker at its C-terminus, such as for linkage to another amino acid sequence, such as another polypeptide. In some of any of the provided embodiments, a DLL3 VHH domain may comprise the linker at its N-terminus, such as for linkage to another amino acid sequence, such as another polypeptide.

In some of any of the provided embodiments, the at least one DLL3 VHH domain comprises the sequence set forth in (i) SEQ ID NO: 244, (ii) a humanized variant of SEQ ID NO: 244, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 244, and binds DLL3.

Provided herein is a multispecific polypeptide construct, comprising: (a) a first component comprising a heterodimeric Fc region comprising a first Fc polypeptide and a second Fc polypeptide and (b) a second component comprising an anti-CD3 antibody or antigen-binding fragment comprising a variable heavy chain region (VH) and a variable light chain region (VL), wherein the VH and VL that comprise the anti-CD3 antibody or antigen binding fragment are linked to opposite polypeptides of the heterodimeric Fc, wherein the first and second components are coupled by a linker, wherein the heterodimeric Fc region is positioned N-terminal to the anti-CD3 antibody; and wherein one or both of the first and second components comprises at least one antigen binding domain comprising a VHH domain that specifically binds DLL3 (DLL3 VHH domain). In particular embodiments, the DLL3 VHH domain can include any of the provided DLL3 VHH domain sequences, including any as described above or elsewhere herein.

In some embodiments, the multispecific polypeptide construct comprises at least (i) a first polypeptide comprising the first Fc polypeptide of the heterodimeric Fc region, the linker and the VH or VL domain of the anti-CD3 antibody or antigen binding fragment; and (ii) a second polypeptide comprising the second Fc polypeptide of the heterodimeric Fc region, the linker, optionally the same linker as present in the first polypeptide, and the other of the VH or VL domain of the anti-CD3 antibody or antigen binding fragment, wherein one or both of the first and second polypeptide comprise the at least one DLL3 VHH domain.

In some embodiments, one or both of the first and second Fc polypeptides of the heterodimeric Fc region comprises at least one modification to induce heterodimerization compared to a polypeptide of a homodimeric Fc region, optionally compared to the Fc polypeptide set forth in SEQ ID NO:8 or an immunologically active fragment thereof. In some embodiments, each of the first and second Fc polypeptides of the heterodimeric Fc region independently comprise at least one amino acid modification. In some embodiments, each of the first and second Fc polypeptides of the heterodimeric Fc region comprise a knob-into-hole modification or comprise a charge mutation to increase electrostatic complementarity of the polypeptides.

In some embodiments, the amino acid modification is a knob-into-hole modification. In one embodiment, the first Fc polypeptide of the heterodimeric Fc region comprises the modification selected from among Thr366Ser, Leu368Ala, Tyr407Val, and combinations thereof and the second Fc polypeptide of the heterodimeric Fc region comprises the modification Thr366Trp. In such an embodiment, the first and second Fc polypeptides can further comprises a modification of a non-cysteine residue to a cysteine residue, wherein the modification of the first Fc polypeptide is at one of the position Ser354 and Tyr349 and the modification of the second Fc polypeptide is at the other of the position Ser354 and Tyr349.

In some embodiments, the amino acid modification is a charge mutation to increase electrostatic complementarity of the polypeptides. In some embodiments, the first and/or second Fc polypeptides or each of the first and second Fc polypeptide comprise a modification in complementary positions, wherein the modification is replacement with an amino acid having an opposite charge to the complementary amino acid of the other polypeptide.

In some of any of the provided embodiments, one of the first or second Fc polypeptide of the heterodimeric Fc region further comprises a modification at residue Ile253. In some embodiments, the modification is Ile253Arg. In some embodiments, one of the first or second Fc polypeptide of the heterodimeric Fc region further comprises a modification at residue His435. In some embodiments, the modification is His435Arg.

In some embodiments, the Fc region of any of the provided polypeptides or constructs comprises a polypeptide that lacks Lys447.

In some embodiments, the Fc region of any of the provided polypeptides or constructs comprises at least one modification to enhance FcRn binding. In some embodiments, the modification is at a position selected from the group consisting of Met252, Ser254, Thr256, Met428, Asn434, and combinations thereof. In some embodiments, the modification is selected from the group consisting of Met252Y, Ser254T, Thr256E, Met428L, Met428V, Asn434S, and combinations thereof. In some embodiments the modification is at position Met252 and at position Met428. In some embodiments, the modification is Met252Y and Met428L. In some embodiments, the modification is Met252Y and Met428V.

In some of any of the provided embodiments, the first Fc polypeptide of the heterodimeric Fc region comprises the sequence of amino acids set forth in any of SEQ ID NOS: 103, 107, 115 or 117, and the second Fc polypeptide of the heterodimeric Fc region comprises the sequence of amino acids set forth in any of SEQ ID NOS: 104, 108, 111, 113, 119 or 121.

In some of any of the provided embodiments, the Fc region of a provided polypeptide or construct comprises a polypeptide comprising at least one amino acid modification that reduces effector function and/or reduces binding to an effector molecule selected from an Fc gamma receptor or C1q. In some embodiments, the one or more amino acid modification is deletion of one or more of Glu233, Leu234 or Leu235.

In some of any of the provided embodiments, the first Fc polypeptide of the heterodimeric Fc region comprises the sequence of amino acids set forth in any of SEQ ID NOS: 105, 109, 116 or 118 and the second Fc polypeptide of the heterodimeric Fc region comprises the sequence of amino acids set forth in any of SEQ ID NOS: 106, 110, 112, 114, 120 or 122.

In some of any of the provided embodiments, the anti-CD3 antibody or antigen binding fragment is monovalent. In some embodiments, the anti-CD3 antibody or antigen binding fragment is an Fv antibody fragment. In some embodiments, the Fv antibody fragment comprises a disulfide stabilized anti-CD3 binding Fv fragment (dsFv).

In some embodiments, the anti-CD3 antibody or antigen binding fragment is not a single chain antibody, for example is not a single chain variable fragment (scFv).

In some embodiments, the anti-CD3 antibody or antigen-binding fragment comprises a VH CDR1 comprising the amino acid sequence TYAMN (SEQ ID NO: 29); a VH CDR2 comprising the amino acid sequence RIRSKYNNYATYYADSVKD (SEQ ID NO: 30); a VH CDR3 comprising the amino acid sequence HGNFGNSYVSWFAY (SEQ ID NO: 31), a VL CDR1 comprising the amino acid sequence RSSTGAVTTSNYAN (SEQ ID NO: 32); a VL CDR2 comprising the amino acid sequence GTNKRAP (SEQ ID NO: 33); and a VL CDR3 comprising the amino acid sequence ALWYSNLWV (SEQ ID NO: 34). In some embodiments, the anti-CD3 antibody or antigen-binding fragment comprises: a VH having the amino acid sequence of any of SEQ ID NOS: 35-65 or a sequence that exhibits at least 90%, 91%, 92%, 93%, 94%, 95%, 96%, 97%, 98% or 99% sequence identity to any of SEQ ID NOS: 35-65; and a VL having the amino acid sequence of any of SEQ ID NOS: 66-84 and 368 or a sequence that exhibits at least 90%, 91%, 92%, 93%, 94%, 95%, 96%, 97%, 98% or 99% sequence identity to any of SEQ ID NOS: 66-84 and 368. In some embodiments, the anti-CD3 antibody or antigen-binding fragment comprises the amino acid sequence of SEQ ID NO: 47 and the amino acid sequence of SEQ ID NO: 75. In some embodiments, the anti-CD3 antibody or antigen-binding fragment comprises the amino acid sequence of SEQ ID NO: 47 and the amino acid sequence of SEQ ID NO: 368.

In some embodiments, the VL of the anti-CD3 antibody or antigen binding fragment is linked to the first Fc polypeptide of the heterodimeric Fc and the VH of the anti-CD3 antibody or antigen binding fragment is linked to the second Fc polypeptide of the heterodimeric Fc.

In some embodiments, the at least one DLL3 VHH domain is positioned amino-terminally relative to the Fc region and/or carboxy-terminally relative to the CD3 binding region of the multispecific polypeptide construct.

In some embodiments, the multispecific polypeptide construct comprises a first DLL3 VHH domain that specifically binds DLL3 and a second DLL3 VHH domain that specifically binds DLL3. In particular embodiments, the first DLL3 VHH domain and the second DLL3 VHH domain independently can include any of the provided DLL3 VHH domain sequences, including any as described above or elsewhere herein. In some embodiments, the first and second DLL3 VHH domain are the same. In some embodiments, the first and second DLL3 VHH domains are different. In some embodiments, the first and second DLL3 VHH domain bind a distinct or non-overlapping epitope of DLL3 and/or do not compete for binding to DLL3.

In some embodiments, the first or second DLL3 VHH domain is positioned amino-terminally relative to the Fc region of the multispecific construct and the other of the first or second DLL3 VHH domain is positioned carboxy-terminally relative to the CD3 binding region of the multispecific construct.

In some embodiments of any of the provided multispecific polypeptide constructs, the first component comprises in order of N-terminus to C-terminus a first DLL3 VHH domain that binds DLL3, the first Fc polypeptide of the heterodimeric Fc region, the linker, the VH or VL domain of the anti-CD3 antibody or antigen binding fragment and a second DLL3 VHH domain that binds DLL3; and the second polypeptide comprises in order of N-terminus to C-terminus the second Fc polypeptide of the heterodimeric Fc region, the linker, optionally the same linker as present in the first component, and the other of the VH or VL domain of the anti-CD3 antibody or antigen binding fragment.

In some embodiments, one or both of the first and second component comprises at least one co-stimulatory receptor binding region (CRBR) that binds a co-stimulatory receptor. In some embodiments, the at least one co-stimulatory receptor binding region (CRBR) is positioned amino-terminally relative to the Fc region and/or carboxy-terminally relative to the CD3 binding region of the multispecific polypeptide construct. In some embodiments, the multispecific polypeptide construct comprises only one co-stimulatory receptor binding region (CRBR).

In some embodiments of any of the provided multispecific polypeptide constructs, the first component comprises in order of N-terminus to C-terminus a first DLL3 VHH domain that binds DLL3, the first Fc polypeptide of the heterodimeric Fc region, the linker, the VH or VL domain of the anti-CD3 antibody or antigen binding fragment and a second DLL3 VHH domain that binds DLL3; and the second component comprises the CRBR and comprises in order of N-terminus to C-terminus the second Fc polypeptide of the heterodimeric Fc region, the linker, optionally the same linker as present in the first component, the other of the VH or VL domain of the anti-CD3 antibody or antigen binding fragment, wherein the CRBR is positioned amino-terminally relative to the Fc region or carboxy-terminally relative to the anti-CD3 antibody or antigen binding fragment of the second component.

In some embodiments, the at least one co-stimulatory receptor binding region (CRBR) is or comprises the extracellular domain or binding fragment thereof of the native cognate binding partner of the co-stimulatory receptor, or a variant thereof that exhibits binding activity to the co-stimulatory receptor. In some embodiments, the at least one co-stimulatory receptor binding region (CRBR) is an antibody or antigen-binding fragment thereof selected from the group consisting of a Fab fragment, a F(ab')2 fragment, an Fv fragment, a scFv, a scAb, a dAb, a single domain heavy chain antibody, and a single domain light chain antibody. In some embodiments, the antibody or antigen-binding fragment thereof is a Fv, a scFv, a Fab, a single domain antibody (VHH domain), a VNAR, or a VHH. In some embodiments, the antibody or antigen-binding fragment is an VHH domain. In some embodiments, the VHH domain is a human or humanized VHH domain.

In some of any of the provided embodiments, the at least one co-stimulatory receptor binding region (CRBR) binds a co-stimulatory receptor selected from among 41BB (CD137), OX40 (CD134), CD27, glucocorticoid-induced TNFR-related protein (GITR), CD28, ICOS, CD40, B-cell activating factor receptor (BAFF-R), B-cell maturation antigen (BCMA), Transmembrane activator and CAML interactor (TACI), and NKG2D. In some embodiments, the at least one co-stimulatory receptor binding region (CRBR) binds a co-stimulatory receptor selected from among 41BB (CD137), OX40 (CD134), and glucocorticoid-induced TNFR-related protein (GITR).

In some embodiments, the at least one co-stimulatory receptor binding region (CRBR) comprises the sequence of amino acids set forth in SEQ ID NO:210 or a sequence that has at least 85%, 86%, 87%, 88%, 89%, 90%, 91%, 92%, 93%, 94%, 95%, 96%, 97%, 98%, or 99% sequence identity to the sequence set forth in SEQ ID NO:210 and binds 4-1BB.

In some embodiments, at least one co-stimulatory receptor binding region (CRBR) comprises the sequence of amino acids set forth in SEQ ID NO:210 and binds 4-1BB.

In some embodiments, at least one co-stimulatory receptor binding region (CRBR) comprises the sequence of amino acids set forth in SEQ ID NO:470 and binds 4-1BB.

In some embodiments, one or both of the first and second components comprises at least one inhibitory receptor binding region (IRBR) that binds an inhibitory receptor. In some embodiments, the at least one inhibitory receptor binding region (IRBR) is positioned amino-terminally relative to the Fc region and/or carboxy-terminally relative to the CD3 binding region of the multispecific polypeptide construct. In some embodiments, the multispecific polypeptide construct comprises only one inhibitory receptor binding region (IRBR).

In some embodiments of any of the provided multispecific polypeptide constructs, the first component comprises in order of N-terminus to C-terminus a first DLL3 VHH domain that binds DLL3, the first Fc polypeptide of the heterodimeric Fc region, the linker, the VH or VL domain of the anti-CD3 antibody or antigen binding fragment and a second DLL3 VHH domain that binds DLL3; and the second component comprises the IRBR and comprises in order of N-terminus to C-terminus the second Fc polypeptide of the heterodimeric Fc region, the linker, optionally the same linker as present in the first component, the other of the VH or VL domain of the anti-CD3 antibody or antigen binding fragment, wherein the IRBR is positioned amino-terminally relative to the Fc region or carboxy-terminally relative to the anti-CD3 antibody or antigen-binding fragment of the second component.

In some embodiments, the at least one IRBR is or comprises the extracellular domain or binding fragment thereof of the native cognate binding partner of the inhibitory receptor, or a variant thereof that exhibits binding activity to the inhibitory receptor. In some embodiments, the at least one IRBR is an antibody or antigen-binding fragment thereof selected from the group consisting of a Fab fragment, a F(ab')2 fragment, an Fv fragment, a scFv, a scAb, a dAb, a single domain heavy chain antibody, and a single domain light chain antibody. In some embodiments, the antibody or antigen-binding fragment thereof is a Fv, a scFv, a Fab, a single domain antibody (VHH domain), a VNAR, or a VHH. In some embodiments, the antibody or antigen-binding fragment is an VHH domain. In some embodiments, the VHH domain is a human or humanized VHH domain. In some embodiments, the at least one IRBR binds a inhibitory receptor selected from among PD-1, CTLA-4, TIGIT, VISTA and TIM3. In some embodiments, the at least one IRBR binds PD-1.

In some of any of the provided embodiments of a multispecific polypeptide construct, the first component comprises in order of N-terminus to C-terminus a first DLL3 VHH domain that binds DLL3, the first Fc polypeptide of the heterodimeric Fc region, the linker, the VH or VL domain of the anti-CD3 antibody or antigen binding fragment and a second DLL3 VHH domain that binds DLL3; and the second component comprises comprises in order of N-terminus to C-terminus one of the IRBR or the CRBR, the second Fc polypeptide of the heterodimeric Fc region, the linker, optionally the same linker as present in the first component, the other of the VH or VL domain of the anti-CD3 antibody or antigen binding fragment, and the other of the CRBR or IRBR.

In some of any of the provided embodiments, the linker is a peptide or polypeptide linker. In some embodiments, the linker is 3, 4, 5, 6, 7, 8, 9, 10, 11, 12, 13, 14, 15, 16, 17, 18, 19 or 20 amino acids in length.

In some embodiments, the linker is a non-cleavable linker, such as a linker that comprises GS, GGS, GGGGS (SEQ ID NO: 125), GGGGGS (SEQ ID NO: 126) and combinations thereof. In some embodiments, the linker is or comprises the sequence GGGGGSGGGGGSGGGGS (SEQ ID NO: 127).

In some embodiments, the linker is a cleavable linker, such as a polypeptide that functions as a substrate for a protease. In some embodiments, the protease is produced by an immune effector cell, by a tumor, or by cells present in the tumor microenvironment. In some embodiments, the protease is produced by an immune effector cell and the immune effector cell is an activated T cell, a natural killer (NK) cell, or an NK T cell. In some embodiments, the protease is a matriptase, a matrix metalloprotease (MMP), granzyme B, or combinations thereof. In some embodiments, the cleavable linker comprises the amino acid sequence GGSGGGGIEPDIGGSGGS (SEQ ID NO: 171).

Provided herein is an isolated single domain antibody that binds DLL3 and that contains any of the DLL3 VHH domain sequences provided herein, including any as described above or elsewhere herein.

Provided herein is an isolated single domain antibody that binds DLL3, comprising a complementarity determining region 1 (CDR1) comprising an amino acid sequence selected from the group consisting of SEQ ID NO: 319, 320, 321, 322, 323, 324, 325, 326, 327, 328, 329, 330, 331, 332, 333, 334, 335 and 456; a complementarity determining region 2 (CDR2) comprising an amino acid sequence selected from the group consisting of SEQ ID NO: 336, 337, 338, 339, 340, 341, 342, 343, 344, 345, 346, 347, 348, 349, 350, 351, 352, 353, 384, 410, and 411; and a complementarity determining region 3 (CDR3) comprising an amino acid sequence selected from the group consisting of SEQ ID NO: 354, 355, 356, 357, 358, 359, 360, 361, 362, 363, 364, 365, 366 and 367, 395, and 412-415.

Provided herein are polynucleotides encoding any of the DLL3-binding polypeptides constructs provided herein.

Also provided herein are polynucleotides encoding any of the multispecific polypeptide constructs provided herein, or a first or second polypeptide thereof. In some embodiments, the polynucleotide includes a first nucleid acid encoding the first polypeptide and a second nucleic acid encoding a second polypeptide of a provided multispecific polypeptide construct, wherein the first and second nucleic acid sequence are separated by an internal ribosome entry site (IRES), or a nucleic acid encoding a self-cleaving peptide or a peptide that causes ribosome skipping, such as a T2A, a P2A, a E2A or an F2A.

Also provided are polynucleotides encoding any of the provided single domain antibodies.

Also provided are vector, such as expression vectors, encoding any of the provided polynucleotides.

Provided herein is a cell comprising any of the provided polynucleotide or polynucleotides or any of the provided vector or vectors.

Provided herein is a method of producing a polypeptide including introducing into a cell any of the provided polynucleotide or polynucleotides or a vector or vectors and culturing the cell under conditions to produce the multispecific polypeptide construct. Provided herein is a polypeptide produced by any of the methods provided herein.

Provided herein is an engineered immune cell, comprising a chimeric antigen receptor comprising an extracellular domain comprising any of the provided DLL3 VHH domain sequence single domain antibodies; a transmembrane domain; and an intracellular signaling domain.

Provided herein is a pharmaceutical composition comprising any of the provided DLL3-binding polypeptides, multispecific polypeptide constructs, single domain antibodies or engineered immune cells.

Provided herein is a method of stimulating or inducing an immune response in a subject, the method comprising administering, to a subject in need thereof, any of the provided DLL3-binding polypeptides, multispecific polypeptide constructs, single domain antibodies or engineered immune cells, or pharmaceutical compositions.

Also provided herein is a method of treating a disease or condition in a subject, the method comprising administering, to a subject in need thereof, a therapeutically effective amount of any of the DLL3-binding polypeptides described herein, any of the multispecific polypeptide constructs described herein, any of the single domain antibodies described herein, any of the engineered immune cells described herein, or any of the pharmaceutical compositions described herein.

BRIEF DESCRIPTION OF THE DRAWINGS

FIG. 2A shows binding of 3G3 and humanized variants thereof on SHP-77. FIG. 2B shows binding of 5A7 and humanized variants thereof on SHP-77. FIG. 2C shows binding of 3C5 and humanized variants thereof on SHP-77. FIG. 2D shows binding of 6C5 and humanized variants thereof on SHP-77. FIGS. 2E-G show binding of 5A8 and humanized variants thereof on SHP-77 (FIGS. 2E and 2F) and DLL3 transfected 293FS (FL) (FIG. 2G). FIG. 2H shows binding of 10D9 and humanized variants thereof on SHP-77. FIG. 2I shows binding of 10E5 and humanized variants thereof on SHP-77.

FIGS. 2J and 2K show binding of 8E7 and humanized variants thereof on SHP-77 and DLL3 transfected 293FS cells, respectively. FIG. 2L shows binding of 6F1 and humanized variants thereof on SHP-77. Herein the DLL3 sdAbs were operably linked to a human Fc.

FIG. 31A demonstrates the ability of the representative DLL3-targeting constrained CD3 engaging construct to elicit T-cell mediated cytotoxicity in the presence of DLL3-positive SHP-77 cells. FIGS. 31B-31E demonstrate the ability of the representative DLL3-targeting constrained CD3 engaging construct to elicit T cell activation in the presence of DLL3-positive SHP-77 cells, as assessed by: expression of CD25 on CD4+ T cells (FIG. 31B), CD69 expression on CD4+ T cells (FIG. 31C), CD25 expression on CD8+ T cells (FIG. 31D) and CD69 expression on CD8+ T cells (FIG. 31E).

FIGS. 37A and 37B depict mean fluorescence intensity (MFI) of the GFP reporter when the TAA positive cell line A375 or the TAA negative cell line CCRF-CEM, respectively, were co-cultured with Jurkat CD3 NFAT-GFP reporter cells. FIGS. 37C and 37D depict relative luminescent units (RLU) of the luciferase reporter when the TAA positive cell line A375 or the TAA negative cell line CCRF-CEM, respectively, were co-cultured with Jurkat CD3 NFAT-Luciferase reporter cells.

FIG. 38A depicts relative luminescence units (RLU) of the luciferase reporter when DLL3-expressing CHO cells were co-cultured with reporter cells and treated with a titration of DLL3-targeted constructs containing IgG1 Fcs. FIG. 38B depicts RLU of the luciferase reporter when treated with a titration of DLL3-targeted constructs containing IgG1 Fcs in the absence of DLL3-expressing cells.

DETAILED DESCRIPTION

Figure 1:
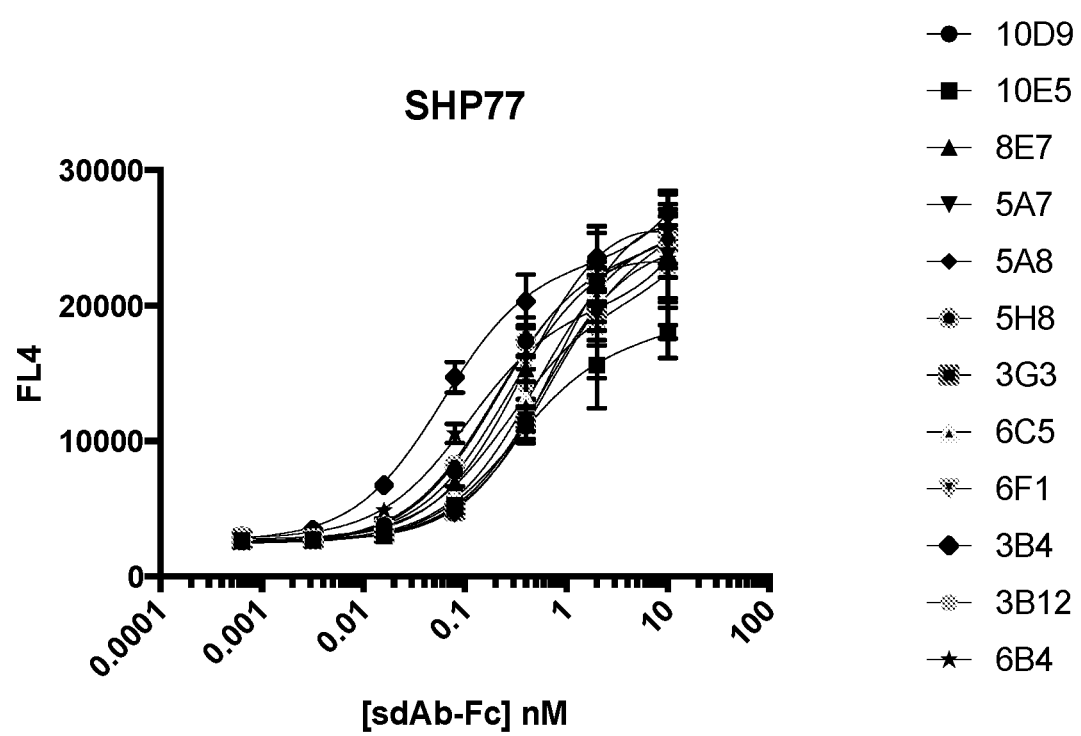
FIG. 1 sets forth a graph depicting the ability of various anti-DLL3 single domain antibodies (sdAb) to bind cell-surface DLL3. Binding was assessed by flow cytometry on the DLL3 positive cell line SHP-77. Herein the DLL3 sdAbs 10D9, 10E5, 8E7, 5A7, 5A8, 5H8, 3G3, 6C5, 6F1, 3B4, 3B12 or 6B4 were operably linked to a human Fc.
Figure 2A:
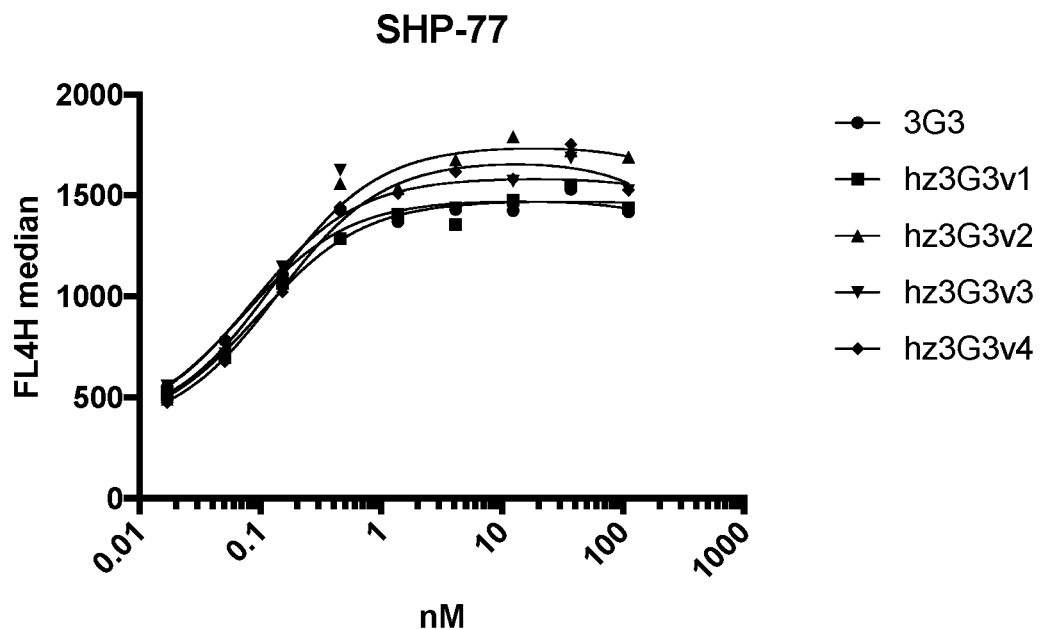
FIGS. 2A-L set forth a series of graphs depicting the ability of sdAb and humanized variants thereof targeting DLL3 to bind cell surface DLL3. Binding was assessed by flow cytometry on the DLL3 positive cell line SHP-77 or HEK-293 freestyle cells transiently transfected with a vector encoding DLL3.
Figure 2B:
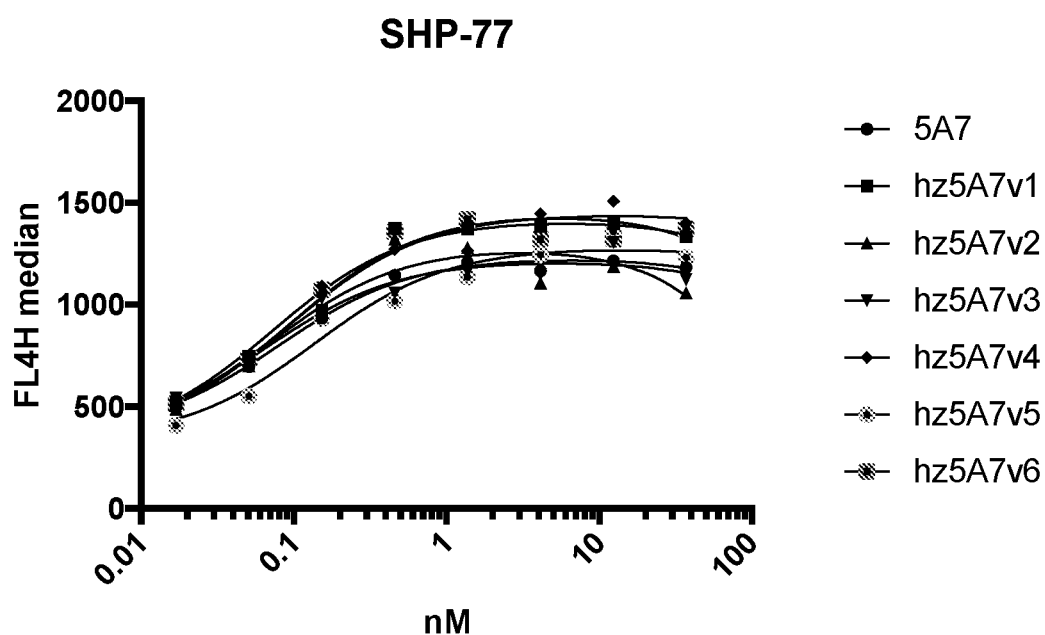
Figure 2C:
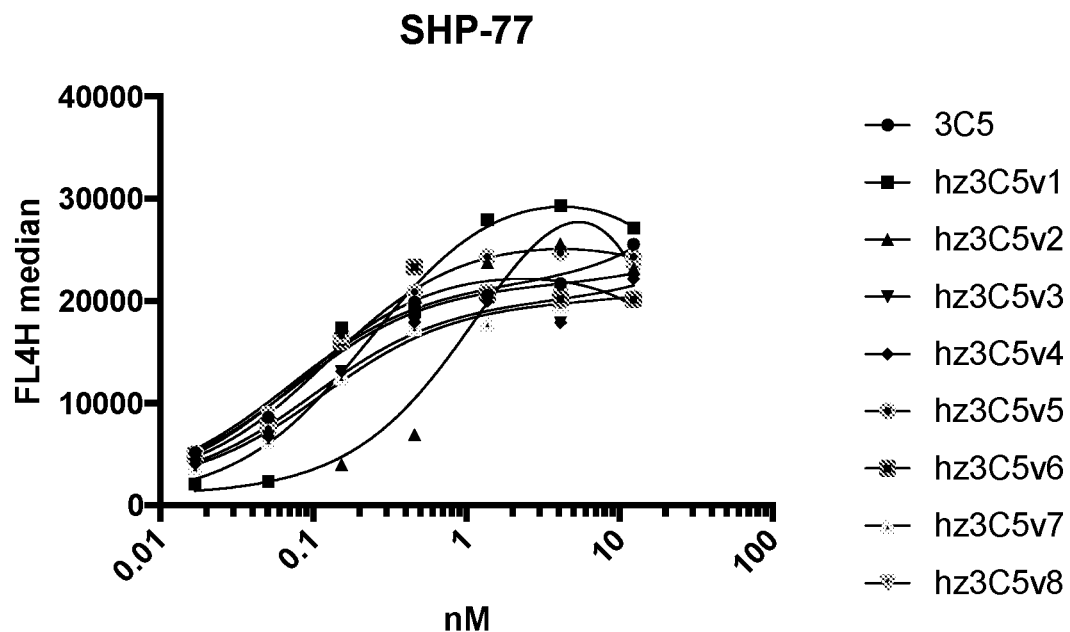
Figure 2D:
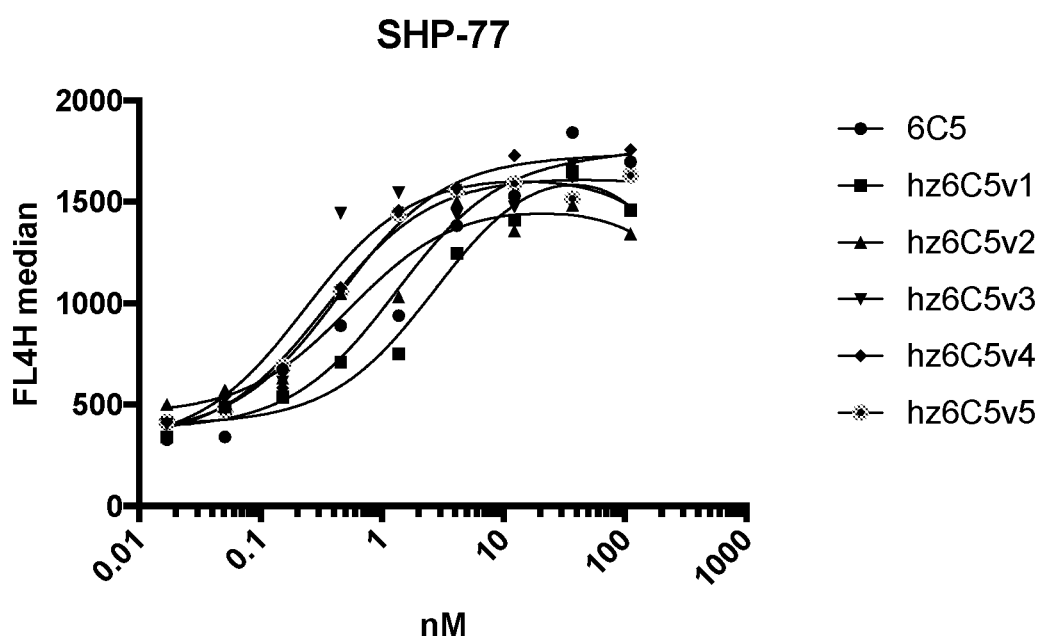
Figure 2E:
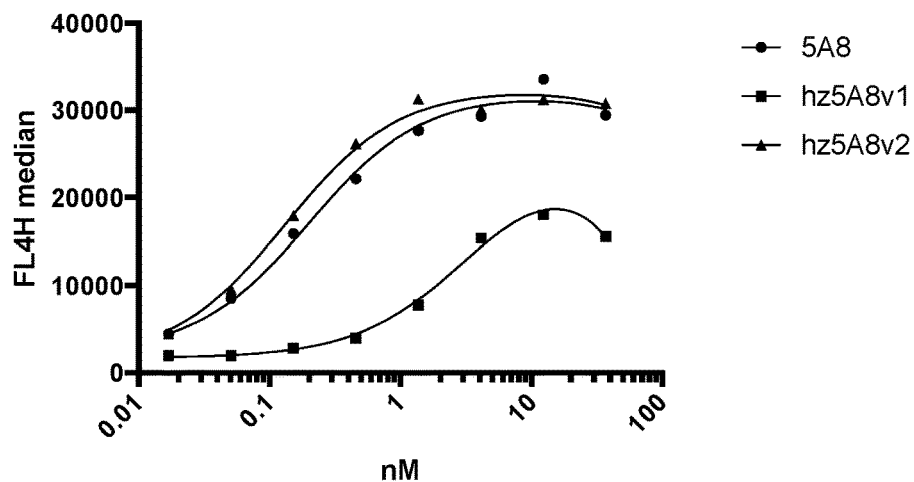
Figure 2F:
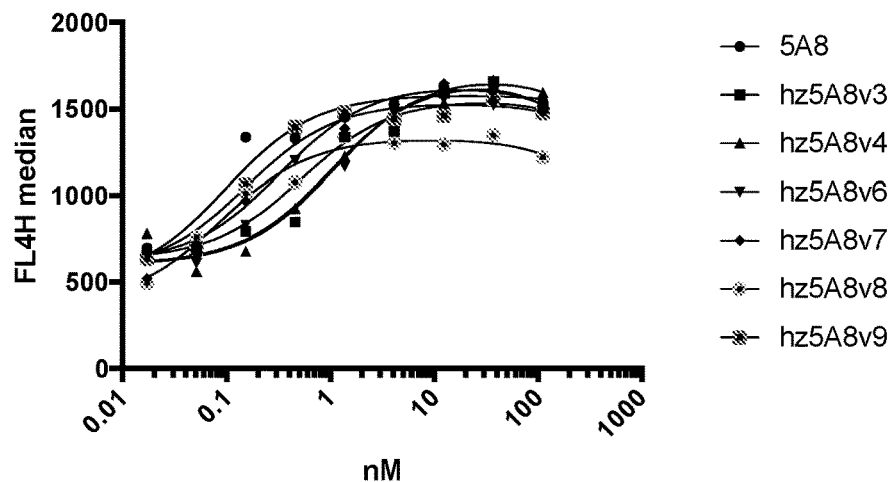
Figure 2G:
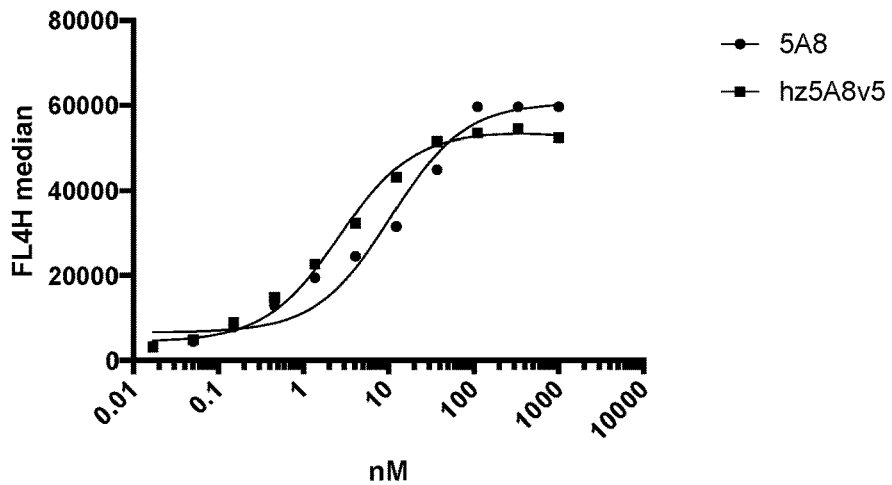
Figure 2H:
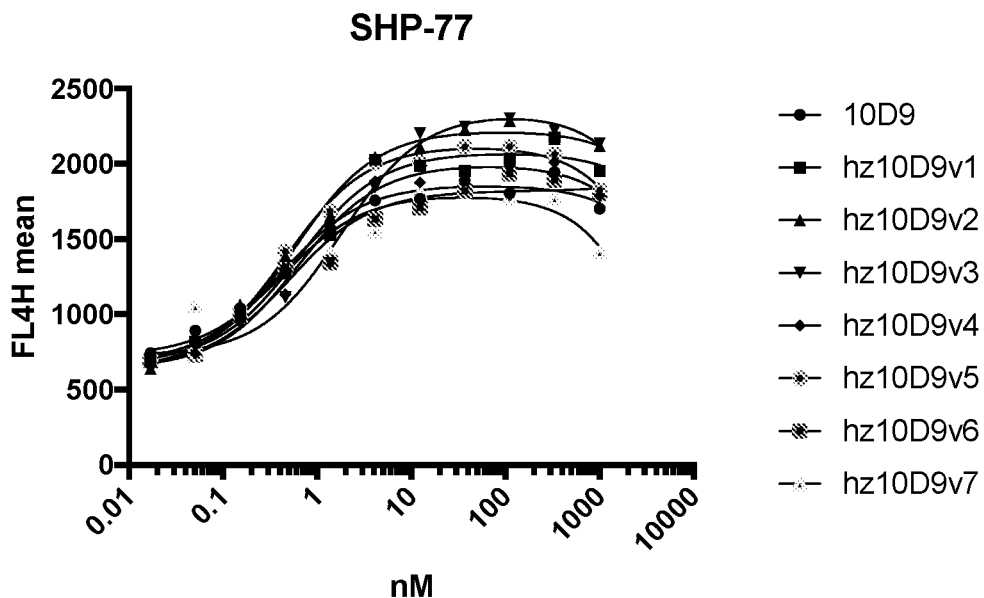
Figure 2I:
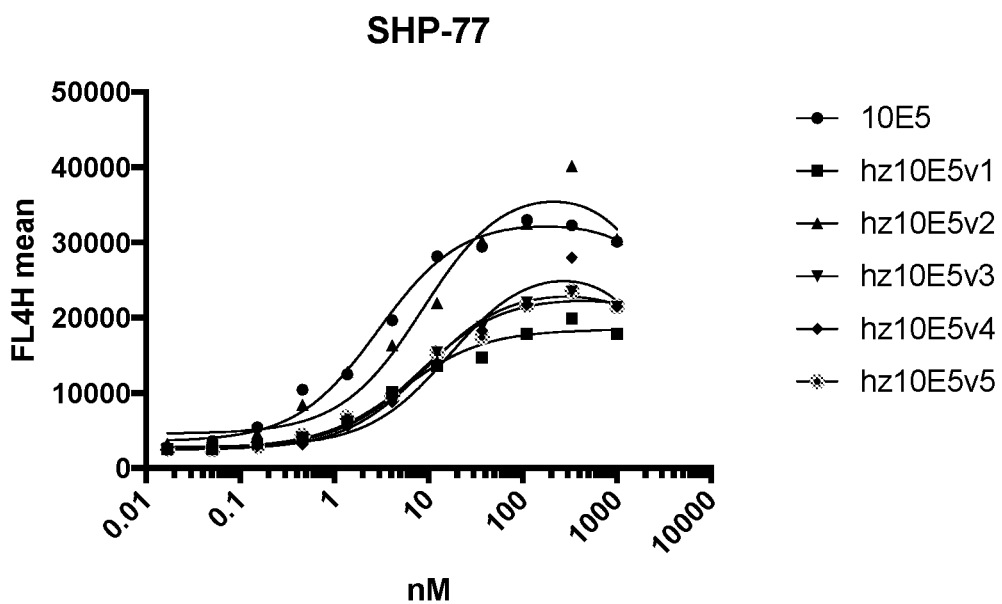
Figure 2J:
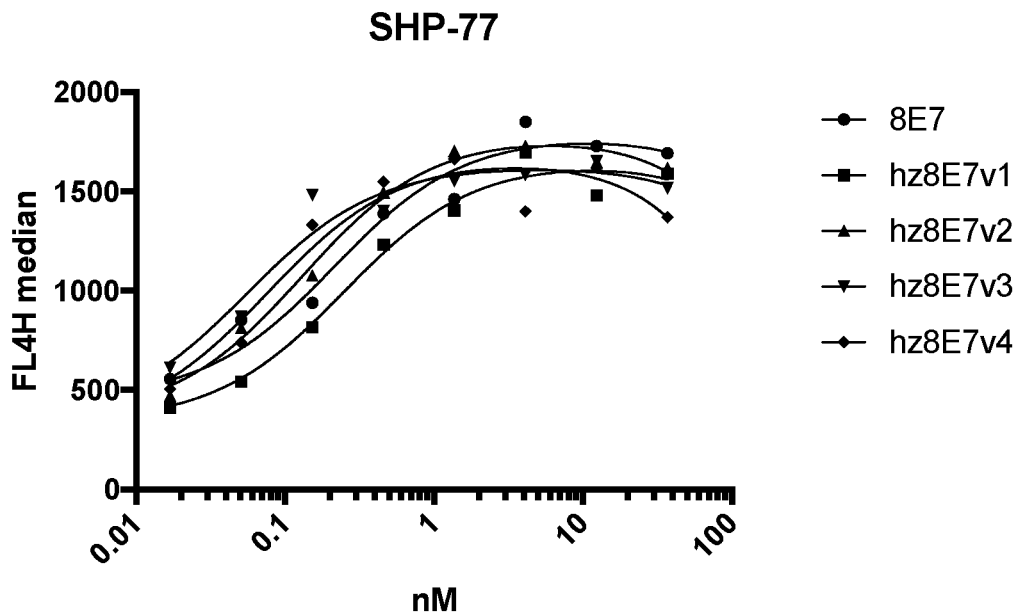
Figure 2K:
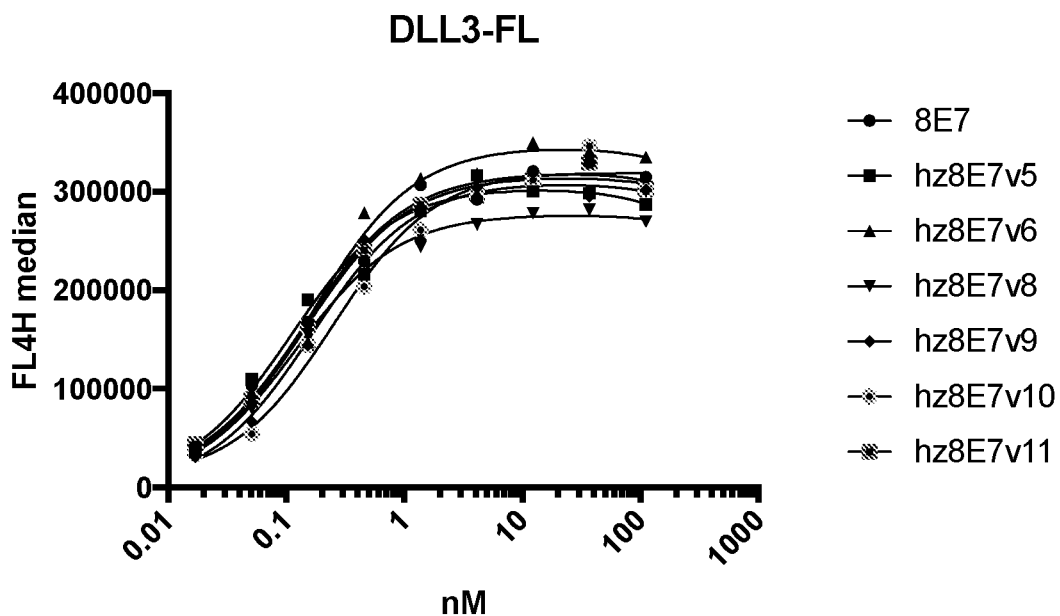
Figure 2L:
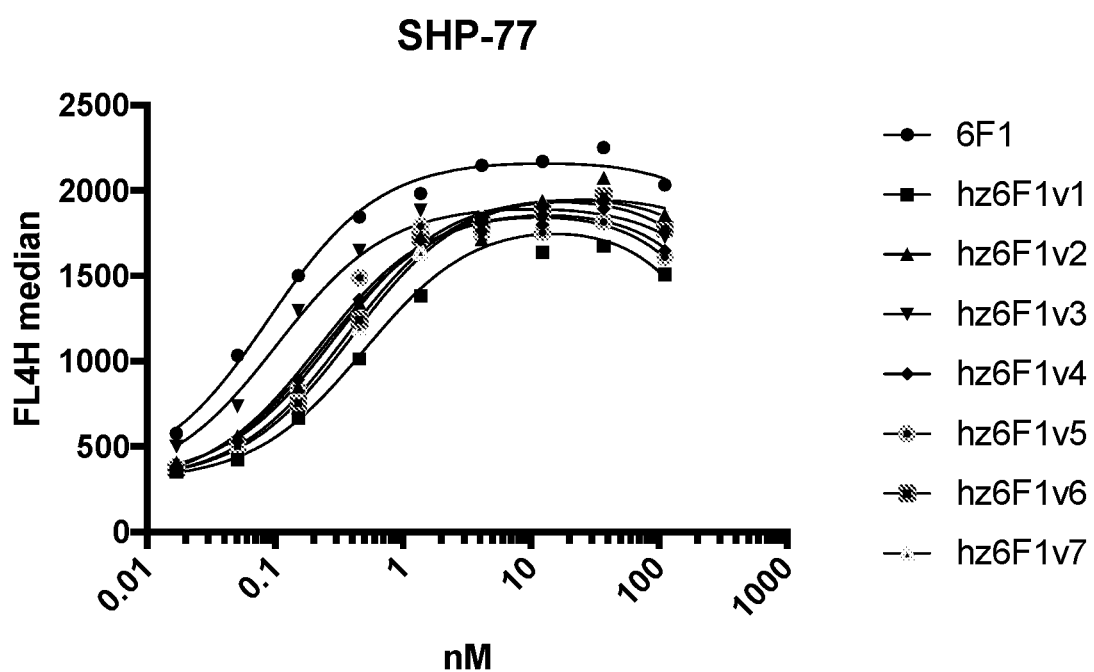
Figure 3A:
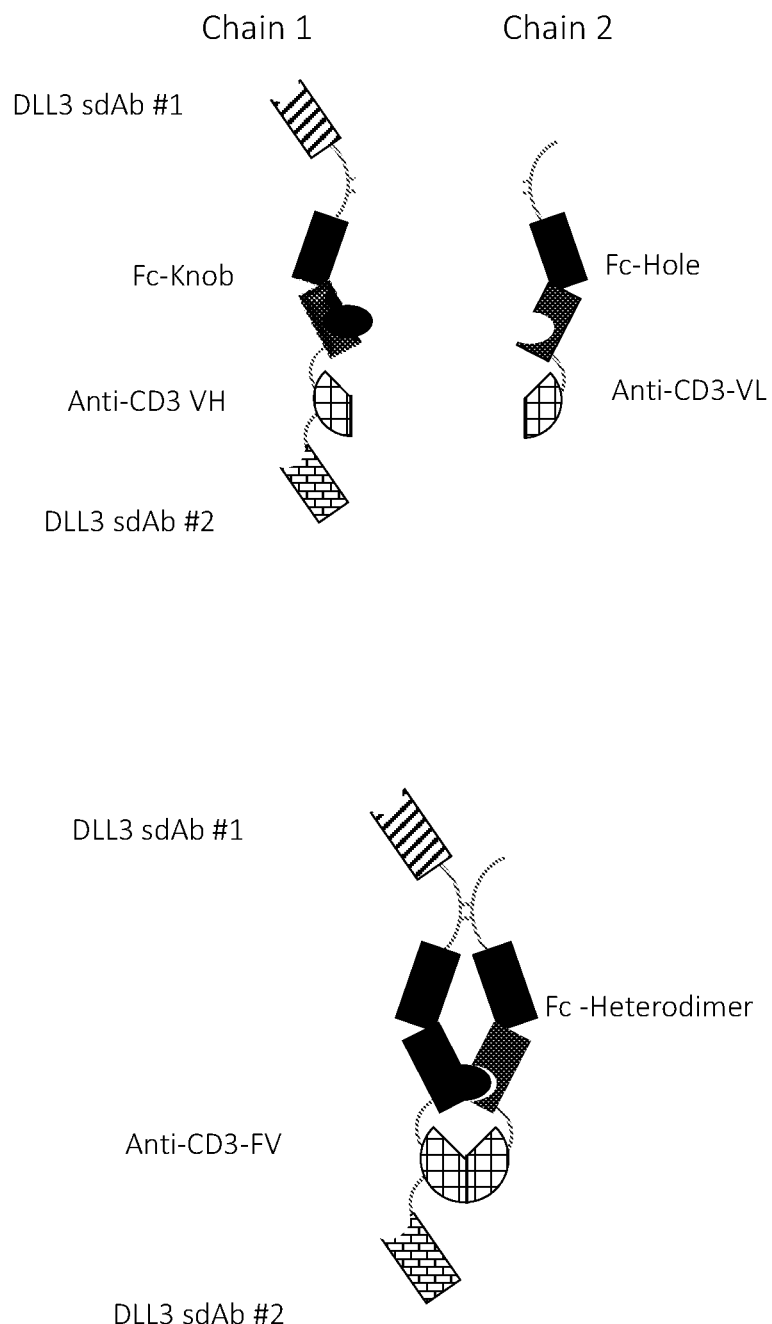
FIGS. 3A-3E depict a series of schematics representing various DLL3-targeted constrained CD3 engaging constructs. The basic components of the DLL3-targeted constrained CD3 engaging constructs of the present disclosure having constrained CD3 binding. The antigen binding domain(s) are positioned at the amino and/or carboxy termini. The Fc region, such as a heterodimeric Fc region, is positioned N-terminal to the CD3 binding region. This positioning of the Fc in close proximity to the CD3 binding region obstructs CD3 binding.
Figure 3B:
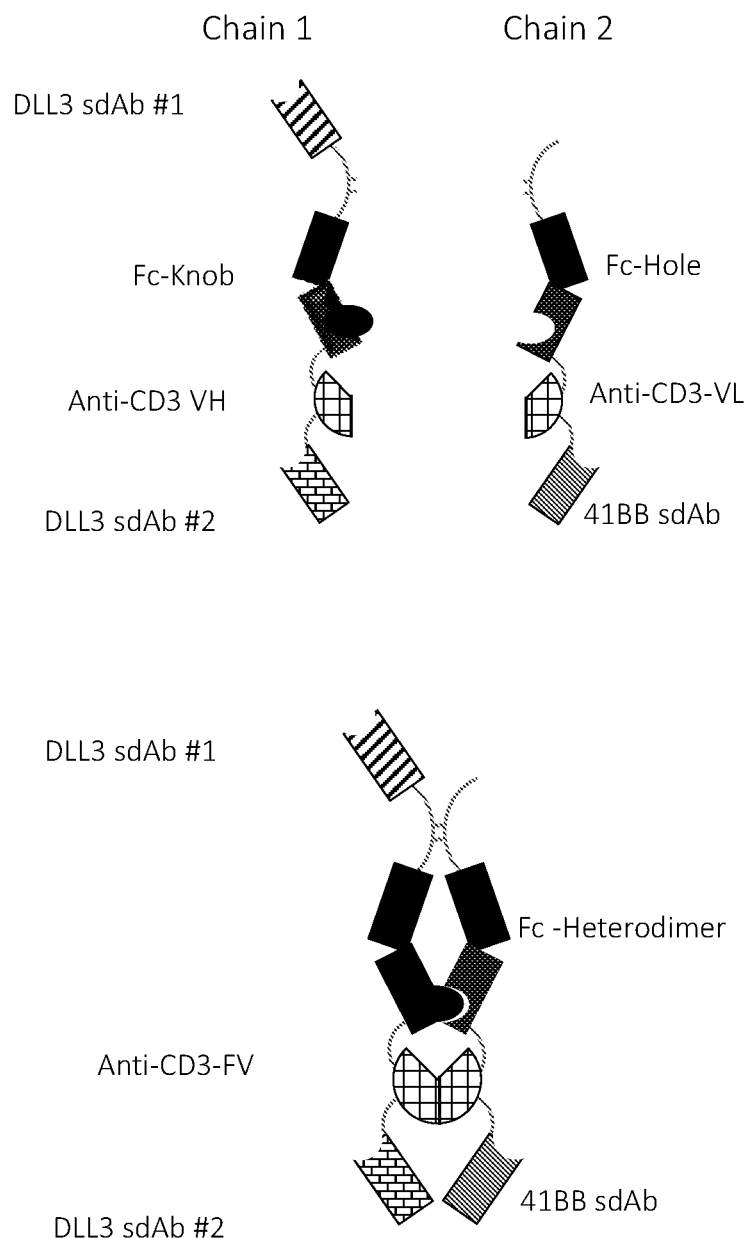
Figure 3C:
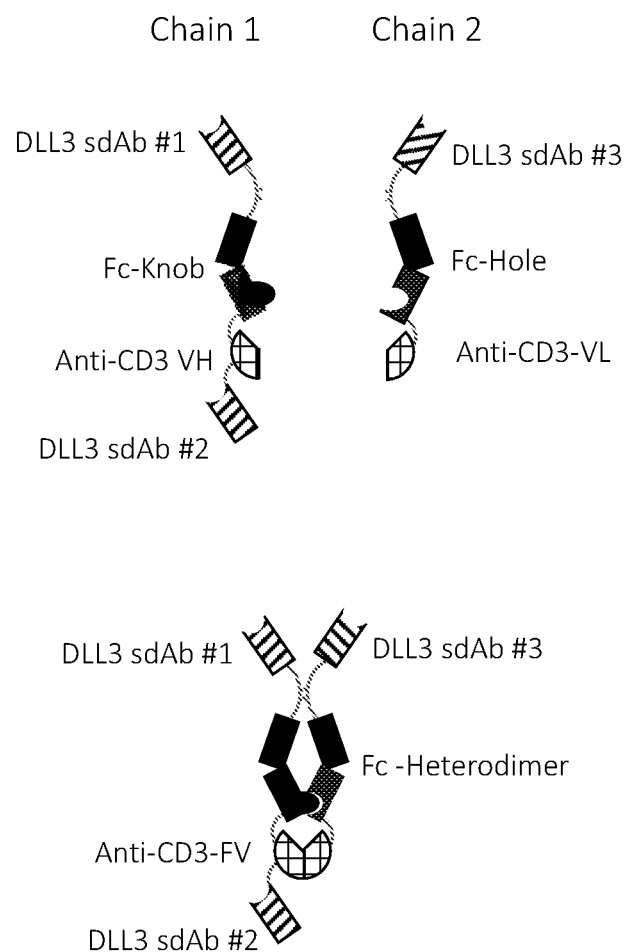
Figure 3D:
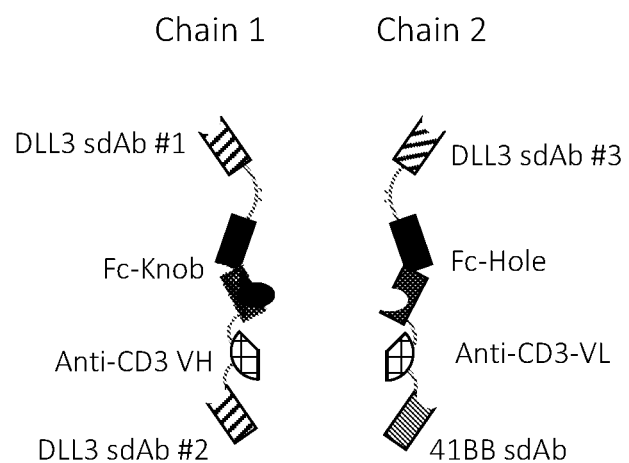
Figure 3D:
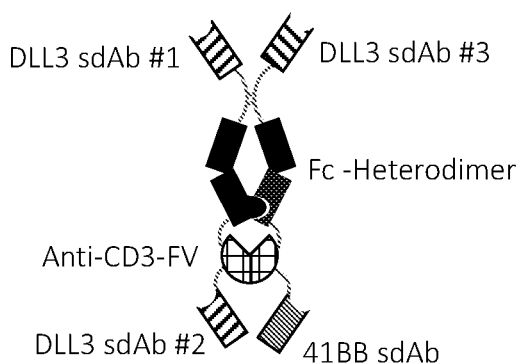
Figure 3E:
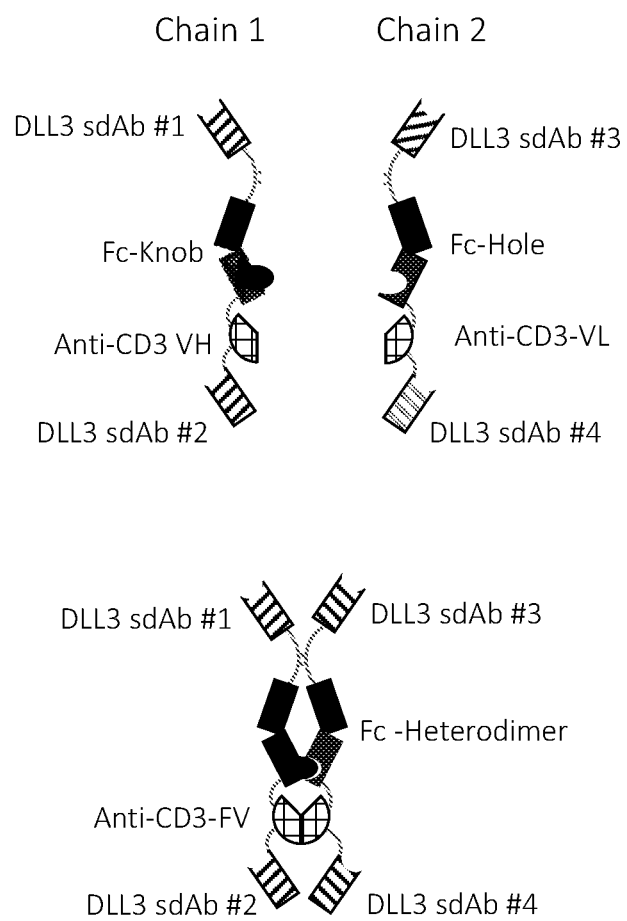
Figure 4A:
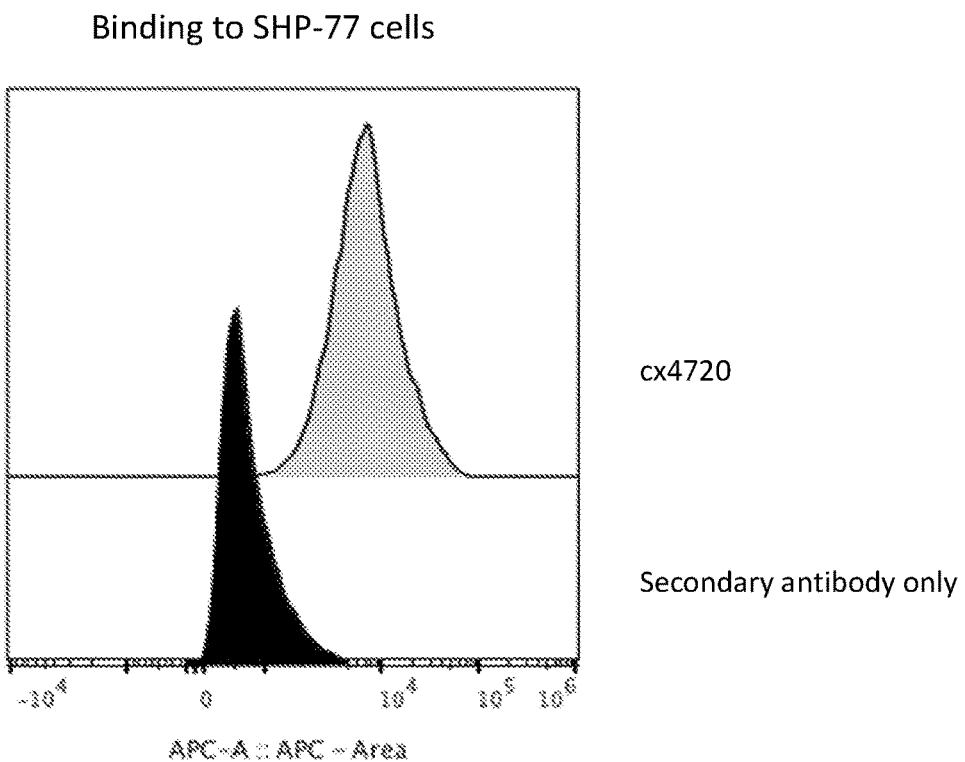
FIGS. 4A-4B demonstrates the binding of DLL3-target constrained CD3 engaging construct cx4720 to DLL3 positive cells, SHP-77 (FIG. 4A) and the lack of binding to primary human T-cells (FIG. 4B). Binding was assessed by flow cytometry using an anti-human IgG APC secondary antibody. The histograms display the normalized cell counts vs fluorescence at 200 nM of each construct, unless otherwise noted.
Figure 4B:
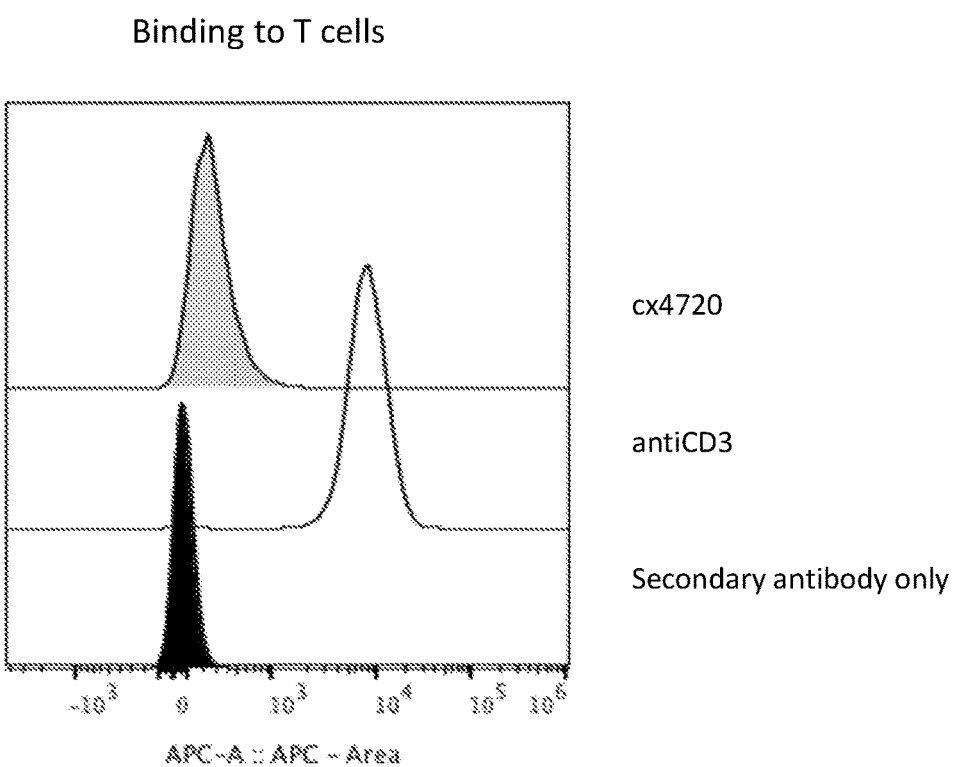
Figure 5A:
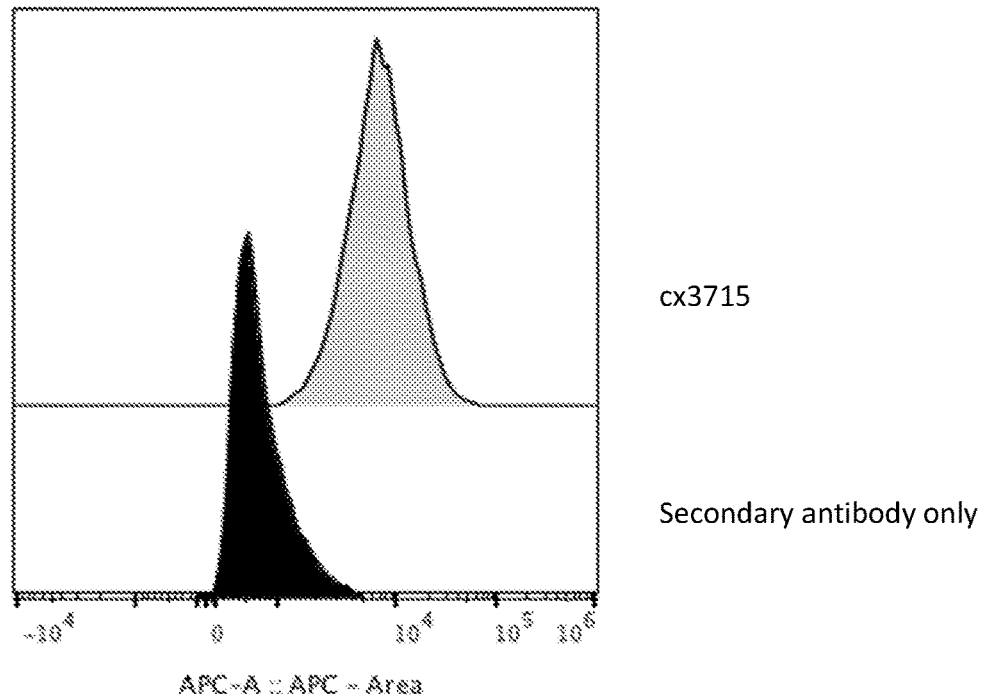
FIGS. 5A-5B demonstrates the binding of DLL3-target constrained CD3 engaging construct cx3715 to DLL3 positive cells, SHP-77 (FIG. 5A) and the lack of binding to primary human T-cells (FIG. 5B). Binding was assessed by flow cytometry using an anti-human IgG APC secondary antibody. The histograms display the normalized cell counts vs fluorescence at 200 nM of each construct, unless otherwise noted.
Figure 5B:
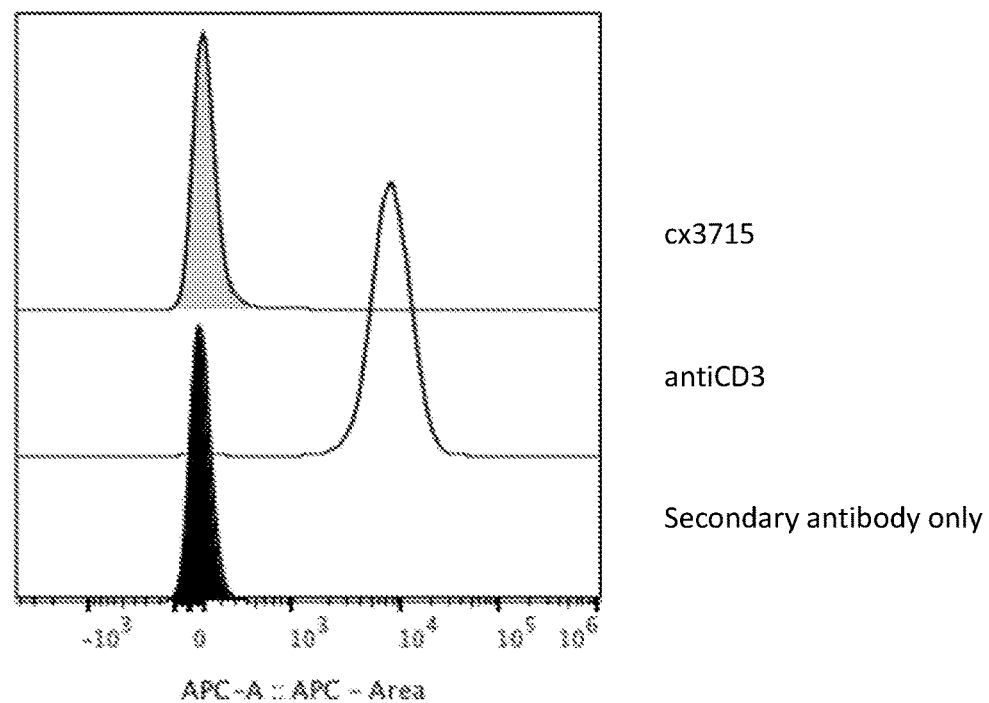
Figure 6A:
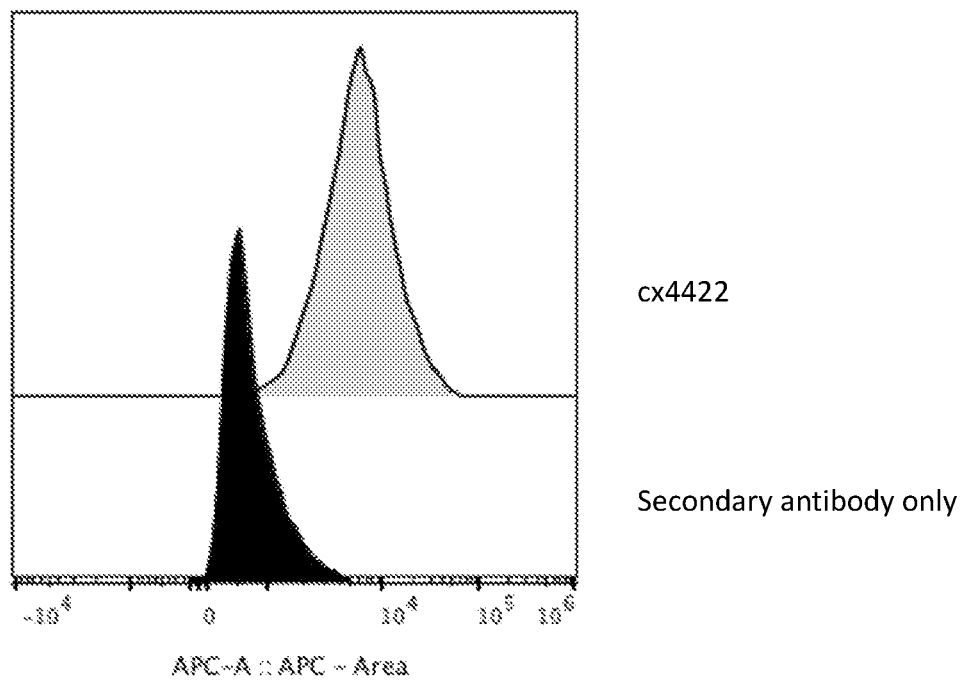
FIG. 6A-6B demonstrates the binding of DLL3-target constrained CD3 engaging construct cx4422 to DLL3 positive cells, SHP-77 (FIG. 6A) and the lack of binding to primary human T-cells (FIG. 6B). Binding was assessed by flow cytometry using an anti-human IgG APC secondary antibody. The histograms display the normalized cell counts vs fluorescence at 200 nM of each construct, unless otherwise noted.
Figure 6B:
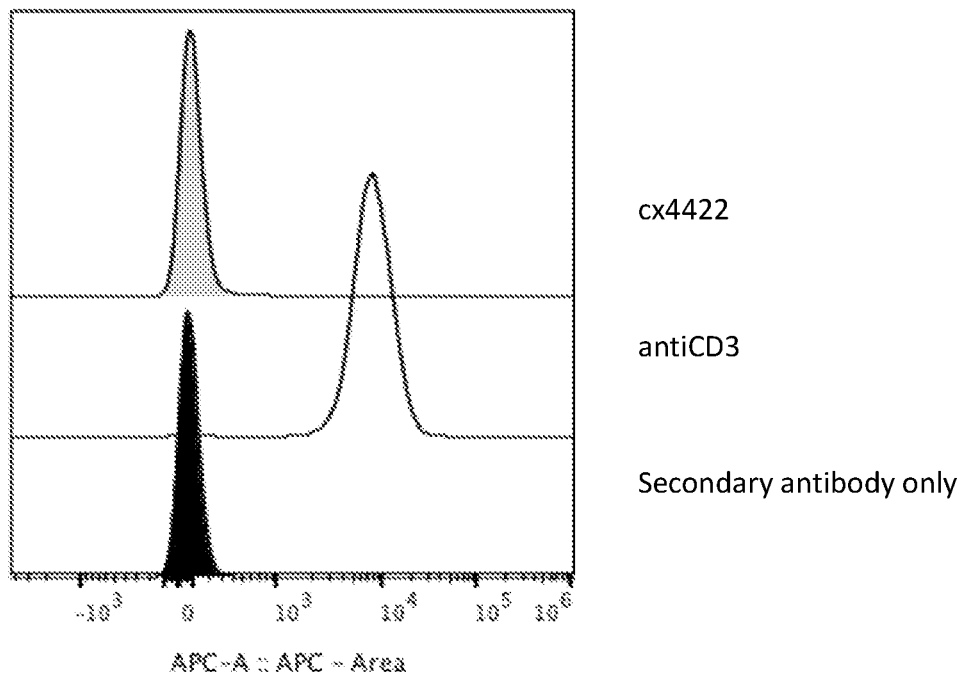
Figure 7A:
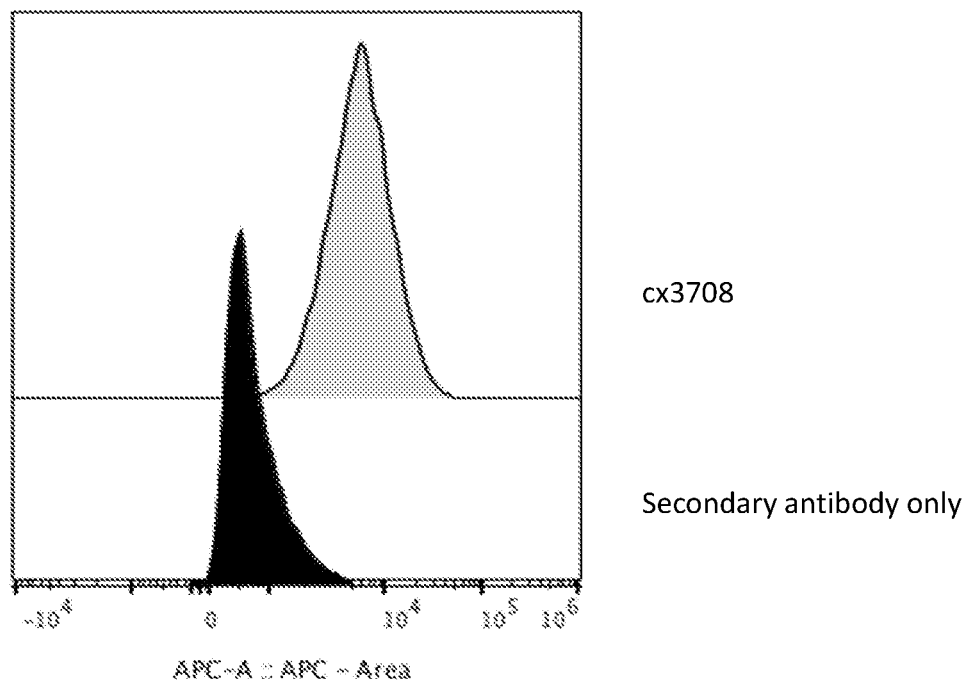
FIGS. 7A-7B demonstrates the binding of DLL3-target constrained CD3 engaging construct cx3708 to DLL3 positive cells, SHP-77 (FIG. 7A) and the lack of binding to primary human T-cells (FIG. 7B). Binding was assessed by flow cytometry using an anti-human IgG APC secondary antibody. The histograms display the normalized cell counts vs fluorescence at 200 nM of each construct, unless otherwise noted.
Figure 7B:
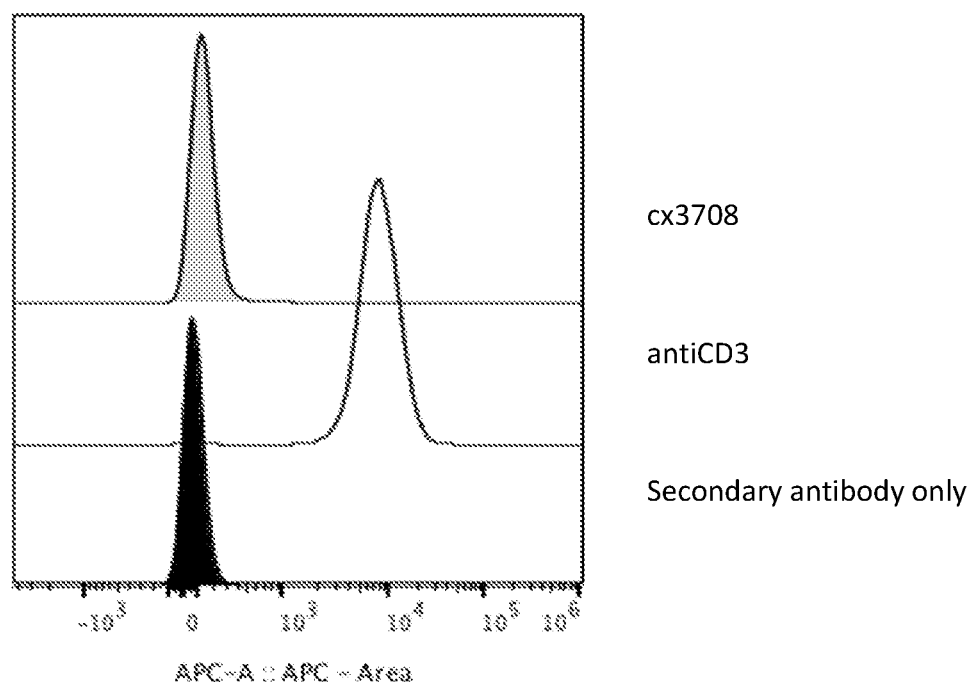
Figure 8A:
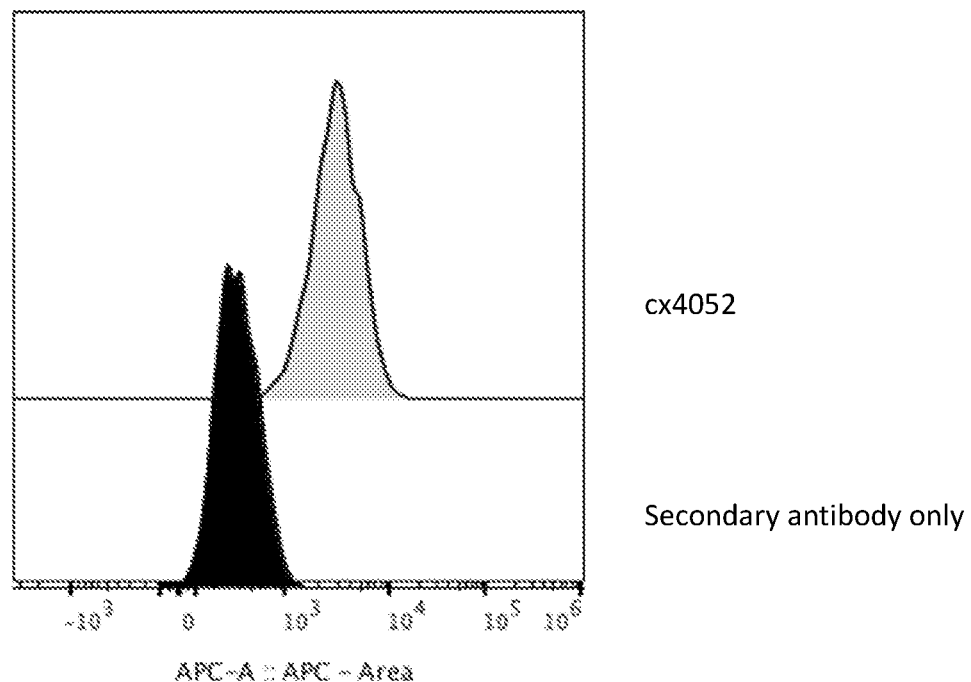
FIGS. 8A-8B demonstrates the binding of DLL3-target constrained CD3 engaging construct cx4052 to DLL3 positive cells, SHP-77 (FIG. 8A) and the lack of binding to primary human T-cells (FIG. 8B). Binding was assessed by flow cytometry using an anti-human IgG APC secondary antibody. The histograms display the normalized cell counts vs fluorescence at 200 nM of each construct, unless otherwise noted.
Figure 8B:
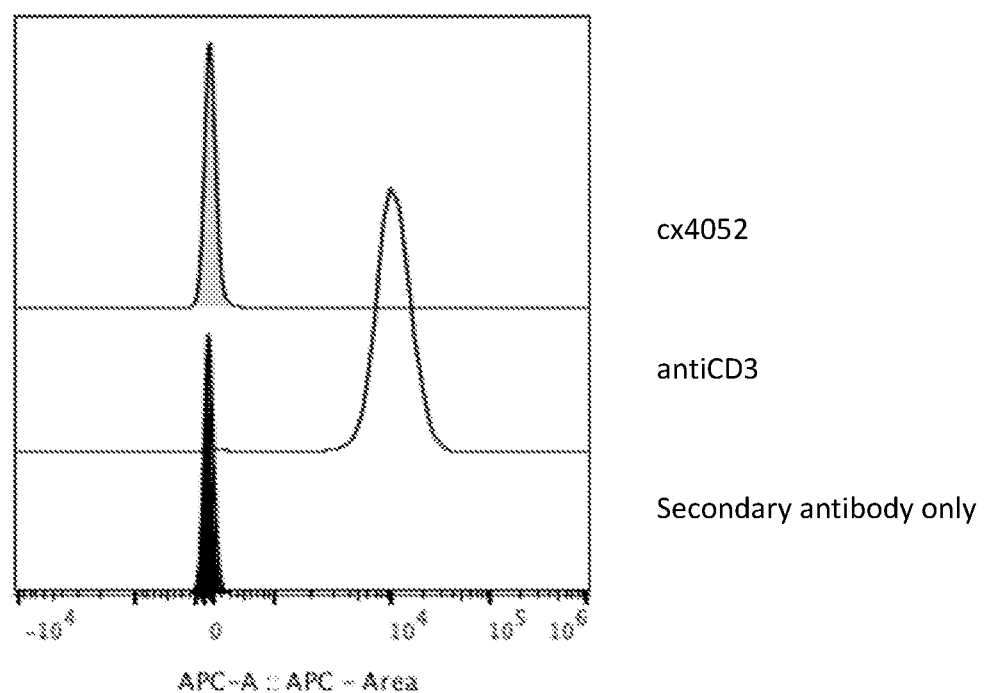
Figure 9A:
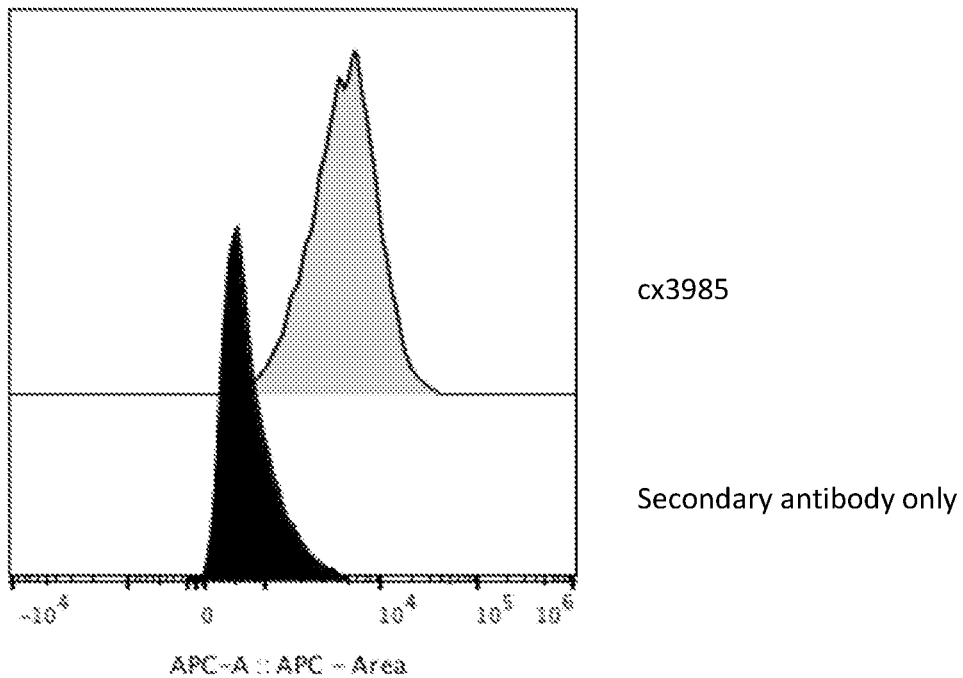
FIGS. 9A-9B demonstrates the binding of DLL3-target constrained CD3 engaging construct cx3985 to DLL3 positive cells, SHP-77 (FIG. 9A) and the lack of binding to primary human T-cells (FIG. 9B). Binding was assessed by flow cytometry using an anti-human IgG APC secondary antibody. The histograms display the normalized cell counts vs fluorescence at 200 nM of each construct, unless otherwise noted.
Figure 9B:
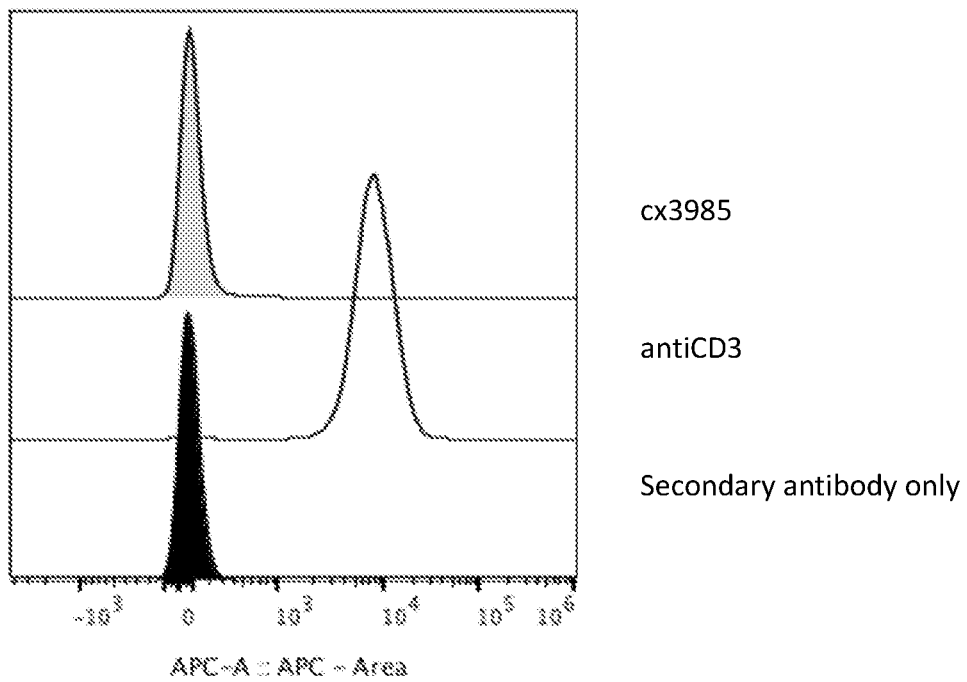
Figure 10A:
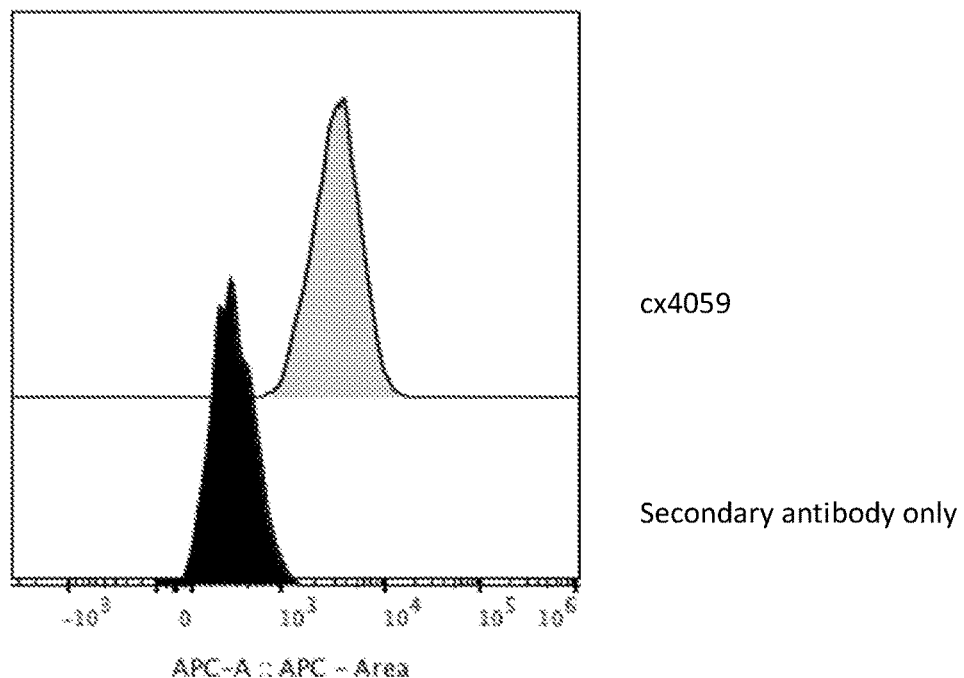
FIGS. 10A-10B demonstrates the binding of DLL3-target constrained CD3 engaging construct cx4059 to DLL3 positive cells, SHP-77 (FIG. 10A) and the lack of binding to primary human T-cells (FIG. 10B). Binding was assessed by flow cytometry using an anti-human IgG APC secondary antibody. The histograms display the normalized cell counts vs fluorescence at 200 nM of each construct, unless otherwise noted.
Figure 10B:
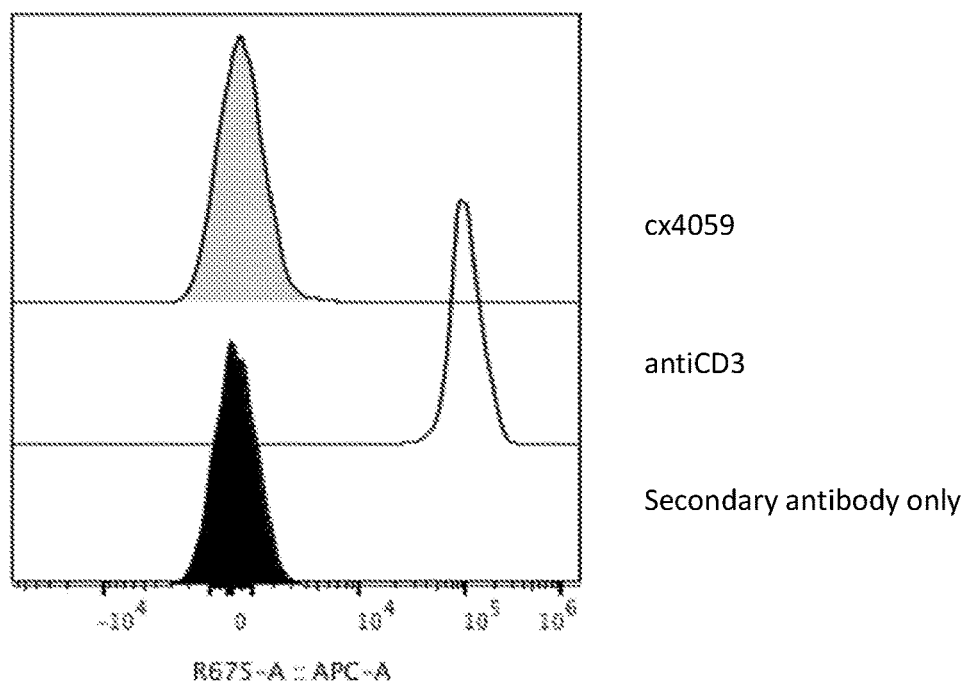
Figure 11A:
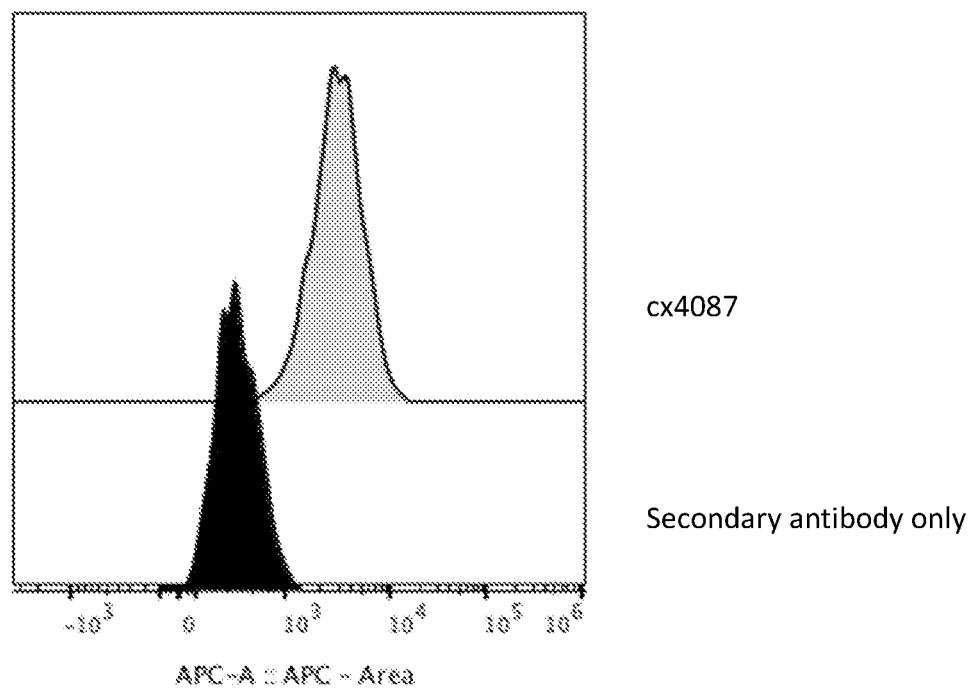
FIGS. 11A-11B demonstrates the binding of DLL3-target constrained CD3 engaging construct cx4087 to DLL3 positive cells, SHP-77 (FIG. 11A) and the lack of binding to primary human T-cells (FIG. 11B). Binding was assessed by flow cytometry using an anti-human IgG APC secondary antibody. The histograms display the normalized cell counts vs fluorescence at 200 nM of each construct, unless otherwise noted.
Figure 11B:
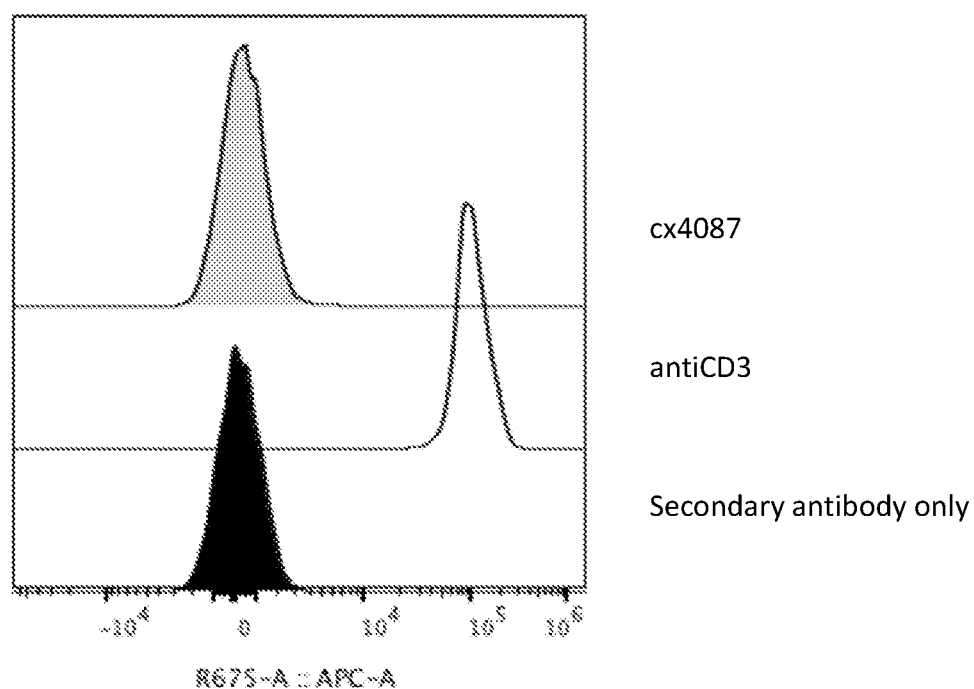
Figure 12A:
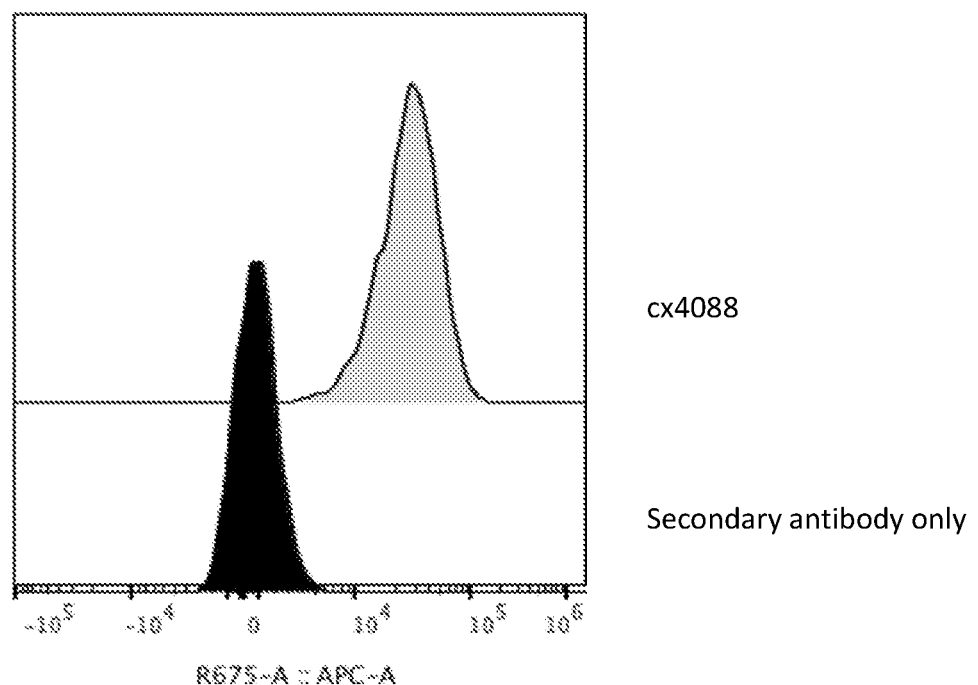
FIGS. 12A-12B demonstrates the binding of DLL3-target constrained CD3 engaging construct cx4088 to DLL3 positive cells, SHP-77 (FIG. 12A) and the lack of binding to primary human T-cells (FIG. 12B). Binding was assessed by flow cytometry using an anti-human IgG APC secondary antibody. The histograms display the normalized cell counts vs fluorescence at 200 nM of each construct, unless otherwise noted.
Figure 12B:
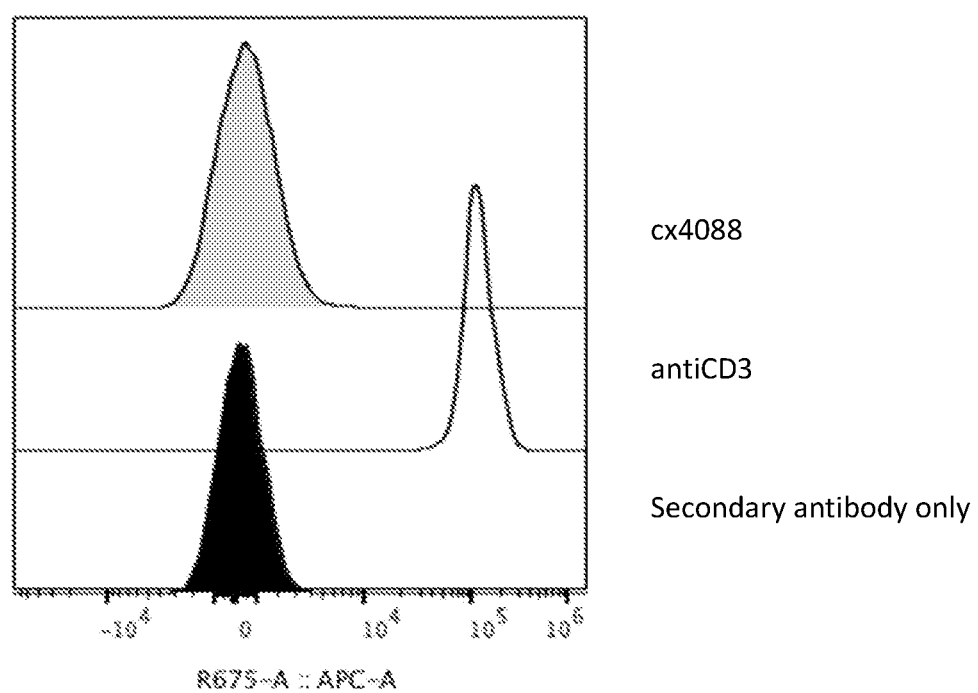
Figure 13A:
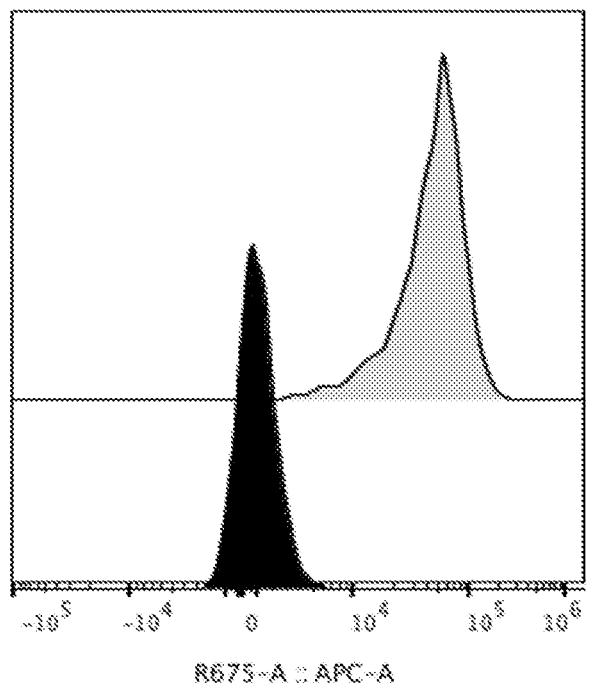
FIGS. 13A-13B demonstrates the binding of DLL3-target constrained CD3 engaging construct cx4895 to DLL3 positive cells, SHP-77 (FIG. 13A) and the lack of binding to primary human T-cells (FIG. 13B). Binding was assessed by flow cytometry using an anti-human IgG APC secondary antibody. The histograms display the normalized cell counts vs fluorescence at 200 nM of each construct, unless otherwise noted.
Figure 13B:
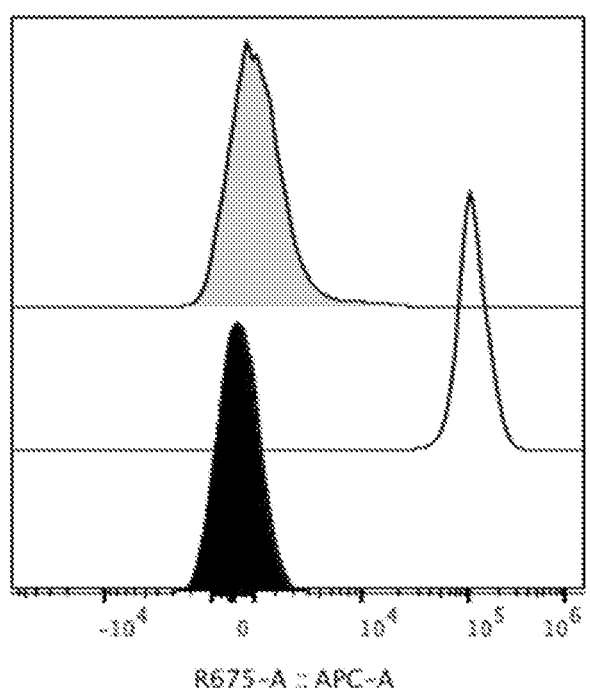
Figure 14A:
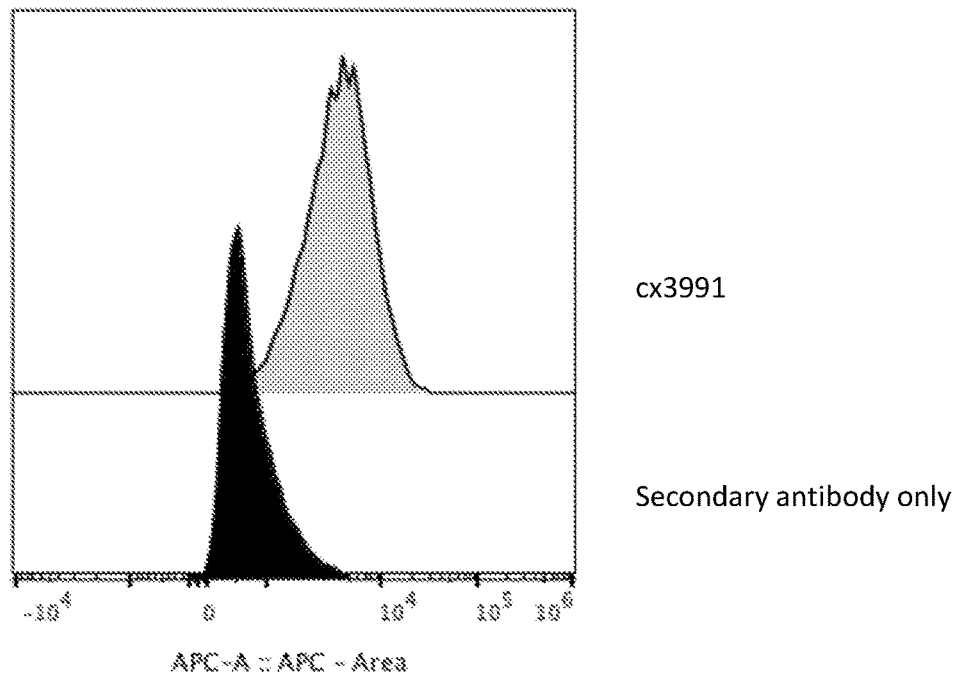
FIGS. 14A-14B demonstrates the binding of DLL3-target constrained CD3 engaging construct cx3991 to DLL3 positive cells, SHP-77 (FIG. 14A) and the lack of binding to primary human T-cells (FIG. 14B). Binding was assessed by flow cytometry using an anti-human IgG APC secondary antibody. The histograms display the normalized cell counts vs fluorescence at 200 nM of each construct, unless otherwise noted.
Figure 14B:
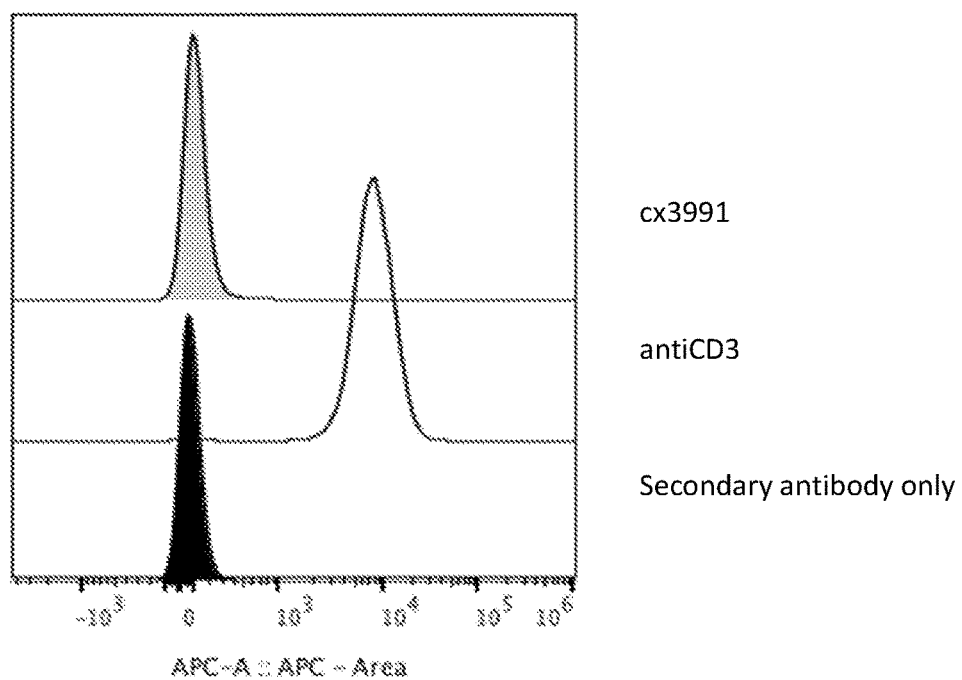
Figure 15A:
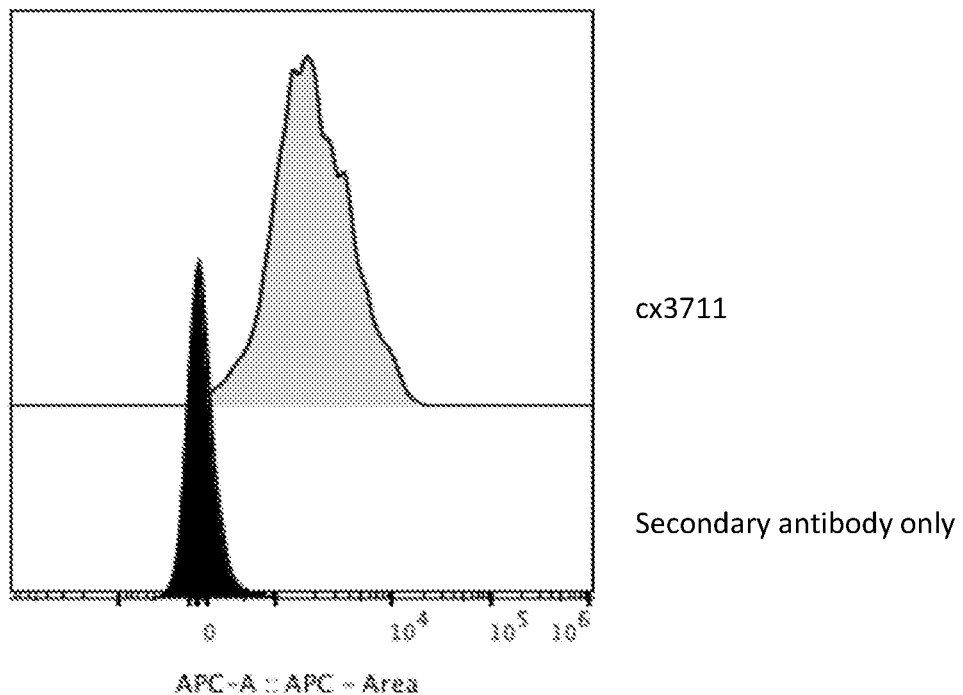
FIGS. 15A-15B demonstrates the binding of DLL3-target constrained CD3 engaging construct cx3711 to DLL3 positive cells, SHP-77 (FIG. 15A) and the lack of binding to primary human T-cells (FIG. 15B). Binding was assessed by flow cytometry using an anti-human IgG APC secondary antibody. The histograms display the normalized cell counts vs fluorescence at 200 nM of each construct, unless otherwise noted.
Figure 15B:
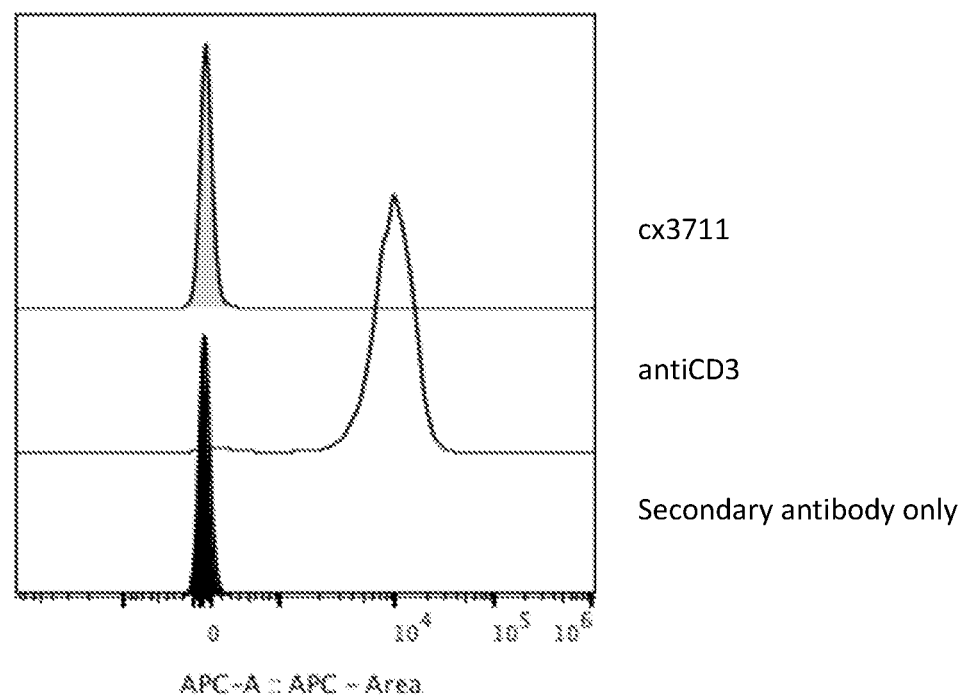
Figure 16A:
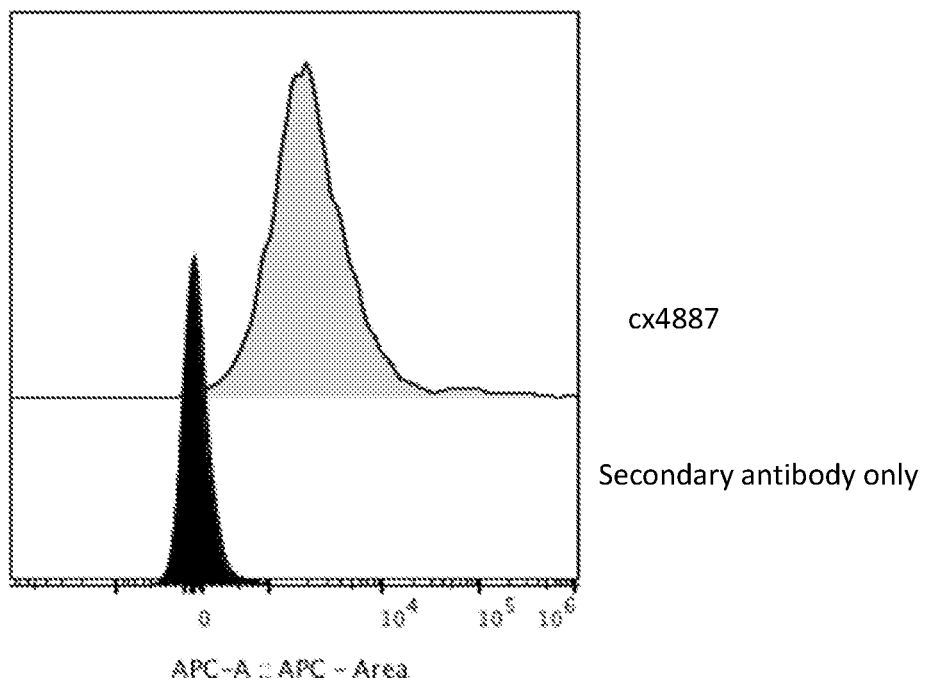
FIGS. 16A-16B demonstrates the binding of DLL3-target constrained CD3 engaging construct cx4887 to DLL3 positive cells, SHP-77 (FIG. 16A) and the lack of binding to primary human T-cells (FIG. 16B). Binding was assessed by flow cytometry using an anti-human IgG APC secondary antibody. The histograms display the normalized cell counts vs fluorescence at 200 nM of each construct, unless otherwise noted.
Figure 16B:
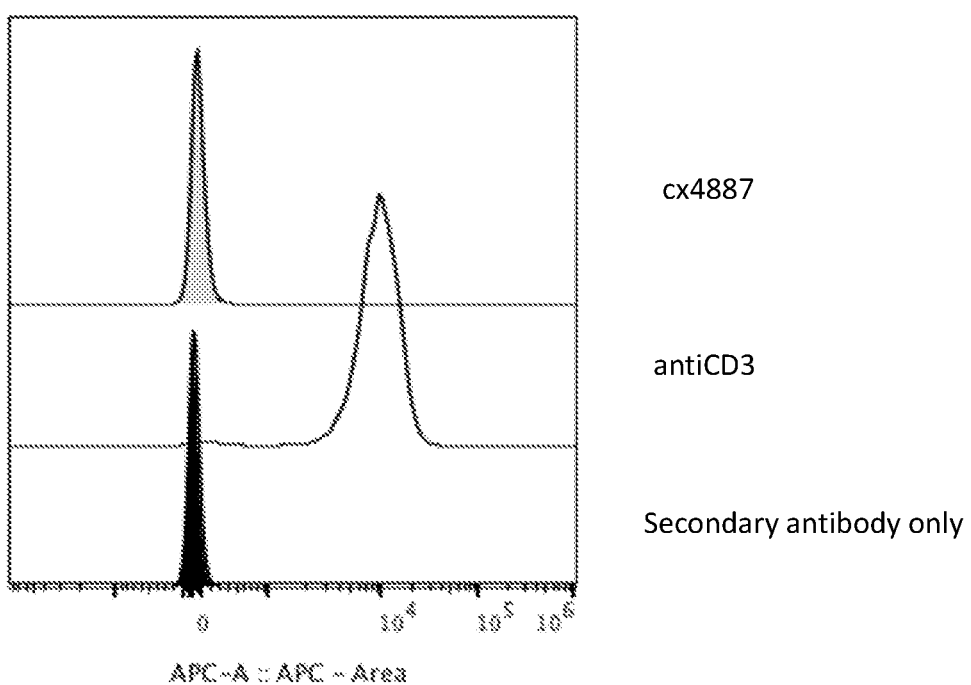
Figure 17A:
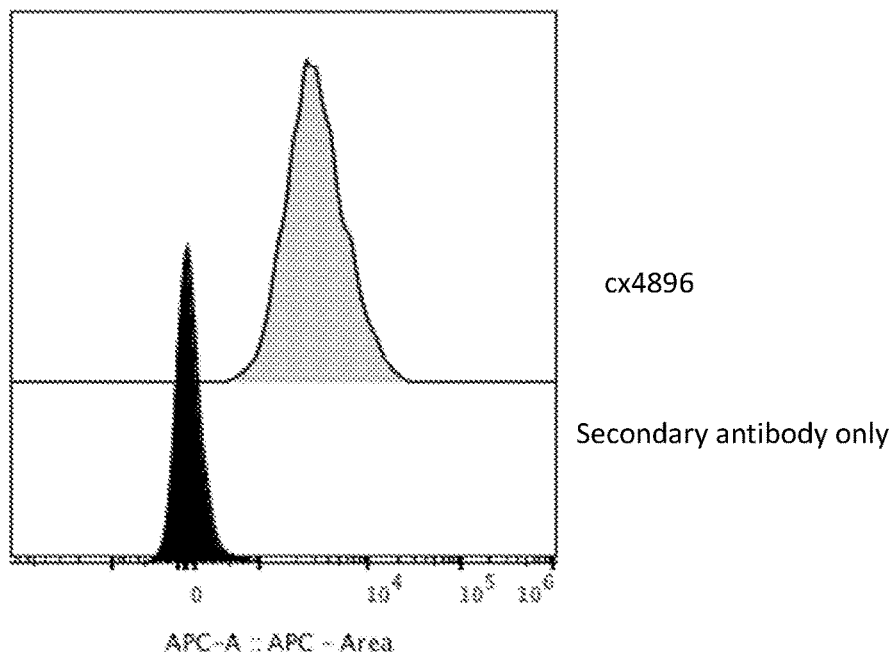
FIGS. 17A-17B demonstrates the binding of DLL3-target constrained CD3 engaging construct cx4896 to DLL3 positive cells, SHP-77 (FIG. 17A) and the lack of binding to primary human T-cells (FIG. 17B). Binding was assessed by flow cytometry using an anti-human IgG APC secondary antibody. The histograms display the normalized cell counts vs fluorescence at 200 nM of each construct, unless otherwise noted.
Figure 17B:
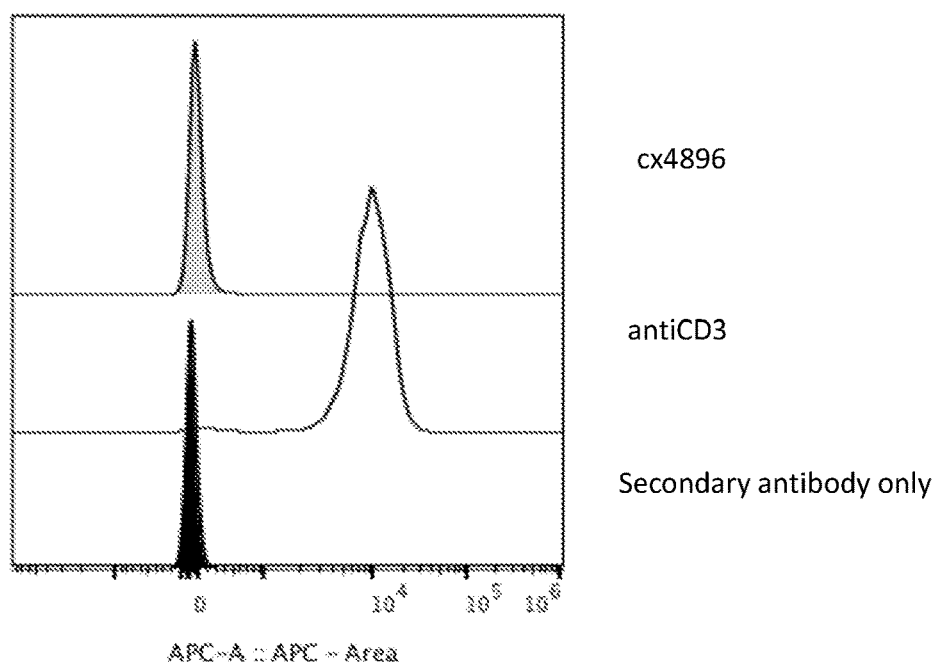
Figure 18A:
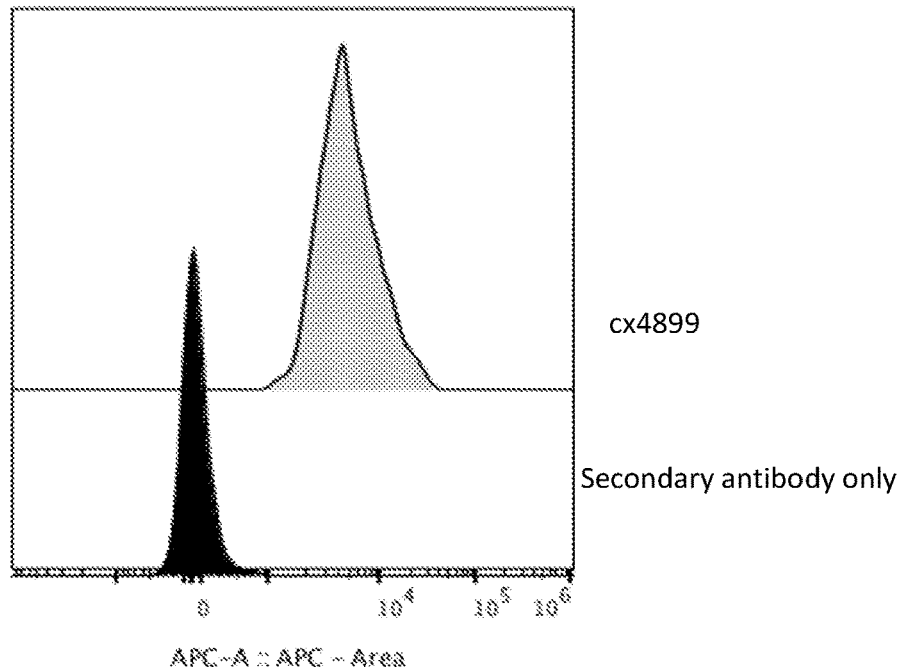
FIGS. 18A-18B demonstrates the binding of DLL3-target constrained CD3 engaging construct cx4899 to DLL3 positive cells, SHP-77 (FIG. 18A) and the lack of binding to primary human T-cells (FIG. 18B). Binding was assessed by flow cytometry using an anti-human IgG APC secondary antibody. The histograms display the normalized cell counts vs fluorescence at 200 nM of each construct, unless otherwise noted.
Figure 18B:
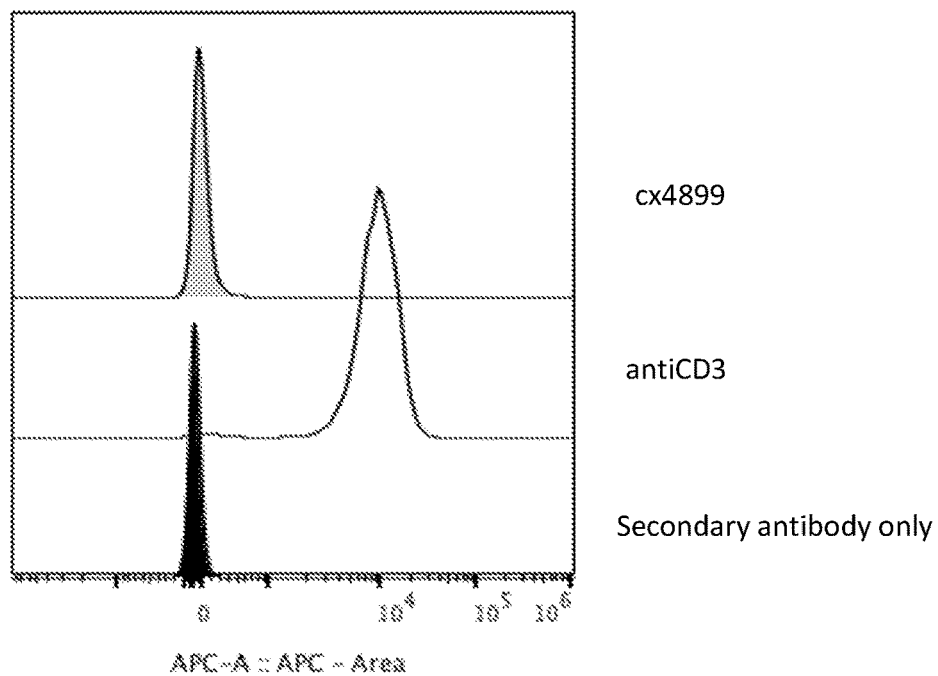
Figure 19A:
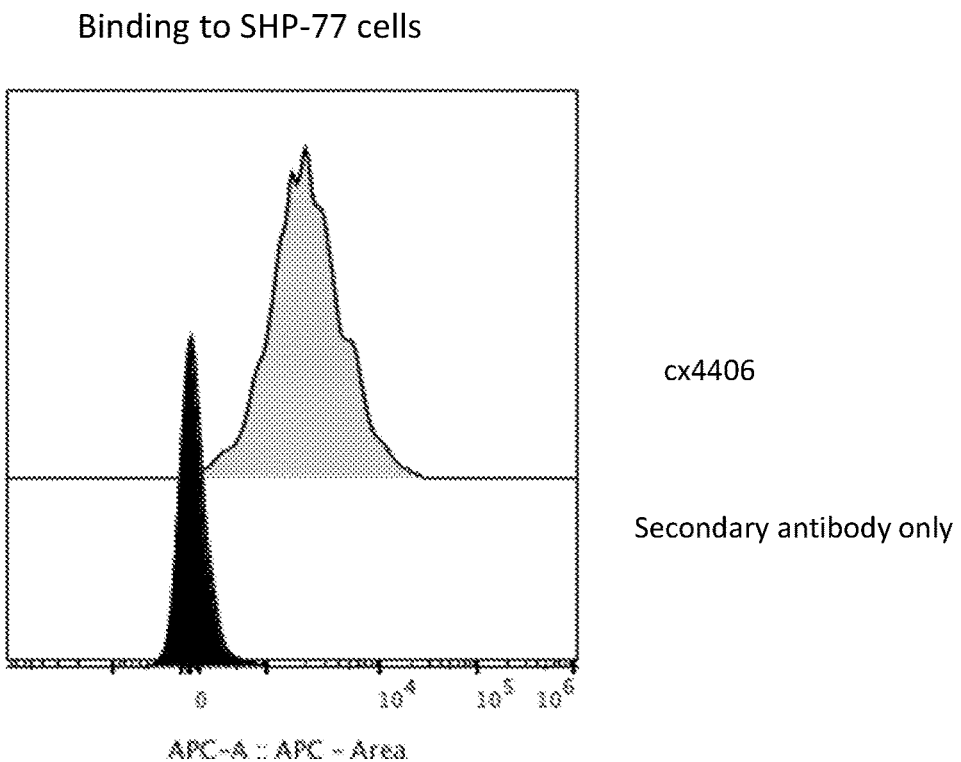
FIGS. 19A-19B demonstrates the binding of DLL3-target constrained CD3 engaging construct cx4406 to DLL3 positive cells, SHP-77 (FIG. 19A) and the lack of binding to primary human T-cells (FIG. 19B). Binding was assessed by flow cytometry using an anti-human IgG APC secondary antibody. The histograms display the normalized cell counts vs fluorescence at 200 nM of each construct, unless otherwise noted.
Figure 19B:
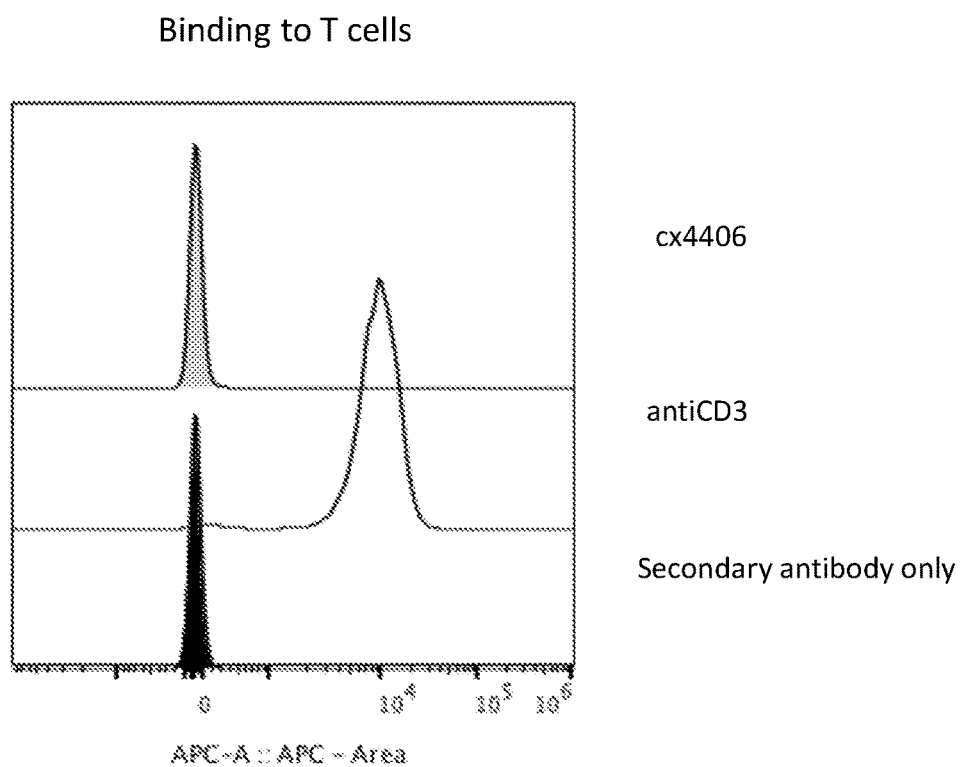
Figure 20A:
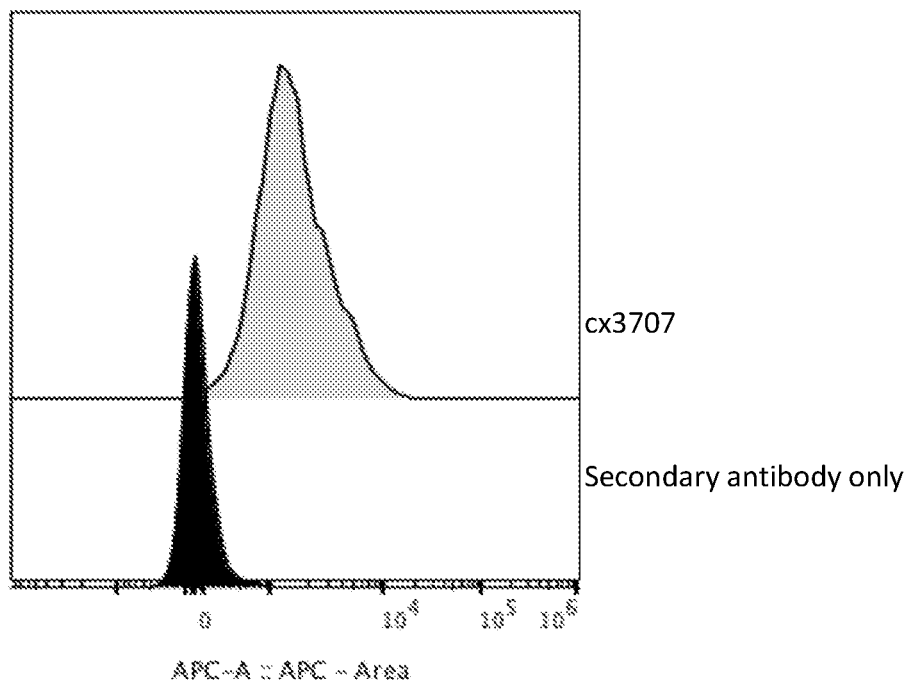
FIGS. 20A-20B demonstrates the binding of DLL3-target constrained CD3 engaging construct cx3707 to DLL3 positive cells, SHP-77 (FIG. 20A) and the lack of binding to primary human T-cells (FIG. 20B). Binding was assessed by flow cytometry using an anti-human IgG APC secondary antibody. The histograms display the normalized cell counts vs fluorescence at 200 nM of each construct, unless otherwise noted.
Figure 20B:
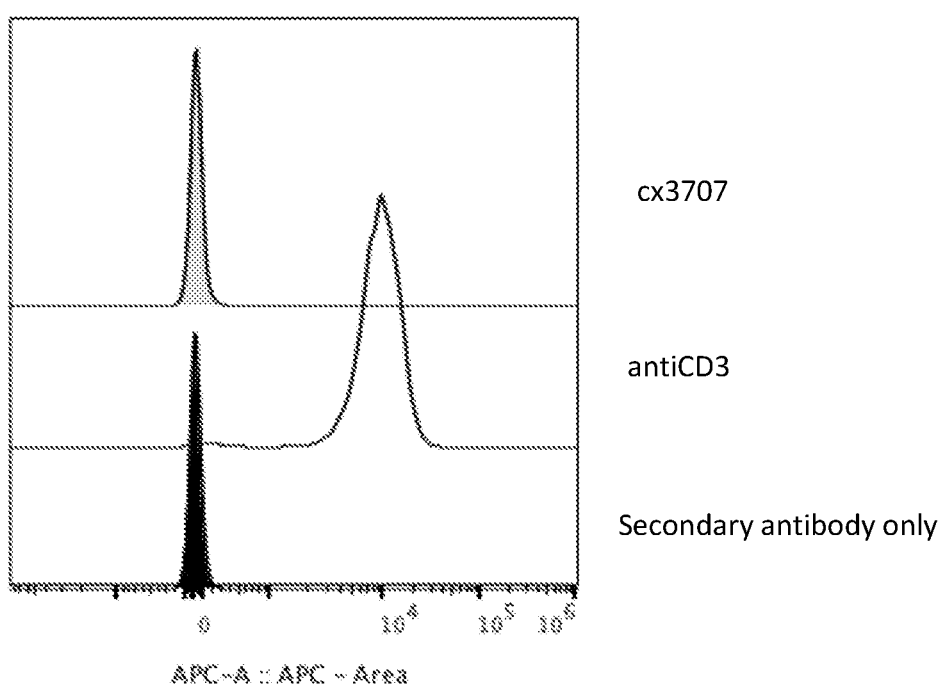
Figure 21A:
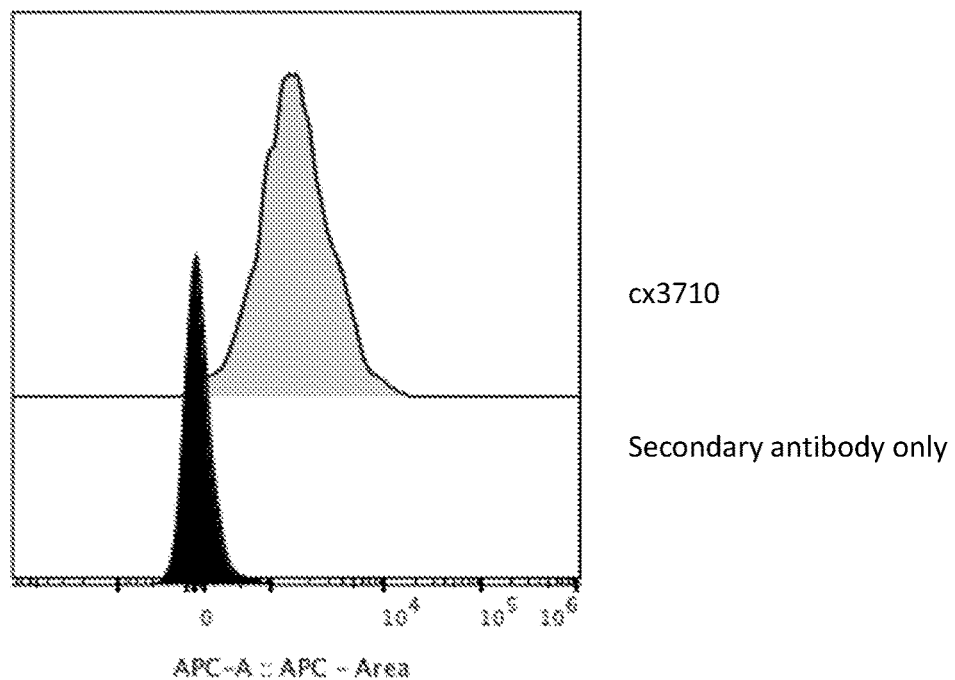
FIGS. 21A-21B demonstrates the binding of DLL3-target constrained CD3 engaging construct cx3710 to DLL3 positive cells, SHP-77 (FIG. 21A) and the lack of binding to primary human T-cells (FIG. 21B). Binding was assessed by flow cytometry using an anti-human IgG APC secondary antibody. The histograms display the normalized cell counts vs fluorescence at 200 nM of each construct, unless otherwise noted.
Figure 21B:
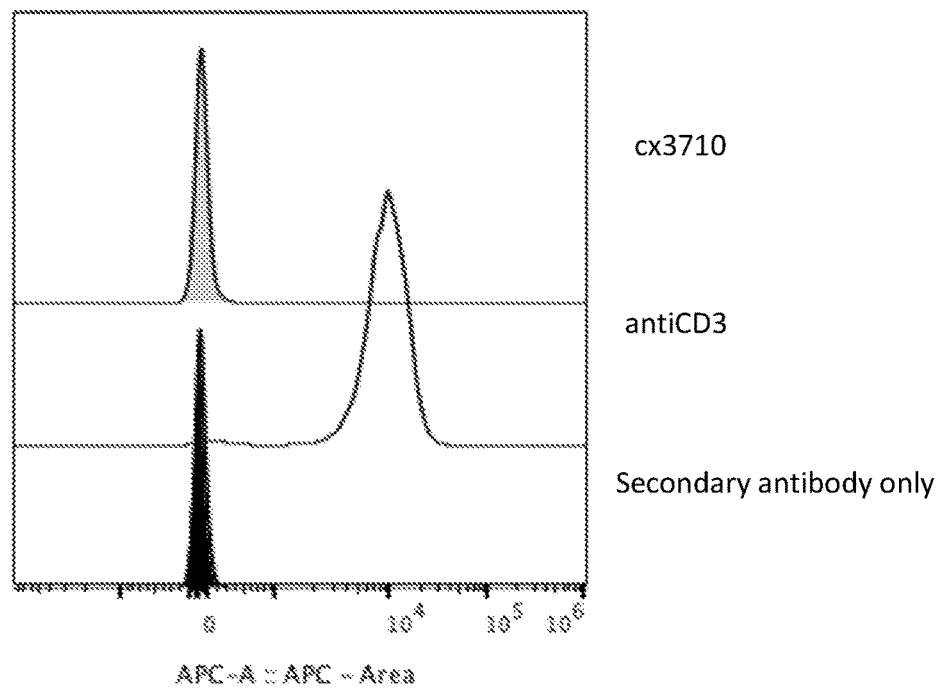
Figure 22A:
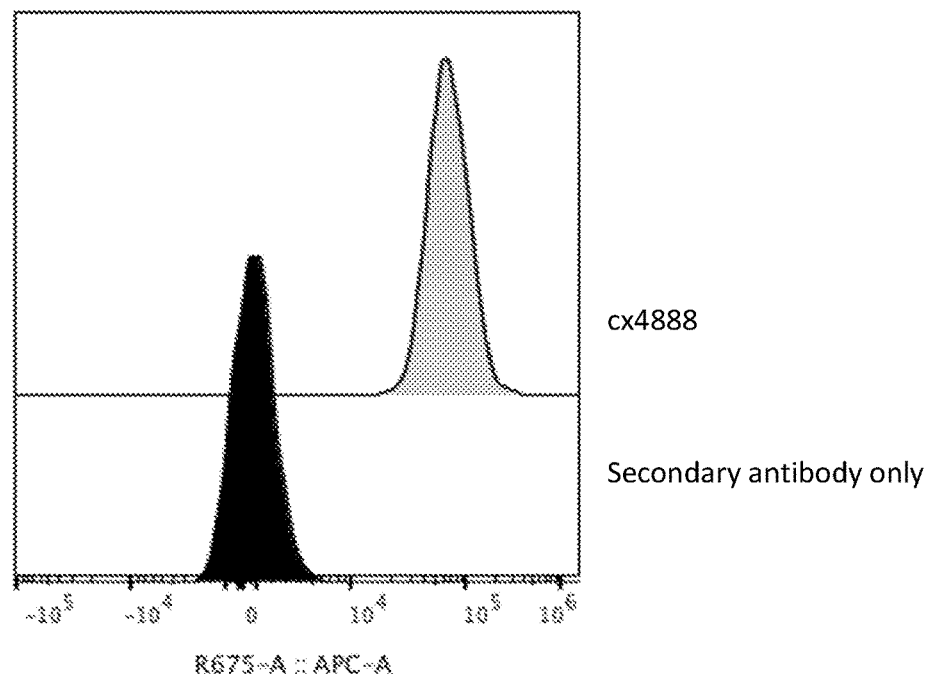
FIGS. 22A-22B demonstrates the binding of DLL3-target constrained CD3 engaging construct cx4888 to DLL3 positive cells, SHP-77 (FIG. 22A) and the lack of binding to primary human T-cells (FIG. 22B). Binding was assessed by flow cytometry using an anti-human IgG APC secondary antibody. The histograms display the normalized cell counts vs fluorescence at 200 nM of each construct, unless otherwise noted.
Figure 22B:
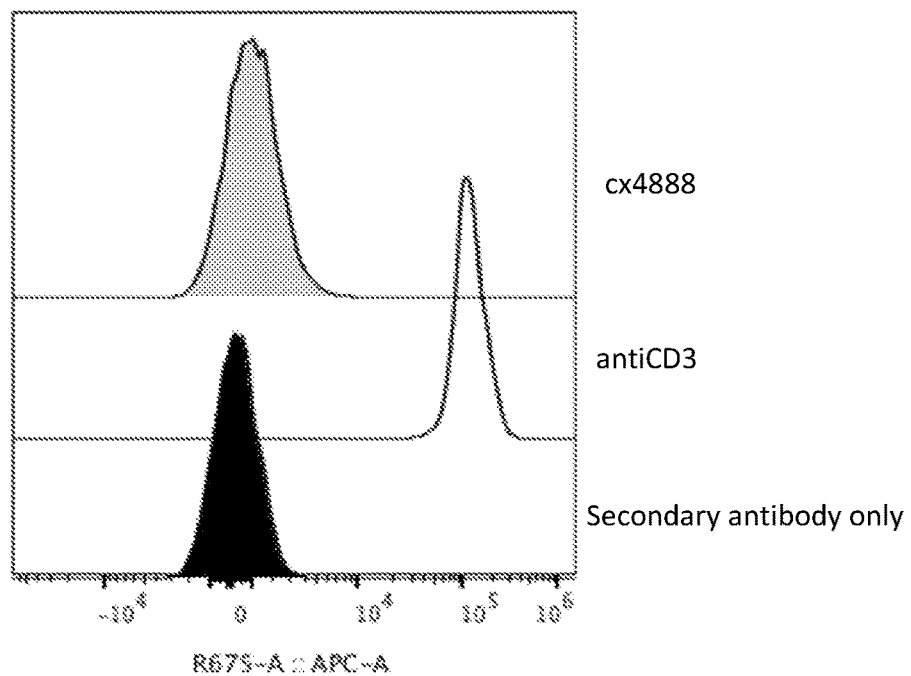
Figure 23A:
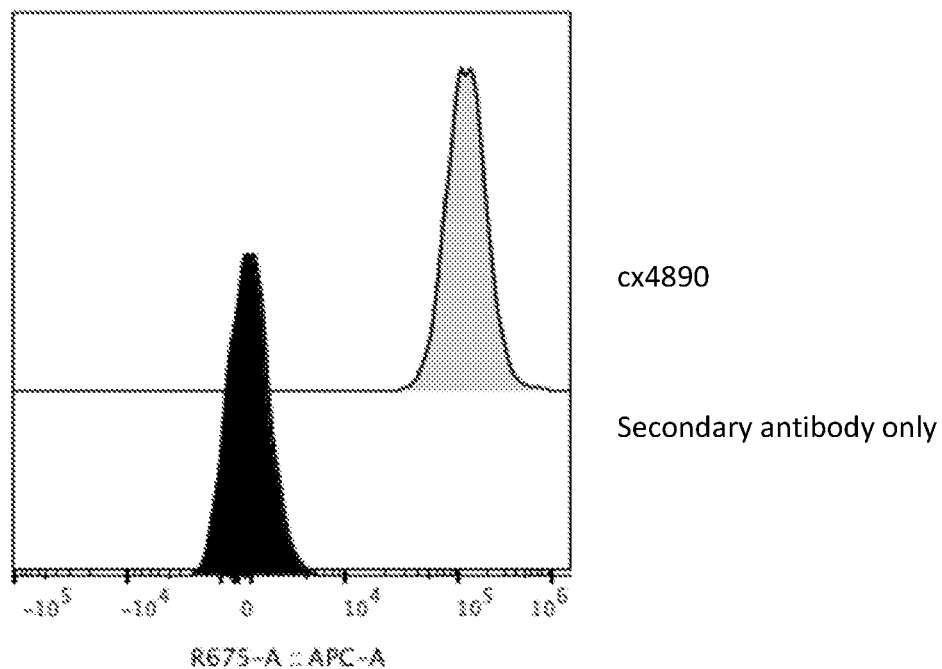
FIGS. 23A-23B demonstrates the binding of DLL3-target constrained CD3 engaging construct cx4890 to DLL3 positive cells, SHP-77 (FIG. 23A) and the lack of binding to primary human T-cells (FIG. 23B). Binding was assessed by flow cytometry using an anti-human IgG APC secondary antibody. The histograms display the normalized cell counts vs fluorescence at 200 nM of each construct, unless otherwise noted.
Figure 23B:
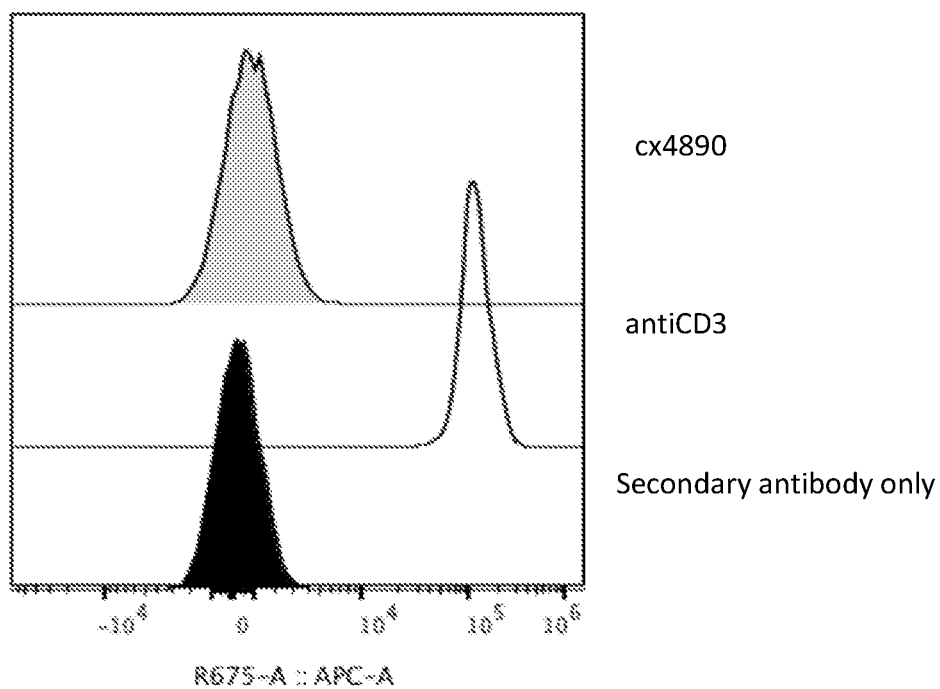

Provided herein are polypeptides that specifically bind to DLL3, hereinafter also called DLL3-binding polypeptides. In some embodiments, the provided binding polypeptides comprise at least one VHH domain that binds DLL3. In some embodiments, a DLL3-binding polypeptide provided herein comprises one, two, three, four, five, six, seven, or eight VHH domains that each individually binds DLL3. In some embodiments, a DLL3-binding polypeptide provided herein comprises one, two, three, or four VHH domains that bind DLL3. In some embodiments, the DLL3-binding polypeptides are monospecific. In some embodiments, the DLL3-binding polypeptides are multispecific. For example, provided DLL3-binding polypeptides include polypeptides that may comprise at least one VHH domain that binds DLL3 and one or more additional binding domains, such as one or more additional VHH domains, that bind one or more target proteins other than DLL3.

In some embodiments, a DLL3-binding polypeptide comprises at least one VHH domain that binds DLL3 and an Fc domain. In some embodiments, a DLL3-binding polypeptide provided herein comprises one, two, three, or four VHH domains that bind DLL3 and an Fc domain. In some embodiments, an Fc domain mediates dimerization of the DLL3-binding polypeptide at physiological conditions such that a dimer is formed that doubles the number of DLL3 binding sites. For example, a DLL3-binding polypeptide comprising three VHH domains that bind DLL3 and an Fc region is trivalent as a monomer, but at physiological conditions, the Fc region may mediate dimerization, such that the DLL3-binding polypeptide exists as a hexavalent dimer under such conditions.

DLL3 is a member of the delta protein ligand family. The delta protein ligand family functions as Notch ligands that are characterized by a DSL domain, EGF repeats, and a transmembrane domain. DLL3 is highly expressed in the fetal brain but not in normal adult tissues. In contrast, DLL3 is expressed on the surface of a wide variety of tumor cells and tumor vasculature including, but not limited to, small cell lung cancer (SCLC), large cell neuroendocrine carcinoma (LCNEC) and ovarian cancers. In the course of normal development, as opposed to the Notch-activating delta protein family members, DLL3 inhibits both cis- and trans-acting Notch pathway activation by interacting with Notch and DLL1 and redirecting or retaining them to late endosomal/lysosomal compartments or the Golgi, respectively, thereby preventing their localization to the cell surface (Chapman et al., 2011, Hum Mol Genet. 20(5):905-16.; Serth et al., 2015, PLoS One. 10(4):e0123776.). Notably, in neuroendocrine tumors, Notch activation suppresses tumor growth (Kunnimalaiyaan and Chen, 2007, Oncologist.

12(5):535-42). These observations suggest that DLL3, by downregulating Notch signaling, might be associated with the neuroendocrine phenotype, thus contributing to neuroendocrine tumorigenesis. DLL3 expression is very limited in normal adult tissue but is widespread in malignant SCLC, LCNEC, melanoma, glioblastoma, extrapulmonary neuroendocrine carcinoma (NEC) (Saunders et al., 2015, Sci Transl Med. 2015, 7(302): 302ra136; Peng et al., 2016, J. Clin. Oncol., 34, no. 15_suppl 11611-11611). In addition, a high level of DLL3 expression on tumor tissue correlated with advanced tumor stage and/or poorer survival in glioblastoma, medullary thyroid and neuroendocrine pancreatic cancer (Peng et al., 2016, J. Clin. Oncol., 34, no. 15_suppl 11611-11611), SCLC and LCNEC (Saunders et al., 2015, Sci Transl Med. 2015, 7(302): 302ra136), as well as some ovarian cancers (Hu et al., 2014, Cancer Res., 74(12): 3282-3293).

An exemplary sequence of canonical human DLL3 is set forth as follows:

MVSPRMSGLLSQTVILALIFLPQTRPAGVFELQIHSFGPGPGPGAPRSP

CSARLPCRLFFRVCLKPGLSEEAAESPCALGAALSARGPVYTEQPGAPA

PDLPLPDGLLQVPFRDAWPGTFSFIIETWREELGDQIGGPAWSLLARVA

GRRRLAAGGPWARDIQRAGAWELRFSYRARCEPPAVGTACTRLCRPRSA

PSRCGPGLRPCAPLEDECEAPLVCRAGCSPEHGFCEQPGECRCLEGWTG

PLCTVPVSTSSCLSPRGPSSATTGCLVPGPGPCDGNPCANGGSCSETPR

SFECTCPRGFYGLRCEVSGVTCADGPCFNGGLCVGGADPDSAYICHCPP

GFQGSNCEKRVDRCSLQPCRNGGLCLDLGHALRCRCRAGFAGPRCEHDL

DDCAGRACANGGTCVEGGGAHRCSCALGFGGRDCRERADPCAARPCAHG

GRCYAHFSGLVCACAPGYMGARCEFPVHPDGASALPAAPPGLRPGDPQR

YLLPPALGLLVAAGVAGAALLLVHVRRRGHSQDAGSRLLAGTPEPSVHA

LPDALNNLRTQEGSGDGPSSSVDWNRPEDVDPQGIYVISAPSIYAREVA

TPLFPPLHTGRAGQRQHLLFPYPSSILSVK(SEQ ID NO: 86, signal sequence underlined)

An exemplary sequence of non-canonical human DLL3 is set forth as follows:

MVSPRMSGLLSQTVILALIFLPQTRPAGVFELQIHSFGPGPGPGAPRSP

CSARLPCRLFFRVCLKPGLSEEAAESPCALGAALSARGPVYTEQPGAPA

PDLPLPDGLLQVPFRDAWPGTFSFIIETWREELGDQIGGPAWSLLARVA

GRRRLAAGGPWARDIQRAGAWELRFSYRARCEPPAVGTACTRLCRPRSA

PSRCGPGLRPCAPLEDECEAPLVCRAGCSPEHGFCEQPGECRCLEGWTG

PLCTVPVSTSSCLSPRGPSSATTGCLVPGPGPCDGNPCANGGSCSETPR

SFECTCPRGFYGLRCEVSGVTCADGPCFNGGLCVGGADPDSAYICHCPP

GFQGSNCEKRVDRCSLQPCRNGGLCLDLGHALRCRCRAGFAGPRCEHDL

DDCAGRACANGGTCVEGGGAHRCSCALGFGGRDCRERADPCAARPCAHG

GRCYAHFSGLVCACAPGYMGARCEFPVHPDGASALPAAPPGLRPGDPQR

-continued

YLLPPALGLLVAAGVAGAALLLVHVRRRGHSQDAGSRLLAGTPEPSVHA

LPDALNNLRTQEGSGDGPSSSVDWNRPEDVDPQGIYVISAPSIYAREA (SEQ ID NO: 87, signal sequence underlined)

In some cases, the provided DLL3 binding polypeptides directly block or inhibit activity of DLL3, which, in some aspects, can be used as a therapeutic to inhibit or reduce tumor cell growth or survival.

A variety of DLL3 polypeptide binding formats are provided. In some examples, DLL3 binding polypeptides include DLL3 VHH-Fc polypeptides. In some embodiments, the Fc is an Fc that exhibits immune effector activity, such as one or more effector functions such as antibody-dependent cellular cytotoxicity (ADCC), antibody-dependent cellular phagocytosis (ADCP) and/or complement-dependent cytotoxicity (CDC).

In some embodiments, the provided DLL3-binding polypeptides can be used to stimulate an immune response in a subject, which, in some aspects, treats a disease or disorder, such as a cancer, in the subject. In some aspects, a DLL3-binding polypeptide provided herein, such as a DLL3-Fc, can bind to DLL3-expressing tumor cells and induce an active immune response against the tumor cells expressing DLL3. In some cases, the active immune response can cause the death of the cancerous cells (e.g., antibody binding to cancer cells inducing apoptotic cell death), or inhibit the growth (e.g., block cells cycle progression) of the cancerous cells. In other cases, a DLL3-binding polypeptide provided herein, such as a DLL3 VHH-Fc, can bind to cancerous cells and antibody dependent cellular cytotoxicity (ADCC) can eliminate cancerous cells to which the DLL3-binding polypeptide binds. In some cases, provided DLL3 VHH-binding polypeptides can also activate both cellular and humoral immune responses and recruit more natural killer cells or increased production of cytokines (e.g., IL-2, IFN-gamma, IL-12, TNF-alpha, TNF-beta, etc.) that further activate an individual's immune system to destroy cancerous cells. In yet another embodiment, DLL3 binding polypeptides, such as DLL3 VHH-Fc, can bind to cancerous cells, and macrophages or other phagocytic cell can opsonize the cancerous cells, such as via CDC or ADCP processes.

In other aspects, also provided herein are VHH-binding polypeptides that exhibit multispecific binding. In some cases, the binding polypeptides include polypeptides that exhibit dual affinity for DLL3 and a T cell antigen, such as CD3. In some aspects, such dual affinity molecules are capable of engaging or activating T cells at the site of a tumor upon binding of tumor-expressed DLL3. In particular, among such molecules provided herein are molecules that exhibit constrained CD3 binding. Also provided herein are engineered cells, such as engineered T cells, that express a chimeric antigen receptor containing a DLL3 binding polypeptide.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The techniques and procedures described or referenced herein are generally well understood and commonly employed using conventional methodology by those skilled in the art, such as, for example, the widely utilized methodologies described in Sambrook et al., Molecular Cloning: A Laboratory Manual 3rd. edition (2001) Cold Spring Harbor Laboratory Press, Cold Spring Harbor, N.Y. CURRENT PROTOCOLS IN MOLECULAR BIOLOGY (F. M. Ausubel, et al. eds., (2003)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)); Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney), ed., 1987); Introduction to Cell and Tissue Culture (J. P. Mather and P. E. Roberts, 1998) Plenum Press; Cell and Tissue Culture Laboratory Procedures (A. Doyle, J. B. Griffiths, and D. G. Newell, eds., 1993-8) J. Wiley and Sons; Handbook of Experimental Immunology (D. M. Weir and C. C. Blackwell, eds.); Gene Transfer Vectors for Mammalian Cells (J. M. Miller and M. P. Calos, eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: A Practical Approach (D. Catty., ed., IRL Press, 1988-1989); Monoclonal Antibodies: A Practical Approach (P. Shepherd and C. Dean, eds., Oxford University Press, 2000); Using Antibodies: A Laboratory Manual (E. Harlow and D. Lane (Cold Spring Harbor Laboratory Press, 1999); The Antibodies (M. Zanetti and J. D. Capra, eds., Harwood Academic Publishers, 1995); and Cancer: Principles and Practice of Oncology (V. T. DeVita et al., eds., J. B. Lippincott Company, 1993); and updated versions thereof.

The section headings used herein are for organizational purposes only and are not to be construed as limiting the subject matter described.

I. DEFINITIONS

Unless otherwise defined, scientific and technical terms used in connection with the present disclosure shall have the meanings that are commonly understood by those of ordinary skill in the art. Further, unless otherwise required by context or expressly indicated, singular terms shall include pluralities and plural terms shall include the singular. For any conflict in definitions between various sources or references, the definition provided herein will control.

It is understood that embodiments of the invention described herein include "consisting" and/or "consisting essentially of" embodiments. As used herein, the singular form "a", "an", and "the" includes plural references unless indicated otherwise. Use of the term "or" herein is not meant to imply that alternatives are mutually exclusive.

In this application, the use of "or" means "and/or" unless expressly stated or understood by one skilled in the art. In the context of a multiple dependent claim, the use of "or" refers back to more than one preceding independent or dependent claim.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X".

The terms "nucleic acid molecule", "nucleic acid" and "polynucleotide" may be used interchangeably, and refer to a polymer of nucleotides. Such polymers of nucleotides may contain natural and/or non-natural nucleotides, and include, but are not limited to, DNA, RNA, and PNA. "Nucleic acid sequence" refers to the linear sequence of nucleotides comprised in the nucleic acid molecule or polynucleotide.

The term "isolated polynucleotide" as used herein shall mean a polynucleotide of genomic, cDNA, or synthetic origin or some combination thereof, which by virtue of its origin (1) is not associated with all or a portion of a polynucleotide found in nature, (2) is operably linked to a polynucleotide that it is not linked to in nature, or (3) does not occur in nature as part of a larger sequence.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present disclosure, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

The term "isolated protein" referred to herein means that a subject protein (1) is free of at least some other proteins with which it would typically be found in nature, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or noncovalent interaction) with portions of a protein with which the "isolated protein" is associated in nature, (6) is operably associated (by covalent or noncovalent interaction) with a polypeptide with which it is not associated in nature, or (7) does not occur in nature. Such an isolated protein can be encoded by genomic DNA, cDNA, mRNA or other RNA, of may be of synthetic origin, or any combination thereof. In certain embodiments, the isolated protein is substantially pure or substantially free from proteins or polypeptides or other contaminants that are found in its natural environment that would interfere with its use (therapeutic, diagnostic, prophylactic, research or otherwise).

As used herein, "substantially pure" means an object species is the predominant species present (i.e., on a molar basis it is more abundant than any other individual species in the composition), and a substantially purified fraction is a composition wherein the object species comprises at least about 50 percent (on a molar basis) of all macromolecular species present. Generally, a substantially pure composition will comprise more than about 80 percent of all macromolecular species present in the composition, for example, in some embodiments, more than about 85%, 90%, 95%, and 99%. In some embodiments, the object species is purified to essential homogeneity (contaminant species cannot be detected in the composition by conventional detection methods) wherein the composition consists essentially of a single macromolecular species.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "specifically binds" to an antigen or epitope is a term that is well understood in the art, and methods to determine such specific binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. A single-domain antibody (sdAb) or VHH-containing polypeptide "specifically binds" or "preferentially binds" to a target if it binds with greater affinity, avidity, more readily, and/or with greater duration than it binds to other substances. For example, a sdAb or VHH-containing polypeptide that specifically or preferentially binds to a DLL3 epitope is a sdAb or VHH-containing polypeptide that binds this epitope with greater affinity, avidity, more readily, and/or with greater duration than it binds to other DLL3 epitopes or non-DLL3 epitopes. It is also understood by reading this definition that; for example, a sdAb or VHH-containing polypeptide that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding. "Specificity" refers to the ability of a binding protein to selectively bind an antigen.

As used herein, the term "epitope" refers to a site on a target molecule (for example, an antigen, such as a protein, nucleic acid, carbohydrate or lipid) to which an antigen-binding molecule (for example, a sdAb or VHH-containing polypeptide) binds. Epitopes often include a chemically active surface grouping of molecules such as amino acids, polypeptides or sugar side chains and have specific three-dimensional structural characteristics as well as specific charge characteristics. Epitopes can be formed both from contiguous and/or juxtaposed noncontiguous residues (for example, amino acids, nucleotides, sugars, lipid moiety) of the target molecule. Epitopes formed from contiguous residues (for example, amino acids, nucleotides, sugars, lipid moiety) typically are retained on exposure to denaturing solvents whereas epitopes formed by tertiary folding typically are lost on treatment with denaturing solvents. An epitope may include but is not limited to at least 3, at least 5 or 8-10 residues (for example, amino acids or nucleotides). In some embodiments, an epitope is less than 20 residues (for example, amino acids or nucleotides) in length, less than 15 residues or less than 12 residues. Two antibodies may bind the same epitope within an antigen if they exhibit competitive binding for the antigen. In some embodiments, an epitope can be identified by a certain minimal distance to a CDR residue on the antigen-binding molecule. In some embodiments, an epitope can be identified by the above distance, and further limited to those residues involved in a bond (for example, a hydrogen bond) between a residue of the antigen-binding molecule and an antigen residue. An epitope can be identified by various scans as well, for example an alanine or arginine scan can indicate one or more residues that the antigen-binding molecule can interact with. Unless explicitly denoted, a set of residues as an epitope does not exclude other residues from being part of the epitope for a particular antigen-binding molecule. Rather, the presence of such a set designates a minimal series (or set of species) of epitopes. Thus, in some embodiments, a set of residues identified as an epitope designates a minimal epitope of relevance for the antigen, rather than an exclusive list of residues for an epitope on an antigen.

A "nonlinear epitope" or "conformational epitope" comprises noncontiguous polypeptides, amino acids and/or sugars within the antigenic protein to which an antigen-binding molecule specific to the epitope binds. In some embodiments, at least one of the residues will be noncontiguous with the other noted residues of the epitope; however, one or more of the residues can also be contiguous with the other residues.

A "linear epitope" comprises contiguous polypeptides, amino acids and/or sugars within the antigenic protein to which an antigen-binding molecule specific to the epitope binds. It is noted that, in some embodiments, not every one of the residues within the linear epitope need be directly bound (or involved in a bond) by the antigen-binding molecule. In some embodiments, linear epitopes can be from immunizations with a peptide that effectively consisted of the sequence of the linear epitope, or from structural sections of a protein that are relatively isolated from the remainder of the protein (such that the antigen-binding molecule can interact, at least primarily), just with that sequence section.

The terms "antibody" and "antigen-binding molecule" are used interchangeably in the broadest sense and encompass various polypeptides that comprise antibody-like antigen-binding domains, including but not limited to conventional antibodies (typically comprising at least one heavy chain and at least one light chain), single-domain antibodies (sdAbs, comprising just one chain, which is typically similar to a heavy chain), VHH-containing polypeptides (polypeptides comprising at least one heavy chain only antibody variable domain, or VHH), and fragments of any of the foregoing so long as they exhibit the desired antigen-binding activity. In some embodiments, an antibody comprises a dimerization domain. Such dimerization domains include, but are not limited to, heavy chain constant domains (comprising CH1, hinge, CH2, and CH3, where CH1 typically pairs with a light chain constant domain, CL, while the hinge mediates dimerization) and Fc domains (comprising hinge, CH2, and CH3, where the hinge mediates dimerization).

The term antibody also includes, but is not limited to, chimeric antibodies, humanized antibodies, and antibodies of various species such as camelid (including llama), shark, mouse, human, cynomolgus monkey, etc.

The term "variable region" or "variable domain" refers to the domain of an antibody heavy or light chain that is involved in binding the antibody to antigen. The variable regions of the heavy chain and light chain ($V_H$ and $V_L$, respectively) of a native antibody generally have similar structures, with each domain comprising four conserved framework regions (FRs) and three CDRs. (See, e.g., Kindt et al. Kuby Immunology, 6th ed., W. H. Freeman and Co., page 91 (2007). A single $V_H$ or $V_L$ domain may be sufficient to confer antigen-binding specificity, e.g. a single domain antibody, such as a VHH. Furthermore, antibodies that bind a particular antigen may be isolated using a $V_H$ or $V_L$ domain from an antibody that binds the antigen to screen a library of complementary $V_L$ or $V_H$ domains, respectively. See, e.g., Portolano et al., J. Immunol. 150:880-887 (1993); Clarkson et al., Nature 352:624-628 (1991).

An "antibody fragment" or "antigen-binding fragment" refers to a molecule other than a conventional or intact antibody that comprises a portion of a conventional or intact antibody containing at least a variable region that binds an antigen. Examples of antibody fragments include but are not limited to Fv, single chain Fvs (sdFvs), Fab, Fab', Fab'-SH, F(ab')$_2$; diabodies; linear antibodies; a single-domain antibodies comprising only the V$_H$ region (VHH).

As used herein, "monovalent" with reference to a binding molecule refers to binding molecules that have a single antigen recognition site that is specific for a target antigen. Examples of monovalent binding molecules include, for example, a monovalent antibody fragment, a proteinaceous binding molecule with antibody-like binding properties or an MHC molecule. Examples of monovalent antibody fragments include, but are not limited to, a Fab fragment, an Fv fragment, and a single-chain Fv fragment (scFv).

The terms "single domain antibody", "sdAb," "VHH" are used interchangeably herein to refer to an antibody having a single monomeric domain antigen binding/recognition domain. Such antibodies include a camelid antibody or shark antibody. In some embodiments, a VHH comprises three CDRs and four framework regions, designated FR1, CDR1, FR2, CDR2, FR3, CDR3, and FR4. In some embodiments, a VHH may be truncated at the N-terminus or C-terminus such that it comprise only a partial FR1 and/or FR4, or lacks one or both of those framework regions, so long as the VHH substantially maintains antigen binding and specificity.

The term "VHH-containing polypeptide" refers to a polypeptide that comprises at least one VHH domain. In some embodiments, a VHH polypeptide comprises two, three, or four or more VHH domains, wherein each VHH domain may be the same or different. In some embodiments, a VHH-containing polypeptide comprises an Fc domain. In some such embodiments, the VHH polypeptide may form a dimer. Nonlimiting structures of VHH-containing polypeptides include VHH$_1$-Fc, VHH$_1$-VHH$_2$-Fc, and VHH$_1$-VHH$_2$-VHH$_3$-Fc, wherein VHH$_1$, VHH$_2$, and VHH$_3$ may be the same or different. In some embodiments of such structures, one VHH may be connected to another VHH by a linker, or one VHH may be connected to the Fc by a linker. In some such embodiments, the linker comprises 1-20 amino acids, preferably 1-20 amino acids predominantly composed of glycine and, optionally, serine. In some embodiments, when a VHH-containing polypeptide comprises an Fc, it forms a dimer. Thus, the structure VHH$_1$-VHH$_2$-Fc, if it forms a dimer, is considered to be tetravalent (i.e., the dimer has four VHH domains). Similarly, the structure VHH$_1$-VHH$_2$-VHH$_3$-Fc, if it forms a dimer, is considered to be hexavalent (i.e., the dimer has six VHH domains).

As used herein, a DLL3-binding polypeptide is a polypeptide or protein that specifically binds DLL3. Typically, a DLL3-binding polypeptide herein is a VHH-containing polypeptide containing at least one VHH domain that binds DLL3. A DLL3-binding polypeptide includes conjugates, including fusion proteins. A DLL3-binding polypeptide includes fusion proteins, including those containing an Fc domain. In some embodiments, a DLL3-binding polypeptide contains two, three, or four or more VHH domains that each specifically bind to DLL3, wherein each VHH domain may be the same or different. In some embodiments, a DLL3-binding polypeptide is multivalent. In some embodiments, a DLL3-binding polypeptide is multispecific. In some cases, a DLL3-binding polypeptide may contain one or more additional domains that bind to one or more further or additional antigens other than DLL3.

The term "monoclonal antibody" refers to an antibody (including an sdAb or VHH-containing polypeptide) of a substantially homogeneous population of antibodies, that is, the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. Thus, a sample of monoclonal antibodies can bind to the same epitope on the antigen. The modifier "monoclonal" indicates the character of the antibody as being obtained from a substantially homogeneous population of antibodies, and is not to be construed as requiring production of the antibody by any particular method. For example, the monoclonal antibodies may be made by the hybridoma method first described by Kohler and Milstein, 1975, Nature 256:495, or may be made by recombinant DNA methods such as described in U.S. Pat. No. 4,816,567. The monoclonal antibodies may also be isolated from phage libraries generated using the techniques described in McCafferty et al., 1990, Nature 348:552-554, for example.

The term "CDR" denotes a complementarity determining region as defined by at least one manner of identification to one of skill in the art. The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme); Al-Lazikani et al., (1997) JMB 273, 927-948 ("Chothia" numbering scheme); MacCallum et al., J. Mol. Biol. 262:732-745 (1996), "Antibody-antigen interactions: Contact analysis and binding site topography," J. Mol. Biol. 262, 732-745." ("Contact" numbering scheme); Lefranc M P et al., "IMGT unique numbering for immunoglobulin and T cell receptor variable domains and Ig superfamily V-like domains," Dev Comp Immunol, 2003 January; 27(1):55-77 ("IMGT" numbering scheme); Honegger A and Plückthun A, "Yet another numbering scheme for immunoglobulin variable domains: an automatic modeling and analysis tool," J Mol Biol, 2001 Jun. 8; 309(3):657-70, ("Aho" numbering scheme); and Martin et al., "Modeling antibody hypervariable loops: a combined algorithm," PNAS, 1989, 86(23):9268-9272, ("AbM" numbering scheme).

The boundaries of a given CDR or FR may vary depending on the scheme used for identification. For example, the Kabat scheme is based on structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme. The AbM scheme is a compromise between Kabat and Chothia definitions based on that used by Oxford Molecular's AbM antibody modeling software.

In some embodiments, CDRs can be defined in accordance with any of the Chothia numbering schemes, the Kabat numbering scheme, a combination of Kabat and Chothia, the AbM definition, and/or the contact definition. A VHH comprises three CDRs, designated CDR1, CDR2, and CDR3. Table 1, below, lists exemplary position boundaries of CDR-H1, CDR-H2, CDR-H3 as identified by Kabat, Chothia, AbM, and Contact schemes, respectively. For CDR-H1, residue numbering is listed using both the Kabat and Chothia numbering schemes. FRs are located between CDRs, for example, with FR-H1 located before CDR-H1, FR-H2 located between CDR-H1 and CDR-H2, FR-H3 located between CDR-H2 and CDR-H3 and so forth. It is noted that because the shown Kabat numbering scheme places insertions at H35A and H35B, the end of the Chothia CDR-H1 loop when numbered using the shown Kabat numbering convention varies between H32 and H34, depending on the length of the loop.

TABLE 1

Boundaries of CDRs according to various numbering schemes.

| CDR | Kabat | Chothia | AbM | Contact |
|---|---|---|---|---|
| CDR-H1 (Kabat Numbering[1]) | H31--H35B | H26--H32 ... 34 | H26--H35B | H30--H35B |
| CDR-H1 (Chothia Numbering[2]) | H31--H35 | H26--H32 | H26--H35 | H30--H35 |
| CDR-H2 | H50--H65 | H52--H56 | H50--H58 | H47--H58 |
| CDR-H3 | H95--H102 | H95--H102 | H95--H102 | H93--H101 |

[1]Kabat et al. (1991), "Sequences of Proteins of Immunological Interest," 5th Ed. Public Health Service, National Institutes of Health, Bethesda, MD
[2]Al-Lazikani et al., (1997) JMB 273, 927-948

Thus, unless otherwise specified, a "CDR" or "complementary determining region," or individual specified CDRs (e.g., CDR-H1, CDR-H2, CDR-H3), of a given antibody or region thereof, such as a variable region thereof, should be understood to encompass a (or the specific) complementary determining region as defined by any of the aforementioned schemes. For example, where it is stated that a particular CDR (e.g., a CDR-H3) contains the amino acid sequence of a corresponding CDR in a given VHH amino acid sequence, it is understood that such a CDR has a sequence of the corresponding CDR (e.g., CDR-H3) within the VHH, as defined by any of the aforementioned schemes. In some embodiments, specific CDR sequences are specified. Exemplary CDR sequences of provided antibodies are described using various numbering schemes (see e.g. Table 1), although it is understood that a provided antibody can include CDRs as described according to any of the other aforementioned numbering schemes or other numbering schemes known to a skilled artisan.

As used herein, "conjugate," "conjugation" or grammatical variations thereof refers the joining or linking together of two or more compounds resulting in the formation of another compound, by any joining or linking methods known in the art. It can also refer to a compound which is generated by the joining or linking together two or more compounds. For example, a VHH domain linked directly or indirectly to one or more chemical moieties or polypeptide is an exemplary conjugate. Such conjugates include fusion proteins, those produced by chemical conjugates and those produced by any other methods.

An immunoglobulin Fc fusion ("Fc-fusion"), such as VHH-Fc, is a molecule comprising one or more VHH domains operably linked to an Fc region of an immunoglobulin. An immunoglobulin Fc region may be linked indirectly or directly to one or more VHH domains. Various linkers are known in the art and can optionally be used to link an Fc to a fusion partner to generate an Fc-fusion. In some such embodiments, the linker comprises 1-20 amino acids, preferably 1-20 amino acids predominantly composed of glycine and, optionally, serine. Fc-fusions of identical species can be dimerized to form Fc-fusion homodimers, or using non-identical species to form Fc-fusion heterodimers. In some embodiments, the Fc is a mammalian Fc such as human Fc.

The term "heavy chain constant region" as used herein refers to a region comprising at least three heavy chain constant domains, $C_H1$, hinge, $C_H2$, and $C_H3$. Of course, non-function-altering deletions and alterations within the domains are encompassed within the scope of the term "heavy chain constant region," unless designated otherwise. Nonlimiting exemplary heavy chain constant regions include γ, δ, and α. Nonlimiting exemplary heavy chain constant regions also include ε and μ. Each heavy constant region corresponds to an antibody isotype. For example, an antibody comprising a γ constant region is an IgG antibody, an antibody comprising a δ constant region is an IgD antibody, and an antibody comprising an a constant region is an IgA antibody. Further, an antibody comprising a μ constant region is an IgM antibody, and an antibody comprising an E constant region is an IgE antibody. Certain isotypes can be further subdivided into subclasses. For example, IgG antibodies include, but are not limited to, IgG1 (comprising a $\gamma_1$ constant region), IgG2 (comprising a $\gamma_2$ constant region), IgG3 (comprising a $\gamma_3$ constant region), and IgG4 (comprising a $\gamma_4$ constant region) antibodies; IgA antibodies include, but are not limited to, IgA1 (comprising an $\alpha_1$ constant region) and IgA2 (comprising an $\alpha_2$ constant region) antibodies; and IgM antibodies include, but are not limited to, IgM1 and IgM2.

A "Fc region" as used herein refers to a portion of a heavy chain constant region comprising CH2 and CH3. In some embodiments, an Fc region comprises a hinge, CH2, and CH3. In various embodiments, when an Fc region comprises a hinge, the hinge mediates dimerization between two Fc-containing polypeptides. An Fc region may be of any antibody heavy chain constant region isotype discussed herein. In some embodiments, an Fc region is an IgG1, IgG2, IgG3, or IgG4.

A "functional Fc region" possesses an "effector function" of a native sequence Fc region. Exemplary "effector functions" include Fc receptor binding; C1q binding and complement dependent cytotoxicity (CDC); Fc receptor binding; antibody-dependent cell-mediated cytotoxicity (ADCC); phagocytosis; down regulation of cell surface receptors (for example B-cell receptor); and B-cell activation, etc. Such effector functions generally require the Fc region to be combined with a binding domain (for example, an antibody variable domain) and can be assessed using various assays.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification. In some embodiments, a "variant Fc region" comprises an amino acid sequence which differs from that of a native sequence Fc region by virtue of at least one amino acid modification, yet retains at least one effector function of the native sequence Fc region. In some embodiments, the variant Fc region has at least one amino acid substitution compared to a native sequence Fc region or to the Fc region of a parent polypeptide, for example, from about one to about ten amino acid substitutions, and preferably, from about one to about five amino acid substitutions in a native sequence Fc region or in the Fc region of the parent polypeptide. In some embodiments, the variant Fc region herein will possess at least about 80% sequence identity with a native sequence Fc region and/or with an Fc region of a parent polypeptide, at least about 90% sequence identity therewith, at least about 95%, at least about 96%, at least about 97%, at least about 98%, or at least about 99% sequence identity therewith.

In general, the numbering of the residues in an immunoglobulin heavy chain or portion thereof, such as an Fc region, is that of the EU index as in Kabat et al., *Sequences of Proteins of Immunological Interest*, 5th Ed. Public Health Service, National Institutes of Health, Bethesda, Md. (1991). The "EU index as in Kabat" refers to the residue numbering of the human IgG1 EU antibody.

"Fc receptor" or "FcR" describes a receptor that binds to the Fc region of an antibody. In some embodiments, an FcγR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain Inhibiting receptor FcγRIIB contains an immunoreceptor tyrosine-based inhibition motif (ITIM) in its cytoplasmic domain. (See, for example, Daeron, Annu. Rev. Immunol. 15:203-234 (1997)). FcRs are reviewed, for example, in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. For example, the term "Fc receptor" or "FcR" also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)) and regulation of homeostasis of immunoglobulins. Methods of measuring binding to FcRn are known (see, for example, Ghetie and Ward, *Immunol. Today* 18(12):592-598 (1997); Ghetie et al., *Nature Biotechnology,* 15(7):637-640 (1997); Hinton et al., *J. Biol. Chem.* 279(8):6213-6216 (2004); WO 2004/92219 (Hinton et al.).

An "acceptor human framework" as used herein is a framework comprising the amino acid sequence of a heavy chain variable domain ($V_H$) framework derived from a human immunoglobulin framework or a human consensus framework, as discussed herein. An acceptor human framework derived from a human immunoglobulin framework or a human consensus framework can comprise the same amino acid sequence thereof, or it can contain amino acid sequence changes. In some embodiments, the number of amino acid changes are fewer than 10, or fewer than 9, or fewer than 8, or fewer than 7, or fewer than 6, or fewer than 5, or fewer than 4, or fewer than 3, across all of the human frameworks in a single antigen binding domain, such as a VHH.

As used herein, a "chimeric antigen receptor" or "CAR" refers to an engineered receptor, which introduces an antigen specificity, via an antigen binding domain, onto cells to which it is engineered (for example T cells such as naive T cells, central memory T cells, effector memory T cells or combination thereof) thus combining the antigen binding properties of the antigen binding domain with the T cell activity (e.g. lytic capacity and self renewal) of T cells. A CAR typically includes an extracellular antigen-binding domain (ectodomain), a transmembrane domain and an intracellular signaling domain. The intracellular signaling domain generally contains at least one ITAM signaling domain, e.g. derived from CD3zeta, and optionally at least one costimulatory signaling domain, e.g. derived from CD28 or 4-1BB. In a CAR provided herein, a VHH domain forms the antigen binding domain and is located at the extracellular side when expressed in a cell.

"Affinity" refers to the strength of the sum total of noncovalent interactions between a single binding site of a molecule (for example, an antibody or VHH-containing polypeptide) and its binding partner (for example, an antigen). The affinity or the apparent affinity of a molecule X for its partner Y can generally be represented by the dissociation constant ($K_D$) or the $K_{D-apparent}$, respectively. Affinity can be measured by common methods known in the art (such as, for example, ELISA $K_D$, KinExA, flow cytometry, and/or surface plasmon resonance devices), including those described herein. Such methods include, but are not limited to, methods involving BIAcore®, Octet®, or flow cytometry.

The term "$K_D$", as used herein, refers to the equilibrium dissociation constant of an antigen-binding molecule/antigen interaction. When the term "$K_D$" is used herein, it includes $K_D$ and $K_{D-apparent}$.

In some embodiments, the $K_D$ of the antigen-binding molecule is measured by flow cytometry using an antigen-expressing cell line and fitting the mean fluorescence measured at each antibody concentration to a non-linear one-site binding equation (Prism Software graphpad). In some such embodiments, the $K_D$ is $K_{D-apparent}$.

The term "biological activity" refers to any one or more biological properties of a molecule (whether present naturally as found in vivo, or provided or enabled by recombinant means). Biological properties include, but are not limited to, binding a ligand, inducing or increasing cell proliferation (such as T cell proliferation), and inducing or increasing expression of cytokines.

An "affinity matured" VHH-containing polypeptide refers to a VHH-containing polypeptide with one or more alterations in one or more CDRs compared to a parent VHH-containing polypeptide that does not possess such alterations, such alterations resulting in an improvement in the affinity of the VHH-containing polypeptide for antigen.

A "humanized VHH" as used herein refers to a VHH in which one or more framework regions have been substantially replaced with human framework regions. In some instances, certain framework region (FR) residues of the human immunoglobulin are replaced by corresponding non-human residues. Furthermore, the humanized VHH can comprise residues that are found neither in the original VHH nor in the human framework sequences, but are included to further refine and optimize VHH or VHH-containing polypeptide performance. In some embodiments, a humanized VHH-containing polypeptide comprises a human Fc region. As will be appreciated, a humanized sequence can be identified by its primary sequence and does not necessarily denote the process by which the antibody was created.

The term "substantially similar" or "substantially the same," as used herein, denotes a sufficiently high degree of similarity between two or more numeric values such that one of skill in the art would consider the difference between the two or more values to be of little or no biological and/or statistical significance within the context of the biological characteristic measured by said value. In some embodiments the two or more substantially similar values differ by no more than about any one of 5%, 10%, 15%, 20%, 25%, or 50%.

A polypeptide "variant" means a biologically active polypeptide having at least about 80% amino acid sequence identity with the native sequence polypeptide after aligning the sequences and introducing gaps, if necessary, to achieve the maximum percent sequence identity, and not considering any conservative substitutions as part of the sequence identity. Such variants include, for instance, polypeptides wherein one or more amino acid residues are added, or deleted, at the N- or C-terminus of the polypeptide. In some embodiments, a variant will have at least about 80% amino acid sequence identity. In some embodiments, a variant will have at least about 90% amino acid sequence identity. In some embodiments, a variant will have at least about 95% amino acid sequence identity with the native sequence polypeptide.

As used herein, "percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared.

An amino acid substitution may include but are not limited to the replacement of one amino acid in a polypeptide with another amino acid. Exemplary substitutions are shown in Table 2 Amino acid substitutions may be introduced into an antibody of interest and the products screened for a desired activity, for example, retained/improved antigen binding, decreased immunogenicity, or improved ADCC or CDC.

TABLE 2

| Original Residue | Exemplary Substitutions |
| --- | --- |
| Ala (A) | Val; Leu; Ile |
| Arg (R) | Lys; Gln; Asn |
| Asn (N) | Gln; His; Asp, Lys; Arg |
| Asp (D) | Glu; Asn |
| Cys (C) | Ser; Ala |
| Gln (Q) | Asn; Glu |
| Glu (E) | Asp; Gln |
| Gly (G) | Ala |
| His (H) | Asn; Gln; Lys; Arg |
| Ile (I) | Leu; Val; Met; Ala; Phe; Norleucine |
| Leu (L) | Norleucine; Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (W) | Tyr; Phe |
| Tyr (Y) | Trp; Phe; Thr; Ser |
| Val (V) | Ile; Leu; Met; Phe; Ala; Norleucine |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

The term "vector" is used to describe a polynucleotide that can be engineered to contain a cloned polynucleotide or polynucleotides that can be propagated in a host cell. A vector can include one or more of the following elements: an origin of replication, one or more regulatory sequences (such as, for example, promoters and/or enhancers) that regulate the expression of the polypeptide of interest, and/or one or more selectable marker genes (such as, for example, antibiotic resistance genes and genes that can be used in colorimetric assays, for example, β-galactosidase). The term "expression vector" refers to a vector that is used to express a polypeptide of interest in a host cell.

A "host cell" refers to a cell that may be or has been a recipient of a vector or isolated polynucleotide. Host cells may be prokaryotic cells or eukaryotic cells. Exemplary eukaryotic cells include mammalian cells, such as primate or non-primate animal cells; fungal cells, such as yeast; plant cells; and insect cells. Nonlimiting exemplary mammalian cells include, but are not limited to, NSO cells, PER.C6® cells (Crucell), and 293 and CHO cells, and their derivatives, such as 293-6E, CHO-DG44, CHO-K1, CHO-S, and CHO-DS cells. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) a provided herein.

The term "isolated" as used herein refers to a molecule that has been separated from at least some of the components with which it is typically found in nature or produced. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide.

Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, for example, in the case of an RNA polynucleotide. Thus, a DNA polynucleotide that is contained in a vector inside a host cell may be referred to as "isolated".

The terms "individual" and "subject" are used interchangeably herein to refer to an animal; for example a mammal. The term patient includes human and veterinary subjects. In some embodiments, methods of treating mammals, including, but not limited to, humans, rodents, simians, felines, canines, equines, bovines, porcines, ovines, caprines, mammalian laboratory animals, mammalian farm animals, mammalian sport animals, and mammalian pets, are provided. The subject can be male or female and can be any suitable age, including infant, juvenile, adolescent, adult, and geriatric subjects. In some examples, an "individual" or "subject" refers to an individual or subject in need of treatment for a disease or disorder. In some embodiments, the subject to receive the treatment can be a patient, designating the fact that the subject has been identified as having a disorder of relevance to the treatment, or being at adequate risk of contracting the disorder. In particular embodiments, the subject is a human, such as a human patient.

A "disease" or "disorder" as used herein refers to a condition where treatment is needed and/or desired.

The term "tumor cell", "cancer cell", "cancer", "tumor", and/or "neoplasm", unless otherwise designated, are used herein interchangeably and refer to a cell (or cells) exhibiting an uncontrolled growth and/or abnormal increased cell survival and/or inhibition of apoptosis which interferes with the normal functioning of bodily organs and systems. Included in this definition are benign and malignant cancers, polyps, hyperplasia, as well as dormant tumors or micrometastases.

The terms "cancer" and "tumor" encompass solid and hematological/lymphatic cancers and also encompass malignant, pre-malignant, and benign growth, such as dysplasia. Also, included in this definition are cells having abnormal proliferation that is not impeded (e.g. immune evasion and immune escape mechanisms) by the immune system (e.g. virus infected cells). Exemplary cancers include, but are not limited to: basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intraepithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (such as that associated with brain tumors), and Meigs' syndrome.

The term "non-tumor cell" as used herein refers to a normal cells or tissue. Exemplary non-tumor cells include, but are not limited to: T-cells, B-cells, natural killer (NK) cells, natural killer T (NKT) cells, dendritic cells, monocytes, macrophages, epithelial cells, fibroblasts, hepatocytes, interstitial kidney cells, fibroblast-like synoviocytes, osteoblasts, and cells located in the breast, skeletal muscle, pancreas, stomach, ovary, small intestines, placenta, uterus, testis, kidney, lung, heart, brain, liver, prostate, colon, lymphoid organs, bone, and bone-derived mesenchymal stem cells. The term "a cell or tissue located in the periphery" as used herein refers to non-tumor cells not located near tumor cells and/or within the tumor microenvironment.

The term "cells or tissue within the tumor microenvironment" as used herein refers to the cells, molecules, extracellular matrix and/or blood vessels that surround and/or feed a tumor cell. Exemplary cells or tissue within the tumor microenvironment include, but are not limited to: tumor vasculature; tumor-infiltrating lymphocytes; fibroblast reticular cells; endothelial progenitor cells (EPC); cancer-associated fibroblasts; pericytes; other stromal cells; components of the extracellular matrix (ECM); dendritic cells; antigen presenting cells; T-cells; regulatory T-cells (Treg cells); macrophages; neutrophils; myeloid-derived suppressor cells (MDSCs) and other immune cells located proximal to a tumor. Methods for identifying tumor cells, and/or cells/tissues located within the tumor microenvironment are well known in the art, as described herein, below.

In some embodiments, an "increase" or "decrease" refers to a statistically significant increase or decrease, respectively. As will be clear to the skilled person, "modulating" can also involve effecting a change (which can either be an increase or a decrease) in affinity, avidity, specificity and/or selectivity of a target or antigen, for one or more of its ligands, binding partners, partners for association into a homomultimeric or heteromultimeric form, or substrates; effecting a change (which can either be an increase or a decrease) in the sensitivity of the target or antigen for one or more conditions in the medium or surroundings in which the target or antigen is present (such as pH, ion strength, the presence of co-factors, etc.); and/or cellular proliferation or cytokine production, compared to the same conditions but without the presence of a test agent. This can be determined in any suitable manner and/or using any suitable assay known per se or described herein, depending on the target involved.

As used herein, "an immune response" is meant to encompass cellular and/or humoral immune responses that are sufficient to inhibit or prevent onset or ameliorate the symptoms of disease (for example, cancer or cancer metastasis). "An immune response" can encompass aspects of both the innate and adaptive immune systems.

As used herein, the terms "treating," "treatment," or "therapy" of a disease, disorder or condition is an approach for obtaining beneficial or desired clinical results. "Treatment" as used herein, covers any administration or application of a therapeutic for disease in a mammal, including a human. For purposes of this disclosure, beneficial or desired clinical results include, but are not limited to, any one or more of: alleviation of one or more symptoms, diminishment of extent of disease, preventing or delaying spread (for example, metastasis, for example metastasis to the lung or to the lymph node) of disease, preventing or delaying recurrence of disease, delay or slowing of disease progression, amelioration of the disease state, inhibiting the disease or progression of the disease, inhibiting or slowing the disease or its progression, arresting its development, and remission (whether partial or total). Also encompassed by "treatment" is a reduction of pathological consequence of a proliferative disease. The methods provided herein contemplate any one or more of these aspects of treatment. In-line with the above, the term treatment does not require one-hundred percent removal of all aspects of the disorder.

As used herein in the context of cancer, the terms "treatment" or, "inhibit," "inhibiting" or "inhibition" of cancer refers to at least one of: a statistically significant decrease in the rate of tumor growth, a cessation of tumor growth, or a reduction in the size, mass, metabolic activity, or volume of the tumor, as measured by standard criteria such as, but not limited to, the Response Evaluation Criteria for Solid Tumors (RECIST), or a statistically significant increase in progression free survival (PFS) or overall survival (OS).

"Ameliorating" means a lessening or improvement of one or more symptoms as compared to not administering a therapeutic agent. "Ameliorating" also includes shortening or reduction in duration of a symptom.

"Preventing," "prophylaxis," or "prevention" of a disease or disorder refers to administration of a pharmaceutical composition, either alone or in combination with another compound, to prevent the occurrence or onset of a disease or disorder or some or all of the symptoms of a disease or disorder or to lessen the likelihood of the onset of a disease or disorder.

The terms "inhibition" or "inhibit" refer to a decrease or cessation of any phenotypic characteristic or to the decrease or cessation in the incidence, degree, or likelihood of that characteristic. To "reduce" or "inhibit" is to decrease, reduce or arrest an activity, function, and/or amount as compared to a reference. In some embodiments, by "reduce" or "inhibit" is meant the ability to cause an overall decrease of 10% or greater. In some embodiments, by "reduce" or "inhibit" is meant the ability to cause an overall decrease of 50% or greater. In some embodiments, by "reduce" or "inhibit" is meant the ability to cause an overall decrease of 75%, 85%, 90%, 95%, or greater. In some embodiments, the amount noted above is inhibited or decreased over a period of time, relative to a control over the same period of time.

As used herein, "delaying development of a disease" means to defer, hinder, slow, retard, stabilize, suppress and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

"Preventing," as used herein, includes providing prophylaxis with respect to the occurrence or recurrence of a disease in a subject that may be predisposed to the disease but has not yet been diagnosed with the disease. Unless otherwise specified, the terms "reduce", "inhibit", or "prevent" do not denote or require complete prevention over all time, but just over the time period being measured.

The term "anti-cancer agent" is used herein in its broadest sense to refer to agents that are used in the treatment of one or more cancers. Exemplary classes of such agents in include, but are not limited to, chemotherapeutic agents, anti-cancer biologics (such as cytokines, receptor extracellular domain-Fc fusions, and antibodies), radiation therapy, CAR-T therapy, therapeutic oligonucleotides (such as antisense oligonucleotides and siRNAs) and oncolytic viruses.

The term "biological sample" means a quantity of a substance from a living thing or formerly living thing. Such substances include, but are not limited to, blood, (for example, whole blood), plasma, serum, urine, amniotic fluid, synovial fluid, endothelial cells, leukocytes, monocytes, other cells, organs, tissues, bone marrow, lymph nodes and spleen.

The term "control" or "reference" refers to a composition known to not contain an analyte ("negative control") or to contain an analyte ("positive control"). A positive control can comprise a known concentration of analyte.

The terms "effective amount" or "therapeutically effective amount" refer to a quantity and/or concentration of a composition containing an active ingredient (e.g. sdAb or VHH-containing polypeptide) that when administered into a patient either alone (i.e., as a monotherapy) or in combination with additional therapeutic agents, yields a statistically significant decrease in disease progression as, for example, by ameliorating or eliminating symptoms and/or the cause of the disease. An effective amount may be an amount that relieves, lessens, or alleviates at least one symptom or biological response or effect associated with a disease or disorder, prevents progression of the disease or disorder, or improves physical functioning of the patient. A therapeutically effective amount of a composition containing an active agent may vary according to factors such as the disease state, age, sex, and weight of the individual, and the ability of the active agent to elicit a desired response in the individual. A therapeutically effective amount is also one in which any toxic or detrimental effects of the active agent are outweighed by the therapeutically beneficial effects. A therapeutically effective amount may be delivered in one or more administrations. A therapeutically effective amount refers to an amount effective, at dosages and for periods of time necessary, to achieve the desired therapeutic and/or prophylactic result.

As used herein, a composition refers to any mixture of two or more products, substances, or compounds, including cells. It may be a solution, a suspension, liquid, powder, a paste, aqueous, non-aqueous or any combination thereof.

The terms "pharmaceutical formulation" and "pharmaceutical composition" refer to a preparation which is in such form as to permit the biological activity of the active ingredient(s) to be effective, and which contains no additional components which are unacceptably toxic to a subject to which the formulation would be administered. Hence, it is a composition suitable for pharmaceutical use in a mammalian subject, often a human. A pharmaceutical composition typically comprises an effective amount of an active agent (e.g., sdAb or VHH-containing polypeptide) and a carrier, excipient, or diluent. The carrier, excipient, or diluent is typically a pharmaceutically acceptable carrier, excipient or diluent, respectively. Such formulations may be sterile.

A "pharmaceutically acceptable carrier" refers to a non-toxic solid, semisolid, or liquid filler, diluent, encapsulating material, formulation auxiliary, or carrier conventional in the art for use with a therapeutic agent that together comprise a "pharmaceutical composition" for administration to a subject. A pharmaceutically acceptable carrier is non-toxic to recipients at the dosages and concentrations employed and are compatible with other ingredients of the formulation. The pharmaceutically acceptable carrier is appropriate for the formulation employed.

Administration "in combination with" one or more further therapeutic agents includes simultaneous (concurrent) and sequential administration in any order.

The term "concurrently" is used herein to refer to administration of two or more therapeutic agents, where at least part of the administration overlaps in time, or where the administration of one therapeutic agent falls within a short period of time relative to administration of the other therapeutic agent, or wherein the therapeutic effect of both agents overlap for at least a period of time.

The term "sequentially" is used herein to refer to administration of two or more therapeutic agents that does not overlap in time, or wherein the therapeutic effects of the agents do not overlap.

As used herein, "in conjunction with" refers to administration of one treatment modality in addition to another treatment modality. As such, "in conjunction with" refers to administration of one treatment modality before, during, or after administration of the other treatment modality to the individual.

The term "package insert" is used to refer to instructions customarily included in commercial packages of therapeutic products, that contain information about the indications, usage, dosage, administration, combination therapy, contraindications and/or warnings concerning the use of such therapeutic products.

An "article of manufacture" is any manufacture (for example, a package or container) or kit comprising at least one reagent, for example, a medicament for treatment of a disease or disorder (for example, cancer), or a probe for specifically detecting a biomarker described herein. In some embodiments, the manufacture or kit is promoted, distributed, or sold as a unit for performing the methods described herein.

The terms "label" and "detectable label" mean a moiety attached, for example, to an antibody or antigen to render a reaction (for example, binding) between the members of the specific binding pair, detectable. The labeled member of the specific binding pair is referred to as "detectably labeled." Thus, the term "labeled binding protein" refers to a protein with a label incorporated that provides for the identification of the binding protein. In some embodiments, the label is a detectable marker that can produce a signal that is detectable by visual or instrumental means, for example, incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Examples of labels for polypeptides include, but are not limited to, the following: radioisotopes or radionuclides (for example, $^3H$, $^{14}C$, $^{35}S$, $^{90}Y$, $^{99}Tc$, $^{111}In$, $^{125}I$, $^{131}I$, $^{177}Lu$, $^{166}Ho$, or $^{153}Sm$); chromogens, fluorescent labels (for example, FITC, rhodamine, lanthanide phosphors), enzymatic labels (for example, horseradish peroxidase, luciferase, alkaline phosphatase); chemiluminescent markers; biotinyl groups; predetermined polypeptide epitopes recognized by a secondary reporter (for example, leucine zipper pair sequences, binding sites for secondary antibodies, metal binding domains, epitope tags); and magnetic agents, such as gadolinium chelates. Representative examples of labels commonly employed for immunoassays include moieties that produce light, for example, acridinium compounds, and moieties that produce fluorescence, for example, fluorescein. In this regard, the moiety itself may not be detectably labeled but may become detectable upon reaction with yet another moiety.

II. VHH Domains Binding DLL3

Provided herein are DLL3-binding polypeptides that are VHH-containing polypeptides containing at least one VHH domain that specifically binds to DLL3. In some embodiments, the VHH domain binds human DLL3. In some of any of the provided embodiments, the VHH domain binds DLL3 having the sequence set forth in SEQ ID NO: 86 or a mature form thereof lacking the signal sequence. In some of any of the provided embodiments, the VHH domain binds DLL3 having the sequence set forth in SEQ ID NO: 87 or a mature form thereof lacking the signal sequence.

In some embodiments, the VHH-containing polypeptides incorporate multiple copies of a VHH domain provided herein. In such embodiments, the VHH-containing polypeptide may incorporate multiple copies of the same VHH domain. In some embodiments, the VHH-containing polypeptides may incorporate multiple copies of a VHH domain that are different but that recognize the same epitope on DLL3. The VHH-containing polypeptides can be formatted in a variety of formats, including any as described in Section III below.

A VHH domain is an antibody fragment that is a single monomeric variable antibody domain that is able to bind selectively to a specific antigen. With a molecular weight of only 12-15 kDa, VHH domains (also called single-domain antibodies) are much smaller than common antibodies (150-160 kDa) which are composed of two heavy protein chains and two light chains, and even smaller than Fab fragments (~50 kDa, one light chain and half a heavy chain) and single-chain variable fragments (~25 kDa, two variable domains, one from a light and one from a heavy chain).

Single domain antibodies are antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be derived from any species including, but not limited to mouse, human, camel, llama, alpaca, vicuna, guanaco, shark, goat, rabbit, and/or bovine. In some embodiments, a single domain antibody as used herein is a naturally occurring single domain antibody known as heavy chain antibody devoid of light chains. For clarity reasons, this variable domain derived from a heavy chain antibody naturally devoid of light chain is known herein as a VHH to distinguish it from the conventional VH of four chain immunoglobulins. Such a VHH molecule can be derived from antibodies raised in Camelidae species, for example in camel, llama, dromedary, alpaca, vicuna and guanaco. Other species besides Camelidae may produce heavy chain antibodies naturally devoid of light chain; such VHHs are within the scope of the disclosure.

Methods for the screening of VHH domains, including VHH-binding polypeptides, that possess the desired specificity for DLL3 include, but are not limited to, enzyme linked immunosorbent assay (ELISA), enzymatic assays, flow cytometry, and other immunologically mediated techniques known within the art.

Among the provided VHH domains provided herein are DLL3 VHH (llama-derived) and humanized sequences, such as any described below.

In some embodiments, a VHH domain that binds DLL3 may be humanized. Humanized antibodies (such as VHH-containing polypeptides) are useful as therapeutic molecules because humanized antibodies reduce or eliminate the human immune response to non-human antibodies, which can result in an immune response to an antibody therapeutic, and decreased effectiveness of the therapeutic. Generally, a humanized antibody comprises one or more variable domains in which CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (for example, the antibody from which the CDR residues are derived), for example, to restore or improve antibody specificity or affinity.

Humanized antibodies and methods of making them are reviewed, for example, in Almagro and Fransson, (2008) *Front. Biosci.* 13: 1619-1633, and are further described, for example, in Riechmann et al., (1988) *Nature* 332:323-329; Queen et al., (1989) *Proc. Natl Acad. Sci. USA* 86: 10029-10033; U.S. Pat. Nos. 5,821,337, 7,527,791, 6,982,321, and 7,087,409; Kashmiri et al., (2005) *Methods* 36:25-34; Padlan, (1991) *Mol. Immunol.* 28:489-498 (describing "resurfacing"); Dall'Acqua et al., (2005) *Methods* 36:43-60 (describing "FR shuffling"); and Osbourn et al., (2005) *Methods* 36:61-68 and Klimka et al., (2000) *Br. J. Cancer,* 83:252-260 (describing the "guided selection" approach to FR shuffling).

Human framework regions that can be used for humanization include but are not limited to: framework regions selected using the "best-fit" method (see, for example, Sims et al. (1993) *J. Immunol.* 151:2296); framework regions derived from the consensus sequence of human antibodies of a particular subgroup of heavy chain variable regions (see, for example, Carter et al. (1992) *Proc. Natl. Acad. Sci. USA,* 89:4285; and Presta et al. (1993) *J. Immunol,* 151:2623); human mature (somatically mutated) framework regions or human germline framework regions (see, for example, Almagro and Fransson, (2008) *Front. Biosci.* 13:1619-1633); and framework regions derived from screening FR libraries (see, for example, Baca et al., (1997) *J. Biol. Chem.* 272: 10678-10684 and Rosok et al., (1996) *J. Biol. Chem.* 271:22611-22618). Typically, the FR regions of a VHH are replaced with human FR regions to make a humanized VHH. In some embodiments, certain FR residues of the human FR are replaced in order to improve one or more properties of the humanized VHH. VHH domains with such replaced residues are still referred to herein as "humanized."

Provided herein is a VHH domain that binds DLL3 in which the VHH domain comprises a CDR1, CDR2, and CDR3 contained in a VHH amino acid sequences selected from any of SEQ ID NO: 102, 244-318, 401-409, 416, 455 and 476-480-488, 507-518, or an amino acid sequence that has at least 90%, 91%, 92%, 93%, 94%, 95%, 96%, 97%, 98%, or 99% sequence identity to the $V_H H$ region amino acid selected from any one of SEQ ID NOs: 102, 244-318, 401-409, 416, 455 and 476-480-488, 507-518. In some embodiments, a DLL3 VHH domain provided herein contains a CDR1 set forth in any one of SEQ ID NOS: 319-335 or 456, a CDR2 set forth in any one of SEQ ID NOS: 336-353, 384, 410, and 411 and a CDR3 set forth in any one of SEQ ID NOS: 354-367, 395, and 412-415. In some embodiments, a DLL3 VHH domain has the amino acid sequence set forth in any of SEQ ID NOS: 102, 244-318, 401-409, 416, 455 and 476-480-488, 507-518 or an amino acid sequence that has at least 90%, 91%, 92%, 93%, 94%, 95%, 96%, 97%, 98%, or 99% sequence identity to the $V_H H$ region amino acid selected from any one of SEQ ID NO: 102, 244-318, 401-409, 416, 455 and 476-480-488, 507-518. In some embodiments, the DLL3 VHH domain has the sequence of amino acids set forth in any one of SEQ ID NO: 102, 244-318, 401-409, 416, 455 and 476-480-488, 507-518.

Provided herein is a VHH domain that binds DLL3 in which the VHH domain comprises a CDR1, CDR2, and CDR3 contained in a VHH amino acid sequences selected from any of SEQ ID NO:244-318 and 455, or an amino acid sequence that has at least 90%, 91%, 92%, 93%, 94%, 95%, 96%, 97%, 98%, or 99% sequence identity to the $V_H H$ region amino acid selected from any one of SEQ ID NOs: 244-318 and 455. In some embodiments, a DLL3 VHH domain provided herein contains a CDR1 set forth in any one of SEQ ID NOS: 319-335, a CDR2 set forth in any one of SEQ ID NOS: 336-353 and a CDR3 set forth in any one of SEQ ID NOS: 354-367. Among the provided DLL3 VHH domain has the amino acid sequence set forth in any of SEQ ID NOS: 1-114 or an amino acid sequence that has at least 90%, 91%, 92%, 93%, 94%, 95%, 96%, 97%, 98%, or 99% sequence identity to the $V_H H$ region amino acid selected from any one of SEQ ID NO:244-318. In some embodiments, the DLL3 VHH domain has the sequence of amino acids set forth in any one of SEQ ID NO:244-318 and 455.

In some embodiments, a DLL3 VHH domain provided herein contains a CDR1, CDR2, CDR3 contained in a VHH domain set forth in SEQ ID NO:244, or an amino acid sequence that has at least 90%, 91%, 92%, 93%, 94%, 95%, 96%, 97%, 98%, or 99% sequence identity to the VHH region amino acid selected set forth in SEQ ID NO:244. In some embodiments, the DLL3 VHH domain has the amino acid sequence set forth in SEQ ID NO:244 or an amino acid sequence that has at least 90%, 91%, 92%, 93%, 94%, 95%, 96%, 97%, 98%, or 99% sequence identity to the amino acid selected set forth in SEQ ID NO: 244. In some embodiments, the DLL3 VHH domain is a humanized variant of the amino acid sequence set forth in SEQ ID NO:244.

In some embodiments, a DLL3 VHH domain provided herein contains a CDR1 set forth in any one of SEQ ID NOS: 319, 320, 321, 322, 323, 324, 325, 326, a CDR2 set forth in any one of SEQ ID NOS: 336, 337, 338 and a CDR3 set forth in SEQ ID NO: 354.

In some embodiments, the DLL3 VHH domain provided herein contains a CDR1, CDR2, and CDR3 set forth in any one of SEQ ID NO: 319, 336 and 354, respectively. In some embodiments, the DLL3 VHH domain provided herein contains a CDR1, CDR2 and CDR3 set forth in any one of SEQ ID NO: 319, 337 and 354, respectively. In some embodiments, the DLL3 VHH domain provided herein contains a CDR1, CDR2 and CDR3 set forth in any one of SEQ ID NO: 319, 338 and 354, respectively. In some embodiments, the DLL3 VHH domain provided herein contains a CDR1, CDR2 and CDR3 set forth in any one of SEQ ID NO: 320, 338 and 354, respectively. In some embodiments, the DLL3 VHH domain provided herein contains a CDR1, CDR2 and CDR3 set forth in any one of SEQ ID NO: 321, 338 and 354, respectively. In some embodiments, the DLL3 VHH domain provided herein contains a CDR1, CDR2 and CDR3 set forth in any one of SEQ ID NO: 322, 338 and 354, respectively. In some embodiments, the DLL3 VHH domain provided herein contains a CDR1, CDR2 and CDR3 set forth in any one of SEQ ID NO: 323, 338 and 354, respectively. In some embodiments, the DLL3 VHH domain provided herein contains a CDR1, CDR2 and CDR3 set forth in any one of SEQ ID NO: 324, 338 and 354, respectively. In some embodiments, the DLL3 VHH domain provided herein contains a CDR1, CDR2 and CDR3 set forth in any one of SEQ ID NO: 325, 338 and 354, respectively. In some embodiments, the DLL3 VHH domain provided herein contains a CDR1, CDR2 and CDR3 set forth in any one of SEQ ID NO: 326, 338 and 354, respectively.

In some aspects, a VHH domain that binds DLL3 comprises a CDR1, CDR2 and CDR2 contained in a VHH amino acid sequences selected from any of SEQ ID NO: 245-257, or an amino acid sequence that has at least 90%, 91%, 92%, 93%, 94%, 95%, 96%, 97%, 98%, or 99% sequence identity to the $V_HH$ region amino acid selected from any one of SEQ ID NOs: 245-257.

In some cases, the provided DLL3 VHH domain is a humanized variant that has the amino acid sequence set forth in any of SEQ ID NOS: 245-257 or an amino acid sequence that has at least 90%, 91%, 92%, 93%, 94%, 95%, 96%, 97%, 98%, or 99% sequence identity to the $V_HH$ region amino acid selected from any one of SEQ ID NOs: 245-257. In some embodiments, the DLL3 humanized VHH domain has the sequence of amino acids set forth in any one of SEQ ID NOS: 245-257.

In some embodiments, a DLL3 VHH domain provided herein contains a CDR1, CDR2, CDR3 contained in a VHH domain set forth in SEQ ID NO: 258, or an amino acid sequence that has at least 90%, 91%, 92%, 93%, 94%, 95%, 96%, 97%, 98%, or 99% sequence identity to the VHH region amino acid selected set forth in SEQ ID NO: 258. In some embodiments, the DLL3 VHH domain has the amino acid sequence set forth in SEQ ID NO:258 or an amino acid sequence that has at least 90%, 91%, 92%, 93%, 94%, 95%, 96%, 97%, 98%, or 99% sequence identity to the amino acid selected set forth in SEQ ID NO: 258. In some embodiments, the DLL3 VHH domain is a humanized variant of the amino acid sequence set forth in SEQ ID NO: 258.

In some embodiments, a DLL3 VHH domain provided herein contains a CDR1 set forth in SEQ ID NO: 327, a CDR2 set forth in SEQ ID NO: 339 and a CDR3 set forth in SEQ ID NO: 355.

In some embodiments, the DLL3 VHH domain provided herein contains a CDR1, CDR2, and CDR3 set forth in any one of SEQ ID NO: 327, 339 and 335, respectively.

In some aspects, a VHH domain that binds DLL3 comprises a CDR1, CDR2, and CDR3 contained in a VHH amino acid sequences selected from any of SEQ ID NO: 259-263, or an amino acid sequence that has at least 90%, 91%, 92%, 93%, 94%, 95%, 96%, 97%, 98%, or 99% sequence identity to the $V_HH$ region amino acid selected from any one of SEQ ID NOs: 259-263.

In some cases, the provided DLL3 VHH domain is a humanized variant that has the amino acid sequence set forth in any of SEQ ID NOS: 259-263 or an amino acid sequence that has at least 90%, 91%, 92%, 93%, 94%, 95%, 96%, 97%, 98%, or 99% sequence identity to the VHH region amino acid selected from any one of SEQ ID NOs: 259-263. In some embodiments, the DLL3 humanized VHH domain has the sequence of amino acids set forth in any one of SEQ ID NOS: 259-263.

In some embodiments, a DLL3 VHH domain provided herein contains a CDR1, CDR2, CDR3 contained in a VHH domain set forth in SEQ ID NO: 264, or an amino acid sequence that has at least 90%, 91%, 92%, 93%, 94%, 95%, 96%, 97%, 98%, or 99% sequence identity to the VHH region amino acid selected set forth in SEQ ID NO: 264. In some embodiments, the DLL3 VHH domain has the amino acid sequence set forth in SEQ ID NO: 264 or an amino acid sequence that has at least 90%, 91%, 92%, 93%, 94%, 95%, 96%, 97%, 98%, or 99% sequence identity to the amino acid selected set forth in SEQ ID NO: 264. In some embodiments, the DLL3 VHH domain is a humanized variant of the amino acid sequence set forth in SEQ ID NO: 264.

In some embodiments, a DLL3 VHH domain provided herein contains a CDR1 set forth in SEQ ID NOs: 328, 329, or 456, a CDR2 set forth in SEQ ID NO: 340 and a CDR3 set forth in SEQ ID NO: 356.

In some embodiments, the DLL3 VHH domain provided herein contains a CDR1, CDR2, and CDR3 set forth in any one of SEQ ID NO: 328, 340, 356, respectively. In some embodiments, the DLL3 VHH domain provided herein contains a CDR1, CDR2, and CDR3 set forth in any one of SEQ ID NO: 329, 340, 356, respectively. In some embodiments, the DLL3 VHH domain provided herein contains a CDR1, CDR2, and CDR3 set forth in any one of SEQ ID NO: 456, 340, 356, respectively.

In some aspects, a VHH domain that binds DLL3 comprises a CDR1, CDR2, and CDR3 contained in a VHH amino acid sequences selected from any of SEQ ID NO: 265-274, 416, 455, or 476-478, or an amino acid sequence that has at least 90%, 91%, 92%, 93%, 94%, 95%, 96%, 97%, 98%, or 99% sequence identity to the VHH region amino acid selected from any one of SEQ ID NOs: 265-274, 416, 455, or 476-478.

In some cases, the provided DLL3 VHH domain is a humanized variant that has the amino acid sequence set forth in any of SEQ ID NOS: 265-274, 416, 455, or 476-478 or an amino acid sequence that has at least 90%, 91%, 92%, 93%, 94%, 95%, 96%, 97%, 98%, or 99% sequence identity to the VHH region amino acid selected from any one of SEQ ID NOs: 265-274, 416, 455, or 476-478. In some embodiments, the DLL3 humanized VHH domain has the sequence of amino acids set forth in any one of SEQ ID NOS: 265-274, 416, 455, or 476-478.

In some embodiments, a DLL3 VHH domain provided herein contains a CDR1, CDR2, CDR3 contained in a VHH domain set forth in SEQ ID NO: 275, or an amino acid sequence that has at least 90%, 91%, 92%, 93%, 94%, 95%, 96%, 97%, 98%, or 99% sequence identity to the VHH region amino acid selected set forth in SEQ ID NO: 275. In some embodiments, the DLL3 VHH domain has the amino acid sequence set forth in SEQ ID NO: 275 or an amino acid sequence that has at least 90%, 91%, 92%, 93%, 94%, 95%, 96%, 97%, 98%, or 99% sequence identity to the amino acid selected set forth in SEQ ID NO: 105. In some embodiments, the DLL3 VHH domain is a humanized variant of the amino acid sequence set forth in SEQ ID NO: 275.

In some embodiments, a DLL3 VHH domain provided herein contains a CDR1 set forth in SEQ ID NO: 320, a CDR2 set forth in SEQ ID NO: 341 and a CDR3 set forth in SEQ ID NO:357.

In some aspects, a VHH domain that binds DLL3 comprises a CDR1, CDR2, and CDR3 contained in a VHH amino acid sequences selected from any of SEQ ID NO: 276-279 or 479, or an amino acid sequence that has at least 90%, 91%, 92%, 93%, 94%, 95%, 96%, 97%, 98%, or 99% sequence identity to the $V_HH$ region amino acid selected from any one of SEQ ID NOs: 276-279 or 479.

In some cases, the provided DLL3 VHH domain is a humanized variant that has the amino acid sequence set forth in any of SEQ ID NOS: 276-279 or 479 or an amino acid sequence that has at least 90%, 91%, 92%, 93%, 94%, 95%, 96%, 97%, 98%, or 99% sequence identity to the $V_HH$ region amino acid selected from any one of SEQ ID NOs: 276-279 or 479. In some embodiments, the DLL3 humanized VHH domain has the sequence of amino acids set forth in any one of SEQ ID NOS: 276-279 or 479.

In some embodiments, a DLL3 VHH domain provided herein contains a CDR1, CDR2, CDR3 contained in a VHH domain set forth in SEQ ID NO: 280, or an amino acid sequence that has at least 90%, 91%, 92%, 93%, 94%, 95%, 96%, 97%, 98%, or 99% sequence identity to the VHH region amino acid selected set forth in SEQ ID NO: 280. In some embodiments, the DLL3 VHH domain has the amino acid sequence set forth in SEQ ID NO: 280 or an amino acid sequence that has at least 90%, 91%, 92%, 93%, 94%, 95%, 96%, 97%, 98%, or 99% sequence identity to the amino acid selected set forth in SEQ ID NO: 280. In some embodiments, the DLL3 VHH domain is a humanized variant of the amino acid sequence set forth in SEQ ID NO: 280.

In some embodiments, a DLL3 VHH domain provided herein contains a CDR1 set forth in SEQ ID NO: 330, a CDR2 set forth in SEQ ID NO: 342 and a CDR3 set forth in SEQ ID NO: 358.

In some aspects, a VHH domain that binds DLL3 comprises a CDR1, CDR2, and CDR3 contained in a VHH amino acid sequences selected from any of SEQ ID NO: 281-286, or an amino acid sequence that has at least 90%, 91%, 92%, 93%, 94%, 95%, 96%, 97%, 98%, or 99% sequence identity to the $V_HH$ region amino acid selected from any one of SEQ ID NOs: 281-286.

In some cases, the provided DLL3 VHH domain is a humanized variant that has the amino acid sequence set forth in any of SEQ ID NOS: 281-286 or an amino acid sequence that has at least 90%, 91%, 92%, 93%, 94%, 95%, 96%, 97%, 98%, or 99% sequence identity to the $V_HH$ region amino acid selected from any one of SEQ ID NOs: 281-286. In some embodiments, the DLL3 humanized VHH domain has the sequence of amino acids set forth in any one of SEQ ID NOS: 281-286.

In some embodiments, a DLL3 VHH domain provided herein contains a CDR1, CDR2, CDR3 contained in a VHH domain set forth in SEQ ID NO: 287, or an amino acid sequence that has at least 90%, 91%, 92%, 93%, 94%, 95%, 96%, 97%, 98%, or 99% sequence identity to the VHH region amino acid selected set forth in SEQ ID NO: 287. In some embodiments, the DLL3 VHH domain has the amino acid sequence set forth in SEQ ID NO: 287 or an amino acid sequence that has at least 90%, 91%, 92%, 93%, 94%, 95%, 96%, 97%, 98%, or 99% sequence identity to the amino acid selected set forth in SEQ ID NO: 287. In some embodiments, the DLL3 VHH domain is a humanized variant of the amino acid sequence set forth in SEQ ID NO: 287.

In some embodiments, a DLL3 VHH domain provided herein contains a CDR1 set forth in SEQ ID NO: 320, a CDR2 set forth in any one of SEQ ID NOS: 345, 346, 347, and a CDR3 set forth in any one of SEQ ID NOS: 359, 360, 361.

In some embodiments, the DLL3 VHH domain provided herein contains a CDR1, CDR2, and CDR3 set forth in any one of SEQ ID NO: 320, 345 and 359, respectively. In some embodiments, the DLL3 VHH domain provided herein contains a CDR1, CDR2 and CDR3 set forth in any one of SEQ ID NO: 320, 346, and 359, respectively. In some embodiments, the DLL3 VHH domain provided herein contains a CDR1, CDR2 and CDR3 set forth in any one of SEQ ID NO: 320, 347, and 359, respectively. In some embodiments, the DLL3 VHH domain provided herein contains a CDR1, CDR2 and CDR3 set forth in any one of SEQ ID NO: 320, 345 and 360, respectively. In some embodiments, the DLL3 VHH domain provided herein contains a CDR1, CDR2 and CDR3 set forth in any one of SEQ ID NO: 320, 345 and 361, respectively. In some embodiments, the DLL3 VHH domain provided herein contains a CDR1, CDR2 and CDR3 set forth in any one of SEQ ID NO: 320, 347 and 360, respectively.

In some aspects, a VHH domain that binds DLL3 comprises a CDR1, CDR2 and CDR2 contained in a VHH amino acid sequences selected from any of SEQ ID NO: 288-298 or 102, or an amino acid sequence that has at least 90%, 91%, 92%, 93%, 94%, 95%, 96%, 97%, 98%, or 99% sequence identity to the $V_HH$ region amino acid selected from any one of SEQ ID NOs: 288-298 or 102.

In some cases, the provided DLL3 VHH domain is a humanized variant that has the amino acid sequence set forth in any of SEQ ID NOS: 288-298 or 102 or an amino acid sequence that has at least 90%, 91%, 92%, 93%, 94%, 95%, 96%, 97%, 98%, or 99% sequence identity to the $V_HH$ region amino acid selected from any one of SEQ ID NOs: 288-298 or 102. In some embodiments, the DLL3 humanized VHH domain has the sequence of amino acids set forth in any one of SEQ ID NOS: 288-298 or 102.

In some embodiments, a DLL3 VHH domain provided herein contains a CDR1, CDR2, CDR3 contained in a VHH domain set forth in SEQ ID NO: 299, or an amino acid sequence that has at least 90%, 91%, 92%, 93%, 94%, 95%, 96%, 97%, 98%, or 99% sequence identity to the VHH region amino acid selected set forth in SEQ ID NO: 299. In some embodiments, the DLL3 VHH domain has the amino acid sequence set forth in SEQ ID NO: 299 or an amino acid sequence that has at least 90%, 91%, 92%, 93%, 94%, 95%, 96%, 97%, 98%, or 99% sequence identity to the amino acid selected set forth in SEQ ID NO: 299. In some embodiments, the DLL3 VHH domain is a humanized variant of the amino acid sequence set forth in SEQ ID NO: 299.

In some embodiments, a DLL3 VHH domain provided herein contains a CDR1 set forth in SEQ ID NO: 331, a CDR2 set forth in any one of SEQ ID NOS: 348, 349, 350, and a CDR3 set forth in SEQ ID NOS: 356.

In some embodiments, the DLL3 VHH domain provided herein contains a CDR1, CDR2, and CDR3 set forth in any one of SEQ ID NO: 331, 348 and 356, respectively. In some embodiments, the DLL3 VHH domain provided herein contains a CDR1, CDR2 and CDR3 set forth in any one of SEQ ID NO: 331, 349 and 356, respectively. In some embodiments, the DLL3 VHH domain provided herein contains a CDR1, CDR2 and CDR3 set forth in any one of SEQ ID NO: 331, 350 and 356, respectively.

In some aspects, a VHH domain that binds DLL3 comprises a CDR1, CDR2 and CDR2 contained in a VHH amino acid sequences selected from any of SEQ ID NOs: 300-305 or 480, or an amino acid sequence that has at least 90%, 91%, 92%, 93%, 94%, 95%, 96%, 97%, 98%, or 99% sequence identity to the $V_HH$ region amino acid selected from any one of SEQ ID NOs: 300-305 or 480.

In some cases, the provided DLL3 VHH domain is a humanized variant that has the amino acid sequence set forth in any of SEQ ID NOS: 300-305 or 480 or an amino acid sequence that has at least 90%, 91%, 92%, 93%, 94%, 95%, 96%, 97%, 98%, or 99% sequence identity to the $V_HH$ region amino acid selected from any one of SEQ ID NOs: 300-305 or 480. In some embodiments, the DLL3 humanized VHH domain has the sequence of amino acids set forth in any one of SEQ ID NOS: 300-305 or 480.

In some embodiments, a DLL3 VHH domain provided herein contains a CDR1, CDR2, CDR3 contained in a VHH domain set forth in SEQ ID NO: 306, or an amino acid sequence that has at least 90%, 91%, 92%, 93%, 94%, 95%, 96%, 97%, 98%, or 99% sequence identity to the VHH region amino acid selected set forth in SEQ ID NO: 306. In some embodiments, the DLL3 VHH domain has the amino acid sequence set forth in SEQ ID NO: 306 or an amino acid sequence that has at least 90%, 91%, 92%, 93%, 94%, 95%, 96%, 97%, 98%, or 99% sequence identity to the amino acid selected set forth in SEQ ID NO: 306. In some embodiments, the DLL3 VHH domain is a humanized variant of the amino acid sequence set forth in SEQ ID NO: 306.

In some embodiments, a DLL3 VHH domain provided herein contains a CDR1, CDR2, CDR3 contained in a VHH domain set forth in SEQ ID NO: 507, or an amino acid sequence that has at least 90%, 91%, 92%, 93%, 94%, 95%, 96%, 97%, 98%, or 99% sequence identity to the VHH region amino acid selected set forth in SEQ ID NO: 507. In some embodiments, the DLL3 VHH domain has the amino acid sequence set forth in SEQ ID NO: 507 or an amino acid sequence that has at least 90%, 91%, 92%, 93%, 94%, 95%, 96%, 97%, 98%, or 99% sequence identity to the amino acid selected set forth in SEQ ID NO: 507. In some embodiments, the DLL3 VHH domain is a humanized variant of the amino acid sequence set forth in SEQ ID NO: 507.

In some embodiments, a DLL3 VHH domain provided herein contains a CDR1 set forth in SEQ ID NO: 332, a CDR2 set forth in any one of SEQ ID NOS: 348, 349, 350, and a CDR3 set forth in SEQ ID NOS: 362.

In some embodiments, the DLL3 VHH domain provided herein contains a CDR1, CDR2, and CDR3 set forth in any one of SEQ ID NO: 332, 348 and 362, respectively. In some embodiments, the DLL3 VHH domain provided herein contains a CDR1, CDR2 and CDR3 set forth in any one of SEQ ID NO: 332, 349 and 362, respectively. In some embodiments, the DLL3 VHH domain provided herein contains a CDR1, CDR2 and CDR3 set forth in any one of SEQ ID NO: 332, 350 and 362, respectively.

In some aspects, a VHH domain that binds DLL3 comprises a CDR1, CDR2 and CDR2 contained in a VHH amino acid sequences selected from any of SEQ ID NOs: 307-313, or an amino acid sequence that has at least 90%, 91%, 92%, 93%, 94%, 95%, 96%, 97%, 98%, or 99% sequence identity to the $V_HH$ region amino acid selected from any one of SEQ ID NOs: 307-313.

In some cases, the provided DLL3 VHH domain is a humanized variant that has the amino acid sequence set forth in any of SEQ ID NOS: 307-313 or an amino acid sequence that has at least 90%, 91%, 92%, 93%, 94%, 95%, 96%, 97%, 98%, or 99% sequence identity to the $V_HH$ region amino acid selected from any one of SEQ ID NOs: 307-313. In some embodiments, the DLL3 humanized VHH domain has the sequence of amino acids set forth in any one of SEQ ID NOS: 307-313.

In some aspects, a VHH domain that binds DLL3 comprises a CDR1, CDR2 and CDR2 contained in a VHH amino acid sequences selected from any of SEQ ID NOs: 508-514, or an amino acid sequence that has at least 90%, 91%, 92%, 93%, 94%, 95%, 96%, 97%, 98%, or 99% sequence identity to the $V_HH$ region amino acid selected from any one of SEQ ID NOs: 508-514.

In some cases, the provided DLL3 VHH domain is a humanized variant that has the amino acid sequence set forth in any of SEQ ID NOS: 508-514 or an amino acid sequence that has at least 90%, 91%, 92%, 93%, 94%, 95%, 96%, 97%, 98%, or 99% sequence identity to the $V_HH$ region amino acid selected from any one of SEQ ID NOs: 508-514. In some embodiments, the DLL3 humanized VHH domain has the sequence of amino acids set forth in any one of SEQ ID NOS: 508-514.

In some embodiments, a DLL3 VHH domain provided herein contains a CDR1, CDR2, CDR3 contained in a VHH domain set forth in SEQ ID NO: 401, or an amino acid sequence that has at least 90%, 91%, 92%, 93%, 94%, 95%, 96%, 97%, 98%, or 99% sequence identity to the VHH region amino acid selected set forth in SEQ ID NO: 401. In some embodiments, the DLL3 VHH domain has the amino acid sequence set forth in SEQ ID NO: 401 or an amino acid sequence that has at least 90%, 91%, 92%, 93%, 94%, 95%, 96%, 97%, 98%, or 99% sequence identity to the amino acid selected set forth in SEQ ID NO: 401. In some embodiments, the DLL3 VHH domain is a humanized variant of the amino acid sequence set forth in SEQ ID NO: 401.

In some embodiments, a DLL3 VHH domain provided herein contains a CDR1 set forth in SEQ ID NO: 320, a CDR2 set forth in any one of SEQ ID NOS: 384, 410, 411 and a CDR3 set forth in any one of SEQ ID NOS: 395, 412, 413, 414, 415.

In some embodiments, the DLL3 VHH domain provided herein contains a CDR1, CDR2, and CDR3 set forth in any one of SEQ ID NO: 320, 384 and 395, respectively. In some embodiments, the DLL3 VHH domain provided herein contains a CDR1, CDR2 and CDR3 set forth in any one of SEQ ID NO: 320, 410 and 395, respectively. In some embodiments, the DLL3 VHH domain provided herein contains a CDR1, CDR2 and CDR3 set forth in any one of SEQ ID NO: 320, 411 and 395, respectively. In some embodiments, the DLL3 VHH domain provided herein contains a CDR1, CDR2 and CDR3 set forth in any one of SEQ ID NO: 320, 384 and 412, respectively. In some embodiments, the DLL3 VHH domain provided herein contains a CDR1, CDR2 and CDR3 set forth in any one of SEQ ID NO: 320, 384 and 413, respectively. In some embodiments, the DLL3 VHH domain provided herein contains a CDR1, CDR2 and CDR3 set forth in any one of SEQ ID NO: 320, 384 and 414, respectively. In some embodiments, the DLL3 VHH domain provided herein contains a CDR1, CDR2 and CDR3 set forth in any one of SEQ ID NO: 320, 384 and 415, respectively.

In some aspects, a VHH domain that binds DLL3 comprises a CDR1, CDR2 and CDR2 contained in a VHH amino acid sequences selected from any of SEQ ID NOs: 402-409, or an amino acid sequence that has at least 90%, 91%, 92%, 93%, 94%, 95%, 96%, 97%, 98%, or 99% sequence identity to the $V_HH$ region amino acid selected from any one of SEQ ID NOs: 402-409. In some aspects, a VHH domain that binds DLL3 comprises a CDR1, CDR2 and CDR2 contained in a VHH amino acid sequences selected from any of SEQ ID NOs: 481-488, or an amino acid sequence that has at least 90%, 91%, 92%, 93%, 94%, 95%, 96%, 97%, 98%, or 99% sequence identity to the $V_HH$ region amino acid selected from any one of SEQ ID NOs: 481-488.

In some cases, the provided DLL3 VHH domain is a humanized variant that has the amino acid sequence set forth in any of SEQ ID NOS: 402-409 or an amino acid sequence that has at least 90%, 91%, 92%, 93%, 94%, 95%, 96%, 97%, 98%, or 99% sequence identity to the $V_HH$ region amino acid selected from any one of SEQ ID NOs: 402-409. In some embodiments, the DLL3 humanized VHH domain has the sequence of amino acids set forth in any one of SEQ ID NOS: 402-409. In some cases, the provided DLL3 VHH domain is a humanized variant that has the amino acid sequence set forth in any of SEQ ID NOS: 481-488 or an amino acid sequence that has at least 90%, 91%, 92%, 93%, 94%, 95%, 96%, 97%, 98%, or 99% sequence identity to the V$_H$H region amino acid selected from any one of SEQ ID NOs: 481-488. In some embodiments, the DLL3 humanized VHH domain has the sequence of amino acids set forth in any one of SEQ ID NOS: 481-488.

III. Fusion Proteins and Conjugates Containing DLL3-Binding Polypeptides

Provided herein are fusion proteins and conjugates containing DLL3-binding polypeptides containing at least one VHH domain that specifically binds DLL3 linked, directly or indirectly, to one or more additional domains or moieties. In some embodiments, the fusion protein or conjugate of the present disclosure is composed of a single polypeptide. In other embodiments, the fusion protein or conjugate of the present disclosure is composed of more than one polypeptide. In some embodiments, the DLL3-binding polypeptide of the present disclosure incorporates at least one VHH domain that specifically binds DLL3. In some aspects, the DLL3-binding polypeptide is multivalent. In some embodiments, the DLL3-binding polypeptides include two or more copies of a VHH domain that specifically binds DLL3, for example, three or more, four or more, five or more, or six or more copies of a VHH domain that specifically binds DLL3. In certain aspects, the DLL3-binding polypeptide is multi-specific. For example, in some cases, the one or more additional domain may be one or more additional binding domain that binds to one or more further antigen or protein.

In some embodiments, the DLL3-binding polypeptides of the present disclosure include two or more polypeptide sequences that are operably linked via amino acid linkers. In some embodiments, these linkers are composed predominately of the amino acids Glycine and Serine, denoted as GS-linkers herein. The GS-linkers of the fusion proteins of the present disclosure can be of various lengths, for example, 5, 6, 7, 8, 9, 10, 11, 12, 13, 14, 15, 16, 17, 18, 19, 20 amino acids in length. In some embodiments, the GS-linker comprises an amino acid sequence selected from the group consisting of GGSGGS, i.e., (GGS)$_2$ (SEQ ID NO: 1); GGSGGGSGGS, i.e., (GGS)$_3$ (SEQ ID NO: 2); GGSGGSGGSGGS, i.e., (GGS)$_4$ (SEQ ID NO: 3); and GGSGGSGGSGGSGGS, i.e., (GGS)$_5$ (SEQ ID NO: 4). In some embodiments, the linker is a flexible linker comprising Glycine residues, such as, by way of non-limiting example, GG, GGG, GGGG (SEQ ID NO: 5), GGGGG (SEQ ID NO: 6), and GGGGGG (SEQ ID NO: 7). In some embodiments, the DLL3-binding polypeptide includes a combination of a GS-linker and a Glycine linker. In some embodiments, the linker is (GGGGS)$_n$, wherein n is 1 to 5 (SEQ ID NO:123); (GGGGGS)$_n$, wherein n is 1 to 4 (SEQ ID NO:124); GGGGS (SEQ ID NO:125); GGGGGS (SEQ ID NO:126); GGGGGSGGGGGSGGGGS (SEQ ID NO:127); GGGGSGGGGSGGGGS (SEQ ID NO:128); GGSGGGGSGGGGSGGGGS (SEQ ID NO:129); or PGGGG (SEQ ID NO:450). In some embodiments, the linker is a GG linker. In some embodiments, the DLL3-binding polypeptide includes a combination of a GS-linker and a Glycine linker.

A. Fc Fusions

Provided herein is a DLL3-binding polypeptide that is a fusion protein containing at least one VHH domain that binds DLL3 provided herein and an Fc domain. In some embodiments, a DLL3-binding polypeptide provided herein comprises one, two, three, or four VHH domains that bind DLL3 and an Fc domain.

In some embodiments, incorporation of an immunoglobulin Fc region into the fusion protein can, in some aspects, be composed of two polypeptides that together form a dimer. In some embodiments, an Fc domain mediates dimerization of the DLL3-binding polypeptide at physiological conditions, such as when expressed from a cell, such that a dimer is formed that doubles the number of DLL3 binding sites. For example, a DLL3-binding polypeptide comprising three VHH domains that bind DLL3 and an Fc region is trivalent as a monomer, but the Fc region may mediate dimerization, such that the DLL3-binding polypeptide exists as a hexavalent dimer under such conditions. In some embodiments, a DLL3 VHH domain is fused to an IgG Fc region and in these embodiments, the fusion protein is bivalent having two DLL3 VHH domains per molecule. In some embodiments, two DLL3 binding domains (2×) are fused to an IgG Fc region and in these embodiments, the fusion protein is tetravalent having four DLL3 VHH domains per molecule. In some embodiments, three DLL3 VHH domain (3×) are fused to an IgG Fc region and in these embodiments, the fusion protein is hexavalent having six DLL3 VHH domains per molecule.

In some embodiments, the multivalent DLL3-binding polypeptide is bivalent. In some embodiments, the bivalent DLL3-binding polypeptide of the disclosure includes two copies of a DLL3-binding polypeptide having the following structure: (DLL3 VHH)-Linker-Fc. In some embodiments, the multivalent DLL3-binding polypeptide is tetravalent. In some embodiments, the tetravalent DLL3-binding polypeptide of the disclosure includes two copies of a DLL3-polypeptide having the following structure: (DLL3 VHH)-Linker-(DLL3 VHH)-Linker-Fc. In some embodiments, the multivalent DLL3-binding polypeptide is hexavalent. In some embodiments, the hexavalent DLL3-binding polypeptide of the disclosure includes two copies of a DLL3-binding polypeptide having the following structure: (DLL3 VHH)-Linker-(DLL3 VHH)-Linker-(DLL3 VHH)-Linker-Fc.

In some cases, the CH3 domain of the Fc region can be used as homodimerization domain, such that the resulting fusion protein is formed from two identical polypeptides. In other cases, the CH3 dimer interface region of the Fc region can be mutated so as to enable heterodimerization. For example, a heterodimerization domain can be incorporated into the fusion protein such that the construct is an asymmetric fusion protein.

In any of the provided embodiments, a DLL3 VHH domain can be any as described above. In come embodiments, the DLL3 VHH domain is a humanized VHH domain that binds DLL3.

In various embodiments, an Fc domain included in a DLL3-binding polypeptide is a human Fc domain, or is derived from a human Fc domain. In some embodiments, the fusion protein contains an immunoglobulin Fc region. In some embodiments, the immunoglobulin Fc region is an IgG isotype selected from the group consisting of IgG1 isotype, IgG2 isotype, IgG3 isotype, and IgG4 subclass.

In some embodiments, the immunoglobulin Fc region or immunologically active fragment thereof is an IgG isotype. For example, the immunoglobulin Fc region of the fusion protein is of human IgG1 isotype, having an amino acid sequence:

(SEQ ID NO: 8)
```
PAPELLGGPS VFLFPPKPKD TLMISRTPEV TCVVVDVSHE

DPEVKFNWYV DGVEVHNAKT KPREEQYNST YRVVSVLTVL

HQDWLNGKEY KCKVSNKALP APIEKTISKA KGQPREPQVY

TLPPSRDELT KNQVSLTCLV KGFYPSDIAV EWESNGQPEN

NYKTTPPVLD SDGSFFLYSK LTVDKSRWQQ GNVFSCSVMH

EALHNHYTQK SLSLSPGK
```

In some embodiments, the immunoglobulin Fc region or immunologically active fragment thereof comprises a human IgG1 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 8.

In some embodiments where the fusion protein of the disclosure includes an Fc polypeptide, the Fc polypeptide is mutated or modified. In some cases, the mutations include one or more amino acid substitutions to reduce an effector function of the Fc polypeptide. Various examples of mutations to Fc polypeptides to alter, such as reduce, effector function are known, including any as described below. In some embodiments, reference to amino acid substitutions in an Fc region is by EU numbering by Kabat (also called Kabat numbering) unless described with reference to a specific SEQ ID NO. EU numbering is known and is according to the most recently updated IMGT Scientific Chart (IMGT®, the international ImMunoGeneTics information system®, http://www.imgtorg/IMGTScientific-Chart/Numbering/Hu_IGHGnber.html (created: 17 May 2001, last updated: 10 Jan. 2013) and the EU index as reported in Kabat, E. A. et al. Sequences of Proteins of Immunological interest. 5th ed. US Department of Health and Human Services, NIH publication No. 91-3242 (1991).

In some embodiments, an Fc region that exhibits reduced effector functions may be a desirable candidate for applications in which DLL3 or CD3 binding is desired yet certain effector functions (such as CDC and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the multispecific polypeptide constructs and/or cleaved components thereof lack FcγR binding (hence likely lacking ADCC activity), but retains FcRn binding ability. The primary cells for mediating ADCC, NK cells, express FcγRIII only, whereas monocytes express FcγRI, FcγRII and FcγRIII. Non-limiting examples of in vitro assays to assess ADCC activity of a molecule of interest is described in U.S. Pat. No. 5,500,362 (see, e.g., Hellstrom, I. et al. Proc. Nat'l Acad. Sci. USA 83:7059-7063 (1986)) and Hellstrom, I et al., Proc. Nat'l Acad. Sci. USA 82:1499-1502 (1985); U.S. Pat. No. 5,821,337 (see Bruggemann, M. et al., J. Exp. Med. 166: 1351-1361 (1987)). Alternatively, non-radioactive assay methods may be employed (see, for example, ACTI™ non-radioactive cytotoxicity assay for flow cytometry (CellTechnology, Inc. Mountain View, Calif.; and CytoTox 96™ non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. Proc. Nat'l Acad. Sci. USA 95:652-656 (1998). C1q binding assays may also be carried out to confirm that the multispecific polypeptide construct or cleaved components thereof is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., J. Immunol. Methods 202:163 (1996); Cragg, M. S. et al., Blood 101:1045-1052 (2003); and Cragg, M. S. and M. J. Glennie, Blood 103:2738-2743 (2004)). FcRn binding and in vivo clearance/half-life determinations can also be performed using methods known in the art (see, e.g., Petkova, S. B. et al., Int'l. Immunol. 18(12):1759-1769 (2006)).

In some embodiments, the human IgG Fc region is modified to alter antibody-dependent cellular cytotoxicity (ADCC) and/or complement-dependent cytotoxicity (CDC), e.g., the amino acid modifications described in Natsume et al., 2008 Cancer Res, 68(10): 3863-72; Idusogie et al., 2001 J Immunol, 166(4): 2571-5; Moore et al., 2010 mAbs, 2(2): 181-189; Lazar et al., 2006 PNAS, 103(11): 4005-4010, Shields et al., 2001 JBC, 276(9): 6591-6604; Stavenhagen et al., 2007 Cancer Res, 67(18): 8882-8890; Stavenhagen et al., 2008 Advan. Enzyme Regul., 48: 152-164; Alegre et al, 1992 J Immunol, 148: 3461-3468; Reviewed in Kaneko and Niwa, 2011 Biodrugs, 25(1):1-11.

Examples of mutations that enhance ADCC include modification at Ser239 and Ile332, for example Ser239Asp and Ile332Glu (S239D, I332E). Examples of mutations that enhance CDC include modifications at Lys326 and Glu333. In some embodiments, the Fc region is modified at one or both of these positions, for example Lys326Ala and/or Glu333Ala (K326A and E333A) using the Kabat numbering system.

In some embodiments, the Fc region of the fusion protein is altered at one or more of the following positions to reduce Fc receptor binding: Leu 234 (L234), Leu235 (L235), Asp265 (D265), Asp270 (D270), Ser298 (S298), Asn297 (N297), Asn325 (N325), Ala327 (A327) or Pro329 (P329). For example, Leu 234Ala (L234A), Leu235Ala (L235A), Leu235Glu (L235E), Asp265Asn (D265N), Asp265Ala (D265A), Asp270Asn (D270N), Ser298Asn (S298N), Asn297Ala (N297A), Pro329Ala (P329A) or Pro239Gly (P329G), Asn325Glu (N325E) or Ala327Ser (A327S). In preferred embodiments, modifications within the Fc region reduce binding to Fc-receptor-gamma receptors while have minimal impact on binding to the neonatal Fc receptor (FcRn).

In some embodiments, the human IgG1 Fc region is modified at amino acid Asn297 (Kabat Numbering) to prevent glycosylation of the fusion protein, e.g., Asn297Ala (N297A) or Asn297Asp (N297D). In some embodiments, the Fc region of the fusion protein is modified at amino acid Leu235 (Kabat Numbering) to alter Fc receptor interactions, e.g., Leu235Glu (L235E) or Leu235Ala (L235A). In some embodiments, the Fc region of the fusion protein is modified at amino acid Leu234 (Kabat Numbering) to alter Fc receptor interactions, e.g., Leu234Ala (L234A). In some embodiments, the Fc region of the fusion protein is modified at amino acid Leu234 (Kabat Numbering) to alter Fc receptor interactions, e.g., Leu235Glu (L235E). In some embodiments, the Fc region of the fusion protein is altered at both amino acids 234 and 235, e.g., Leu234Ala and Leu235Ala (L234A/L235A) or Leu234Val and Leu235Ala (L234V/L235A). In some embodiments, the Fc region of the fusion protein is altered at amino acids 234, 235, and 297, e.g., Leu234Ala, Leu235Ala, Asn297Ala (L234A/L235A/N297A). In some embodiments, the Fc region of the fusion protein is altered at amino acids at 234, 235, and 329, e.g., Leu234Ala, Leu235Ala, Pro239Ala (L234A/L235A/P329A). In some embodiments, the Fc region of the fusion protein is modified at amino acid Asp265 (Kabat Numbering) to alter Fc receptor interactions, e.g Asp265Ala (D265A). In some embodiments, the Fc region of the fusion protein is modified at amino acid Pro329 (Kabat Numbering) to alter Fc receptor interactions, e.g Pro329Ala (P329A) or Pro329Gly (P329G). In some embodiments, the Fc region of the fusion protein is altered at both amino acids 265 and 329, e.g., Asp265Ala and Pro329Ala (D265A/P329A) or Asp265Ala and Pro329Gly (D265A/P329G). In some embodiments, the Fc region of the fusion protein is altered at amino acids at 234, 235, and 265, e.g., Leu234Ala, Leu235Ala, Asp265Ala (L234A/L235A/D265A). In some embodiments, the Fc region of the fusion protein is altered at amino acids at 234, 235, and 329, e.g., Leu234Ala, Leu235Ala, Pro329Gly (L234A/L235A/P329G). In some embodiments, the Fc region of the fusion protein is altered at amino acids at 234, 235, 265 and 329, e.g., Leu234Ala, Leu235Ala, Asp265Ala, Pro329Gly (L234A/L235A/D265A/P329G). In some embodiments, the Fc region of the fusion protein is altered at Gly235 to reduce Fc receptor binding. For example, wherein Gly235 is deleted from the fusion protein. In some embodiments, the human IgG1 Fc region is modified at amino acid Gly236 to enhance the interaction with CD32A, e.g., Gly236Ala (G236A). In some embodiments, the human IgG1 Fc region lacks Lys447 (EU index of Kabat et al 1991 Sequences of Proteins of Immunological Interest).

In some embodiments, the Fc region of the fusion protein is lacking an amino acid at one or more of the following positions to reduce Fc receptor binding: Glu233 (E233), Leu234 (L234), or Leu235 (L235). In some embodiments, the Fc region of the fusion protein is lacking an amino acid at one or more of the following positions Glu233 (E233), Leu234 (L234), or Leu235 (L235), and is modified at one or more of Asp265 (D265), Asn297 (N297), or Pro329 (P329), to reduce Fc receptor binding. For example, an Fc region included in a DLL3-binding polypeptide is derived from a human Fc domain, and comprises a three amino acid deletion in the lower hinge corresponding to IgG1 E233, L234, and L235. In some aspects, such Fc polypeptides do not engage FcγRs and thus are referred to as "effector silent" or "effector null." For example, Fc deletion of these three amino acids reduces the complement protein C1q binding. In some embodiments, a polypeptide with an Fc region with Fc deletion of these three amino acids retains binding to FcRn and therefore has extended half-life and transcytosis associated with FcRn mediated recycling. Such a modified Fc region is referred to as "Fc xELL" or "Fc deletion" and has the following amino acid sequence:

```
                                             (SEQ ID NO: 9)
  PAPGGPSVFL FPPKPKDTLM ISRTPEVTCV VVDVSHEDPE

VKFNWYVDGV EVHNAKTKPR EEQYNSTYRV VSVLTVLHQD

WLNGKEYKCK VSNKALPAPI EKTISKAKGQ PREPQVYTLP

PSRDELTKNQ VSLTCLVKGF YPSDIAVEWE SNGQPENNYK

TTPPVLDSDG SFFLYSKLTV DKSRWQQGNV FSCSVMHEAL

HNHYTQKSLS LSPGK
```

In some embodiments, the immunoglobulin Fc region or immunologically active fragment thereof comprises a human IgG1 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 9.

In some embodiments, the human IgG Fc region is modified to enhance FcRn binding. Examples of Fc mutations that enhance binding to FcRn are Met252Tyr, Ser254Thr, Thr256Glu (M252Y, S254T, T256E, respectively) (Kabat numbering, Dall'Acqua et al 2006, J. Biol Chem Vol. 281(33) 23514-23524), Met428Leu and Asn434Ser (M428L, N434S) (Zalevsky et al 2010 Nature Biotech, Vol. 28(2) 157-159), or Met252Ile, Thr256Asp, Met428Leu (M252I, T256D, M428L, respectively), (EU index of Kabat et al 1991 Sequences of Proteins of Immunological Interest).

In some embodiments, the Fc domain included in a DLL3-binding polypeptide is derived from a human Fc domain and comprises mutations M252Y and M428V, herein referred to as "Fc-YV". In some embodiments, the mutated or modified Fc polypeptide includes the following mutations: M252Y and M428L using the Kabat numbering system. In some embodiments, such mutations enhance binding to FcRn at the acidic pH of the endosome (near 6.5), while losing detectable binding at neutral pH (about 7.2), allowing for enhanced FcRn mediated recycling and extended half-life.

In particular embodiments of multispecific polypeptide constructs provides herein, the Fc domain included in a DLL3-binding polypeptide is derived from a human Fc domain and comprises mutations to induce heterodimerization. In some embodiments, such mutations include those referred to as "knob" and "hole" mutations. For example, having an amino acid modification within the CH3 domain at Thr366, which when replaced with a more bulky amino acid, e.g., Try (T366W), is able to preferentially pair with a second CH3 domain having amino acid modifications to less bulky amino acids at positions Thr366, Leu368, and Tyr407, e.g., Ser, Ala and Val, respectively (T366S/L368A/Y407V). In some embodiments, the "knob" Fc domain comprises the mutation T366W. In some embodiments, the "hole" Fc domain comprises mutations T366S, L368A, and Y407V. Heterodimerization via CH3 modifications can be further stabilized by the introduction of a disulfide bond, for example by changing Ser354 to Cys (S354C) and Y349 to Cys (Y349C) on opposite CH3 domains (Reviewed in Carter, 2001 Journal of Immunological Methods, 248: 7-15). In some embodiments, Fc domains used for heterodimerization comprise additional mutations, such as the mutation S354C on a first member of a heterodimeric Fc pair that forms an asymmetric disulfide with a corresponding mutation Y349C on the second member of a heterodimeric Fc pair. In some embodiments, one member of a heterodimeric Fc pair comprises the modification H435R or H435K to prevent protein A binding while maintaining FcRn binding. In some embodiments, one member of a heterodimeric Fc pair comprises the modification H435R or H435K, while the second member of the heterodimeric Fc pair is not modified at H435. In various embodiments, the hole Fc domain comprises the modification H435R or H435K (referred to as "hole-R" in some instances when the modification is H435R), while the knob Fc domain does not. In some instances, the hole-R mutation improves purification of the heterodimer over homodimeric hole Fc domains that may be present.

In some embodiments, the human IgG Fc region is modified to prevent dimerization. In these embodiments, the fusion proteins of the present disclosure are monomeric. For example modification at residue Thr366 to a charged residue, e.g. Thr366Lys, Thr366Arg, Thr366Asp, or Thr366Glu (T366K, T366R, T366D, or T366E, respectively), prevents CH3-CH3 dimerization.

In some embodiments, the immunoglobulin Fc region or immunologically active fragment of the fusion protein is of human IgG2 isotype, having an amino acid sequence:

```
                                            (SEQ ID NO: 10)
PAPPVAGPSV FLFPPKPKDT LMISRTPEVT CVVVDVSHED

PEVQFNWYVD GVEVHNAKTK PREEQFNSTF RVVSVLTVVH

QDWLNGKEYK CKVSNKGLPA PIEKTISKTK GQPREPQVYT

LPPSREEMTK NQVSLTCLVK GFYPSDISVE WESNGQPENN

YKTTPPMLDS DGSFFLYSKL TVDKSRWQQG NVFSCSVMHE

ALHNHYTQKS LSLSPGK
```

In some embodiments, the fusion or immunologically active fragment thereof comprises a human IgG2 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 10.

In some embodiments, the human IgG2 Fc region is modified at amino acid Asn297 (e.g. to prevent to glycosylation of the antibody, e.g., Asn297Ala (N297A) or Asn297Asp (N297D). In some embodiments, the human IgG2 Fc region is lacks Lys447 (EU index of Kabat et al 1991 Sequences of Proteins of Immunological Interest).

In some embodiments, the immunoglobulin Fc region or immunologically active fragment of the fusion protein is of human IgG3 isotype, having an amino acid sequence:

```
                                            (SEQ ID NO: 11)
PAPELLGGPS VFLFPPKPKD TLMISRTPEV TCVVVDVSHE

DPEVQFKWYV DGVEVHNAKT KPREEQYNST FRVVSVLTVL

HQDWLNGKEY KCKVSNKALP APIEKTISKT KGQPREPQVY

TLPPSREEMT KNQVSLTCLV KGFYPSDIAV EWESSGQPEN

NYNTTPPMLD SDGSFFLYSK LTVDKSRWQQ GNIFSCSVMH

EALHNRFTQK SLSLSPGK
```

In some embodiments, the antibody or immunologically active fragment thereof comprises a human IgG3 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 11.

In some embodiments, the human IgG3 Fc region is modified at amino acid Asn297 (Kabat Numbering) to prevent to glycosylation of the antibody, e.g., Asn297Ala (N297A) or Asn297Asp (N297D). In some embodiments, the human IgG3 Fc region is modified at amino acid 435 to extend the half-life, e.g., Arg435His (R435H). In some embodiments, the human IgG3 Fc region is lacks Lys447 (EU index of Kabat et al 1991 Sequences of Proteins of Immunological Interest).

In some embodiments, the immunoglobulin Fc region or immunologically active fragment of the fusion protein is of human IgG4 isotype, having an amino acid sequence:

```
                                            (SEQ ID NO: 12)
PAPEFLGGPS VFLFPPKPKD TLMISRTPEV TCVVVDVSQE

DPEVQFNWYV DGVEVHNAKT KPREEQFNST YRVVSVLTVL

HQDWLNGKEY KCKVSNKGLP SSIEKTISKA KGQPREPQVY

TLPPSQEEMT KNQVSLTCLV KGFYPSDIAV EWESNGQPEN

NYKTTPPVLD SDGSFFLYSR LTVDKSRWQE GNVFSCSVMH

EALHNHYTQK SLSLSLGK
```

In some embodiments, the antibody or immunologically active fragment thereof comprises a human IgG4 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 12.

In some embodiments, the immunoglobulin Fc region or immunologically active fragment of the fusion protein is of human IgG4 isotype, having an amino acid sequence:

```
                                            (SEQ ID NO: 13)
PAPELLGGPS VFLFPPKPKD TLMISRTPEV TCVVVDVSQE

DPEVQFNWYV DGVEVHNAKT KPREEQFNST YRVVSVLTVL

HQDWLNGKEY KCKVSNKGLP SSIEKTISKA KGQPREPQVY

TLPPSQEEMT KNQVSLTCLV KGFYPSDIAV EWESNGQPEN

NYKTTPPVLD SDGSFFLYSR LTVDKSRWQE GNVFSCSVMH

EALHNHYTQK SLSLSLGK
```

In some embodiments, the antibody or immunologically active fragment thereof comprises a human IgG4 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 13.

In some embodiments, the human IgG4 Fc region is modified at amino acid 235 to alter Fc receptor interactions, e.g., Leu235Glu (L235E). In some embodiments, the human IgG4 Fc region is modified at amino acid Asn297 (Kabat Numbering) to prevent to glycosylation of the antibody, e.g., Asn297Ala (N297A) or Asn297Asp (N297D). In some embodiments, the human IgG4 Fc region is lacks Lys447 (EU index of Kabat et al 1991 Sequences of Proteins of Immunological Interest).

In some embodiments, the fusion protein contains a polypeptide derived from an immunoglobulin hinge region. The hinge region can be selected from any of the human IgG subclasses. For example, the fusion protein may contain a modified IgG1 hinge having the sequence of EPKSSDKTHTCPPC (SEQ ID NO: 14), where in the Cys220 that forms a disulfide with the C-terminal cysteine of the light chain is mutated to serine, e.g., Cys220Ser (C220S). In other embodiments, the fusion protein contains a truncated hinge having a sequence DKTHTCPPC (SEQ ID NO: 15).

In some embodiments, the fusion protein has a modified hinge from IgG4, which is modified to prevent or reduce strand exchange, e.g., Ser228Pro (S228P), having the sequence ESKYGPPCPPC (SEQ ID NO: 16). In some embodiments, the fusion protein contains linker polypeptides. In other embodiments, the fusion protein contains linker and hinge polypeptides.

In some embodiments, the Fc region lacks or has reduced Fucose attached to the N-linked glycan-chain at N297. There are numerous ways to prevent fucosylation, including but not limited to production in a FUT8 deficient cell line; addition inhibitors to the mammalian cell culture media, for example Castanospermine; and metabolic engineering of the production cell line.

In some embodiments, the Fc region is engineered to eliminate recognition by pre-existing antibodies found in humans. In some embodiments, VHH-containing polypeptides of the present disclosure are modified by mutation of position Leu11, for example Leu11Glu (L11E) or Leu11Lys (L11K). In other embodiments, single domain antibodies of the present disclosure are modified by changes in carboxy-terminal region, for example the terminal sequence has the sequence GQGTLVTVKPGG (SEQ ID NO: 17) or GQGTLVTVEPGG (SEQ ID NO: 18) or modification thereof. In some embodiments, the VHH-containing polypeptides of the present disclosure are modified by mutation of position 11 and by changes in carboxy-terminal region.

In some embodiments, the one or more polypeptides of the fusion proteins of the present disclosure are operably linked via amino acid linkers. In some embodiments, these linkers are composed predominately of the amino acids Glycine and Serine, denoted as GS-linkers herein. The GS-linkers of the fusion proteins of the present disclosure can be of various lengths, for example, 5, 6, 7, 8, 9, 10, 11, 12, 13, 14, 15, 16, 17, 18, 19, 20 amino acids in length.

In some embodiments, the GS-linker comprises an amino acid sequence selected from the group consisting of GGSGGS, i.e., (GGS)$_2$ (SEQ ID NO: 1); GGSGGSGGS, i.e., (GGS)$_3$ (SEQ ID NO: 2); GGSGGSGGSGGS, i.e., (GGS)$_4$ (SEQ ID NO: 3); and GGSGGSGGSGGSGGS, i.e., (GGS)$_5$ (SEQ ID NO: 4). In some embodiments, the linker is a flexible linker is a glycine linker comprising Glycine residues, such as, by way of non-limiting example, GG, GGG, GGGG (SEQ ID NO: 5), GGGGG (SEQ ID NO: 6), and GGGGGG (SEQ ID NO: 7). In some embodiments, the linker is (GGGGS)$_n$, wherein n is 1 to 5 (SEQ ID NO:123); (GGGGGS)$_n$, wherein n is 1 to 4 (SEQ ID NO:124); GGGGS (SEQ ID NO:125); GGGGGS (SEQ ID NO:126); GGGGGSGGGGGSGGGGGS (SEQ ID NO:127); GGGGSGGGGSGGGGS (SEQ ID NO:128); GGSGGGGSGGGGSGGGGS (SEQ ID NO:129); or PGGGG (SEQ ID NO:450). In some embodiments, the fusion proteins can include a combination of a GS-linker and a Glycine linker.

B. Conjugates

Provided herein are conjugates containing at least one VHH domain that specifically binds DLL3 provided herein and one or more further moiety. The further moiety can be a therapeutic agent, such as a cytotoxic agent, or can be a detection agent. In some embodiments, the moiety can be a targeting moiety, a small molecule drug (non-polypeptide drug of less than 500 Daltons molar mass), a toxin, a cytostatic agent, a cytotoxic agent, an immunosuppressive agent, a radioactive agent suitable for diagnostic purposes, a radioactive metal ion for therapeutic purposes, a prodrug-activating enzyme, an agent that increases biological half-life, or a diagnostic or detectable agent.

In some embodiments, the conjugate is an antibody drug conjugate (ADC, also called immunoconjugates) containing one or more DLL3 VHH domain provided herein conjugated to a therapeutic agent, which is either cytotoxic, cytostatic or otherwise provides some therapeutic benefit. In some embodiments, the cytotoxic agent is a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate). In some embodiments, provided antibody drug conjugates of the present disclosure allow targeted-delivery of the drug moiety to tumors. In some cases, this can result in targeted killing of the tumor cell.

In some embodiments, there is provided a DLL3-binding conjugate comprising at least one DLL3 VHH domain provided herein conjugated with a therapeutic agent. In some embodiments, the therapeutic agent includes, for example, daunomycin, doxorubicin, methotrexate, and vindesine (Rowland et al., Cancer Immunol. Immunother. 21:183-187, 1986). In some embodiments, the therapeutic agent has an intracellular activity. In some embodiments, the DLL3-binding conjugate is internalized and the therapeutic agent is a cytotoxin that blocks the protein synthesis of the cell, therein leading to cell death. In some embodiments, the therapeutic agent is a cytotoxin comprising a polypeptide having ribosome-inactivating activity including, for example, gelonin, bouganin, saporin, ricin, ricin A chain, bryodin, diphtheria toxin, restrictocin, *Pseudomonas* exotoxin A and variants thereof. In some embodiments, where the therapeutic agent is a cytotoxin comprising a polypeptide having a ribosome-inactivating activity, the DLL3-binding conjugate must be internalized upon binding to the target cell in order for the protein to be cytotoxic to the cells.

In some embodiments, there is provided a DLL3-binding conjugate comprising at least one DLL3 VHH domain provided herein conjugated with a toxin. In some embodiments, the toxin includes, for example, bacterial toxins such as diphtheria toxin, plant toxins such as ricin, small molecule toxins such as geldanamycin (Mandler et al., J. Nat. Cancer Inst. 92(19):1573-1581 (2000); Mandler et al., Bioorganic & Med. Chem. Letters 10:1025-1028 (2000); Mandler et al., Bioconjugate Chem. 13:786-791 (2002)), maytansinoids (EP 1391213; Liu et al., Proc. Natl. Acad. Sci. USA 93:8618-8623 (1996)), and calicheamicin (Lode et al., Cancer Res. 58:2928 (1998); Hinman et al., Cancer Res. 53:3336-3342 (1993)). The toxins may exert their cytotoxic and cytostatic effects by mechanisms including tubulin binding, DNA binding, or topoisomerase inhibition.

In some embodiments, there is provided a DLL3-binding conjugate comprising at least one DLL3 VHH domain provided herein conjugated with a label, which can generate a detectable signal, indirectly or directly. These IgSF conjugates can be used for research or diagnostic applications, such as for the in vivo detection of cancer. The label is preferably capable of producing, either directly or indirectly, a detectable signal. For example, the label may be radio-opaque or a radioisotope, such as 3H, 14C, 32P, 35S, 123I, 125I, 131I; a fluorescent (fluorophore) or chemiluminescent (chromophore) compound, such as fluorescein isothiocyanate, rhodamine or luciferin; an enzyme, such as alkaline phosphatase, β-galactosidase or horseradish peroxidase; an imaging agent; or a metal ion. In some embodiments, the label is a radioactive atom for scintigraphic studies, for example 99Tc or 123I, or a spin label for nuclear magnetic resonance (NMR) imaging (also known as magnetic resonance imaging, MRI), such as zirconium-89, iodine-123, iodine-131, indium-111, fluorine-19, carbon-13, nitrogen-15, oxygen-17, gadolinium, manganese or iron. Zirconium-89 may be complexed to various metal chelating agents and conjugated to antibodies, e.g., for PET imaging (WO 2011/056983).

The DLL3-binding conjugates may be prepared using any methods known in the art. See, e.g., WO 2009/067800, WO 2011/133886, and U.S. Patent Application Publication No. 2014322129, incorporated by reference herein in their entirety.

In some embodiments, the attachment can be covalent or non-covalent, e.g., via a biotin-streptavidin non-covalent interaction. In some embodiments, 1, 2, 3, 4, 5 or more moieties, which can be the same or different, are conjugated, linked or fused to a DLL3 VHH domain to form a DLL3-binding conjugate. In some embodiments, such moieties can be attached to the VHH domain using various molecular biological or chemical conjugation and linkage methods known in the art and described below. In some embodiments, linkers such as peptide linkers, cleavable linkers, non-cleavable linkers or linkers that aid in the conjugation reaction, can be used to link or conjugate the effector moieties to the variant polypeptide or immunomodulatory protein.

In some embodiments, a DLL3 VHH domain is conjugated to one or more moieties, e.g. about 1 to about 20 drug moieties per VHH, through a linker (L). In some embodiments, the DLL3-binding conjugate comprises the following components: (VHH domain), $(L)_q$ and $(moiety)_m$, wherein the VHH domain is any of the described VHH domains capable of specifically binding DLL3 as described; L is a linker for linking the protein or polypeptide to the moiety; m is at least 1; q is 0 or more; and the resulting DLL3-binding conjugate binds to DLL3. In particular embodiments, m is 1 to 4 and q is 0 to 8.

The linker may be composed of one or more linker components. For covalent attachment of the antibody and the drug moiety the linker typically has two reactive functional groups, i.e. bivalency in a reactive sense. Bivalent linker reagents which are useful to attach two or more functional or biologically active moieties, such as peptides, nucleic acids, drugs, toxins, antibodies, haptens, and reporter groups are known, and methods have been described their resulting conjugates (Hermanson, G. T. (1996) Bioconjugate Techniques; Academic Press: New York, p 234-242).

Exemplary linker components include 6-maleimidocaproyl ("MC"), maleimidopropanoyl ("MP"), valine-citrulline ("val-cit"), a alanine-phenylalanine ("ala-phe"), p-aminobenzyloxycarbonyl ("PAB"), N-Succinimidyl 4-(2-pyridylthio)pentanoate ("SPP"), N-Succinimidyl 4-(N-maleimidomethyl)cyclohexane-I carboxylate ("SMCC"), and N-Succinimidyl (4-iodo-acetyl)aminobenzoate ("SIAB").

In some embodiments, the linker may comprise amino acid residues. Exemplary amino acid linker components include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline Amino acid linker components can be designed and optimized in their selectivity for enzymatic cleavage by a particular enzyme, for example, a tumor-associated protease, cathepsin B, C and D, at a plasmin protease.

Conjugates of a VHH domain and cytotoxic agent can be made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl substrate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene).

The antibody drug conjugate can be prepared by a variety of methods, such as organic chemistry reactions, conditions, and reagents known to those skilled in the art. In one embodiments, methods include: (1) reaction of a nucleophilic group of a VHH domain with a bivalent linker reagent, to form VHH-L, via a covalent bond, followed by reaction with a drug moiety D; and (2) reaction of a nucleophilic group of a drug moiety with a bivalent linker reagent, to form D-L, via a covalent bond, followed by reaction with the nucleophilic group of a VHH domain.

Nucleophilic groups on antibodies, including VHH domains, include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues).

Conjugates, such as antibody drug conjugates, may also be produced by modification of an antibody, such as a VHH domain, to introduce electrophilic moieties, which can react with nucleophilic substituents on the linker reagent or drug. The sugars of glycosylated antibodies may be oxidized, e.g., with periodate oxidizing reagents, to form aldehyde or ketone groups which may lead with the amine group of linker reagents or drug moieties. The resulting imine Schiff base groups may form a stable linkage, or may be reduced, e.g., by borohydride reagents to form stable amine linkages. In one embodiment, reaction of the carbohydrate portion of a glycosylated antibody with either glactose oxidase or sodium meta-periodate may yield carbonyl (aldehyde and ketone) groups in the protein that can react with appropriate groups on the drug (Hermanson, Bioconjugate Techniques). In another embodiment, proteins containing N-terminal serine or threonine residues can react with sodium meta-periodate, resulting in production of an aldehyde in place of the first amino acid. Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBi esters, haloformates, and acid halides; (ii) alkyl and benzyl halides such as haloacetamides; (iii) aldehydes, ketones, carboxyl, and maleimide groups.

Alternatively, a fusion protein containing a VHH domain and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

C. Multispecific Formats

Provided herein are DLL3-binding polypeptides that are multispecific containing at least one VHH domain that binds DLL3 and one or more additional binding domains. Typically, the one or more additional domains bind to a second antigen or protein other than DLL3. In some embodiments, the one or more additional domain is an antibody or antigen-binding fragment specific for the second antigen or protein. In some embodiments, the additional domain is a VHH domain.

In some embodiments, a multispecific DLL3-binding polypeptide comprises at least one VHH domain that binds DLL3 and at least one additional binding domain that binds a second antigen or protein. In some embodiments, this second antigen is a tumor associated antigen (TAA) or tumor microenvironment associated antigen (TMEAA). In some embodiments, this second antigen is an immunomodulatory antigen, wherein said antigen is involved with enhancing or dampening a signaling pathway in an immune cell.

In some cases, a multispecific DLL3-binding polypeptide can further contain an Fc domain, such as any described above. In some embodiments, a multispecific DLL3-binding polypeptide provided herein at least one VHH domains that bind DLL3, at least one additional binding domain that binds a second antigen or protein, and an Fc domain. In some embodiments, an Fc domain mediates dimerization of the multispecific DLL3-binding polypeptide at physiological conditions such that a dimer is formed that doubles the number of binding sites for DLL3 and for the additional antigen or protein.

Non-limiting exemplary multispecific DLL3-binding polypeptides are described below.

1. Bispecific T Cells Engager

In some embodiments, the DLL3-binding polypeptide is a bispecific construct that is or comprises at least one DLL3 VHH domain provided herein and at least one additional binding molecule capable of binding to a surface molecule expressed on a T cell. In some embodiments, the surface molecule is an activating component of a T cell, such as a component of the T cell receptor complex. In particular aspects, the surface molecule is an activating T cell antigen that is expressed on a T cell and is capable of inducing T cell activation upon interaction with an antigen binding molecule. For example, in some aspects, interaction of an antigen binding molecule with an activating T cell antigen may induce T cell activation by triggering the signaling cascade of the T cell receptor complex. Suitable assays to measure T cell activation are known, and include any assay to measure or assess proliferation, differentiation, cytokine secretion, cytotoxic activity and/or expression of one or more activation marker. In some embodiments, the simultaneous or near simultaneous binding of such a DLL3-binding polypeptide to both of its targets, DLL3 expressed on target cell and a T cell molecule expressed on a T cell, e.g. activating T cell antigen, can result in a temporary interaction between the target cell and T cell, thereby resulting in activation, e.g. cytotoxic activity, of the T cell and subsequent lysis of the target cell.

In some embodiments, the T surface molecule, such as activating T cell antigen, is CD3 or is CD2. Specifically, a provided bispecific DLL3-binding polypeptide is capable of specifically binding an activating T cell antigen expressed on a human T cell, such as human CD3 or human CD3. In particular aspects, the additional binding domain that is specific to the activating T cell antigen (e.g. CD3 or CD2) is an antibody or antigen-binding fragment. In some embodiments, a DLL3-binding polypeptide can be a bispecific antibody T cell-engager containing at least one DLL3 VHH domain that specifically binds to DLL3 and an additional binding molecule that is an antibody or antigen-binding fragment specific for an activating component of a T cell (e.g. a T cell surface molecule, e.g. CD3 or CD2).

Among bispecific antibody T cell-engagers are bispecific T cell engager (BiTE) molecules, which contain tandem scFv molecules fused by a flexible linker (see e.g. Nagorsen and Bauerle, Exp Cell Res 317, 1255-1260 (2011); tandem scFv molecules fused to each other via, e.g. a flexible linker, and that further contain an Fc domain composed of a first and a second subunit capable of stable association (WO2013026837); diabodies and derivatives thereof, including tandem diabodies (Holliger et al, Prot Eng 9, 299-305 (1996); Kipriyanov et al, J Mol Biol 293, 41-66 (1999)); dual affinity retargeting (DART) molecules that can include the diabody format with a C-terminal disulfide bridge; or triomabs that include whole hybrid mouse/rat IgG molecules (Seimetz et al, Cancer Treat Rev 36, 458-467 (2010). Similar formats of any of the above molecules can be generated using any of the DLL3 VHH domains provided herein.

In some embodiments, the additional binding domain specific to an activating T cell antigen is an antigen-binding fragment selected from a Fab fragment, a F(ab')$_2$ fragment, an Fv fragment, a scFv, disulfide stabilized Fv fragment (dsFv), a scAb, a dAb, a single domain heavy chain antibody (VHH), or a single domain light chain antibody. In some embodiments, the additional binding domain is monovalent for binding the activating T cell antigen, such as CD2 or CD3.

In some embodiments, the additional binding domain is capable of binding to CD3 or a CD3 complex. A CD3 complex is a complex of at least five membrane-bound polypeptides in mature T-lymphocytes that are non-covalently associated with one another and with the T-cell receptor. The CD3 complex includes the gamma, delta, epsilon, zeta, and eta chains (also referred to as subunits). In some embodiments, the additional binding molecule is an antibody or antigen-binding fragment capable of specifically binding to CD3 or a CD3 complex, also called a CD3-binding domain. In some embodiments, the CD3-binding domain capable of binding CD3 or a CD3 complex includes one or more copies of an anti-CD3 Fab fragment, an anti-CD3 F(ab')$_2$ fragment, an anti-CD3 Fv fragment, an anti-CD3 scFv, an anti-CD3 dsFv, an anti-CD3 scAb, an anti-CD3 dAb, an anti-CD3 single domain heavy chain antibody (VHH), and an anti-CD3 single domain light chain antibody. In some embodiments, the anti-CD3 binding domain is monovalent for binding CD3.

In some cases, the CD3-binding domain recognizes the CD3ε-chain. In some embodiments, the anti-CD3ε binding domain includes one or more copies of an anti-CD3ε Fab fragment, an anti-CD3ε F(ab')$_2$ fragment, an anti-CD3ε Fv fragment, an anti-CD3ε scFv, an anti-CD3ε dsFv, an anti-CD3ε scAb, an anti-CD3ε dAb, an anti-CD3ε single domain heavy chain antibody (VHH), and an anti-CD3ε single domain light chain antibody. In some embodiments, the anti-CD3ε binding domain is monovalent for binding CD3ε.

Exemplary monoclonal antibodies against CD3 or a CD3 complex include, but are not limited to, OKT3, SP34, UCHT1 or 64.1, or an antigen-binding fragment thereof (See e.g., June, et al., J. Immunol. 136:3945-3952 (1986); Yang, et al., J. Immunol. 137:1097-1100 (1986); and Hayward, et al., Immunol. 64:87-92 (1988)). In some aspects, clustering of CD3 on T cells, e.g., by immobilized or cell-localized or tethered anti-CD3-antibodies, leads to T cell activation similar to the engagement of the T cell receptor but independent from its clone typical specificity. In one embodiment, the CD3-binding domain monovalently and specifically binds a CD3 antigen, and is derived from OKT3 (ORTHOCLONE-OKT3™ (muromonab-CD3); humanized OKT3 (U.S. Pat. No. 7,635,475 and published international application No. WO2005040220); SP34 (Pessano et ai. The EMBO Journal. 4: 337-344, 1985); humanized variant of SP34 (WO2015001085); Teplizumab™ (MGA031, Eli Lilly); an anti-CD3 binding molecule described in US2011/0275787; UCHT1 (Pollard et al. 1987 J Histochem Cytochem. 35(11):1329-38; WO2000041474); NI0401 (WO2007/033230); visilizumab (U.S. Pat. No. 5,834,597); BC-3 (Anasetti et al., Transplantation 54: 844 (1992); H2C (described in PCT publication no. WO2008/119567); V9 (described in Rodrigues et al., Int J Cancer Suppl 7, 45-50 (1992) and U.S. Pat. No. 6,054,297)). Other anti-CD3 antibodies also can be used in the constructs provided herein, including any described in International published PCT application Nos. WO199404679, WO2008119567, WO2015095392, WO2016204966; WO2019133761; published patent application Nos. US20170369563, US20180194842, US20180355038; U.S. Pat. Nos. 7,728,114, 7,381,803, 7,994,289.

In some embodiments, the CD3-binding domain contains a variable heavy (VH) chain set forth in SEQ ID NO:19 and/or a variable light chain set forth in SEQ ID NO:20, or VH and/or VL sequences having at least 60%, 70%, 80%, 90%, 95%, 97%, 98%, 99% identity with these sequences and specifically binds CD3. In some embodiments, the CD3-binding domain contains a CDRH1, CDRH2 and CDRH3 of the variable heavy (VH) chain set forth in SEQ ID NO:19 and a CDRL1, CDRL2 and CDRL3 variable light chain set forth in SEQ ID NO:20. In some cases, the CD3-binding region comprises a humanized version of the VH sequence set forth in SEQ ID NO:19 and a humanized version of the VL sequence set forth in SEQ ID NO:20. In some embodiments a CD3-binding region can contain a humanized OKT3 derived VH domain sequence set forth in any one of SEQ ID NOs 21, 22, 23 and/or a VL domain sequence set forth in any one of SEQ ID NOs 24, 25, 26, or VH and/or VL sequences having at least 60%, 70%, 80%, 90%, 95%, 97%, 98%, 99% identity with these sequences and specifically binds CD3. In some embodiments, the CD3-binding domain is a Fab, scFv, Fv or dsFv, in which is contained any combination of the above VH and VL sequence, particularly any combination of a VH sequence set forth in any of SEQ ID NOS: 21, 22, 23 and a VL sequence set forth in any of SEQ ID NOS: 24, 25, 26.

In some embodiments, the anti-CD3ε binding domain includes a VH CDR1 sequence that includes at least the amino acid sequence TYAMN (SEQ ID NO: 29); a VH CDR2 sequence that includes at least the amino acid sequence RIRSKYNNYATYYADSVKD (SEQ ID NO: 30); a VH CDR3 sequence that includes at least the amino acid sequence HGNFGNSYVSWFAY (SEQ ID NO: 31), a VL CDR1 sequence that includes at least the amino acid sequence RSSTGAVTTSNYAN (SEQ ID NO: 32); a VL CDR2 sequence that includes at least the amino acid sequence GTNKRAP (SEQ ID NO: 33); and a VL CDR3 sequence that includes at least the amino acid sequence ALWYSNLWV (SEQ ID NO: 34). In some embodiments, the CD3-binding domain is a Fab, scFv, Fv or dsFv, in which is contained a VH CDR1 sequence that includes at least the amino acid sequence TYAMN (SEQ ID NO: 29); a VH CDR2 sequence that includes at least the amino acid sequence RIRSKYNNYATYYADSVKD (SEQ ID NO: 30); a VH CDR3 sequence that includes at least the amino acid sequence HGNFGNSYVSWFAY (SEQ ID NO: 31), a VL CDR1 sequence that includes at least the amino acid sequence RSSTGAVTTSNYAN (SEQ ID NO: 32); a VL CDR2 sequence that includes at least the amino acid sequence GTNKRAP (SEQ ID NO: 33); and a VL CDR3 sequence that includes at least the amino acid sequence ALWYSNLWV (SEQ ID NO: 34).

In some embodiments, the CD3-binding domain contains a variable heavy (VH) chain set forth in SEQ ID NO:27 and/or a variable light chain set forth in SEQ ID NO:28, or VH and/or VL sequences having at least 60%, 70%, 80%, 90%, 95%, 97%, 98%, 99% identity with these sequences and specifically binds to CD3. In some embodiments, the CD3-binding domain contains a CDRH1, CDRH2 and CDRH3 of the variable heavy (VH) chain set forth in SEQ ID NO:27 and a CDRL1, CDRL2 and CDRL3 variable light chain set forth in SEQ ID NO:28. In some embodiments, the CD3-binding domain contains a CDRH1, CDRH2 and CDRH3 set forth in SEQ ID NOs:29, 30 and 31, respectively and a CDRL1, CDRL2 and CDRL3 variable light chain set forth in SEQ ID NO:32, 33, and 34, respectively. In some cases, the CD3-binding region comprises a humanized version of the VH sequence set forth in SEQ ID NO:27 and a humanized version of the VL sequence set forth in SEQ ID NO:28. In some embodiments a CD3-binding region can contain a humanized VH domain sequence set forth in any one of SEQ ID NOs 35-65, 453, 454, or 460, and/or a VL domain sequence set forth in any one of SEQ ID NOs: 66-84, 368, 451, or 452 or VH and/or VL sequences having at least 60%, 70%, 80%, 90%, 95%, 97%, 98%, 99% identity with these sequences and specifically binds to CD3. In some embodiments, the anti-CD3ε binding domain thereof includes a variable heavy chain (VH) comprising the amino acid sequence of SEQ ID NO: 47 and a variable light chain (VL) comprising the amino acid sequence of SEQ ID NO: 75.

In some embodiments, the CD3-binding domain is a Fab, scFv, Fv or dsFv, in which is contained any combination of the above VH and VL sequence, particularly any combination of a VH sequence set forth in any of SEQ ID NOS: 35-65, 453, 454, or 460, and a VL sequence set forth in any of SEQ ID NOS: 66-84, 368, 451, or 452. In some embodiments, the anti-CD3 binding domain is a Fab, scFv, Fv or dsFv, in which is contained a variable heavy chain (VH) comprising the amino acid sequence of SEQ ID NO: 47 and a variable light chain (VL) comprising the amino acid sequence of SEQ ID NO: 75.

In some embodiments, the CD3-binding domain contains a variable heavy (VH) chain set forth in SEQ ID NO:519, 520, 523, or 524. In some embodiments, the CD3-binding domain contains a variable light (VL) chain set forth in SEQ ID NO:521, 522, 525, or 526.

The provided bispecific constructs can be formatted in any of a number of formats containing the at least one DLL3 VHH domain and the at least one additional domain specific to an activating T cell antigen, such as a CD3-binding domain.

In one embodiment, the bispecific construct is a bispecific single-domain antibody-linked Fab (S-Fab) containing at least one DLL3 VHH domain as described linked, directly or indirectly to a Fab antigen binding fragment specific to a T cell activating antigen, e.g. CD3, such as an anti-CD3 Fab. The Fab against a T cell activating antigen, e.g. anti-CD3 Fab, can contain any of the VH and VL sequences as described. In some embodiments, the DLL3 VHH domain is linked to the C-terminus of the VH or VL chain of an anti-CD3 Fab. In some embodiments, the S-Fab can be further modified, such as by conjugation with polyethylene glycol (PEG), N-(2-hydroxypropyl) methacrylamide (HPMA) copolymers, proteins (such as albumin), polyglutamic acid or PASylation (Pan et al. (2018) International Journal of Nanomedicine, 2018:3189-3201).

In another embodiment, the bispecific construct is a scFv-single domain antibody in which the construct contains at least one DLL3 VHH as described linked, directly or indirectly, to an scFv containing a VH and a VL of an antigen binding domain specific to a T cell activating antigen, e.g. CD3. The scFv against a T cell activating antigen, e.g. anti-CD3 scFv, can contain any of the VH and VL sequences as described. In some embodiments, the VHH domain and the scFv are connected by a linker, such as a peptide linker. In some embodiments, the peptide linker can be a peptide linker as described herein. In some embodiments, the VHH domain and the scFv are each connected, optionally through a hinge region or a linker (e.g. peptide linker), to an Fc region, such as an N-terminus of an Fc region. The Fc region can be any described herein, such as a human Fc region or a variant thereof, e.g. a human IgG1 Fc region or a variant thereof. In particular examples, the Fc region is formed by variant Fc domains, e.g. variant human IgG1 domains, that are mutated or modified to promote heterodimerization in which different polypeptides can be dimerized to yield a heterodimer.

In a further embodiment, the CD3-binding domain is a single domain antibody, such as is a VHH domain that specifically binds to CD3. Single domain antibodies, including VHH domains that bind to CD3 are known, see e.g. published U.S. patent application No. US20160280795. In some embodiments, the CD3-binding domain is an anti-CD3 VHH set forth in SEQ ID NO:85, or a sequence that exhibits at least 60%, 70%, 80%, 90%, 95%, 97%, 98%, 99% identity with SEQ ID NO:85 and specifically binds to CD3. In such aspects, a bispecific construct provided herein can include at least one DLL3 VHH domain and at least one CD3 VHH domain. For formatting the constructs, in some cases, each VHH domain is connected, optionally through a hinge region or linker (e.g. peptide linker), to an Fc region, such as an N-terminus of an Fc region. The Fc region can be any described herein, such as a human Fc region or a variant thereof, e.g. a human IgG1 Fc region or a variant thereof. In particular examples, the Fc region is formed by variant Fc domains, e.g. variant human IgG1 domains, that are mutated or modified to promote heterodimerization in which different polypeptides can be dimerized to yield a heterodimer.

In the above embodiments, exemplary modifications of an Fc region to promote heterodimerization are known, including any as described below, e.g. Table 3. In some embodiments, one Fc polypeptide of a heterodimeric Fc comprises the sequence of amino acids set forth in any of SEQ ID NOS:103, 107, 115, 117, 440, or 446 and the other Fc polypeptide of the heterodimeric Fc contains the sequence of amino acids set forth in any of SEQ ID NOS:104, 108, 111, 113, 119, 121, 441, 444, or 448. In some embodiments, one Fc polypeptide of a heterodimeric Fc comprises the sequence of amino acids set forth in any of SEQ ID NOS: 105, 109, 116, 118, 442, or 447 and the other Fc polypeptide of the heterodimeric Fc comprises the sequence of amino acids set forth in any of SEQ ID NOS: 106, 110, 112, 114, 120, 122, 443, 445, or 449.

2. Constrained CD3 Multispecific Construct

In some embodiments, the DLL3-binding polypeptide is a multispecific polypeptide construct that is a constrained T-cell engaging fusion protein. In particular aspects, the constrained multispecific constructs provided herein bind an activating T cell antigen, such as a CD3, and DLL3. The constrained multispecific polypeptide constructs provided herein include at least a first component that includes an immunoglobulin Fc region, a second component that includes one or more copies of at least a binding domain that binds CD3 (referred to herein as an anti-CD3 binding domain or a CD3 binding domain, which are terms that are used interchangeably herein), and a linker, such as a polypeptide linker, that joins the first component and the second component. In the provided multispecific polypeptide constructs, one or both of the first and second components contain at least one DLL3 VHH domain, which, when engaged upon binding to antigen, render the constrained CD3 binding region substantially able to bind CD3. FIGS. 3A-3E depict exemplary formats of a constrained multispecific construct.

In some embodiments, the constrained multispecific polypeptide constructs provided herein exist in two states in terms of capacity to bind CD3 and subsequently activate T-cells: (1) the "inactive" state occurs when there is no binding of any or all of the antigen binding domain(s) to DLL3, such that the CD3 binding is constrained and T-cell interaction is obviated or reduced, and (2) the "active" state occurs upon antigen binding by any or all of the antigen binding domain(s), such that the CD3 binding region is able to bind CD3 and the T-cell interaction is allowed.

In some embodiments, the Fc region is linked to the CD3 binding domain via a linker or linkers. In some embodiments, the Fc region is linked to the CD3 binding region via a non-cleavable linker or linkers. In some embodiments, the Fc region is linked to the CD3 binding region via a cleavable linker or an otherwise labile linker or linkers. In some embodiments, cleavable linker is a linker that can be specifically cleaved in the presence of a protease. In some aspects, enhanced CD3 binding occurs following cleavage of the cleavable linker. In some such aspects, the "active" state can be further amplified via several mechanisms, including via cleavage of the linker joining the CD3 binding region and the Fc region. In some embodiments, the cleavable linker is a linker that contains a substrate recognition site for a protease. In some embodiments, wherein the Fc region and the CD3 binding region are linked by a cleavable linker, enhanced CD3 binding may occur following cleavage within the linker(s).

Further, in aspects wherein the Fc region and the CD3 binding region are operably linked by a cleavable linker, cleavage of the linker(s) between the Fc region and the CD3 binding region may separate the constrained multispecific polypeptide constructs into a first and second component. Depending on the composition of the constrained multispecific polypeptide construct, the first and second component may have distinct functionalities. In some embodiments, the Fc region is a region that exhibits one or more effector functions, such as ADCC, CDC or ADCP functions. In such examples, the constrained multispecific polypeptide constructs of the disclosure can be used to produce a self-amplifying system. For example, in some aspects, the incorporation of a protease cleavable linker between the Fc and the components of the CD3 binding domain enables for amplification of the T-cell activating capacity by allowing full exposure of the CD3 binding domain. Depending on the specific linker included, the amplification step can be mediated by tumor associated proteases or by granzymes released following antigen dependent-T-cell activation. If a tumor protease cleavable linker is included the amplification is mediated by the tumor or tumor-microenvironment.

Whereas, if a granzyme B cleavable linker is included the amplification may be self-mediated by T-cells following antigen-dependent activation. Furthermore, in cases wherein an effector enabled Fc is included in the construct, amplification may be mediated by granzymes released from NK cell that occurs through an ADCC mechanism.

The provided constrained multispecific polypeptide constructs include a configuration in which the first component containing the Fc region is N-terminal to the second component containing the CD3 binding region. In such an embodiment, the first and second components are joined via a linker that is C-terminal to the end of the Fc region. In some embodiments, the at least one DLL3 VHH domain is positioned on the amino-terminal (N-term) region of the multispecific polypeptide construct. In some embodiments, the at least one DLL3 VHH domain is positioned on the carboxy-terminal (C-term) region of the multispecific polypeptide construct. In some embodiments, the constrained multispecific polypeptide construct contains at least two DLL3 VHH domains that are positioned on both the N- and C-terminal regions of the multispecific polypeptide construct.

In some embodiments, the constrained multispecific polypeptide construct is a dimer, in which dimerization is formed by covalent or non-covalent interactions between two polypeptide chains. In some embodiments, the two polypeptide chains are covalently bonded to each other by, for example, interchain disulfide bonds. In some embodiments, the Fc region mediates dimerization via interchain disulfide bonds. In particular embodiments, a constrained multispecific polypeptide construct contains a heterodimeric Fc region in which, in some cases, the polypeptide chains of the multispecific polypeptide construct are different (heterodimer). In particular examples of a heterodimeric multispecific polypeptide construct, the CD3-binding region is a two chain polypeptide containing a VH and a VL chain, such as is an Fv antibody fragment containing the VH and VL. In some embodiments, the Fv antibody fragment includes a disulfide stabilized anti-CD3 binding Fv fragment (dsFv).

In some embodiments, a constrained multispecific polypeptide construct is formed from or includes two polypeptides, including a first polypeptide comprising a first Fc polypeptide of a heterodimeric Fc region, a linker (e.g. cleavable or non-cleavable linker), a VH domain of an anti-CD3 antibody or antigen binding fragment (e.g. Fv); and a second polypeptide comprising a second Fc polypeptide of the heterodimeric Fc region, the linker (e.g. the cleavable or non-cleavable linker), a VL domain of the anti-CD3 antibody or antigen binding fragment (e.g. Fv). In some embodiments, the first polypeptide contains one or two VHH domains that bind to DLL3. In some embodiments, the second polypeptide contains one or two VHH domains that bind to DLL3. In some embodiments, a constrained multispecific polypeptide construct contains at least two DLL3 VHH domains. In some cases, at least one DLL3 VHH domain is located N-terminally to the Fc polypeptide and at least one DLL3 VHH domain is located C-terminally to the chain of the CD3-binding region.

In some embodiments, the first polypeptide or second polypeptide or both the first and second polypeptide further include a co-stimulatory receptor binding region (CRBR) that binds a co-stimulatory receptor. In some embodiments, the CRBR of the first and/or second polypeptide can be located N-terminally to the Fc polypeptide and/or C-terminally to the chain of the CD3-binding region.

In some embodiments, a constrained multispecific polypeptide construct contains at least two VHH domains that bind DLL3 and at least one co-stimulatory receptor binding region (CRBR) that binds a co-stimulatory receptor. In some embodiments, a constrained multispecific polypeptide construct contains (1) a first polypeptide comprising in order of N-terminus to C-terminus: a first DLL3 VHH domain, the first Fc polypeptide of a heterodimeric Fc region, a linker (e.g. a cleavable linker), a chain (e.g. VH or VL) of an anti-CD3 antibody or antigen binding fragment (e.g. Fv or dsFv), and a second DLL3 VHH domain; and (2) a second polypeptide comprising in order of N-terminus to C-terminus: the second Fc polypeptide of the heterodimeric Fc region, the same linker (e.g. same cleavable linker), the other chain (other of the VH or VL) of the anti-CD3 antibody or antigen binding fragment, and a co-stimulatory receptor binding region (CRBR) that binds a co-stimulatory receptor.

In some embodiments, the first polypeptide or second polypeptide or both the first and second polypeptide further include an inhibitory receptor binding region (IRBR) that binds an inhibitory receptor. In some embodiments, the IRBR of the first and/or second polypeptide can be located N-terminally to the Fc polypeptide and/or C-terminally to the chain of the CD3-binding region.

In some embodiments, a constrained multispecific polypeptide construct contains at least two VHH domains that bind DLL3 and at least one inhibitory receptor binding region (IRBR) that binds an inhibitory receptor. In some embodiments, a constrained multispecific polypeptide construct contains (1) a first polypeptide comprising in order of N-terminus to C-terminus: a first DLL3 VHH domain, the first Fc polypeptide of a heterodimeric Fc region, a linker (e.g. a cleavable or non-cleavable linker), a chain (e.g. VH or VL) of an anti-CD3 antibody or antigen binding fragment (e.g. Fv or dsFv), and a second DLL3 VHH domain; and (2) a second polypeptide comprising in order of N-terminus to C-terminus: the second Fc polypeptide of the heterodimeric Fc region, the same linker (e.g. same cleavable linker), the other chain (other of the VH or VL) of the anti-CD3 antibody or antigen binding fragment, and an inhibitory receptor binding region (IRBR) that binds an inhibitory receptor.

In some embodiments, at least one of the first polypeptide or second polypeptide further include a co-stimulatory receptor binding region (CRBR) that binds a co-stimulatory receptor and at least one of the first polypeptide or second polypeptide further includes an inhibitory receptor binding region (IRBR) that binds an inhibitory receptor. In some embodiments, the CRBR of the first and/or second polypeptide can be located N-terminally to the Fc polypeptide and/or C-terminally to the chain of the CD3-binding region. In some embodiments, the IRBR of the first and/or second polypeptide can be located N-terminally to the Fc polypeptide and/or C-terminally to the chain of the CD3-binding region.

In some embodiments, a constrained multispecific polypeptide construct contains at least two VHH domains that bind DLL3, a co-stimulatory receptor binding region (CRBR) that binds a co-stimulatory receptor and an inhibitory receptor binding region (IRBR) that binds an inhibitory receptor. In some embodiments, a constrained multispecific polypeptide construct contains (1) a first polypeptide comprising in order of N-terminus to C-terminus: a first DLL3 VHH domain, the first Fc polypeptide of a heterodimeric Fc region, a linker (e.g. a cleavable or non-cleavable linker), a chain (e.g. VH or VL) of an anti-CD3 antibody or antigen binding fragment (e.g. Fv or dsFv), and a second DLL3 VHH domain; and (2) a second polypeptide comprising in order of N-terminus to C-terminus: one of an IRBR or CRBR, the second Fc polypeptide of the heterodimeric Fc region, the same linker (e.g. same cleavable or non-cleavable linker), the other chain (other of the VH or VL) of the anti-CD3 antibody or antigen binding fragment, and the other of the IRBR or CRBR.

Each of the components of the multispecific polypeptide constructs of the disclosure is described in more detail below.

a. DLL3 VHH Antigen Binding Domain

A constrained multispecific polypeptide construct of the disclosure includes at least one DLL3 VHH domain from among any provided herein. In some embodiments, the DLL3 VHH domain comprises the sequence of amino acids set forth in any of SEQ ID NOS: 244-318. In some embodiments, the DLL3 VHH domain comprises the sequence of amino acids set forth in any of SEQ ID NOS: 244-318, 401-409, 416, or 455. In some embodiments, the DLL3 VHH domain comprises the sequence of amino acids set forth in any of SEQ ID NOS: 102, 244-318, 401-409, 416, 455 and 476-480-488, 507-518.

In particular embodiments, a constrained multispecific polypeptide construct contains at least two DLL3 domain. In some cases, at least one DLL3 VHH domain is positioned amino terminally relative to an Fc polypeptide of the heterodimeric Fc and at least one DLL3 VHH domain is positioned carboxy-terminally relative to VH or VL chain of the CD3 binding region.

In aspects of a constrained multispecific polypeptide construct containing at least two or containing two DLL3 VHH domains, each of the DLL3 VHH domains can bind to the same or an overlapping epitope on DLL3.

In aspects of a constrained multispecific polypeptide construct containing at least two or containing two DLL3 VHH domains, each of the DLL3 VHH domains can bind to a different or a non-overlapping epitope on DLL3.

In some embodiments, the first and second DLL3 VHH domain bind a distinct or non-overlapping epitope of DLL3 and/or do not compete for binding to DLL3.

In some cases, the first sdAb VHH domain comprises the amino acid sequence set forth in any one of 264, 287, 299, 306, or 318, a humanized variant thereof, or a sequence of amino acids that exhibits at least 85%, 86%, 87%, 88%, 89%, 90%, 91%, 92%, 93%, 94%, 95%, 96%, 97%, 98%, or 99% sequence identity to any of 264, 287, 299, 306, or 318, and binds DLL3; and the second sdAbVHH domain comprises the amino acid sequence set forth in any one of 244, 258, 275, 280, 314, 316 or 317, a humanized variant thereof, or a sequence of amino acids that exhibits at least 85%, 86%, 87%, 88%, 89%, 90%, 91%, 92%, 93%, 94%, 95%, 96%, 97%, 98%, or 99% sequence identity to any of 244, 258, 275, 280, 314, 316 or 317 and binds DLL3.

In some cases, the first VHH domain comprises the amino acid sequence set forth in any one of SEQ ID NOs: 251, 264, 267, 268, 287, 299, 306, 314, 318, 455, 507, 517 a humanized variant thereof, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOs: 251, 264, 267, 268, 287, 299, 306, 314, 318, 455, 507, 517, and binds DLL3; and the second VHH domain comprises the amino acid sequence set forth in any one of SEQ ID NOs: 244, 251, 258, 267, 275, 280, 314, 315, 316, 317, 318, 455, 515, 516, 517, 518, or a humanized variant thereof, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOs: 244, 251, 258, 267, 275, 280, 314, 315, 316, 317, 318, 455, 515, 516, 517, 518, and binds DLL3.

In some cases, the first sdAb VHH domain comprises the amino acid sequence set forth in SEQ ID NO: 264 or a humanized variant thereof set forth in any of SEQ ID NOs:265-455, SEQ ID NO: 287 or a humanized variant thereof set forth in any of SEQ ID NOs:288-298, SEQ ID NO: 299 or a humanized variant thereof set forth in any of SEQ ID NOs: 300-305, SEQ ID NO: 306 or a humanized variant thereof set forth in any of SEQ ID NOs: 307-313, or SEQ ID NO: 318; and the second sdAbVHH domain comprises the amino acid sequence set forth in SEQ ID NO: 244 or a humanized variant thereof set forth in any of SEQ ID NOs:245-257, SEQ ID NO: 258 or a humanized variant thereof set forth in any of SEQ ID NOs: 259-263, SEQ ID NO: 275 or a humanized variant thereof set forth in any of SEQ ID NOs: 276-279, SEQ ID NO: 280 or a humanized variant thereof set forth in any of SEQ ID NOs: 281-286, SEQ ID NO: 314, SEQ ID NO: 316, or SEQ ID NO: 317.

In some cases, the first VHH domain comprises the amino acid sequence set forth in SEQ ID NO: 264 or a humanized variant thereof set forth in any of SEQ ID NOs: 265-274, 416, 455, or 476-478, SEQ ID NO: 287 or a humanized variant thereof set forth in any of SEQ ID NOs:102, 288-298, SEQ ID NO: 299 or a humanized variant thereof set forth in any of SEQ ID NOs: 300-305 or 480, SEQ ID NO: 306 or a humanized variant thereof set forth in any of SEQ ID NOs: 307-313, SEQ ID NO: 507 or a humanized variant thereof set forth in any of SEQ ID NOs: 508-514, SEQ ID NO: 318, or SEQ ID NO 517; and the second VHH domain comprises the amino acid sequence set forth in SEQ ID NO: 244 or a humanized variant thereof set forth in any of SEQ ID NOs:245-257, SEQ ID NO: 258 or a humanized variant thereof set forth in any of SEQ ID NOs: 259-263, SEQ ID NO: 275 or a humanized variant thereof set forth in any of SEQ ID NOs: 276-279 or 479, SEQ ID NO: 280 or a humanized variant thereof set forth in any of SEQ ID NOs: 281-286, SEQ ID NO: 314, SEQ ID NO: 316, SEQ ID NO:515, SEQ ID NO:516, or SEQ ID NO: 317.

In some embodiments, the first sdAbVHH domain and second sdAbVHH domain comprise the amino acid sequence selected from SEQ ID NO: 244 and SEQ ID NO: 264; SEQ ID NO: 314 and SEQ ID NO: 318; SEQ ID NO: 244 and SEQ ID NO: 306; SEQ ID NO: 314 and SEQ ID NO: 306; SEQ ID NO: 314 and SEQ ID NO: 299; SEQ ID NO: 251 and SEQ ID NO: 268; SEQ ID NO: 251 and SEQ ID NO: 267; SEQ ID NO: 275 and SEQ ID NO: 318; SEQ ID NO: 314 and SEQ ID NO: 287; SEQ ID NO: 314 and SEQ ID NO: 264; SEQ ID NO: 316 and SEQ ID NO: 318; SEQ ID NO: 317 and SEQ ID NO: 318; or SEQ ID NO: 244 and SEQ ID NO: 318. In some embodiments, the first sdAbVHH domain and second sdAbVHH domain comprises the amino acid sequences set forth in SEQ ID NO: 315 and SEQ ID NO:318. In some embodiments, the first sdAbVHH domain and second sdAbVHH domain comprises the amino acid sequences set forth in SEQ ID NO: 251 and SEQ ID NO:455.

In some embodiments, the first VHH domain and second VHH domain comprise the amino acid sequence selected from SEQ ID NO: 244 and SEQ ID NO: 264; SEQ ID NO: 314 and SEQ ID NO: 318; SEQ ID NO: 314 and SEQ ID NO: 517; SEQ ID NO: 244 and SEQ ID NO: 306; SEQ ID NO: 244 and SEQ ID NO: 507; SEQ ID NO: 314 and SEQ ID NO: 306; SEQ ID NO: 314 and SEQ ID NO: 507; SEQ ID NO: 314 and SEQ ID NO: 299; SEQ ID NO: 251 and SEQ ID NO: 268; SEQ ID NO: 251 and SEQ ID NO: 267;

SEQ ID NO: 275 and SEQ ID NO: 318; 275 and SEQ ID NO: 517; SEQ ID NO: 314 and SEQ ID NO: 287; SEQ ID NO: 314 and SEQ ID NO: 264; SEQ ID NO: 314 and SEQ ID NO: 314; SEQ ID NO: 315 and SEQ ID NO: 264; SEQ ID NO: 518 and SEQ ID NO: 264; SEQ ID NO: 316 and SEQ ID NO: 318; SEQ ID NO: 515 and SEQ ID NO: 517; SEQ ID NO: 318 and SEQ ID NO: 318; SEQ ID NO: 517 and SEQ ID NO: 517; SEQ ID NO: 317 and SEQ ID NO: 318; SEQ ID NO: 516 and SEQ ID NO: 517; SEQ ID NO:251 and SEQ ID NO:455; SEQ ID NO: 244 and SEQ ID NO: 517; or SEQ ID NO: 244 and SEQ ID NO: 318. In some embodiments, the first VHH domain and second VHH domain comprises the amino acid sequences set forth in SEQ ID NO: 315 and SEQ ID NO:318. In some embodiments, the first VHH domain and second VHH domain comprises the amino acid sequences set forth in SEQ ID NO: 518 and SEQ ID NO:517. In some embodiments, the first VHH domain and second VHH domain comprises the amino acid sequences set forth in SEQ ID NO: 251 and SEQ ID NO:455.

In some embodiments, a constrained multispecific polypeptide construct contains at least one DLL3 VHH domains, such as any provided herein, and at least one further antigen binding domain specific to another tumor associated antigen (TAA). In some embodiments, the at least one further antigen binding domain includes one or more copies of an antibody or an antigen-binding fragment thereof selected from the group consisting of a Fab fragment, a F(ab')$_2$ fragment, an Fv fragment, a scFv, a scAb, a dAb, a single domain heavy chain antibody, and a single domain light chain antibody. In particular embodiments, the further TAA antigen binding domain is a single chain antibody. In some examples, the single chain is an scFv, a scAb, a single domain heavy chain antibody, or a single domain light chain antibody. For example, in some cases, the further TAA antigen binding domain includes one or more single domain antibody (sdAb) fragments, for example V$_H$H, V$_{NAR}$, engineered V$_H$ or V$_K$ domains. V$_H$Hs can be generated from natural camelid heavy chain only antibodies, genetically modified rodents that produce heavy chain only antibodies, or naïve/synthetic camelid or humanized camelid single domain antibody libraries. V$_{NAR}$S can be generated from cartilaginous fish heavy chain only antibodies. Various methods have been implemented to generate monomeric sdAbs from conventionally heterodimeric V$_H$ and V$_K$ domains, including interface engineering and selection of specific germline families.

In some embodiments, the further TAA is selected from the group consisting of 1-92-LFA-3, 5T3, Alpha-4 integrin, Alpha-V integrin, alpha4beta1 integrin, alpha4beta7 integrin, AGR2, Anti-Lewis-Y, Apelin J receptor, APRIL, B7-H3, B7-H4, BAFF, BTLA, C5 complement, C-242, CA9, CA19-9, (Lewis a), Carbonic anhydrase 9, CD2, CD3, CD6, CD9, CD11a, CD19, CD20, CD22, CD24, CD25, CD27, CD28, CD30, CD33, CD38, CD40, CD40L, CD41, CD44, CD44v6, CD47, CD51, CD52, CD56, CD64, CD70, CD71, CD74, CD80, CD81, CD86, CD95, CD117, CD123, CD125, CD132, (IL-2RG), CD133, CD137, CD138, CD166, CD172A, CD248, CDH6, CEACAM5 (CEA), CEACAM6 (NCA-90), CLAUDIN-3, CLAUDIN-4, cMet, Collagen, Cripto, CSFR, CSFR-1, CTLA-4, CTGF, CXCL10, CXCL13, CXCR1, CXCR2, CXCR4, CYR61, DL44, DLK1, DLL4, DPP-4, DSG1, EDA, EDB, EGFR, EGFRviii, Endothelin B receptor (ETBR), ENPP3, EpCAM, EPHA2, EPHB2, ERBB3, F protein of RSV, FAP, FGF-2, FGF8, FGFR1, FGFR2, FGFR3, FGFR4, FLT-3, Folate receptor alpha (FRα), GAL3ST1, G-CSF, G-CSFR, GD2, GITR, GLUT1, GLUT4, GM-CSF, GM-CSFR, GP Hb/IIIc receptors, Gp130, GPIIB/IIIA, GPNMB, GRP78, HER2/neu, HER3, HER4, HGF, hGH, HVEM, Hyaluronidase, ICOS, IFNalpha, IFNbeta, IFNgamma, IgE, IgE Receptor (FceRI), IGF, IGF1R, IL1B, IL1R, IL2, IL11, IL12, IL12p40, IL-12R, IL-12Rbeta1, IL13, IL13R, IL15, IL17, IL18, IL21, IL23, IL23R, IL27/IL27R (wsx1), IL29, IL-31R, IL31/IL31R, IL2R, IL4, IL4R, IL6, IL6R, Insulin Receptor, Jagged Ligands, Jagged 1, Jagged 2, KISS1-R, LAG-3, LIF-R, Lewis X, LIGHT, LRP4, LRRC26, Ly6G6D, LyPD1, MCSP, Mesothelin, MRP4, MUC1, Mucin-16 (MUC16, CA-125), Na/K ATPase, NGF, Nicastrin, Notch Receptors, Notch 1, Notch 2, Notch 3, Notch 4, NOV, OSM-R, OX-40, PAR2, PDGF-AA, PDGF-BB, PDGFRalpha, PDGFRbeta, PD-1, PD-L1, PD-L2, Phosphatidylserine, P1GF, PSCA, PSMA, PSGR, RAAG12, RAGE, SLC44A4, Sphingosine 1 Phosphate, STEAP1, STEAP2, TAG-72, TAPA1, TEM-8, TGFbeta, TIGIT, TIM-3, TLR2, TLR4, TLR6, TLR7, TLR8, TLR9, TMEM31, TNFalpha, TNFR, TNFRS12A, TRAIL-R1, TRAIL-R2, Transferrin, Transferrin receptor, TRK-A, TRK-B, uPAR, VAP1, VCAM-1, VEGF, VEGF-A, VEGF-B, VEGF-C, VEGF-D, VEGFR1, VEGFR2, VEGFR3, VISTA, WISP-1, WISP-2, and WISP-3.

In some embodiments, the antigen binding domain, such as a DLL3 VHH domain, is linked, directly or indirectly via a linker, to the Fc region and/or to the CD3 binding region. In some embodiments, linkage is via a linker. In some embodiments, the linker is a linking peptide (LP), which can include any flexible or rigid linker as described. In some embodiments, the linker is selected from the group consisting of GGSGGS, i.e., (GGS)$_2$ (SEQ ID NO: 1); GGSGGSGGS, i.e., (GGS)$_3$ (SEQ ID NO: 2); GGSGGSGGSGGS, i.e., (GGS)$_4$ (SEQ ID NO: 3); and GGSGGSGGSGGSGGS, i.e., (GGS)$_5$ (SEQ ID NO: 4). In some embodiments, the linker is a flexible linker comprising Glycine residues, such as, by way of non-limiting example, GG, GGG, GGGG (SEQ ID NO: 5), GGGGG (SEQ ID NO: 6), and GGGGGG (SEQ ID NO: 7). In some embodiments, the linker is (GGGGS)$_n$, wherein n is 1 to 5 (SEQ ID NO:123); (GGGGGS)$_n$, wherein n is 1 to 4 (SEQ ID NO:124); GGGGS (SEQ ID NO:125); GGGGGS (SEQ ID NO:126); GGGGGSGGGGSGGGGS (SEQ ID NO:127); GGGGSGGGGSGGGGS (SEQ ID NO:128); or GGSGGGSGGGGSGGGGS (SEQ ID NO:129). In some embodiments, the linker includes a combination of a GS-linker and a Glycine linker.

b. Fc Region

A constrained multispecific polypeptide construct includes an immunoglobulin Fc region. Generally, the constrained multispecific polypeptide construct is a dimer formed by polypeptides, each containing an Fc. The Fc polypeptide can be any as set forth above. In particular embodiments, the Fc region is formed by Fc domains that are mutated or modified to promote heterodimerization in which different polypeptides can be dimerized to yield a heterodimer. Thus, in some embodiments, the dimer is a heterodimer in which two polypeptide chains of the multispecific polypeptide construct are different.

Various methods are known for promoting heterodimerization of complementary Fc polypeptides, see e.g. Ridgway et al, Protein Eng. 9:617-621 (1996); Merchant et al, Nat. Biotechnol. 16(7): 677-81 (1998); Moore et al. (2011) MAbs, 3:546-57; Von Kreudenstein et al. MAbs, (2013) 5:646-54; Gunasekaran et al. (2010) J. Biol. Chem., 285:19637-46; Leaver-Fay et al. (2016) Structure, 24:641-51; Ha et al. (2016) Frontiers in Immunology, 7:1; Davis et al. (2010) Protein Eng Des Sel, 23:195-202; published international PCT Appl. No. WO 1998/050431, WO 2009/089004, WO2011143545 WO 2014/067011, WO 2012/058768, WO2018027025; published U.S. patent Appl. No. US20140363426, US20150307628, US20180016354, US20150239991; and U.S. patent Nos. U.S. Pat. Nos. 5,731,168, 7,183,076, 9,701,759, 9,605,084, and 9,650,446. Methods to promote heterodimerization of Fc chains include mutagenesis of the Fc region, such as by including a set of "knob-into-hole" mutations or including mutations to effect electrostatic steering of the Fc to favor attractive interactions among different polypeptide chains. For example, in some embodiments, the Fc polypeptides of a heterodimer includes a mutation to alter charge polarity across the Fc dimer interface such that coexpression of electrostatically matched Fc chains support favorable attractive interactions thereby promoting desired Fc heterodimer formation, whereas unfavorable repulsive charge interactions suppress unwanted Fc homodimer formation (Guneskaran et al. (2010) JBC, 285: 19637-19646). When co-expressed in a cell, association between the chains is possible but the chains do not substantially self-associate due to charge repulsion. Other strategies for generating a heterodimeric Fc include mixing human IgG and IgA CH3 domain segments to create a complementary CH3 heterodimer, which is referred to as a SEED Fc.

Methods and variants for heterodimerization also include those described in published international PCT App. WO2014/145806, including "knobs and holes" mutations (also called "skew" variants), mutations that relate to "electrostatic steering" or "charge pairs," and pI variants. Heterodimeric variants also include any as described in U.S. published Appl. No. US2012/0149876 or US2018/011883.

In some embodiments, to promote heterodimerization both polypeptides of the Fc heterodimer contain paired or complementary amino acid modifications. Exemplary paired amino acid modification of polypeptides of an Fc fusion are set forth in Table 3.

TABLE 3

Paired amino acids of Heterodimeric Fc

| First Fc polypeptide | Second Fc Polypeptide |
|---|---|
| T366W | T366S/L368W/Y407V |
| T366W/S354C | T366S/L368A/Y407V/Y349C |
| S364H/F405A | Y349T/Y349F |
| T350V/L351Y/F405A/Y407V | T350V/T366L/K392L/T394W |
| K360D/D399M/Y407A | E345R/Q347R/T366V/K409V |
| K409D/K392D | D399K/E356K |
| K360E/K409W | Q347R/D399V/F405T |
| L360E/K409W/Y349C | Q347R/399V/F405T/S354C |
| K370E/K409W | E357N/D399V/F405T |

In some embodiments, modifications include introduction of a protuberance (knob) into a first Fc polypeptide and a cavity (hole) into a second Fc polypeptide such that the protuberance is positionable in the cavity to promote complexing of the first and second Fc-containing polypeptides. Amino acids targeted for replacement and/or modification to create protuberances or cavities in a polypeptide are typically interface amino acids that interact or contact with one or more amino acids in the interface of a second polypeptide.

In some embodiments, a first Fc polypeptide that is modified to contain protuberance (hole) amino acids include replacement of a native or original amino acid with an amino acid that has at least one side chain which projects from the interface of the first Fc polypeptide and is therefore positionable in a compensatory cavity (hole) in an adjacent interface of a second polypeptide. Most often, the replacement amino acid is one which has a larger side chain volume than the original amino acid residue. One of skill in the art knows how to determine and/or assess the properties of amino acid residues to identify those that are ideal replacement amino acids to create a protuberance. In some embodiments, the replacement residues for the formation of a protuberance are naturally occurring amino acid residues and include, for example, arginine (R), phenylalanine (F), tyrosine (Y), or tryptophan (W). In some examples, the original residue identified for replacement is an amino acid residue that has a small side chain such as, for example, alanine, asparagine, aspartic acid, glycine, serine, threonine, or valine.

In some embodiments, a second Fc polypeptide that is modified to contain a cavity (hole) is one that includes replacement of a native or original amino acid with an amino acid that has at least one side chain that is recessed from the interface of the second polypeptide and thus is able to accommodate a corresponding protuberance from the interface of a first polypeptide. Most often, the replacement amino acid is one which has a smaller side chain volume than the original amino acid residue. One of skill in the art knows how to determine and/or assess the properties of amino acid residues to identify those that are ideal replacement residues for the formation of a cavity. Generally, the replacement residues for the formation of a cavity are naturally occurring amino acids and include, for example, alanine (A), serine (S), threonine (T) and valine (V). In some examples, the original amino acid identified for replacement is an amino acid that has a large side chain such as, for example, tyrosine, arginine, phenylalanine, or tryptophan.

The CH3 interface of human IgG1, for example, involves sixteen residues on each domain located on four anti-parallel β-strands which buries 1090 Å2 from each surface (see e.g., Deisenhofer et al. (1981) Biochemistry, 20:2361-2370; Miller et al., (1990) J Mol. Biol., 216, 965-973; Ridgway et al., (1996) Prot. Engin., 9: 617-621; U.S. Pat. No. 5,731,168). Modifications of a CH3 domain to create protuberances or cavities are described, for example, in U.S. Pat. No. 5,731,168; International Patent Applications WO98/50431 and WO 2005/063816; and Ridgway et al., (1996) Prot. Engin., 9: 617-621. In some examples, modifications of a CH3 domain to create protuberances or cavities are typically targeted to residues located on the two central anti-parallel β-strands. The aim is to minimize the risk that the protuberances which are created can be accommodated by protruding into the surrounding solvent rather than being accommodated by a compensatory cavity in the partner CH3 domain.

For example, in some embodiments the heterodimeric Fc includes a polypeptide having an amino acid modification within the CH3 domain at Thr366, which when replaced with a more bulky amino acid, e.g., Try (T366W), is able to preferentially pair with a second CH3 domain having amino acid modifications to less bulky amino acids at positions Thr366, Leu368, and Tyr407, e.g., Ser, Ala and Val, respectively (T366S/L368A/Y407V). Heterodimerization via CH3 modifications can be further stabilized by the introduction of a disulfide bond, for example by changing Ser354 to Cys (S354C) and Tyr349 to Cys (Y349C) on opposite CH3 domains (Reviewed in Carter, 2001 Journal of Immunological Methods, 248: 7-15).

In particular embodiments, a multispecific polypeptide construct contains a first and second Fc able to mediate Fc heterodimerization contains a first Fc polypeptide containing mutations T366W and S354C and a second Fc polypeptide containing mutations T366S, L368A, Y407V and Y349C. In some embodiments, the first Fc polypeptide is selected from an Fc polypeptide comprising the sequence set forth in SEQ ID NO: 440 or 446 and the second Fc polypeptide is selected from an Fc polypeptide comprising the sequence set forth in SEQ ID NO: 441, 444 or 448. In some embodiments, the first Fc polypeptide is or comprises the sequence of amino acids set forth in any of SEQ ID NOS:103, 107, 115 or 117 and the second Fc polypeptide is or comprises the sequence of amino acids set forth in any of SEQ ID NOS:104, 108, 111, 113, 119 or 121.

In some embodiments, the Fc polypeptide exhibits features providing Fc-mediated effector functions. In particular examples, the first Fc polypeptide is or comprises the sequence set forth in SEQ ID NOs:440 and a second Fc polypeptide that is or comprises SEQ ID NO: 441 or 444. In some embodiments, the first Fc polypeptide is or comprises the sequence set forth in SEQ ID NO: 103 and the second Fc polypeptide is or comprises the sequence set forth in SEQ ID NO: 104 or 111. In some embodiments, the first Fc polypeptide is or comprises the sequence set forth in SEQ ID NO: 107 and the second Fc polypeptide is or comprises the sequence set forth in SEQ ID NO: 108 or 113. The first and second Fc polypeptide can be formatted on either polypeptide chain of the construct.

In some embodiments, one or both of the first and second Fc polypeptides can further include one or more amino acid mutations to further reduce one or more Fc effector functions, such as reduced Fc receptor binding. Exemplary mutations to reduce Fc effector functions include any as described. In some embodiments, the modification can be a deletion of one or more positions Glu233 (E233), Leu234 (L234), or Leu235 (L235), such as a deletion of amino acids Glu233 (E233), Leu234 (L234), and Leu235 (L235). In some embodiments, the first Fc polypeptide is selected from an Fc polypeptide comprising the sequence set forth in SEQ ID NO: 442 or 447 and the second Fc polypeptide is selected from an Fc polypeptide comprising the sequence set forth in SEQ ID NO: 443, 445 or 449. In some embodiments, the first Fc polypeptide is or comprises the sequence of amino acids set forth in any of SEQ ID NOS:105, 109, 116 or 118 and the second Fc polypeptide is or comprises the sequence of amino acids set forth in any of SEQ ID NOS: 106, 110, 112, 114, 120 or 122.

In particular examples, the first Fc polypeptide is or comprises the sequence set forth in SEQ ID NOs:442 and a second Fc polypeptide that is or comprises SEQ ID NO: 443 or 445. In some embodiments, the first Fc polypeptide is or comprises the sequence set forth in SEQ ID NO: 105 and the second Fc polypeptide is or comprises the sequence set forth in SEQ ID NO: 106 or 112. In some embodiments, the first Fc polypeptide is or comprises the sequence set forth in SEQ ID NO: 109 and the second Fc polypeptide is or comprises the sequence set forth in SEQ ID NO: 110 or 114. The first and second Fc polypeptide can be formatted on either polypeptide chain of the construct.

In some embodiments, the first Fc polypeptide or second Fc polypeptide further includes mutations M252Y and/or M428V. In particular examples, the first Fc polypeptide is or comprises the sequence set forth in SEQ ID NO:446 and the second Fc polypeptide is or comprises the sequence set forth in SEQ ID NO:448. In some embodiments, the first Fc polypeptide is or comprises the sequence set forth in SEQ ID NO:115 and the second Fc polypeptide is or comprises the sequence set forth in SEQ ID NO: 119. In some embodiments, the first Fc polypeptide is or comprises the sequence set forth in SEQ ID NO:117 and the second Fc polypeptide is or comprises the sequence set forth in SEQ ID NO: 121. In other examples, the first Fc polypeptide is or comprises the sequence set forth in SEQ ID NO:447 and the second Fc polypeptide is or comprises the sequence set forth in SEQ ID NO:449. In some embodiments, the first Fc polypeptide is or comprises the sequence set forth in SEQ ID NO:116 and the second Fc polypeptide is or comprises the sequence set forth in SEQ ID NO: 120. In some embodiments, the first Fc polypeptide is or comprises the sequence set forth in SEQ ID NO:118 and the second Fc polypeptide is or comprises the sequence set forth in SEQ ID NO: 122. The first and second Fc polypeptide can be formatted on either polypeptide chain of the construct.

Additional examples of variants that can facilitate the promotion of heterodimers are any combination or pair of steric variants (e.g. skew variants) of a first Fc polypeptide and a second Fc polypeptide from among: S364K/E357Q and L368D/K370S; L368D/K370S and S364K; L368E/K370S and S364K; T411T/E360E/Q362E and D401K; L368D/K370S and S364K/E357L, K370S and S364K/E357Q and T366S/L368A/Y407V and T366W or 3665/L368A/Y407V/Y349C and T366W/S354C), where each pair represents mutations in the first Fc polypeptide and second Fc polypeptide. In particular embodiments, a provided construct contains a first and second Fc polypeptide containing the pair of mutations L368D/K370S and S364K and E357Q.

An additional mechanism that can be used in the generation of heterodimers is sometimes referred to as "electrostatic steering" as described in Gunasekaran et al., J. Biol. Chem. 285(25):19637 (2010). This is sometimes referred to herein as "charge pairs". In this embodiment, electrostatics are used to skew the formation towards heterodimerization. As those in the art will appreciate, these may also have an effect on pI, and thus on purification, and thus could in some cases also be considered pI variants. However, as these were generated to force heterodimerization and were not used as purification tools, they are classified as "steric variants". In one embodiments, a first Fc polypeptide can contain mutations D221E/P228E/L368E and a second Fc polypeptide can contain mutations D221R/P228R/K409R. In another embodiments, a first Fc polypeptide can contain mutations C220E/P228E/368E and a second Fc polypeptide can contain mutations C220R/E224R/P228R/K409R.

In some embodiments, heterodimerization can be facilitated by pI variants. In some aspects, a pI variant can include those that increase the pI of the protein (basic changes). In other aspects, the pI variant can include those that decrease the pI of the protein (acidic changes). In some cases, all combinations of these variants can be done, including combinations in which one Fc polypeptide may be wild type, or a variant that does not display a significantly different pI from wild-type, and the other Fc polypeptide can be either more basic or more acidic. Alternatively, each Fc polypeptide can be changed, one to more basic and one to more acidic. In some embodiments, at least one Fc polypeptide is a negative pI variant Fc containing mutations Q295E/N384D/Q418E/N421D.

In some embodiments, a combination of steric heterodimerization variants (e.g. knob and hole) and pI or charge pair variants can be used.

In particular embodiments, the provided constructs contains (a) a first Fc polypeptide comprising the skew variants S364K/E357Q; and b) a second Fc polypeptide containing skew variants L368D/K370S and the pI variants N208D/Q295E/N384D/Q418E/N421D. In some embodiments, one or both of the first and second polypeptide can contain further mutations to reduce Fc effector activity, such as the exemplary mutations E233P/L234V/L235A/G236del/S267K. An example of such a first Fc polypeptide and a second Fc polypeptide able to mediate Fc heterodimeriztion comprise the sequences set forth in SEQ ID NOs:472 and 473. The first and second Fc polypeptide can be formatted on either polypeptide chain of the construct.

The resulting constrained multispecific polypeptide constructs can be purified by any suitable method such as, for example, by affinity chromatography over Protein A or Protein G columns Where two nucleic acid molecules encoding different polypeptides are transformed into cells, formation of homo- and heterodimers will occur. Conditions for expression can be adjusted so that heterodimer formation is favored over homodimer formation.

Techniques for recovery of heterodimers from homodimers based on a differential affinity of the heterodimers for an affinity reagent are known. In some aspects, such techniques include designing a heterodimer so that one of the Fc polypeptide chains does not bind to the affinity reagent protein A. In some cases, one of the polypeptide chain can contain one or more amino acid substitution to abrogate or reduce affinity for the protein A reagent in one of the polypeptides of the Fc heterodimer, see e.g. WO2017134440, WO2010151792, Jendeberg et al. (Jendeberg et al., (1997) J. Immunol. Methods, 201(1): 25-34. In some of these embodiments, the Fc region may be modified at the protein-A binding site on one member of the heterodimer so as to prevent protein-A binding and thereby enable more efficient purification of the heterodimeric fusion protein. An exemplary modification within this binding site is Ile253, for example Ile253Arg (I253R). In some embodiments, the modification may be H435R or H435R/Y436F. In some embodiments, an Fc polypeptide of an Fc heterodimer can contain a modification so that it is capable of binding protein A but not protein G (pA+/pG−). Exemplary pA+/pG− amino acid modifications include an Fc containing serine at position 428, serine at position 434 and optionally histidine at position 436, with reference to human IgG1 or comprising these residues at the corresponding positions in human IgG 2, 3, or 4. In some aspects, such amino acid modifications in one IgG Fc polypeptide at positions 428, 434 and optionally 436 reduces or prevents the binding of protein G, enhancing the purification of the protein.

In some embodiments, any of such modifications to confer differential affinity to an affinity reagent can be combined with any one or more other amino acid modifications described above. For example, the I253R modification may be combined with either the T366S/L368A/Y407V modifications or with the T366W modifications. The T366S/L368A/Y407V modified Fc is capable of forming homodimers as there is no steric occlusion of the dimerization interface as there is in the case of the T336W modified Fc. Therefore, in some embodiments, the I253R modification is combined with the T366S/L368A/Y407V modified Fc to disallow purification any homodimeric Fc that may have formed. Similar modifications can be employed by combining T366S/L368A/Y407V and H453R.

In some embodiments, the Fc regions of the heterodimeric molecule additionally can contain one or more other Fc mutation, such as any described above. In some embodiments, the heterodimer molecule contains an Fc region with a mutation that reduces effector function. In some embodiments, the Fc region is altered to provide reduced Fc-mediated effector functions, such as via reduced Fc receptor binding, e.g. binding to FcγR binding but generally not FcRn binding.

In some embodiments, the Fc region is mutated in one or more of the following positions to reduce Fc receptor binding: Glu233 (E233), Leu234 (L234), or Leu235 (L235). The one or more mutations can include E233P, L234V and/or L235A.

In particular embodiments, the mutations of the Fc region to reduce Fc effector function, e.g. via reducing Fc receptor binding to FcγR, include mutations from among any of G236R/L328R, E233P/L234V/L235A/G236del/S239K, E233P/L234V/L235A/G236del/S267K, E233P/L234V/L235A/G236del/S239K/A327G, E233P/L234V/L235A/G236del/S267K/A327G or E233P/L234V/L235A/G236del, D265A/P329A, D265A/P329G, D265A/N297A, L234V/L235A/D265A, L234V/L235A/N297A, L234V/L235A/P329A, or L234V/L235A/P329G.

In some embodiments, one Fc polypeptide of a heterodimeric Fc comprises the sequence of amino acids set forth in any of SEQ ID NOS: 440 (e.g. SEQ ID NO:103 or 107), 446 (e.g. SEQ ID NO:115 or 117), and the other Fc polypeptide of the heterodimeric Fc contains the sequence of amino acids set forth in any of SEQ ID NOS: 441 (e.g. SEQ ID NO:104 or 108), 444 (e.g. SEQ ID NO:111 or 113), 448 (e.g. SEQ ID NO:119 or 121). In some embodiments, one Fc polypeptide of a heterodimeric Fc comprises the sequence of amino acids set forth in any of SEQ ID NOS: 442 (SEQ ID NO:105 or 109), 447 (e.g. SEQ ID NO:116 or 118) and the other Fc polypeptide of the heterodimeric Fc comprises the sequence of amino acids set forth in any of SEQ ID NOS: 443 (e.g. SEQ ID NO:106 or 110), 445 (e.g. SEQ ID NO:112 or 114), 449 (e.g. SEQ ID NO:120 or 122).

In some embodiments, the Fc region of the provided multispecific polypeptide constructs exhibit one or more effector functions. In some cases, the Fc region is capable of providing Fc-mediated effector functions, such as for example, ADCC (e.g., release of granzyme B by NK cells), ADCP, and/or CDC. In general, the Fc region is responsible for effector functions, such as complement-dependent cytotoxicity (CDC) and antibody-dependent cell cytotoxicity (ADCC), in addition to the antigen-binding capacity, which is the main function of immunoglobulins. Additionally, the FcRn sequence present in the Fc region plays the role of regulating the IgG level in serum by increasing the in vivo half-life by conjugation to an in vivo FcRn receptor. In some embodiments in which the multispecific polypeptide constructs contain a cleavable linker, cleavage of the linker can produce two components that each have biological activity: the CD3-binding region that is able to bind and engage CD3 on a T cell, which, in some aspects, also can contain a CRBR for inducing a costimulatory signal on the T cell and/or an IRBR for inducing an inhibitory signal on the T cell; and the Fc region linked to the DLL3 VHH domain that can exhibit target-specific effector function. In particular embodiments provided herein, the multispecific polypeptide constructs contain a non-cleavable linker and may, in some aspects, not exhibit an independent Fc-mediated effector function.

In some embodiments, the Fc region includes an Fc polypeptide that is mutated or modified to alter one or more effector functions. Thus, in some cases, effector functions such as on or more of ADCC, ADCP and/or CDC can be altered, such as reduced or enhanced, in an Fc for use with the provided constrained multispecific polypeptide constructs. Exemplary mutations to reduce effector function include any as described above.

In some embodiments, an IgG1 Fc polypeptide or a variant thereof such as any described below can be made in a G1 ml or G1 m3 allotype. In some embodiments, the Fc region can contain amino acids of the human G1 ml allotype, such as residues containing Asp (D) and Leu (L) at positions 356 and 358, e.g. as set forth in SEQ ID NO:8. In some cases, an Fc polypeptide can contain amino acid substitutions E356D and M358L to reconstitute residues of allotype G1 ml. In other embodiments, the Fc region can contain amino acids of the human G1 m3 allotype, such as residues Glu (E) and Met (M) at positions 356 and 358 by EU numbering, e.g. as set forth in SEQ ID NOS: 472 and 473. In some cases, an Fc polypeptide can contain amino acid substitutions D356E and L358M to reconstitute residues of allotype G1 m3.

c. CD3 Binding Domain

A constrained multispecific polypeptide construct includes one or more copies of an anti-CD3 binding domain. The anti-CD3 binding domains of the disclosure activate T cells via engagement of CD3 or a member of the CD3 complex on the T cells. In preferred embodiments, the anti-CD3 binding domains of the disclosure specifically bind the epsilon chain of CD3, also known as CD3ε. The anti-CD3ε binding domains of the disclosure activate T cells via engagement of CD3ε on the T cells. The anti-CD3 binding domains of the disclosure agonize, stimulate, activate, and/or otherwise augment CD3-mediated T cell activation. Biological activities of CD3 include, for example, T cell activation and other signaling through interaction between CD3 and the antigen-binding subunits of the T-Cell Receptor (TCR). For example, the anti-CD3 binding domains of the disclosure completely or partially activate T cells via engagement of CD3ε on T cells by partially or completely modulating, e.g., agonizing, stimulating, activating or otherwise augmenting CD3-mediated T cell activation.

The CD3 binding domain can be any as described above. In particular embodiments, the CD3 binding domain is an an Fv antibody fragment that binds CD3ε (referred to herein as an anti-CD3ε Fv fragment). In some embodiments, the anti-CD3ε Fv antibody fragment is a disulfide stabilized anti-CD3 binding Fv fragment (dsFv). In some embodiments, the anti-CD3 binding domain is monovalent for binding CD3.

In some embodiments, the CD3 binding region is an Fv antibody fragment containing a variable heavy chain (Hv, also called VH) and variable light chain (Lv, also called VL), such as any as described. In aspects of such embodiments, the immunoglobulin Fc region is a heterodimeric Fc region containing two different Fc polypeptides capable of heterodimeric association between both polypeptides of the Fc heterodimer, such as any as described. In such embodiments, the variable heavy chain (VH) and variable light chain (VL) of the CD3 binding region are linked on opposite chains of the heterodimeric Fc.

In some embodiments, the CD3 binding region is an Fv or dsFv of SP34 (Pessano et ai. The EMBO Journal. 4: 337-344, 1985) or of a humanized variant of SP34 (WO2015001085).

In some embodiments, the anti-CD3ε binding domain thereof is an Fv, such as a dsFv fragment, that includes a combination of heavy chain variable amino acid sequence and a light chain variable amino acid sequence. In some embodiments, the CD3-binding domain is an Fv or dsFv fragment in which is contained a VH CDR1 sequence that includes at least the amino acid sequence TYAMN (SEQ ID NO: 29); a VH CDR2 sequence that includes at least the amino acid sequence RIRSKYNNYATYYADSVKD (SEQ ID NO: 30); a VH CDR3 sequence that includes at least the amino acid sequence HGNFGNSYVSWFAY (SEQ ID NO: 31), a VL CDR1 sequence that includes at least the amino acid sequence RSSTGAVTTSNYAN (SEQ ID NO: 32); a VL CDR2 sequence that includes at least the amino acid sequence GTNKRAP (SEQ ID NO: 33); and a VL CDR3 sequence that includes at least the amino acid sequence ALWYSNLWV (SEQ ID NO: 34). In some embodiments, the anti-CD3ε binding domain thereof is an Fv, such as a dsFv fragment, that includes a heavy chain variable amino acid sequence selected from the group of SEQ ID NO: 35-65 and a light chain variable amino acid sequence selected from the group consisting of SEQ ID NO: 66-84 or 368.

In some embodiments, the anti-CD3ε binding domain includes a VH CDR1 sequence that is at least 90%, 91%, 92%, 93%, 94%, 95%, 96%, 97%, 98%, 99% or more identical to the amino acid sequence TYAMN (SEQ ID NO: 29); a VH CDR2 sequence that is at least 90%, 91%, 92%, 93%, 94%, 95%, 96%, 97%, 98%, 99% or more identical to the amino acid sequence RIRSKYNNYATYYADSVKD (SEQ ID NO: 30); a VH CDR3 sequence that is at least 90%, 91%, 92%, 93%, 94%, 95%, 96%, 97%, 98%, 99% or more identical to the amino acid sequence HGNFGNSYVSWFAY (SEQ ID NO: 31), a VL CDR1 sequence that is at least 90%, 91%, 92%, 93%, 94%, 95%, 96%, 97%, 98%, 99% or more identical to the amino acid sequence RSSTGAVTTSNYAN (SEQ ID NO: 32); a VL CDR2 sequence that is at least 90%, 91%, 92%, 93%, 94%, 95%, 96%, 97%, 98%, 99% or more identical to the amino acid sequence GTNKRAP (SEQ ID NO: 33); and a VL CDR3 sequence that is at least 90%, 91%, 92%, 93%, 94%, 95%, 96%, 97%, 98%, 99% or more identical to the amino acid sequence ALWYSNLWV (SEQ ID NO: 34).

In some embodiments, the anti-CD3ε binding domain includes a VH CDR1 sequence that includes at least the amino acid sequence GFTFNTYAMN (SEQ ID NO: 461); a VH CDR2 sequence that includes at least the amino acid sequence RIRSKYNNYATY (SEQ ID NO: 462); a VH CDR3 sequence that includes at least the amino acid sequence HGNFGNSYVSWFAY (SEQ ID NO: 31), a VL CDR1 sequence that includes at least the amino acid sequence RSSTGAVTTSNYAN (SEQ ID NO: 32); a VL CDR2 sequence that includes at least the amino acid sequence GTNKRAP (SEQ ID NO: 33); and a VL CDR3 sequence that includes at least the amino acid sequence ALWYSNLWV (SEQ ID NO: 34).

In some embodiments, the anti-CD3ε binding domain includes a VH CDR1 sequence that is at least 90%, 91%, 92%, 93%, 94%, 95%, 96%, 97%, 98%, 99% or more identical to the amino acid sequence GFTFNTYAMN (SEQ ID NO: 461); a VH CDR2 sequence that is at least 90%, 91%, 92%, 93%, 94%, 95%, 96%, 97%, 98%, 99% or more identical to the amino acid sequence RIRSKYNNYATY (SEQ ID NO: 462); a VH CDR3 sequence that is at least 90%, 91%, 92%, 93%, 94%, 95%, 96%, 97%, 98%, 99% or more identical to the amino acid sequence HGNFGNSYVSWFAY (SEQ ID NO: 31), a VL CDR1 sequence that is at least 90%, 91%, 92%, 93%, 94%, 95%, 96%, 97%, 98%, 99% or more identical to the amino acid sequence RSSTGAVTTSNYAN (SEQ ID NO: 32); a VL CDR2 sequence that is at least 90%, 91%, 92%, 93%, 94%, 95%, 96%, 97%, 98%, 99% or more identical to the amino acid sequence GTNKRAP (SEQ ID NO: 33); and a VL CDR3 sequence that is at least 90%, 91%, 92%, 93%, 94%, 95%, 96%, 97%, 98%, 99% or more identical to the amino acid sequence ALWYSNLWV (SEQ ID NO: 34).

In some embodiments, the anti-CD3ε binding domain includes a VH CDR1 sequence that includes at least the amino acid sequence GFTFNTYAMN (SEQ ID NO: 461); a VH CDR2 sequence that includes at least the amino acid sequence RIRSKYNNYATY (SEQ ID NO: 462); a VH CDR3 sequence that includes at least the amino acid sequence HGNFGNSYVSWFAY (SEQ ID NO: 31), a VL CDR1 sequence that includes at least the amino acid sequence GSSTGAVTTSNYAN (SEQ ID NO: 468); a VL CDR2 sequence that includes at least the amino acid sequence GTNKRAP (SEQ ID NO: 469); and a VL CDR3 sequence that includes at least the amino acid sequence ALWYSNHWV (SEQ ID NO: 464).

In some embodiments, the anti-CD3ε binding domain includes a VH CDR1 sequence that is at least 90%, 91%, 92%, 93%, 94%, 95%, 96%, 97%, 98%, 99% or more identical to the amino acid sequence GFTFNTYAMN (SEQ ID NO: 461); a VH CDR2 sequence that is at least 90%, 91%, 92%, 93%, 94%, 95%, 96%, 97%, 98%, 99% or more identical to the amino acid sequence RIRSKYNNYATY (SEQ ID NO: 462); a VH CDR3 sequence that is at least 90%, 91%, 92%, 93%, 94%, 95%, 96%, 97%, 98%, 99% or more identical to the amino acid sequence HGNFGN-SYVSWFAY (SEQ ID NO: 31), a VL CDR1 sequence that is at least 90%, 91%, 92%, 93%, 94%, 95%, 96%, 97%, 98%, 99% or more identical to the amino acid sequence GSSTGAVTTSNYAN (SEQ ID NO: 468); a VL CDR2 sequence that is at least 90%, 91%, 92%, 93%, 94%, 95%, 96%, 97%, 98%, 99% or more identical to the amino acid sequence GTNKRAP (SEQ ID NO: 469); and a VL CDR3 sequence that is at least 90%, 91%, 92%, 93%, 94%, 95%, 96%, 97%, 98%, 99% or more identical to the amino acid sequence ALWYSNHWV (SEQ ID NO: 464).

In some embodiments, the anti-CD3ε binding domain includes a VH CDR1 sequence that includes at least the amino acid sequence GFTFSTYAMN (SEQ ID NO: 466); a VH CDR2 sequence that includes at least the amino acid sequence RIRSKYNNYATY (SEQ ID NO: 467); a VH CDR3 sequence that includes at least the amino acid sequence HGNFGDSYVSWFAY (SEQ ID NO: 463), a VL CDR1 sequence that includes at least the amino acid sequence GSSTGAVTTSNYAN (SEQ ID NO: 468); a VL CDR2 sequence that includes at least the amino acid sequence GTNKRAP (SEQ ID NO: 469); and a VL CDR3 sequence that includes at least the amino acid sequence ALWYSNHWV (SEQ ID NO: 464).

In some embodiments, the anti-CD3ε binding domain includes a VH CDR1 sequence that is at least 90%, 91%, 92%, 93%, 94%, 95%, 96%, 97%, 98%, 99% or more identical to the amino acid sequence GFTFSTYAMN (SEQ ID NO: 466); a VH CDR2 sequence that is at least 90%, 91%, 92%, 93%, 94%, 95%, 96%, 97%, 98%, 99% or more identical to the amino acid sequence RIRSKYNNYATY (SEQ ID NO: 467); a VH CDR3 sequence that is at least 90%, 91%, 92%, 93%, 94%, 95%, 96%, 97%, 98%, 99% or more identical to the amino acid sequence HGNFGDSYVSWFAY (SEQ ID NO: 463), a VL CDR1 sequence that is at least 90%, 91%, 92%, 93%, 94%, 95%, 96%, 97%, 98%, 99% or more identical to the amino acid sequence GSSTGAVTTSNYAN (SEQ ID NO: 468); a VL CDR2 sequence that is at least 90%, 91%, 92%, 93%, 94%, 95%, 96%, 97%, 98%, 99% or more identical to the amino acid sequence GTNKRAP (SEQ ID NO: 469); and a VL CDR3 sequence that is at least 90%, 91%, 92%, 93%, 94%, 95%, 96%, 97%, 98%, 99% or more identical to the amino acid sequence ALWYSNHWV (SEQ ID NO: 464).

In some embodiments, the anti-CD3ε binding domain includes a CDR3 that includes at least amino acids VLWYSNRWV (SEQ ID NO:465). In some embodiments, the anti-CD3ε binding domain includes a CDR3 that is at least 90%, 91%, 92%, 93%, 94%, 95%, 96%, 97%, 98%, 99% or more identical to the amino acids VLWYSNRWV (SEQ ID NO:465).

In some embodiments, the anti-CD3ε binding domain includes one or more copies of an antibody or an antigen-binding fragment thereof selected from the group consisting of a Fab fragment, a F(ab')$_2$ fragment, an Fv fragment, a scFv, a scAb, a dAb, a single domain heavy chain antibody, and a single domain light chain antibody. In some embodiments, the anti-CD3 binding domain includes an Fv antibody fragment that binds CD3ε (referred to herein as an anti-CD3ε Fv fragment). In some embodiments, the anti-CD3ε Fv antibody fragment is a disulfide stabilized anti-CD3 binding Fv fragment (dsFv). In some embodiments, the anti-CD3 binding domain is monovalent for binding CD3.

In some embodiments, the CD3 binding region is not a single chain antibody. For example, in some aspects, the CD3 binding region is not a single chain variable fragment (scFv).

In some embodiments, the CD3 binding region is an Fv antibody fragment containing a variable heavy chain (Hv, also called VH) and variable light chain (Lv, also called VL), such as any as described. In aspects of such embodiments, the immunoglobulin Fc region is a heterodimeric Fc region containing two different Fc polypeptides capable of heterodimeric association between both polypeptides of the Fc heterodimer, such as any as described in Section III.C.2.b. In such embodiments, the variable heavy chain (VH) and variable light chain (VL) of the CD3 binding region are linked on opposite chains of the heterodimeric Fc.

In some embodiments, the anti-CD3ε binding domain thereof includes a combination of a heavy chain variable region amino acid sequence and a light chain variable region amino acid sequence comprising an amino acid sequence selected from the group of SEQ ID NO: 27, 28, 35-84, 368, 451-454, and 460. In some embodiments, the anti-CD3ε binding domain thereof includes a combination of a heavy chain variable region amino acid sequence selected from the group of SEQ ID NO: 27, 35-65, 453 454, and 460 and a light chain variable region amino acid sequence comprising an amino acid sequence selected from the group of SEQ ID NO: 28, 66-84, 368, 451 and 452.

In some embodiments, the anti-CD3ε binding domain thereof is an Fv fragment that includes a combination of heavy chain variable amino acid sequence and a light chain variable amino acid sequence. In some embodiments, the anti-CD3ε binding domain thereof is an Fv fragment that includes a combination of heavy chain variable amino acid sequence and a light chain variable amino acid sequence comprising an amino acid sequence that is at least 90%, 91%, 92%, 93%, 94%, 95%, 96%, 97%, 98%, 99% or more identical to an amino acid sequence selected from the group consisting of SEQ ID NOs: 35-84, 368, 451-454 and 460. In some embodiments, the anti-CD3ε binding domain thereof is an Fv fragment that includes a combination of heavy chain variable amino acid sequence and a light chain variable amino acid sequence comprising an amino acid sequence selected from the group consisting of SEQ ID NOs: 35-84, 368, 451-454 and 460. In some embodiments, the anti-CD3ε binding domain thereof is an Fv fragment that includes a combination of heavy chain variable amino acid sequence selected from the group of SEQ ID NO: 35-65, 453, 454, and 460 and light chain variable amino acid sequence selected from the group consisting of SEQ ID NO: 66-84, 368, 451 and 452. In some embodiments, the anti-CD3ε binding domain thereof is an Fv fragment that includes a combination of heavy chain variable amino acid sequence that is at least 90%, 91%, 92%, 93%, 94%, 95%, 96%, 97%, 98%, 99% or more identical to an amino acid sequence selected from the group consisting of SEQ ID NO: 35-65, 453, 454, and 460 and a light chain variable amino acid sequence that is at least 90%, 91%, 92%, 93%, 94%, 95%, 96%, 97%, 98%, 99% or more identical to an amino acid sequence selected from the group consisting of SEQ ID NO: 66-84, 368, 451 and 452.

In some embodiments, the anti-CD3ε binding domain thereof is an Fv or dsFv fragment that includes a heavy chain variable amino acid sequence that is at least 90%, 91%, 92%, 93%, 94%, 95%, 96%, 97%, 98%, 99% or more identical to an amino acid sequence selected from the group consisting of SEQ ID NO: 35-65, 453, 454, and 460 and an amino acid sequence that is at least 90%, 91%, 92%, 93%, 94%, 95%, 96%, 97%, 98%, 99% or more identical to an amino acid sequence selected from the group consisting of SEQ ID NO: 66-84 or 368, 451 and 452. In some embodiments, the anti-CD3 binding domain is an Fv or dsFv, in which is contained a variable heavy chain (VH) comprising the amino acid sequence of SEQ ID NO: 47 and a variable light chain (VL) comprising the amino acid sequence of SEQ ID NO: 75. In some embodiments, the anti-CD3 binding domain is an Fv or dsFv, in which is contained a variable heavy chain (VH) comprising the amino acid sequence of SEQ ID NO: 47 and a variable light chain (VL) comprising the amino acid sequence of SEQ ID NO: 368.

In some embodiments, the anti-CD3ε binding domain thereof is an Fv fragment that includes a combination of heavy chain variable amino acid sequence and a light chain variable amino acid sequence. In some embodiments, the anti-CD3ε binding domain thereof is an Fv fragment that includes a combination of heavy chain variable amino acid sequence and a light chain variable amino acid sequence comprising an amino acid sequence that is at least 90%, 91%, 92%, 93%, 94%, 95%, 96%, 97%, 98%, 99% or more identical to an amino acid sequence selected from the group consisting of SEQ ID NOs: 27, 28, 35-84, 368, 451-454, 460. In some embodiments, the anti-CD3ε binding domain thereof is an Fv fragment that includes a combination of heavy chain variable amino acid sequence and a light chain variable amino acid sequence comprising an amino acid sequence selected from the group consisting of SEQ ID NOs: 27, 28, 35-84, 368, 451-454, 460. In some embodiments, the anti-CD3ε Fv antibody fragment includes a combination of a heavy chain variable amino acid sequence that is at least 90%, 91%, 92%, 93%, 94%, 95%, 96%, 97%, 98%, 99% or more identical to an amino acid sequence selected from the group consisting of SEQ ID NO: 27, 35-65, 453, 454, and 460 and a light chain variable amino acid sequence that is at least 90%, 91%, 92%, 93%, 94%, 95%, 96%, 97%, 98%, 99% or more identical to an amino acid sequence selected from the group consisting of SEQ ID NO: 28, 66-84, 368, 451 and 452. In some embodiments, the anti-CD3ε Fv antibody fragment includes a combination of a heavy chain variable amino acid sequence selected from the group of SEQ ID NO: 27, 35-65, 453, 454, and 460 and a light chain variable amino acid sequence selected from the group consisting of SEQ ID NO: 28, 66-84, 368, 451 and 452.

In some embodiments, the anti-CD3ε Fv antibody fragment includes a combination of a heavy chain variable amino acid sequence that is at least 90%, 91%, 92%, 93%, 94%, 95%, 96%, 97%, 98%, 99% or more identical to an amino acid sequence selected from the group consisting of SEQ ID NO: 27, 35-46, 48-50, 453, 454, and 460 and a light chain variable amino acid sequence that is at least 90%, 91%, 92%, 93%, 94%, 95%, 96%, 97%, 98%, 99% or more identical to an amino acid sequence selected from the group consisting of SEQ ID NO: 28, 66, 68-74, 76, 78, 80, 368, 451, and 452. In some embodiments, the anti-CD3ε Fv antibody fragment includes a combination of a heavy chain variable amino acid sequence selected from the group of SEQ ID NO: 27, 35-46, 48-50, 454 454, and 460 and a light chain variable amino acid sequence selected from the group consisting of SEQ ID NO: 28, 66, 68-74, 76, 78, 80, 451, and 452.

In some embodiments, the anti-CD3ε Fv antibody fragment includes a combination of a heavy chain variable amino acid sequence that is at least 90%, 91%, 92%, 93%, 94%, 95%, 96%, 97%, 98%, 99% or more identical to an amino acid sequence selected from the group consisting of SEQ ID NO: 27, 35-46, 48-50, 453 454, and 460 and a light chain variable amino acid sequence that is at least 90%, 91%, 92%, 93%, 94%, 95%, 96%, 97%, 98%, 99% or more identical to an amino acid sequence selected from the group consisting of SEQ ID NO: 28, 66, 68-74, 76, 78, 80, 368, 451, and 452. In some embodiments, the anti-CD3ε Fv antibody fragment includes a combination of a heavy chain variable amino acid sequence selected from the group of SEQ ID NO: 27, 35-46, 48-50, 454 454, and 460 and a light chain variable amino acid sequence selected from the group consisting of SEQ ID NO: 28, 66, 68-74, 76, 78, 80, 368, 451, and 452.

In some embodiments, the anti-CD3ε binding domain thereof includes a variable heavy chain (VH) comprising an amino acid sequence that is at least 90%, 91%, 92%, 93%, 94%, 95%, 96%, 97%, 98%, 99% or more identical to the amino acid sequence of SEQ ID NO:27. In some embodiments, the anti-CD3ε binding domain includes a variable light chain (VL) comprising an amino acid sequence that is at least 90%, 91%, 92%, 93%, 94%, 95%, 96%, 97%, 98%, 99% or more identical to the amino acid sequence of SEQ ID NO: 28. In some embodiments, the anti-CD3ε binding domain thereof includes a variable heavy chain (VH) comprising an amino acid sequence that is at least 90%, 91%, 92%, 93%, 94%, 95%, 96%, 97%, 98%, 99% or more identical to the amino acid sequence of SEQ ID NO: 27 and a variable light chain (VL) comprising an amino acid sequence that is at least 90%, 91%, 92%, 93%, 94%, 95%, 96%, 97%, 98%, 99% or more identical to the amino acid sequence of SEQ ID NO: 28. In some embodiments, the anti-CD3ε binding domain thereof includes a variable heavy chain (VH) comprising the amino acid sequence of SEQ ID NO: 27. In some embodiments, the anti-CD3ε binding domain includes a variable light chain (VL) comprising the amino acid sequence of SEQ ID NO: 28. In some embodiments, the anti-CD3ε binding domain thereof includes a variable heavy chain (VH) comprising the amino acid sequence of SEQ ID NO: 27 and a variable light chain (VL) comprising the amino acid sequence of SEQ ID NO: 28.

In some embodiments, the anti-CD3ε binding domain thereof includes a variable heavy chain (VH) comprising an amino acid sequence that is at least 90%, 91%, 92%, 93%, 94%, 95%, 96%, 97%, 98%, 99% or more identical to the amino acid sequence of SEQ ID NO: 453. In some embodiments, the anti-CD3ε binding domain includes a variable light chain (VL) comprising an amino acid sequence that is at least 90%, 91%, 92%, 93%, 94%, 95%, 96%, 97%, 98%, 99% or more identical to the amino acid sequence of SEQ ID NO: 451. In some embodiments, the anti-CD3ε binding domain thereof includes a variable heavy chain (VH) comprising an amino acid sequence that is at least 90%, 91%, 92%, 93%, 94%, 95%, 96%, 97%, 98%, 99% or more identical to the amino acid sequence of SEQ ID NO: 453 and a variable light chain (VL) comprising an amino acid sequence that is at least 90%, 91%, 92%, 93%, 94%, 95%, 96%, 97%, 98%, 99% or more identical to the amino acid sequence of SEQ ID NO: 451. In some embodiments, the anti-CD3ε binding domain thereof includes a variable heavy chain (VH) comprising the amino acid sequence of SEQ ID NO: 453. In some embodiments, the anti-CD3ε binding domain includes a variable light chain (VL) comprising the amino acid sequence of SEQ ID NO: 451. In some embodiments, the anti-CD3ε binding domain thereof includes a variable heavy chain (VH) comprising the amino acid sequence of SEQ ID NO: 453 and a variable light chain (VL) comprising the amino acid sequence of SEQ ID NO: 451.

In particular embodiments, the Fv is a disulfide stabilized Fv fragment (dsFv) in which the the Vii-V$_L$ heterodimer is stabilized by an interchain disulfide bond. In some embodiments, the interchain disulfide bond is engineered by mutation of position in framework positions of the VH and/or VL chain. In some embodiments, the disulfide stabilized anti-CD3 Fv comprises an anti-CD3 VH with the mutation 44 to Cys and an anti-CD3 VL with the mutation 100 to Cys by Kabat numbering. For example, in some embodiments, the VH chain contains the mutation G44C and the VL chain contains the mutation G100C, each by kabat numbering. In some embodiments, the disulfide stabilized anti-CD3 Fv comprises an anti-CD3 VH with the mutation at position 105 to Cys and an anti-CD3 VL with the mutation position 43 to Cys by Kabat numbering.

In some embodiments, the anti-CD3ε Fv antibody fragment includes a combination of a heavy chain variable amino acid sequence that is at least 90%, 91%, 92%, 93%, 94%, 95%, 96%, 97%, 98%, 99% or more identical to an amino acid sequence selected from the group consisting of SEQ ID NO: 47, 52-65, 454, or 460 and a light chain variable amino acid sequence that is at least 90%, 91%, 92%, 93%, 94%, 95%, 96%, 97%, 98%, 99% or more identical to an amino acid sequence selected from the group consisting of SEQ ID NO: 67, 75, 77, 79, 81-84, 368, or 452. In some of any such embodiments, the anti-CD3 Fv is a dsFv that has a VH chain containing the mutation G44C and a VL chain containing the mutation G100C, each by kabat numbering. In some embodiments, the anti-CD3ε Fv antibody fragment includes a combination of a heavy chain variable amino acid sequence selected from the group of SEQ ID NO: 47, 52-65, 454, or 460 and a light chain variable amino acid sequence selected from the group consisting of SEQ ID NO: 67, 75, 77, 79, 81-84, 368, or 452.

In some embodiments, the anti-CD3ε binding domain thereof includes a variable heavy chain (VH) comprising an amino acid sequence that is at least 90%, 91%, 92%, 93%, 94%, 95%, 96%, 97%, 98%, 99% or more identical to the amino acid sequence of SEQ ID NO: 47 In some embodiments, the anti-CD3ε binding domain includes a variable light chain (VL) comprising an amino acid sequence that is at least 90%, 91%, 92%, 93%, 94%, 95%, 96%, 97%, 98%, 99% or more identical to the amino acid sequence of SEQ ID NO: 75. In some embodiments, the anti-CD3ε binding domain thereof includes a variable heavy chain (VH) comprising an amino acid sequence that is at least 90%, 91%, 92%, 93%, 94%, 95%, 96%, 97%, 98%, 99% or more identical to the amino acid sequence of SEQ ID NO: 47 and a variable light chain (VL) comprising an amino acid sequence that is at least 90%, 91%, 92%, 93%, 94%, 95%, 96%, 97%, 98%, 99% or more identical to the amino acid sequence of SEQ ID NO: 75. In some of any such embodiments, the anti-CD3 Fv is a dsFv that has a VH chain containing the mutation G44C and a VL chain containing the mutation G100C, each by kabat numbering. In some embodiments, the anti-CD3ε binding domain thereof includes a variable heavy chain (VH) comprising the amino acid sequence of SEQ ID NO: 47. In some embodiments, the anti-CD3ε binding domain includes a variable light chain (VL) comprising the amino acid sequence of SEQ ID NO: 75. In some embodiments, the anti-CD3ε binding domain thereof includes a variable heavy chain (VH) comprising the amino acid sequence of SEQ ID NO: 47 and a variable light chain (VL) comprising the amino acid sequence of SEQ ID NO: 75.

In some embodiments, the anti-CD3ε binding domain thereof includes a variable heavy chain (VH) comprising an amino acid sequence that is at least 90%, 91%, 92%, 93%, 94%, 95%, 96%, 97%, 98%, 99% or more identical to the amino acid sequence of SEQ ID NO: 454. In some embodiments, the anti-CD3ε binding domain includes a variable light chain (VL) comprising an amino acid sequence that is at least 90%, 91%, 92%, 93%, 94%, 95%, 96%, 97%, 98%, 99% or more identical to the amino acid sequence of SEQ ID NO: 452. In some embodiments, the anti-CD3ε binding domain thereof includes a variable heavy chain (VH) comprising an amino acid sequence that is at least 90%, 91%, 92%, 93%, 94%, 95%, 96%, 97%, 98%, 99% or more identical to the amino acid sequence of SEQ ID NO: 454 and a variable light chain (VL) comprising an amino acid sequence that is at least 90%, 91%, 92%, 93%, 94%, 95%, 96%, 97%, 98%, 99% or more identical to the amino acid sequence of SEQ ID NO: 452. In some of any such embodiments, the anti-CD3 Fv is a dsFv that has a VH chain containing the mutation G44C and a VL chain containing the mutation G100C, each by kabat numbering. In some embodiments, the anti-CD3ε binding domain thereof includes a variable heavy chain (VH) comprising the amino acid sequence of SEQ ID NO: 454. In some embodiments, the anti-CD3ε binding domain includes a variable light chain (VL) comprising the amino acid sequence of SEQ ID NO: 452. In some embodiments, the anti-CD3ε binding domain thereof includes a variable heavy chain (VH) comprising the amino acid sequence of SEQ ID NO: 454 and a variable light chain (VL) comprising the amino acid sequence of SEQ ID NO: 452.

In some embodiments, the anti-CD3ε binding domain thereof includes a variable heavy chain (VH) comprising an amino acid sequence that is at least 90%, 91%, 92%, 93%, 94%, 95%, 96%, 97%, 98%, 99% or more identical to the amino acid sequence of SEQ ID NO: 460. In some embodiments, the anti-CD3ε binding domain includes a variable light chain (VL) comprising an amino acid sequence that is at least 90%, 91%, 92%, 93%, 94%, 95%, 96%, 97%, 98%, 99% or more identical to the amino acid sequence of SEQ ID NO: 452. In some embodiments, the anti-CD3ε binding domain thereof includes a variable heavy chain (VH) comprising an amino acid sequence that is at least 90%, 91%, 92%, 93%, 94%, 95%, 96%, 97%, 98%, 99% or more identical to the amino acid sequence of SEQ ID NO: 460 and a variable light chain (VL) comprising an amino acid sequence that is at least 90%, 91%, 92%, 93%, 94%, 95%, 96%, 97%, 98%, 99% or more identical to the amino acid sequence of SEQ ID NO: 452. In some of any such embodiments, the anti-CD3 Fv is a dsFv that has a VH chain containing the mutation G44C and a VL chain containing the mutation G100C, each by kabat numbering. In some embodiments, the anti-CD3ε binding domain thereof includes a variable heavy chain (VH) comprising the amino acid sequence of SEQ ID NO: 460. In some embodiments, the anti-CD3ε binding domain includes a variable light chain (VL) comprising the amino acid sequence of SEQ ID NO: 452. In some embodiments, the anti-CD3ε binding domain thereof includes a variable heavy chain (VH) comprising the amino acid sequence of SEQ ID NO: 460 and a variable light chain (VL) comprising the amino acid sequence of SEQ ID NO: 452.

d. Linker

A constrained multispecific polypeptide constructs contain a linker that joins or couples the first component containing the immunoglobulin Fc region and the second component containing the CD3 binding region. In some embodiments, the linker is positioned at the end of the C-terminal region of the Fc region, such that the Fc region is N-terminal to the CD3 binding region. It is understood that because the provided constrained multispecific polypeptide constructs are multimers, such as dimers containing a first and second polypeptide that together form the first and second component, the provided constructs include a linker joining the Fc portion and the CD3 binding region of the first and a linker joining the Fc portion and the CD3 binding region of the second polypeptide. In some embodiments, the first polypeptide includes a first Fc polypeptide of a heterodimeric Fc region, a linker, and a first domain (e.g. VH) of a CD3 binding region, and the second polypeptide includes a second Fc polypeptide of the heterodimeric Fc region, a linker and second domain (e.g. VL) of the CD3 binding region. Typically, the linkers present in the first and second polypeptides of the constrained multispecific polypeptide construct are the same. Thus, in some embodiments, each domain of the CD3 binding domain is linked via a linker, such as the same linker, to opposite polypeptides of the Fc, such as heterodimeric Fc.

Various polypeptide linkers for use in fusion proteins are known (see e.g. Chen et al. (2013) Adv. Drug. Deliv. 65:1357-1369; and International PCT publication No. WO 2014/099997, WO2000/24884; U.S. Pat. Nos. 5,258,498; 5,525,491; 5,525,491, 6,132,992).

In some embodiments, the linker is chosen so that, when the CD3 binding region is joined to the Fc region of the multispecific polypeptide conjugate, the CD3 binding region is constrained and not able to, or not substantially able to, bind or engage CD3 on the surface of a cell, e.g. T cell, upon contact of the multispecific polypeptide construct with the cell. Various assays can be employed to assess binding or engagement of CD3 by the multispecific polypeptide construct, including assays to assess T cell binding, NFAT activation using a reporter system, cytolytic T cell activity, cytokine production and/or expression of T cell activation markers. Exemplary assays are shown in the provided Examples. Typically, the linker also is one that ensures correct folding of the polypeptide construct, does not exhibit a charge that would be inconsistent with the activity or function of the linked polypeptides or form bonds or other interactions with amino acid residues in one or more of the domains that would impede or alter activity of the linked polypeptides. In some embodiments, the linker is a polypeptide linker. The polypeptide linker can be a flexible linker or a rigid linker or a combination of both. In some aspects, the linker is a short, medium or long linker. In some embodiments, the linker is up to 40 amino acids in length. In some embodiments, the linker is up to 25 amino acids in length. In some embodiments, the linker is at least or is at least about 2 amino acids in length. In some aspects, a suitable length is, e.g., a length of at least one and typically fewer than about 40 amino acid residues, such as 2-25 amino acid residues, 5-20 amino acid residues, 5-15 amino acid residues, 8-12 amino acid. In some embodiments, the linker is from or from about 2 to 24 amino acids, 2 to 20 amino acids, 2 to 18 amino acids, 2 to 14 amino acids, 2 to 12 amino acids, 2 to 10 amino acids, 2 to 8 amino acids, 2 to 6 amino acids, 6 to 24 amino acids, 6 to 20 amino acids, 6 to 18 amino acids, 6 to 14 amino acids, 6 to 12 amino acids, 6 to 10 amino acids, 6 to 8 amino acids, 8 to 24 amino acids, 8 to 20 amino acids, 8 to 18 amino acids, 8 to 14 amino acids, 8 to 12 amino acids, 8 to 10 amino acids, 10 to 24 amino acids, 10 to 20 amino acids, 10 to 18 amino acids, 10 to 14 amino acids, 10 to 12 amino acids, 12 to 24 amino acids, 12 to 20 amino acids, 12 to 18 amino acids, 12 to 14 amino acids, 14 to 24 amino acids, 14 to 20 amino acids, 14 to 18 amino acids, 18 to 24 amino acids, 18 to 20 amino acids or 20 to 24 amino acids. In some embodiments, the linker is 2, 3, 4, 5, 6, 7, 8, 9, 10, 11, 12, 13, 14, 15, 16, 17, 18, 19 or 20 amino acids in length.

In certain aspects, the longer the linker length, the greater the CD3 binding when the multispecific polypeptide conjugate is bounds to its antigen, e.g. TAA. Thus, in some aspects, the linker is greater than 12 amino acids in length, such as greater than 13, 14, 15, 16, 17 or 18 amino acids in length. In some embodiments, the linker is 12 to 40 amino acids in length, 12 to 30 amino acids, 12 to 24 amino acids, 12 to 18 acids, 12 to 15 amino acids, 15 to 40 amino acids, 15 to 30 amino acids, 15 to 24 amino acids, 15 to 18 amino acids, 18 to 40 amino acids, 18 to 30 amino acids, 18 to 24 amino acids, 24 to 40 amino acids, 24 to 30 amino acids or 30 to 40 amino acids.

The linkers can be naturally occurring, synthetic or a combination of both. Particularly suitable linker polypeptides predominantly include amino acid residues selected from Glycine (Gly), Serine (Ser), Alanine (Ala), and Threonine (Thr). For example, the linker may contain at least 75% (calculated on the basis of the total number of residues present in the peptide linker), such as at least 80%, at least 85%, or at least 90% of amino acid residues selected from Gly, Ser, Ala, and Thr. The linker may also consist of Gly, Ser, Ala and/or Thr residues only. In some embodiments, the linker contains 1-25 glycine residues, 5-20 glycine residues, 5-15 glycine residues, or 8-12 glycine residues. In some aspects, suitable peptide linkers typically contain at least 50% glycine residues, such as at least 75% glycine residues. In some embodiments, a peptide linker comprises glycine residues only. In some embodiments, a peptide linker comprises glycine and serine residues only.

In some embodiments, these linkers are composed predominately of the amino acids Glycine and Serine, denoted as GS-linkers herein. In some embodiments, the linker contains $(GGS)_n$, wherein n is 1 to 10, such as 1 to 5, for example 1 to 3, such as $GGS(GGS)_n$ (SEQ ID NO:474), wherein n is 0 to 10. In particular embodiments, the linker contains the sequence $(GGGGS)_n$ (SEQ ID NO: 123), wherein n is 1 to 10 or n is 1 to 5, such as 1 to 3. In further embodiments, the linker contains $(GGGGGS)_n$ (SEQ ID NO:124), wherein n is 1 to 4, such as 1 to 3. The linker can include combinations of any of the above, such as repeats of 2, 3, 4, or 5 GS, GGS, GGGGS, and/or GGGGGS linkers may be combined. In some embodiments, such a linker is 2, 3, 4, 5, 6, 7, 8, 9, 10, 11, 12, 13, 14, 15, 16, 17, 18 or 19 amino acids in length.

In some embodiments, the linker is (in one-letter amino acid code): GGS, GGGGS (SEQ ID NO: 125), or GGGGGS (SEQ ID NO: 126). In some embodiments, the GS-linker comprises an amino acid sequence of GGSGGS, i.e., (GGS)$_2$ (SEQ ID NO: 1); GGSGGSGGS, i.e., (GGS)$_3$ (SEQ ID NO: 2); GGSGGSGGSGGS, i.e., (GGS)$_4$ (SEQ ID NO: 3); GGSGGSGGSGGSGGS, i.e., (GGS)$_5$ (SEQ ID NO: 4); GGGGGSGGGGGSGGGGGS, i.e., (G5S)$_3$ (SEQ ID NO: 127), GGSGGGGSGGGGSGGGGS (SEQ ID NO: 129) and GGGGSGGGGSGGGGS (SEQ ID NO:128). In some embodiments, the linker is GGGG (SEQ ID NO:5). In some of any of the above examples, serine can be replaced with alanine (e.g., (Gly4Ala) or (Gly3Ala)).

In some embodiments, the linker includes a peptide linker having the amino acid sequence Gly$_x$Xaa-Gly$_y$-Xaa-Gly$_z$ (SEQ ID NO:130), wherein each Xaa is independently selected from Alanine (Ala), Valine (Val), Leucine (Leu), Isoleucine (Ile), Methionine (Met), Phenylalanine (Phe), Tryptophan (Trp), Proline (Pro), Glycine (Gly), Serine (Ser), Threonine (Thr), Cysteine (Cys), Tyrosine (Tyr), Asparagine (Asn), Glutamine (Gln), Lysine (Lys), Arginine (Arg), Histidine (His), Aspartate (Asp), and Glutamate (Glu), and wherein x, y, and z are each integers in the range from 1-5. In some embodiments, each Xaa is independently selected from the group consisting of Ser, Ala, and Thr. In a specific variation, each of x, y, and z is equal to 3 (thereby yielding a peptide linker having the amino acid sequence Gly-Gly-Gly-Xaa-Gly-Gly-Gly-Xaa-Gly-Gly-Gly (SEQ ID NO:131), wherein each Xaa is selected as above.

In some embodiments, the linker is serine-rich linkers based on the repetition of a (SSSSG)$_y$ (SEQ ID NO:132) motif where y is at least 1, though y can be 2, 3, 4, 5, 6, 7, 8 and 9.

In some cases, it may be desirable to provide some rigidity into the peptide linker. This may be accomplished by including proline residues in the amino acid sequence of the peptide linker. Thus, in some embodiments, a linker comprises at least one proline residue in the amino acid sequence of the peptide linker. For example, a peptide linker can have an amino acid sequence wherein at least 25% (e.g., at least 50% or at least 75%) of the amino acid residues are proline residues. In one particular embodiment, the peptide linker comprises proline residues only.

In some aspects, a peptide linker comprises at least one cysteine residue, such as one cysteine residue. For example, in some embodiments, a linker comprises at least one cysteine residue and amino acid residues selected from the group consisting of Gly, Ser, Ala, and Thr. In some such embodiments, a linker comprises glycine residues and cysteine residues, such as glycine residues and cysteine residues only. Typically, only one cysteine residue will be included per peptide linker. One example of a specific linker comprising a cysteine residue includes a peptide linker having the amino acid sequence Gly$_m$-Cys-Gly$_n$, wherein n and m are each integers from 1-12, e.g., from 3-9, from 4-8, or from 4-7. In a specific variation, such a peptide linker has the amino acid sequence GGGGG-C-GGGGG (SEQ ID NO: 133).

In some embodiments, the linker of the fusion protein is a structured or constrained linker. In particular embodiments, the structured linker contains the sequence (AP)$_n$ or (EAAAK)$_n$ (SEQ ID NO:134), wherein n is 2 to 20, preferably 4 to 10, including but not limited to, AS-(AP)$_n$-GT (SEQ ID NO:135) or AS-(EAAAK)$_n$-GT (SEQ ID NO:136), wherein n is 2 to 20, such as 2, 3, 4, 5, 6, 7, 8, 9, 10, 11, 12, 13, 14 or 15. In other embodiments, the linker comprises the sequences (GGGGA)$_n$ (SEQ ID NO:137), (PGGGS)$_n$ (SEQ ID NO:138), (AGGGS)$_n$ (SEQ ID NO:139) or GGS-(EGKSSGSGSESKST)$_n$-GGS (SEQ ID NO:140, wherein n is 2 to 20), (ADAAP)$_n$ (SEQ ID NO:527, wherein n is 2 to 20), (ADAAP)$_n$-G (SEQ ID NO:528, wherein n is 2 to 20), (GEPQG)$_n$ (SEQ ID NO:529, wherein n is 2 to 20), (GEPQG)$_n$-G (SEQ ID NO:530, wherein n is 2 to 20), (AGGEP)$_n$ (SEQ ID NO:531, wherein n is 2 to 20), (AGGEP)$_n$-G (SEQ ID NO:532, wherein n is 2 to 20), (AGSEP)$_n$ (SEQ ID NO:533, wherein n is 2 to 20), (AGSEP)$_n$-G (SEQ ID NO:534, wherein n is 2 to 20), (GGGEQ)$_n$ (SEQ ID NO:535, wherein n is 2 to 20), (GGGEQ)$_n$-G (SEQ ID NO:536, wherein n is 2 to 20). In some embodiments, the linker is SSSASASSA (SEQ ID NO:141), GSPGSPG (SEQ ID NO:142), ATTTGSSPGPT (SEQ ID NO:143), ADAAPADAAPG (SEQ ID NO:537), GEPQGGEPQGG (SEQ ID NO:538), AGGEPAGGEPG (SEQ ID NO:539), AGSEPAGSEPG (SEQ ID NO:540), or GGGEQGGGEQG (SEQ ID NO:541). In some embodiments, such linkers, by virtue of their structure, may be more resistant to proteolytic degradation, thereby offering an advantage when injected in vivo. In some embodiments, such linkers are negatively charged and may be better suited for dampening the binding of the CD3 binding domain to CD3. In some embodiments, the linker is not a cleavable linker, also called non-cleavable linker. In some embodiments, the linker is not a cleavable by a protease. In some embodiments, a linker that is not a cleavable linker or that is not cleavable by a protease is one that is generally stable for in vivo delivery or recombinant production. In some aspects, a linker that is not cleavable by a protease includes those that do not contain at least one peptide bond which preferably lies within a cleavable peptide sequence or recognition site of a protease. In particular embodiments, a non-cleavable linker is not a target substrate for a protease, such that it is not preferentially or specifically cleaved by a protease compared to a linker that contains a substrate recognition site for the same protease.

In some embodiments, the linker does not contains a substrate recognition site or cleavage site for a particular protease, which is the sequence recognized by the active site of a protease that is cleaved by a protease. Typically, for example, for a serine protease, a cleavage sequence is made up of the P1-P4 and P1'-P4' amino acids in a substrate, where cleavage occurs after the P1 position. Typically, a cleavage sequence for a serine protease is six residues in length to match the extended substrate specificity of many proteases, but can be longer or shorter depending upon the protease. Typically, the linker does not include a P1-P1' scissile bond sequence that is recognized by a protease. In some aspects, a non-cleavable linker or a linker that does not contain a substrate recognition site that is specifically recognized for cleavage by a protease is one whose cleavage by a protease is substantially less than cleavage of a target substrate of the protease.

In some embodiments, the linker is a cleavable linker. In some aspects, a cleavable linker is a linker, such as any described above, that further includes a sequence that is a substrate for a protease due to the presence of at least one bond that can be broken under physiological conditions. In some cases, a cleavable linker is susceptible to or sensitive to cleavage under specific conditions that exist in vivo, such as following exposure to an extracellular protease, including those present in cellular environments in vivo. In some cases, the protease may be present in a particular physiological microenvironment, such as the tumor microenvironment, thereby restricting the sites at which cleavage may occur.

A protease typically exhibits specificity or preference for cleavage of a particular target substrate compared to another non-target substrate. Such a degree of specificity can be determined based on the rate constant of cleavage of a sequence, e.g. linker, which is a measure of preference of a protease for its substrate and the efficiency of the enzyme. Any method to determine the rate of increase of cleavage over time in the presence of various concentrations of substrate can be used to calculate the specificity constant. For example, a substrate is linked to a fluorogenic moiety, which is released upon cleavage by a protease. By determining the rate of cleavage at different protease concentrations the specificity constant for cleavage ($k_{cat}/K_m$) can be determined for a particular protease towards a particular linker. In some embodiments, a cleavable linker is a linker that is capable of being specifically cleaved by a protease at a rate of about at least $1 \times 10^4 \, M^{-1}S^{-1}$, or at least $5 \times 10^4 \, M^{-1}S$, at least $10 \times 10^4 \, M^{-1}S$. at least $10 \times 10^5 \, M^{-1}S$ or more.

In some embodiments, a constrained multispecific polypeptide constructs of the disclosure include a cleavable linker that joins the first and second components. In some embodiments, the cleavable linker includes an amino acid sequence that can serve as a substrate for a protease, usually an extracellular protease. For example, the cleavable linker may include a cleavage sequence containing at least one peptide bond which preferably lies within a cleavable peptide sequence of a protease. Suitable proteases include, for example, matrix metalloproteases (MMP), cysteine proteases, serine proteases and plasmin activators, which are formed or activated in intensified manner in diseases such as rheumatoid arthritis or cancer, leading to excessive tissue degradation, inflammations and metastasis. In particular embodiments, the protease is a protease that is produced by a tumor, an activated immune effector cell (e.g. a T cell or a NK cell), or a cell in a tumor microenvironment. In some embodiments, the protease is a granzyme B, a matriptase or an MMP, such as MMP-2.

The cleavable linker may be selected based on a protease that is produced by a tumor that is in proximity to cells that express the target and/or produced by a tumor that is co-localized in tissue with the desired target of the multispecific polypeptide constructs. There are reports in the literature of increased levels of proteases having known substrates in a number of cancers, e.g., solid tumors. See, e.g., La Rocca et al, (2004) British J. of Cancer 90(7): 1414-1421.

In some embodiments, the cleavable linker that joins the first and second component of a constrained multispecific polypeptide construct is cleaved by a protease produced by an immune effector cell that is activated by one of the components. For example, multispecific polypeptide constructs that encompass an effector enabled or enhanced IgG Fc region are capable of eliciting ADCC when engaged with the target antigen. Central to ADCC is the release of granzyme B and perforin from the effector cells, namely NK cells and cytotoxic T-cells. Upon release granzyme B enters the target cell in a perforin dependent manner wherein it mediates apoptosis. Importantly, granzyme B is active within the extracellular synapse between the effector cell and the target cell. In some embodiments, the cleavable linker that joins the first and second component multispecific polypeptide construct is cleaved by granzyme B. Granzyme B is released during effector cell activation mediated by one of the components of the multispecific polypeptide construct. In some embodiments, granzyme B and other proteases can be produced by immune effector cells, including activated T cells or NK cells. In some embodiments, activation of T cells by CD3 engagement upon binding of a TAA by a multispecific polypeptide construct may release such proteases, which then can cleave a specific cleavable linker thereby potentiating or increasing activity of the CD3 binding molecule to engage CD3. In some embodiments, the cleavage can amplify or increase the activity achieved by the multispecific construct when bound to TAA in an uncleaved state.

Exemplary substrates include but are not limited to substrates cleavable by one or more of the following enzymes or proteases: ADAMS, ADAMTS, e.g. ADAMS; ADAMS; ADAM10; ADAM12; ADAM15; ADAM17/TACE; ADAMDEC1; ADAMTS1; ADAMTS4; ADAMTS5; aspartate proteases, e.g., BACE or Renin; aspartic cathepsins, e.g., Cathepsin D or Cathepsin E; Caspases, e.g., Caspase 1, Caspase 2, Caspase 3, Caspase 4, Caspase 5, Caspase 6, Caspase 7, Caspase 8, Caspase 9, Caspase 10, or Caspase 14; cysteine cathepsins, e.g., Cathepsin B, Cathepsin C, Cathepsin K, Cathepsin L, Cathepsin S, Cathepsin V/L2, Cathepsin X/Z/P; Cysteine proteinases, e.g., Cruzipain; Legumain; Otubain-2; KLKs, e.g., KLK4, KLK5, KLK6, KLK7, KLK8, KLK10, KLK11, KLK13, or KLK14; Metallo proteinases, e.g., Meprin; Neprilysin; PSMA; BMP-1; MMPs, e.g., MMP1, MMP2, MMP3, MMP7, MMP8, MMP9, MMP10, MMP11, MMP12, MMP13, MMP14, MMP15, MMP16, MMP17, MMP19, MMP20, MMP23, MMP24, MMP26, or MMP27, serine proteases, e.g., activated protein C, Cathepsin A, Cathepsin G, Chymase, coagulation factor proteases (e.g., FVIIa, FIXa, FXa, FXIa, FXIIa), Elastase, granzyme B, Guanidinobenzoatase, HtrAl, Human Neutrophil Elastase, Lactoferrin, Marapsin, NS3/4A, PACE4, Plasmin, PSA, tPA, Thrombin, Tryptase, uPA; Type II Transmembrane Serine Proteases (TTSPs), e.g., DESC1, DPP-4, FAP, Hepsin, Matriptase-2, Matriptase, TMPRSS2, TMPRSS3, or TMPRSS4; and any combination thereof.

In some embodiments, the cleavable linker is cleaved by multiple proteases, e.g., 2 or more proteases, 3 or more proteases, 4 or more proteases, and so on.

In some embodiments, the cleavable linker is selected for use with a specific protease, for example a protease that is known to be produced by a tumor that is in proximity to cells that express the target and/or produced by a tumor that is co-localized with the target of the multispecific polypeptide construct.

In some embodiments, the cleavable linker contains a substrate recognition site or cleavage site for a particular protease, which is the sequence recognized by the active site of a protease that is cleaved by a protease. Typically, for example, for a serine protease, a cleavage sequence is made up of the P1-P4 and P1'-P4' amino acids in a substrate, where cleavage occurs after the P1 position. Typically, a cleavage sequence for a serine protease is six residues in length to match the extended substrate specificity of many proteases, but can be longer or shorter depending upon the protease. Typically, the cleavable linker includes a P1-PP scissile bond sequence that is recognized by a protease. In some aspects, the cleavable linker is engineered to introduce a peptide bond able to be cleaved by a specific protease, for example by introducing a substrate recognition site sequence or cleavage sequence of the protease.

In some embodiments, the cleavable linker includes a combination of two or more substrate sequences. In some embodiments, each substrate sequence is cleaved by the same protease. In some embodiments, at least two of the substrate sequences are cleaved by different proteases. In some embodiments, the cleavable linker comprises an amino acid that is a substrate for granzyme B. In some embodiments, a granzyme B cleavable linker contains an amino acid sequence having the general formula P4 P3 P2 P1 ↓ P1' (SEQ ID NO: 144), wherein P4 is amino acid I, L, Y, M, F, V, or A; P3 is amino acid A, G, S, V, E, D, Q, N, or Y; P2 is amino acid H, P, A, V, G, S, or T; P1 is amino acid D or E; and P1' is amino acid I, L, Y, M, F, V, T, S, G or A. In some embodiments, a granzyme B cleavable linker contains an amino acid sequence having the general formula P4 P3 P2 P1 ↓ P1' (SEQ ID NO: 145), wherein P4 is amino acid I or L; P3 is amino acid E; P2 is amino acid P or A; P1 is amino acid D; and P1' is amino acid I, V, T, S, or G.

In some embodiments, the substrate for granzyme B comprises the amino acid sequence LEAD (SEQ ID NO: 146), LEPD (SEQ ID NO: 147), or LEAE (SEQ ID NO:148). In some embodiments, the cleavable linker contains the amino acid sequence the cleavable linker comprises the amino acid sequence IEPDI (SEQ ID NO:149), LEPDG (SEQ ID NO:150), LEADT (SEQ ID NO:151), IEPDG (SEQ ID NO:152), IEPDV (SEQ ID NO:153), IEPDS (SEQ ID NO:154), IEPDT (SEQ ID NO:155), IEPDP (SEQ ID NO:471, or LEADG (SEQ ID NO:144).

In some embodiments, the cleavable linker comprises an amino acid that is a substrate for matriptase. In some embodiments, the cleavable linker comprises the sequence P1QAR↓(A/V) (SEQ ID NO: 156), wherein P1 is any amino acid. In some embodiments, the cleavable linker comprises the sequence RQAR(A/V) (SEQ ID NO: 157). In some embodiments, the substrate for matriptase comprises the amino acid sequence RQAR (SEQ ID NO: 158). In some embodiments, the cleavable linker comprises the amino acid sequence RQARV (SEQ ID NO: 159).

In some embodiments, the cleavable linker comprises an amino acid that is a substrate for one or more matrix metalloproteases (MMPs). In some embodiments, the MMP is MMP-2. In some embodiments, the cleavable linker contains. the general formula P3 P2 P1 ↓ P1' (SEQ ID NO: 160), wherein P3 is P, V or A; P2 is Q or D; P1 is A or N; and P1' is L, I or M. In some embodiments, the cleavable linker contains the general formula P3 P2 P1 ↓ P1' (SEQ ID NO: 161), wherein P3 is P; P2 is Q or D; P1 is A or N; and P1' is L or I. In some embodiments, the substrate for MMP comprises the amino acid sequence PAGL (SEQ ID NO: 162).

In some embodiments, the cleavable linker comprises a combination of an amino acid sequence that is a substrate for granzyme B and an amino acid sequence that is a substrate for matriptase. In some embodiments, the cleavable linker comprises a combination of the amino acid sequence LEAD (SEQ ID NO: 146) and the amino acid sequence RQAR (SEQ ID NO: 158).

In some embodiments, the cleavable linker comprises a combination of an amino acid sequence that is a substrate for granzyme B and an amino acid sequence that is a substrate for MMP. In some embodiments, the cleavable linker comprises a combination of the amino acid sequence LEAD (SEQ ID NO: 146) and the amino acid sequence PAGL (SEQ ID NO: 162).

In some embodiments, the cleavable linker comprises a combination of an amino acid sequence that is a substrate for matriptase and an amino acid sequence that is a substrate for MMP. In some embodiments, the cleavable linker comprises a combination of the amino acid sequence RQAR (SEQ ID NO: 158) and the amino acid sequence PAGL (SEQ ID NO: 162).

In some embodiments, the cleavable linker comprises a combination of an amino acid sequence that is a substrate for granzyme B, an amino acid sequence that is a substrate for matriptase, and an amino acid sequence that is a substrate for MMP. In some embodiments, the cleavable linker comprises a combination of an amino acid sequence that is a substrate for granzyme B and an amino acid sequence that is a substrate for MMP. In some embodiments, the cleavable linker comprises a combination of the amino acid sequence LEAD (SEQ ID NO: 146), the amino acid sequence RQAR (SEQ ID NO: 158), and the amino acid sequence PAGL (SEQ ID NO: 162).

The cleavable linker can include any known linkers. Examples of cleavable linkers are described in Be'liveau et al. (2009) FEBS Journal, 276; U.S. published application Nos. US20160194399; US20150079088; US20170204139; US20160289324; US20160122425; US20150087810; US20170081397; U.S. Pat. No. 9,644,016.

In some embodiments, the cleavable linker comprises an amino acid sequence selected from the group consisting of TGLEADGSPAGLGRQARVG (SEQ ID NO: 163); TGLEADGSRQARVGPAGLG (SEQ ID NO: 164); TGSPAGLEADGSRQARVGS (SEQ ID NO: 165); TGPAGLGLEADGSRQARVG (SEQ ID NO: 166); TGRQARVGLEADGSPAGLG (SEQ ID NO: 167); TGSRQARVGPAGLEADGS (SEQ ID NO: 168); and TGPAGLGSRQARVGLEADGS (SEQ ID NO:169); GPAGLGLEPDGSRQARVG (SEQ ID NO: 170); GGSGGGGIEPDIGGSGGS (SEQ ID NO: 171); GGSGGGGLEADTGGSGGS (SEQ ID NO: 172); GSIEPDIGS (SEQ ID NO: 173); GSLEADTGS (SEQ ID NO: 174); GGSGGGGIEPDGGGSGGS (SEQ ID NO: 175); GGSGGGGIEPDVGGSGGS (SEQ ID NO: 176); GGSGGGGIEPDSGGSGGS (SEQ ID NO: 177); GGSGGGGIEPDTGGSGGS (SEQ ID NO: 178); GGGSLEPDGSGS (SEQ ID NO: 179); and GPAGLGLEADGSRQARVG (SEQ ID NO: 180), GGEGGGGSGGSGGGS (SEQ ID NO: 181); GSSAGSEAGGSGQAGVGS (SEQ ID NO: 182); GGSGGGGLEAEGSGGGGS (SEQ ID NO: 183); GGSGGGGIEPDPGGSGGS(SEQ ID NO: 184); TGGSGGGGIEPDIGGSGGS (SEQ ID NO: 185).

e. Costimulatory Binding Domain

A multispecific polypeptide constructs of the present disclosure include one or more co-stimulatory receptor binding region (CRBR) that binds a costimulatory receptor. In some embodiments, the one or more CRBR of the provided multispecific polypeptide constructs bind a co-stimulatory receptor expressed on T cells. In some embodiments, the co-stimulatory receptor is upregulated, induced, or expressed on the surface of an activated T cell. In some aspects, the CRBR binds a co-stimulatory receptor and stimulates the co-stimulatory receptor. In some embodiments, agonistic binding of the co-stimulatory receptor to the CRBR of the multispecific polypeptide induces downstream signaling in the T cell to potentiate or enhance T cell activation or functionalities following engagement of CD3. In some embodiments, the CRBR, or independently each of the CRBRs, is an antibody or antigen binding fragment, a natural cognate binding partner of the co-stimulatory receptor, an Anticalin (engineered lipocalin), a Darpin, a Fynomer, a Centyrin (engineered fibroneticin III domain), a cystine-knot domain, an Affilin, an Affibody, or an engineered CH3 domain.

In some embodiments, the CRBR, or independently each of the CRBRs, such as the first CRBR and the second CRBRs, includes one or more copies of an antibody or an antigen-binding fragment thereof. In some embodiments, the CRBR or independently each of the CRBRs, such as the first antigen-binding domain and the second CRBRs, includes one or more copies of an antibody or an antigen-binding fragment thereof selected from the group consisting of a Fab fragment, a F(ab')₂ fragment, an Fv fragment, a scFv, a scAb, a dAb, a single domain heavy chain antibody, and a single domain light chain antibody.

In some embodiments, the CRBR, or independently each of the CRBRs, such as the first CRBR and the second CRBRs, is a single chain antibody. In some examples, the single chain is an scFv, a scAb, a single domain heavy chain antibody, or a single domain light chain antibody. In some embodiments, the CRBR, or independently each of the CRBRs, such as the first CRBR and the second CRBR, is a single chain antibody. In some examples, the single chain is an scFv, a scAb, a single domain heavy chain antibody, or a single domain light chain antibody.

In some embodiments, the CRBR, or independently each of the CRBRs, such as the first CRBR and the second CRBR, includes one or more single domain antibody (sdAb) fragments, for example $V_H H$, $V_{NAR}$, engineered $V_H$ or $V_K$ domains. $V_H Hs$ can be generated from natural camelid heavy chain only antibodies, genetically modified rodents that produce heavy chain only antibodies, or naïve/synthetic camelid or humanized camelid single domain antibody libraries. $V_{NAR}s$ can be generated from cartilaginous fish heavy chain only antibodies. Various methods have been implemented to generate monomeric sdAbs from conventionally heterodimeric $V_H$ and $V_K$ domains, including interface engineering and selection of specific germline families.

In some embodiments, the CRBR, or independently each of the CRBRs such as the first CRBR and/or the second CRBR, of the multispecific polypeptide constructs contains at least one sdAb or an scFv that binds a costimulatory receptor. In some embodiments, the at least one scFv or sdAb that binds a costimulatory receptor is positioned amino-terminally relative to the Fc region and/or carboxy-terminally relative to the CD3 binding region of the multispecific polypeptide construct. In some embodiments, the multispecific polypeptide construct contains only one scFv or sdAb that binds to a costimulatory receptor, which can be positioned either amino-terminally relative to the Fc region and/or carboxy-terminally relative to the CD3 binding region. In some embodiments, the multispecific polypeptide construct contains two scFv or sdAb that bind to a costimulatory receptor, positioned amino-terminally relative to the Fc region and/or carboxy-terminally relative to the CD3 binding region.

In some embodiments, the multispecific polypeptide construct is formed from or includes two polypeptides, including a first polypeptide comprising a first Fc polypeptide of a heterodimeric Fc region, a linker, a VH domain of an anti-CD3 antibody or antigen binding fragment (e.g. Fv), and an scFv or sdAb that binds to a costimulatory receptor; and a second polypeptide comprising a second Fc polypeptide of the heterodimeric Fc region, the linker, a VL domain of the anti-CD3 antibody or antigen binding fragment (e.g. Fv) and, optionally, another, the same or different, scFv or sdAb that binds to a costimulatory receptor. The scFv or sdAb that binds the costimulatory receptor can be positioned amino terminally relative to an Fc polypeptide of the heterodimeric Fc and/or carboxy-terminally relative to a VH or VL chain of the CD3 binding region. At least one of the first and/or second polypeptide of the multispecific polypeptide construct also includes an antigen binding domain that binds a TAA or a chain thereof as described in Section II.4. In some embodiments, the antigen binding domain that binds a TAA is a scFv or sdAb and is included as part of the first and/or second polypeptide of the multispecific polypeptide construct. In some embodiments, the antigen binding domain that binds a TAA is a Fab, and the multispecific polypeptide construct is additionally formed from a third polypeptide where at least the first and second polypeptide include a chain of the Fab that binds TAA (e.g. VH-CH1 or VL-CL of a Fab) and the third polypeptide contains the other chain of the Fab that binds TAA (e.g. the other of VH-CH1 or VL-CL of a Fab).

In some embodiments, the CRBR or independently each of the CRBRs, such as the first CRBR and/or the second CRBRs, contains more than one chain. In some embodiments, the CRBR or independently each of the CRBRs, such as the first CRBR and/or the second CRBRs, of the multispecific polypeptide constructs contains VH and VL sequences assembled as FABs.

In some embodiments, the antigen binding domain or independently each of the antigen binding domains, such as the first antigen-binding domain and/or the second antigen binding domains, of the multispecific polypeptide constructs contains a VH-CH1 (Fd) and a VL-CL of a Fab antibody that binds a costimulatory receptor. In some embodiments, the Fab antibody containing a VH-CH1 (Fd) and a VL-CL is positioned amino-terminally relative to the Fc region and/or carboxy-terminally relative to the CD3 binding region of the multispecific polypeptide construct. In some embodiments, the multispecific polypeptide construct contains only one Fab antibody, containing a VH-CH1 (Fd) or VL-CL, that binds to a costimulatory receptor, which can be positioned either amino-terminally relative to the Fc region and/or carboxy-terminally relative to the CD3 binding region. In some embodiments, the multispecific polypeptide construct contains two Fab antibody fragments, each containing a VH-CH1 (Fd) and VL-CL, that binds to a costimulatory receptor, in which one is positioned amino-terminally relative to the Fc region and the other is positioned carboxy-terminally relative to the CD3 binding region.

In some embodiments, the multispecific polypeptide construct is formed from or includes three or more polypeptides, including a first polypeptide comprising a first Fc polypeptide of a heterodimeric Fc region, a linker and a VH-CH1 (Fd) or VL-CL of a Fab antibody fragment that binds to a costimulatory receptor; a second polypeptide comprising a second Fc polypeptide of the heterodimeric Fc region, the linker and, optionally, the same VH-CH1 (Fd) or VL-CL of the Fab antibody fragment that binds to a costimulatory receptor, and a third polypeptide comprising the other of the VH-CH1 (Fd) or VL-CL of the Fab antibody fragment that binds to the costimulatory receptor. The first, second and/or third polypeptide of the multispecific polypeptide construct also can include a DLL3 VHH domain, such as any as described.

In some embodiments, the CRBR, or independently each of the CRBRs, is or includes a natural (native) cognate binding partner of the co-stimulatory receptor (e.g. a natural ligand), or a variant thereof that exhibits binding activity to the co-stimulatory receptor.

In some embodiments, the one or more CRBR of the provided multispecific polypeptide constructs bind a co-stimulatory receptor expressed on T cells. In some embodiments, there are more than one CRBR that binds to a costimulatory receptor and each of the CRBRs, such as the first CRBR and the second CRBR, bind the same co-stimulatory receptor. In some embodiments, each of the CRBRs, such as the first CRBR and the CRBRs, bind a different co-stimulatory receptor. In some embodiments, each of the CRBRs, such as the first CRBR and the second CRBR bind a different epitope on the same co-stimulatory receptor. In some embodiments, each of the CRBRs, such as the first antigen-CRBR and the CRBR, bind the same epitope on the same co-stimulatory receptor.

In some embodiments, the CRBR, or independently each of the CRBRs that binds a co-stimulatory receptor results in monovalent, bivalent, trivalent, or tetravalent binding to the co-stimulatory receptor.

In some embodiments, the co-stimulatory receptor is expressed on T cells, such as primary T cells obtained from a subject. In some embodiments, the co-stimulatory receptor is expressed on human T cells, such as primary human T cells obtained from a human subject.

In some embodiments, the co-stimulatory receptor is a member of the tumor necrosis factor (TNF) receptor family. In some embodiments, the costimulatory receptor is a member of the immunoglobulin superfamily (IgSF). In some embodiments, the costimulatory receptor is a member of the B7 family of receptors.

In some embodiments, the co-stimulatory receptor is selected from the group consisting of 41BB (CD137), OX40 (CD134), CD27, glucocorticoid-induced TNFR-related protein (GITR), CD28, ICOS, CD40, B-cell activating factor receptor (BAFF-R), B-cell maturation antigen (BCMA), Transmembrane activator and CAML interactor (TACI), and NKG2D. In some embodiments, the co-stimulatory receptor is selected from 41BB, OX40, GITR, ICOS, or CD28. In some embodiments, the co-stimulatory receptor is selected from 41BB, OX40, or GITR.

In some embodiments, the costimulatory receptor is 41BB. In some embodiments, the costimulatory receptor is OX40. In some embodiments, the costimulatory receptor is GITR. In some embodiments, the costimulatory receptor is ICOS. In some embodiments, the costimulatory receptor is CD28.

In some embodiments, the CRBR of the multispecific polypeptide is or comprises an agonistic binding molecule to the co-stimulatory receptor. The CRBR can bind to the co-stimulatory receptor and initiate, induce, or stimulate a reaction or activity that is similar to or the same as that initiated, induced, or stimulated by the receptor's natural ligand. In some aspects, the binding of the CRBR to the co-stimulatory receptor induces or stimulates a downstream signal that is more than 5%, more than 10%, more than 20%, more than 30%, more than 40%, more than 50%, more than 60%, more than 70%, more than 80%, more than 90%, or more than 100% of the signal that is initiated, induced, or stimulated by the receptor's natural ligand.

In some embodiments, the one or more CRBR is an antibody or fragment thereof that binds to the co-stimulatory receptor 41BB (CD137), OX40 (CD134), CD27, glucocorticoid-induced TNFR-related protein (GITR), CD28, ICOS, CD40, B-cell activating factor receptor (BAFF-R), B-cell maturation antigen (BCMA). In some embodiments, the one or more CRBR is an antibody or fragment thereof that binds to the co-stimulatory receptor 41BB, OX40, GITR, ICOS, or CD28. In some embodiments, the one or more CRBR is an antibody or fragment thereof that binds to the co-stimulatory receptor 41BB, OX40, or GITR. Exemplary polypeptides for binding 41BB, OX40 and GITR are described in PCT publication. No. WO2017123650, WO2017123673, and WO2017015623, respectively. In some embodiments, the one or more CRBR is a single domain antibody (sdAb) that binds the co-stimulatory receptor, such as those described in PCT publication. No. WO2017123650, WO2017123673, and WO2017015623.

In some examples, the co-stimulatory receptor binding region (CRBR) binds or comprises a natural cognate binding partner of 41BB (CD137), OX40 (CD134), CD27, glucocorticoid-induced TNFR-related protein (GITR), CD28, ICOS, CD40, B-cell activating factor receptor (BAFF-R), B-cell maturation antigen (BCMA), Transmembrane activator and CAML interactor (TACI), NKG2D. In some embodiments, the natural cognate binding partner is selected from 41BB ligand (41BBL), OX40L (CD252), CD70, GITR Ligand/TNFSF18, CD80 (B7-1), CD86 (B7-2), ICOS Ligand (ICOSL), CD154 (CD40L), B-cell activating factor (BAFF), A proliferation-inducing ligand (APRIL), NKG2D ligands, or a functional fragment thereof.

In some embodiments, the co-stimulatory receptor binding region (CRBR) is an antibody or antigen binding fragment that binds 41BB. In particular examples, the CRBR that binds 4-1BB is a single domain antibody. In some embodiments, the sdAb contains a CDR1 GFSFSINAMG (set forth in SEQ ID NO:457), a CDR2 AIESGRNTV (set forth in SEQ ID NO:458) and a CDR3 LKGNRVVSPSVAY (set forth in SEQ ID NO: 459). Examples of sdAb that target 41BB are described in PCT publication. No. WO2017123650.

Exemplary sequences of CRBRs are set forth in Table 4.

In some embodiments, at least one CRBR, or independently each CRBR, binds the co-stimulatory receptor 41BB. In some examples, the CRBR is or contains an antibody or antigen binding fragment specific to or that binds 41BB, such as a sdAb or fragments containing a VH and VL (e.g. scFv). In some embodiments, at least on CRBR, or independently each CRBR, is a natural ligand of 41BB or is a functional binding fragment thereof. Exemplary 41BB-binding CRBRs are set forth in any of SEQ ID NOS: 186-210 and 470. In some embodiments, a 41BB-binding CRBR is a functional fragment of 41BB ligand (41BBL) containing the extracellular domain or a truncated portion thereof, such as corresponding to amino acids 50-254 of UniProt. No. P41273, e.g. as set forth in SEQ ID NO:186, or a truncated portion or fragment thereof set forth in any of SEQ ID NOS:202-209. In some embodiments, at least one CRBR, or independently each CRBR, is an anticalin set forth in any one of SEQ ID NOS:193-201. In some embodiments, a sdAb, such as a VHH, contains a CDR1, a CDR2, and a CDR3 having a sequence set forth in SEQ ID NO:457, 458, and 459, respectively. A 41BB-binding CRBR, such as a sdAb, can include the sequence set forth in SEQ ID NO:210. A 41BB-binding CRBR, such as a sdAb, can include the sequence set forth in SEQ ID NO:470. In some embodiments, the 4-1BB-binding domain contains an antigen binding antibody fragment containing a VH and a VL, such as a single chain fragment in which the VH and VL are separated by a linker, for example an scFv. In some embodiments, the 41BB binding CRBR contains a VH set forth in any of SEQ ID NOS: 187, 189 and 191, and a VL set forth in any of SEQ ID NO: 188, 190, or 192. The CRBRs, or independently each CRBR, in a provided multispecific polypeptide construct can have at least 85%, 85%, 87%, 88%, 89%, 90%, 91%, 92%, 93%, 94%, 95%, 96%, 97%, 98% or 99% sequence identity to any of the foregoing SEQ ID Nos and bind 41BB.

In some embodiments, at least one CRBR, or independently each CRBR, binds the co-stimulatory receptor OX40. In some examples, the CRBR is or contains an antibody or antigen binding fragment specific to or that binds OX40, such as a sdAb or fragments containing a VH and VL (e.g. scFv). In some embodiments, at least on CRBR, or independently each CRBR, is a natural ligand of OX40 or is a functional binding fragment thereof. Exemplary of such OX40-binding CRBRs are set forth in any of SEQ ID NOS: 211-220. In some embodiments, the OX40-binding CRBR contains an VH set forth in any of SEQ ID NOS: 216 and 218, and a VL set forth in any of SEQ ID NO: 217 and 219.

The CRBRs, or independently each CRBR, in a provided multispecific polypeptide construct can have at least 85%, 85%, 87%, 88%, 89%, 90%, 91%, 92%, 93%, 94%, 95%, 96%, 97%, 98% or 99% sequence identity to any of the foregoing SEQ ID Nos and bind OX40.

In some embodiments, at least one CRBR, or independently each CRBR, binds the co-stimulatory receptor GITR. In some examples, the CRBR is or contains an antibody or antigen binding fragment specific to or that binds GITR, such as a sdAb or fragments containing a VH and VL (e.g. scFv). In some embodiments, at least one CRBR, or independently each CRBR, is a natural ligand of GITR or is a functional binding fragment thereof. Exemplary of such GITR-binding CRBRs are set forth in any of SEQ ID NOS: 221-230. In some embodiments, the GITR binding CRBR contains a VH set forth in any of SEQ ID NOS: 222, 224, 226, and 228 and a VL set forth in any of SEQ ID NO: 223, 225, 227, and 229. The CRBRs, or independently each CRBR, in a provided multispecific polypeptide construct can have at least 85%, 85%, 87%, 88%, 89%, 90%, 91%, 92%, 93%, 94%, 95%, 96%, 97%, 98% or 99% sequence identity to any of the foregoing SEQ ID Nos and bind GITR.

In some embodiments, at least one CRBR, or independently each CRBR, binds the co-stimulatory receptor CD27. In some examples, the CRBR is or contains an antibody or antigen binding fragment specific to or that binds CD27, such as a sdAb or fragments containing a VH and VL (e.g. scFv). In some embodiments, at least one CRBR, or independently each CRBR, is a natural ligand of CD27 or is a functional binding fragment thereof. Exemplary of such CD27-binding CRBRs are set forth in any of SEQ ID NOS: 231. In some embodiments, the CD27 binding CRBR contains a VH set forth SEQ ID NO: 232 and a VL set forth in SEQ ID NO: 233. The CRBRs, or independently each CRBR, in a provided multispecific polypeptide construct can have at least 85%, 85%, 87%, 88%, 89%, 90%, 91%, 92%, 93%, 94%, 95%, 96%, 97%, 98% or 99% sequence identity to any of the foregoing SEQ ID Nos and bind CD27.

In some embodiments, at least one CRBR, or independently each CRBR, binds the co-stimulatory receptor ICOS. In some examples, the CRBR is or contains an antibody or antigen binding fragment specific to or that binds ICOS, such as a sdAb or fragments containing a VH and VL (e.g. scFv). In some embodiments, at least one CRBR, or independently each CRBR, is a natural ligand of ICOS or is a functional binding fragment thereof. An exemplary ICOS-binding CRBR sequence is set forth in SEQ ID NO: 234.

In some embodiments, at least one CRBR, or independently each CRBR, binds the co-stimulatory receptor CD28. In some examples, the CRBR is or contains an antibody or antigen binding fragment specific to or that binds CD28, such as a sdAb or fragments containing a VH and VL (e.g. scFv). In some embodiments, at least one CRBR, or independently each CRBR, is a natural ligand of CD28 or is a functional binding fragment thereof. An exemplary CD28-binding CRBR sequence is set forth in SEQ ID NO: 235.

TABLE 4

Exemplary CRBR Sequences

| CRBR | Format | Reference | SEQ ID NO |
|---|---|---|---|
| 41BB binding CRBR Sequences | | | |
| 41BBL | Natural Ligand | UniProt accession no. P41273 | 186 |
| PF-05082566 | VH | US 2012/0237498 (SEQ ID NO: 43) | 187 |
|  | VL | US 2012/0237498 (SEQ ID NO: 45) | 188 |
| BMS663513 | VH | WO 2005/035584 (SEQ ID NO: 9) | 189 |
|  | VL | WO 2005/035584 (SEQ ID NO: 6) | 190 |
| MSB7 | VH | US 2017/0226215 (SEQ ID NO: 138) | 191 |
|  | VL | US 2017/0226215 (SEQ ID NO: 28) | 192 |
| 41BB Anticalin | Anticalin | WO 2016/177762 (SEQ ID NO: 12) | 193 |
| 41BB Anticalin | Anticalin | WO 2016/177762 (SEQ ID NO: 13) | 194 |
| 41BB Anticalin | Anticalin | WO 2016/177762 (SEQ ID NO: 14) | 195 |
| 41BB Anticalin | Anticalin | WO 2016/177762 (SEQ ID NO: 15) | 196 |
| 41BB Anticalin | Anticalin | WO 2016/177762 (SEQ ID NO: 16) | 197 |
| 41BB Anticalin | Anticalin | WO 2016/177762 (SEQ ID NO: 17) | 198 |
| 41BB Anticalin | Anticalin | WO 2016/177762 (SEQ ID NO: 18) | 199 |
| 41BB Anticalin | Anticalin | WO 2016/177762 SEQ ID NO: 19) | 200 |
| 41BB Anticalin | Anticalin | WO 2016/177762 (SEQ ID NO: 20) | 201 |
| 71-254 of human 41BBL | 41BB ligand | WO 2017/167672 (SEQ ID NO: 3) | 202 |
| 85-254 of human 41BBL | 41BB ligand | WO 2017/167672 (SEQ ID NO: 4) | 203 |
| 80-254 of human 41BBL | 41BB ligand | WO 2017/167672 (SEQ ID NO: 5) | 204 |
| 52-254 of human 41BBL | 41BB ligand | WO 2017/167672 (SEQ ID NO: 6) | 205 |
| 71-248 of human 41BBL | 41BB ligand | WO 2017/167672 (SEQ ID NO: 7) | 206 |
| 85-248 of human 41BBL | 41BB ligand | WO 2017/167672 (SEQ ID NO: 8 | 207 |
| 80-248 of human 41BBL | 41BB ligand | WO 2017/167672 (SEQ ID NO: 9) | 208 |
| 52-248 of human 41BBL | 41BB ligand | WO 2017/167672 (SEQ ID NO: 10) | 209 |
| 41BB sdAb | sdAb | US 2017/0198050 | 210 |
| 41BB sdAb | sdAb |  | 470 |
| OX40-binding CRBR Sequences | | | |
| OX40 ligand | Natural Ligand | UniProt accession no. P23510 | 211 |
| OX40 ligand | Natural Ligand | U.S. Pat. No. 7,959,925 (SEQ ID NO: 2) | 212 |
| human OX40L: 51-183 | Natural Ligand | WO 2017/167672 (SEQ ID NO: 11) | 213 |
| Human Ox40L: 51-183 N90D | Natural Ligand | WO 2017/167672 (SEQ ID NO: 12) | 214 |
| Human OX40L: 52-183 | Natural Ligand | WO 2017/167672 (SEQ ID NO: 13) | 215 |
| 1A07 | VH | US 2015/0307617 (SEQ ID NO: 56) | 216 |
|  | VL | US 2015/0307617 (SEQ ID NO: 59) | 217 |
| 1949 | VH | WO 2016/179517 (SEQ ID NO: 16) | 218 |
|  | VL | WO 2016/179517 | 219 |

TABLE 4-continued

Exemplary CRBR Sequences

| CRBR | Format | Reference | SEQ ID NO |
|---|---|---|---|
| 1D10v1 | sdAb | U.S. Pat. No. 9,006,399 | 220 |
| GITR-binding CRBR Sequences | | | |
| GITR ligand | Natural Ligand | UniProt no. Q9UNG2 | 221 |
| 36E5 | VH | US 2014/0348841 (SEQ ID NO: 104) | 222 |
|  | VL | US 2014/0348841 (SEQ ID NO: 105) | 223 |
| TRX-518 | VH | US 2013/0183321 (SEQ ID NO: 54) | 224 |
|  | VL | US 2013/0183321 (SEQ ID NO: 44) | 225 |
| 5H7v2 | VH | US 2015/0064204 (SEQ ID NO: 282) | 226 |
|  | VL | US 2015/0064204 (SEQ ID NO: 134) | 227 |
| 41G5v2 | VH | US 2015/0064204 (SEQ ID NO: 312) | 228 |
|  | VL | US 2015/0064204 (SEQ ID NO: 124) | 229 |
| C06v3 | sdAb | US 2017/0022284 (SEQ ID NO: 59) | 230 |
| CD27-binding CRBR Sequences | | | |
| CD70-ECD | Natural Ligand | UniProt no. P32970 | 231 |
| 1F5 | VH | US 2011/0274685 | 232 |
|  | VL | US 2011/0274685 | 233 |
| CD28-binding CRBR Sequences | | | |
| CD28 sdAb | sdAb |  | 235 |
| ICOS-binding CRBR Sequences | | | |
| ICOS sdAb | sdAb |  | 234 |

In some embodiments, the one or more CRBR is linked, directly or indirectly via a linker, to the Fc region and/or to the CD3 binding region. In some embodiments, linkage is via a linker. In some embodiments, the linker is a linking peptide (LP), which can include any flexible or rigid linker as described herein, although generally the peptide linking the CRBR or regions is not a cleavable liker.

In some embodiments, the multispecific polypeptide construct comprises a linking peptide (LP) between the CRBR and the Fc region. In some embodiments, the multispecific polypeptide construct comprises a linking peptide (LP) between the CD3 binding region and the CRBR.

f. Inhibitory Receptor Binding Regions (IRBR)

The multispecific polypeptide constructs of the present disclosure include one or more inhibitor receptor binding region (IRBR) that binds an inhibitory receptor. In some embodiments, the one or more IRBR of the provided multispecific polypeptide constructs bind an inhibitory receptor expressed on T cells. In some embodiments, the inhibitory receptor is upregulated, induced, or expressed on the surface of an activated T cell. In some aspects, the IRBR blocks an interaction between the inhibitory receptor and its ligand, thereby reducing, suppressing or decreasing an inhibitory signal in the cell to which the IRBR binds, e.g. T cell. In some embodiments, the IRBR, or independently each of the IRBRs, is an antibody or antigen binding fragment, a natural cognate binding partner of the inhibitory receptor, an Anticalin (engineered lipocalin), a Darpin, a Fynomer, a Centyrin (engineered fibroneticin III domain), a cystine-knot domain, an Affilin, an Affibody, or an engineered CH3 domain.

In some embodiments, the IRBR, or independently each of the IRBRs, such as the first IRBR and the second IRBR, includes one or more copies of an antibody or an antigen-binding fragment thereof. In some embodiments, the IRBR or independently each of the IRBRs, such as the first IRBR and the second IRBR, includes one or more copies of an antibody or an antigen-binding fragment thereof selected from the group consisting of a Fab fragment, a F(ab')2 fragment, an Fv fragment, a scFv, a scAb, a dAb, a single domain heavy chain antibody, and a single domain light chain antibody.

In some embodiments, the IRBR, or independently each of the IRBRs, such as the first IRBR and the second IRBR, is a single chain antibody. In some examples, the single chain is an scFv, a scAb, a single domain heavy chain antibody, or a single domain light chain antibody.

In some embodiments, the IRBR, or independently each of the IRBRs, such as the first IRBR and the second IRBR, includes one or more single domain antibody (sdAb) fragments, for example VHH, VNAR, engineered VH or VK domains. VHHs can be generated from natural camelid heavy chain only antibodies, genetically modified rodents that produce heavy chain only antibodies, or naïve/synthetic camelid or humanized camelid single domain antibody libraries. VNARs can be generated from cartilaginous fish heavy chain only antibodies. Various methods have been implemented to generate monomeric sdAbs from conventionally heterodimeric VH and VK domains, including interface engineering and selection of specific germline families.

In some embodiments, the IRBR, or independently each of the IRBRs such as the first IRBR and/or the second IRBR, of the multispecific polypeptide constructs contains at least one sdAb or an scFv that binds an inhibitory receptor. In some embodiments, the at least one scFv or sdAb that binds an inhibitory receptor is positioned amino-terminally relative to the Fc region and/or carboxy-terminally relative to the CD3 binding region of the multispecific polypeptide construct. In some embodiments, the multispecific polypeptide construct contains only one scFv or sdAb that binds to an inhibitory receptor, which can be positioned either amino-terminally relative to the Fc region and/or carboxy-terminally relative to the CD3 binding region. In some embodiments, the multispecific polypeptide construct contains two scFv or sdAb that bind to an inhibitory receptor, positioned amino-terminally relative to the Fc region and/or carboxy-terminally relative to the CD3 binding region.

In some embodiments, the multispecific polypeptide construct is formed from or includes two polypeptides, including a first polypeptide comprising a first Fc polypeptide of a heterodimeric Fc region, a linker, a VH domain of an anti-CD3 antibody or antigen binding fragment (e.g. Fv), and an scFv or sdAb that binds to an inhibitory receptor; and a second polypeptide comprising a second Fc polypeptide of the heterodimeric Fc region, the linker, a VL domain of the anti-CD3 antibody or antigen binding fragment (e.g. Fv) and, optionally, another, the same or different, scFv or sdAb that binds to an inhibitory receptor. The scFv or sdAb that binds the inhibitory receptor can be positioned amino terminally relative to an Fc polypeptide of the heterodimeric Fc and/or carboxy-terminally relative to a VH or VL chain of the CD3 binding region. At least one of the first and/or second polypeptide of the multispecific polypeptide construct also includes an antigen binding domain that binds a TAA or a chain thereof as described in Section II.4. In some embodiments, the antigen binding domain that binds a TAA is a scFv or sdAb and is included as part of the first and/or second polypeptide of the multispecific polypeptide construct. In some embodiments, the antigen binding domain that binds a TAA is a Fab, and the multispecific polypeptide construct is additionally formed from a third polypeptide where at least the first and second polypeptide include a chain of the Fab that binds TAA (e.g. VH-CH1 or VL-CL of a Fab) and the third polypeptide contains the other chain of the Fab that binds TAA (e.g. the other of VH-CH1 or VL-CL of a Fab).

In some embodiments, the multispecific polypeptide construct is formed from or includes two polypeptides, including a first polypeptide comprising in order: a first antigen binding domain specific for a TAA, a first Fc polypeptide of a heterodimeric Fc region, a linker, a VH domain of an anti-CD3 antibody or antigen binding fragment (e.g. Fv), and a second antigen binding domain specific for a TAA; and a second polypeptide containing the IRBR and comprising in order: a second Fc polypeptide of the heterodimeric Fc region, the linker, a VL domain of the anti-CD3 antibody or antigen binding fragment (e.g. Fv), wherein the IRBR is positioned amino terminally to the Fc region and/or C-terminally to the CD3 binding region. In some embodiments, the IRBR is positioned on the second polypeptide carboxyterminally to the CD3 binding region. In some embodiments, the IRBR is positioned on the second polypeptide amino-terminally to the Fc region. In some embodiments, the IRBR is positioned amino terminally to the Fc region and C-terminally to the CD3 binding region. In some embodiments, the first and second antigen binding domain is specific to a TAA are the same. In some embodiments, the first and second antigen binding domain is specific to a TAA are different. In some embodiments, the first antigen binding domain and the second antigen binding domain bind a different TAA. In some embodiments, the first antigen binding domain and the second antigen binding domain bind a distinct or non-overlapping epitope of the same TAA and/or compete for binding to the same TAA.

In some embodiments, the IRBR or independently each of the IRBRs, such as the first IRBR and/or the second IRBR, contains more than one chain. In some embodiments, the IRBR or independently each of the IRBRs, such as the first IRBR and/or the second IRBR, of the multispecific polypeptide constructs contains VH and VL sequences assembled as FABs.

In some embodiments, the antigen binding domain or independently each of the antigen binding domains, such as the first antigen-binding domain and/or the second antigen binding domains, of the multispecific polypeptide constructs contains a VH-CH1 (Fd) and a VL-CL of a Fab antibody that binds an inhibitory receptor. In some embodiments, the Fab antibody containing a VH-CH1 (Fd) and a VL-CL is positioned amino-terminally relative to the Fc region and/or carboxy-terminally relative to the CD3 binding region of the multispecific polypeptide construct. In some embodiments, the multispecific polypeptide construct contains only one Fab antibody, containing a VH-CH1 (Fd) or VL-CL, that binds to an inhibitory receptor, which can be positioned either amino-terminally relative to the Fc region and/or carboxy-terminally relative to the CD3 binding region. In some embodiments, the multispecific polypeptide construct contains two Fab antibody fragments, each containing a VH-CH1 (Fd) and VL-CL, that binds to an inhibitory receptor, in which one is positioned amino-terminally relative to the Fc region and the other is positioned carboxyterminally relative to the CD3 binding region.

In some embodiments, the multispecific polypeptide construct is formed from or includes three or more polypeptides, including a first polypeptide comprising a first Fc polypeptide of a heterodimeric Fc region, a linker and a VH-CH1 (Fd) or VL-CL of a Fab antibody fragment that binds to an inhibitory receptor; a second polypeptide comprising a second Fc polypeptide of the heterodimeric Fc region, the linker and, optionally, the same VH-CH1 (Fd) or VL-CL of the Fab antibody fragment that binds to a inhibitory receptor, and a third polypeptide comprising the other of the VH-CH1 (Fd) or VL-CL of the Fab antibody fragment that binds to the inhibitory receptor. The first, second and/or third polypeptide of the multispecific polypeptide construct also can include an antigen binding domain that binds a TAA or a chain thereof as described in Section II.4. In some embodiments, the antigen binding domain that binds a TAA is a scFv or sdAb and is included as part of the first and/or second polypeptide of the multispecific polypeptide construct. In some embodiments, the antigen binding domain that binds a TAA is a Fab, and the multispecific polypeptide construct is additionally formed from a fourth polypeptide where at least a first and second polypeptide includes a chain of the Fab that binds TAA (e.g. VH-CH1 or VL-CL of a Fab) and the fourth polypeptide contains the other chain of the Fab that binds TAA (e.g. the other of VH-CH1 or VL-CL of a Fab).

In some embodiments, the IRBR, or independently each of the IRBRs, is or includes a natural (native) cognate binding partner of the inhibitor receptor (e.g. a natural ligand), or a variant thereof that exhibits binding activity to the inhibitory receptor.

In some embodiments, the one or more IRBR of the provided multispecific polypeptide constructs bind a inhibitory receptor expressed on T cells. In some embodiments, there are more than one IRBR that binds to an inhibitory receptor and each of the IRBRs, such as the first IRBR and the second IRBR, bind the same co-stimulatory receptor. In some embodiments, each of the IRBRs, such as the first IRBR and the second IRBR, bind a different inhibitory receptor. In some embodiments, each of the IRBRs, such as the first IRBR and the second IRBR bind a different epitope on the same inhibitory receptor. In some embodiments, each of the IRBRs, such as the first IRBR and the second IRBR, bind the same epitope on the same inhibitory receptor.

In some embodiments, the IRBR, or independently each of the IRBRs that binds a inhibitory receptor results in monovalent, bivalent, trivalent, or tetravalent binding to the inhibitory receptor.

In some embodiments, the inhibitory receptor is expressed on T cells, such as primary T cells of a subject. In some embodiments, the inhibitory receptor is expressed on human T cells, such as primary human T cells of a human subject.

In some embodiments, the inhibitory receptor is a member of the tumor necrosis factor (TNF) receptor family. In some embodiments, the inhibitory receptor is a member of the immunoglobulin superfamily (IgSF).

In some embodiments, the inhibitory receptor is Programmed cell death protein 1 (PD-1), cytotoxic T-lymphocyte associated protein 4 (CTLA-4), T cell immunoreceptor with Ig and ITIM domains (TIGIT), V-domain immunoglobulin suppressor of T cell activation (VISTA), T cell immunoglobulin and mucin-domain containing-3 (TIM3), or lymphocyte activation gene 3 (LAG3). In some embodiments, the one or more IRBR is an antibody or fragment thereof that binds to the inhibitor receptor PD-1, CTLA-4, TIGIT, VISTA, TIM3 or LAG3. In particular embodiments, the antibody or antigen-binding fragment is humanized or is human.

In some examples, the inhibitory receptor binding region (IRBR) binds or comprises a natural cognate binding partner of PD-1, CTLA-4, TIGIT, VISTA, or TIM3. In some embodiments, the natural cognate binding partner is selected from PD-L1, PD-L2, CD80, CD86, CD155, CD112, or VSIG-3/IGSF11, or a functional fragment thereof.

In some examples, the IRBR contains an antibody fragment, such as an scFv, that contains a variable light (VL) chain and a variable heavy (VH) chain of an antibody that that binds an inhibitory receptor, such as PD-1, CTLA-4, TIGIT, VISTA, or TIM3. In some examples, the IRBR contains a single domain antibody or a VHH domain that specifically binds an inhibitory receptor, such as a PD-1, CTLA-4, TIGIT, VISTA, or TIM3, see e.g. described in PCT publication No. WO2018068695 or WO2018068201.

In some embodiments, the inhibitory receptor is PD-1. In come embodiments, the one or more IRBR is an antibody fragment that binds to PD-1.

In some embodiments, the IRBR is or contains a VHH domain that binds PD-1 comprising a CDR1, CDR2 and CDR3 contained in a VHH amino acid sequences selected from any of SEQ ID NO: 417-433, 439, 489-506 or an amino acid sequence that has at least 90%, 91%, 92%, 93%, 94%, 95%, 96%, 97%, 98%, or 99% sequence identity to the VHH region amino acid selected from any one of SEQ ID NOs: 417-433, 439, 489-506 and binds PD-1.

In some embodiments, the IRBR is or contains a VHH domain that contains a CDR1, CDR2, CDR3 contained in a VHH domain set forth in SEQ ID NO:439, or an amino acid sequence that has at least 90%, 91%, 92%, 93%, 94%, 95%, 96%, 97%, 98%, or 99% sequence identity to the VHH region amino acid selected set forth in SEQ ID NO: 439 and that binds PD-1. In some embodiments, the IRBR is or contains a VHH domain that has the amino acid sequence set forth in SEQ ID NO: 439 or an amino acid sequence that has at least 90%, 91%, 92%, 93%, 94%, 95%, 96%, 97%, 98%, or 99% sequence identity to the amino acid selected set forth in SEQ ID NO: 439 and that binds PD-1. In some embodiments, IRBR is or contains a VHH domain that is a humanized variant of the amino acid sequence set forth in SEQ ID NO: 439.

In some embodiments, an IRBR that binds PD-1 has a VHH domain that comprises a CDR1 set forth in any one of SEQ ID NOS: 434, 435 or 436, a CDR2 set forth in SEQ ID NO: 437 and a CDR3 set forth in SEQ ID NO: 438.

In some embodiments, an IRBR that binds PD-1 has a VHH domain that contains a CDR1, CDR2, and CDR3 set forth in SEQ ID NOs: 435, 437, and 438, respectively. In some embodiments, an IRBR that binds PD-1 has a VHH domain that contains a CDR1, CDR2 and CDR3 set forth in SEQ ID NOs: 434, 437, and 438, respectively. In some embodiments, the an IRBR that binds PD-1 has a VHH domain that contains a CDR1, CDR2 and CDR3 set forth in SEQ ID NOs: 436, 437, and 438, respectively.

In some aspects, the IRBR is or contains a VHH domain that contains a CDR1, CDR2 and CDR3 contained in a VHH amino acid sequence selected from any of SEQ ID NO:417-433, or an amino acid sequence that has at least 90%, 91%, 92%, 93%, 94%, 95%, 96%, 97%, 98%, or 99% sequence identity to the VHH region amino acid selected from any one of SEQ ID NOs: 417-433 and that binds PD-1.

In some cases, the IRBR contains a VHH domain that is a humanized variant that has the amino acid sequence set forth in any of SEQ ID NOS: 417-433 or an amino acid sequence that has at least 90%, 91%, 92%, 93%, 94%, 95%, 96%, 97%, 98%, or 99% sequence identity to the VHH region amino acid selected from any one of SEQ ID NOs: 417-433 and that binds PD-1. In some embodiments, the IRBR is or contains a VHH domain sequence that is a humanized VHH domain having the sequence of amino acids set forth in any one of SEQ ID NOS: 417-433.

In some embodiments, the IRBR is or contains a VHH domain that contains a CDR1, CDR2, CDR3 contained in a VHH domain set forth in SEQ ID NO:489, or an amino acid sequence that has at least 90%, 91%, 92%, 93%, 94%, 95%, 96%, 97%, 98%, or 99% sequence identity to the VHH region amino acid selected set forth in SEQ ID NO: 489 and that binds PD-1. In some embodiments, the IRBR is or contains a VHH domain that has the amino acid sequence set forth in SEQ ID NO: 489 or an amino acid sequence that has at least 90%, 91%, 92%, 93%, 94%, 95%, 96%, 97%, 98%, or 99% sequence identity to the amino acid selected set forth in SEQ ID NO: 489 and that binds PD-1. In some embodiments, IRBR is or contains a VHH domain that is a humanized variant of the amino acid sequence set forth in SEQ ID NO: 489.

In some embodiments, an IRBR that binds PD-1 has a VHH domain that comprises a CDR1 set forth in any one of SEQ ID NOS: 434, 435 or 436, a CDR2 set forth in SEQ ID NO: 437 and a CDR3 set forth in SEQ ID NO: 438.

In some embodiments, an IRBR that binds PD-1 has a VHH domain that contains a CDR1, CDR2, and CDR3 set forth in SEQ ID NOs: 435, 437, and 438, respectively. In some embodiments, an IRBR that binds PD-1 has a VHH domain that contains a CDR1, CDR2 and CDR3 set forth in SEQ ID NOs: 434, 437, and 438, respectively. In some embodiments, the an IRBR that binds PD-1 has a VHH domain that contains a CDR1, CDR2 and CDR3 set forth in SEQ ID NOs: 436, 437, and 438, respectively.

In some aspects, the IRBR is or contains a VHH domain that contains a CDR1, CDR2 and CDR3 contained in a VHH amino acid sequence selected from any of SEQ ID NO: 490-506, or an amino acid sequence that has at least 90%, 91%, 92%, 93%, 94%, 95%, 96%, 97%, 98%, or 99% sequence identity to the VHH region amino acid selected from any one of SEQ ID NOs: 490-506 and that binds PD-1.

In some cases, the IRBR contains a VHH domain that is a humanized variant that has the amino acid sequence set forth in any of SEQ ID NOS: 490-506 or an amino acid sequence that has at least 90%, 91%, 92%, 93%, 94%, 95%, 96%, 97%, 98%, or 99% sequence identity to the VHH region amino acid selected from any one of SEQ ID NOs: 490-506 and that binds PD-1. In some embodiments, the IRBR is or contains a VHH domain sequence that is a humanized VHH domain having the sequence of amino acids set forth in any one of SEQ ID NOS: 490-506.

In some embodiments, the one or more IRBR is linked, directly or indirectly via a linker, to the Fc region and/or to the CD3 binding region. In some embodiments, linkage is via a linker. In some embodiments, the linker is a linking peptide (LP), which can include any flexible or rigid linker as described, such as in Section II.3, although generally the peptide linking the IRBR or regions is not a cleavable liker.

In some embodiments, the multispecific polypeptide construct comprises a linking peptide (LP) between the IRBR and the Fc region. In some embodiments, the multispecific polypeptide construct comprises a linking peptide (LP) between the CD3 binding region and the IRBR.

In some embodiments, the multispecific polypeptide construct comprises more than one IRBR. In some embodiments, the multispecific polypeptide construct comprises a first linking peptide (LP1) between the first IRBR and the Fc region. In some embodiments, the multispecific polypeptide construct comprises a second linking peptide (LP2) between the CD3 binding region and the second IRBR. In some embodiments, the multispecific polypeptide construct comprises a first linking peptide (LP1) between the first IRBR and the Fc region and a second linking peptide (LP2) between the CD3 binding region and the second CRBR. In some aspects, the multispecific polypeptide construct has the structural arrangement from N-terminus to C-terminus as follows: IRBR and/or antigen binding domain-LP1-Fc region-linker-CD3 binding region-LP2-IRBR and/or antigen binding domain. In some embodiments, the two linking peptides are not identical to each other.

In some embodiments, the LP (e.g., LP1 or LP2) is independently a peptide of about 1 to 20 amino acids in length. In some embodiments, the LP1 or LP2 is independently a peptide that is or comprises any Gly-Ser linker as set forth in SEQ ID NOs: 1-4, 125-127, 129 or GGS.

In some embodiments, the multispecific polypeptide construct contains both a CRBR and an IRBR. In some embodiments, one of the CRBR or IRBR is positioned amino-terminally relative to the Fc region and the other of the CRBR or IRBR is positioned carboxy-terminally relative to the CD3 binding region of the multispecific polypeptide construct. In some embodiments, the CRBR and IRBR are present on different polypeptide of a heterodimeric multispecific polypeptide construct, in which at least one of the polypeptides also contains the at least one antigen binding domain specific to a TAA. In some embodiments, the CRBR and IRBR are present on the same polypeptide (first polypeptide) of a heterodimeric multispecific polypeptide construct and the at least one antigen binding domain specific to a TAA is on the other (or second) polypeptide of the heterodimeric multispecific polypeptide construct.

In some embodiments, the multispecific polypeptide construct is formed from or includes two polypeptides. In some aspects, the first polypeptide comprises in order: a first antigen binding domain specific for a TAA, a first Fc polypeptide of a heterodimeric Fc region, a linker, a VH domain of an anti-CD3 antibody or antigen binding fragment (e.g. Fv), and a second antigen binding domain specific for a TAA; and a second polypeptide comprising in order: one of the IRBR or CRBR, a second Fc polypeptide of the heterodimeric Fc region, the linker, a VL domain of the anti-CD3 antibody or antigen binding fragment (e.g. Fv), and the other of the IRBR or CRBR. In some embodiments, the IRBR is positioned on the second polypeptide carboxy-terminally to the CD3 binding region and the CRBR is positioned on the second polypeptide amino-terminally to the Fc region. In some embodiments, the IRBR is positioned on the second polypeptide amino-terminally to the Fc region and the CRBR is positioned on the second polypeptide carboxy-terminally to the CD3 binding region. In some embodiments, the first and second antigen binding domain is specific to a TAA are the same. In some embodiments, the first and second antigen binding domain is specific to a TAA are different. In some embodiments, the first antigen binding domain and the second antigen binding domain bind a different TAA. In some embodiments, the first antigen binding domain and the second antigen binding domain bind a distinct or non-overlapping epitope of the same TAA and/or compete for binding to the same TAA.

3. NK Recruitment

In some embodiments, the DLL3-binding polypeptide is a bispecific construct that is or comprises at least one DLL3 VHH domain provided herein and at least one additional binding molecule capable of binding to a surface molecule expressed on a Natural Killer (NK) cells and/or recruiting NK cells. In particular aspects, the multispecific construct is bispecific for DLL3 and the NK cell surface molecule. In some embodiments, the surface molecule is CD16 (FcγRIII). Specifically, a provided bispecific DLL3-binding polypeptide is capable of specifically binding an an NK activating receptor expressed on a human NK cells cell, such as human CD16a.

CD16, a low affinity receptor for the Fc portion of some IgGs known to be involved in antibody-dependent cellular cytotoxicity (ADCC), is the best-characterized membrane receptor responsible for triggering of target cell lysis by NK cells (Mandelboim et al., 1999, PNAS 96:5640-5644). Generally, a large majority (approximately 90%) of human NK cells express CD56 at low density (CD56dim) and FcγRIII (CD16) at a high level (Cooper et al., 2001, Trends Immunol. 22:633-640). Human FcγRIII exists as two isoforms, CD16a (FcγRIIIA) and CD16b (FcγRIIIB), that share 96% sequence identity in their extracellular immunoglobulin-binding regions (van de Winkel and Capel, 1993, Immunol. Today 14(5):215-221). In particular embodiments, the additional binding molecule is capable of specifically binding CD16a.

CD16a is expressed on macrophages, mast cells, and NK cells as a transmembrane receptor. On NK cells, the alpha chain of CD16a associates with the immunoreceptor tyrosine-based activation motif (ITAM) containing FcεRI γ-chain and/or the T-cell receptor (TCR)/CD3 ζ-chain to mediate signalling (Wirthmueller et al., 1992, J. Exp. Med. 175:1381-1390). The interaction of CD16a with different combinations of homo- and hetero-dimers of the γ and ζ chains has been observed in NK cells, indicating the ability to mediate signaling via different signaling pathways via variations of the CD16a complex in NK cells (Anderson et al., 1990, PNAS 87(6):2274-2278; Ackerly et al., 1992, Int. J. Cancer Suppl. 7:11-14). FcγR-expressing effector cells have been shown to be involved in destroying tumor cells via ADCC. For example, engagement of CD16a, such as with an agonist binding molecule capable of specifically binding CD16a can result in activating of NK cells expressing CD16a, thereby eliciting a biological response, in particular a signaling response. In some cases, the binding molecule is capable of triggering cell killing, in a manner analogous to antibody-dependent cellular cytotoxicity (ADCC), by virtue of its binding to such cells.

In particular example, DLL3-binding polypeptides include bispecific molecules that can specifically bind to DLL3 and to CD16a may target NK cells to cells bearing such antigen, so that the cell bearing the antigen may be eradicated via NK cell mediated cell killing. For example, a binding molecule that specifically binds DLL3 expressed on a tumor cell may target NK-cells to the tumor cell. In some cases, activation of the NK cell caused by the binding molecule binding to CD16a can lead to killing of the tumor cells.

In some embodiments, the additional binding domain specific to an activating NK cell receptor, such as CD16a, is an antigen-binding fragment selected from a Fab fragment, a F(ab')$_2$ fragment, an Fv fragment, a scFv, disulfide stabilized Fv fragment (dsFv), a scAb, a dAb, a single domain heavy chain antibody (VHH), or a single domain light chain antibody. In some embodiments, the additional binding domain is monovalent for binding the activating T NK cell receptor, such as CD16a.

In some cases, the additional binding domain recognizes CD16a. In some embodiments, the anti-CD16a binding domain includes one or more copies of an anti-CD16a Fab fragment, an anti-CD16a F(ab')$_2$ fragment, an anti-CD16a Fv fragment, an anti-CD16a scFv, an anti-CD16a dsFv, an anti-CD16a scAb, an anti-CD16a dAb, an anti-CD16a single domain heavy chain antibody (VHH), and an anti-CD16a single domain light chain antibody. In some embodiments, the anti-CD16a binding domain is monovalent for binding CD16a. In some embodiments, the BH73-binding polypeptide is a bispecific construct that binds BH73 and agonizes the activity of CD16a.

Antibodies and antigen-binding fragments thereof specific for CD16a are known and include, for example, NM3E2 (McCall et al. (1999) Mol. Immunol., 36:433-045. Other anti-CD16a antibodies also can be used in the constructs provided herein, including any described in published U.S. patent application No. US10160280795; U.S. Pat. No. 9,701,750; Behar et al. (2008) Protein Eng Des Sel. 21:1-10; Arndt et al., (1999) Blood 94:2562-2568. In particular examples, the anti-CD16a is an anti-CD16a scFv. In some embodiments, the anti-CD16a is an anti-CD16a antibody included in a T and Ab molecule (see e.g. Reush et al. (2014) Mabs, 6:727-738). In some aspects, the anti-CD16a is an anti-CD16a or antigen binding fragment, such as an scFv, described in U.S. Pat. No. 9,035,026.

The provided bispecific constructs can be formatted in any of a number of formats containing the at least one DLL3 VHH domain and the at least one additional domain specific to an activating NK cell receptor, such as a CD16a-binding domain.

In one embodiment, the bispecific construct is a bispecific single-domain antibody-linked Fab (S-Fab) containing at least one DLL3 VHH domain as described linked, directly or indirectly to a Fab antigen binding fragment specific to an NK cell activating receptor, e.g. CD16a, such as an anti-CD16a Fab. In some embodiments, the DLL3 VHH domain is linked to the C-terminus of the VH or VL chain of an anti-C16a Fab. In some embodiments, the S-Fab can be further modified, such as by conjugation with polyethylene glycol (PEG), N-(2-hydroxypropyl) methacrylamide (HPMA) copolymers, proteins (such as albumin), polyglutamic acid or PASylation (Pan et al. (2018) International Journal of Nanomedicine, 2018:3189-3201).

In another embodiment, the bispecific construct is a scFv-single domain antibody in which the construct contains at least one DLL3 VHH as described linked, directly or indirectly, to an scFv containing a VH and a VL of an antigen binding domain specific to an NK cell activating receptor, e.g. CD16a. The scFv against an NK cell activating receptor, e.g. anti-CD16a scFv, can contain any of the VH and VL sequences as described. In some embodiments, the VHH domain and the scFv are connected by a linker, such as a peptide linker. In some embodiments, the peptide linker can be a peptide linker as described herein. In some embodiments, the VHH domain and the scFv are each connected, optionally through a hinge region or a linker (e.g. peptide linker), to an Fc region, such as an N-terminus of an Fc region. The Fc region can be any described herein, such as a human Fc region or a variant thereof, e.g. a human IgG1 Fc region or a variant thereof. In particular examples, the Fc region is formed by variant Fc domains, e.g. variant human IgG1 domains, that are mutated or modified to promote heterodimerization in which different polypeptides can be dimerized to yield a heterodimer.

In a further embodiment, the antigen binding domain specific to an NK cell activating receptor, e.g. CD16a, is a single domain antibody, such as is a VHH domain that specifically binds to CD16a. Single domain antibodies, including VHH domains that bind to CD16a are known, see e.g. published U.S. patent application No. US20160280795. In such aspects, a bispecific construct provided herein can include at least one DLL3 VHH domain and at least one CD16a VHH domain. For formatting the constructs, in some cases, each VHH domain is connected, optionally through a hinge region or linker (e.g. peptide linker), to an Fc region, such as an N-terminus of an Fc region. The Fc region can be any described herein, such as a human Fc region or a variant thereof, e.g. a human IgG1 Fc region or a variant thereof. In particular examples, the Fc region is formed by variant Fc domains, e.g. variant human IgG1 domains, that are mutated or modified to promote heterodimerization in which different polypeptides can be dimerized to yield a heterodimer.

In the above embodiments, exemplary modifications of an Fc region to promote heterodimerization are known, including any as described below, e.g. Table 3. In some embodiments, one Fc polypeptide of a heterodimeric Fc comprises the sequence of amino acids set forth in any of SEQ ID NOS: 103, 107, 115, 117, 440, or 446 and the other Fc polypeptide of the heterodimeric Fc contains the sequence of amino acids set forth in any of SEQ ID NOS: 104, 108, 111, 113, 119 121, 441, 444, or 448. In some embodiments, one Fc polypeptide of a heterodimeric Fc comprises the sequence of amino acids set forth in any of SEQ ID NOS: 105, 109, 116, 118, 442, or 447 and the other Fc polypeptide of the heterodimeric Fc comprises the sequence of amino acids set forth in any of SEQ ID NOS: 106, 110, 112, 114, 120, 122, 443, 445, or 449.

4. Cytokine Fusion and/or Cytokine Receptor Targeting

In some embodiments, the DLL3-binding polypeptide is a multispecific polypeptide construct that is a cytokine-antibody fusion protein (also called a DLL3 VHH-cytokine fusion). In some aspects, at least one DLL3 VHH domain provided herein is linked, directly or indirectly, to at least one cytokine, such as to an interferon. In particular embodiments, the cytokine is an interferon capable of exhibiting anti-proliferative activity, apoptotic activity and/or anti-viral activity. In some embodiments, the interferon of a DLL3 VHH-cytokine fusion provided herein is capable of binding to a receptor composed of IFNAR1 and/or 2. Any of a variety of assays can be used to assess the effect of such fusion proteins on binding IFNAR1 and/or 2, reducing or decreasing the growth rather and/or proliferation rate of a cancer cell, reducing tumor size, eliminating tumors or inducing the death of a cancer cell (e.g. via apoptosis). Such assays in include in vitro assays with various cancer cell lines known to express DLL3 or in vivo assays employing animal tumor models.

In some embodiments, the interferon is a type I interferon, such as a human type I interferon or a variant thereof. In some aspects, the human type I interferon is a variant that is a truncated human type I interferon or a human mutant type I interferon. In some embodiments, the type I interferon or variant thereof is a wild-type human IFN-alpha (IFN-alpha; alpha2 and natural higher affinity variants such as alpha 14), interferon beta (IFN-beta) as well as mutants and/or truncated forms thereof. In some embodiments, the interferon is a type II interferon, such as a human type II interferon or a variant thereof. In some aspects, the human type II interferon is a variant that is a truncated human type II interferon or a human mutant type II interferon. In some embodiments, the type II interferon or variant thereof is a wild-type human interferon gamma (IFN-gamma) as well as mutants and/or truncated forms thereof. In some embodiments, the provided cytokine-antibody fusion proteins can be used to inhibit the growth and/or proliferation of target cells (e.g. cancer cells) that express or overexpress DLL3.

In some embodiments, the DLL3 VHH-cytokine fusion protein is similar in format to any as described in International PCT published application No. WO2014194100; U.S. Pat. No. 9,803,021; Valedkarimi et al. (2017) Biomed Pharmacother., 95:731-742; or Young et al. (2014) Semin Oncol., 41:623-636.

In particular embodiments, the interferon, e.g. a type I interferon, such as a human type I interferon (e.g. IFN-alpha, IFN-beta, or IFN-gamma) is one that possesses the endogenous binding affinity and/or activity of the native or wild-type interferon, preferably at a level of at least 60%, or of at least or at least about 80%, such as at least 90%, 95%, 98%, 99%, 100%, or a level greater than the native wild-type interferon (in its isolated form).

Interferons and interferon mutants are a well known and well characterized group of cytokines (see e.g., WO 2002/095067; WO 2002/079249; WO 2002/101048; WO 2002/095067; WO 2002/083733; WO 2002/086156; WO 2002/083733; WO 2003/000896; WO 2002/101048; WO 2002/079249; WO 2003/000896; WO 2004/022593; WO2004/022747; WO 2003/023032; WO 2004/022593 and also in Kim et al. (2003) Cancer Lett. 189(2): 183-188; Hussain et al. (2000) J. Interferon Cytokine Res. 20(9): 763-768; Hussain et al. (1998) J. Interferon Cytokine Res. 18(7): 469-477; Nyman et al. (1988) Biochem. J. 329 (Pt 2): 295-302; Golovleva et al. (1997) J. Interferon Cytokine Res. 17(10): 637-645; Hussain et al. (1997) J. Interferon Cytokine Res. 17(9): 559-566; Golovleva et al. (1997) Hum. Hered. 47(4): 185-188; Kita et al. (1991) J. Interferon Cytokine Res. 17(3): 135-140; Golovleva et al. (1996) Am. J. Hum. Genet. 59(3): 570-578; Hussain et al. (1996) J. Interferon Cytokine Res. 16(7): 523-529; Linge et al. (1995) Biochim Biophys Acta. Any of such can be used in the provided cytokine-antibody fusion proteins.

In some embodiments, the interferon is a human type I interferon. Alleles of the human interferon family of genes/proteins are known, see e.g. Pestka (10983) Arch Biochem Biophys., 221:1-37; Diaz et al. (1994) Genomics, 22:540-52; Pestka (1986) Meth. Enzymol, 199: 3-4; and Krause et al. (2000) J. Biol. Chem., 275:22995-3004.

In some embodiments, the interferon is a full-length IFN-alpha (e.g. human IFN-alpha), a full-length IFN-beta (e.g. human IFN-beta) or a full-length IFN-gamma (e.g. human IFN-gamma). In some embodiments, the interferon is a biologically active truncated IFN-alpha (e.g. human IFN-alpha), a biologically active truncated IFN-beta (e.g. human IFN-beta) or a biologically active truncated IFN-gamma (e.g. human IFN-gamma). In some embodiments, a biologically active truncated interferon contains a contiguous sequence of amino acids of a wild-type or native interferon that is truncated at the N- and/or C-terminus and comprises a length that is at least or at least about 50%, 55%, 60%, 65%, 70%, 75%, 80%, 85%, 90% or more the length of the native or wild-type interferon. Any of a variety of standard assays for assessing biological activity of an interferon can be used. For example, IFN-alpha activity can be assayed by measuring antiviral activity against a particular test virus. Kits for assaying for IFN-alpha activity are commercially available (see, e.g., ILITE™ alphabeta kit by Neutekbio, Ireland). In some aspects, the IFN-alpha is an IFN-αa (e.g. Acc. No. CAA23805), IFN-a-c (Acc. No. P01566), IFN-a-d (Acc. No. AAB59403); IFNa-5 (Acc. No. CAA26702); IFNa-6 (Acc. No. AA26704); IFNa-4 (Acc. No. NP_066546); IFNa-4b (Acc. No. CAA26701); IFNa-I (Acc. No. AAA52725); IFNa-J (Acc. No. CAA23792); IFNa-H (Acc. No. CAA23794); IFNa-F (Acc. No. AAA52718); IFNa-7 (Acc. No. CAA26903), or is a biologically active fragment thereof. In some aspects, the IFN-beta is IFN-beta set forth in Acc. No. AAC41702 or is a biologically active fragment thereof. In some aspects, the IFN-gamma is IFN-gamma set forth in Acc. No. P01579 or is a biologically active fragment thereof.

In some embodiments, a provided DLL3 VHH-cytokine fusion contains a variant or mutant interferon alpha 2 (IFNa2) is contemplated. Certain mutants include a mutation of the His at position 57, and/or the E at position 58, and/or the Q at position 61. In certain embodiments the mutants include the mutation H57Y, and/or E58N, and/or Q61S. In certain embodiments the mutants include a mutated IFNa2 having the mutations H57Y, E58N, and Q61S (YNS) (see, e.g., Kalie et al. (2007) J. Biol. Chem., 282: 11602-11611). In other embodiments mutants include a mutation of the His at position 57, and/or the E at position 58, and/or the Q at position 61 to A (alanine). In certain embodiments the mutants include a mutated IFNa2 having the mutations H57A, E58A, and Q61A (HEQ) (see, e.g., Jaitin et al. (2006) Mol. Cellular Biol, 26(5): 1888-1897). In certain embodiments the mutant interferon comprises a mutation of His at position 57 to A, Y, or M, and/or a mutation of E at position 58 to A, or N, or D, or L, and/or a mutation of Q at position 61 to A, or S, or L, or D.

In certain embodiments mutant include mutants of interferon alpha 8 (IFN-α8), such as variants with amino acid replacement corresponding to R145 to V, I, or L, and/or A146 to N, or S, and/or M149 to Y, e.g. R145V/A146N/M149Y), R145I/A146S/M149Y or R145L/A146S/M149Y (see, e.g., Yamamoto et. al. (2009) J. Interferon & cytokine Res, 29: 161-170.

In some embodiments, a provided DLL3 VHH-cytokine fusion contains a mutant or variant IFN-beta containing a serine substituted for the naturally occurring cysteine at amino acid 17 (see, e.g., Hawkins et al. (1985) Cancer Res., 45, 5914-5920).

In some embodiments, a provided DLL3 VHH-cytokine fusion contains a truncated interferon. In one embodiment, a truncated interferon includes a human IFN-alpha with deletions of up to the first 15 amino-terminal amino acid residues and/or up to the last 10-13 carboxyl-terminal amino acid residues, which has been shown to retain activity of the native or wild-type human IFN-alpha (see e.g. Ackerman (1984) Proc. Natl. Acad. Sci, USA, 81: 1045-1047). In some embodiments, a truncated human IFN-alpha has 1, 2, 3, 4, 5, 6, 7, 8, 9, 10, 11, 12 or 13 carboxyl terminal amino acid residues deleted and/or 1, 2, 3, 4, 5, 6, 7, 8, 9, 10, 11, 12, 13, 14, or 15 amino terminal amino acid residues deleted.

In some embodiments, a provided DLL3 VHH-cytokine fusion contains a truncated interferon, such as described in published U.S. patent appl. No. US2009/0025106. In some embodiments, a provided DLL3 VHH-cytokine fusion contains a truncated IFN-gamma containing N- and/or C-terminal deletions, such as described in Lundell et al. (1991) Protein Neg., 4:335-341; Pan et al. (1987, Eur. J. Biochem., 166:145-149); WO.

In some embodiments, the interferon, e.g. human interferon, is a mutant interferon that is resistant to proteolysis compared to the unmodified, typically wild-type protein, see e.g. U.S. Pat. Nos. 7,998,469; 8,052,964; 4,832,959; 6,120,762; WO1992/008737; and EP219781.

In aspects of the provided DLL3 VHH-cytokine fusion proteins, the antibody and the cytokine, e.g. interferon, are attached directly or are attached indirectly via a linker, such as a peptide linker. The attachment can be to the N- or C-terminus of the VHH domain, so long as the attachment does not interfere with binding of the antibody to DLL3. Any linker, e.g. peptide linker, described herein can be used. In some embodiments, the linker is a GS-linker that comprises an amino acid sequence selected from the group consisting of GGSGGS, i.e., $(GGS)_2$ (SEQ ID NO: 1); GGSGGSGGS, i.e., $(GGS)_3$ (SEQ ID NO: 2); GGSGGSGGSGGS, i.e., $(GGS)_4$ (SEQ ID NO: 3); and GGSGGSGGSGGSGGS, i.e., $(GGS)_5$ (SEQ ID NO: 4). In some embodiments, the linker is a flexible linker comprising Glycine residues, such as, by way of non-limiting example, GG, GGG, GGGG (SEQ ID NO: 5), GGGGG (SEQ ID NO: 6), and GGGGGG (SEQ ID NO: 7). In some embodiments, the fusion proteins can include a combination of a GS-linker and a Glycine linker.

D. Chimeric Receptors and Engineered Cells

Provided herein are chimeric antigen receptors (CARs) having an extracellular domain comprising one or more of the DLL3 VHH domains provided herein, such as any of the sequences of a DLL3 VHH domain provided herein. CAR constructs provided herein include an extracellular domain containing the one or more DLL3 VHH, a transmembrane domain and an intracellular signaling region. The one or more DLL3 VHH domain which form the antigen binding unit of the CAR "binds" or is "capable of binding", i.e. targets, DLL3 with sufficient affinity such the CAR is useful in therapy in targeting a cell or tissue expressing DLL3.

CARs are synthetic receptors typically containing an extracellular targeting/binding moiety that is associated with one or more signaling domains in a single fusion molecule, and that is expressed on the surface of a cell, such as a T cell. Thus, CARs combine antigen-specificity and T cell activating properties in a single fusion molecule. First generation CARs typically included the cytoplasmic region of the CD3zeta or Fc 1 receptor y chain as their signaling domain. First generation CARs have been tested in phase I clinical studies in patients with ovarian cancer, renal cancer, lymphoma, and neuroblastoma, where they have induced modest responses (reviewed in Sadelain et al., Curr Opin Immunol, 21 (2): 215-223, 2009). Second generation CARs, which contain the signalling domains of a costimulatory molecule, such as CD28, and CD3zeta, provide dual signalling to direct combined activating and co-stimulatory signals. Third generation CARs are more complex with three or more signaling domains (reviewed in Sadelain et al., Cancer Discovery (3), 388-398, 2013 and Dotti et al, Immuno. Rev, 257 (1), 1-36, 2014).

In some embodiments, a provided CAR contains at least one antigen binding domain comprising a DLL3 VHH domain that targets or is capable of specifically binding DLL3. In some embodiments, the CAR contains at least two antigen binding domains (where at least one comprises a DLL3 VHH domain) which target one or more antigen. In one embodiment, the antigen binding domain of a CAR comprises two or at least two DLL3 VHH domains that are specific for DLL3, thus providing a bivalent binding molecule. In one embodiment, the antigen binding domain comprises two or at least two DLL3 VHH domains that are specific for DLL3, but bind to different epitopes on said antigen. In such cases, the antigen binding domain comprises a first DLL3 VHH domain that binds to a first epitope of DLL3 and a second VHH domain that binds to a second epitope of DLL3. The epitopes may be overlapping. Thus, in some embodiments, the antigen binding domain is biparatopic and the CAR is a biparatopic CAR. In yet another embodiment, the antigen binding domain comprises two DLL3 VHH domains that are specific for DLL3 and bind to the same epitopes on DLL3.

The transmembrane domain of a CAR provided herein is a domain that typically crosses or is capable of crossing or spanning the plasma membrane and is connected, directly or indirectly (e.g. via a spacer, such as an immunoglobulin hinge sequence) to the extracellular antigen binding domain and the endoplasmic portion containing the intracellular signaling domain. In one embodiment, the transmembrane domain of the CAR is a transmembrane region of a transmembrane protein (for example Type I transmembrane proteins), an artificial hydrophobic sequence or a combination thereof. In one embodiment, the transmembrane domain comprises the CD3zeta domain or CD28 transmembrane domain. Other transmembrane domains will be apparent to those of skill in the art and may be used in connection with embodiments of a CAR provided herein.

The intracellular signaling region of a CAR provided herein contains one or more intracellular signaling domain that transmits a signal to a T cell upon engagement of the antigen binding domain of the CAR, such as upon binding antigen. In some embodiments, the intracellular region contains an intracellular signaling domain that is or contains an ITAM signaling domain. Exemplary intracellular signaling domains include, for example, a signaling domain derived from ζ chain of the T-cell receptor complex or any of its homologs (e.g., η chain, FcsRIy and β chains, MB 1 (Iga) chain, B29 (Ig) chain, etc.), human CD3zeta chain, CD3 polypeptides (Δ, δ and ε), syk family tyrosine kinases (Syk, ZAP 70, etc.), src family tyrosine kinases (Lck, Fyn, Lyn, etc.) and other molecules involved in T-cell transduction, such as CD2, CD5, OX40 and CD28. In particular embodiments, the intracellular signaling region contains an intracellular signaling domain derived from the human CD3 zeta chain.

In some embodiments, the endodomain comprises at CD3-zeta signaling domain. In some embodiments, the CD3-zeta signaling domain comprises the sequence of amino acids set forth in SEQ ID NO: 236 or a sequence of amino acids that exhibits at least 85%, 86%, 87%, 88%, 89%, 90%, 91%, 92%, 93%, 94%, 95%, 96%, 97%, 98% or 99% or more sequence identity to SEQ ID NO: 236 and retains the activity of T cell signaling.

In some embodiments, the intracellular signaling region of a CAR can further contain an intracellular signaling domain derived from a costimulatory molecule. In such examples, such a signaling domain may enhance CAR-T cell activity, such as via enhancement of proliferation, survival and/or development of memory cells, after antigen specific engagement, for example, compared to a CAR that only contains an ITAM containing signaling domain, e.g. CD3 zeta. In some embodiments, the co-stimulatory domain is a functional signaling domain obtained from a protein selected from: CD28, CD137 (4-IBB), CD134 (OX40), DapIO, CD27, CD2, CD5, ICAM-1, LFA-1 (CD11a/CD18), Lck, TNFR-I, TNFR-II, Fas, CD30, CD40 or combinations thereof. In particular embodiments, the costimulatory signaling domain is derived or obtained from a human protein. In some aspects, the costimulatory signaling domain is derived or obtained from human CD28 or human CD137 (4-IBB).

In some embodiments, the costimulatory signaling domain is a derived from CD28 or 4-1BB and comprises the sequence of amino acids set forth in any of SEQ ID NOS: 237-240 or a sequence of amino acids that exhibits at least 85%, 86%, 87%, 88%, 89%, 90%, 91%, 92%, 93%, 94%, 95%, 96%, 97%, 98% or 99% or more sequence identity to SEQ ID NO: 237-240 and retains the activity of T cell costimulatory signaling.

In particular embodiments, the CAR further comprises a hinge or spacer region which connects the extracellular antigen binding domain and the transmembrane domain. This hinge or spacer region can be used to achieve different lengths and flexibility of the resulting CAR. Examples of the a hinge or spacer region that can be used include, but are not limited to, Fc fragments of antibodies or fragments or derivatives thereof, hinge regions of antibodies, or fragments or derivatives thereof, $C_H2$ regions of antibodies, $C_H3$ regions of antibodies, artificial spacer sequences, for example peptide sequences, or combinations thereof. Other hinge or spacer region will be apparent to those of skill in the art and may be used. In one embodiment, the hinge is an IgG4 hinge or a CD8A hinge.

In some embodiments, the spacer and transmembrane domain are the hinge and transmembrane domain derived from CD8, such as having an exemplary sequence set forth in SEQ ID NO: 241-243 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 241-243.

Also provided herein is an isolated nucleic acid construct comprising at least one nucleic acid encoding a CAR as provided herein. In some aspects, the construct is an expression vector for expression of the CAR in a cell. The expression vector may be a viral vector. Viral vector technology is well known in the art and is described, for example, in Sambrook et al. (Molecular Cloning: A Laboratory Manual, Cold Spring Harbor Laboratory, New York, 2013). A number of viral based systems have been developed for gene transfer into mammalian cells. For example, retroviruses such as, adenovirus vectors are used. In one embodiment, a lentivirus vector is used.

In a further aspect, also provided is an isolated cell or cell population comprising one or more nucleic acid construct as described above. Also provided is an isolated cell or cell population that has been genetically modified to express a CAR provided herein. Thus, provided herein are genetically engineered cells which comprise, such as stably express, a CAR provided herein. In one embodiment, the cell is selected from the group consisting of a T cell, a Natural Killer (NK) cell, a cytotoxic T lymphocyte (CTL), a regulatory T cell, hematopoietic stem cells and/or pluripotent embryonic/induced stem cells. In some cases, the cell is a T cell, such as a CD4 and/or CD8 T cell. In some embodiments, the cells are autologous to the subject. For example, in some embodiments, T cells may be isolated from a patient (also called primary T cells) for engineering, e.g. transfection or transduction, with a CAR nucleic acid construct.

In an exemplary example, primary T-cells can be purified ex vivo (CD4 cells or CD8 cells or both) and stimulated with a TCR/CD28 agonists, such as anti-CD3/anti-CD28 coated beads. After a 2 or 3 day activation process, a recombinant expression vector encoding the CAR can be stably introduced into the primary T cells through standard lentiviral or retroviral transduction protocols or plasmid electroporation strategies. Cells can be monitored for CAR expression by, for example, flow cytometry using anti-epitope tag or antibodies that cross-react with native parental molecule. T-cells that express the CAR can be enriched through sorting with anti-epitope tag antibodies or enriched for high or low expression depending on the application.

The CAR engineered T-cells can be assayed for appropriate function by a variety of means. In some cases, in vitro cytotoxicity, proliferation, or cytokine assays (e.g., IFN-gamma expression) can be used to assess the function of engineered T-cells. Exemplary standard endpoints are percent lysis of a tumor line, proliferation of the engineered T-cell, or IFN-gamma protein expression in culture supernatant. In some cases, the ability to stimulate activation of T cells upon stimulation of the CAR, e.g. via antigen, can be assessed, such as by monitoring expression of activation markers such as CD69, CD44, or CD62L, proliferation and/or cytokine production.

Also provided herein are methods for the prevention and/or treatment of a disease or condition in a subject, such as a cancer, that includes administering to a subject engineered cells comprising a CAR provided herein. Generally, the subject is in need of treatment for the disease or condition. pharmaceutically active amount of a cell and/or of a pharmaceutical composition of the invention.

IV. Polypeptide Expression and Production

Nucleic acid molecules comprising polynucleotides that encode any of the provided sdAb and DLL3-binding polypeptides are provided. In some embodiments, the provided nucleic acid sequences and particularly DNA sequences encode fusion proteins as provided herein. In any of the foregoing embodiments, the nucleic acid molecule may also encode a leader sequence that directs secretion of the DLL3-binding polypeptide, which leader sequence is typically cleaved such that it is not present in the secreted polypeptide. The leader sequence may be a native heavy chain (or VHH) leader sequence, or may be another heterologous leader sequence.

Nucleic acid molecules can be constructed using recombinant DNA techniques conventional in the art. In some embodiments, a nucleic acid molecule is an expression vector that is suitable for expression in a selected host cell.

Vectors comprising nucleic acids that encode the DLL3-binding polypeptides described herein are provided. Such vectors include, but are not limited to, DNA vectors, phage vectors, viral vectors, retroviral vectors, etc. In some embodiments, a vector is selected that is optimized for expression of polypeptides in a desired cell type, such as CHO or CHO-derived cells, or in NSO cells. Exemplary such vectors are described, for example, in Running Deer et al., *Biotechnol. Prog.* 20:880-889 (2004).

In particular, a DNA vector that encodes a desired DLL3-binding polypeptides, such as a fusion protein, can be used to facilitate the methods of preparing the DLL3-binding polypeptides described herein and to obtain significant quantities. The DNA sequence can be inserted into an appropriate expression vector, i.e., a vector which contains the necessary elements for the transcription and translation of the inserted protein-coding sequence. A variety of host-vector systems may be utilized to express the protein-coding sequence. These include mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage DNA, plasmid DNA or cosmid DNA. Depending on the host-vector system utilized, any one of a number of suitable transcription and translation elements may be used.

The disclosure also provides methods of producing a DLL3-binding polypeptides by culturing a cell under conditions that lead to expression of the polypeptide, wherein the cell comprises an isolated nucleic acid molecule encoding a DLL3-binding polypeptide described herein, and/or vectors that include these isolated nucleic acid sequences.

In some embodiments, a DLL3-binding polypeptide may be expressed in prokaryotic cells, such as bacterial cells; or in eukaryotic cells, such as fungal cells (such as yeast), plant cells, insect cells, and mammalian cells. Such expression may be carried out, for example, according to procedures known in the art. Exemplary eukaryotic cells that may be used to express polypeptides include, but are not limited to, COS cells, including COS 7 cells; 293 cells, including 293-6E cells; CHO cells, including CHO-S, DG44. Lec13 CHO cells, and FUT8 CHO cells; PER.C6® cells (Crucell); and NSO cells. In some embodiments, the DLL3-binding polypeptides may be expressed in yeast. See, e.g., U.S. Publication No. US 2006/0270045 A1. In some embodiments, a particular eukaryotic host cell is selected based on its ability to make desired post-translational modifications to the polypeptide. For example, in some embodiments, CHO cells produce polypeptides that have a higher level of sialylation than the same polypeptide produced in 293 cells.

Introduction of one or more nucleic acids (such as vectors) into a desired host cell may be accomplished by any method, including but not limited to, calcium phosphate transfection, DEAE-dextran mediated transfection, cationic lipid-mediated transfection, electroporation, transduction, infection, etc. Nonlimiting exemplary methods are described, for example, in Sambrook et al., Molecular Cloning, A Laboratory Manual, 3$^{rd}$ ed. Cold Spring Harbor Laboratory Press (2001). Nucleic acids may be transiently or stably transfected in the desired host cells, according to any suitable method.

Host cells comprising any of the nucleic acids or vectors described herein are also provided. In some embodiments, a host cell that expresses an DLL3-binding polypeptide described herein is provided. The DLL3-binding polypeptides expressed in host cells can be purified by any suitable method. Such methods include, but are not limited to, the use of affinity matrices or hydrophobic interaction chromatography. Suitable affinity ligands include the ROR1 ECD and agents that bind Fc regions. For example, a Protein A, Protein G, Protein A/G, or an antibody affinity column may be used to bind the Fc region and to purify a DLL3-binding polypeptide that comprises an Fc region. Hydrophobic interactive chromatography, for example, a butyl or phenyl column, may also suitable for purifying some polypeptides such as antibodies. Ion exchange chromatography (for example anion exchange chromatography and/or cation exchange chromatography) may also suitable for purifying some polypeptides such as antibodies. Mixed-mode chromatography (for example reversed phase/anion exchange, reversed phase/cation exchange, hydrophilic interaction/anion exchange, hydrophilic interaction/cation exchange, etc.) may also suitable for purifying some polypeptides such as antibodies. Many methods of purifying polypeptides are known in the art.

In some embodiments, the DLL3-binding polypeptide is produced in a cell-free system. Nonlimiting exemplary cell-free systems are described, for example, in Sitaraman et al., *Methods Mol. Biol.* 498: 229-44 (2009); Spirin, *Trends Biotechnol.* 22: 538-45 (2004); Endo et al., *Biotechnol. Adv.* 21: 695-713 (2003).

In some embodiments, DLL3-binding polypeptides prepared by the methods described above are provided. In some embodiments, the DLL3-binding polypeptide is prepared in a host cell. In some embodiments, the DLL3-binding polypeptide is prepared in a cell-free system. In some embodiments, the DLL3-binding polypeptide is purified. In some embodiments, a cell culture media comprising an DLL3-binding polypeptide is provided.

In some embodiments, compositions comprising antibodies prepared by the methods described above are provided. In some embodiments, the composition comprises a DLL3-binding polypeptide prepared in a host cell. In some embodiments, the composition comprises a DLL3-binding polypeptide prepared in a cell-free system. In some embodiments, the composition comprises a purified DLL3-binding polypeptide.

V. Pharmaceutical Compositions and Formulations

Provided herein are pharmaceutical compositions containing any of the DLL3-binding polypeptides provided herein or engineered cells expressing the same. In some embodiments, DLL3-binding polypeptides, such as fusion proteins of the disclosure (also referred to herein as "active compounds"), and derivatives, fragments, analogs and homologs thereof, can be incorporated into pharmaceutical compositions suitable for administration. In some embodiments, engineered cells expressing a chimeric receptor, such as a chimeric antigen receptor, containing a DLL3-binding polypeptide provided herein can be incorporated into pharmaceutical compositions suitable for administration.

Such compositions typically contain a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Suitable examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the disclosure is formulated to be compatible with its intended route of administration. Examples of routes of administration include parenteral, e.g., intravenous, intradermal, subcutaneous, intratumoral, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved, and the limitations inherent in the art of compounding such an active compound for the treatment of individuals.

The pharmaceutical compositions can be included in a kit, container, pack, or dispenser together with instructions for administration. These pharmaceutical compositions can be included in diagnostic kits with instructions for use.

Pharmaceutical compositions are administered in an amount effective for treatment or prophylaxis of the specific indication. The therapeutically effective amount is typically dependent on the weight of the subject being treated, his or her physical or health condition, the extensiveness of the condition to be treated, or the age of the subject being treated. In some embodiments, the pharmaceutical composition may be administered in an amount in the range of about 50 µg/kg body weight to about 50 mg/kg body weight per dose. In some embodiments, the pharmaceutical composition may be administered in an amount in the range of about 100 µg/kg body weight to about 50 mg/kg body weight per dose. In some embodiments, the pharmaceutical composition may be administered in an amount in the range of about 100 µg/kg body weight to about 20 mg/kg body weight per dose. In some embodiments, the pharmaceutical composition may be administered in an amount in the range of about 0.5 mg/kg body weight to about 20 mg/kg body weight per dose.

In some embodiments, the pharmaceutical composition may be administered in an amount in the range of about 10 mg to about 1,000 mg per dose. In some embodiments, the pharmaceutical composition may be administered in an amount in the range of about 20 mg to about 500 mg per dose. In some embodiments, the pharmaceutical composition may be administered in an amount in the range of about 20 mg to about 300 mg per dose. In some embodiments, the pharmaceutical composition may be administered in an amount in the range of about 20 mg to about 200 mg per dose.

The pharmaceutical composition may be administered as needed to subjects. In some embodiments, an effective dose of the pharmaceutical composition is administered to a subject one or more times. In various embodiments, an effective dose of the pharmaceutical composition is administered to the subject once a month, less than once a month, such as, for example, every two months, every three months, or every six months. In other embodiments, an effective dose of the pharmaceutical composition is administered more than once a month, such as, for example, every two weeks, every week, twice per week, three times per week, daily, or multiple times per day. An effective dose of the pharmaceutical composition is administered to the subject at least once. In some embodiments, the effective dose of the pharmaceutical composition may be administered multiple times, including for periods of at least a month, at least six months, or at least a year. In some embodiments, the pharmaceutical composition is administered to a subject as-needed to alleviate one or more symptoms of a condition.

VI. Methods of Treatment and Uses

The DLL3-binding polypeptides or engineered cells expressing the same described herein are useful in a variety of therapeutic, diagnostic and prophylactic indications. For example, the DLL3-binding polypeptides or engineered cells are useful in treating a variety of diseases and disorders in a subject. Such methods and uses include therapeutic methods and uses, for example, involving administration of the molecules or engineered cells, or compositions containing the same, to a subject having a disease, condition, or disorder, such as a tumor or cancer. In some embodiments, the molecule ore engineered cell is administered in an effective amount to effect treatment of the disease or disorder. Uses include uses of molecules containing the DLL3-binding polypeptides or engineered cells in such methods and treatments, and in the preparation of a medicament in order to carry out such therapeutic methods. In some embodiments, the methods are carried out by administering the DLL3-binding polypeptides or engineered cells, or compositions comprising the same, to the subject having or suspected of having the disease or condition. In some embodiments, the methods thereby treat the disease or condition or disorder in the subject.

In one embodiment, a DLL3-binding polypeptide or engineered cell of the disclosure may be used as therapeutic agents. Such agents will generally be employed to diagnose, prognose, monitor, treat, alleviate, and/or prevent a disease or pathology in a subject. A therapeutic regimen is carried out by identifying a subject, e.g., a human patient or other mammal suffering from (or at risk of developing) a disorder using standard methods. In some cases, a subject is selected that is known, suspected or that has been identified as having a tumor expressing DLL3. A DLL3-binding polypeptide or engineered cell is administered to the subject. A DLL3-binding polypeptide or engineered cell is administered to the subject and will generally have an effect due to its binding with the target(s).

In some embodiments, a provided DLL3 polypeptide multi-specific polypeptide construct or engineered cell is capable of modulating, e.g. increasing, an immune response when administered to a subject, such as by engagement of CD3 and/or a CD3 signal in a cell. In some embodiments, provided herein is a method of modulating an immune response in a subject by administering a therapeutically effective amount of a provided multispecific construction or engineered cell, or pharmaceutical compositions thereof. In some embodiments, the method of modulating an immune response increases or enhances an immune response in a subject. For example, the increase or enhanced response may be an increase in cell-mediated immunity. In some examples, the method increases T-cell activity, such as cytolytic T-cell (CTL) activity. In some embodiments, the modulated (e.g., increased) immune response is against a tumor or cancer.

In some embodiments, administration of a DLL3-binding polypeptide, such as an DLL3-Fc fusion protein or a multispecific construction containing an Fc region, may activate innate immune cells via engagement of FcγRs through the Fc-region of the multispecific polypeptide construct. Administration of such multispecific polypeptide constructs may agonize, stimulate, activate, and/or augment innate immune cell effector functions, including ADCC, cytokine release, degranulation and/or ADCP. In the case of a constrained multispecific polypeptide construct, administration of such multispecific polypeptide constructs may activate T-cells once the linker(s) joining the first and second component is cleaved by a protease and/or upon binding of DLL3 on a target cell (e.g. tumor cell), thereby allowing the anti-CD3 binding portion to bind CD3ε on the T cells. In some cases, administration of the multispecific polypeptide constructs may agonize, stimulate, activate, and/or augment CD3-mediated T cell activation, cytotoxicity, cytokine release and/or proliferation.

In some embodiments, the provided methods are for treating a disease or condition in a subject by administering a therapeutically effective amount of any of the provided DLL3-binding polypeptides or engineered cells or pharmaceutical compositions thereof. In some embodiments, the disease or condition is a tumor or a cancer. Generally, alleviation or treatment of a disease or disorder involves the lessening of one or more symptoms or medical problems associated with the disease or disorder. For example, in the case of cancer, the therapeutically effective amount of the drug can accomplish one or a combination of the following: reduce the number of cancer cells; reduce the tumor size; inhibit (i.e., to decrease to some extent and/or stop) cancer cell infiltration into peripheral organs; inhibit tumor metastasis; inhibit, to some extent, tumor growth; and/or relieve to some extent one or more of the symptoms associated with the cancer. In some embodiments, a composition of this disclosure can be used to prevent the onset or reoccurrence of the disease or disorder in a subject, e.g., a human or other mammal, such as a non-human primate, companion animal (e.g., cat, dog, horse), farm animal, work animal, or zoo animal. The terms subject and patient are used interchangeably herein.

In some embodiments, the DLL3-binding polypeptides or engineered cells, or pharmaceutical compositions thereof, can be used to inhibit growth of mammalian cancer cells (such as human cancer cells). A method of treating cancer can include administering an effective amount of any of the pharmaceutical compositions described herein to a subject with cancer. The effective amount of the pharmaceutical composition can be administered to inhibit, halt, or reverse progression of cancers. Human cancer cells can be treated in vivo, or ex vivo. In ex vivo treatment of a human patient, tissue or fluids containing cancer cells are treated outside the body and then the tissue or fluids are reintroduced back into the patient. In some embodiments, the cancer is treated in a human patient in vivo by administration of the therapeutic composition into the patient.

Non-liming examples of disease include: all types of cancers (breast, lung, colorectal, prostate, melanomas, head and neck, pancreatic, etc.), rheumatoid arthritis, Crohn's disuse, SLE, cardiovascular damage, ischemia, etc. For example, indications would include leukemias, including T-cell acute lymphoblastic leukemia (T-ALL), lymphoblastic diseases including multiple myeloma, and solid tumors, including lung, colorectal, prostate, pancreatic, and breast, including triple negative breast cancer. For example, indications include bone disease or metastasis in cancer, regardless of primary tumor origin; breast cancer, including by way of non-limiting example, ER/PR+ breast cancer, Her2+ breast cancer, triple-negative breast cancer; colorectal cancer; endometrial cancer; gastric cancer; glioblastoma; head and neck cancer, such as esophageal cancer; lung cancer, such as by way of non-limiting example, non-small cell lung cancer; multiple myeloma ovarian cancer; pancreatic cancer; prostate cancer; sarcoma, such as osteosarcoma; renal cancer, such as by way of nonlimiting example, renal cell carcinoma; and/or skin cancer, such as by way of nonlimiting example, squamous cell cancer, basal cell carcinoma, or melanoma. In some embodiments, the cancer is a squamous cell cancer. In some embodiments, the cancer is a skin squamous cell carcinoma. In some embodiments, the cancer is an esophageal squamous cell carcinoma. In some embodiments, the cancer is a head and neck squamous cell carcinoma. In some embodiments, the cancer is a lung squamous cell carcinoma.

In some embodiments, the DLL3-binding polypeptides or engineered cells, or pharmaceutical compositions thereof, or are useful in treating, alleviating a symptom of, ameliorating and/or delaying the progression of a cancer or other neoplastic condition. In some embodiments, the cancer is bladder cancer, breast cancer, uterine/cervical cancer, ovarian cancer, prostate cancer, testicular cancer, esophageal cancer, gastrointestinal cancer, pancreatic cancer, colorectal cancer, colon cancer, kidney cancer, head and neck cancer, lung cancer, stomach cancer, germ cell cancer, bone cancer, liver cancer, thyroid cancer, skin cancer, neoplasm of the central nervous system, lymphoma, leukemia, myeloma, sarcoma, and virus-related cancer. In certain embodiments, the cancer is a metastatic cancer, refractory cancer, or recurrent cancer.

In some embodiments, a therapeutically effective amount of a DLL3-binding polypeptide, such as a fusion protein or multispecific polypeptide construct, of the disclosure relates generally to the amount needed to achieve a therapeutic objective. Typically, precise amount of the compositions of the present disclosure to be administered can be determined by a physician with consideration of individual differences in age, weight, tumor size, extent of infection or metastasis, and condition of the patient (subject).

In some embodiments, a therapeutically effective dose may be, by way of nonlimiting example, from about 0.01 µg/kg body weight to about 10 mg/kg body weight. In some embodiments, the therapeutically effective dose may be, by way of nonlimiting example, from about 0.01 mg/kg body weight to about 5-10 mg/kg body weight. Common dosing frequencies may range, for example, from twice daily to once a week.

In some embodiments, a therapeutic amount of an engineered cell composition of the present disclosure is administered. It can generally be stated that a pharmaceutical composition comprising engineered cells, e.g., T cells, as described herein may be administered at a dosage of $10^4$ to $10^9$ cells/kg body weight, such as $10^5$ to $10^6$ cells/kg body weight, including all integer values within those ranges. Engineered cell compositions, such as T cell compositions, may also be administered multiple times at these dosages. The cells can be administered by using infusion techniques that are commonly known in immunotherapy (see, e.g., Rosenberg et al, New Eng. J. of Med. 319: 1676, 1988). The optimal dosage and treatment regime for a particular patient can readily be determined by one skilled in the art of medicine by monitoring the patient for signs of disease and adjusting the treatment accordingly.

Efficaciousness of treatment is determined in association with any known method for diagnosing or treating the particular disorder. Methods for the screening of DLL3-binding polypeptides, or engineered cells containing the same, that possess the desired specificity include, but are not limited to, enzyme linked immunosorbent assay (ELISA) and other immunologically mediated techniques known within the art. A variety of means are known for determining if administration of the provided DLL3-binding polypeptides or engineered cells sufficiently modulates immunological activity by eliminating, sequestering, or inactivating immune cells mediating or capable of mediating an undesired immune response; inducing, generating, or turning on immune cells that mediate or are capable of mediating a protective immune response; changing the physical or functional properties of immune cells; or a combination of these effects. Examples of measurements of the modulation of immunological activity include, but are not limited to, examination of the presence or absence of immune cell populations (using flow cytometry, immunohistochemistry, histology, electron microscopy, polymerase chain reaction (PCR)); measurement of the functional capacity of immune cells including ability or resistance to proliferate or divide in response to a signal (such as using T-cell proliferation assays and pepscan analysis based on 3H-thymidine incorporation following stimulation with anti-CD3 antibody, anti-T-cell receptor antibody, anti-CD28 antibody, calcium ionophores, PMA (phorbol 12-myristate 13-acetate) antigen presenting cells loaded with a peptide or protein antigen; B cell proliferation assays); measurement of the ability to kill or lyse other cells (such as cytotoxic T cell assays); measurements of the cytokines, chemokines, cell surface molecules, antibodies and other products of the cells (e.g., by flow cytometry, enzyme-linked immunosorbent assays, Western blot analysis, protein microarray analysis, immunoprecipitation analysis); measurement of biochemical markers of activation of immune cells or signaling pathways within immune cells (e.g., Western blot and immunoprecipitation analysis of tyrosine, serine or threonine phosphorylation, polypeptide cleavage, and formation or dissociation of protein complexes; protein array analysis; DNA transcriptional, profiling using DNA arrays or subtractive hybridization); measurements of cell death by apoptosis, necrosis, or other mechanisms (e.g., annexin V staining, TUNEL assays, gel electrophoresis to measure DNA laddering, histology; fluorogenic caspase assays, Western blot analysis of caspase substrates); measurement of the genes, proteins, and other molecules produced by immune cells (e.g., Northern blot analysis, polymerase chain reaction, DNA microarrays, protein microarrays, 2-dimensional gel electrophoresis, Western blot analysis, enzyme linked immunosorbent assays, flow cytometry); and measurement of clinical symptoms or outcomes such as improvement of autoimmune, neurodegenerative, and other diseases involving self-proteins or self-polypeptides (clinical scores, requirements for use of additional therapies, functional status, imaging studies) for example, by measuring relapse rate or disease severity.

The provided DLL3-binding polypeptides are also useful in a variety of diagnostic and prophylactic formulations. In one embodiment, a DLL3-binding polypeptide is administered to patients that are at risk of developing one or more of the aforementioned disorders. A patient's or organ's predisposition to one or more of the disorders can be determined using genotypic, serological or biochemical markers.

In another embodiment of the disclosure, a DLL3-binding polypeptide or engineered cell is administered to human individuals diagnosed with a clinical indication associated with one or more of the aforementioned disorders. Upon diagnosis, such a therapeutic agent is administered to mitigate or reverse the effects of the clinical indication.

Combination Therapy

DLL3-binding polypeptides or engineered cells of the present disclosure can be administered alone or in combination with other modes of treatment, such as other anticancer agents. They can be provided before, substantially contemporaneous with, or after other modes of treatment (i.e., concurrently or sequentially). In some embodiments, the method of treatment described herein can further include administering: radiation therapy, chemotherapy, vaccination, targeted tumor therapy, CAR-T therapy, oncolytic virus therapy, cancer immunotherapy, cytokine therapy, surgical resection, chromatin modification, ablation, cryotherapy, an antisense agent against a tumor target, a siRNA agent against a tumor target, a microRNA agent against a tumor target or an anti-cancer/tumor agent, or a biologic, such as an antibody, cytokine, or receptor extracellular domain-Fc fusion.

In some embodiments, a DLL3-binding polypeptide provided herein is given concurrently with one or more chemotherapeutic agent, CAR-T (chimeric antigen receptor T-cell) therapy, oncolytic virus therapy, cytokine therapy, and/or agents that target other checkpoint molecules, such as PD1, PD-L1, LAG3, TIM3, VISTA, gpNMB, B7H4, HHLA2, CD73, CTLA4, TIGIT, etc.

In some embodiments, the DLL3-binding polypeptide or engineered cells of the present disclosure is used in combination with other anti-tumor agents, such as anti-HER-2 antibodies, anti-CD20 antibodies, an epidermal growth factor receptor (EGFR) antagonist (e.g., a tyrosine kinase inhibitor), HER1/EGFR inhibitor (e.g., erlotinib (TARCEVA®), platelet derived growth factor inhibitors (e.g., GLEEVEC® (Imatinib Mesylate)), a COX-2 inhibitor (e.g., celecoxib), interferons, CTLA4 inhibitors (e.g., anti-CTLA antibody ipilimumab (YERVOY®)), PD-1 inhibitors (e.g., anti-PD1 antibodies, BMS-936558), PDL1 inhibitors (e.g., anti-PDL1 antibodies, MPDL3280A), PDL2 inhibitors (e.g., anti-PDL2 antibodies), cytokines, antagonists (e.g., neutralizing antibodies) that bind to one or more of the following targets ErbB2, ErbB3, ErbB4, PDGFR-beta, BlyS, APRIL, BCMA, PD-1, PDL1, PDL2, CTLA4, or VEGF receptor(s), TRAIL/Apo2, and other bioactive and organic chemical agents, etc.

In some embodiments, a DLL3-binding polypeptide or engineered cell provided herein is given concurrently with a PD-1/PD-L1 therapy. Examples of PD-1/PD-L1 therapy include nivolumab (BMS); pidilizumab (CureTech, CT-011), pembrolizumab (Merck); durvalumab (Medimmune/AstraZeneca); atezolizumab (Genentech/Roche); avelumab (Pfizer); AMP-224 (Amplimmune); BMS-936559; AMP-514 (Amplimmune); MDX-1105 (Merck); TSR-042 (Tesaro/AnaptysBio, ANB-011); STI-A1010 (Sorrento Therapeutics); STI-A1110 (Sorrento Therapeutics); and other agents that are directed against programmed death-1 (PD-1) or programmed death ligand 1 (PD-L1).

In some embodiments, the DLL3-binding polypeptide or engineered cell of the present disclosure may be used in combination with a chemotherapeutic agent. Examples of chemotherapeutic agents include, but are not limited to, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem Int'l. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane;

folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, OR); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Illinois), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluorometlhylornithine (DMFO); retinoids such as retinoic acid; capecitabine; combretastatin; leucovorin (VL); oxaliplatin, including the oxaliplatin treatment regimen (FOLFOX); inhibitors of PKC-alpha, Raf, H-Ras, EGFR (e.g., erlotinib)) (TARCEVA® and VEGF-A that reduce cell proliferation and pharmaceutically acceptable salts, acids or derivatives of any of the above.

Further nonlimiting exemplary chemotherapeutic agents include anti-hormonal agents that act to regulate or inhibit hormone action on cancers such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON® toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® (aldesleukin) rIL-2; LURTOTECAN® topoisomerase 1 inhibitor; ABARELIX® GnRH agoninst; and pharmaceutically acceptable salts, acids or derivatives of any of the above.

In some embodiments, the DLL3-binding polypeptide and the additional agent are formulated into a single therapeutic composition, and the DLL3-binding polypeptide and additional agent are administered simultaneously. Alternatively, the DLL3-binding polypeptide or engineered cell and the additional agent are separate from each other, e.g., each is formulated into a separate therapeutic composition, and the DLL3-binding polypeptide or engineered cell and the additional agent are administered simultaneously, or the DLL3-binding polypeptide or engineered cell and the additional agent are administered at different times during a treatment regimen. For example, the DLL3-binding polypeptide or engineered cell is administered prior to the administration of the additional agent, the DLL3-binding polypeptide or engineered cell is administered subsequent to the administration of the additional agent, or the DLL3-binding polypeptide or engineered cell and the additional agent are administered in an alternating fashion. The DLL3-binding polypeptide and additional agent may be administered in single doses or in multiple doses.

In some embodiments, the DLL3-binding polypeptide or engineered cell and the additional agent(s) are administered simultaneously. For example, the DLL3-binding polypeptide and the additional agent(s) can be formulated in a single composition or administered as two or more separate compositions. In some embodiments, the DLL3-binding polypeptide or engineered cell and the additional agent(s) are administered sequentially, or the DLL3-binding polypeptide or engineered cell and the additional agent are administered at different times during a treatment regimen.

VII. Exemplary Embodiments

Among the provided embodiments are:
1. A DLL3-binding polypeptide construct, comprising at least one heavy chain only variable domain (DLL3 VHH domain) that specifically binds DLL3 and one or more additional binding domain that binds to a target other than DLL3.
2. The DLL3-binding polypeptide construct of embodiment 1, wherein the at least one DLL3 VHH domain comprises a complementarity determining region 1 (CDR1) comprising an amino acid sequence selected from the group consisting of SEQ ID NO: 319, 320, 321, 322, 323, 324, 325, 326, 327, 328, 329, 330, 331, 332, 333, 334, 335 and 456; a complementarity determining region 2 (CDR2) comprising an amino acid sequence selected from the group consisting of SEQ ID NO: 336, 337, 338, 339, 340, 341, 342, 343, 344, 345, 346, 347, 348, 349, 350, 351, 352, 353, 384, 410, and 411; and a complementarity determining region 3 (CDR3) comprising an amino acid sequence selected from the group consisting of SEQ ID NO: 354, 355, 356, 357, 358, 359, 360, 361, 362, 363, 364, 365, 366, 367, 395, and 412-415, and binds DLL3.
3. A DLL3-binding polypeptide construct, comprising at least one heavy chain only variable domain (DLL3 VHH domain) that specifically binds DLL3 comprising a complementarity determining region 1 (CDR1) comprising an amino acid sequence selected from the group consisting of SEQ ID NO: 319, 320, 321, 322, 323, 324, 325, 326, 327, 328, 329, 330, 331, 332, 333, 334, 335 and 456; a complementarity determining region 2 (CDR2) comprising an amino acid sequence selected from the group consisting of SEQ ID NO: 336, 337, 338, 339, 340, 341, 342, 343, 344, 345, 346, 347, 348, 349, 350, 351, 352, 353, 384, 410, and 411; and a complementarity determining region 3 (CDR3) comprising an amino acid sequence selected from the group consisting of SEQ ID NO: 354, 355, 356, 357, 358, 359, 360, 361, 362, 363, 364, 365, 366, 367, 395, and 412-415, and binds DLL3.

4. The DLL3-binding polypeptide construct of any of embodiments 1-3, wherein the DLL3 is a human DLL3.

5. The DLL3-binding polypeptide construct of any of embodiments 1-4, wherein the at least one DLL3 VHH domain is humanized.

6. The DLL3-binding polypeptide construct of any of embodiments 1, 2, 4 and 5, wherein the one or more additional binding domains binds to an activating receptor on an immune cell.

7. The DLL3-binding polypeptide polypeptide construct of embodiment 6, wherein the immune cell is a T cell.

8. The DLL3-binding polypeptide construct of embodiment 6 or embodiment 7, wherein the activating receptor is CD3 (CD3ε).

9. The DLL3-binding polypeptide construct of embodiment 8 that is bispecific for DLL3 and CD3.

10. The DLL3-binding polypeptide construct of embodiment 9, wherein the immune cell is a Natural Killer (NK) cell.

11. The DLL3-binding polypeptide construct of embodiment 6 or embodiment 10, wherein the activating receptor is CD16 (CD16a).

12. The DLL3-binding polypeptide construct of embodiment 11 that is bispecific for DLL3 and CD16a.

13. The DLL3-binding polypeptide construct of any of embodiments 1, 2, 4 and 5, wherein the one or more additional binding domain binds to a cytokine receptor.

14. The DLL3-binding polypeptide construct of any of embodiments 1, 2 and 4-13, wherein the one or more additional binding domain comprises an antibody or antigen-binding fragment thereof.

15. The DLL3-binding polypeptide construct of any of embodiments 1, 2 and 4-14, wherein the one or more additional binding domain is monovalent.

16. The DLL3-binding polypeptide construct of embodiment 14 or embodiment 15, wherein the antibody or antigen-binding fragment thereof is an Fv, a disulfide-stabilized Fv (dsFv), scFv, a Fab, a single domain antibody (sdAb), a VNAR, or a VHH.

17. The DLL3-binding polypeptide construct of embodiment 13, wherein the one or more additional binding domain is a cytokine or is a truncated fragment or variant thereof capable of binding to the cytokine receptor.

18. The DLL3-binding polypeptide construct of embodiment 17, wherein the cytokine is an interferon, or is a truncated fragment or variant of an interferon.

19. The DLL3-binding polypeptide construct of embodiment 18, wherein the interferon is a type I interferon or a type II interferon, is a truncated fragment or variant of a type I interferon or is a truncated fragment or variant of a type II interferon.

20. The DLL3-binding polypeptide construct of embodiment 19, wherein: the type I interferon is an IFN-alpha or an IFN-beta or is a truncated fragment or variant thereof; or the type II interferon is an IFN-gamma or is a truncated fragment or variant thereof.

21. The DLL3-binding polypeptide construct of any of embodiments 1-20, wherein the polypeptide comprises an immunoglobulin Fc region.

22. The DLL3-binding polypeptide construct of any of embodiments 1, 2 and 4-21, wherein the polypeptide construct comprises an immunoglobulin Fc region that links the at least one VHH domain and the one or more additional binding domain.

23. The DLL3-binding polypeptide construct of any of embodiments 1-22 that is a dimer.

24. The DLL3-binding polypeptide construct of any of embodiments 21-23, wherein the Fc region is a homodimeric Fc region.

25. The DLL3-binding polypeptide construct of any of embodiments 21-24, wherein the Fc region comprises the sequence of amino acids set forth in any of SEQ ID NOS: 8, 10, 11, 12 or 13, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOS: 8, 10, 11, 12 or 13.

26. The DLL3-binding polypeptide construct of any of embodiments 21-24, wherein the Fc region is a human IgG1.

27. The DLL3-binding polypeptide construct of embodiment 26, wherein the Fc region comprises the sequence of amino acids set forth in SEQ ID NO: 8 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 8.

28. The DLL3-binding polypeptide construct of any of embodiments 21-23, wherein the Fc region is a heterodimeric Fc region.

29. The DLL3-binding polypeptide construct of any of embodiments 21-28, wherein the Fc region exhibits effector function.

30. The DLL3-binding polypeptide construct of any of embodiments 21-29, wherein the Fc region comprises a polypeptide comprising one or more amino acid modification that reduces effector function and/or reduces binding to an effector molecule selected from an Fc gamma receptor or C1q.

31. The DLL3-binding polypeptide construct of embodiment 30, wherein the one or more amino acid modification is deletion of one or more of Glu233, Leu234 or Leu235.

32. The DLL3-binding polypeptide construct of embodiment 30 or embodiment 31, wherein the Fc region comprises the sequence of amino acids set forth in SEQ ID NO: 9 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 9.

33. The DLL3-binding polypeptide construct of any of embodiments 1-32, wherein the at least one DLL3 VHH domain comprises the VHH domain sequence set forth in any of SEQ ID NOS: 102, 244-275, 277-300, 302-305, 314, 401, 416, 455, 476-480-488, and 507-518, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOS: 102, 244-275, 277-300, 302-305, 314, 401, 416, 455, 476-480-488, and 507-518, and binds DLL3.

34. The DLL3-binding polypeptide construct of any of embodiments 1-33, wherein the at least one DLL3 VHH domain comprises the sequence set forth in (i) SEQ ID NO: 244, (ii) a humanized variant of SEQ ID NO: 244, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 244, and binds DLL3.

35. The DLL3-binding polypeptide of any of embodiments 1-34, wherein the at least one DLL3 VHH domain comprises a CDR1 comprising an amino acid sequence selected from the group consisting of SEQ ID NO: 319, 320, 321, 322, 323, 324, 325 and 326; a CDR2 comprising an amino acid sequence selected from the group consisting of SEQ ID NO: 336, 337 and 338; and a CDR3 comprising an amino acid sequence set forth in SEQ ID NO: 354, and binds DLL3.

36. The DLL3-binding polypeptide construct of any of embodiments 1-35, wherein the at least one DLL3 VHH domain comprises a CDR1, CDR2 and CDR3 set forth in SEQ ID NOS: 319, 336 and 354, respectively; SEQ ID NOS: 319, 337 and 354, respectively; SEQ ID NOS: 319, 338 and 354, respectively; SEQ ID NOS: 320, 338 and 354, respectively; SEQ ID NOS: 321, 338 and 354, respectively; SEQ ID NOS: 322, 338 and 354, respectively; SEQ ID NOS: 323, 338 and 354, respectively; SEQ ID NOS: 324, 338 and 354, respectively; SEQ ID NOS: 325, 338 and 354, respectively; or SEQ ID NOS: 326, 338 and 354, respectively, and binds DLL3.

37. The DLL3-binding polypeptide construct of any of embodiments 1-36, wherein the at least one DLL3 VHH domain comprises the sequence of amino acids set forth in any one of SEQ ID NOs: 245-257 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 245-257, and binds DLL3.

38. The DLL3-binding polypeptide construct of embodiments 1-37, wherein the at least one DLL3 VHH domain comprises the sequence of amino acids set forth in any one of SEQ ID NOS: 245-257, and binds DLL3.

39. The DLL3-binding polypeptide construct of any of embodiments 1-33, wherein the at least one DLL3 VHH domain comprises the sequence set forth in (i) SEQ ID NO:258, (ii) a humanized variant of SEQ ID NO: 258, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 258, and binds DLL3.

40. The DLL3-binding polypeptide of any of embodiments 1-33 and 39, wherein the at least one DLL3 VHH domain comprising a CDR1 comprising an amino acid sequence set forth in SEQ ID NO: 327; a CDR2 comprising an amino acid sequence set forth in SEQ ID NO: 339; and a CDR3 comprising an amino acid sequence set forth in SEQ ID NO: 355, and binds DLL3.

41. The DLL3-binding polypeptide construct of any of embodiments 1-33, 39 and 40, wherein the at least one DLL3 VHH domain comprises a CDR1, CDR2 and CDR3 set forth in SEQ ID NO: 327, 339 and 335, respectively, and binds DLL3.

42. The DLL3-binding polypeptide construct of any of embodiments 1-33 and 39-41, wherein the at least one DLL3 VHH domain comprises the sequence of amino acids set forth in any one of SEQ ID NOs: 259-263 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 259-263, and binds DLL3.

43. The DLL3-binding polypeptide construct of embodiments 1-33 and 39-42, wherein the at least one DLL3 VHH domain comprises the sequence of amino acids set forth in any one of SEQ ID NOS: 259-263, and binds DLL3.

44. The DLL3-binding polypeptide construct of any of embodiments 1-33, wherein the at least one DLL3 VHH domain comprises the sequence set forth in (i) SEQ ID NO: 264 (ii) a humanized variant of SEQ ID NO: 264, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 264, and binds DLL3.

45. The DLL3-binding polypeptide construct of any of embodiments 1-33 and 44, wherein the at least one DLL3 VHH domain comprises a CDR1 comprising an amino acid sequence set forth in SEQ ID NO: 328, 329 or 456; a CDR2 comprising an amino acid sequence set forth in SEQ ID NO: 340; and a CDR3 comprising an amino acid sequence set forth in SEQ ID NO: 356, and binds DLL3.

46. The DLL3-binding polypeptide construct of any of embodiments 1-33, 44 and 45, wherein the at least one DLL3 VHH domain comprises a CDR1, CDR2 and CDR3 set forth in SEQ ID NOS: 328, 340 and 356, respectively; SEQ ID NOS: 329, 340 and 356, respectively, or SEQ ID NOS: 456, 340 and 356, respectively, and binds DLL3.

47. The DLL3-binding polypeptide construct of any of embodiments 1-33 and 44-46, wherein the at least one DLL3 VHH domain comprises the sequence of amino acids set forth in any one of SEQ ID NOs: 265-274, 416, 455, or 476-478 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 265-274, 416, 455, or 476-478, and binds DLL3.

48. The DLL3-binding polypeptide construct of embodiments 1-33 and 44-47, wherein the at least one DLL3 VHH domain comprises the sequence of amino acids set forth in any one of SEQ ID NOS: 265-274, 416, 455, or 476-478, and binds DLL3.

49. The DLL3-binding polypeptide construct of any of embodiments 1-33, wherein the at least one DLL3 VHH domain comprises the sequence set forth in (i) SEQ ID NO: 275 (ii) a humanized variant of SEQ ID NO: 275, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 275, and binds DLL3.

50. The DLL3-binding polypeptide construct of any of embodiments 1-33 and 49, wherein the at least one DLL3 VHH domain comprising a CDR1 comprising an amino acid sequence set forth in SEQ ID NO: 320; a CDR2 comprising an amino acid sequence set forth in SEQ ID NO: 341; and a CDR3 comprising an amino acid sequence set forth in SEQ ID NO: 357, and binds DLL3.

51. The DLL3-binding polypeptide construct of any of embodiments 1-33, 49 and 50, wherein the at least one DLL3 VHH domain comprises the sequence of amino acids set forth in any one of SEQ ID NOs: 277-279 and 479 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 277-279 and 479, and binds DLL3.

52. The DLL3-binding polypeptide construct of embodiments 1-33 and 49-51, wherein the at least one DLL3

VHH domain comprises the sequence of amino acids set forth in any one of SEQ ID NOS: 277-279 and 479, and binds DLL3.

53. The DLL3-binding polypeptide construct of any of embodiments 1-33, wherein the at least one DLL3 VHH domain comprises the sequence set forth in (i) SEQ ID NO: 280 (ii) a humanized variant of SEQ ID NO: 280, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 280, and binds DLL3.

54. The DLL3-binding polypeptide construct of any of embodiments 1-33 and 53, wherein the at least one DLL3 VHH domain comprising a CDR1 comprising an amino acid sequence set forth in SEQ ID NO: 330; a CDR2 comprising an amino acid sequence set forth in SEQ ID NO: 342; and a CDR3 comprising an amino acid sequence set forth in SEQ ID NO: 358, and binds DLL3.

55. The DLL3-binding polypeptide construct of any of embodiments 1-33, 53 and 54, wherein the at least one DLL3 VHH domain comprises the sequence of amino acids set forth in any one of SEQ ID NOs: 281-286 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 281-286, and binds DLL3.

56. The DLL3-binding polypeptide construct of embodiments 1-33 and 53-55, wherein the at least one DLL3 VHH domain comprises the sequence of amino acids set forth in any one of SEQ ID NOS: 281-286, and binds DLL3.

57. The DLL3-binding polypeptide construct of any of embodiments 1-33, wherein the at least one DLL3 VHH domain comprises the sequence set forth in (i) SEQ ID NO: 287, (ii) a humanized variant of SEQ ID NO: 287, or (iii) a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 287, and binds DLL3.

58. The DLL3-binding polypeptide construct of any of embodiments 1-33 and 57, wherein the at least one DLL3 VHH domain comprises a CDR1 comprising an amino acid sequence set forth in SEQ ID NO: 320; a CDR2 comprising an amino acid sequence selected from the group consisting of SEQ ID NO: 345, 346 and 347; and a CDR3 comprising an amino acid sequence selected from the group consisting of SEQ ID NO: 359, 360, and 361, and binds DLL3.

59. The DLL3-binding polypeptide construct of any of embodiments 1-33, and 57-58, wherein the at least one DLL3 VHH domain comprises a CDR1, CDR2 and CDR3 set forth in SEQ ID NOS: 320, 345 and 359, respectively; SEQ ID NOS: 320, 346, and 359, respectively; SEQ ID NOS: 320, 347, and 359, respectively; SEQ ID NOS: 320, 345 and 360, respectively; SEQ ID NOS: 320, 345 and 361, respectively; or SEQ ID NOS: 320, 347 and 360, respectively, and binds DLL3.

60. The DLL3-binding polypeptide construct of any of embodiments 1-33, and 57-59 wherein the at least one DLL3 VHH domain comprises the sequence of amino acids set forth in any one of SEQ ID NOs: 288-298 or 102 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 288-298 or 102, and binds DLL3.

61. The DLL3-binding polypeptide construct of embodiments 1-33, and 57-60, wherein the at least one DLL3 VHH domain comprises the sequence of amino acids set forth in any one of SEQ ID NOS: 288-298 or 102, and binds DLL3.

62. The DLL3-binding polypeptide construct of any of embodiments 1-33, wherein the at least one DLL3 VHH domain comprises the sequence set forth in (i) SEQ ID NO: 299, (ii) a humanized variant of SEQ ID NO: 299, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 299, and binds DLL3.

The DLL3-binding polypeptide of any of embodiments 1-33 and 62, wherein the at least one DLL3 VHH domain comprises a CDR1 comprising an amino acid sequence set forth in SEQ ID NO: 331; a CDR2 comprising an amino acid sequence selected from the group consisting of SEQ ID NO: 348, 349 and 350; and a CDR3 comprising an amino acid sequence set forth in SEQ ID NO: 356, and binds DLL3.

64. The DLL3-binding polypeptide construct of any of embodiments 1-33, and 62-63, wherein the at least one DLL3 VHH domain comprises a CDR1, CDR2 and CDR3 set forth in SEQ ID NOS: 331, 348 and 356, respectively; SEQ ID NOS: 331, 349 and 356, respectively; or SEQ ID NOS: 331, 350 and 356, respectively, and binds DLL3.

65. The DLL3-binding polypeptide construct of any of embodiments 1-33, and 62-64 wherein the at least one DLL3 VHH domain comprises the sequence of amino acids set forth in any one of SEQ ID NOs: 300, 302-305, and 480 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 300, 302-305, and 480, and binds DLL3.

66. The DLL3-binding polypeptide construct of embodiments 1-33, and 62-65, wherein the at least one DLL3 VHH domain comprises the sequence of amino acids set forth in any one of SEQ ID NOS: 300, 302-305, and 480, and binds DLL3.

67. The DLL3-binding polypeptide construct of any of embodiments 1-33, wherein the at least one DLL3 VHH domain comprises the sequence set forth in (i) SEQ ID NO: 507, (ii) a humanized variant of SEQ ID NO: 507, or (iii) a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 507, and binds DLL3.

68. The DLL3-binding polypeptide construct of any of embodiments 1-33 and 67, wherein the at least one DLL3 VHH domain comprises a CDR1 comprising an amino acid sequence set forth in SEQ ID NO: 332; a CDR2 comprising an amino acid sequence selected from the group consisting of SEQ ID NO: 348, 349 and 350; and a CDR3 comprising an amino acid sequence set forth in SEQ ID NO: 362, and binds DLL3.

69. The DLL3-binding polypeptide construct of any of embodiments 1-33, and 67-68, wherein the at least one DLL3 VHH domain comprises a CDR1, CDR2 and CDR3 set forth in SEQ ID NOS: 332, 348 and 362, respectively; SEQ ID NOS: 332, 349 and 362, respectively; or SEQ ID NOS: 332, 350 and 362.

70. The DLL3-binding polypeptide construct of any of embodiments 1-33, and 67-69 wherein the at least one DLL3 VHH domain comprises the sequence of amino acids set forth in any one of SEQ ID NOs: 508-514 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 508-514, and binds DLL3.

71. The DLL3-binding polypeptide construct of embodiments 1-33, and 67-70, wherein the at least one DLL3 VHH domain comprises the sequence of amino acids set forth in any one of SEQ ID NOS: 508-514, and binds DLL3.

72. The DLL3-binding polypeptide construct of any of embodiments 1-33, wherein the at least one DLL3 VHH domain comprises the sequence set forth in (i) SEQ ID NO: 401, (ii) a humanized variant of SEQ ID NO: 401, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 401, and binds DLL3.

73. The DLL3-binding polypeptide construct of any of embodiments 1-33 and 72, wherein the at least one DLL3 VHH domain comprises a CDR1 comprising an amino acid sequence set forth in SEQ ID NO: 320; a CDR2 comprising an amino acid sequence selected from the group consisting of SEQ ID NO: 384, 410 and 411; and a CDR3 comprising an amino acid sequence selected from the group consisting of SEQ ID NO: 395, 412, 413, 414 and 415, and binds DLL3.

74. The DLL3-binding polypeptide construct of any of embodiments 1-33, and 72-73, wherein the at least one DLL3 VHH domain comprises a CDR1, CDR2 and CDR3 set forth in SEQ ID NOS: 320, 384 and 395, respectively; SEQ ID NOS: 320, 410 and 395, respectively; SEQ ID NOS: 320, 411 and 395, respectively; SEQ ID NOS: 320, 384 and 412, respectively; SEQ ID NOS: 320, 384 and 413, respectively; SEQ ID NOS: 320, 384 and 414, respectively; or SEQ ID NOS: 320, 384 and 415, and binds DLL3.

75. The DLL3-binding polypeptide construct of any of embodiments 1-33, and 72-74 wherein the at least one DLL3 VHH domain comprises the sequence of amino acids set forth in any one of SEQ ID NOs: 481-488 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 481-488, and binds DLL3.

76. The DLL3-binding polypeptide construct of embodiments 1-33, and 72-75, wherein the at least one DLL3 VHH domain comprises the sequence of amino acids set forth in any one of SEQ ID NOS: 481-488, and binds DLL3.

77. The DLL3-binding polypeptide construct of any of embodiments 1-33, wherein the at least one DLL3 VHH domain comprises the sequence set forth in (i) SEQ ID NO: 314, 518, 515, 516 or 517 (ii) a humanized variant of SEQ ID NO: 314, 518, 515, 516 or 517, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 314, 518, 515, 516 or 517, and binds DLL3.

78. The DLL3-binding polypeptide construct of any of embodiments 1-33 and 77, wherein the at least one DLL3 VHH domain comprises a CDR1, CDR2 and CDR3 set forth in SEQ ID NOS: 333, 351, and 363, respectively; 334, 352 and 364, respectively; 320, 353 and 365, respectively; 334, 339 and 366, respectively; or 335, 348 and 367, respectively, and binds DDL3.

79. The DLL3-binding polypeptide construct of any of embodiments 1-33, 77 and 78, wherein the at least one DLL3 VHH domain is set forth in SEQ ID NO: 314, 518, 515, 516 or 517, and binds DLL3.

80. A multispecific polypeptide construct, comprising: (a) a first component comprising a heterodimeric Fc region comprising a first Fc polypeptide and a second Fc polypeptide and (b) a second component comprising an anti-CD3 antibody or antigen-binding fragment comprising a variable heavy chain region (VH) and a variable light chain region (VL), wherein: the VH and VL that comprise the anti-CD3 antibody or antigen binding fragment are linked to opposite polypeptides of the heterodimeric Fc; the first and second components are coupled by a linker, wherein the heterodimeric Fc region is positioned N-terminal to the anti-CD3 antibody; and one or both of the first and second components comprises at least one antigen binding domain comprising a VHH domain that specifically binds DLL3 (DLL3 VHH domain).

81. The multispecific polypeptide construct of embodiment 80, wherein the multispecific polypeptide construct comprises at least (i) a first polypeptide comprising the first Fc polypeptide of the heterodimeric Fc region, the linker and the VH or VL domain of the anti-CD3 antibody or antigen binding fragment; and (ii) a second polypeptide comprising the second Fc polypeptide of the heterodimeric Fc region, the linker, optionally the same linker as present in the first polypeptide, and the other of the VH or VL domain of the anti-CD3 antibody or antigen binding fragment, wherein one or both of the first and second polypeptide comprise the at least one DLL3 VHH domain. 82. The multispecific polypeptide construct of embodiment 80 or embodiment 81, wherein one or both of the first and second Fc polypeptides of the heterodimeric Fc region comprises at least one modification to induce heterodimerization compared to a polypeptide of a homodimeric Fc region, optionally compared to the Fc polypeptide set forth in SEQ ID NO:8 or an immunologically active fragment thereof.

83. The multispecific polypeptide construct of embodiment 82, wherein each of the first and second Fc polypeptides of the heterodimeric Fc region independently comprise at least one amino acid modification.

84. The multispecific polypeptide construct of embodiment 83, wherein each of the first and second Fc polypeptides of the heterodimeric Fc region comprise a knob-into-hole modification or comprise a charge mutation to increase electrostatic complementarity of the polypeptides.

85. The multispecific polypeptide construct of embodiment 84, wherein the amino acid modification is a knob-into-hole modification.

86. The multispecific polypeptide construct of any of embodiments 80-85, wherein the first Fc polypeptide of the heterodimeric Fc region comprises the modification selected from among Thr366Ser, Leu368Ala, Tyr407Val, and combinations thereof and the second Fc polypeptide of the heterodimeric Fc region comprises the modification Thr366Trp.

87. The multispecific polypeptide construct of embodiment 86, wherein the first and second Fc polypeptides further comprises a modification of a non-cysteine residue to a cysteine residue, wherein the modification of the first Fc polypeptide is at one of the position Ser354 and Tyr349 and the modification of the second Fc polypeptide is at the other of the position Ser354 and Tyr349.

88. The multispecific polypeptide construct of any of embodiments 80-84, wherein the amino acid modification is a charge mutation to increase electrostatic complementarity of the polypeptides.

89. The multispecific polypeptide construct of any of embodiments 80-84 and 88, wherein the first and/or second Fc polypeptides or each of the first and second Fc polypeptide comprise a modification in complementary positions, wherein the modification is replacement with an amino acid having an opposite charge to the complementary amino acid of the other polypeptide.

90. The multispecific polypeptide construct of any of embodiments 60-69, wherein one of the first or second Fc polypeptide of the heterodimeric Fc region further comprises a modification at residue Ile253.

91. The multispecific polypeptide construct of embodiment 90, wherein the modification is Ile253Arg.

92. The multispecific polypeptide construct of any of embodiments 80-91, wherein one of the first or second Fc polypeptide of the heterodimeric Fc region further comprises a modification at residue His435.

93. The multispecific polypeptide construct of embodiment 92, wherein the modification is His435Arg.

94. The multispecific polypeptide construct of any of embodiments 80-93, wherein the Fc region comprises a polypeptide that lacks Lys447.

95. The multispecific polypeptide construct of any of embodiments 80-94, wherein the Fc region comprises a polypeptide comprising at least one modification to enhance FcRn binding.

96. The multispecific polypeptide construct of embodiment 95, wherein the modification is at a position selected from the group consisting of Met252, Ser254, Thr256, Met428, Asn434, and combinations thereof.

97. The multispecific polypeptide construct of embodiment 96, wherein the modification is selected from the group consisting of Met252Y, Ser254T, Thr256E, Met428L, Met428V, Asn434S, and combinations thereof.

98. The multispecific polypeptide construct of embodiment 96, wherein the modification is at position Met252 and at position Met428.

99. The multispecific polypeptide construct of embodiment 98, wherein the modification is Met252Y and Met428L.

100. The multispecific polypeptide construct of embodiment 76, wherein the modification is Met252Y and Met428V.

101. The multispecific polypeptide construct of any of embodiments 80-100, wherein the first Fc polypeptide of the heterodimeric Fc region comprises the sequence of amino acids set forth in any of SEQ ID NOS: 103, 107, 115 or 117, and the second Fc polypeptide of the heterodimeric Fc region comprises the sequence of amino acids set forth in any of SEQ ID NOS: 104, 108, 111, 113, 119 or 121.

102. The multispecific polypeptide construct of any of embodiments 1-101, wherein the Fc region comprises a polypeptide comprising at least one amino acid modification that reduces effector function and/or reduces binding to an effector molecule selected from an Fc gamma receptor or C1q.

103. The multispecific polypeptide construct of embodiment 102, wherein the one or more amino acid modification is deletion of one or more of Glu233, Leu234 or Leu235.

104. The multispecific polypeptide construct of any of embodiments 80-103, wherein the first Fc polypeptide of the heterodimeric Fc region comprises the sequence of amino acids set forth in any of SEQ ID NOS: 105, 109, 116 or 118 and the second Fc polypeptide of the heterodimeric Fc region comprises the sequence of amino acids set forth in any of SEQ ID NOS: 106, 110, 112, 114, 120 or 122.

105. The multispecific polypeptide construct of any of embodiment 80-104, wherein the anti-CD3 antibody or antigen binding fragment is monovalent.

106. The multispecific polypeptide construct of any of embodiments 80-105, wherein the anti-CD3 antibody or antigen-binding fragment is not a single chain antibody, optionally is not a single chain variable fragment (scFv). 107. The multispecific polypeptide construct of any of embodiments 80-106, wherein the anti-CD3 antibody or antigen binding fragment is an Fv antibody fragment.

108. The multispecific polypeptide construct of embodiment 107, wherein the Fv antibody fragment comprises a disulfide stabilized anti-CD3 binding Fv fragment (dsFv).

109. The multispecific polypeptide construct of any of embodiments 80-108, wherein the anti-CD3 antibody or antigen-binding fragment comprises a VH CDR1 comprising the amino acid sequence TYAMN (SEQ ID NO: 29); a VH CDR2 comprising the amino acid sequence RIRSKYNNYATYYADSVKD (SEQ ID NO: 30); a VH CDR3 comprising the amino acid sequence HGNFGNSYVSWFAY (SEQ ID NO: 31), a VL CDR1 comprising the amino acid sequence RSSTGAVTTSNYAN (SEQ ID NO: 32); a VL CDR2 comprising the amino acid sequence GTNKRAP (SEQ ID NO: 33); and a VL CDR3 comprising the amino acid sequence ALWYSNLWV (SEQ ID NO: 34).

110. The multispecific polypeptide construct of any of embodiments 80-109, wherein the anti-CD3 antibody or antigen-binding fragment comprises: a VH having the amino acid sequence of any of SEQ ID NOS: 35-65 or a sequence that exhibits at least 90%, 91%, 92%, 93%, 94%, 95%, 96%, 97%, 98% or 99% sequence identity to any of SEQ ID NOS: 35-65; and a VL having the amino acid sequence of any of SEQ ID NOS: 66-84 and 368 or a sequence that exhibits at least 90%, 91%, 92%, 93%, 94%, 95%, 96%, 97%, 98% or 99% sequence identity to any of SEQ ID NOS: 66-84 and 368.

111. The multispecific polypeptide construct of any of embodiments 80-110, wherein the anti-CD3 antibody or antigen-binding fragment comprises the amino acid sequence of SEQ ID NO: 47 and the amino acid sequence of SEQ ID NO: 75.

112. The multispecific polypeptide construct of any of embodiments 80-110, wherein the anti-CD3 antibody or antigen-binding fragment comprises the amino acid sequence of SEQ ID NO: 47 and the amino acid sequence of SEQ ID NO: 368.

113. The multispecific polypeptide construct of any of embodiment 80-112, wherein the at least one DLL3 VHH domain is positioned amino-terminally relative to the Fc region and/or carboxy-terminally relative to the CD3 binding region of the multispecific polypeptide construct.

114. The multispecific polypeptide construct of any of embodiments 80-113, wherein the multispecific polypeptide construct comprises a first DLL3 VHH domain that specifically binds DLL3 and a second DLL3 VHH domain that specifically binds DLL3.

115. The multispecific polypeptide construct of embodiment 114, wherein the first or second DLL3 VHH domain is positioned amino-terminally relative to the Fc region of the multispecific construct and the other of the first or second DLL3 VHH domain is positioned carboxy-terminally relative to the CD3 binding region of the multispecific construct.

116. The multispecific polypeptide construct of embodiment 114 or embodiment 115, wherein
the first component comprises in order of N-terminus to C-terminus a first DLL3 VHH domain that binds DLL3, the first Fc polypeptide of the heterodimeric Fc region, the linker, the VH or VL domain of the anti-CD3 antibody or antigen binding fragment and a second DLL3 VHH domain that binds DLL3; and the second polypeptide comprises in order of N-terminus to C-terminus the second Fc polypeptide of the heterodimeric Fc region, the linker, optionally the same linker as present in the first component, and the other of the VH or VL domain of the anti-CD3 antibody or antigen binding fragment.

117. The multispecific polypeptide construct of any of embodiments 114-116, wherein the first and second DLL3 VHH domain are the same.

118. The multispecific polypeptide construct of any of embodiments 114-116, wherein the first and second DLL3 VHH domain are different.

119. The multispecific polypeptide construct of embodiment 118, wherein the first and second DLL3 VHH domain bind a distinct or non-overlapping epitope of DLL3 and/or do not compete for binding to DLL3.

120. The multispecific polypeptide construct of embodiment 119, wherein:
the first VHH domain comprises the amino acid sequence set forth in any one of 251, 264, 267, 268, 287, 299, 507, 314, 517, or 455, a humanized variant thereof, or a sequence of amino acids that exhibits at least 85%, 86%, 87%, 88%, 89%, 90%, 91%, 92%, 93%, 94%, 95%, 96%, 97%, 98%, or 99% sequence identity to any of 251, 264, 267, 268, 287, 299, 507, 314, 517, or 455, and binds DLL3; and the second VHH domain comprises the amino acid sequence set forth in any one of 244, 251, 258, 267, 275, 280, 314, 518, 515, 516, 517, 455, or a humanized variant thereof, or a sequence of amino acids that exhibits at least 85%, 86%, 87%, 88%, 89%, 90%, 91%, 92%, 93%, 94%, 95%, 96%, 97%, 98%, or 99% sequence identity to any of 244, 251, 258, 267, 275, 280, 314, 518, 515, 516, 517, 455, and binds DLL3.

121. The multispecific polypeptide construct of embodiment 119 or 120, wherein:
the first VHH domain and second VHH domain comprise the amino acid sequence selected from SEQ ID NO: 244 and SEQ ID NO: 264; SEQ ID NO: 314 and SEQ ID NO: 517; SEQ ID NO: 244 and SEQ ID NO: 507; SEQ ID NO: 314 and SEQ ID NO: 507; SEQ ID NO: 314 and SEQ ID NO: 314; SEQ ID NO: 314 and SEQ ID NO: 299; SEQ ID NO:518 and SEQ ID NO: 264; SEQ ID NO: 251 and SEQ ID NO: 268; SEQ ID NO: 251 and SEQ ID NO: 267; SEQ ID NO: 275 and SEQ ID NO: 517; SEQ ID NO: 314 and SEQ ID NO: 287; SEQ ID NO: 314 and SEQ ID NO: 264; SEQ ID NO: 515 and SEQ ID NO: 517; SEQ ID NO: 516 and SEQ ID NO: 517; SEQ ID NO: 517 and SEQ ID NO: 517; SEQ ID NO:251 and SEQ ID NO:455; or SEQ ID NO: 244 and SEQ ID NO: 517.

122. The multispecific polypeptide construct of any of embodiments 80-121, wherein the at least one DLL3 VHH domain, or each of the first and second DLL3 VHH domain, independently comprises the VHH domain sequence set forth in any of SEQ ID NOS: 102, 244-275, 277-300, 302-305, 314, 401, 416, 455, 476-488, or 507-518, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOS: 102, 244-275, 277-300, 302-305, 314, 401, 416, 455, 476-488, or 507-518, and binds DLL3.

123. The multispecific polypeptide construct of any of embodiments 80-122, wherein the at least one DLL3 VHH domain, or each of the first and second DLL3 VHH domain, independently comprises the sequence set forth in (i) SEQ ID NO: 244, (ii) a humanized variant of SEQ ID NO: 244, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 244, and binds DLL3.

124. The multispecific polypeptide construct of any of embodiments 80-123, wherein the at least one DLL3 VHH domain, or each of the first and second DLL3 VHH domain, independently comprises a CDR1 comprising an amino acid sequence selected from the group consisting of SEQ ID NO: 319, 320, 321, 322, 323, 324, 325 and 326; a CDR2 comprising an amino acid sequence selected from the group consisting of SEQ ID NO: 336, 337 and 338; and a CDR3 comprising an amino acid sequence set forth in SEQ ID NO: 354, and binds DLL3.

125. The multispecific construct of any of embodiments 80-124, wherein the at least one DLL3 VHH domain, or each of the first and second DLL3 VHH domain, independently comprises a CDR1, CDR2 and CDR3 set forth in SEQ ID NOS: 319, 336 and 354, respectively; SEQ ID NOS: 319, 337 and 354, respectively; SEQ ID NOS: 319, 338 and 354, respectively; SEQ ID NOS: 320, 338 and 354, respectively; SEQ ID NOS: 321, 338 and 354, respectively; SEQ ID NOS: 322, 338 and 354, respectively; SEQ ID NOS: 323, 338 and 354, respectively; SEQ ID NOS: 324, 338 and 354, respectively; SEQ ID NOS: 325, 338 and 354, respectively; or SEQ ID NOS: 326, 338 and 354, respectively, and binds DLL3.

126. The multispecific polypeptide construct of any of embodiments 80-125, wherein the at least one DLL3 VHH domain, or each of the first and second DLL3 VHH domain, independently comprises the sequence of amino acids set forth in any one of SEQ ID NOs: 245-257 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 245-257, and binds DLL3.

127. The multispecific polypeptide construct of any of embodiments 80-126, wherein the at least one DLL3 VHH domain, or each of the first and second DLL3

VHH domain, independently comprises the sequence of amino acids set forth in any one of SEQ ID NOS: 245-257, and binds DLL3.

128. The multispecific polypeptide construct of any of embodiments 80-122, wherein the at least one DLL3 VHH domain, or each of the first and second DLL3 VHH domain, independently comprises the sequence set forth in (i) SEQ ID NO:258, (ii) a humanized variant of SEQ ID NO: 258, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 258, and binds DLL3.

129. The multispecific polypeptide construct of any of embodiments 80-122 and 128, wherein the at least one DLL3 VHH domain, or each of the first and second DLL3 VHH domain, independently comprises a CDR1 comprising an amino acid sequence set forth in SEQ ID NO: 327; a CDR2 comprising an amino acid sequence set forth in SEQ ID NO: 339; and a CDR3 comprising an amino acid sequence set forth in SEQ ID NO: 355, and binds DLL3.

130. The multispecific polypeptide construct of any of embodiments 80-122, 128 and 129, wherein the at least one DLL3 VHH domain, or each of the first and second DLL3 VHH domain, independently comprises a CDR1, CDR2 and CDR3 set forth in SEQ ID NO: 327, 339 and 335, respectively, and binds DLL3.

131. The multispecific polypeptide construct of any of embodiments 80-122 and 128-130, wherein the at least one DLL3 VHH domain, or each of the first and second DLL3 VHH domain, independently comprises the sequence of amino acids set forth in any one of SEQ ID NOs: 259-263 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 259-263, and binds DLL3.

132. The multispecific polypeptide construct of embodiments 80-122 and 128-131, wherein the at least one DLL3 VHH domain, or each of the first and second DLL3 VHH domain, independently comprises the sequence of amino acids set forth in any one of SEQ ID NOS: 259-263, and binds DLL3.

133. The multispecific polypeptide construct of any of embodiments 80-122, wherein the at least one DLL3 VHH domain, or each of the first and second DLL3 VHH domain, independently comprises the sequence set forth in (i) SEQ ID NO: 264 (ii) a humanized variant of SEQ ID NO: 264, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 264, and binds DLL3.

134. The multispecific polypeptide construct of any of embodiments 80-122 and 133, wherein the at least one DLL3 VHH domain, or each of the first and second VHH domain, independently comprises a CDR1 comprising an amino acid sequence set forth in SEQ ID NO: 328, 329 or 456; a CDR2 comprising an amino acid sequence set forth in SEQ ID NO: 340; and a CDR3 comprising an amino acid sequence set forth in SEQ ID NO: 356, and binds DLL3.

135. The multispecific polypeptide construct of any of embodiments 80-122, 133 and 134, wherein the at least one DLL3 VHH domain, or each of the first and second DLL3 VHH domain, independently comprises a CDR1, CDR2 and CDR3 set forth in SEQ ID NOS: 328, 340 and 356, respectively; or SEQ ID NOS: 329, 340 and 356, respectively; or SEQ ID NOS: 456, 340 and 356, respectively, and binds DLL3.

136. The multispecific polypeptide construct of any of embodiments 80-122 and 133-135, wherein the at least one DLL3 VHH domain, or each of the first and second DLL3 VHH domain, independently comprises the sequence of amino acids set forth in any one of SEQ ID NOs: 265-274, 416, 455, or 476-478 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 265-274, 416, 455, or 476-478, and binds DLL3.

137. The multispecific polypeptide construct of embodiments 80-122 and 133-136, wherein the at least one DLL3 VHH domain, or each of the first and second DLL3 VHH domain, independently comprises the sequence of amino acids set forth in any one of SEQ ID NOS: 265-274, 416, 455, or 476-478, and binds DLL3.

138. The multispecific polypeptide construct of any of embodiments 80-122, wherein the at least one DLL3 VHH domain, or each of the first and second DLL3 VHH domain, independently comprises the sequence set forth in (i) SEQ ID NO: 275 (ii) a humanized variant of SEQ ID NO: 275, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 275, and binds DLL3.

139. The multispecific polypeptide construct of any of embodiments 80-122 and 138, wherein the at least one DLL3 VHH domain, or each of the first and second DLL3 VHH domain, independently comprises a CDR1 comprising an amino acid sequence set forth in SEQ ID NO: 320; a CDR2 comprising an amino acid sequence set forth in SEQ ID NO: 341; and a CDR3 comprising an amino acid sequence set forth in SEQ ID NO: 357, and binds DLL3.

140. The multispecific polypeptide construct of any of embodiments 80-122, 138 and 139, wherein the at least one DLL3 VHH domain, or each of the first and second VHH domain, independently comprises the sequence of amino acids set forth in any one of SEQ ID NOs: 277-279 and 479 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 277-279 and 479, and binds DLL3.

141. The multispecific polypeptide construct of any of embodiments 80-122 and 138-140, wherein the at least one DLL3 VHH domain, or each of the first and second DLL3 VHH domain, independently comprises the sequence of amino acids set forth in any one of SEQ ID NOS: 277-279 and 479, and binds DLL3.

142. The multispecific polypeptide construct of any of embodiments 80-122, wherein the at least one DLL3 VHH domain, or each of the first and second DLL3 VHH domain, independently comprises the sequence set forth in (i) SEQ ID NO: 280 (ii) a humanized variant of SEQ ID NO:110, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 280, and binds DLL3.

143. The multispecific polypeptide construct of any of embodiments 80-122 and 142, wherein the at least one DLL3 VHH domain, or each of the first and second DLL3 VHH domain, independently comprises a CDR1 comprising an amino acid sequence set forth in SEQ ID NO: 330; a CDR2 comprising an amino acid sequence set forth in SEQ ID NO: 342; and a CDR3 comprising an amino acid sequence set forth in SEQ ID NO: 358, and binds DLL3.

144. The multispecific polypeptide construct of any of embodiments 80-122, 142 and 143, wherein the at least one DLL3 VHH domain, or each of the first and second VHH domain, independently comprises the sequence of amino acids set forth in any one of SEQ ID NOs: 281-286 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 281-286, and binds DLL3.

145. The multispecific polypeptide construct of any of embodiments 80-122 and 142-144, wherein the at least one DLL3 VHH domain, or each of the first and second DLL3 VHH domain, independently comprises the sequence of amino acids set forth in any one of SEQ ID NOS: 281-286, and binds DLL3.

146. The multispecific polypeptide construct of any of embodiments 80-122, wherein the at least one DLL3 VHH domain, or each of the first and second DLL3 VHH domain, independently comprises the sequence set forth in (i) SEQ ID NO: 287, (ii) a humanized variant of SEQ ID NO: 287, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 287, and binds DLL3.

147. The multispecific polypeptide construct of any of embodiments 80-122 and 146, wherein the at least one DLL3 VHH domain, or each of the first and second DLL3 VHH domain, independently comprises a CDR1 comprising an amino acid sequence set forth in SEQ ID NO: 320; a CDR2 comprising an amino acid sequence selected from the group consisting of SEQ ID NO: 345, 346 and 347; and a CDR3 comprising an amino acid sequence selected from the group consisting of SEQ ID NO: 359, 360, and 361, and binds DLL3.

148. The multispecific polypeptide construct of any of embodiments 80-122, 146 and 147, wherein the at least one DLL3 VHH domain comprises a CDR1, CDR2 and CDR3 set forth in SEQ ID NOS: 320, 345 and 359, respectively; SEQ ID NOS: 320, 346, and 359, respectively; SEQ ID NOS: 320, 347, and 359, respectively; SEQ ID NOS: 320, 345 and 360, respectively; SEQ ID NOS: 320, 345 and 361, respectively; or SEQ ID NOS: 320, 347 and 360, respectively, and binds DLL3.

149. The multispecific polypeptide construct of any of embodiments 80-122 and 146-148, wherein the at least one DLL3 VHH domain, or each of the first and second DLL3 VHH domain, independently comprises the sequence of amino acids set forth in any one of SEQ ID NOs: 288-298 or 102 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 288-298 or 102, and binds DLL3.

150. The multispecific polypeptide construct of embodiments 80-122 and 146-149, wherein the at least one DLL3 VHH domain, or each of the first and second DLL3 VHH domain, independently comprises the sequence of amino acids set forth in any one of SEQ ID NOS: 288-298 or 102, and binds DLL3.

151. The multispecific polypeptide construct of any of embodiments 80-122, wherein the at least one DLL3 VHH domain, or each of the first and second DLL3 VHH domain, independently comprises the sequence set forth in (i) SEQ ID NO: 299, (ii) a humanized variant of SEQ ID NO: 299, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 299, and binds DLL3.

152 The multispecific polypeptide construct of any of embodiments 80-122 and 151, wherein the at least one DLL3 VHH domain, or each of the first and second DLL3 VHH domain, independently comprises a CDR1 comprising an amino acid sequence set forth in SEQ ID NO: 331; a CDR2 comprising an amino acid sequence selected from the group consisting of SEQ ID NO: 348, 349 and 350; and a CDR3 comprising an amino acid sequence set forth in SEQ ID NO: 356, and binds DLL3.

153. The multispecific polypeptide construct of any of embodiments 80-122, 151 and 152, wherein the at least one DLL3 VHH domain comprises a CDR1, CDR2 and CDR3 set forth in SEQ ID NOS: 331, 348 and 356, respectively; SEQ ID NOS: 331, 349 and 356, respectively; or SEQ ID NOS: 331, 350 and 356, respectively, and binds DLL3.

154. The multispecific polypeptide construct of any of embodiments 80-122 and 151-153, wherein the at least one DLL3 VHH domain, or each of the first and second DLL3 VHH domain, independently comprises the sequence of amino acids set forth in any one of SEQ ID NOs: 300, 302-305, and 480 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 300, 302-305, and 480, and binds DLL3.

155. The multispecific polypeptide construct of embodiments 80-122 and 151-154, wherein the at least one DLL3 VHH domain, or each of the first and second DLL3 VHH domain, independently comprises the sequence of amino acids set forth in any one SEQ ID NOS: 300, 302-305, and 480, and binds DLL3.

156. The multispecific polypeptide construct of any of embodiments 80-122, wherein the at least one DLL3 VHH domain, or each of the first and second DLL3 VHH domain, independently comprises the sequence set forth in (i) SEQ ID NO: 507, (ii) a humanized variant of SEQ ID NO: 507, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 507, and binds DLL3.

157. The multispecific polypeptide construct of any of embodiments 80-122 and 156, wherein the at least one DLL3 VHH domain, or each of the first and second DLL3 VHH domain, independently comprises a CDR1 comprising an amino acid sequence set forth in SEQ ID NO: 332; a CDR2 comprising an amino acid sequence selected from the group consisting of SEQ ID NO: 348, 349 and 350; and a CDR3 comprising an amino acid sequence set forth in SEQ ID NO: 362, and binds DLL3.

158. The multispecific polypeptide construct of any of embodiments 80-122, 156 and 157, wherein the at least one DLL3 VHH domain comprises a CDR1, CDR2 and CDR3 set forth in SEQ ID NOS: 332, 348 and 362, respectively; SEQ ID NOS: 332, 349 and 362, respectively; or SEQ ID NOS: 332, 350 and 362, and binds DLL3.

159. The multispecific polypeptide construct of any of embodiments 80-122 and 156-158, wherein the at least one DLL3 VHH domain, or each of the first and second DLL3 VHH domain, independently comprises the sequence of amino acids set forth in any one of SEQ ID NOs: 508-514 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 508-514, and binds DLL3.

160. The multispecific polypeptide construct of embodiments 80-122 and 156-159, wherein the at least one DLL3 VHH domain, or each of the first and second DLL3 VHH domain, independently comprises the sequence of amino acids set forth in any one SEQ ID NOS: 508-514, and binds DLL3.

161. The multispecific polypeptide construct of any of embodiments 80-122, wherein the at least one DLL3 VHH domain, or each of the first and second DLL3 VHH domain, independently comprises the sequence set forth in (i) SEQ ID NO: 401, (ii) a humanized variant of SEQ ID NO: 401, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 401, and binds DLL3.

162. The multispecific polypeptide construct of any of embodiments 80-122 and 161, wherein the at least one DLL3 VHH domain, or each of the first and second DLL3 VHH domain, independently comprises a CDR1 comprising an amino acid sequence set forth in SEQ ID NO: 320; a CDR2 comprising an amino acid sequence selected from the group consisting of SEQ ID NO: 384, 410 and 411; and a CDR3 comprising an amino acid sequence selected from the group consisting of SEQ ID NO: 395, 412, 413, 414 and 415, and binds DLL3.

163. The multispecific polypeptide construct of any of embodiments 80-122, 161 and 162, wherein the at least one DLL3 VHH domain comprises a CDR1, CDR2 and CDR3 set forth in SEQ ID NOS: 320, 384 and 395, respectively; SEQ ID NOS: 320, 410 and 395, respectively; SEQ ID NOS: 320, 411 and 395, respectively; SEQ ID NOS: 320, 384 and 412, respectively; SEQ ID NOS: 320, 384 and 413, respectively; SEQ ID NOS: 320, 384 and 414, respectively; or SEQ ID NOS: 320, 384 and 415, and binds DLL3.

164. The multispecific polypeptide construct of any of embodiments 80-122 and 161-163, wherein the at least one DLL3 VHH domain, or each of the first and second DLL3 VHH domain, independently comprises the sequence of amino acids set forth in any one of SEQ ID NOs: 481-488, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 481-488, and binds DLL3.

165. The multispecific polypeptide construct of embodiments 80-122 and 161-164, wherein the at least one DLL3 VHH domain, or each of the first and second DLL3 VHH domain, independently comprises the sequence of amino acids set forth in any one SEQ ID NOS: 481-488, and binds DLL3.

166. The multispecific polypeptide construct of any of embodiments 80-122, wherein the at least one DLL3 VHH domain, or each of the first and second VHH domain, independently comprises the sequence set forth in (i) SEQ ID NO: 314, 518, 515, 516 or 517, (ii) a humanized variant of SEQ ID NO: 314, 518, 515, 516 or 517, or (iii) a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 314, 518, 515, 516 or 517, and binds DLL3.

167. The multispecific polypeptide construct of any of embodiments 80-122 and 166, wherein the at least one DLL3 VHH domain, or each of the first and second DLL3 VHH domain, independently comprises a CDR1, CDR2 and CDR3 set forth in SEQ ID NOS: 333, 351, and 363, respectively; 334, 352 and 364, respectively; 320, 353 and 365, respectively; 334, 339 and 366, respectively; or 335, 348 and 367, respectively, and binds DDL3.

168. The multispecific polypeptide construct of any of embodiments 80-122, 166 and 167, wherein the at least one DLL3 VHH domain, or each of the first and second DLL3 VHH domain, independently is set forth in SEQ ID NO: 314, 518, 515, 516 or 517, and binds DLL3.

169. The multispecific polypeptide construct of any of embodiments 80-168, wherein one or both of the first and second component comprises at least one co-stimulatory receptor binding region (CRBR) that binds a co-stimulatory receptor.

170. The multispecific polypeptide construct of embodiment 169, wherein the at least one co-stimulatory receptor binding region (CRBR) is positioned amino-terminally relative to the Fc region and/or carboxy-terminally relative to the CD3 binding region of the multispecific polypeptide construct.

171. The multispecific polypeptide construct of embodiment 169 or embodiment 170, wherein the multispecific polypeptide construct comprises only one co-stimulatory receptor binding region (CRBR).

172. The multispecific polypeptide construct of any of embodiments 169-171, wherein:
the first component comprises in order of N-terminus to C-terminus a first DLL3 VHH domain that binds DLL3, the first Fc polypeptide of the heterodimeric Fc region, the linker, the VH or VL domain of the anti-CD3 antibody or antigen binding fragment and a second DLL3 VHH domain that binds DLL3; and the second component comprises the CRBR and comprises in order of N-terminus to C-terminus the second Fc polypeptide of the heterodimeric Fc region, the linker, optionally the same linker as present in the first component, the other of the VH or VL domain of the anti-CD3 antibody or antigen binding fragment, wherein the CRBR is positioned amino-terminally relative to the Fc region or carboxy-terminally relative to the anti-CD3 antibody or antigen binding fragment of the second component.

173. The multispecific polypeptide construct of any of embodiments 169-172, wherein the at least one co-stimulatory receptor binding region (CRBR) is or comprises the extracellular domain or binding fragment thereof of the native cognate binding partner of the co-stimulatory receptor, or a variant thereof that exhibits binding activity to the co-stimulatory receptor.

174. The multispecific polypeptide construct of any of embodiments 169-173, wherein the at least one costimulatory receptor binding region (CRBR) is an antibody or antigen-binding fragment thereof selected from the group consisting of a Fab fragment, a F(ab')2 fragment, an Fv fragment, a scFv, a scAb, a dAb, a single domain heavy chain antibody, and a single domain light chain antibody.

175. The multispecific polypeptide construct of embodiment 174, wherein the antibody or antigen-binding fragment thereof is a Fv, a scFv, a Fab, a single domain antibody (VHH domain), a VNAR, or a VHH.

176. The multispecific polypeptide construct of embodiment 174 or embodiment 175, wherein the antibody or antigen-binding fragment is an VHH domain.

177. The multispecific polypeptide construct of embodiment 176, wherein the VHH domain is a human or humanized VHH domain.

178. The multispecific polypeptide construct of any of embodiments 169-177, wherein the at least one co-stimulatory receptor binding region (CRBR) binds a co-stimulatory receptor selected from among 41BB (CD137), OX40 (CD134), CD27, glucocorticoid-induced TNFR-related protein (GITR), CD28, ICOS, CD40, B-cell activating factor receptor (BAFF-R), B-cell maturation antigen (BCMA), Transmembrane activator and CAML interactor (TACI), and NKG2D.

179. The multispecific polypeptide construct of any of embodiments 169-178, wherein the at least one co-stimulatory receptor binding region (CRBR) binds a co-stimulatory receptor selected from among 41BB (CD137), OX40 (CD134), and glucocorticoid-induced TNFR-related protein (GITR).

180. The multispecific polypeptide construct of any of embodiments 169-179, wherein the at least one co-stimulatory receptor binding region (CRBR) comprises the sequence of amino acids set forth in SEQ ID NO:210 or a sequence that has at least 85%, 86%, 87%, 88%, 89%, 90%, 91%, 92%, 93%, 94%, 95%, 96%, 97%, 98%, or 99% sequence identity to the sequence set forth in SEQ ID NO:210 and binds 4-1BB.

181. The multispecific polypeptide construct of any of embodiments 80-180, wherein one or both of the first and second components comprises at least one inhibitory receptor binding region (IRBR) that binds an inhibitory receptor.

182. The multispecific polypeptide construct of embodiment 181, wherein the at least one inhibitory receptor binding region (IRBR) is positioned amino-terminally relative to the Fc region and/or carboxy-terminally relative to the CD3 binding region of the multispecific polypeptide construct.

183. The multispecific polypeptide construct of embodiment 181 or embodiment 182, wherein the multispecific polypeptide construct comprises only one inhibitory receptor binding region (IRBR).

184. The multispecific polypeptide construct of any of embodiments 181-183, wherein:
the first component comprises in order of N-terminus to C-terminus a first DLL3 VHH domain that binds DLL3, the first Fc polypeptide of the heterodimeric Fc region, the linker, the VH or VL domain of the anti-CD3 antibody or antigen binding fragment and a second DLL3 VHH domain that binds DLL3; and
the second component comprises the IRBR and comprises in order of N-terminus to C-terminus the second Fc polypeptide of the heterodimeric Fc region, the linker, optionally the same linker as present in the first component, the other of the VH or VL domain of the anti-CD3 antibody or antigen binding fragment, wherein the IRBR is positioned amino-terminally relative to the Fc region or carboxy-terminally relative to the anti-CD3 antibody or antigen-binding fragment of the second component.

185. The multispecific polypeptide construct of any of embodiments 181-184, wherein the at least one IRBR) is or comprises the extracellular domain or binding fragment thereof of the native cognate binding partner of the inhibitory receptor, or a variant thereof that exhibits binding activity to the inhibitory receptor.

186. The multispecific polypeptide construct of any of embodiments 181-185, wherein the at least one IRBR is an antibody or antigen-binding fragment thereof selected from the group consisting of a Fab fragment, a F(ab')2 fragment, an Fv fragment, a scFv, a scAb, a dAb, a single domain heavy chain antibody, and a single domain light chain antibody.

187. The multispecific polypeptide construct of embodiment 186, wherein the antibody or antigen-binding fragment thereof is a Fv, a scFv, a Fab, a single domain antibody (VHH domain), a VNAR, or a VHH.

188. The multispecific polypeptide construct of embodiment 186 or embodiment 187, wherein the antibody or antigen-binding fragment is an VHH domain.

189. The multispecific polypeptide construct of embodiment 188, wherein the VHH domain is a human or humanized VHH domain.

190. The multispecific polypeptide construct of any of embodiments 181-189, wherein the at least one IRBR binds a inhibitory receptor selected from among PD-1, CTLA-4, TIGIT, VISTA and TIM3.

191. The multispecific polypeptide construct of any of embodiments 181-189, wherein the at least one IRBR binds PD-1.

192. The multispecific polypeptide construct of any of embodiments 181-191, wherein:
the first component comprises in order of N-terminus to C-terminus a first DLL3 VHH domain that binds DLL3, the first Fc polypeptide of the heterodimeric Fc region, the linker, the VH or VL domain of the anti-CD3 antibody or antigen binding fragment and a second DLL3 VHH domain that binds DLL3; and
the second component comprises comprises in order of N-terminus to C-terminus one of the IRBR or the CRBR, the second Fc polypeptide of the heterodimeric Fc region, the linker, optionally the same linker as present in the first component, the other of the VH or VL domain of the anti-CD3 antibody or antigen binding fragment, and the other of the CRBR or IRBR.

193. The multispecific polypeptide construct of any of embodiments 80-192, wherein the linker is a peptide or polypeptide linker, optionally wherein the linker is 3, 4, 5, 6, 7, 8, 9, 10, 11, 12, 13, 14, 15, 16, 17, 18, 19 or 20 amino acids in length.

194. The multispecific polypeptide construct of any of embodiments 80-193, wherein the linker is a non-cleavable linker 195. The multispecific polypeptide construct of embodiment 194, wherein the non-cleavable linker comprises GS, GGS, GGGGS (SEQ ID NO: 125), GGGGGS (SEQ ID NO: 126) and combinations thereof.

196. The multispecific polypeptide construct of any of embodiments 80-195, wherein the linker is or comprises the sequence GGGGGSGGGGGSGGGGGS (SEQ ID NO: 127).

197. The multispecific polypeptide construct of any of embodiments 80-193, wherein the linker is a cleavable linker.
198. The multispecific polypeptide construct of embodiment 197, wherein the cleavable linker is a polypeptide that functions as a substrate for a protease.
199. The multispecific polypeptide construct of embodiment 198, wherein the protease is produced by an immune effector cell, by a tumor, or by cells present in the tumor microenvironment.
200. The multispecific polypeptide construct of embodiment 198 or embodiment 199, wherein the protease is produced by an immune effector cell and the immune effector cell is an activated T cell, a natural killer (NK) cell, or an NK T cell.
201. The multispecific polypeptide construct of any of embodiments 198-200, wherein the protease is selected from among matriptase, a matrix metalloprotease (MMP), granzyme B, and combinations thereof.
202. The multispecific polypeptide construct of embodiment 201, wherein the protease is granzyme B.
203. The multispecific polypeptide construct of any of embodiments 198-202, wherein the cleavable linker comprises the amino acid sequence GGSGGGGIEP-DIGGSGGS (SEQ ID NO: 171).
204. An isolated single domain antibody that binds DLL3, comprising a complementarity determining region 1 (CDR1) comprising an amino acid sequence selected from the group consisting of SEQ ID NO: 319, 320, 321, 322, 323, 324, 325, 326, 327, 328, 329, 330, 331, 332, 333, 334, 335 and 456; a complementarity determining region 2 (CDR2) comprising an amino acid sequence selected from the group consisting of SEQ ID NO: 336, 337, 338, 339, 340, 341, 342, 343, 344, 345, 346, 347, 348, 349, 350, 351, 352, 353, 384, 410, and 411; and a complementarity determining region 3 (CDR3) comprising an amino acid sequence selected from the group consisting of SEQ ID NO: 354, 355, 356, 357, 358, 359, 360, 361, 362, 363, 364, 365, 366, 367, 395, and 412-415.
205. The isolated single domain antibody of embodiment 204, comprising the amino acid sequence set forth in any of SEQ ID NOS: 102, 244-275, 277-300, 302-305, 314, 401, 416, 455, 476-480-488, and 507-518, or a sequence of amino acids that exhibits at least 85%, 86%, 87%, 88%, 89%, 90%, 91%, 92%, 93%, 94%, 95%, 96%, 97%, 98%, or 99% sequence identity to any of any of SEQ ID NOS: 102, 244-275, 277-300, 302-305, 314, 401, 416, 455, 476-480-488, and 507-518 and binds DLL3.
206. The isolated single domain antibody of embodiment 204 or embodiment 205, wherein the single domain antibody comprises the sequence set forth in (i) SEQ ID NO: 244, (ii) a humanized variant of SEQ ID NO:244, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 244, and binds DLL3.
207. The isolated single domain antibody of any of embodiments 204-206, wherein the sdAb comprises a CDR1 comprising an amino acid sequence selected from the group consisting of SEQ ID NO: 319, 320, 321, 322, 323, 324, 325 and 326; a CDR2 comprising an amino acid sequence selected from the group consisting of SEQ ID NO: 336, 337 and 338; and a CDR3 comprising an amino acid sequence set forth in SEQ ID NO: 354, and binds DLL3.
208. The isolated single domain antibody of any of embodiments 204-207, wherein the sdAb comprises a CDR1, CDR2 and CDR3 set forth in SEQ ID NOS: 319, 336 and 354, respectively; SEQ ID NOS: 319, 337 and 354, respectively; SEQ ID NOS: 319, 338 and 354, respectively; SEQ ID NOS: 320, 338 and 354, respectively; SEQ ID NOS: 321, 338 and 354, respectively; SEQ ID NOS: 322, 338 and 354, respectively; SEQ ID NOS: 323, 338 and 354, respectively; SEQ ID NOS: 324, 338 and 354, respectively; SEQ ID NOS: 325, 338 and 354, respectively; or SEQ ID NOS: 326, 338 and 354, respectively, and binds DLL3.
209. The isolated single domain antibody of any of embodiments 204-208, wherein the sdAb comprises the sequence of amino acids set forth in any one of SEQ ID NOs: 245-257 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 245-257, and binds DLL3.
210. The isolated single domain antibody of any of embodiments 204-209, wherein the sdAb comprises the sequence of amino acids set forth in any one of SEQ ID NOS: 245-257, and binds DLL3.
211. The isolated single domain antibody of embodiment 204 or embodiment 205, wherein the sdAb comprises the sequence set forth in (i) SEQ ID NO:258, (ii) a humanized variant of SEQ ID NO: 258, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 258, and binds DLL3.
212. The isolated single domain antibody of any of embodiments 204, 205 and 211, wherein the sdAb comprising a CDR1 comprising an amino acid sequence set forth in SEQ ID NO: 327; a CDR2 comprising an amino acid sequence set forth in SEQ ID NO: 339; and a CDR3 comprising an amino acid sequence set forth in SEQ ID NO: 355, and binds DLL3.
213. The isolated single domain antibody of any of embodiments 204, 205, 211, and 212, wherein the sdAb comprises a CDR1, CDR2 and CDR3 set forth in SEQ ID NO: 327, 339 and 335, respectively, and binds DLL3.
214. The isolated single domain antibody of any of embodiments 204, 205 and 211-213, wherein the sdAb comprises the sequence of amino acids set forth in any one of SEQ ID NOs: 259-263 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 259-263, and binds DLL3.
215. The isolated single domain antibody of any of embodiments 204, 205 and 211-214, wherein the sdAb comprises the sequence of amino acids set forth in any one of SEQ ID NOS: 259-263, and binds DLL3.
216. The isolated single domain antibody of embodiment 204 or embodiment 205, wherein the sdAb comprises the sequence set forth in (i) SEQ ID NO: 264 (ii) a humanized variant of SEQ ID NO: 264, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 264, and binds DLL3.
217. The isolated single domain antibody of embodiment 204, embodiment 205 or embodiment 216, wherein the sdAb comprises a CDR1 comprising an amino acid sequence selected from the group consisting of SEQ ID NO: 328, 329 or 456; a CDR2 comprising an amino acid sequence set forth in SEQ ID NO: 340; and a CDR3 comprising an amino acid sequence set forth in SEQ ID NO: 356, and binds DLL3.

218. The isolated single domain antibody of any of embodiments 204, 205 and 216-217, wherein the sdAb comprises a CDR1, CDR2 and CDR3 set forth in SEQ ID NOS: 328, 340 and 356, respectively; or SEQ ID NOS: 329, 340 and 356, respectively; SEQ ID NOS: 456, 340 and 356, respectively, and binds DLL3.

219. The isolated single domain antibody of any of embodiments 204, 205 and 216-218, wherein the sdAb comprises the sequence of amino acids set forth in any one of SEQ ID NOs: 265-274, 416, 455, or 476-478 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 265-274, 416, 455, or 476-478, and binds DLL3.

220. The isolated single domain antibody of any of embodiments 204, 205 and 216-219, wherein the at least one DLL3 sdAb comprises the sequence of amino acids set forth in any one of SEQ ID NOS: 265-274, 416, 455, or 476-478, and binds DLL3.

221. The isolated single domain antibody of embodiment 204 or embodiment 205, wherein the sdAb comprises the sequence set forth in (i) SEQ ID NO: 275 (ii) a humanized variant of SEQ ID NO: 275, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 275, and binds DLL3.

222. The isolated single domain antibody of embodiment 204, 205 or 221, wherein the sdAb comprising a CDR1 comprising an amino acid sequence set forth in SEQ ID NO: 320; a CDR2 comprising an amino acid sequence set forth in SEQ ID NO: 341; and a CDR3 comprising an amino acid sequence set forth in SEQ ID NO: 357, and binds DLL3.

223. The isolated single domain antibody of any of embodiments 204, 205 and 221-222, wherein the sdAb comprises the sequence of amino acids set forth in any one of SEQ ID NOs: 277-279 and 479 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 277-279 and 479, and binds DLL3.

224. The isolated single domain antibody of any of embodiments 204, 205 and 221-223, wherein the sdAb comprises the sequence of amino acids set forth in any one of SEQ ID NOS: 277-279 and 479.

225. The isolated single domain antibody of embodiment 204 or embodiment 205, wherein the sdAb comprises the sequence set forth in (i) SEQ ID NO: 280 (ii) a humanized variant of SEQ ID NO: 280, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 280, and binds DLL3.

226. The isolated single domain antibody of any of embodiments 204, 205 and 225, wherein the sdAb comprising a CDR1 comprising an amino acid sequence set forth in SEQ ID NO: 330; a CDR2 comprising an amino acid sequence set forth in SEQ ID NO: 342; and a CDR3 comprising an amino acid sequence set forth in SEQ ID NO: 358, and binds DLL3.

227. The isolated single domain antibody of any of embodiments 204, 205 and 225-226, wherein the sdAb comprises the sequence of amino acids set forth in any one of SEQ ID NOs: 281-286 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 281-286, and binds DLL3.

228. The isolated single domain antibody of any of embodiments 204, 205 and 225-227, wherein the sdAb comprises the sequence of amino acids set forth in any one of SEQ ID NOS: 281-286, and binds DLL3.

229. The isolated single domain antibody of embodiment 204 or embodiment 205, wherein the sdAb comprises the sequence set forth in (i) SEQ ID NO: 287, (ii) a humanized variant of SEQ ID NO: 287, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 287, and binds DLL3.

230. The isolated single domain antibody of any of embodiments 204, 205 and 229, wherein the sdAb comprising a CDR1 comprising an amino acid sequence set forth in SEQ ID NO: 320; a CDR2 comprising an amino acid sequence selected from the group consisting of SEQ ID NO: 345, 346 and 347; and a CDR3 comprising an amino acid sequence selected from the group consisting of SEQ ID NO: 359, 360, and 361, and binds DLL3.

231. The isolated single domain antibody of any of embodiments 204, 205 and 229-230, wherein the sdAb comprises a CDR1, CDR2 and CDR3 set forth in SEQ ID NOS: 320, 345 and 359, respectively; SEQ ID NOS: 320, 346, and 359, respectively; SEQ ID NOS: 320, 347, and 359, respectively; SEQ ID NOS: 320, 345 and 360, respectively; SEQ ID NOS: 320, 345 and 361, respectively; or SEQ ID NOS: 320, 347 and 360, respectively, and binds DLL3.

232. The isolated single domain antibody of any of embodiments 204, 205 and 229-231, wherein the sdAb comprises the sequence of amino acids set forth in any one of SEQ ID NOs: 288-298 or 102 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 288-298 or 102, and binds DLL3.

233. The isolated single domain antibody of any of embodiments 204, 205 and 229-232, wherein the sdAb comprises the sequence of amino acids set forth in any one of SEQ ID NOS: 288-298 or 102, and binds DLL3.

234. The isolated single domain antibody of embodiment 204 or embodiment 205, wherein the sdAb comprises the sequence set forth in (i) SEQ ID NO: 299, (ii) a humanized variant of SEQ ID NO: 299, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 299, and binds DLL3.

235 The isolated single domain antibody of any of embodiments 204, 205 and 234, wherein the sdAb comprising a CDR1 comprising an amino acid sequence set forth in SEQ ID NO: 331; a CDR2 comprising an amino acid sequence selected from the group consisting of SEQ ID NO: 348, 349 and 350; and a CDR3 comprising an amino acid sequence set forth in SEQ ID NO: 356, and binds DLL3.

236. The isolated single domain antibody of any of embodiments 204, 205 and 234-235, wherein the sdAb comprises a CDR1, CDR2 and CDR3 set forth in SEQ ID NOS: 331, 348 and 356, respectively; SEQ ID NOS: 331, 349 and 356, respectively; or SEQ ID NOS: 331, 350 and 356, respectively, and binds DLL3.

237. The isolated single domain antibody of any of embodiments 204, 205 and 234-236, wherein the sdAb comprises the sequence of amino acids set forth in any one of SEQ ID NOs: 300, 302-305, and 480 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 300, 302-305, and 480, and binds DLL3.

238. The isolated single domain antibody of any of embodiments 204, 205 and 234-237, wherein the sdAb comprises the sequence of amino acids set forth in any one of SEQ ID NOS: 300, 302-305, and 480, and binds DLL3.

239. The isolated single domain antibody of embodiment 204 or embodiment 205, wherein the sdAb comprises the sequence set forth in (i) SEQ ID NO: 507, (ii) a humanized variant of SEQ ID NO: 507, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 507, and binds DLL3.

240. The isolated single domain antibody of any of embodiments 204, 205 and 239, wherein the sdAb comprising a CDR1 comprising an amino acid sequence set forth in SEQ ID NO: 332; a CDR2 comprising an amino acid sequence selected from the group consisting of SEQ ID NO: 348, 349 and 350; and a CDR3 comprising an amino acid sequence set forth in SEQ ID NO: 362, and binds DLL3.

241. The isolated single domain antibody of any of embodiments 204, 205 and 239-240, wherein the sdAb comprises a CDR1, CDR2 and CDR3 set forth in SEQ ID NOS: 332, 348 and 362, respectively; SEQ ID NOS: 332, 349 and 362, respectively; or SEQ ID NOS: 332, 350 and 362, and binds DLL3.

242. The isolated single domain antibody of any of embodiments 204, 205 and 239-241, wherein the sdAb comprises the sequence of amino acids set forth in any one of SEQ ID NOs: 508-514 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 508-514, and binds DLL3.

243. The isolated single domain antibody of any of embodiments 204, 205 and 239-242, wherein the sdAb comprises the sequence of amino acids set forth in any one of SEQ ID NOS: 508-514, and binds DLL3.

244. The isolated single domain antibody of embodiment 204 or embodiment 205, wherein the sdAb comprises the sequence set forth in (i) SEQ ID NO: 401, (ii) a humanized variant of SEQ ID NO: 401, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 401, and binds DLL3.

245. The isolated single domain antibody of any of embodiments 204, 205 and 244, wherein the sdAb comprising a CDR1 comprising an amino acid sequence set forth in SEQ ID NO: 320; a CDR2 comprising an amino acid sequence selected from the group consisting of SEQ ID NO: 384, 410 and 411; and a CDR3 comprising an amino acid sequence selected from the group consisting of SEQ ID NO: 395, 412, 413, 414 and 415, and binds DLL3.

246. The isolated single domain antibody of any of embodiments 204, 205 and 244-245, wherein the sdAb comprises a CDR1, CDR2 and CDR3 set forth in SEQ ID NOS: 320, 384 and 395, respectively; SEQ ID NOS: 320, 410 and 395, respectively; SEQ ID NOS: 320, 411 and 395, respectively; SEQ ID NOS: 320, 384 and 412, respectively; SEQ ID NOS: 320, 384 and 413, respectively; SEQ ID NOS: 320, 384 and 414, respectively; or SEQ ID NOS: 320, 384 and 415, and binds DLL3.

247. The isolated single domain antibody of any of embodiments 204, 205 and 244-246, wherein the sdAb comprises the sequence of amino acids set forth in any one of SEQ ID NOs: 481-488 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 481-488, and binds DLL3.

248. The isolated single domain antibody of any of embodiments 204, 205 and 244-247, wherein the sdAb comprises the sequence of amino acids set forth in any one of SEQ ID NOS: 481-488, and binds DLL3.

249. The isolated single domain antibody of embodiment 204 or embodiment 205, wherein the sdAb comprises the sequence set forth in (i) SEQ ID NO: 314, 518, 515, 516 or 517 (ii) a humanized variant of SEQ ID NO: 314, 518, 515, 516 or 517, or (iii) a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 314, 518, 515, 516 or 517, and binds DLL3.

250. The isolated single domain antibody of any of embodiments 204, 205 and 249, wherein the at least one DLL3 sdAb comprises a CDR1, CDR2 and CDR3 set forth in SEQ ID NOS: 333, 351, and 363, respectively; 334, 352 and 364, respectively; 320, 353 and 365, respectively; 334, 339 and 366, respectively; or 335, 348 and 367, respectively, and binds DDL3.

251. A polynucleotide(s) encoding the DLL3-binding polypeptide construct of any of embodiments 1-79.

252. A polynucleotide(s) encoding the multispecific polypeptide construct of any of embodiments 80-203.

253. A polynucleotide, comprising a first nucleic acid sequence encoding a first polypeptide of a multispecific construct of any of embodiments 80-203 and a second nucleic acid sequence encoding a second polypeptide of the multispecific construct, wherein the first and second nucleic acid sequence are separated by an internal ribosome entry site (IRES), or a nucleic acid encoding a self-cleaving peptide or a peptide that causes ribosome skipping.

254. The polynucleotide of embodiment 253, wherein the first nucleic acid sequence and second nucleic acid sequence are operably linked to the same promoter.

255. The polynucleotide of embodiment 254, wherein the nucleic acid encoding a self-cleaving peptide or a peptide that causes ribosome skipping is selected from a T2A, a P2A, a E2A or a F2A.

256. A polynucleotide encoding the single domain antibody of any of embodiments 204-250.

257. A vector, comprising the polynucleotide of any of embodiments 251-256.

258. The vector of embodiment 257 that is an expression vector.

259. The vector of embodiment 257 or embodiment 258 that is a viral vector or a eukaryotic vector, optionally wherein the eukaryotic vector is a mammalian vector.

260. A cell, comprising polynucleotide or polynucleotides of any of embodiments 251-256, or a vector or vectors of any of embodiments 257-259.

261. The cell of embodiment 260, wherein the cell is recombinant or isolated.

262. The cell of embodiment 261, wherein the cell is a mammalian cell.

263. A method of producing a polypeptide, the method comprising introducing into a cell a polynucleotide or polynucleotides of any of embodiments 251-256 or a vector or vectors of any of embodiments 257-259 and culturing the cell under conditions to produce the multispecific polypeptide construct.

264. The method of embodiment 263, further comprising isolating or purifying the polypeptide from the cell.

265. A polypeptide produced by the method of embodiment 263 or embodiment 264.

266. An engineered immune cell, comprising a chimeric antigen receptor comprising: an extracellular domain comprising the single domain antibody of any of embodiments 204-250; a transmembrane domain; and an intracellular signaling domain.

267. The engineered immune cell of embodiment 266, wherein the cell is a lymphocyte.

268. The engineered immune cell of embodiment 266 or embodiment 267, wherein the cell is a T cell or a natural killer (NK) cell.

269. The engineered immune cell of any of embodiments 266-268, wherein the intracellular signaling domain comprises an immunoreceptor tyrosine-based activation motif (ITAM) signaling domain.

270. The engineered immune cell of any of embodiments 266-269, wherein the intracellular signaling domain is or comprises a CD3zeta signaling domain, optionally a human CD3zeta signaling domain.

271. The engineered immune cell of embodiment 269 or embodiment 270, wherein the intracellular signaling domain further comprises a signaling domain of a costimulatory molecule.

272. The engineered immune cell of embodiment 271, wherein the costimulatory molecule is CD28, ICOS, 41BB or OX40, optionally a human CD28, a human ICOS, a human 41BB or a human OX40.

273. A pharmaceutical composition comprising the DLL3-binding polypeptide construct of any of embodiments 1-79, the multispecific polypeptide construct of any of embodiments 80-203, the single domain antibody of any of embodiments 204-250 or the engineered immune cell of any of embodiments 266-272.

274. The pharmaceutical composition of embodiment 273, comprising a pharmaceutically acceptable carrier.

275. The pharmaceutical composition of embodiment 273 or embodiment 274 that is sterile.

276. A method of stimulating or inducing an immune response in a subject, the method comprising administering, to a subject in need thereof, the DLL3-binding polypeptide construct of any of embodiments 1-79, the multispecific polypeptide construct of any of embodiments 80-203, the single domain antibody of any of embodiments 204-250 or the engineered immune cell of any of embodiments 266-272 or a pharmaceutical composition of embodiment 273-275.

277. The method of embodiment 276, wherein the immune response is increased against a tumor or cancer, optionally a tumor or a cancer that expresses DLL3.

278. The method of embodiment 276 or embodiment 277, wherein the method treats a disease or condition in the subject.

279. A method of treating a disease or condition in a subject, the method comprising administering, to a subject in need thereof, a therapeutically effective amount of the DLL3-binding polypeptide construct of any of embodiments 1-79, the multispecific polypeptide construct of any of embodiments 80-203, the single domain antibody of any of embodiments 204-250 or the engineered immune cell of any of embodiments 266-272 or a pharmaceutical composition of embodiment 273-275.

280. The method of embodiment 278 or embodiment 279, wherein the disease or condition is a tumor or a cancer.

281. The method of any of embodiments 276-277, wherein said subject is a human.

VIII. EXAMPLES

The following examples are included for illustrative purposes only and are not intended to limit the scope of the invention.

Example 1: Generation of DLL3 sdAb

Single domain antibodies targeting human DLL3 were generated via immunization of llamas and alpaca. Llamas and alpacas were immunized with a recombinant version of the human DLL3 extracellular domain (ECD; amino acids 27-492 of human DLL3, e.g. UniProt No. Q9NYJ7) set forth as follows (SEQ ID NO:475):

```
AGVFELQIHSFGPGPGPGAPRSPCSARLPCRLFFRVCLKPGLSEEAAES

PCALGAALSARGPVYTEQPGAPAPDLPLPDGLLQVPFRDAWPGTFSFII

ETWREELGDQIGGPAWSLLARVAGRRRLAAGGPWARDIQRAGAWELRFS

YRARCEPPAVGTACTRLCRPRSAPSRCGPGLRPCAPLEDECEAPLVCRA

GCSPEHGFCEQPGECRCLEGWTGPLCTVPVSTSSCLSPRGPSSATTGCL

VPGPGPCDGNPCANGGSCSETPRSFECTCPRGFYGLRCEVSGVTCADGP

CFNGGLCVGGADPDSAYICHCPPGFQGSNCEKRVDRCSLQPCRNGGLCL

DLGHALRCRCRAGFAGPRCEHDLDDCAGRACANGGTCVEGGGAHRCSCA

LGFGGRDCRERADPCAARPCAHGGRCYAHFSGLVCACAPGYMGARCEFP

VHPDGASALPAAPPGLRPGDPQRYL
```

Following the development of specific anti-DLL3 antibody titers, llama/alpaca peripheral blood mononuclear cells (PBMCs) were isolated from 500 mL of blood from the immunized animal and total mRNA was isolated using the Qiagen RNeasy Maxi Kit and subsequently converted to first strand cDNA using Thermo Superscript IV Reverse Transcriptase and oligo-dT priming. Single domain antibody (sdAb; also called VHH) sequences were specifically amplified via PCR using the cDNA as template and cloned into a yeast surface display vector as sdAb-Fc-AGA2 fusion proteins. The Fc was a human IgG1 Fc (set forth in SEQ ID NO:8) or, in some cases, a variant thereof with reduced effector function (Fc xELL; SEQ ID NO:9).

Yeast libraries displaying these sdAbs were enriched using recombinant forms of the DLL3 ECD via magnetic bead isolation followed by fluorescence activated cell sorting (FACS). Sorted yeast were plated out and isolated colonies were picked into 96-well blocks and grown in media that switched the expression from surface displayed sdAb-Fc to secretion into the media. Supernatants from the 96-well yeast secretion cultures were applied to SHP-77 cells (DLL3 positive) or CCRF-CEM cells (DLL3 negative), washed, treated with fluorophore labelled anti-human Fc secondary antibody, and analyzed by 96-well flow cytometry.

Binders to DLL3 positive cells and not to DLL3 negative cells were cloned into mammalian expression vectors as sdAb-Fcs, expressed by transient transfection in HEK293 freestyle cells (293F cells) or CHO cells using polyethylenimine. Recombinant protein secreted into the supernatant was collected after 3-7 days, purified by protein A chromatography, and quantitated by absorbance at 280 nm.

Exemplary identified sdAbs are set forth in Table E1A. In some cases, the sdAbs can include a flexible linker (e.g. GG) for linkage to another polypeptide, such as an Fc or another sdAb.

(DLL3 293FS). A titration series of the fusion protein was incubated with the DLL3-expressing cell lines (approximately $2.5 \times 10^4$ to $5 \times 10^4$ cells/well) for 30 minutes at 4 degrees Celsius in FACS Buffer (PBS 1% BSA, 0.1% $NaN_3$ pH 7.4) in 96-well plates. Following three wash steps in FACS buffer, an APC-conjugated anti-human Fcγ specific secondary antibody (Jackson ImmunoResearch) was added and incubated for 30 minutes at 4 degrees Celsius. Following three additional wash steps in FACS buffer bound antibody was detected via flow cytometry (IQue Intellicyte).

FIG. 1 sets forth binding results for exemplary DLL3 sdAbs, namely 10D9 (SEQ ID NO: 244), 10E5 (SEQ ID NO: 258), 8E7 (SEQ ID NO: 264), 3G3 (SEQ ID NO: 275), 5A7 (SEQ ID NO: 280), 5A8 (SEQ ID NO: 287), 6C5 (SEQ ID NO: 299), 6F1 (SEQ ID NO: 507, such as SEQ ID NO:306), 3B4 (SEQ ID NO: 314), 5H8 (SEQ ID NO: 515, such as set forth in SEQ ID NO:316), 3B12 (SEQ ID NO: 516, such as set forth in SEQ ID NO:317) and 6B4 (SEQ ID NO: 517, such as set forth in SEQ ID NO:318).

An epitope binning assay for binding to DLL3 were carried out using exemplary generated sdAbs to test antibodies pairwise for blocking of another's binding to the epitope of an antigen. Results are set forth in Table E1B:

TABLE E1A

DLL3 sdAbs

| Clone name | CDR1 | SEQ ID NO | CDR2 | SEQ ID NO | CDR3 | SEQ ID NO | VHH SEQ ID NO |
|---|---|---|---|---|---|---|---|
| L10D9 | GSILSINAMG | 319 | GFTGDGNTI | 336 | DVQLFSRDYEFY | 354 | 244 |
| L10E5 | GFTLDDYTIG | 327 | CISSSGGSTY | 339 | YCPVVVGPELGYDY | 355 | 258 |
| L8E7 | EIITSDKSVG | 328 | GISNVGSTN | 340 | RDFENEY | 356 | 264 |
| L3G3 | GSIFSINAMG | 320 | GFTGDGMTK | 341 | DVFTDRDHVDWY | 357 | 275 |
| L5A7 | GSDFSINAIG | 330 | GFTGDGVTT | 342 | DVKIGGDYEWF | 358 | 280 |
| L5A8 | GSIFSINAMG | 320 | VVSSDGRTT | 345 | REWYSDSDWRDY | 359 | 287 |
| L6C5 | EITFSDKTVG | 331 | VISNVDSTN | 348 | RDFENEY | 356 | 299 |
| L6F1 | EIIFSDKTVG | 332 | VISNVDSTN | 348 | RDFESEY | 362 | 306 507 |
| 3B4 | GSDFSINAMG | 333 | GFTGDGNPI | 351 | DVKIGGDYEWY | 363 | 314 |
| 6A1 | GFSLDDYTIG | 334 | CISSSGGSTY | 352 | WCGVATMTEDLPFDY | 364 | 315 518 |
| 5H8 | GSIFSINAMG | 320 | GFTSEGSAK | 353 | DIFSDRDHVDWY | 365 | 316 515 |
| 3B12 | GFSLDDYTIG | 334 | CISSSGGSTY | 339 | YCPVTIADELGFDY | 366 | 317 516 |
| 6B4 | EITLSDKTVG | 335 | VISNVDSTN | 348 | RDFEAEY | 367 | 318 517 |
| 3C5 | GSIFSINAMG | 320 | GFTGDGSTK | 384 | DVQLLNSDYEFY | 395 | 401 |

Example 2: Binding of sdAb to DLL3 Expressing Cells by Flow Cytometry

Specificity and relative affinity were assessed for purified sdAb-Fcs on DLL3-expressing cells. Binding of DLL3-sdAb-Fc fusion proteins was assessed by flow cytometry using DLL3-expressing cell lines, lung carcinoma cell line (SHP-77), or a 293FS cell line transfected with DLL3

TABLE E1B

| Epitope Binning | |
|---|---|
| 10D9 | BIN2 |
| 10E5 | BIN2 |
| 8E7 | BIN1 |
| 3G3 | BIN2 |

TABLE E1B-continued

| Epitope Binning | |
|---|---|
| 5A7 | BIN2 |
| 5A8 | BIN1 |
| 6C5 | BIN1 |
| 6F1 | BIN1 |
| 3B4 | BIN2 |
| 5H8 | BIN2 |
| 3B12 | BIN2 |
| 6B4 | BIN1 |

Example 3: Humanization of Camelid Derived DLL3 sdAb

Exemplary camelid derived DLL3 sdAbs, L10D9 (SEQ ID NO:244), L10E5 SEQ ID NO:258), L8E7 (SEQ ID NO: 264), L3G3 (SEQ ID NO:275), L5A7 (SEQ ID NO:280), L5A8 (SEQ ID NO:287), L6C5 (SEQ ID NO:299), and L6F1 (SEQ ID NO:507) were humanized using the human VH3-23 germline as scaffold. Camelid residues that contribute to solubility, specificity, stability and/or affinity remained unmodified. In addition all humanized variants contained the modification of Leu11Glu (L11E) and the carbox-terminal modifications of Ser112Lys (S112K) and Ser113Pro (S113P) as these are known prevent or reduce the recognition of pre-existing ADA directed toward sdAbs (as described in US20160207981)

Table E2 sets forth exemplary DLL3 sdAbs humanized variants. In some cases, the sdAbs can include a flexible linker (e.g. GG) for linkage to another polypeptide, such as an Fc or another sdAb.

TABLE E2

DLL3 sdAbs Humaized Variants

| Clone name | CDR1 | SEQ ID NO | CDR2 | SEQ ID NO | CDR3 | SEQ ID NO | VHH SEQ ID NO |
|---|---|---|---|---|---|---|---|
| 10D9 Humanized Variants | | | | | | | |
| hz10D9v1 | GSILSINAMG | 319 | GFTGDGNTI | 336 | DVQLFSRDYEFY | 354 | 245 |
| hz10D9v2 | GSILSINAMG | 319 | GFTGDGNTI | 336 | DVQLFSRDYEFY | 354 | 246 |
| hz10D9v3 | GSILSINAMG | 319 | GFTGEGNTI | 337 | DVQLFSRDYEFY | 354 | 247 |
| hz10D9v4 | GSILSINAMG | 319 | GFTGDTNTI | 338 | DVQLFSRDYEFY | 354 | 248 |
| hz10D9v5 | GSILSINAMG | 319 | GFTGDTNTI | 338 | DVQLFSRDYEFY | 354 | 249 |
| hz10D9v6 | GSILSINAMG | 319 | GFTGDTNTI | 338 | DVQLFSRDYEFY | 354 | 250 |
| hz10D9v7 | GSIFSINAMG | 320 | GFTGDTNTI | 338 | DVQLFSRDYEFY | 354 | 251 |
| hz10D9v8 | GFTFSINAMG | 321 | GFTGDTNTI | 338 | DVQLFSRDYEFY | 354 | 252 |
| hz10D9v9 | GFTFSSYAMG | 322 | GFTGDTNTI | 338 | DVQLFSRDYEFY | 354 | 253 |
| hz10D9v10 | GSIFSSNAMG | 323 | GFTGDTNTI | 338 | DVQLFSRDYEFY | 354 | 254 |
| hz10D9v11 | GFIFSSYAMG | 324 | GFTGDTNTI | 338 | DVQLFSRDYEFY | 354 | 255 |
| hz10D9v12 | GSIFSIYAMG | 325 | GFTGDTNTI | 338 | DVQLFSRDYEFY | 354 | 256 |
| hz10D9v13 | GFIFSINAMG | 326 | GFTGDTNTI | 338 | DVQLFSRDYEFY | 354 | 257 |
| 10E5 Humanized Variants | | | | | | | |
| hz10E5v1 | GFTLDDYTIG | 327 | CISSSGGSTY | 339 | YCPVVVGPELGYDY | 355 | 259 |
| hz10E5v2 | GFTLDDYTIG | 327 | CISSSGGSTY | 339 | YCPVVVGPELGYDY | 355 | 260 |
| hz10E5v3 | GFTLDDYTIG | 327 | CISSSGGSTY | 339 | YCPVVVGPELGYDY | 355 | 261 |
| hz10E5v4 | GFTLDDYTIG | 327 | CISSSGGSTY | 339 | YCPVVVGPELGYDY | 355 | 262 |
| hz10E5v5 | GFTLDDYTIG | 327 | CISSSGGSTY | 339 | YCPVVVGPELGYDY | 355 | 263 |
| 8E7 Humanized Variants | | | | | | | |
| hz8E7v1 | EIITSDKSVG | 328 | GISNVGSTN | 340 | RDFENEY | 356 | 265 |
| hz8E7v2 | EIITSDKSVG | 328 | GISNVGSTN | 340 | RDFENEY | 356 | 266 |
| hz8E7v3 | EIITSDKSVG | 328 | GISNVGSTN | 340 | RDFENEY | 356 | 267 |
| hz8E7v4 | EIITSDKSVG | 328 | GISNVGSTN | 340 | RDFENEY | 356 | 268 |
| hz8E7v5 | EIITSDKSVG | 328 | GISNVGSTN | 340 | RDFENEY | 356 | 416 |

TABLE E2-continued

DLL3 sdAbs Humaized Variants

| Clone name | CDR1 | SEQ ID NO | CDR2 | SEQ ID NO | CDR3 | SEQ ID NO | VHH SEQ ID NO |
|---|---|---|---|---|---|---|---|
| hz8E7v6 | EIIFSDKSVG | 329 | GISNVGSTN | 340 | RDFENEY | 356 | 269 |
| hz8E7v8 | EIITSDKSVG | 328 | GISNVGSTN | 340 | RDFENEY | 356 | 270 |
| hz8E7v9 | EIITSDKSVG | 328 | GISNVGSTN | 340 | RDFENEY | 356 | 271 |
| hz8E7v10 | EIITSDKSVG | 328 | GISNVGSTN | 340 | RDFENEY | 356 | 272 |
| hz8E7v11 | EIITSDKSVG | 328 | GISNVGSTN | 340 | RDFENEY | 356 | 273 |
| hz8E7v12 | EIITSDKSVG | 328 | GISNVGSTN | 340 | RDFENEY | 356 | 274 |
| hz8E7v13 | EIITSDKSMG | 456 | GISNVGSTN | 340 | RDFENEY | 356 | 476 |
| hz8E7v14 | EIITSDKSVG | 328 | GISNVGSTN | 340 | RDFENEY | 356 | 477 |
| hz8E7v15 | EIITSDKSMG | 456 | GISNVGSTN | 340 | RDFENEY | 356 | 488 |
| hz8E7v16 | EIITSDKSMG | 456 | GISNVGSTN | 340 | RDFENEY | 356 | 455 |

3G3 Humanized Variants

| Clone name | CDR1 | SEQ ID NO | CDR2 | SEQ ID NO | CDR3 | SEQ ID NO | VHH SEQ ID NO |
|---|---|---|---|---|---|---|---|
| hz3G3v1 | GSIFSINAMG | 320 | GFTGDGMTK | 341 | DVFTDRDHVDWY | 357 | 276 479 |
| hz3G3v2 | GSIFSINAMG | 320 | GFTGDGMTK | 341 | DVFTDRDHVDWY | 357 | 277 |
| hz3G3v3 | GSIFSINAMG | 320 | GFTGDGMTK | 341 | DVFTDRDHVDWY | 357 | 278 |
| hz3G3v4 | GSIFSINAMG | 320 | GFTGDGMTK | 341 | DVFTDRDHVDWY | 357 | 279 |

5A7 Humanized Variants

| Clone name | CDR1 | SEQ ID NO | CDR2 | SEQ ID NO | CDR3 | SEQ ID NO | VHH SEQ ID NO |
|---|---|---|---|---|---|---|---|
| hz5A7v1 | GSDFSINAIG | 330 | GFTGDGVTT | 342 | DVKIGGDYEWF | 358 | 281 |
| hz5A7v2 | GSDFSINAIG | 330 | GFTGDTVTT | 343 | DVKIGGDYEWF | 358 | 282 |
| hz5A7v3 | GSDFSINAIG | 330 | GFTGEGVTT | 344 | DVKIGGDYEWF | 358 | 283 |
| hz5A7v4 | GSDFSINAIG | 330 | GFTGDGVTT | 342 | DVKIGGDYEWF | 358 | 284 |
| hz5A7v5 | GSDFSINAIG | 330 | GFTGDGVTT | 342 | DVKIGGDYEWF | 358 | 285 |
| hz5A7v6 | GSDFSINAIG | 330 | GFTGDGVTT | 342 | DVKIGGDYEWF | 358 | 286 |

5A8 Humanized Variants

| Clone name | CDR1 | SEQ ID NO | CDR2 | SEQ ID NO | CDR3 | SEQ ID NO | VHH SEQ ID NO |
|---|---|---|---|---|---|---|---|
| hz5A8v1 | GSIFSINAMG | 320 | VVSSDGRTT | 345 | REWYSDSDWRDY | 359 | 288 |
| hz5A8v2 | GSIFSINAMG | 320 | VVSSDGRTT | 345 | REWYSDSDWRDY | 359 | 289 |
| hz5A8v3 | GSIFSINAMG | 320 | VVSSDGRTT | 345 | REWYSDSDWRDY | 359 | 290 |
| hz5A8v4 | GSIFSINAMG | 320 | VVSSDGRTT | 345 | REWYSDSDWRDY | 359 | 102 |
| hz5A8v5 | GSIFSINAMG | 320 | VVSSDGRTT | 345 | REWYSDSDWRDY | 359 | 291 |
| hz5A8v6 | GSIFSINAMG | 320 | VVSSEGRTT | 346 | REWYSDSDWRDY | 359 | 292 |
| hz5A8v7 | GSIFSINAMG | 320 | VVSSDARTT | 347 | REWYSDSDWRDY | 359 | 293 |
| hz5A8v8 | GSIFSINAMG | 320 | VVSSDGRTT | 345 | REWYSDADWRDY | 360 | 294 |
| hz5A8v9 | GSIFSINAMG | 320 | VVSSDGRTT | 345 | REWYSESDWRDY | 361 | 295 |
| hz5A8v10 | GSIFSINAMG | 320 | VVSSDARTT | 347 | REWYSDADWRDY | 360 | 296 |
| hz5A8v11 | GSIFSINAMG | 320 | VVSSDGRTT | 345 | REWYSDSDWRDY | 359 | 297 |
| hz5A8v12 | GSIFSINAMG | 320 | VVSSDGRTT | 345 | REWYSDSDWRDY | 359 | 298 |

TABLE E2-continued

DLL3 sdAbs Humaized Variants

| Clone name | CDR1 | SEQ ID NO | CDR2 | SEQ ID NO | CDR3 | SEQ ID NO | VHH SEQ ID NO |
|---|---|---|---|---|---|---|---|
| 6C5 Humanized Variants ||||||||
| hz6C5v1 | EITFSDKTVG | 331 | VISNVDSTN | 348 | RDFENEY | 356 | 300 |
| hz6C5v2 | EITFSDKTVG | 331 | VISNVDSTN | 348 | RDFENEY | 356 | 301 480 |
| hz6C5v3 | EITFSDKTVG | 331 | VISNVDSTN | 348 | RDFENEY | 356 | 302 |
| hz6C5v4 | EITFSDKTVG | 331 | VISNVDSTN | 348 | RDFENEY | 356 | 303 |
| hz6C5v5 | EITFSDKTVG | 331 | VISNVESTN | 349 | RDFENEY | 356 | 304 |
| hz6C5v6 | EITFSDKTVG | 331 | VISNVDATN | 350 | RDFENEY | 356 | 305 |
| 6F1 Humanized Variants ||||||||
| hz6F1v1 | EIIFSDKTVG | 332 | VISNVDSTN | 348 | RDFESEY | 362 | 307 508 |
| hz6F1v2 | EIIFSDKTVG | 332 | VISNVDSTN | 348 | RDFESEY | 362 | 308 509 |
| hz6F1v3 | EIIFSDKTVG | 332 | VISNVDSTN | 348 | RDFESEY | 362 | 309 510 |
| hz6F1v4 | EIIFSDKTVG | 332 | VISNVDSTN | 348 | RDFESEY | 362 | 310 511 |
| hz6F1v5 | EIIFSDKTVG | 332 | VISNVDSTN | 348 | RDFESEY | 362 | 311 512 |
| hz6F1v6 | EIIFSDKTVG | 332 | VISNVESTN | 349 | RDFESEY | 362 | 312 513 |
| hz6F1v7 | EIIFSDKTVG | 332 | VISNVDATN | 350 | RDFESEY | 362 | 313 514 |
| 3C5 Humanized Variants ||||||||
| hz3C5v1 | GSIFSINAMG | 320 | GFTGDGSTK | 384 | DVQLLNSDYEFY | 395 | 402 481 |
| hz3C5v2 | GSIFSINAMG | 320 | GFTGDGSTK | 384 | DVQLLNSDYEFY | 395 | 403 482 |
| hz3C5v3 | GSIFSINAMG | 320 | GFTGDTSTK | 410 | DVQLLNSDYEFY | 395 | 404 483 |
| hz3C5v4 | GSIFSINAMG | 320 | GFTGEGSTK | 411 | DVQLLNSDYEFY | 395 | 405 484 |
| hz3C5v5 | GSIFSINAMG | 320 | GFTGDGSTK | 384 | DVQLLSSDYEFY | 412 | 406 485 |
| hz3C5v6 | GSIFSINAMG | 320 | GFTGDGSTK | 384 | DVQLLTSDYEFY | 413 | 407 486 |
| hz3C5v7 | GSIFSINAMG | 320 | GFTGDGSTK | 384 | DVQLLQSDYEFY | 414 | 408 487 |
| hz3C5v8 | GSIFSINAMG | 320 | GFTGDGSTK | 384 | DVQLLNTDYEFY | 415 | 409 488 |

Humanized variants of the DLL3 sdAbs were tested for their ability to bind DLL3 expressing cells substantially as described in Example 2, and binding was compared to the parental sdAb. SHP-77 cells, which endogenously express DLL3, were used in these studies. Results are shown in FIGS. 2A-L, which confirm binding of the humanized variants. In some cases, binding was increased compared to the parental sdAb.

Example 4: Method of Producing DLL3-Targeted Constrained CD3 Binding Proteins Multispecific polypeptide constructs were generated containing a disulfide stabilized anti-CD3 Fv binding region that exhibits constrained CD3 binding, a heterodimeric Fc domain, and one or more DLL3 sdAb described above positioned amino-terminally relative to the Fc region and/or carboxy-terminally relative to the CD3 binding region. The multispecific constructs were generated in various configurations, as shown in FIG. 3A-3E. In some cases, the multispecific polypeptide constructs contained at least one co-stimulatory receptor binding region (CRBR) positioned amino-terminally relative to the Fc region and/or carboxy-terminally relative to the CD3 binding region. An exemplary CRBR is a sdAb targeting a 4-1BB co-stimulatory receptor (e.g. containing a CDR1, a CDR2 and a CDR3 set forth in SEQ ID Nos: 457, 458 and 459, respectively; e.g. set forth in SEQ ID NO:210).

In the exemplary constructs, polynucleotides encoding at least a first polypeptide chain and a second polypeptide chain of the heterodimeric multispecific polypeptide construct were generated and cloned into a plasmid for expression. The first polypeptide chain generally included in order, from the N-terminus to C-terminus, an Fc hole polypeptide (e.g. set forth in SEQ ID NO:112, or in some cases SEQ ID NO:114); a cleavable or a non-cleavable linker, such as one containing one or more substrate recognition sites for a protease; and a variable light (VL) domain of a dsFv anti-CD3 antibody (e.g. set forth in SEQ ID NO:75). The second polypeptide chain generally included in order, from the N-terminus to C-terminus, an Fc knob polypeptide (e.g. set forth in SEQ ID NO: 105, or in some cases SEQ ID NO:109); the same cleavable linker or the same non-cleavable linker as the first polypeptide chain; and a variable heavy domain of a dsFv anti-CD3 antibody (e.g. set forth in SEQ ID NO:47). The constructs were generated with the exemplary non-cleavable linker, GGGGGSGGGGGSGGGGGS (SEQ ID NO:127), or the exemplary cleavable linker, GGSGGGGIEPDIGGSGGS (SEQ ID NO:171) containing a substrate recognition site for granzyme B. One or both of the polypeptide chains additionally encoded one or more DLL3 sdAb amino terminal to the Fc domain and/or carboxy terminal to the CD3 binding region, and/or a co-stimulatory receptor binding domain amino terminal to the Fc domain and/or carboxy terminal to the CD3 binding region, in various configurations.

Separate plasmids encoding each chain of a heterodimeric constrained CD3 binding protein were transiently transfected at an equimolar ratio into mammalian cells (either HEK293 or CHO) using polyethylenimine. Recombinant protein secreted into the supernatant was collected after 3-7 days, and purified by protein A chromatography, followed by either preparative size exclusion chromatography (SEC) or flow-through hydrophobic interaction chromatography (HIC). Heterodimeric protein was selectively purified owing to a mutation designed into one chain of the heterodimeric Fc at position I253R or H435R (usually the hole-Fc) such that it did not bind protein A. The second chromatography step on SEC (AKTA with Superdex-200 resin) or FT-HIC (AKTA with butyl/phenyl sepharose) was used to remove undesired cross-paired species containing two heterodimeric Fcs that were more hydrophobic and twice the expected molecular weight.

The method favored production of heterodimeric multispecific polypeptide constructs, containing properly paired species of heterodimeric Fc and the disulfide stabilized anti-CD3 Fv as described (e.g. anti-CD3 VH with the mutation G44C as set forth in SEQ ID NO: 47 and VL with the mutation G100C as set forth in SEQ ID NO:75). Purified heterodimeric constrained CD3 binding protein was stable and did not accumulate cross-paired species upon prolonged incubation at 4 degrees Celsius or increased protein concentration.

Table E3 sets forth exemplary generated constrained multispecific constructs:

TABLE E3

| DLL3 VHH Constrained Multispecific Constructs | | | | | | |
|---|---|---|---|---|---|---|
| Construct | Chain | N-term sdAb (Target) (SEQ ID NO) | Fc | Linker | CD3 Binding Domain | C-term sdAb (Target) (SEQ ID NO) |
| cx4720 | 1 | 10D9 (DLL3) (244) | xELL-Knob | (G5S)3 | Con1 VH | 8E7 (DLL3) (264) |
| | 2 | — | xELL-Hole | (G5S)3 | Con1 VL | RH3v5 (41BB) (e.g. 210) |
| cx3715 | 1 | 3B4 (DLL3) (314) | hFc-Knob | IEPDI | Con1 VH | 6B4 (DLL3) (517, e.g. 318) |
| | 2 | — | hFc-Hole | IEPDI | Con1 VL | RH3v5 (41BB) (e.g. 210) |
| cx4422 | 1 | 10D9 (DLL3) (244) | hFc-Knob | IEPDI | Con1 VH | 6F1 (DLL3) (507, e.g. 306) |
| | 2 | — | hFc-Hole | IEPDI | Con1 VL | — |
| cx3708 | 1 | 3B4 (DLL3) (314) | hFc-Knob | IEPDI | Con1 VH | 6B4 (DLL3) (517, e.g. 318) |
| | 2 | — | hFc-Hole | IEPDI | Con1 VL | — |
| cx3985 | 1 | 3B4 (DLL3) (314) | hFc-Knob | IEPDI | Con1 VH | 6F1 (DLL3) (507, e.g. 306) |
| | 2 | — | hFc-Hole | IEPDI | Con1 VL | — |
| cx3991 | 1 | 3B4 (DLL3) (314) | hFc-Knob | IEPDI | Con1 VH | 6C5 (DLL3) (299) |
| | 2 | — | hFc-Hole | IEPDI | Con1 VL | — |

TABLE E3-continued

DLL3 VHH Constrained Multispecific Constructs

| Construct | Chain | N-term sdAb (Target) (SEQ ID NO) | Fc | Linker | CD3 Binding Domain | C-term sdAb (Target) (SEQ ID NO) |
|---|---|---|---|---|---|---|
| cx4888 | 1 | hz10D9v7 (DLL3) (251) | xELL-Knob | (g5s)3 | Con1 VH | hz8E7v4 (DLL3) (268) |
| | 2 | — | xELL-Hole | (g5s)3 | Con1 VL | RH3v5 (41BB) (e.g. 210) |
| cx4890 | 1 | 10D9 (DLL3) (244) | xELL-Knob | (g5s)3 | Con1 VH | 8E7 (DLL3) (264) |
| | 2 | — | xELL-Hole | (g5s)3 | Con1 VL | — |
| cx4887 | 1 | hz10D9v7 (DLL3) (251) | xELL-Knob | (g5s)3 | Con1 VH | hz8E7v4 (DLL3) (268) |
| | 2 | — | xELL-Hole | (g5s)3 | Con1 VL | — |
| cx4895 | 1 | 10D9 (DLL3) (244) | xELL-Knob | (g5s)3 | Con1 VH | 8E7 (DLL3) (264) |
| | 2 | — | xELL-Hole | (g5s)3 | Con1 VL | RH3v5 (41BB) (e.g. 210) |
| cx4899 | 1 | hz8E7v3 (DLL3) (267) | xELL-Knob | (g5s)3 | Con1 VH | hz10D9v7 (DLL3) (251) |
| | 2 | — | xELL-Hole | (g5s)3 | Con1 VL | — |
| cx4896 | 1 | 10D9v7 (DLL3) (251) | xELL-Knob | (g5s)3 | Con1 VH | hz8E7v3 (DLL3) (267) |
| | 2 | — | xELL-Hole | (g5s)3 | Con1 VL | RH3v5 (41BB) (e.g. 210) |
| cx4052 | 1 | 3G3 (DLL3) (275) | hFc -Knob | IEPDI | Con1 VH | 6B4 (DLL3) (517, e.g. 318) |
| | 2 | — | hFc -Hole | IEPDI | Con1 VL | — |
| cx4087 | 1 | 3B4 (DLL3) (314) | hFc -Knob | IEPDI | Con1 VH | 5A8 (DLL3) (287) |
| | 2 | — | hFc -Hole | IEPDI | Con1 VL | — |
| cx4088 | 1 | 3B4 (DLL3) (314) | hFc -Knob | IEPDI | Con1 VH | 8E7 (DLL3) (264) |
| | 2 | — | hFc -Hole | IEPDI | Con1 VL | — |
| cx4059 | 1 | 5H8 (DLL3) (515, e.g. 316) | hFc -Knob | IEPDI | Con1 VH | 6B4 (DLL3) (517, e.g. 318) |
| | 2 | — | hFc -Hole | IEPDI | Con1 VL | — |
| cx4049 | 1 | 3B12 (DLL3) (516, e.g. 317) | hFc -Knob | IEPDI | Con1 VH | 6B4 (DLL3) (517, e.g. 318) |
| | 2 | — | hFc -Hole | IEPDI | Con1 VL | — |
| cx4050 | 1 | 6A1 (DLL3) (518, e.g. 315) | hFc -Knob | IEPDI | Con1 VH | 6B4 (DLL3) (517, e.g. 318) |
| | 2 | — | hFc -Hole | IEPDI | Con1 VL | — |
| cx4060 | 1 | 10D9 (DLL3) (244) | hFc -Knob | IEPDI | Con1 VH | 6B4 (DLL3) (517, e.g. 318) |
| | 2 | — | hFc -Hole | IEPDI | Con1 VL | — |
| cx3711 | 1 | 6B4 (DLL3) (517, e.g. 318) | hFc -Knob | IEPDI | Con1 VH | 3B4 (DLL3) (314) |
| | 2 | — | hFc -Hole | IEPDI | Con1 VL | — |
| cx4406 | 1 | 10D9 (DLL3) (244) | hFc -Knob | IEPDI | Con1 VH | 8E7 (DLL3) (264) |
| | 2 | — | hFc -Hole | IEPDI | Con1 VL | — |
| cx3707 | 1 | 6B4 (DLL3) (517, e.g. 318) | hFc -Knob | IEPDI | Con1 VH | 6B4 (DLL3) (517, e.g. 318) |
| | 2 | — | hFc -Hole | IEPDI | Con1 VL | — |
| cx3710 | 1 | 3B4 (DLL3) (314) | hFc -Knob | IEPDI | Con1 VH | 3B4 (DLL3) (314) |
| | 2 | — | hFc -Hole | IEPDI | Con1 VL | — |

Example 5: Comparison of Binding to Isolated Primary T-Cells Vs. DLL3-Expressing Cancer Cells Binding of exemplary DLL3-targeting constrained CD3 engaging constructs of the disclosure, referred to herein as cx4720, cx3715, cx4422, cx3708, cx4052, cx3985, cx4059, cx4087, cx4088, cx4895, cx3991, cx3711, cx4887, cx4896, cx4899, cx4406, cx3707, cx3710, cx4888 and cx4890, to CD3 on the surface of primary T cells was assessed via flow cytometry (SONY SA3800 spectral analyzer) using T-cell that were negatively enriched from PBMCs isolated from healthy human donor leukopaks. Representative DLL3-targeting constrained CD3 engaging constructs were assessed for binding to T cells and DLL3 expressing cells (SHP-77). Bound cx4720, cx3715, cx4422, cx3708, cx4052, cx3985, cx4059, cx4087, cx4088, cx4895, cx3991, cx3711, cx4887, cx4896, cx4899, cx4406, cx3707, cx3710, cx4888 and cx4890 was detected with fluorophore-conjugated secondary antibodies specific for the human Fc and binding was measured by flow cytometry. Cells incubated with secondary antibody only served as negative controls.

As shown in FIGS. 4A to 23A, the exemplary DLL3-targeting constrained CD3 engagers (cx4720, cx3715, cx4422, cx3708, cx4052, cx3985, cx4059, cx4087, cx4088, cx4895, cx3991, cx3711, cx4887, cx4896, cx4899, cx4406, cx3707, cx3710, cx4888 and cx4890) were found to bind SHP-77 cells expressing DLL3. However, as shown in FIGS. 4B to 23B, the same constructs were not able to bind to T cells in isolation.

Table E4 summarizes the affinity of exemplary molecules for DLL3 or CD3, as determined from flow cytometry, in these studies.

TABLE E4

Construct Binding Affinity

| Construct # | Affinity DLL3 | Affinity CD3 |
|---|---|---|
| cx4720 | 0.115 nM | >200 nM |
| cx3715 | 0.044 nM | >200 nM |
| cx4422 | 0.183 nM | >200 nM |
| cx3708 | 0.138 nM | >200 nM |
| cx3985 | 0.084 nM | >200 nM |
| cx3991 | 0.155 nM | >200 nM |
| cx4888 | 0.134 nM | >200 nM |
| cx4890 | 0.062 nM | >200 nM |
| cx4887 | 0.410 nM | >200 nM |
| cx4895 | 0.065 nM | >200 nM |
| cx4899 | 0.397 nM | >200 nM |
| cx4896 | 0.339 nM | >200 nM |
| cx4052 | 0.186 nM | >200 nM |
| cx4087 | 0.597 nM | >200 nM |
| cx4088 | 0.093 nM | >200 nM |
| cx4059 | 0.134 nM | >200 nM |
| cx4049 | ND | ND |
| cx4050 | ND | ND |
| cx4060 | ND | ND |
| cx3711 | 0.357 nM | >200 nM |
| cx4406 | 0.320 nM | >200 nM |
| cx3707 | 0.208 nM | >200 nM |
| cx3710 | 0.315 nM | >200 nM |

Example 6: Assessment of DLL3-Dependent CD3 Reporter T Cell Activation Using a Reporter Assay This example describes assessment of the ability of various representative DLL3-targeting constrained CD3 engaging constructs, referred to herein as cx3707, cx3710, cx3708, cx3711, cx4720, cx4422, cx3715, cx3985, cx3991, cx4894, cx4888, cx4890, cx4887, cx4895, cx4899, cx4052, cx4083, cx4087, cx4088, cx4059, cx4049, cx4050, cx4060, and cx4896, to activate a CD3 NFAT reporter Jurkat cell line in co-culture with DLL3-expressing SHP-77 cells or a DLL3 negative cell line, HEK-293 freestyle cells. These assays were used to demonstrate that while T-cell binding via the CD3-binding domain is restricted or inhibited on isolated T cells (as shown in Example 5), once the DLL3-targeted constrained CD3 engaging constructs provided herein are bound to a cognate antigen, they are capable of engaging T-cells and mediating T-cell activation.

Antigen targeting constrained CD3 engaging constructs were titrated onto co-cultures of target cells and engineered Jurkat cells that express NFAT-driven green fluorescence protein (GFP). Engagement of CD3 results in NFAT signaling and production of green fluorescence. For reporter assays utilizing adherent target cells, target cells were seeded, allowed to settle at room temperature for uniform distribution, and incubated for several hours at 37° C. to permit adherence (or partial adherence) prior to addition of reporter cells and antigen targeting constrained CD3 engaging constructs. Assay plates were serially imaged using an IncuCyte ZOOM system and CD3 reporter cell activation was determined by measuring total green object integrated intensity. As shown in FIGS. 24A-24B and 25A-25D, assessed DLL3-targeted constrained CD3 engaging constructs induced reporter activity in cultures containing DLL3 positive cells (SHP-77) (FIGS. 24A, 25A, 25C), but no measurable reporter activity was observed when T cells were cultured with DLL3 negative cell lines (293 FS) (FIGS. 24B, 25B, 25D).

Figure 24A:
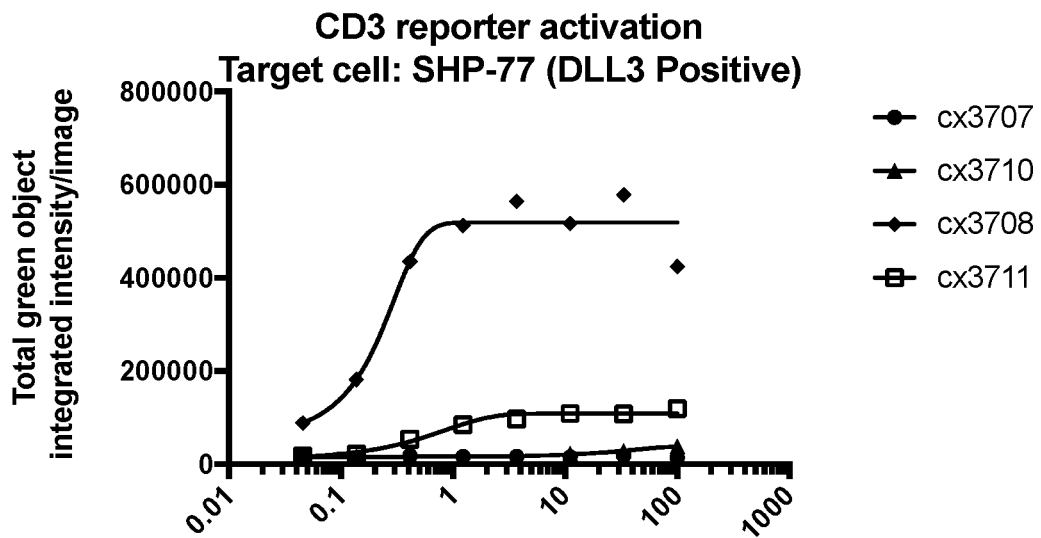
FIGS. 24A-24B depict graphs demonstrating the ability of DLL3-targeted constrained CD3 engaging constructs to elicit DLL3-dependent T-cell activation. A Jurkat CD3 NFAT-GFP reporter cell line was used to monitor T-cell activation. SHP-77 cells (FIG. 24A) and HEK-293 freestyle cells (FIG. 24B) were used as antigen positive and negative cell lines, respectively.
Figure 24B:
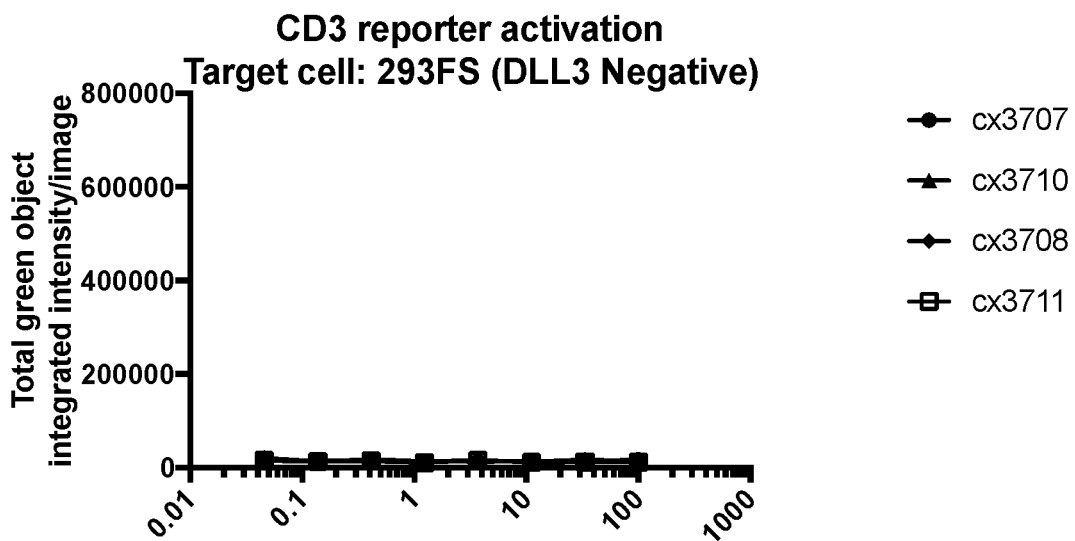
Figure 25A:
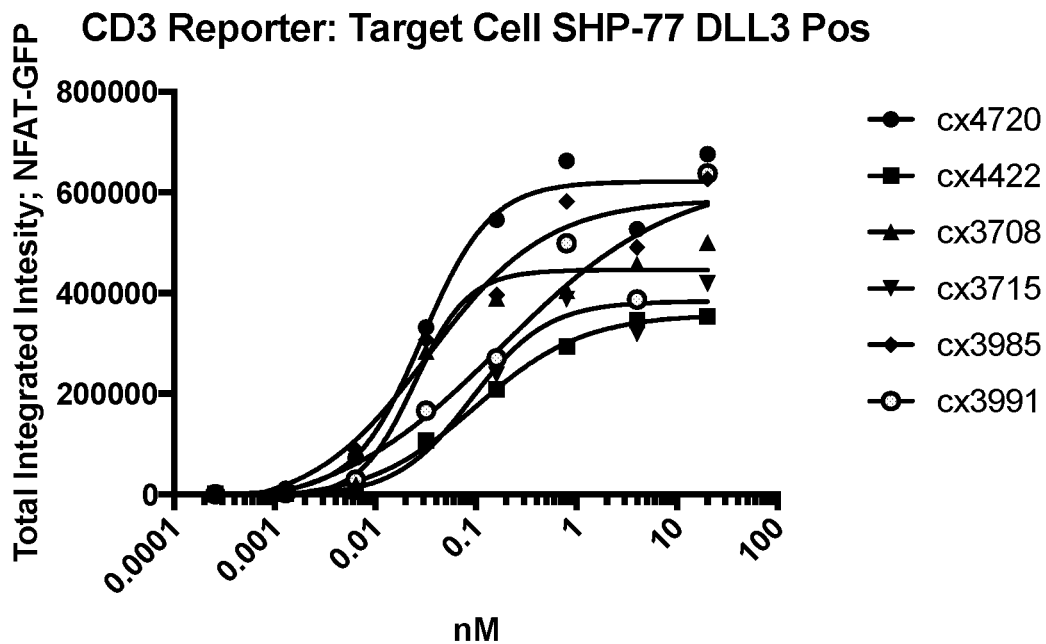
FIGS. 25A-25D depict graphs demonstrating the ability of bi-epitopic DLL3-targeted constrained CD3 engaging constructs to elicit DLL3-dependent T-cell activation. A Jurkat CD3 NFAT-GFP reporter cell line was used to monitor T-cell activation. SHP-77 cells (FIGS. 22A and 22C) and HEK-293 freestyle cells (FIGS. 22B and 22D) were used as antigen positive and negative cell lines, respectively.
Figure 25B:
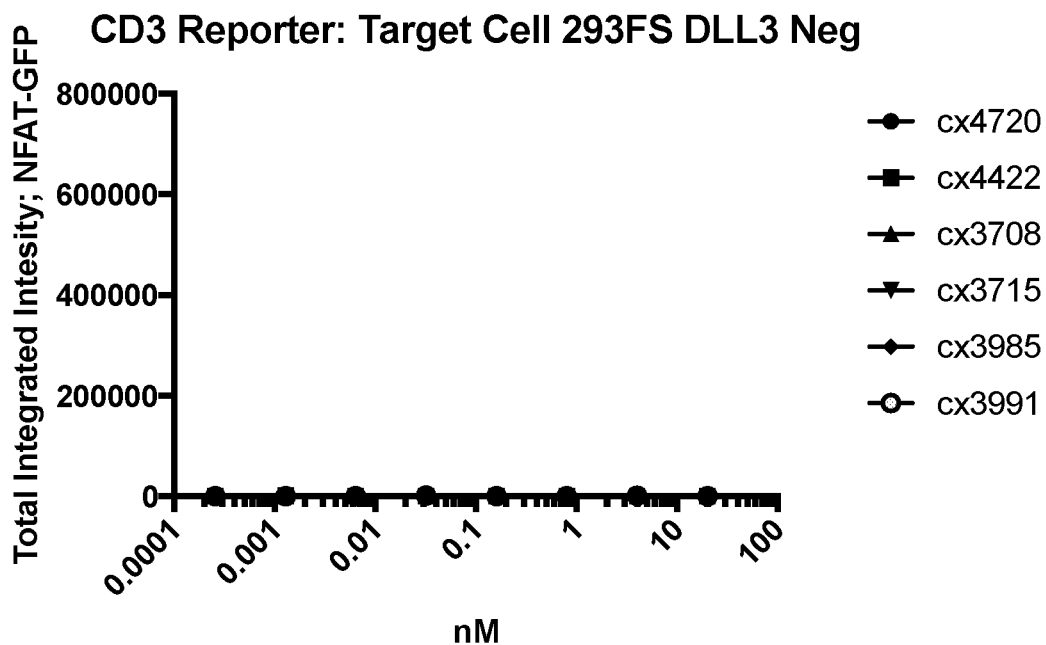
Figure 25C:
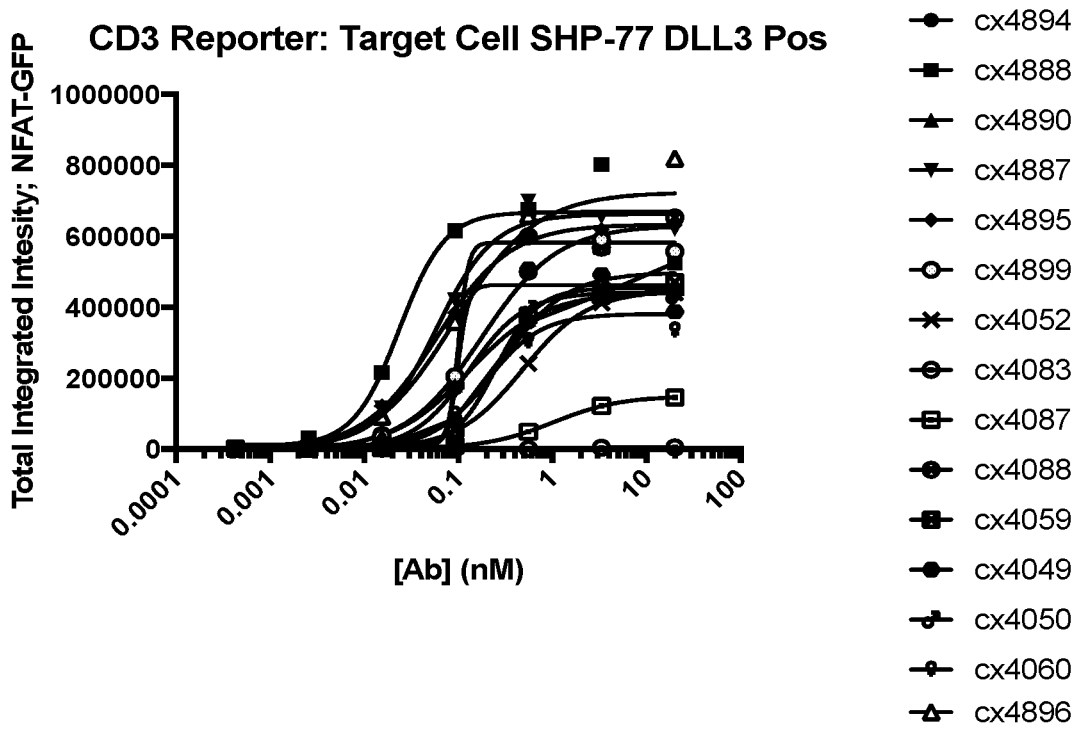
Figure 25D:
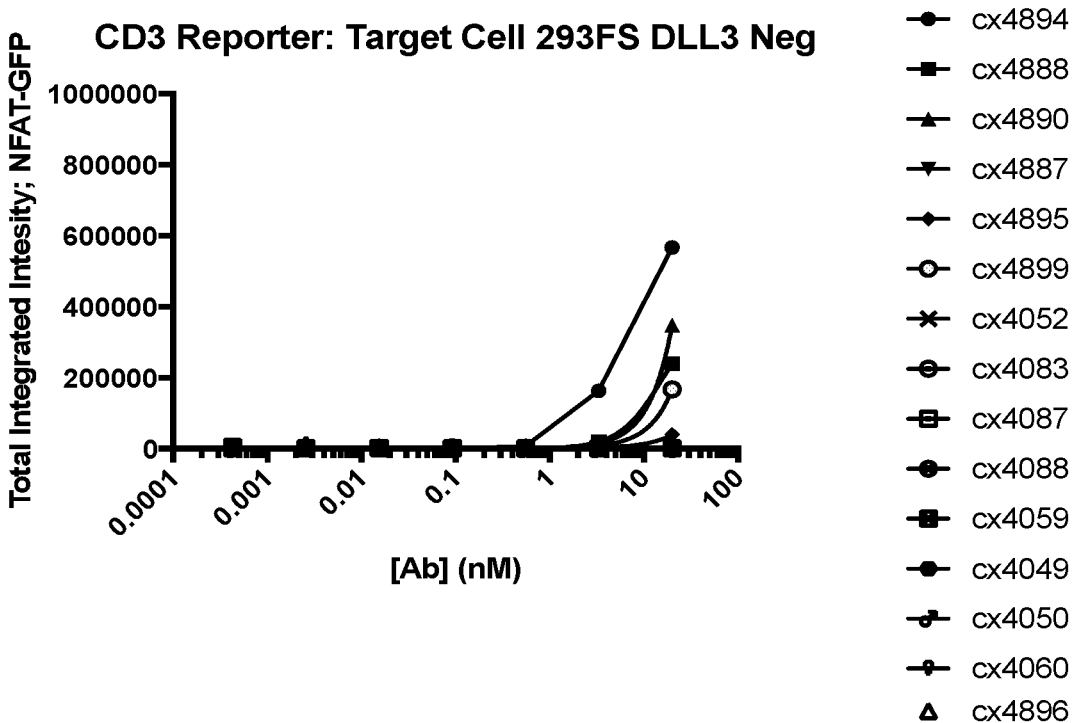

FIG. 24A depicts results from targeting two distinct epitopes on DLL3, and are consistent with an observation that the location of the specific DLL3-targeted sdAB within the constrained CD3 engaging construct may impact binding. cx3707 contains two copies of the DLL3-targeted sdAb, 6B4. cx3710 contains two copies of the the DLL3-targeted sdAb, 3B4. Thus cx3707 and cx3710 are bivalent in DLL3 targeting and each recognize a single epitope on DLL3, albeit distinct epitopes from each other. cx3708 and cx3711 each contain one copy of 3B4 and one copy of 6B4 and therefore bind DLL3 in bivalent bi-epitopic targeting manner. cx3708 has 3B4 positioned N-terminal to the Fc and 6B4 positioned C-terminal to the CD3 binding domain. Conversely, cx3711 has 6B4 positioned N-terminal to the Fc and 3B4 positioned C-terminal to the CD3 binding domain. The constructs capable of bi-epitoptic DLL3 binding (cx3708 and cx3711) are superior to the constructs capable of only mono-epitopic DLL3 binding (cx3707 and cx3710) in their capacity to activate T-cells, as evidenced using a Jurkat CD3-NFAT-GFP reporter. Notably, the positioning of the specific sdAbs within also impacts activity as cx3708 is substantially better at mediating T-cell activation compared to cx3711. Furthermore, constructs containing the combination of DLL3-targeted sdAbs 10D9 and 8E7, and humanized variants thereof, were found to mediate strong CD3 signaling as shown in FIG. 25.

Example 7: Assessment of Functional Activity

This Example describes the assessment and characterization of the tested DLL3-target constrained CD3 engaging constructs in human primary T cell in vitro assays.

1. T Cell-Mediated Cytotoxicity

Target cells were fluorescently labeled with CytoID red. For cytotoxicity assays utilizing adherent target cells SHP-77 or HEK-293FS, target cells were seeded, allowed to settle at room temperature for uniform distribution, and incubated for 24 hours at 37° C. to permit adherence prior to addition of other assay components. Primary T cells were negatively enriched from PBMCs isolated from healthy human donor leukopaks and added at a 10:1-40:1 T cell-to-target cell ratio. Green caspase-3/7 reagent was added, which fluorescently labeled nuclear DNA of cells undergoing apoptosis. Antibodies were titrated onto the co-culture and assay plates were serially imaged using an IncuCyte ZOOM system. Target cell death was determined by measuring total red/green overlap object area.

Figure 26A:
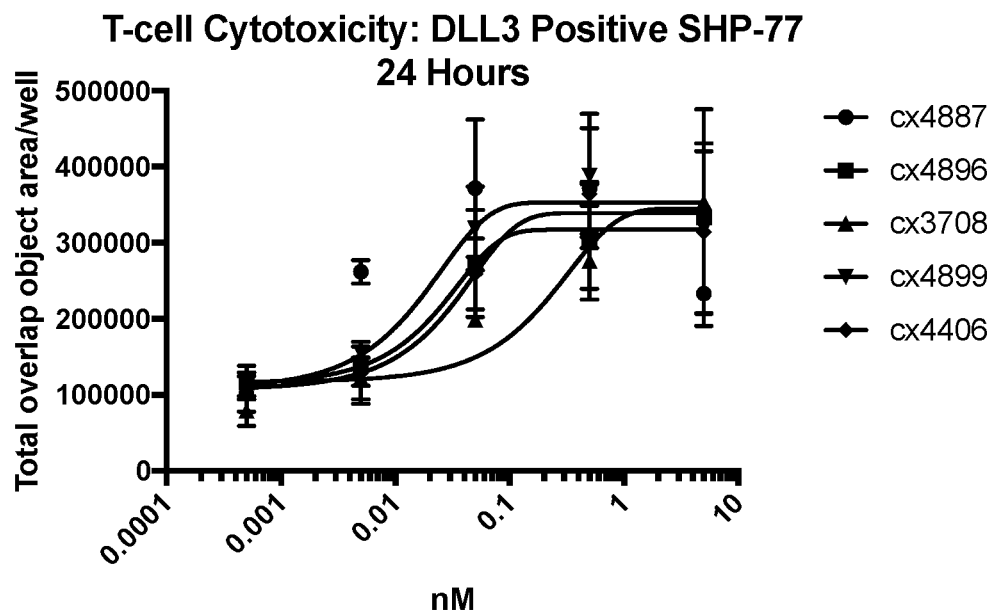
FIGS. 26A-26B depict graphs demonstrating the ability of DLL3-targeted constrained CD3 engaging constructs to mediate antigen specific T-cell cytotoxicity on DLL3 positive SHP-77 cells (FIG. 26A), and DLL3 negative HEK-293 Freestyle cells (FIG. 26B).
Figure 26B:
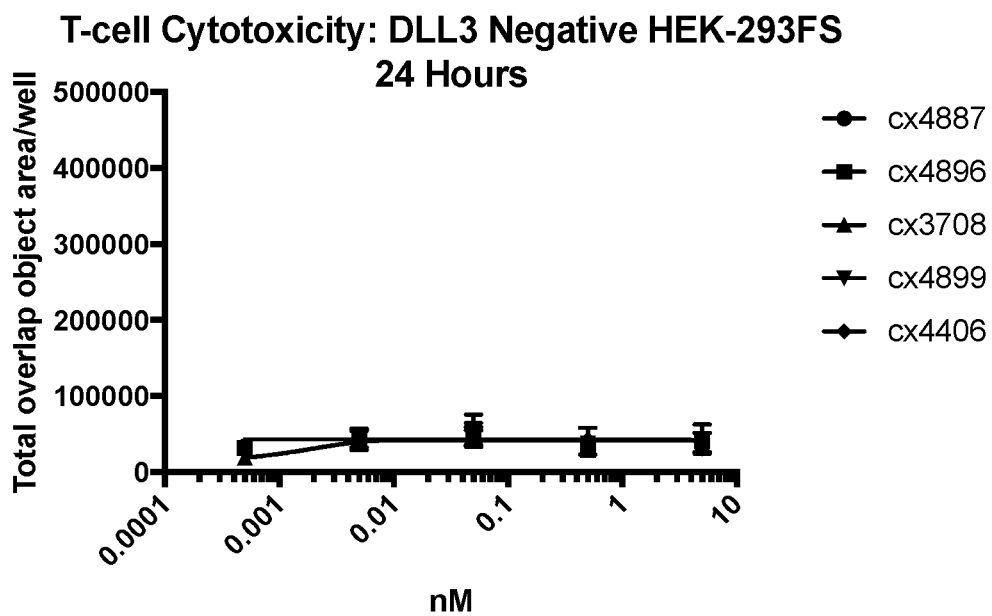
Figure 27A:
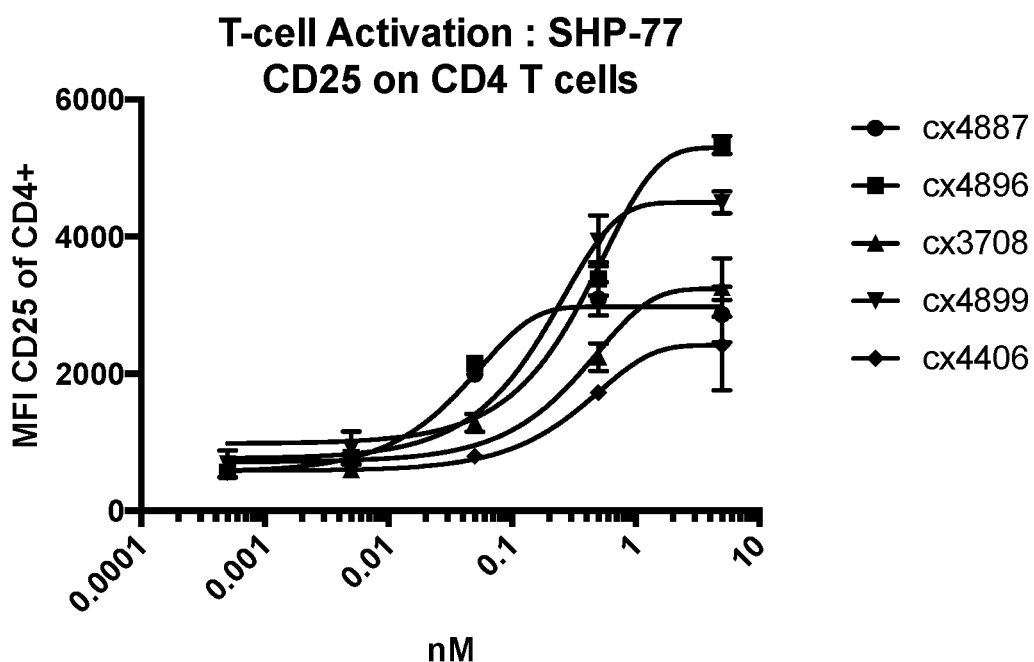
FIGS. 27A-27D depict graphs demonstrating the ability of DLL3-targeted constrained CD3 engaging constructs to mediate antigen specific T-cell activation on DLL3 positive SHP-77 cells (FIGS. 27A and 27C), and DLL3 negative HEK-293 Freestyle cells (FIGS. 27B and 27D)
Figure 27B:
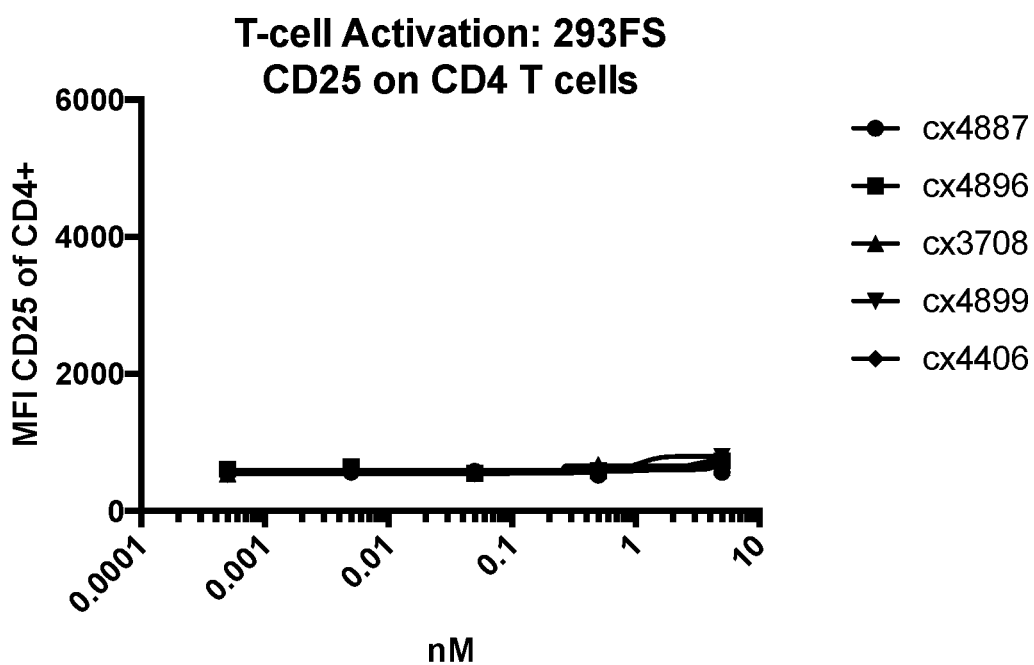
Figure 27C:
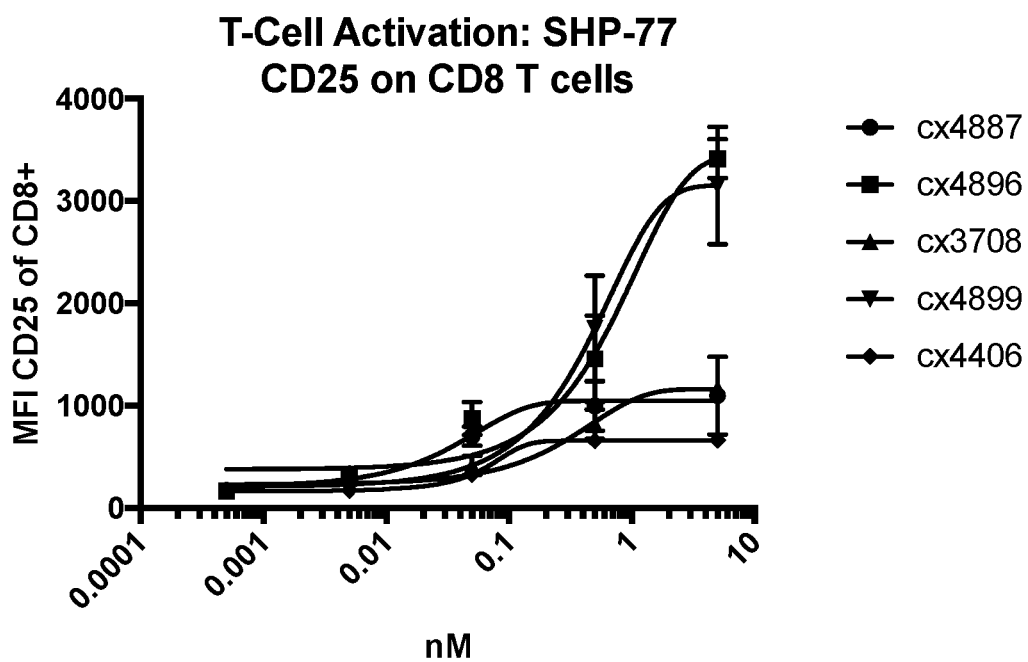
Figure 27D:
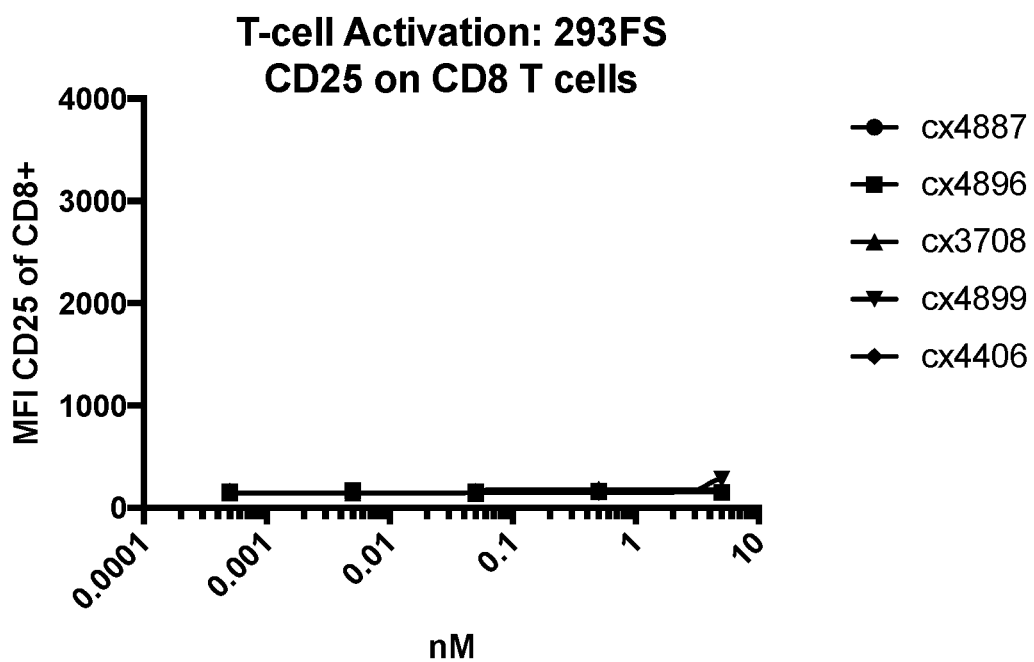

As shown in FIGS. 26A-26B, exemplary DLL3-targeted constrained CD3 engaging constructs, cx4887, cx4896, cx3708, cx4899, and cx4406 induced potent T-cell-mediated cytotoxicity of an antigen positive cell line (SHP-77) but not an antigen negative cell line (HEK-293FS), consistent with the capacity to potently induce antigen-dependent T-cell activation. These observations support that the antigen-targeted constrained CD3 format provided herein exhibit reduced T-cell binding in isolation while maintaining potent DLL3-dependent T-cell cytotoxicity inducing capacities. Notably, cx4887, which contains the humanized variants of DLL3-targeted sdAbs hz10D9v7 and hz8E7v3 positioned at the N and C-termini, respectively, elicited potent T-cell mediated cytotoxicity.

2. T Cell Activation

To assess T cell activation, cells from T cell-mediated cytotoxicity assays were collected and stained with a live/dead stain and fluorophore-conjugated anti-CD4, anti-CD8, and/or anti-CD25 antibodies. Cells were analyzed using a SONY SA3800 spectral analyzer and CD4+ or CD8+ T cell activation was determined by measuring expression levels of CD25.

FIGS. 27A-27B and FIGS. 27C-27D depict results for CD25 expression on CD4 T cells and CD8 T cells, respectively, upon culture of T cells with DLL3 positive (SHP-77) or DLL3 negative cell lines (HEK-293FS) in the presence of exemplary constructs. As shown in FIGS. 27A-27D, exemplary DLL3-targeted constrained CD3 engaging constructs, cx4887, cx4896, cx3708, cx4899, and cx4406 mediated DLL3-dependent T-cell activation via CD3 binding. Thus, the results demonstrated that the DLL3-targeting constrained CD3 engaging constructs of the present invention induced potent antigen-dependent activation of both CD4 and CD8 T-cells as evidenced by enhanced CD25 expression.

3. T Cell Cytokine Production (ELISA)

Figure 28:
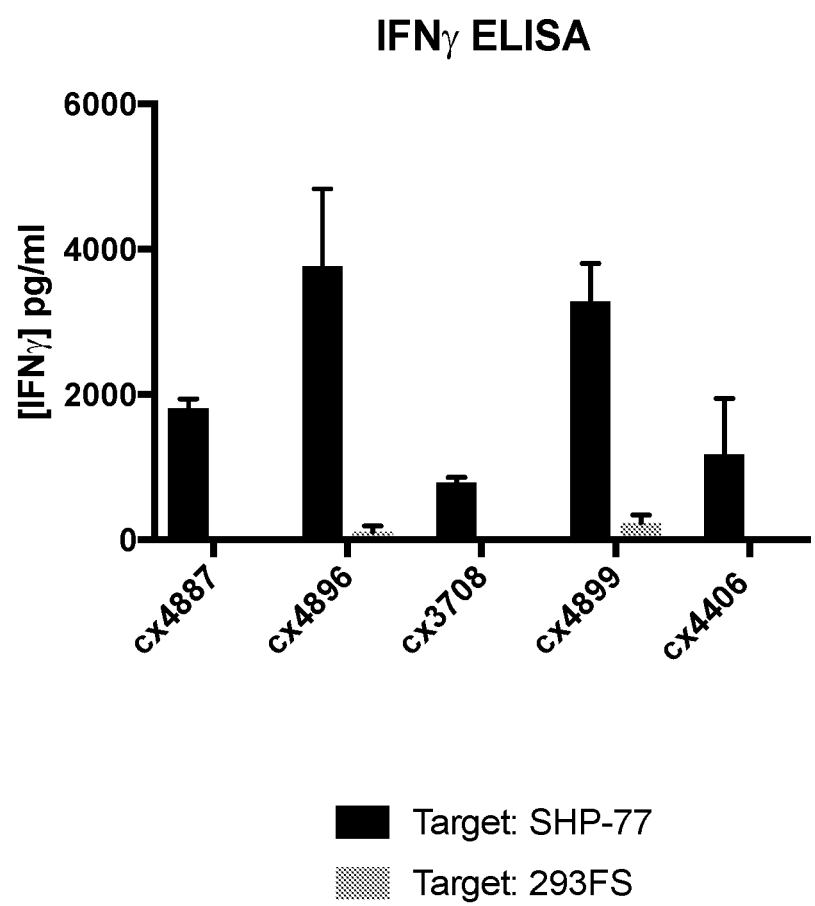
FIG. 28 demonstrates the ability of DLL3-targeted constrained CD3 engaging constructs to elicit cytokine production from T cells in an antigen-dependent manner. Cytokine production was monitored using an ELISA method.

Supernatants from T cell-mediated cytotoxicity assays were analyzed for IFNγ content by sandwich ELISA (BioLegend, USA). The manufacturer's instructions were followed and a standard curve was generated from which cytokine concentration values of supernatant samples were interpolated. Samples that had absorbance values below the lower limit of detection were assigned a cytokine concentration equal to half that of the lowest standard concentration. FIG. 28 shows that exemplary DLL3-targeted constrained CD3 engaging constructs, cx4887, cx4896, cx3708, cx4899, and cx4406 elicit IFNγ production by T-cells in an antigen dependent manner.

Example 8: Generation of Additional Constructs with Constrained CD3 Binding

Figure 29A:
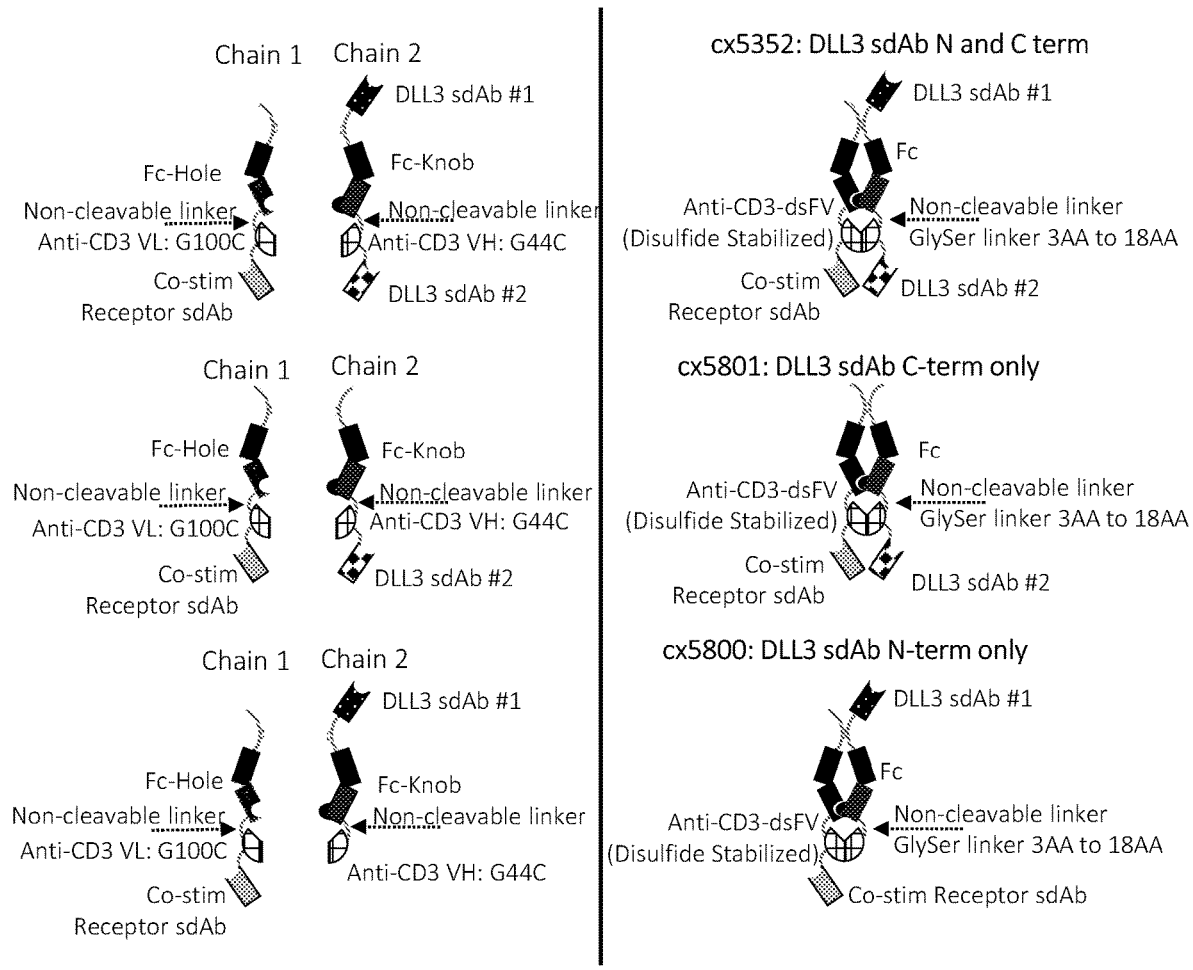
FIG. 29A is a schematic of three DLL3-targeting constrained CD3 constructs composed of two polypeptides, Chain 1 and Chain 2. Chain 1 contains a heterodimeric Fc "hole", linked via a non-cleavable linker to an anti-CD3 VL domain modified at G100C linked to a co-stimulatory receptor targeting sdAb. Chain 2 contains either a DLL3-targeted sdAb, linked to a complementary heterodimeric Fc "knob", linked via the linker as above to an anti-CD3 VH domain modified at G44C linked to second DLL3-targeted sdAb (top); a heterodimeric Fc "knob", linked via the linker as above to an anti-CD3 VH domain modified at G44C linked to a DLL3-targeted sdAb (middle); or a DLL3-targeted sdAb, linked to a complementary heterodimeric Fc "knob", linked via the linker as above to an anti-CD3 VH domain modified by G44C (bottom). The resulting constructs engage DLL3 either in bivalent (top) or monovalent (middle and bottom) manner. All the constructs herein express contain a co-stimulatory receptor targeting sdAb.
Figure 29B:
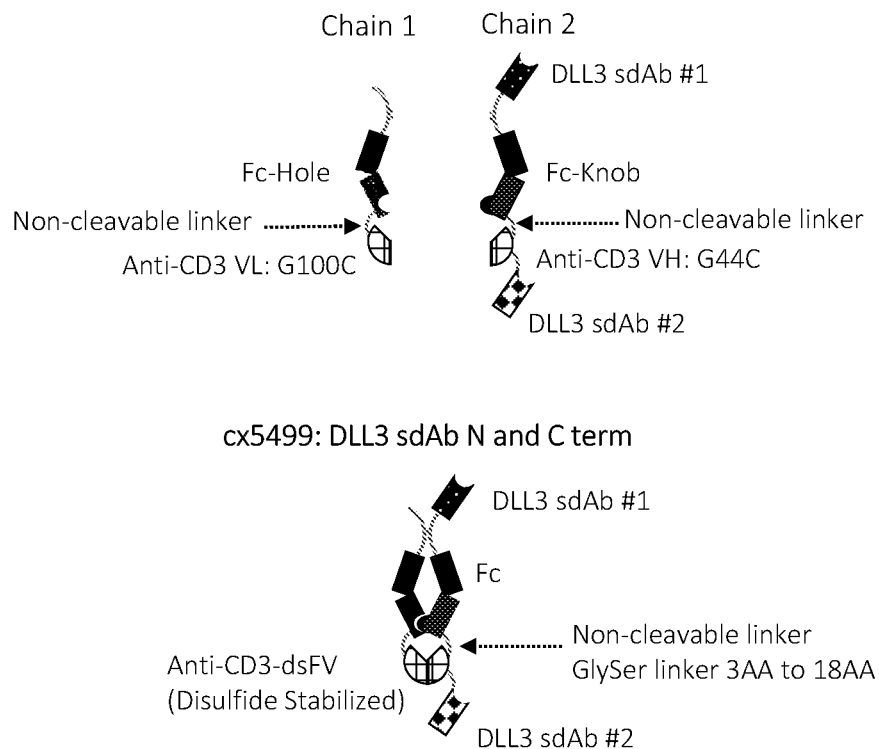
FIG. 29B is a schematic of a DLL3-targeting constrained CD3 construct, cx5499, composed of two polypeptides, Chain 1 and Chain 2. cx5499 is identical to cx5352 shown in FIG. 29A (top), but lacking a co-stimulatory receptor-targeting sdAb on the C-terminus of Chain 1. When co-expressed, the CD3 binding domain is properly assembled via the association of the VL:VH on the hole and knob, respectively. VH:VL interaction is stabilized by an engineered disulfide bond between the modified residues G44C in the VH domain and G100C in the VL domain.

Example 8 describes the generation and expression of multispecific polypeptide constructs containing a CD3 binding region that exhibits constrained CD3 binding. The multispecific constructs were generated in various configurations, as shown in FIGS. 29A and 29B, to contain a heterodimeric Fc region of an immunoglobulin coupled by a linker (e.g. a non-cleavable linker) to the CD3 binding region, and one or more antigen binding domains that binds a tumor associated antigen (TAA) positioned amino-terminally relative to the Fc region and/or carboxy-terminally relative to the CD3 binding region of the multispecific polypeptide construct.

A. Design and Generation of Constructs

Polynucleotides encoding at least a first polypeptide chain and a second polypeptide chain of the heterodimeric multispecific polypeptide construct were generated and cloned into a plasmid for expression. The first polypeptide chain generally included in order, from the N-terminus to C-terminus, a first Fc polypeptide (e.g. an Fc hole polypeptide); a non-cleavable linker; and a variable light (VL) domain of an anti-CD3 antibody. The second polypeptide chain generally included in order, from the N-terminus to C-terminus, a second Fc polypeptide (e.g. an Fc knob polypeptide); the same non-cleavable linker as the first polypeptide chain; and a variable heavy (VH) domain of an anti-CD3 antibody. The anti-CD3 antibody included either a disulfide-stabilized (dsFv) antibody (anti-CD3 VH with the mutation G44C and VL with the mutation G100C) or contained a non-disulfide stabilized Fv antibody, as set forth in Table E5. Various exemplary Fc polypeptide pairs to facilitate heterodimerization of the polypeptide chains were used as set forth in Table E5. One or both of the polypeptide chains additionally encoded one or more TAA antigen binding domain amino-terminal to the Fc domain and/or carboxy-terminal to the CD3 binding region, in various configurations. Similar constructs can be generated using other heterodimeric Fc configurations, including other knob-into-hole configurations, such as any as described; other CD3-binding regions, including other anti-CD3 antibodies, including dsFv or other monovalent fragments; or other TAA antigen-binding fragments, such as scFv, sdAb or Fab formats can also be used.

Among generated constructs, the non-cleavable linker included linkers ranging from 3-18 amino acids in size. Examples of non-cleavable linkers used in exemplary generated molecules were

GGS,

GGSGGS, (SEQ ID NO: 1)

GGSGGSGGS, (SEQ ID NO: 2)

GGSGGSGGSGGS, (SEQ ID NO: 3)

GGSGGSGGSGGSGGS, (SEQ ID NO: 4)

and

GGGGSGGGGSGGGGS (SEQ ID NO: 127)

or

GGSGGGGSGGGGSGGGGS. (SEQ ID NO: 129)

Any antigen binding domain that binds to a TAA can be employed in the provided multispecific polypeptide constructs. Exemplary generated proteins contained an antigen binding domain that binds Delta-like 3 (DLL3). The antigen-binding domain can include single chain fragments (e.g. sdAb or scFv) or two chain antigen-binding fragments (Fabs). When the TAA was provided as a single chain fragment, e.g. sdAb or scFv, the TAA antigen binding domain was linked at the N-terminus to one or both polypeptide chains of the Fc heterodimer (e.g. hole and/or knob) by a peptide linker, e.g. PGGGG (SEQ ID NO:450) and/or was linked at the C-terminus to one or both domains (e.g. VH and/or VL) of the CD3 binding region by a peptide linker, e.g. GGGG (SEQ ID NO:5). Other similar peptide linkers can be employed.

Multispecific polypeptide constructs were generated containing 1, 2, or 3 TAA antigen binding domains, such as to provide for monovalent, bivalent, or trivalent binding, respectively. In constructs engineered with more than one DLL3-targeting sdAb TAA binding domain, the TAA antigen binding domains were different, such that the generated multispecific polypeptide constructs exhibited specificity for at least two different epitopes of the same TAA (bi-epitopic).

Among the generated proteins were constructs in which the TAA antigen binding domains were composed as single domain antibodies (sdAbs). Polynucleotides were generated to encode polypeptide chains of exemplary multispecific polypeptide constructs containing non-cleavable linkers. These included sdAb-containing constructs designated cx5352, cx5800, cx5801, and cx5499, targeting DLL-3 as depicted in FIGS. 29A and 29B. The constructs were engineered with a disulfide linkage stabilizing the VH and VL domains of the anti-CD3 antibody. Notably, some of the exemplary constructs generated additionally contained a sdAb (containing a CDR1, a CDR2 and a CDR3 set forth in SEQ ID Nos: 457, 458 and 459, respectively; e.g. set forth in SEQ ID NO:210) targeting a 4-1BB co-stimulatory receptor (e.g. cx5352, cx5800, cx5801). cx5499 was not engineered to contain a sdAb targeting a co-stimulatory receptor. A list of exemplary constrained CD3 binding constructs having sdAb and Fab TAA domains is given below in Table E5.

TABLE E5

Exemplary Constrained CD3 engaging constructs

| Construct ID | Chain | N-term sdAb (SEQ ID NO) | Fc (SEQ ID NO) | Linker (SEQ ID NO) | CD3 Binding Domain (SEQ ID NO) | C-term sdAb (SEQ ID NO) | Disulfide Stabilized |
|---|---|---|---|---|---|---|---|
| cx5352 | 1 | DLL3 sdAb 1 (251) | xELL-Knob (105, 109 or 442) | GGGGGSGG GGGSGGGG GS (127) | VH13 (47) | DLL3 sdAb2 (455) | yes |
|  | 2 | None | xELL-Hole (112, 114 or 445) | GGGGGSGG GGGSGGGG GS (127) | VL10 (75) | Co-stim Receptor sdAb |  |
| cx5800 | 1 | DLL3 sdAb 1 (251) | xELL-Knob (SEQ ID NO: 105, 109 or 442) | GGGGGSGG GGGSGGGG GS (127) | VH13 (S47) | None | yes |
|  | 2 | None | xELL-Hole (112, 114 or 445) | GGGGGSGG GGGSGGGG GS (127) | VL10 (75) | Co-stim Receptor sdAb |  |
| cx5801 | 1 | None | xELL-Knob (105, 109 or 442) | GGGGGSGG GGGSGGGG GS (127) | VH13 (47) | DLL3 sdAb 2 (455) | yes |
|  | 2 | None | xELL-Hole (112, 114 or 445) | GGGGGSGG GGGSGGGG GS (127) | VL10 (75) | Co-stim Receptor sdAb |  |
| cx5499 | 1 | DLL3 sdAb1 (251) | xELL-Knob (105, 109 or 442) | GGGGGSGG GGGSGGGG GS (127) | VH13 (47) | DLL3 sdAb 2 (455) | yes |
|  | 2 | None | xELL-Hole (112, 114 or 445) | GGGGGSGG GGGSGGGG GS (127) | VL10 (75) | None |  |

B. Expression and Purification of Generated Constructs

Separate plasmids encoding each chain of the heterodimeric constrained CD3 binding protein were transiently transfected at an equimolar ratio into mammalian cells (either HEK293 or CHO) using polyethylenimine Recombinant protein secreted into the supernatant was collected after 3-14 days, and purified by protein A chromatography, followed by either preparative size exclusion chromatography (SEC) or flow-through hydrophobic interaction chromatography (HIC). In some cases, heterodimeric protein was enriched for during purification due to a mutation designed into one chain of the heterodimeric Fc at position I253R or H435R (e.g. in the hole-Fc) such that it did not bind protein A, and thus homodimers of I253R or H435R were not purified. The second chromatography step by SEC (AKTA with Superdex-200 resin) or FT-HIC (AKTA with butyl/phenyl sepharose) was used to remove undesired cross-paired species containing two heterodimeric Fcs that were more hydrophobic and twice the expected molecular weight.

The method favored production of heterodimeric multispecific polypeptide constructs, containing properly paired species of heterodimeric Fc and the anti-CD3 Fv (e.g. disulfide stabilized anti-CD3 Fv). Purified heterodimeric constrained CD3 binding protein was stable and did not accumulate cross-paired species upon prolonged incubation at 4° C. or increased protein concentration.

Example 9: Assessment of CD3 Constrained Multispecific Constructs Containing Single or Multiple Antigen-Binding DLL3-Targeting Domains This example describes the assessment and characterization of exemplary generated DLL3-targeted constrained CD3 engaging constructs in human primary T cell in vitro assays.

Binding and activity of DLL3-targeted constrained CD3 engaging constructs that were formatted with an anti-DLL3 sdAb (e.g. cx5352, cx5800, cx5801, and cx5499) as the antigen-binding domain(s) were assessed (see FIGS. 29A-B and Table E5). All tested constructs contained a disulfide-stabilized anti-CD3 Fv (dsFv) containing an interchain disulfide bond created by the modification of anti-CD3 VH G44C paired with VL G100C. Further, the DLL-3-targeted constructs were engineered to contain a co-stimulatory receptor sdAb C-terminal to the CD3 dsFv, except for cx5499, which did not contain this co-stimulatory receptor sdAb domain.

A. Binding

Figure 30A:
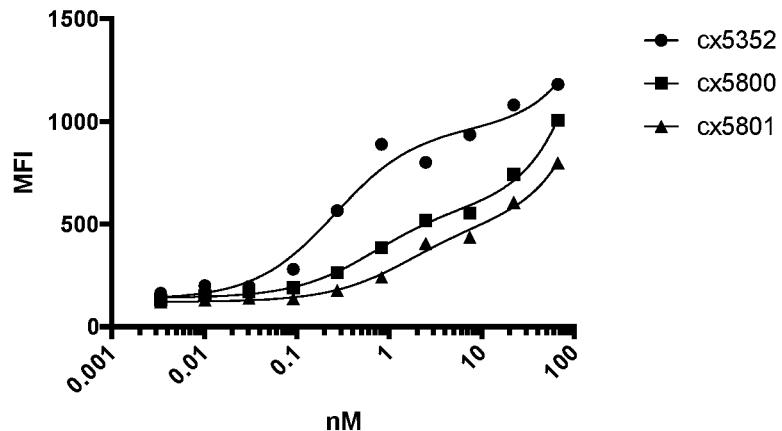
FIGS. 30A-30B demonstrate that the representative monovalent (cx5800 and cx5801) and bivalent (cx5352) DLL3-targeting constrained CD3 engaging constructs bound a DLL3 expressing cell line, SHP-77 (FIG. 30A), but not isolated T cells (FIG. 30B). Binding was assessed by flow cytometry.
Figure 30B:
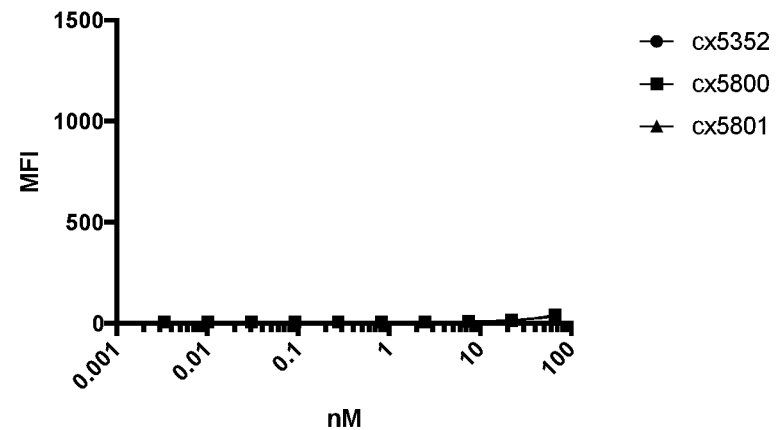

Binding of exemplary multispecific polypeptide constructs of the disclosure containing an antigen-binding domain directed against DLL3 to CD3 on the surface of primary T cells and to DLL3 expressing cells (SHP-77) was assessed by flow cytometry. As shown in FIG. 30A the bivalent DLL3-targeting constrained CD3 engaging constructs, cx5352 displayed higher affinity binding to DLL3 positive, SHP-77 cells compared to the monovalent versions, cx5800 and cx5801. None of the constructs tested displayed binding to DLL3-negative primary T cells, as depicted in FIG. 30B. These binding assays were conducted by flow cytometry, wherein bound constructs were detected using a fluorophore-conjugated anti-human IgG Fc secondary antibody.

B. T Cell Reporter Activity

Figure 30C:
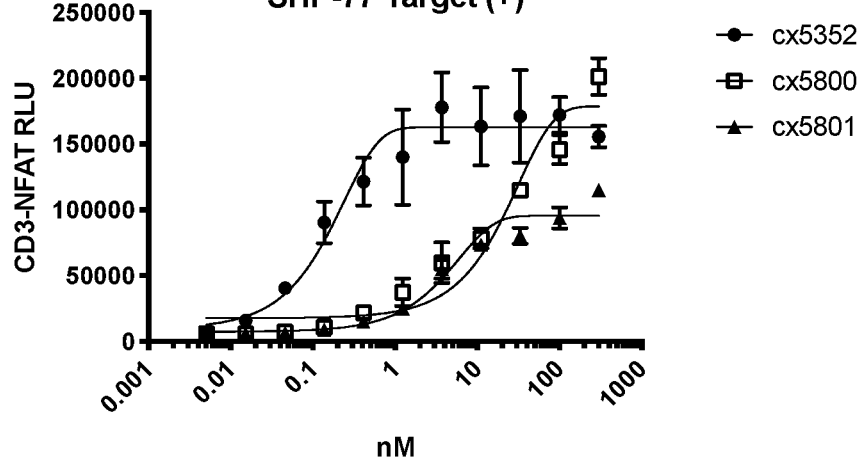
FIG. 30C depicts the ability of representative DLL3-targeting constrained CD3 engaging constructs to agonize CD3 signaling in the presence of DLL3 positive SHP-77 cells. Engaging DLL3 positive cells with a construct that is bivalent and bi-epitopic to DLL3 (cx5352) induced more potent T-cell activation than constructs that are monovalent to DLL3 (cx5800 and cx5801). A Jurkat CD3 NFAT-Luciferase reporter cell line was used to assess CD3 signaling.

T cell activity was assessed in a reporter assay using Jurkat cells expressing NFAT-driven Luciferase. Agonism of CD3 results in NFAT signaling and production of luciferase that can be monitored. NFAT-driven Luciferase CD3 Jurkat reporter cells were co-cultured with SHP-77 (DLL3-positive) target cells in the presence of monovalent and bivalent constructs containing antigen-binding domains against the DLL3 antigen (see FIG. 29A). Specifically, as shown in FIG. 30C, the exemplary bivalent construct cx5352 induced substantially greater luciferase activity in this assay compared to the exemplary monovalent constructs cx5800 and cx5801.

C. Cytotoxicity

Figure 31A:
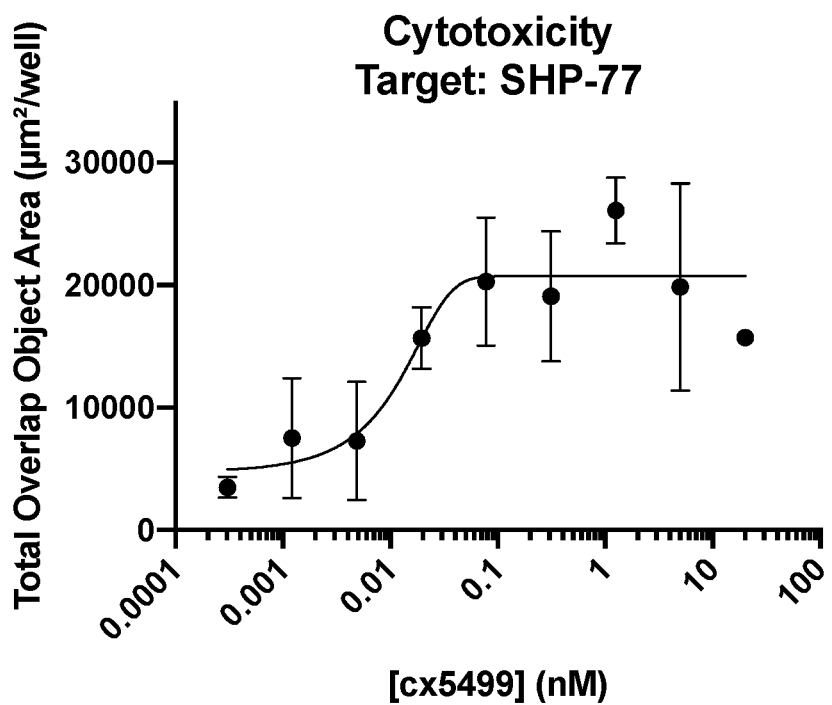
FIGS. 31A-31E demonstrate the ability of a representative DLL3-targeting constrained CD3 engaging construct, cx5499 to elicit T-cell mediated cytotoxicity and T-cell activation in the presence of DLL3-positive SHP-77 cells.

Cytotoxicity in the presence of cx5499, a DLL3-targeted CD3 constrained binding construct formatted with two distinct sdAb binding domains located at its amino and carboxy termini, was assessed. Target cells were the DLL3 expressing cell line, SHP-77. Target cells were seeded at $1.0 \times 10^4$ cells per well, allowed to settle at room temperature for uniform distribution, and incubated for several hours at 37 degrees Celsius. Primary T cells were negatively enriched from PBMCs isolated from healthy human donor leukopaks and added at a 10:1 T cell-to-target cell ratio. Green caspase-3/7 reagent was added, which fluorescently labels nuclear DNA of cells undergoing apoptosis was added. Multispecific constructs with constrained CD3 engaging activity were titrated onto the co-culture and assay plates were serially imaged using an IncuCyte ZOOM system. Target cell death was determined by measuring total red/green overlap object area. As shown in FIG. 31A, cx5499 induced potent T-cell mediated cytotoxicity directed toward the SHP-77 cell line.

D. T Cell Modulation

To further assess T cell modulation, exemplary multispecific CD3 constrained binding constructs were assessed by monitoring the ability of the constructs to modulate T cell activation markers. To assess T cell activation, suspension cells from T cell cytotoxicity assays above, involving culture of T cells with DLL3 positive SHP-77 cells in the presence of cx5499, were collected. Cells were stained with a live/dead stain and fluorophore-conjugated anti-CD4, anti-CD8, anti-CD25 and/or anti-CD69 antibodies. Cells were analyzed using a SONY SA3800 spectral analyzer and CD4+ or CD8+ T cell activation was determined by measuring expression levels of CD25 or CD69 or percent CD25- or CD69-positive.

Figure 31B:
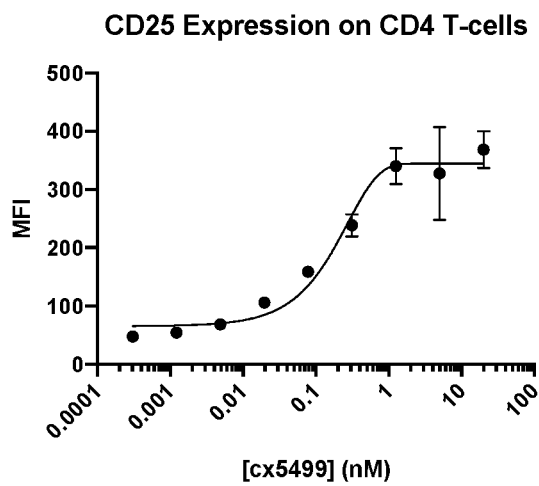
Figure 31C:
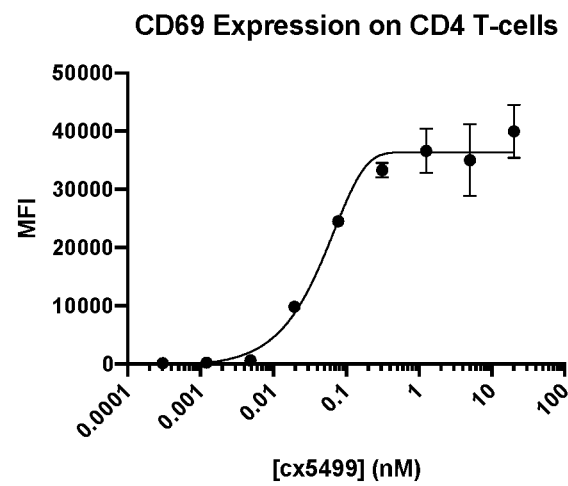
Figure 31D:
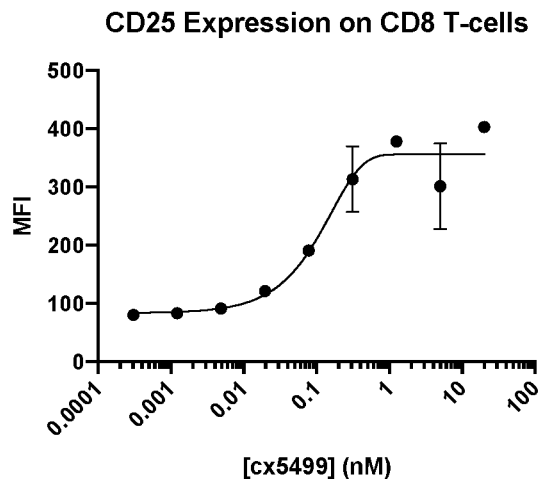
Figure 31E:
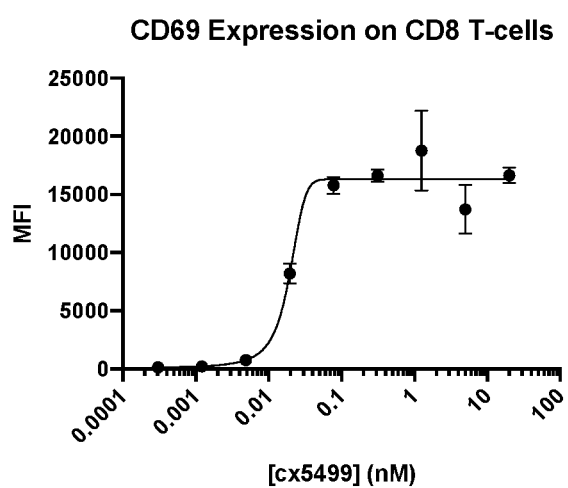

FIG. 31B and FIG. 31D depict results for CD25 expression on CD4 T cells and CD8 T cells, respectively, upon culture of T cells with DLL3 positive, SHP-77 cells, in the presence of an exemplary DLL3-targeted constrained CD3 engaging construct, cx5499. FIG. 31C and FIG. 31E depict results for CD69 expression on CD4 cells and CD8 T cells, respectively, upon culture of T cells with DLL3 positive, SHP-77 cells, in the presence of an exemplary DLL3-targeted constrained CD3 engaging construct, cx5499. The results showed that cx5499 mediated a dose-dependent DLL3-dependent T-cell activation via CD3 binding, as evidenced by increased expression of CD25 and CD69 on CD4+ and CD8+ T cells.

E. Summary

Together, these results demonstrate that constrained anti-CD3 constructs formatted with anti-DLL3 sdAb binding domains and CRBRs are capable of binding to a DLL3-expressing cell line, SHP-77, and eliciting antigen-dependent T-cell activation. This suggests that the constrained anti-CD3 constructs described herein are not specific to a target antigen, but are effective at binding various antigens to elicit T-cell cytotoxicity and activation against target-expressing cells.

Example 10: Effect of Costimulatory Receptor Binding Region in CD3-Constrained Multispecific Constructs Containing DLL3-Targeting Domains To compare activity of a DLL3-targeted construct that contained a CRBR positioned C-terminally at the CD3 binding domain to a construct that did not contain a CRBR, exemplary constructs cx5352 and cx5499, respectively, were tested in various assays to assess their effect on T cell activity (see Table E5).

A. T Cell Reporter Assay

Figure 32:
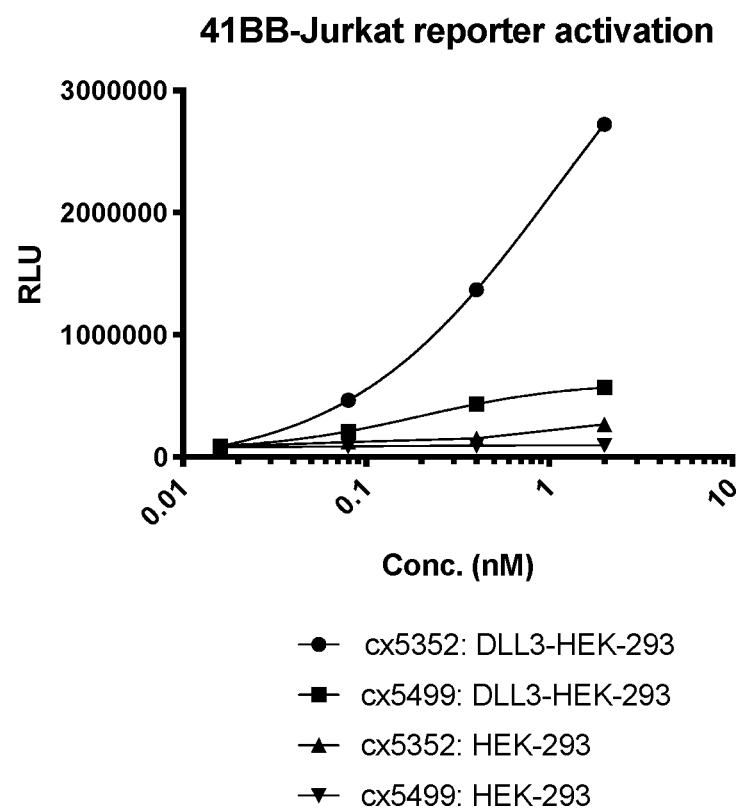
FIG. 32 shows the ability of the DLL3-targeted constrained CD3 engaging construct with a 41BB binding domain, cx5352, but not the same construct lacking a 41BB binding domain, cx5499, to mediate 41BB signaling. DLL3 dependent 41BB signaling was monitored using Jurkat 41BB NFkB-luciferase reporter cells co-cultured with either parental HEK-293 cells or HEK-293 cells transiently expressing a truncated version of DLL3, and activity is shown as relative luciferase units (RLU).

The capacity of constrained CD3 engaging constructs containing a co-stimulatory receptor binding domain to mediate specific agonism of the co-stimulatory signaling pathway was assessed. A Jurkat 41BB NFκB-Luciferase reporter cell was used to test exemplary DLL3-targeting constrained CD3 engaging constructs with either no co-stimulatory receptor binding domain (cx5499) or a 41BB binding domain (cx5352). The reporter cells were co-cultured with either a DLL3 negative cell line, HEK-293, or HEK-293 cells transiently expressing a truncated version of DLL3 (residues 276-618 of SEQ ID NO:86). As shown in FIG. 32, cx5352 displayed DLL3-dependent 41BB agonism in which robust luciferase activity was only observed in the presence of DLL3-expressing cells. A low level of DLL3-dependent NFkB activation was observed with cx5499, indicating that CD3 signaling in this assay may lead to some NFkB activation.

B. Cytotoxic Activity

Primary human T cells were negatively enriched from PBMCs isolated from three different healthy human donor leukopaks and added at a 10:1-40:1 T cell-to-target cell ratio. Herein target cells were labeled as red with the CytoID red, while apoptosis was monitored with the green fluorescent caspase-3/7 substrate; thus apoptotic target cells those that are dual labeled red and green. Assay plates were serially imaged using an IncuCyte ZOOM system. Target cell death was determined by measuring total red/green overlap object area.

Figure 33A:
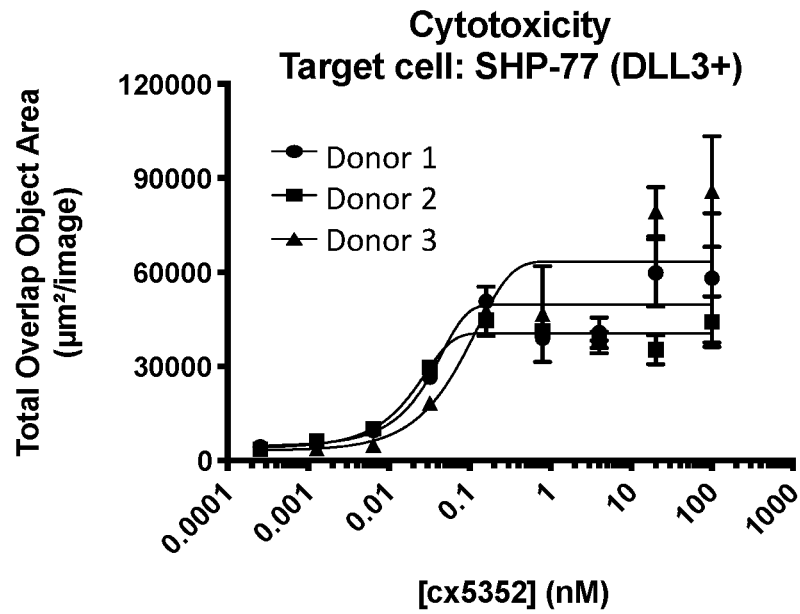
FIGS. 33A-B depict the potency of T-cell-mediated cytotoxicity driven by an exemplary DLL3-targeted constrained CD3 engaging construct with a 41BB binding domain, cx5352, toward a DLL3 positive cell line, SHP-77 (FIG. 33A) or a DLL3 negative cell line, HEK-293FS (FIG. 33B). Three distinct T-cell donors were used as the source of effector cells in this assay.
Figure 33B:
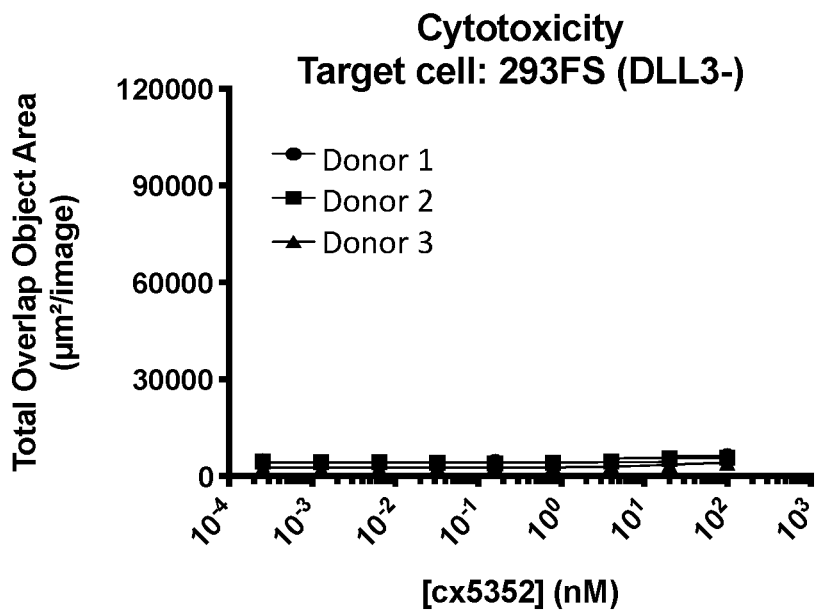

In an exemplary assay, the CD3 engaging construct that was tested included dual DLL3-targeted sdAbs with a 41BB-binding CRBR (cx5352). The target cells were DLL3-expressing SHP-77 cells or 293FS cells that did not express DLL3. As shown in FIG. 33A, cx5352 was capable of eliciting T-cell mediated antigen specific cytotoxicity. No cytotoxicity was observed in the absence of the antigen, as shown by no red/green overlap object area in co-cultures containing DLL3-negative cells (FIG. 33B). This data demonstrates the capacity of an exemplary DLL3-targeted constrained CD3 engaging construct with a 41BB binding domain to elicit T-cell mediated antigen specific cytotoxicity.

Figure 34A:
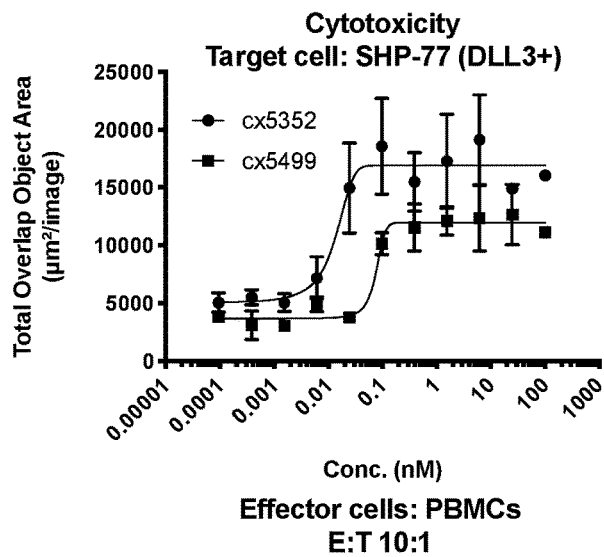
FIGS. 34A-C show differences in potency of T-cell-mediated cytotoxicity driven by exemplary DLL3-targeted constrained CD3 engaging constructs with a 41BB binding domain, cx5352, and without a 41BB binding domain, cx5499. Herein various effector (T cells) to target cells (SHP-77) ratios (effector:target cell ratio) were compared as follows: 10:1 (FIG. 34A), 5:1 (FIG. 34B) or 1.25:1 (FIG. 34C). Human PBMCs were used as the source of T-cells.
Figure 34B:
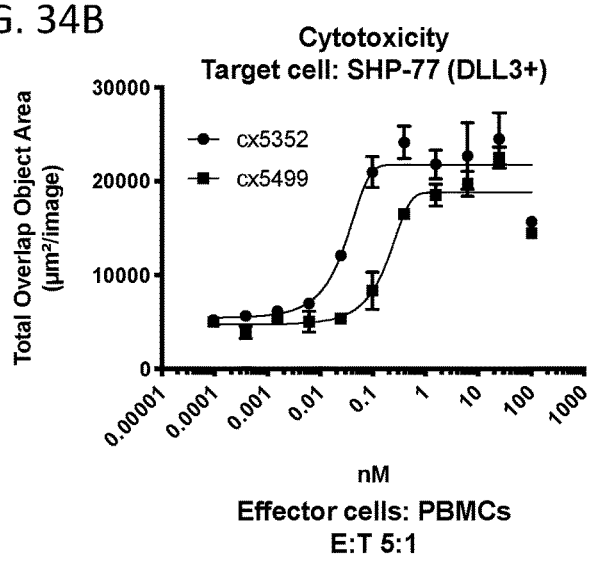
Figure 34C:
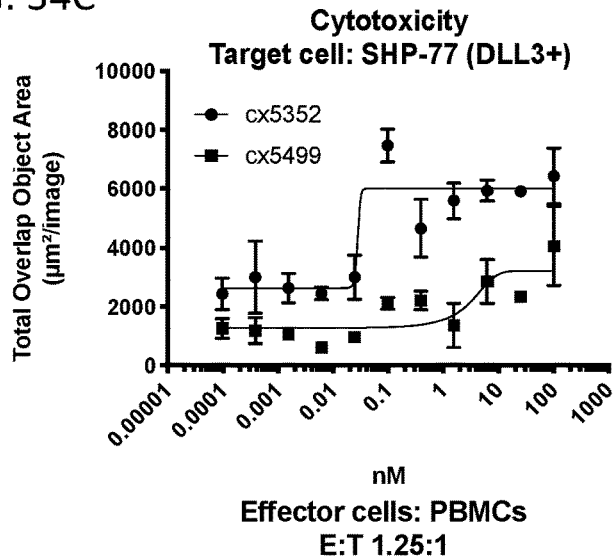

In a similar assay, primary human PBMCs isolated from healthy human donor leukopaks were added at a 10:1, 5:1, or 1.25:1 ratio of effector to target (E:T) cells. The PBMCs were co-cultured with DLL3-expressing SHP-77 target cells and incubated in the presence of increasing concentrations of exemplary constructs containing DLL3-targeted sdAbs with a CRBR (cx5352) and without a CRBR (cx5499). As shown in FIGS. 34A-C, cx5352 displayed enhanced cytotoxicity against target cells at all three E:T ratios analyzed.

C. T Cell Cytokine Expression

Supernatants from a T cell-mediated cytotoxicity assay, carried out substantially as described above with SHP-77 cells as target cells, were analyzed for IFNγ content by sandwich ELISA (BioLegend, USA). The manufacturer's instructions were followed and a standard curve was generated from which cytokine concentration values of supernatant samples were interpolated. Samples that had absorbance values below the lower limit of detection were assigned a cytokine concentration equal to half that of the lowest standard concentration.

Figure 35:
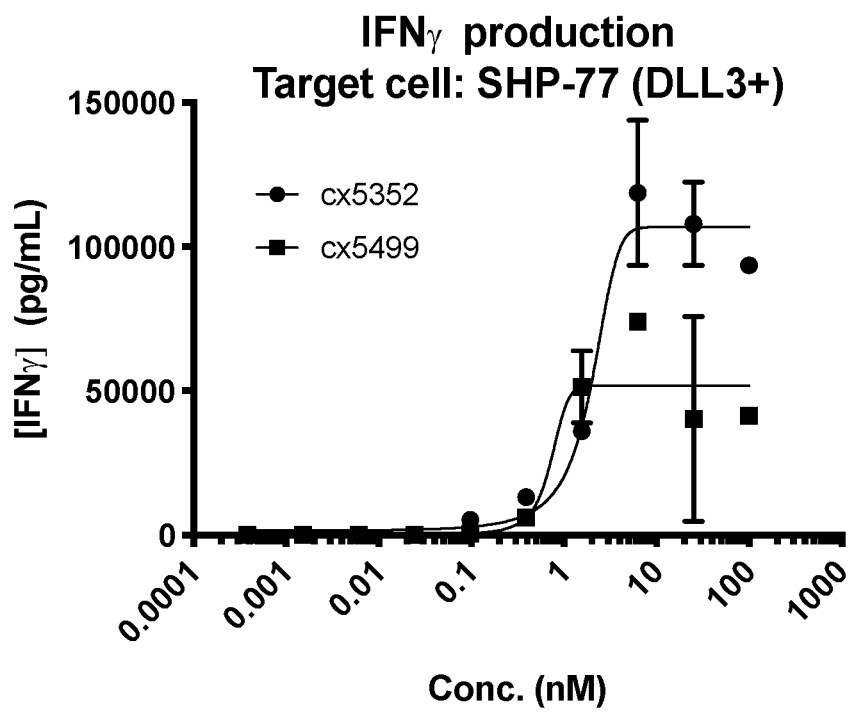
FIG. 35 shows a comparison of IFNγ production by T-cells treated with a titration of representative DLL3-targeted constrained CD3 engaging constructs with a 41BB binding domain, cx5352, and without a 41BB binding domain, cx5499, in the presence of the DLL3 positive cell line SHP-77.

As shown in FIG. 35, the DLL3-targeted constrained CD3 engaging construct incorporating the 41BB binding domain, cx5352, resulted in enhanced IFNγ production by T cells compared to the similar construct lacking the 41BB binding domain, cx5499.

Figure 36A:
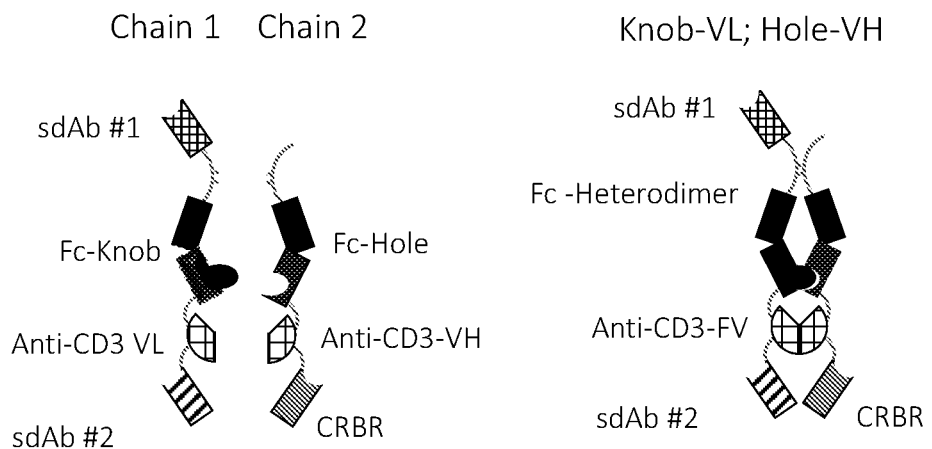
FIGS. 36A-B depict exemplary TAA-targeted constrained CD3 engagers without with a co-stimulatory receptor binding region (CRBR). The constructs have an antigen-targeting sdAb positioned at the N and C-termini of one chain of the heterodimer, the Fc knob, and have a co-stimulatory receptor binding region (CRBR) positioned at the C-termini of the opposite chain of the heterodimer, the Fc hole, but have the VH and VL of the CD3 binding Fv positioned on opposite sides with respect to each other.
Figure 36B:
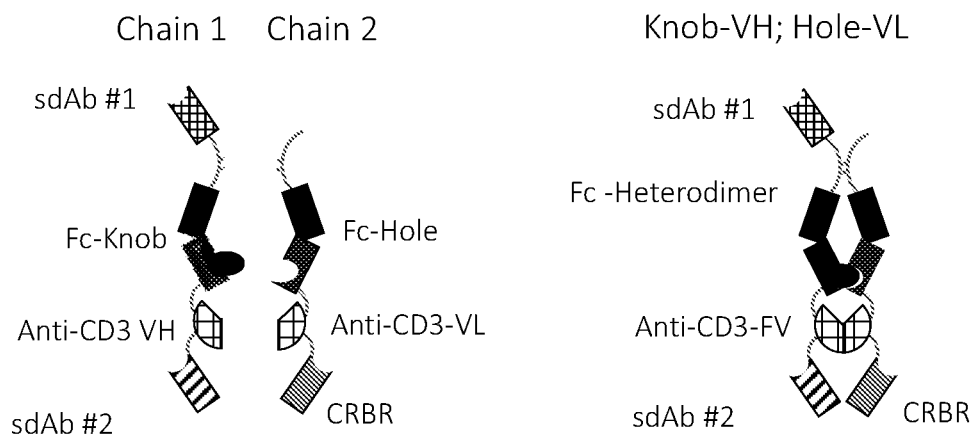

Example 11: Comparison of Orientation of CD3 Binding Region in CD3-Constrained Multispecific Constructs Containing Antigen-Targeting Domains A. Design and Generation of Constructs Multispecific polypeptide constructs were generated as shown in FIGS. 36A-B, to contain a heterodimeric Fc region of an immunoglobulin coupled by a linker (e.g. a non-cleavable linker) to the CD3 binding region, an antigen binding domain (e.g. sdAb) as a CRBR positioned carboxy-terminally relative to the CD3 binding region, and dual antigen binding domains that bind a tumor associated antigen (TAA) positioned amino-terminally relative to the Fc region and carboxy-terminally relative to the CD3 binding region of the multispecific polypeptide construct. The exemplary constructs generated contained a sdAb (containing a CDR1, a CDR2 and a CDR3 set forth in SEQ ID Nos: 457, 458 and 459, respectively; e.g. set forth in SEQ ID NO:210)

Polynucleotides encoding at least a first polypeptide chain and a second polypeptide chain of the heterodimeric multispecific polypeptide construct were generated and cloned into a plasmid for expression. The first polypeptide chain generally included in order, from the N-terminus to C-terminus, a first Fc polypeptide (e.g. an Fc hole polypeptide); a non-cleavable linker; a variable light (VL; FIG. 36B) or variable heavy (VH; FIG. 36A) domain of an anti-CD3 antibody; and an antigen-binding domain (e.g. sdAb) as a CRBR. The second polypeptide chain generally included in order, from the N-terminus to C-terminus, a first antigen-binding domain (e.g. sdAb #1), a second Fc polypeptide (e.g. an Fc knob polypeptide); the same linker as the first polypeptide chain; the other of the variable heavy (VH) or variable light (VL) domain of an anti-CD3 antibody; and a second antigen-binding domain (e.g. sdAb #2). The anti-CD3 antibody included a disulfide-stabilized (dsFv) antibody (anti-CD3 VH with the mutation G44C and VL with the mutation G100C).

Notably, as shown in FIG. 36, the orientation of the anti-CD3 VH and anti-CD3 VL of the CD3 Fv were positioned differently relative to the Fc knob or Fc hole of the heterodimeric Fc region. As shown in FIG. 36A, the construct was generated in which the first polypeptide of the heterodimeric construct had the VL of CD3 Fv positioned C-terminal to the Fc knob and antigen-binding domains on the extreme N and C-termini and the second polypeptide of the heterodimeric construct had the VH of CD3 Fv positioned C-terminal to the Fc Hole and a CRBR sdAb on the extreme C-termini. In contrast, FIG. 36B depicts an exemplary construct in which the first polypeptide of the heterodimeric construct had the VH of CD3 Fv positioned C-terminal to the Fc knob and antigen-binding domains on the extreme N and C-termini and the second polypeptide of the heterodimeric construct had the VL of CD3 Fv positioned C-terminal to the Fc Hole and a CRBR sdAb on the extreme C-termini.

The constructs were expressed as purified substantially as described in Example 8.

B. T Cell Reporter Activity

To compare CD3 engagement, the exemplary constructs were tested in an antigen-dependent CD3 reporter assay by assessing their ability to activate a CD3 NFAT reporter Jurkat cell line in a co-culture with target antigen-expressing cells. Activation was assessed by monitoring either green fluorescent or luciferase reporter signal in Jurkat reporter cells.

Antigen targeting constrained CD3 engaging constructs were titrated onto co-cultures of either A375 cells expressing the target antigen or control CCRF-CEM cells not expressing the target antigen, and engineered Jurkat cells that express NFAT-driven green fluorescence protein (GFP). Engagement of CD3 results in NFAT signaling and production of green fluorescence. For reporter assays utilizing adherent target cells, target cells were seeded, allowed to settle at room temperature for uniform distribution, and incubated for several hours at 37° C. to permit adherence prior to addition of reporter cells and antigen targeting constrained CD3 engaging constructs. Assay plates were serially imaged using an IncuCyte ZOOM system and CD3 reporter cell activation was determined by measuring total green object integrated intensity.

Figure 37A:
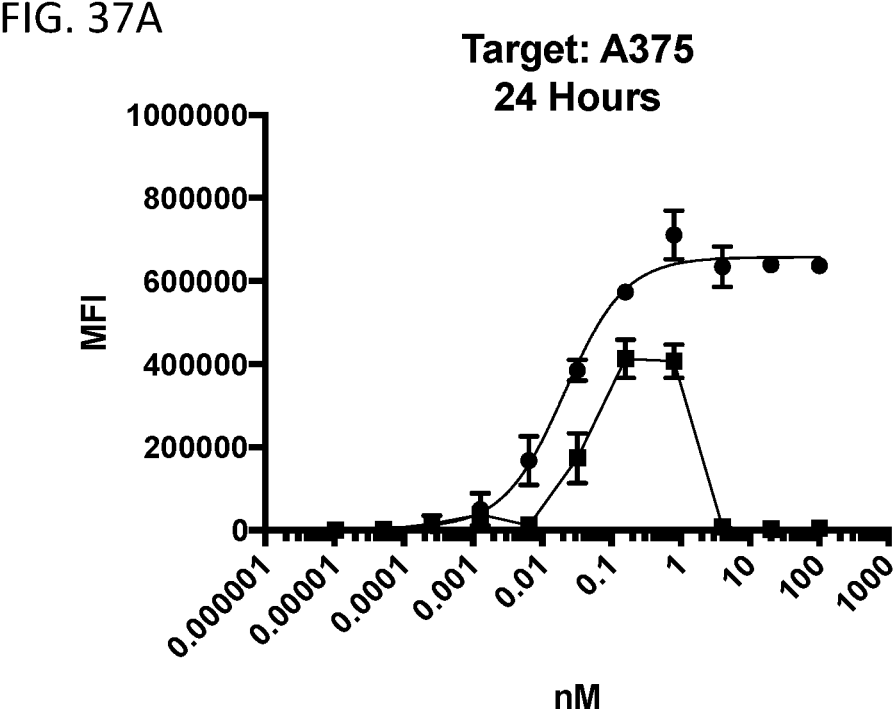
FIGS. 37A-D depict results of a T cell reporter assay for exemplary constructs described in FIG. 36A-B.
Figure 37B:
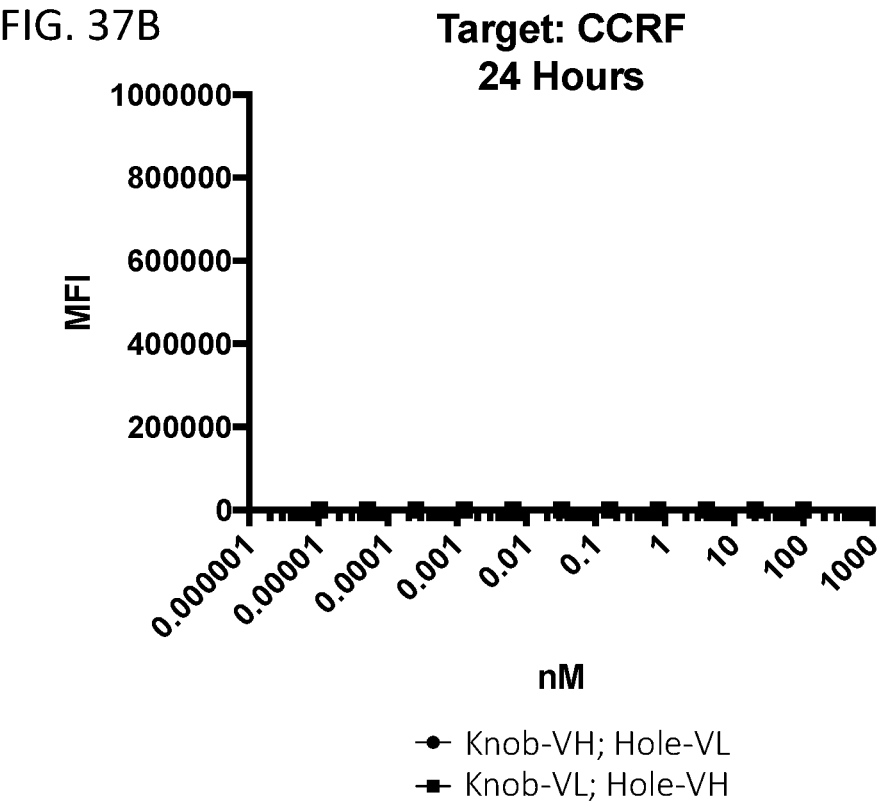

As shown in FIG. 37A, the exemplary antigen-targeted constrained CD3 engaging constructs exhibited capacity to mediate target antigen specific T-cell activation when incubated in reporter T cell co-cultures in the presence of antigen-expressing target cells. Reporter activity, however, was not observed in co-cultures with cells not expressing target antigen (FIG. 37B). Notably, the construct with the Knob-VH; Hole-VL format displayed enhanced T cell activation compared to the construct with the Knob-VL; Hole-VH format.

Figure 37C:
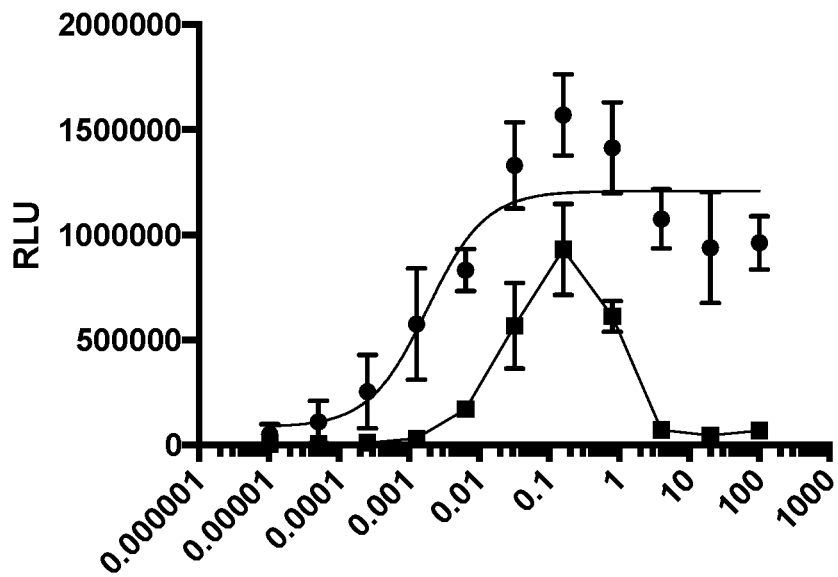
Figure 37D:
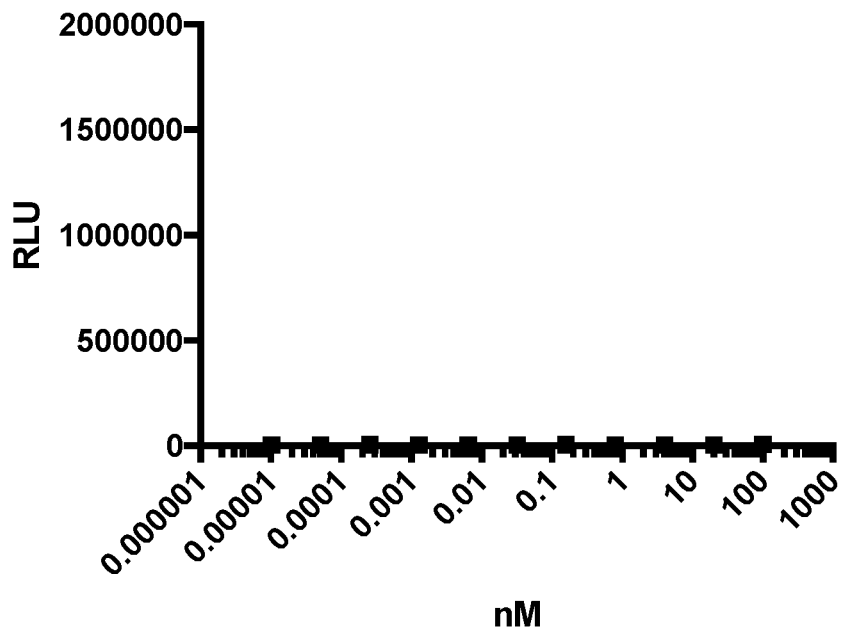

In a similar assay, the same antigen targeting constrained CD3 engaging constructs were titrated onto co-cultures of either A375 cells expressing target antigen or control CCRF-CEM cells not expressing target antigen, and engineered Jurkat cells that express NFAT-driven luciferase. As shown in FIG. 37C, the exemplary antigen-targeted constrained CD3 engaging constructs exhibited capacity to mediate target antigen specific T-cell activation when incubated in reporter T cell co-cultures in the presence of antigen-expressing target cells. Again, reporter activity, was not observed in co-cultures with cells not expressing target antigen (FIG. 37D). As in the GFP reporter assay, the construct with the Knob-VH; Hole-VL format displayed enhanced T cell activation compared to the construct with the Knob-VL; Hole-VH format.

These results are consistent with an observation that enhanced CD3 engagement and activity is observed when the components of the CD3 Fv are oriented so that the VH and VL are positioned C-terminally to the Fc Knob and Fc Hole regions, respectively.

Figure 38A:
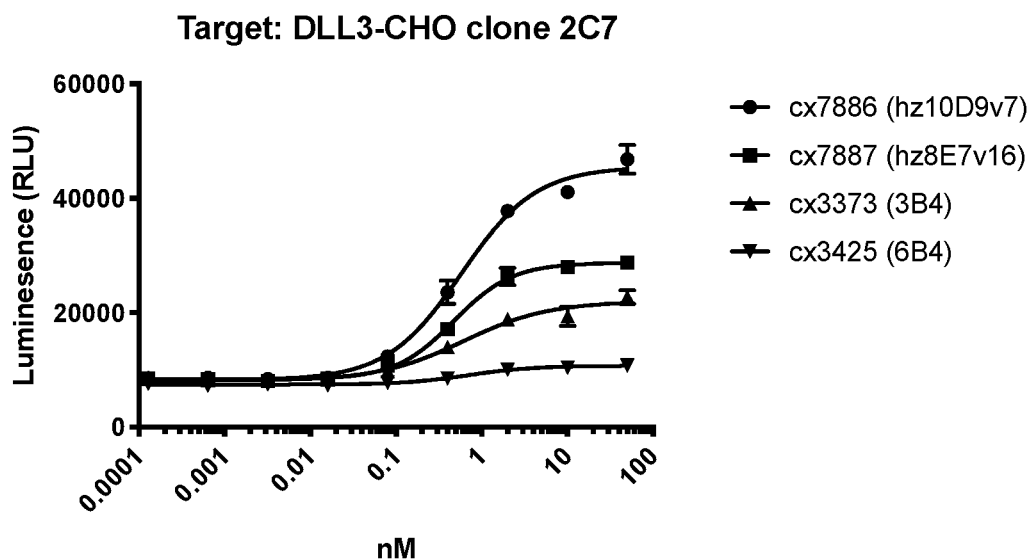
FIGS. 38A-B depict results of a T cell reporter assay using a Jurkat reporter cell line engineered to stably express CD16a with an NFAT-driven luciferase reporter gene.
Figure 38B:
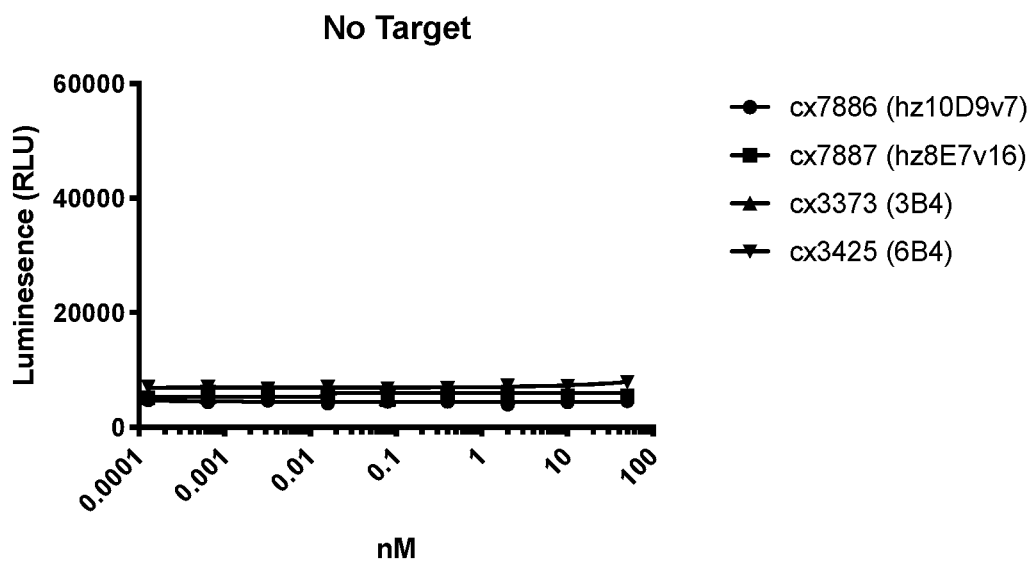

Example 12: Assessment of DLL3-Dependent CD16 Reporter T Cell Activation Using a Reporter Assay This example describes the assessment of the Fc effector function of exemplary DLL3 targeted sdAbs, referred to herein as cx7886, cx7887, cx3373, and cx3425, to activate an NFAT reporter Jurkat cell line in co-culture with DLL3-expressing cells (DLL3-CHO). The Jurkat reporter cell line was engineered to stably express CD16a with an NFAT-driven luciferase reporter gene. Reporter cells were seeded (approximately $6\times10^4$ cells/well) in the presence or absence of DLL3-expressing cells (DLL3-CHO; approximately $3\times10^4$ cells/well). cx7886 (hz10D9v7-Fc), cx7887 (hz8E7v16-Fc), cx3373 (3B4-Fc), or cx3425 (6B4-Fc) were titrated onto the cells and assay plates were incubated at 37 degrees Celsius for six hours, with a final assay volume of 75 microliters. Assay plates were equilibrated to room temperature, 75 microliters of Bio-Glo was added to sample wells, and assay plates were incubated at room temperature for 10 minutes. 100 microliter aliquots were transferred to white 96-well plates and luminescence was measured using a Clariostar microplate reader. FIG. 38A depicts the ability of all constructs to activate CD16 reporter cells in an antigen-dependent manner with cx7886 (hz10D9v7-Fc) and cx7887 (hz8E7v16) inducing greater activation of the reporter cells. As shown in FIG. 38B, no activation was observed in the absence of DLL3-expressing cells.

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

Sequences

| # | SEQUENCE | ANNOTATION |
|---|---|---|
| 1 | GGSGGS | (GGS)2 linker |
| 2 | GGSGGSGGS | (GGS)3 linker |
| 3 | GGSGGSGGSGGS | (GGS)4 linker |
| 4 | GGSGGSGGSGGSGGS | (GGS)5 linker |
| 5 | GGGG | glycine linker |
| 6 | GGGGG | glycine linker |
| 7 | GGGGGG | glycine linker |
| 8 | PAPELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSRDELT KNQVSLTCLV KGFYPSDIAV EWESNGQPEN NYKTTPPVLD SDGSFFLYSK LTVDKSRWQQ GNVFSCSVMH EALHNHYTQK SLSLSPGK | human IgG1 Fc |
| 9 | PAPGGPSVFL FPPKPKDTLM ISRTPEVTCV VVDVSHEDPE VKFNWYVDGV EVHNAKTKPR EEQYNSTYRV VSVLTVLHQD WLNGKEYKCK VSNKALPAPI EKTISKAKGQ PREPQVYTLP PSRDELTKNQ VSLTCLVKGF YPSDIAVEWE SNGQPENNYK TTPPVLDSDG SFFLYSKLTV DKSRWQQGNV FSCSVMHEAL HNHYTQKSLS LSPGK | Fc xELL |
| 10 | PAPPVAGPSV FLFPPKPKDT LMISRTPEVT CVVVDVSHED PEVQFNWYVD GVEVHNAKTK PREEQFNSTF RVVSVLTVVH QDWLNGKEYK CKVSNKGLPA PIEKTISKTK GQPREPQVYT LPPSREEMTK NQVSLTCLVK GFYPSDISVE WESNGQPENN YKTTPPMLDS DGSFFLYSKL TVDKSRWQQG NVFSCSVMHE ALHNHYTQKS LSLSPGK | human IgG2 Fc |
| 11 | PAPELLGGPS VFLFPPKPKD TLMISRTPEV TCVVVDVSHE DPEVQFKWYV DGVEVHNAKT KPREEQYNST FRVVSVLTVL HQDWLNGKEY KCKVSNKALP APIEKTISKT KGQPREPQVY TLPPSREEMT KNQVSLTCLV KGFYPSDIAV EWESSGQPEN NYNTTPPMLD SDGSFFLYSK LTVDKSRWQQ GNIFSCSVMH EALHNRFTQK SLSLSPGK | human IgG Fc |
| 12 | PAPEFLGGPS VFLFPPKPKD TLMISRTPEV TCVVVDVSQE DPEVQFNWYV DGVEVHNAKT KPREEQFNST YRVVSVLTVL HQDWLNGKEY KCKVSNKGLP SSIEKTISKA KGQPREPQVY TLPPSQEEMT KNQVSLTCLV KGFYPSDIAV EWESNGQPEN NYKTTPPVLD SDGSFFLYSR LTVDKSRWQE GNVFSCSVMH EALHNHYTQK SLSLSLGK | human IgG4 Fc |
| 13 | PAPELLGGPS VFLFPPKPKD TLMISRTPEV TCVVVDVSQE DPEVQFNWYV DGVEVHNAKT KPREEQFNST YRVVSVLTVL HQDWLNGKEY KCKVSNKGLP SSIEKTISKA KGQPREPQVY TLPPSQEEMT KNQVSLTCLV KGFYPSDIAV EWESNGQPEN NYKTTPPVLD SDGSFFLYSR LTVDKSRWQE GNVFSCSVMH EALHNHYTQK SLSLSLGK | human IgG4 Fc |

-continued

| # | SEQUENCE | ANNOTATION |
|---|---|---|
| 14 | EPKSSDKTHTCPPC | modified IgG1 hinge |
| 15 | DKTHTCPPC | truncated IgG1 hinge |
| 16 | ESKYGPPCPPC | modified IgG4 hinge |
| 17 | GQGTLVTVKPGG | carboxy-terminal sequence |
| 18 | GQGTLVTVEPGG | carboxy-terminal sequence |
| 19 | QVQLVQSGGG VVQPGRSLRL SCKASGYTFT RYTMHWVRQA PGKGLEWIGYINPSRGYTNY NQKVKDRFTI SRDNSKNTAF LQMDSLRPED TGVYFCARYYDDHYCLDYWG QGTPVTVSS | OKT3 VH |
| 20 | DIQMTQSPSS LSASVGDRVT ITCSASSSVS YMNWYQQTPG KAPKRWIYDTSKLASGVPSR FSGSGSGTDY TFTISSLQPE DIATYYCQQW SSNPFTFGQGTKLQIT | OKT3 VL |
| 21 | QVQLVQSGGG VVQPGRSLRL SCKASGYTFT RYTMHWVRQA PGKGLEWIGYINPSRGYTNY NQKVKDRFTI SRDNSKNTAF LQMDSLRPED TGVYFCARYYDDHYSLDYWG QGTPVTVSS | OKT3 humanized VH |
| 22 | DVQLVQSGAE VKKPGASVKV SCKASGYTFT RYTMHWVRQA PGQGLEWIGYINPSRGYTNY ADSVKGRFTI TTDKSTSTAY MELSSLRSED TATYYCARYYDDHYCLDYWG QGTTVTVSS | OKT3 humanized VH |
| 23 | QVQLVQSGAE LKKPGASVKV SCKASGYTFT RYTMHWVRQA PGQCLEWMGYINPSRGYTNY NQKFKDKATL TADKSTSTAY MELRSLRSDD TAVYYCARYYDDHYSLDYWG QGTLVTVSS | OKT3 humanized VH |
| 24 | QIVLTQSPAI MSASPGEKVT MTCSASSSVS YMNWYQQKSG TSPKRWIYDTSKLASGVPAH FRGSGSGTSY SLTISGMEAE DAATYYCQQW SSNPFTFGSGTKLEIN | OKT3 humanized VL |
| 25 | DIQMTQSPSS LSASVGDRVT ITCRASQSVS YMNWYQQKPG KAPKRWIYDTSKVASGVPAR FSGSGSGTDY SLTINSLEAE DAATYYCQQW SSNPLTFGGGTKVEIK | OKT3 humanized VL |
| 26 | DIQLTQSPSI LSASVGDRVT ITCRASSSVS YMNWYQQKPG KAPKRWIYDTSKVASGVPYR FSGSGSGTEY TLTISSMQPE DFATYYCQQW SSNPLTFGCGTKVEIKRT | OKT3 humanized VL |
| 27 | EVQLVESGGGLVQPKGSLKLSCAASGFTFNTYAMNWVRQAPG KGLEWVARIRSKYNNYATYYADSVKDRFTISRDDSQSILYLQM NNLKTEDTAMYYCVRHGNFGNSYVSWFAYWGQGTLVTVSA | anti-CD3 Hv |
| 28 | QAVVTQESALTTSPGETVTLTCRSSTGAVTTSNYANWVQEKPD HLFTGLIGGTNKRAPGVPARFSGSLIGDKAALTITGAQTEDEAI YFCALWYSNLWVFGGGTKLTVL | anti-CD3 Lv |
| 29 | TYAMN | anti-CD3 VH CDR1 |
| 30 | RIRSKYNNYATYYADSVKD | anti-CD3 VH CDR2 |
| 31 | HGNFGNSYVSWFAY | anti-CD3 VH CDR3 |
| 32 | RSSTGAVTTSNYAN | anti-CD3 VL CDR1 |
| 33 | GTNKRAP | anti-CD3 VL CDR2 |
| 34 | ALWYSNLWV | anti-CD3 VL CDR3 |

| # | SEQUENCE | ANNOTATION |
|---|---|---|
| 35 | EVQLVESGGGLVQPGGSLRLSCAASGFTFSTYAMNWVRQAPG KGLEWVGRIRSKYNNYATYYADSVKDRFTISRDDSKNSLYLQ MNSLKTEDTAVYYCVRHGNFGNSYVSWFAYWGQGTLVTVSS | anti-CD3 VH1 |
| 36 | EVKLVESGGGLVQPGGSLRLSCAASGFTFNTYAMNWVRQAPG KGLEWVARIRSKYNNYATYYADSVKDRFTISRDDSKSSLYLQ MNNLKTEDTAMYYCVRHGNFGNSYVSWFAYWGQGTLVTVSS | anti-CD3 VH2 |
| 37 | EVKLVESGGGLVKPGRSLRLSCAASGFTFNTYAMNWVRQAPG KGLEWVARIRSKYNNYATYYADSVKDRFTISRDDSKSILYLQM NNLKTEDTAMYYCVRHGNFGNSYVSWFAYWGQGTLVTVSS | anti-CD3 VH3 |
| 38 | EVKLVESGGGLVKPGRSLRLSCAASGFTFNTYAMNWVRQAPG KGLEWVARIRSKYNNYATYYADSVKDRFTISRDDSKSILYLQM NSLKTEDTAMYYCVRHGNFGNSYVSWFAYWGQGTLVTVSS | anti-CD3 VH4 |
| 39 | EVKLVESGGGLVKPGRSLRLSCAASGFTFNTYAMNWVRQAPG KGLEWVARIRSKYNNYATYYADSVKDRFTISRDDSKSILYLQM NSLKTEDTAMYYCVRHGNFGNSYVSWFAYWGQGTLVTVSS | anti-CD3 VHS |
| 40 | EVQLLESGGGLVQPGGSLRLSCAASGFTFSTYAMNWVRQAPG KGLEWVSRIRSKYNNYATYYADSVKGRFTISRDDSKNTLYLQ MNSLRAEDTAVYYCVRHGNFGNSYVSWFAYWGQGTLVTVSS | anti-CD3 VH6 |
| 41 | EVQLVESGGGLVQPGGSLRLSCAASGFTFSTYAMSWVRQAPG KGLEWVGRIRSKYNNYATYYADSVKGRFTISRDDSKNTLYLQ MNSLRAEDTAVYYCVRHGNFGDSYVSWFAYWGQGTLVTVSS | anti-CD3 VH7 |
| 42 | EVQLVESGGGLVQPGGSLKLSCAASGFTFNKYAMNWVRQAPG KGLEWVARIRSKYNNYATYYADSVKDRFTISRDDSKNTAYLQ MNNLKTEDTAVYYCVRHGNFGNSYISYWAYWGQGTLVTVS | anti-CD3 VH8 |
| 43 | EVQLVESGGGLVQPGGSLRLSCAASGFTFNTYAMNWVRQAPG KGLEWVARIRSKYNNYATYYADSVKGRFTISRDDSKNTLYLQ MNSLRAEDTAVYYCVRHGNFGNSYVSWFAYWGQGTTVTVSS | anti-CD3 VH9 |
| 44 | EVQLVESGGGLVQPGGSLRLSCAASGFTFNTYAMNWVRQAPG KGLEWVARIRSKYNNYATYYADSVKGRFTISRDDSKNTLYLQ MNSLRAEDTAVYYCVRHGNFGNSYVSYFAYWGQGTTVTVSS | anti-CD3 VH10 |
| 45 | EVQLVESGGGLVQPKGSLKLSCAASGFTFNTYAMNWVRQAPG KGLEWVARIRSKYNNYATYYADSVKDRFTISRDDSQSILYLQM NNLKTEDTAMYYCVRHGNFGNSYVSWFAYWGQGTLVTVSS | anti-CD3 VH11 |
| 46 | EVQLVESGGGLVQPGGSLRLSCAASGFTFNTYAMNWVRQAPG KGLEWVARIRSKYNNYATYYADSVKGRFTISRDDAKNTLYLQ MSSLRAEDTAVYYCVRHGNFGNSYVSWFAYWGQGTLVTVKP | anti-CD3 VH12 |
| 47 | EVQLVESGGGLVQPGGSLRLSCAASGFTFNTYAMNWVRQAPG KCLEWVARIRSKYNNYATYYADSVKGRFTISRDDAKNTLYLQ MSSLRAEDTAVYYCVRHGNFGNSYVSWFAYWGQGTLVTVKP | anti-CD3 VH13 |
| 48 | EVQLVESGGGLVQPGGSLRLSCAASGFTFNTYAMNWVRQAPG KGLEWVARIRSKYNNYATYYADSVKGRFTISRDDAKNTLYLQ MSSLRAEDTAVYYCVRHGNFGNSYVSWFAYWGCGTLVTVKP | anti-CD3 VH14 |
| 49 | EVQLVESGGGLVQPGGSLRLSCAASGFTFSTYAMNWVRQAPG KGLEWVARIRSKYNNYATYYADSVKGRFTISRDDAKNTLYLQ MSSLRAEDTAVYYCVRHGNFGNSYVSWFAYWGQGTLVTVSS | anti-CD3 VH15 |
| 50 | EVQLVESGGGLVQPGGSLRLSCAASGFTFNTYAMNWVRQAPG KGLEWVSRIRSKYNNYATYYADSVKGRFTISRDDAKNTLYLQ MSSLRAEDTAVYYCVRHGNFGNSYVSWFAYWGQGTLVTVSS | anti-CD3 VH16 |
| 51 | EVQLVESGGGLVQPGGSLRLSCAASGFTFSTYAMNWVRQAPG KGLEWVSRIRSKYNNYATYYADSVKGRFTISRDDAKNTLYLQ MSSLRAEDTAVYYCVRHGNFGNSYVSWFAYWGQGTLVTVSS | anti-CD3 VH17 |
| 52 | EVQLVESGGGLVQPGGSLRLSCAASGFTFSTYAMNWVRQAPG KCLEWVARIRSKYNNYATYYADSVKGRFTISRDDAKNTLYLQ MSSLRAEDTAVYYCVRHGNFGNSYVSWFAYWGQGTLVTVSS | anti-CD3 VH18 |

| # | SEQUENCE | ANNOTATION |
|---|---|---|
| 53 | EVQLVESGGGLVQPGGSLRLSCAASGFTFNTYAMNWVRQAPG KCLEWVSRIRSKYNNYATYYADSVKGRFTISRDDAKNTLYLQ MSSLRAEDTAVYYCVRHGNFGNSYVSWFAYWGQGTLVTVSS | anti-CD3 VH19 |
| 54 | EVQLVESGGGLVQPGGSLRLSCAASGFTFSTYAMNWVRQAPG KCLEWVSRIRSKYNNYATYYADSVKGRFTISRDDAKNTLYLQ MSSLRAEDTAVYYCVRHGNFGNSYVSWFAYWGQGTLVTVSS | anti-CD3 VH20 |
| 55 | EVQLVESGGGLVQPGGSLRLSCAASGFTFSTYAMNWVRQAPG KCLEWVGRIRSKYNNYATYYADSVKDRFTISRDDSKNSLYLQ MNSLKTEDTAVYYCVRHGNFGNSYVSWFAYWGQGTLVTVSS | anti-CD3 VH21 |
| 56 | EVKLVESGGGLVQPGGSLRLSCAASGFTFNTYAMNWVRQAPG KCLEWVARIRSKYNNYATYYADSVKDRFTISRDDSKSSLYLQ MNNLKTEDTAMYYCVRHGNFGNSYVSWFAYWGQGTLVTVSS | anti-CD3 VH22 |
| 57 | EVKLVESGGGLVKPGRSLRLSCAASGFTFNTYAMNWVRQAPG KCLEWVARIRSKYNNYATYYADSVKDRFTISRDDSKSILYLQM NNLKTEDTAMYYCVRHGNFGNSYVSWFAYWGQGTLVTVSS | anti-CD3 VH23 |
| 58 | EVKLVESGGGLVKPGRSLRLSCAASGFTFNTYAMNWVRQAPG KCLEWVARIRSKYNNYATYYADSVKDRFTISRDDSKSILYLQM NSLKTEDTAMYYCVRHGNFGNSYVSWFAYWGQGTLVTVSS | anti-CD3 VH24 |
| 59 | EVKLVESGGGLVKPGRSLRLSCAASGFTFNTYAMNWVRQAPG KCLEWVARIRSKYNNYATYYADSVKDRFTISRDDSKSILYLQM NSLKTEDTAMYYCVRHGNFGNSYVSWFAYWGQGTLVTVSS | anti-CD3 VH25 |
| 60 | EVQLLESGGGLVQPGGSLRLSCAASGFTFSTYAMNWVRQAPG KCLEWVSRIRSKYNNYATYYADSVKGRFTISRDDSKNTLYLQ MNSLRAEDTAVYYCVRHGNFGNSYVSWFAYWGQGTLVTVSS | anti-CD3 VH26 |
| 61 | EVQLVESGGGLVQPGGSLRLSCAASGFTFSTYAMSWVRQAPG KCLEWVGRIRSKYNNYATYYADSVKGRFTISRDDSKNTLYLQ MNSLRAEDTAVYYCVRHGNFGDSYVSWFAYWGQGTLVTVSS | anti-CD3 VH27 |
| 62 | EVQLVESGGGLVQPGGSLKLSCAASGFTFNKYAMNWVRQAPG KCLEWVARIRSKYNNYATYYADSVKDRFTISRDDSKNTAYLQ MNNLKTEDTAVYYCVRHGNFGNSYISYWAYWGQGTLVTVS | anti-CD3 VH28 |
| 63 | EVQLVESGGGLVQPGGSLRLSCAASGFTFNTYAMNWVRQAPG KCLEWVARIRSKYNNYATYYADSVKGRFTISRDDSKNTLYLQ MNSLRAEDTAVYYCVRHGNFGNSYVSWFAYWGQGTTVTVSS | anti-CD3 VH29 |
| 64 | EVQLVESGGGLVQPGGSLRLSCAASGFTFNTYAMNWVRQAPG KCLEWVARIRSKYNNYATYYADSVKGRFTISRDDSKNTLYLQ MNSLRAEDTAVYYCVRHGNFGNSYVSYFAYWGQGTTVTVSS | anti-CD3 VH30 |
| 65 | EVQLVESGGGLVQPKGSLKLSCAASGFTFNTYAMNWVRQAPG KCLEWVARIRSKYNNYATYYADSVKDRFTISRDDSQSILYLQM NNLKTEDTAMYYCVRHGNFGNSYVSWFAYWGQGTLVTVSS | anti-CD3 VH31 |
| 66 | QAVVTQESALTTSPGETVTLTCRSSTGAVTTSNYANWVQEKPD HLFTGLIGGTNKRAPGVPARFSGSLIGDKAALTITGAQTEDEAI YFCALWYSNLWVFGGGTKLTVL | anti-CD3 VL1 |
| 67 | QAVVTQEPSLTVSPGGTVTLTCGSSTGAVTTSNYANWVQQKP GKSPRGLIGGTNKRAPGVPARFSGSLLGGKAALTISGAQPEDEA DYYCALWYSNHWVFGCGTKLEIK | anti-CD3 VL2 |
| 68 | QAVVTQEPSLTVSPGGTVTLTCRSSTGAVTTSNYANWVQQKP GQAPRGLIGGTNKRAPWTPARFSGSLLGGKAALTITGAQAEDE ADYYCALWYSNLWVFGGGTKLTVL | anti-CD3 VL3 |
| 69 | QAVVTQEPSFSVSPGGTVTLTCRSSTGAVTTSNYANWVQQTPG QAFRGLIGGTNKRAPGVPARFSGSLIGDKAALTITGAQADDESI YFCALWYSNLWVFGGGTKLTVL | anti-CD3 VL4 |
| 70 | QAVVTQEPSFSVSPGGTVTLTCRSSTGAVTTSNYANWVQQTPG QAFRGLIGGTNKRAPGVPARFSGSILGNKAALTITGAQADDESI YFCALWYSNLWVFGGGTKLTVL | anti-CD3 VL5 |

-continued

| # | SEQUENCE | ANNOTATION |
|---|---|---|
| 71 | QAVVTQEPSFSVSPGGTVTLTCRSSTGAVTTSNYANWVQQTPG<br>QAFRGLIGGTNKRAPGVPARFSGSILGNKAALTITGAQADDESD<br>YYCALWYSNLWVFGGGTKLTVL | anti-CD3 VL6 |
| 72 | QAVVTQEPSLTVSPGGTVTLTCGSSTGAVTTSNYANWVQEKP<br>GQAFRGLIGGTNKRAPGTPARFSGSLLGGKAALTLSGAQPEDE<br>AEYYCALWYSNLWVFGGGTKLTVL | anti-CD3 VL7 |
| 73 | QTVVTQEPSLTVSPGGTVTLTCGSSTGAVTSGNYPNWVQQKPG<br>QAPRGLIGGTKFLAPGTPARFSGSLLGGKAALTLSGVQPEDEAE<br>YYCVLWYSNRWVFGGGTKLTVL | anti-CD3 VL8 |
| 74 | QAVVTQEPSLTVSPGGTVTLTCGSSTGAVTTSNYANWVQQKP<br>GQAFRGLIGGTNKRAPGVPARFSGSLLGGKAALTISGAQPEDE<br>ADYYCALWYSNHWVFGGGTKLEIK | anti-CD3 VL9 |
| 75 | QAVVTQEPSLTVSPGGTVTLTCGSSTGAVTTSNYANWVQQKP<br>GQAFRGLIGGTNKRAPGVPARFSGSLLGGKAALTISGAQPEDE<br>ADYYCALWYSNHWVFGCGTKLEIK | anti-CD3 VL10 |
| 76 | QAVVTQEPSLTVSPGGTVTLTCGSSTGAVTTSNYANWVQQKP<br>GQCFRGLIGGTNKRAPGVPARFSGSLLGGKAALTISGAQPEDE<br>ADYYCALWYSNHWVFGEGTKLEIK | anti-CD3 VL11 |
| 77 | QAVVTQESALTTSPGETVTLTCRSSTGAVTTSNYANWVQEKPD<br>HLFTGLIGGTNKRAPGVPARFSGSLIGDKAALTITGAQTEDEAI<br>YFCALWYSNLWVFGCGTKLTVL | anti-CD3 VL12 |
| 78 | QAVVTQEPSLTVSPGGTVTLTCGSSTGAVTTSNYANWVQQKP<br>GKSPRGLIGGTNKRAPGVPARFSGSLLGGKAALTISGAQPEDEA<br>DYYCALWYSNHWVFGGGTKLEIK | anti-CD3 VL13 |
| 79 | QAVVTQEPSLTVSPGGTVTLTCRSSTGAVTTSNYANWVQQKP<br>GQAPRGLIGGTNKRAPWTPARFSGSLLGGKAALTITGAQAEDE<br>ADYYCALWYSNLWVFGCGTKLTVL | anti-CD3 VL14 |
| 80 | QAVVTQEPSFSVSPGGTVTLTCRSSTGAVTTSNYANWVQQTPG<br>QAFRGLIGGTNKRAPGVPARFSGSLIGDKAALTITGAQADDESI<br>YFCALWYSNLWVFGGGTKLTVL | anti-CD3 VL15 |
| 81 | QAVVTQEPSFSVSPGGTVTLTCRSSTGAVTTSNYANWVQQTPG<br>QAFRGLIGGTNKRAPGVPARFSGSILGNKAALTITGAQADDESI<br>YFCALWYSNLWVFGCGTKLTVL | anti-CD3 VL16 |
| 82 | QAVVTQEPSFSVSPGGTVTLTCRSSTGAVTTSNYANWVQQTPG<br>QAFRGLIGGTNKRAPGVPARFSGSILGNKAALTITGAQADDESD<br>YYCALWYSNLWVFGCGTKLTVL | anti-CD3 VL17 |
| 83 | QAVVTQEPSLTVSPGGTVTLTCGSSTGAVTTSNYANWVQEKP<br>GQAFRGLIGGTNKRAPGTPARFSGSLLGGKAALTLSGAQPEDE<br>AEYYCALWYSNLWVFGCGTKLTVL | anti-CD3 VL18 |
| 84 | QTVVTQEPSLTVSPGGTVTLTCGSSTGAVTSGNYPNWVQQKPG<br>QAPRGLIGGTKFLAPGTPARFSGSLLGGKAALTLSGVQPEDEAE<br>YYCVLWYSNRWVFGCGTKLTVL | anti-CD3 VL19 |
| 85 | QVQLQESGGGLVQAGGSLRLSCAASGRTFSNYHMGWFRQAPG<br>KERELVAAISGSGGSTYYTDSVKGRFTISRNNAKNTMSLQMSN<br>LKPEDTGVYYCTTPTEKGSSIDYWGQGTQVTVSSGRYPYDVPD<br>Y | anti-CD3 VHH |
| 86 | MVSPRMSGLLSQTVILALIFLPQTRPAGVFELQIHSFGPGPGPGA<br>PRSPCSARLPCRLFFRVCLKPGLSEEAAESPCALGAALSARGPV<br>YTEQPGAPAPDLPLPDGLLQVPFRDAWPGTFSFIIETWREELGD<br>QIGGPAWSLLARVAGRRRLAAGGPWARDIQRAGAWELRFSYR<br>ARCEPPAVGTACTRLCRPRSAPSRCGPGLRPCAPLEDECEAPLV<br>CRAGCSPEHGFCEQPGECRCLEGWTGPLCTVPVSTSSCLSPRGP<br>SSATTGCLVPGPGPCDGNPCANGGSCSETPRSFECTCPRGFYGL<br>RCEVSGVTCADGPCFNGGLCVGGADPDSAYICHCPPGFQGSNC<br>EKRVDRCSLQPCRNGGLCLDLGHALRCRCRAGFAGPRCEHDL<br>DDCAGRACANGGTCVEGGGAHRCSCALGFGGRDCRERADPC<br>AARPCAHGGRCYAHFSGLVCACAPGYMGARCEFPVHPDGASA<br>LPAAPPGLRPGDPQRYLLPPALGLLVAAGVAGAALLLVHVRRR<br>GHSQDAGSRLLAGTPEPSVHALPDALNNLRTQEGSGDGPSSV | Canonical DLL3<br>sequence (e.g.,<br>UniProt No.<br>Q9NYJ7) |

| # | SEQUENCE | ANNOTATION |
|---|---|---|
|  | DWNRPEDVDPQGIYVISAPSIYAREVATPLFPPLHTGRAGQRQH LLFPYPSSILSVK |  |
| 87 | MVSPRMSGLLSQTVILALIFLPQTRPAGVFELQIHSFGPGPGPGA PRSPCSARLPCRLFFRVCLKPGLSEEAAESPCALGAALSARGPV YTEQPGAPAPDLPLPDGLLQVPFRDAWPGTFSFIIETWREELGD QIGGPAWSLLARVAGRRRLAAGGPWARDIQRAGAWELRFSYR ARCEPPAVGTACTRLCRPRSAPSRCGPGLRPCAPLEDECEAPLV CRAGCSPEHGFCEQPGECRCLEGWTGPLCTVPVSTSSCLSPRGP SSATTGCLVPGPGPCDGNPCANGGSCSETPRSFECTCPRGFYGL RCEVSGVTCADGPCFNGGLCVGGADPDSAYICHCPPGFQGSNC EKRVDRCSLQPCRNGGLCLDLGHALRCRCRAGFAGPRCEHDL DDCAGRACANGGTCVEGGGAHRCSCALGFGGRDCRERADPC AARPCAHGGRCYAHFSGLVCACAPGYMGARCEFPVHPDGASA LPAAPPGLRPGDPQRYLLPPALGLLVAAGVAGAALLLVHVRRR GHSQDAGSRLLAGTPEPSVHALPDALNNLRTQEGSGDGPSSSV DWNRPEDVDPQGIYVISAPSIYAREA | Non-Canonical DLL3-sequence (e.g. UniProt No. Q9NYJ7-2) |
| 88 | GGSGGS | (GGS)2 linker |
| 89 | GGSGGSGGS | (GGS)3 linker |
| 90 | GGSGGSGGSGGS | (GGS)4 linker |
| 91 | GGSGGSGGSGGSGGS | (GGS)5 linker |
| 92 | GGGG | glycine linker |
| 93 | GGGGG | glycine linker |
| 94 | GGGGGG | glycine linker |
| 95 | GGSGGS | (GGS)2 linker |
| 96 | GGSGGSGGS | (GGS)3 linker |
| 97 | GGSGGSGGSGGS | (GGS)4 linker |
| 98 | GGSGGSGGSGGSGGS | (GGS)5 linker |
| 99 | GGGG | glycine linker |
| 100 | GGGGG | glycine linker |
| 101 | GGGGGG | glycine linker |
| 102 | EVQLVESGGGEVQPGGSLRLSCAASGSIFSINAMGWYRQAPGK QRELVAVVSSDGRTTVAPSVKGRFTISRDNAKNTVSLQMSSLR AEDTAVYYCGVREWYSDSDWRDYEGQGTLVTVKP | hz5A8v4 |
| 103 | DKTHTCPPCPAPELLGGPSVFLFPPKPKDTLMISRTPEVTCVVV DVSHEDPEVKFNWYVDGVEVHNAKTKPREEQYNSTYRVVSV LTVLHQDWLNGKEYKCKVSNKALPAPIEKTISKAKGQPREPQV YTLPPCRDELTKNQVSLWCLVKGFYPSDIAVEWESNGQPENNY KTTPPVLDSDGSFFLYSKLTVDKSRWQQGNVFSCSVMHEALH NHYTQKSLSLSPT | Knob Fc |
| 104 | DKTHTCPPCPAPELLGGPSVFLFPPKPKDTLMRSRTPEVTCVVV DVSHEDPEVKFNWYVDGVEVHNAKTKPREEQYNSTYRVVSV LTVLHQDWLNGKEYKCKVSNKALPAPIEKTISKAKGQPREPQV CTLPPSRDELTKNQVSLSCAVKGFYPSDIAVEWESNGQPENNY KTTPPVLDSDGSFFLVSKLTVDKSRWQQGNVFSCSVMHEALH NHYTQKSLSLSPT | Hole Fc |
| 105 | DKTHTCPPCPAPGGPSVFLFPPKPKDTLMISRTPEVTCVVVDVS HEDPEVKFNWYVDGVEVHNAKTKPREEQYNSTYRVVSVLTVL HQDWLNGKEYKCKVSNKALPAPIEKTISKAKGQPREPQVYTLP PCRDELTKNQVSLWCLVKGFYPSDIAVEWESNGQPENNYKTTP PVLDSDGSFFLYSKLTVDKSRWQQGNVFSCSVMHEALHNHYT QKSLSLSPT | Knob Fc |
| 106 | DKTHTCPPCPAPGGPSVFLFPPKPKDTLMRSRTPEVTCVVVDVS HEDPEVKFNWYVDGVEVHNAKTKPREEQYNSTYRVVSVLTVL HQDWLNGKEYKCKVSNKALPAPIEKTISKAKGQPREPQVCTLP PSRDELTKNQVSLSCAVKGFYPSDIAVEWESNGQPENNYKTTP | Hole Fc |

-continued

| # | SEQUENCE | ANNOTATION |
|---|----------|------------|
| | PVLDSDGSFFLVSKLTVDKSRWQQGNVFSCSVMHEALHNHYT<br>QKSLSLSPT | |
| 107 | DKTHTCPPCPAPELLGGPSVFLFPPKPKDTLMISRTPEVTCVVV<br>DVSHEDPEVKFNWYVDGVEVHNAKTKPREEQYNSTYRVVSV<br>LTVLHQDWLNGKEYKCKVSNKALPAPIEKTISKAKGQPREPQV<br>YTLPPCRDELTKNQVSLWCLVKGFYPSDIAVEWESNGQPENNY<br>KTTPPVLDSDGSFFLYSKLTVDKSRWQQGNVFSCSVMHEALH<br>NHYTQKSLSLSPG | Knob Fc |
| 108 | DKTHTCPPCPAPELLGGPSVFLFPPKPKDTLMRSRTPEVTCVVV<br>DVSHEDPEVKFNWYVDGVEVHNAKTKPREEQYNSTYRVVSV<br>LTVLHQDWLNGKEYKCKVSNKALPAPIEKTISKAKGQPREPQV<br>CTLPPSRDELTKNQVSLSCAVKGFYPSDIAVEWESNGQPENNY<br>KTTPPVLDSDGSFFLVSKLTVDKSRWQQGNVFSCSVMHEALH<br>NHYTQKSLSLSPG | Hole Fc |
| 109 | DKTHTCPPCPAPGGPSVFLFPPKPKDTLMISRTPEVTCVVVDVS<br>HEDPEVKFNWYVDGVEVHNAKTKPREEQYNSTYRVVSVLTVL<br>HQDWLNGKEYKCKVSNKALPAPIEKTISKAKGQPREPQVYTLP<br>PCRDELTKNQVSLWCLVKGFYPSDIAVEWESNGQPENNYKTTP<br>PVLDSDGSFFLYSKLTVDKSRWQQGNVFSCSVMHEALHNHYT<br>QKSLSLSPG | Knob Fc |
| 110 | DKTHTCPPCPAPGGPSVFLFPPKPKDTLMRSRTPEVTCVVVDVS<br>HEDPEVKFNWYVDGVEVHNAKTKPREEQYNSTYRVVSVLTVL<br>HQDWLNGKEYKCKVSNKALPAPIEKTISKAKGQPREPQVCTLP<br>PSRDELTKNQVSLSCAVKGFYPSDIAVEWESNGQPENNYKTTP<br>PVLDSDGSFFLVSKLTVDKSRWQQGNVFSCSVMHEALHNHYT<br>QKSLSLSPG | Hole Fc |
| 111 | DKTHTCPPCPAPELLGGPSVFLFPPKPKDTLMISRTPEVTCVVV<br>DVSHEDPEVKFNWYVDGVEVHNAKTKPREEQYNSTYRVVSV<br>LTVLHQDWLNGKEYKCKVSNKALPAPIEKTISKAKGQPREPQV<br>CTLPPSRDELTKNQVSLSCAVKGFYPSDIAVEWESNGQPENNY<br>KTTPPVLDSDGSFFLVSKLTVDKSRWQQGNVFSCSVMHEALH<br>NRYTQKSLSLSPT | Hole Fc |
| 112 | DKTHTCPPCPAPGGPSVFLFPPKPKDTLMISRTPEVTCVVVDVS<br>HEDPEVKFNWYVDGVEVHNAKTKPREEQYNSTYRVVSVLTVL<br>HQDWLNGKEYKCKVSNKALPAPIEKTISKAKGQPREPQVCTLP<br>PSRDELTKNQVSLSCAVKGFYPSDIAVEWESNGQPENNYKTTP<br>PVLDSDGSFFLVSKLTVDKSRWQQGNVFSCSVMHEALHNRYT<br>QKSLSLSPT | Hole Fc |
| 113 | DKTHTCPPCPAPELLGGPSVFLFPPKPKDTLMISRTPEVTCVVV<br>DVSHEDPEVKFNWYVDGVEVHNAKTKPREEQYNSTYRVVSV<br>LTVLHQDWLNGKEYKCKVSNKALPAPIEKTISKAKGQPREPQV<br>CTLPPSRDELTKNQVSLSCAVKGFYPSDIAVEWESNGQPENNY<br>KTTPPVLDSDGSFFLVSKLTVDKSRWQQGNVFSCSVMHEALH<br>NRYTQKSLSLSPG | Hole Fc |
| 114 | DKTHTCPPCPAPGGPSVFLFPPKPKDTLMISRTPEVTCVVVDVS<br>HEDPEVKFNWYVDGVEVHNAKTKPREEQYNSTYRVVSVLTVL<br>HQDWLNGKEYKCKVSNKALPAPIEKTISKAKGQPREPQVCTLP<br>PSRDELTKNQVSLSCAVKGFYPSDIAVEWESNGQPENNYKTTP<br>PVLDSDGSFFLVSKLTVDKSRWQQGNVFSCSVMHEALHNRYT<br>QKSLSLSPG | Hole Fc |
| 115 | DKTHTCPPCPAPELLGGPSVFLFPPKPKDTLYISRTPEVTCVVVD<br>VSHEDPEVKFNWYVDGVEVHNAKTKPREEQYNSTYRVVSVLT<br>VLHQDWLNGKEYKCKVSNKALPAPIEKTISKAKGQPREPQVYT<br>LPPCRDELTKNQVSLWCLVKGFYPSDIAVEWESNGQPENNYKT<br>TPPVLDSDGSFFLYSKLTVDKSRWQQGNVFSCSVVHEALHNH<br>YTQKSLSLSPT | Knob Fc |
| 116 | DKTHTCPPCPAPGGPSVFLFPPKPKDTLYISRTPEVTCVVVDVS<br>HEDPEVKFNWYVDGVEVHNAKTKPREEQYNSTYRVVSVLTVL<br>HQDWLNGKEYKCKVSNKALPAPIEKTISKAKGQPREPQVYTLP<br>PCRDELTKNQVSLWCLVKGFYPSDIAVEWESNGQPENNYKTTP<br>PVLDSDGSFFLYSKLTVDKSRWQQGNVFSCSVVHEALHNHYT<br>QKSLSLSPT | Knob Fc |
| 117 | DKTHTCPPCPAPELLGGPSVFLFPPKPKDTLYISRTPEVTCVVVD<br>VSHEDPEVKFNWYVDGVEVHNAKTKPREEQYNSTYRVVSVLT | Knob Fc |

| # | SEQUENCE | ANNOTATION |
|---|---|---|
| | VLHQDWLNGKEYKCKVSNKALPAPIEKTISKAKGQPREPQVYT<br>LPPCRDELTKNQVSLWCLVKGFYPSDIAVEWESNGQPENNYKT<br>TPPVLDSDGSFFLYSKLTVDKSRWQQGNVFSCSVVHEALHNH<br>YTQKSLSLSPG | |
| 118 | DKTHTCPPCPAPGGPSVFLFPPKPKDTLYISRTPEVTCVVVDVS<br>HEDPEVKFNWYVDGVEVHNAKTKPREEQYNSTYRVVSVLTVL<br>HQDWLNGKEYKCKVSNKALPAPIEKTISKAKGQPREPQVYTLP<br>PCRDELTKNQVSLWCLVKGFYPSDIAVEWESNGQPENNYKTTP<br>PVLDSDGSFFLYSKLTVDKSRWQQGNVFSCSVVHEALHNHYT<br>QKSLSLSPG | Knob Fc |
| 119 | DKTHTCPPCPAPELLGGPSVFLFPPKPKDTLYISRTPEVTCVVVD<br>VSHEDPEVKFNWYVDGVEVHNAKTKPREEQYNSTYRVVSVLT<br>VLHQDWLNGKEYKCKVSNKALPAPIEKTISKAKGQPREPQVCT<br>LPPSRDELTKNQVSLSCAVKGFYPSDIAVEWESNGQPENNYKT<br>TPPVLDSDGSFFLVSKLTVDKSRWQQGNVFSCSVVHEALHNRY<br>TQKSLSLSPT | Hole Fc |
| 120 | DKTHTCPPCPAPGGPSVFLFPPKPKDTLYISRTPEVTCVVVDVS<br>HEDPEVKFNWYVDGVEVHNAKTKPREEQYNSTYRVVSVLTVL<br>HQDWLNGKEYKCKVSNKALPAPIEKTISKAKGQPREPQVCTLP<br>PSRDELTKNQVSLSCAVKGFYPSDIAVEWESNGQPENNYKTTP<br>PVLDSDGSFFLVSKLTVDKSRWQQGNVFSCSVVHEALHNRYT<br>QKSLSLSPT | Hole Fc |
| 121 | DKTHTCPPCPAPELLGGPSVFLFPPKPKDTLYISRTPEVTCVVVD<br>VSHEDPEVKFNWYVDGVEVHNAKTKPREEQYNSTYRVVSVLT<br>VLHQDWLNGKEYKCKVSNKALPAPIEKTISKAKGQPREPQVCT<br>LPPSRDELTKNQVSLSCAVKGFYPSDIAVEWESNGQPENNYKT<br>TPPVLDSDGSFFLVSKLTVDKSRWQQGNVFSCSVVHEALHNRY<br>TQKSLSLSPG | Hole Fc |
| 122 | DKTHTCPPCPAPGGPSVFLFPPKPKDTLYISRTPEVTCVVVDVS<br>HEDPEVKFNWYVDGVEVHNAKTKPREEQYNSTYRVVSVLTVL<br>HQDWLNGKEYKCKVSNKALPAPIEKTISKAKGQPREPQVCTLP<br>PSRDELTKNQVSLSCAVKGFYPSDIAVEWESNGQPENNYKTTP<br>PVLDSDGSFFLVSKLTVDKSRWQQGNVFSCSVVHEALHNRYT<br>QKSLSLSPG | Hole Fc |
| 123 | (GGGGS)n, wherein n is 1 to 5 | Linker |
| 124 | (GGGGGS)n, wherein n is 1 to 4 | linker |
| 125 | GGGGS | Linker |
| 126 | GGGGGS | Linker |
| 127 | GGGGGSGGGGSGGGGGS | Linker |
| 128 | GGGGSGGGGSGGGGS | Linker |
| 129 | GGSGGGGSGGGGSGGGGS | Linker |
| 130 | GlyxXaa-Glyy-Xaa-Glyz<br>Xaa is independently selected from A, V, L, I, M, F, W, P, G<br>S, T, C, Y, N,Q, K, R, H, D, or E<br>x, y, and z are each integers in the range from 1-5 | Linker |
| 131 | Gly-Gly-Gly-Xaa-Gly-Gly-Gly-Xaa-Gly-Gly-Gly<br>Xaa is independently selected from A, V, L, I, M,F, W, P, G,<br>S, T, C, Y, N,Q, K, R, H, D, or E | Linker |
| 132 | (SSSSG)n<br>n = 1-9 | Linker |
| 133 | GGGGG-C-GGGGG | Linker |
| 134 | (EAAAK)n<br>n = 2-20 | Linker |
| 135 | AS-(AP)n-GT<br>n = 2-20 | Linker |

-continued

| # | SEQUENCE | ANNOTATION |
|---|---|---|
| 136 | AS-(EAAAK)n-GT<br>n = 2-20 | Linker |
| 137 | (GGGGA)n<br>n = 2-20 | Linker |
| 138 | (PGGGS)n<br>n = 2-20 | Linker |
| 139 | (AGGGS)n<br>n = 2-20 | Linker |
| 140 | GGS-(EGKSSGSGSESKST)n-GGS<br>n = 2-20 | Linker |
| 141 | SSSASASSA | Linker |
| 142 | GSPGSPG | Linker |
| 143 | ATTTGSSPGPT | Linker |
| 144 | X1 X2 X3 X4 X5 (P4 P3 P2 P1 ↓ P1')<br>X1 = I, L, Y, M, F, V, or A; (P4 = I, L, Y, M, F, V, or A)<br>X2 = A, G, S, V, E, D, Q, N, or Y; (P3 = A, G, S, V, E, D, Q, N, or Y)<br>X3 = H, P, A, V, G, S, or T; (P2 = H, P, A, V, G, S, or T)<br>X4 = D or E; (P1 = D or E)<br>X5 = I, L, Y, M, F, V, T, S, G or A (P1' = I, L, Y, M, F, V, T, S, G or A) | Linker consensus |
| 145 | X1 E X3 D X5 (P4 P3 P2 P1 ↓ P1')<br>X1 = I or L;(P4 = I or L)<br>(P3 = E)<br>X3 = P or A; (P2 = P or A)<br>X5 = I, V, T, S, or G (P1' = I, V, T, S, or G) | Linker consensus |
| 146 | LEAD | granzyme B substrate |
| 147 | LEPD | Linker |
| 148 | LEAE | Linker |
| 149 | IEPDI | Linker |
| 150 | LEPDG | Linker |
| 151 | LEADT | Linker |
| 152 | IEPDG | Linker |
| 153 | IEPDV | Linker |
| 154 | IEPDS | Linker |
| 155 | IEPDT | Linker |
| 156 | X1QARX5 (P1QAR↓ (A/V))<br>X1 = any amino acid; (P1 is any amino acid)<br>X5 = A or V | Linker consensus |
| 157 | RQARX5 (RQAR(A/V))<br>X5 = A or V | Linker |
| 158 | RQAR | matriptase substrate |
| 159 | RQARV | linker |
| 160 | X1X2 X3 X4 (P3 P2 P1 ↓ P1')<br>X1 = P, V or A; (P3 = P, V or A)<br>X2 = Q or D; (P2 = Q or D)<br>X3 = A or N; (P1 = A or N)<br>X4 = L, I or M (P1' = L, I or M) | Linker consensus |

| # | SEQUENCE | ANNOTATION |
|---|---|---|
| 161 | PX2X3X4 (P3 P2 P1 ↓ P1')<br>(P3 = P)<br>X2 = Q or D; (P2 = Q or D)<br>X3 = A or N; (P1 is A or N)<br>X4 = L or I (P1' is L or I) | Linker consensus |
| 162 | PAGL | MMP substrate |
| 163 | TGLEADGSPAGLGRQARVG | Linker |
| 164 | TGLEADGSRQARVGPAGLG | Linker |
| 165 | TGSPAGLEADGSRQARVGS | Linker |
| 166 | TGPAGLGLEADGSRQARVG | Linker |
| 167 | TGRQARVGLEADGSPAGLG | Linker |
| 168 | TGSRQARVGPAGLEADGS | Linker |
| 169 | TGPAGLGSRQARVGLEADGS | Linker |
| 170 | GPAGLGLEPDGSRQARVG | Linker |
| 171 | GGSGGGGIEPDIGGSGGS | Linker |
| 172 | GGSGGGGLEADTGGSGGS | Linker |
| 173 | GSIEPDIGS | Linker |
| 174 | GSLEADTGS | Linker |
| 175 | GGSGGGGIEPDGGGSGGS | Linker |
| 176 | GGSGGGGIEPDVGGSGGS | Linker |
| 177 | GGSGGGGIEPDSGGSGGS | Linker |
| 178 | GGSGGGGIEPDTGGSGGS | Linker |
| 179 | GGGSLEPDGSGS | Linker |
| 180 | GPAGLGLEADGSRQARVG | Linker |
| 181 | GGEGGGGSGGSGGGS | Linker |
| 182 | GSSAGSEAGGSGQAGVGS | Linker |
| 183 | GGSGGGGLEAEGSGGGGS | Linker |
| 184 | GGSGGGGIEPDPGGSGGS | Linker |
| 185 | TGGSGGGGIEPDIGGSGGS | Linker |
| 186 | ACPWAVSGARASPGSAASPRLREGPELSPDDPAGLLDLRQGMF<br>AQLVAQNVLLIDGPLSWYSDPGLAGVSLTGGLSYKEDTKELV<br>VAKAGVYYVFFQLELRRVVAGEGSGSVSLALHLQPLRSAAGA<br>AALALTVDLPPASSEANSAFGFQGRLLHLSAGQRLGVHLHTEA<br>RARHAWQLTQGATVLGLFRVTPEIPAGLPSPRSE | 41BBL |
| 187 | EVQLVQSGAEVKKPGESLRISCKGSGYSFSTYWISWVRQMPGK<br>GLEWMGKIYPGDSYTNYSPSFQGQVTISADKSISTAYLQWSSL<br>KASDTAMYYCARGYGIFDYWGQGTLVTVSS | 41BB VH |
| 188 | SYELTQPPSVSVSPGQTASITCSGDNIGDQYAHWYQQKPGQSP<br>VLVIYQDKNRPSGIPERFSGSNSGNTATLTISGTQAMDEADYYC<br>ATYTGFGSLAVFGGGTKLTVL | 41BB VL |
| 189 | QVQLQQWGAGLLKPSETLSLTCAVYGGSFSGYYWSWIRQSPE<br>KGLEWIGEINHGGYVTYNPSLESRVTISVDTSKNQFSLKLSSVT<br>AADTAVYYCARDYGPGNYDWYFDLWGRGTLVTVSS | 41BB VH |

| # | SEQUENCE | ANNOTATION |
|---|---|---|
| 190 | EIVLTQSPATLSLSPGERATLSCRASQSVSSYLAWYQQKPGQAP RLLIYDASNRATGIPARFSGSGSGTDFTLTISSLEPEDFAVYYCQ QRSNWPPALTFGGGTKVEIK | 41BB VL |
| 191 | QMQLVQSGAEVKKPGASVKVSCKASGYSFSGYYMHWVRQAP GQGLEWMGWVNPMSGGTNYAQKFQGRVTITRDTSASTAYME LSSLRSEDTAVYYCAREGMAMRLELDKWGQGTLVTVSS | 41BB VH |
| 192 | SYELTQPPSVSVAPGKTARITCGGNNIGSKSVHWYQQKPGQAP VLVIYYDSDRPSGIPERFSGSNSGNTATLTISRVEAGDEADYYC QVWDSSSVVFGGGTQLTVL | 41BB VL |
| 193 | QDSTSDLIPAPPLSKVPLQQNFQDNQFHGKWYVVGQAGNIKLR EDKDPNKMMATIYELKEDKSYNVTGVTFDDKKCTYAISTFVP GSQPGEFTLGKIKSFPGHTSSLVRVVSTNYNQHAMVFFKFVFQ NREEFYITLYGRTKELTSELKENFIRFSKSLGLPENHIVFPVPIDQ CIDG | 41BB Anticalin |
| 194 | QDSTSDLIPAPPLSKVPLQQNFQDNQFHGKWYVVGQAGNIRLR EDKDPIKMMATIYELKEDKSYDVTMVKFDDKKCMYDIVVTFVP GSQPGEFTLGKIKSFPGHTSSLVRVVSTNYNQHAMVFFKFVFQ NREEFYITLYGRTKELTSELKENFIRFSKSLGLPENHIVFPVPIDQ CIDG | 41BB Anticalin |
| 195 | QDSTSDLIPAPPLSKVPLQQNFQDNQFHGKWYVVGQAGNIRLR EDKDPNKMMATIYELKEDKSYDVTAVAFDDKKCTYDIWTFVP GSQPGEFTLGKIKSFPGHTSSLVRVVSTNYNQHAMVFFKFVFQ NREEFYITLYGRTKELTSELKENFIRFSKSLGLPENHIVFPVPIDQ CIDG | 41BB Anticalin |
| 196 | QDSTSDLIPAPPLSKVPLQQNFQDNQFHGKWYVVGQAGNIKLR EDKDPNKMMATIYELKEDKSYDVTAVAFDDKKCTYDIWTFVP GSQPGEFTLGKIKSFPGHTSSLVRVVSTNYNQHAMVFFKFVFQ NREEFYITLYGRTKELTSELKENFIRFSKSLGLPENHIVFPVPIDQ CIDG | 41BB Anticalin |
| 197 | QDSTSDLIPA PPLSKVPLQQ NFQDNQFHGK WYVVGQAGNI KLREDSKMMA TIYELKEDKS YDVTGVSFDD KKCTYAIMTF VPGSQPGEFT LGKIKSFPGH TSSLVRVVST NYNQHAMVFF KFVFQNREEF YITLYGRTKE LTSELKENFI RFSKSLGLPE NHIVFPVPID QCIDG | 41BB Anticalin |
| 198 | QDSTSDLIPA PPLSKVPLQQ NFQDNQFHGK WYVVGQAGNI KLREDKDPVK MMATIYELKE DKSYDVTGVT FDDKKCRYDI STFVPGSQPG EFTFGKIKSF PGHTSSLVRV VSTNYNQHAM VFFKFVFQNR EEFYITLYGR TKELTSELKE NFIRFSKSLG LPENHIVFPV PIDQCIDG | 41BB Anticalin |
| 199 | QDSTSDLIPAPPLSKVPLQQNFQDNQFHGKWYVVGQAGNIRLR EDKDPHKMMATIYELKEDKSYDVTGVTFDDKKCTYAISTFVP GSQPGEFTLGKIKSFPGHTSSLVRVVSTNYNQHAMVFFKFVFQ NREEFYITLYGRTKELTSELKENFIRFSKSLGLPENHIVFPVPIDQ CIDG | 41BB Anticalin |
| 200 | QDSTSDLIPAPPLSKVPLQQNFQDNQFHGKWYVVGQAGNIKLR EDKDPNKMMATIYELKEDKSYDVTGVTFDDKKCTYAISTLVP GSQPGEFTFGKIKSFPGHTSSLVRVVSTNYNQHAMVFFKFVFQ NREEFYITLYGRTKELTSELKENFIRFSKSLGLPENHIVFPVPIDQ CIDG | 41BB Anticalin |
| 201 | QDSTSDLIPAPPLSKVPLQQNFQDNQFHGKWYVVGQAGNIRLR EDKDPSKMMATIYELKEDKSYDVTAVTFDDKKCNYAISTFVPG SQPGEFTLGKIKSFPGHTSSLVRVVSTNYNQHAMVFFKFVFQN REEFYITLYGRTKELTSELKENFIRFSKSLGLPENHIVFPVPIDQC IDG | 41BB Anticalin |
| 202 | REGPELSPDDPAGLLDLRQGMFAQLVAQNVLLIDGPLSWYSDP GLAGVSLTGGLSYKEDTKELVVAKAGVYYVFFQLELRRVVAG EGSGSVSLALHLQPLRSAAGAAALALTVDLPPASSEARNSAFG FQGRLLHLSAGQRLGVHLHTEARARHAWQLTQGATVLGLFRV TPEIPAGLPSPRSE | 71-254 of human 41BBL |
| 203 | LDLRQGMFAQLVAQNVLLIDGPLSWYSDPGLAGVSLTGGLSY KEDTKELVVAKAGVYYVFFQLELRRVVAGEGSGSVSLALHLQ | 85-254 of human 41BBL |

| # | SEQUENCE | ANNOTATION |
|---|---|---|
| | PLRSAAGAAALALTVDLPPASSEARNSAFGFQGRLLHLSAGQR<br>LGVHLHTEARARHAWQLTQGATVLGLFRVTPEIPAGLPSPRSE | |
| 204 | DPAGLLDLRQGMFAQLVAQNVLLIDGPLSWYSDPGLAGVSLT<br>GGLSYKEDTKELVVAKAGVYYVFFQLELRRVVAGEGSGSVSL<br>ALHLQPLRSAAGAAALALTVDLPPASSEARNSAFGFQGRLLHL<br>SAGQRLGVHLHTEARARHAWQLTQGATVLGLFRVTPEIPAGLP<br>SPRSE | 80-254 of human 41BBL |
| 205 | PWAVSGARASPGSAASPRLREGPELSPDDPAGLLDLRQGMFAQ<br>LVAQNVLLIDGPLSWYSDPGLAGVSLTGGLSYKEDTKELVVA<br>KAGVYYVFFQLELRRVVAGEGSGSVSLALHLQPLRSAAGAAA<br>LALTVDLPPASSEARNSAFGFQGRLLHLSAGQRLGVHLHTEAR<br>ARHAWQLTQGATVLGLFRVTPEIPAGLPSPRSE | 52-254 of human 4-1BBL |
| 206 | REGPELSPDDPAGLLDLRQGMFAQLVAQNVLLIDGPLSWYSDP<br>GLAGVSLTGGLSYKEDTKELVVAKAGVYYVFFQLELRRVVAG<br>EGSGSVSLALHLQPLRSAAGAAALALTVDLPPASSEARNSAFG<br>FQGRLLHLSAGQRLGVHLHTEARARHAWQLTQGATVLGLFRV<br>TPEIPAGL | 71-248 of human 41BBL |
| 207 | LDLRQGMFAQLVAQNVLLIDGPLSWYSDPGLAGVSLTGGLSY<br>KEDTKELVVAKAGVYYVFFQLELRRVVAGEGSGSVSLALHLQ<br>PLRSAAGAAALALTVDLPPASSEARNSAFGFQGRLLHLSAGQR<br>LGVHLHTEARARHAWQLTQGATVLGLFRVTPEIPAGL | 85-248 of human 41BBL |
| 208 | DPAGLLDLRQGMFAQLVAQNVLLIDGPLSWYSDPGLAGVSLT<br>GGLSYKEDTKELVVAKAGVYYVFFQLELRRVVAGEGSGSVSL<br>ALHLQPLRSAAGAAALALTVDLPPASSEARNSAFGFQGRLLHL<br>SAGQRLGVHLHTEARARHAWQLTQGATVLGLFRVTPEIPAGL | 80-248 of human 41BBL |
| 209 | PWAVSGARASPGSAASPRLREGPELSPDDPAGLLDLRQGMFAQ<br>LVAQNVLLIDGPLSWYSDPGLAGVSLTGGLSYKEDTKELVVA<br>KAGVYYVFFQLELRRVVAGEGSGSVSLALHLQPLRSAAGAAA<br>LALTVDLPPASSEARNSAFGFQGRLLHLSAGQRLGVHLHTEAR<br>ARHAWQLTQGATVLGLFRVTPEIPAGL | 52-248 of human 41BBL |
| 210 | EVQLLESGGGEVQPGGSLRLSCAASGFSFSINAMGWYRQAPGK<br>RREFVAAIESGRNTVYAESVKGRFTISRDNAKNTVYLQMSSLR<br>AEDTAVYYCGLLKGNRVVSPSVAYWGQGTLVTVKP | 41BB sdAb |
| 211 | QVSHRYPRIQSIKVQFTEYKKEKGFILTSQKEDEIMKVQNNSVII<br>NCDGFYLISLKGYFSQEVNISLHYQKDEEPLFQLKKVRSVNSL<br>VASLTYKDKVYLNVTTDNTSLDDFHVNGGELILIHQNPGEFC<br>VL | OX40 ligand |
| 212 | QVSHRYPRFQ SIKVQFTEYK KEKGFILTSQ KEDEIMKVQN<br>NSVIINCDGF YLISLKGYFS QEVNISLHYQ KDEEPLFQLK<br>KVRSVNSLMV ASLTYKDKVY LNVTTDNTSL DDFHVNGGEL<br>ILIHQNPGEFCVL | OX40 ligand |
| 213 | QVSHRYPRIQSIKVQFTEYKKEKGFILTSQKEDEIMKVQNNSVII<br>NCDGFYLISLKGYFSQEVNISLHYQKDEEPLFQLKKVRSVNSL<br>MVASLTYKDKVYLNVTTDNTSLDDFHVNGGELILIHQNPGEFC<br>VL | OX40 ligand |
| 214 | QVSHRYPRIQ SIKVQFTEYK KEKGFILTSQ KEDEIMKVQN<br>NSVIINCDGF YLISLKGYFS QEVNISLHYQ KDEEPLFQLK<br>KVRSVNSLMV ASLTYKDKVY LNVTTDNTSL DDFHVNGGEL<br>ILIHQNPGEFCVL | OX40 ligand |
| 215 | VSHRYPRIQSIKVQFTEYKKEKGFILTSQKEDEIMKVQNNSVIIN<br>CDGFYLISLKGYFSQEVNISLHYQKDEEPLFQLKKVRSVNSLM<br>VASLTYKDKVYLNVTTDNTSLDDFHVNGGELILIHQNPGEFCV<br>L | OX40 ligand |
| 216 | EVQLVQSGAEVKKPGASVKVSCKASGYTFTDSYMSWVRQAP<br>GQGLEWIGDMYPDNGDSSYNQKFRERVTITRDTSTSTAYLELS<br>SLRSEDTAVYYCVLAPRWYFSVWGQGTLVTVSS | OX40 VH |
| 217 | DIQMTQSPSSLSASVGDRVTITCRASQDISNYLNWYQQKPGKA<br>PKLLIYYTSRLRSGVPSRFSGSGSGTDFTLTISSLQPEDFATYYC<br>QQGHTLPPTFGQGTKVEIKRT | OX40 VL |

-continued

| # | SEQUENCE | ANNOTATION |
|---|----------|------------|
| 218 | EVQLVESGGGLVQPGGSLKLSCAASGFTFSGSAMHWVRQASG KGLEWVGRIRSKANSYATAYAASVKGRFTISRDDSKNTAYLQ MNSLKTEDTAVYYCTSGIYDSSGYDYWGQGTLVTVSS | OX40 VH |
| 219 | DIVMTQSPLSLPVTPGEPASISCRSSQSLLHSNGYNYLDWYLQK PGQSPQLLIYLGSNRASGVPDRFSGSGSGTDFTLKISRVEAEDV GVYYCMQALQTPLTFGGGTKVEIK | OX40 VL |
| 220 | EVQLLESGGGEVQPGGSLRLSCAASGFTFSDAFMYWVRQAPG KGLEWVSSISNRGLKTAYAESVKGRFTISRDNAKNTLYLQMSS LRAEDTAVYYCSRDVGDFRGQGTLVTVKP | OX40 sdAb |
| 221 | QLETAKEPCMAKFGPLPSKWQMASSEPPCVNKVSDWKLEILQ NGLYLIYGQVAPNANYNDVAPFEVRLYKNKDMIQTLTNKSKI QNVGGTYELHVGDTIDLIFNSEHQVLKNNTYWGIILLANPQFIS | GITR ligand |
| 222 | QVQLVESGGGVVQPGRSLRLSCAASGFTFSSYAMSWVRQAPG KGLEWVASISSGGTTYYPDSVKGRFTISRDNSKNTLYLQMNSL RAEDTAVYYCARVGGYYDSMDYWGQGTLVTVSS | GITR VH |
| 223 | EIVLTQSPGTLSLSPGERATLSCRASESVDNYGVSFMNVVYQQK PGQAPRLLIYAASNQGSGIPDRFSGSGSGTDFTLTISRLEPEDFA VYYCQQTKEVTWTFGQGTKVEIK | GITR VL |
| 224 | QVTLRESGPALVKPTQTLTLTCTFSGFSLSTSGMGVGWIRQPPG KALEWLAHIWWDDDKYYQPSLKSRLTISKDTSKNQVVLTMTN MDPVDTATYYCARTRRYFPPAYWGQGTLVTVSS | GITR VH |
| 225 | EIVMTQSPATLSVSPGERATLSCKASQNVGTNVAWYQQKPGQ APRLLIYSASYRYSGIPARFSGSGSGTEFTLTISSLQSEDFAVYYC QQYNTDPLTFGGGTKVEIK | GITR VL |
| 226 | QVQLQESGPGLVKPSETLSLTCTVSGGSISSGGYFWSWIRQPPG KGLEWIGYIYYSGTTYYNPSLKSRVTISDTSKNQFSLKLSSVTA ADTAVYYCARDLFYYDTSGPRGFDPWGQGTLVTVSS | GITR VH |
| 227 | EIVLTQSPGTLSLSPGERATLSCRASQTVSSNYLAWYQQKPGQ APRLLIYGSSTRATGIPDRFSGSGSGTDFTLTISRLEPEDFAVYY CQQYDSSPWTFGQGTKVEIK | GITR VL |
| 228 | QVQLVESGGGVVQPGRSLRLSCAASGFTFSSYGMHWVRQAPG KGLEWVAVIwYPGSNKYYAESVKGRFTISRDNSKNTLYLQMN SLRAEDTAVYYCARGGELGRYYYYGMDVWGQGTTVTVSS | GITR VH |
| 229 | DIQMTQSPSSLSASVGDRVTVTCRASQGIRNDLGWYQQKPGK APKRLIYAASSLQSGVPSRFSGSGSGTEFTLTISSLQPEDFATYY CLQHNNYPWTFGQGTKVDIK | GITR VL |
| 230 | EVQLLESGGGEVQPGGSLRLSCAASGSVFSIDAMGWYRQAPG KQRELVAVLSGISSAKYAASAPGRFTISRDNAKNTVYLQMSSL RAEDTAVYYCYADVSTGWGRDAHGYWGQGTLVTV | GITR sdAb |
| 231 | MPEEGSGCSVRRRPYGCVLRAALVPLVAGLVICLVVCI<u>QRFAQ AQQQLPLESLGWDVAELQLNHTGPQQDPRLYWQGGPALGRSF LHGPELDKGQLRIHRDGIYMVHIQVTLAICSSTTASRHHPTTLA VGICSPASRSISLLRLSFHQGCTIASQRLTPLARGDTLCTNLTGT LLPSRNTDETFFGVQWVRP</u> | UniProt no. P32970; CD70-ECD residues 39-193 (underline) |
| 232 | QVQLVESGGGVVQPGRSLRLSCAASGFTFSSYDMHWVRQAPG KGLEWVAVIWYDGSNKYYADSVKGRFTISRDNSKNTLYLQM NSLRAEDTAVYYCARGSGNWGFFDYWGQGTLVTVSS | CD70 VH |
| 233 | DIQMTQSPSSLSASVGDRVTITCRASQGISRWLAWYQQKPEKA PKSLIYAASSLQSGVPSRFSGSGSGTDFTLTISSLQPEDFATYYC QQYNTYPRTFGQGTKVEIK | CD70 VL |
| 234 | QVQLQQSGGGLVQPGGSLRLSCAASGSIFSINGMGWYRQAPG KERELVAGLTSGGSVTNYADSVKGRFTISRDNAKNTVYLQMN SLKPEDTAVYYCRAEIFTRTGENYYGMDYWGKGTQVTVKP | ICOS sdAb |
| 235 | EVQLVESGGGEVQPGGSLRLSCAASGRMFSNYAMGWFRQAPG KEREFVAAINYRRDAADYAESVKGRFTISRDNAKNTVYLQMN SLRAEDTAVYYCGFTYAGWASSRRDDYNYWGQGTLVTVKP | CD28 sdAb |

| # | SEQUENCE | ANNOTATION |
|---|---|---|
| 236 | RVKFSRSADAPAYQQGQNQLYNELNLGRREEYDVLDKRRGRD PEMGGKPRRKNPQEGLYNELQKDKMAEAYSEIGMKGERRRG KGHDGLYQGLSTATKDTYDALHMQALPPR | CD3zeta signaling domain |
| 237 | KRGRKKLLYIFKQPFMRPVQTTQEEDGCSCRFPEEEEGGCEL | 4-1BB-derived costimulatory domain |
| 238 | SKRSRLLHSDYMNMTPRRPGPTRKHYQPYAPPRDFAAYRS | CD28-derived costimulatory domain |
| 239 | RSKRSRLLHSDYMNMTPRRPGPTRKHYQPYAPPRDFAAYRS | CD28-derived costimulatory domain 2 |
| 240 | FWVRSKRSRLLHSDYMNMTPRRPGPTRKHYQPYAPPRDFAAY RS | CD28-derived costimulatory domain 3 |
| 241 | KPTTTPAPRPPTPAPTIASQPLSLRPEASRPAAGGAVHTRGLDFA SDIYIWAPLAGTCGVLLLSLVITLYC | CD8-derived hinge and transmembrane domain |
| 242 | AKPTTTPAPRPPTPAPTIASQPLSLRPEACRPAAGGAVHTRGLD FACDIYIVVAPLAGTCGVLLLSLVIT | CD8-derived hinge and transmembrane domain |
| 243 | KPTTTPAPRPPTPAPTIASQPLSLRPEACRPAAGGAVHTRGLDF ACDIYIVVAPLAGTCGVLLLSLVIT | CD8 hinge and transmembrane domain |
| 244 | EVQLVQSGGGLVQAGGSLRLSCAASGSILSINAMGWYRQPPGK QREMVAGFTDGNTIYADSVKGRFTISRDNAKNTVYLQMNSL KPEDTAVYYCAADVQLFSRDYEFYWGQGTQVTVKP | L10D9 |
| 245 | EVQLVESGGGEVQPGGSLRLSCAASGSILSINAMGWYRQAPGK QREMVAGFTGDGNTIYAESVKGRFTISRDNAKNTVYLQMSSLR AEDTAVYYCAADVQLFSRDYEFYWGQGTLVTVKP | hz10D9v1 |
| 246 | EVQLVESGGGEVQPGGSLRLSCAASGSILSINAMGWYRQAPGK QRELVAGFTGDGNTIYAESVKGRFTISRDNAKNTVYLQMSSLR AEDTAVYYCAADVQLFSRDYEFYWGQGTLVTVKP | hz10D9v2 |
| 247 | EVQLVESGGGEVQPGGSLRLSCAASGSILSINAMGWYRQAPGK QREMVAGFTGEGNTIYAESVKGRFTISRDNAKNTVYLQMSSLR AEDTAVYYCAADVQLFSRDYEFYWGQGTLVTVKP | hz10D9v3 |
| 248 | EVQLVESGGGEVQPGGSLRLSCAASGSILSINAMGWYRQAPGK QREMVAGFTGDTNTIYAESVKGRFTISRDNAKNTVYLQMSSLR AEDTAVYYCAADVQLFSRDYEFYWGQGTLVTVKP | hz10D9v4 |
| 249 | EVQLVESGGGEVQPGGSLRLSCAASGSILSINAMGWYRQAPGK QRELVAGFTFDTNTIYAESVKGRFTISRDNAKNTVYLQMSSLR AEDTAVYYCAADVQLFSRDYEFYWGQGTLVTVKP | hz10D9v5 |
| 250 | EVQLVESGGGEVQPGGSLRLSCAASGSILSINAMGWYRQPPGK QRELVAGFTGDTNTIYAESVKGRFTISRDNAKNTVYLQMSSLR AEDTAVYYCAADVQLFSRDYEFYWGQGTLVTVKP | hz10D9v6 |
| 251 | EVQLVESGGGEVQPGGSLRLSCAASGSIFSINAMGWYRQAPGK QRELVAGFTGDTNTIYAESVKGRFTISRDNAKNTVYLQMSSLR AEDTAVYYCAADVQLFSRDYEFYWGQGTLVTVKP | hz10D9v7 |
| 252 | EVQLVESGGGEVQPGGSLRLSCAASGFTFSINAMGWYRQAPG KQRELVAGFTGDTNTIYAESVKGRFTISRDNAKNTVYLQMSSL RAEDTAVYYCAADVQLFSRDYEFYWGQGTLVTVKP | hz10D9v8 |
| 253 | EVQLVESGGGEVQPGGSLRLSCAASGFTFSSYAMGWYRQAPG KQRELVAGFTGDTNTIYAESVKGRFTISRDNAKNTVYLQMSSL RAEDTAVYYCAADVQLFSRDYEFYWGQGTLVTVKP | hz10D9v9 |

| # | SEQUENCE | ANNOTATION |
|---|---|---|
| 254 | EVQLVESGGGEVQPGGSLRLSCAASGSIFSSNAMGWYRQAPG KQRELVAGFTGDTNTIYAESVKGRFTISRDNAKNTVYLQMSSL RAEDTAVYYCAADVQLFSRDYEFYWGQGTLVTVKP | hz10D9v10 |
| 255 | EVQLVESGGGEVQPGGSLRLSCAASGFIFSSYAMGWYRQAPG KQRELVAGFTGDTNTIYAESVKGRFTISRDNAKNTVYLQMSSL RAEDTAVYYCAADVQLFSRDYEFYWGQGTLVTVKP | hz10D9v11 |
| 256 | EVQLVESGGGEVQPGGSLRLSCAASGIFSIYAMGWYRQAPGK QRELVAGFTGDTNTIYAESVKGRFTISRDNAKNTVYLQMSSLR AEDTAVYYCAADVQLFSRDYEFYWGQGTLVTVKP | hz10D9v12 |
| 257 | EVQLVESGGGEVQPGGSLRLSCAASGFIFSINAMGWYRQAPGK QRELVAGFTGDTNTIYAESVKGRFTISRDNAKNTVYLQMSSLR AEDTAVYYCAADVQLFSRDYEFYWGQGTLVTVKP | hz10D9v13 |
| 258 | EVQLVQSGGGLVQPGGSLRLSCAASGFTLDDYTIGWFRQFPGK EREGVSCISSSGGSTYYADSVKGRFTISRDNAKNTVWLQMNDL KSEDTAIYYCATYCPVVVGPELGYDYWGQGTQVTVKP | L10E5 |
| 259 | EVQLVESGGGEVQPGGSLRLSCAASGFTLDDYTIGWFRQAPGK EREGVSCISSSGGSTYYAESVKGRFTISRDNAKNTLYLQMSSLR AEDTAVYYCATYCPVVVGPELGYDYWGQGTLVTVKP | hz10E5v1 |
| 260 | EVQLVESGGGEVQPGGSLRLSCAASGFTLDDYTIGWFRQAPGK EREGVSCISSSGGSTYYAESVKGRFTISRDNAKNTVWLQMSSL RAEDTAVYYCATYCPVVVGPELGYDYWGQGTLVTVKP | hz10E5v2 |
| 261 | EVQLVESGGGEVQPGGSLRLSCAASGFTLDDYTIGWFRQAPGK EREGVSCISSSGGSTYYAESVKGRFTISRDNAKNTLYLQMNDL RAEDTAVYYCATYCPVVVGPELGYDYWGQGTLVTVKP | hz10E5v3 |
| 262 | EVQLVESGGGEVQPGGSLRLSCAASGFTLDDYTIGWFRQAPGK EREGVSCISSSGGSTYYAESVKGRFTISRDNAKNTLYLQMSSLK SEDTAIYYCATYCPVVVGPELGYDYWGQGTLVTVKP | hz10E5v4 |
| 263 | EVQLVESGGGEVQPGGSLRLSCAASGFTLDDYTIGWFRQFPGK EREGVSCISSSGGSTYYAESVKGRFTISRDNAKNTLYLQMSSLR AEDTAVYYCATYCPVVVGPELGYDYWGQGTLVTVKP | hz10E5v5 |
| 264 | EVQLQESGGGLVQAGGSLRLSCGPSEIITSDKSVGWWRQAPGK QRNLVAGISNVGSTNYAQSVKGRFTISRDNAKNTLFLQMNSLK PEDTAVYYCYARDFENEYWGRGTQVTVKP | L8E7 |
| 265 | EVQLVESGGGEVQPGGSLRLSCAASEIITSDKSVGWWRQAPGK QRNLVAGISNVGSTNYAESVKGRFTISRDNAKNTLYLQMSSLR AEDTAVYYCYARDFENEYWGQGTLVTVKP | hz8E7v1 |
| 266 | EVQLVESGGGEVQPGGSLRLSCAASEIITSDKSVGWWRQAPGK QRNLVAGISNVGSTNYAQSVKGRFTISRDNAKNTLYLQMSSLR AEDTAVYYCYARDFENEYWGQGTLVTVKP | hz8E7v2 |
| 267 | EVQLVESGGGEVQPGGSLRLSCGPSEIITSDKSVGWWRQAPGK QRNLVAGISNVGSTNYAQSVKGRFTISRDNAKNTLYLQMSSLR AEDTAVYYCYARDFENEYWGQGTLVTVKP | hz8E7v3 |
| 268 | EVQLVESGGGEVQPGGSLRLSCAASEIITSDKSVGWWRQAPGK QRNLVAGISNVGSTNYAQSVKGRFTISRDNAKNTLFLQMSSLR AEDTAVYYCYARDFENEYWGQGTLVTVKP | hz8E7v4 |
| 269 | EVQLVESGGGEVQPGGSLRLSCGPSEIIFSDKSVGWWRQAPGK QRNLVAGISNVGSTNYAQSVKGRFTISRDNAKNTLYLQMSSLR AEDTAVYYCYARDFENEYWGQGTLVTVKP | hz8E7v6 |
| 270 | EVQLVESGGGEVQPGGSLRLSCGPSEIITSDKSVGWYRQAPGK QRNLVAGISNVGSTNYAQSVKGRFTISRDNAKNTLYLQMSSLR AEDTAVYYCYARDFENEYWGQGTLVTVKP | hz8E7v8 |
| 271 | EVQLVESGGGEVQPGGSLRLSCGPSEIITSDKSVGWVRQAPGK QRNLVAGISNVGSTNYAQSVKGRFTISRDNAKNTLYLQMSSLR AEDTAVYYCYARDFENEYWGQGTLVTVKP | hz8E7v9 |

-continued

| # | SEQUENCE | ANNOTATION |
|---|---|---|
| 272 | EVQLVESGGGEVQPGGSLRLSCGPSEIITSDKSVGWWRQAPGK QRELVAGISNVGSTNYAQSVKGRFTISRDNAKNTLYLQMSSLR AEDTAVYYCYARDFENEYWGQGTLVTVKP | hz8E7v10 |
| 273 | EVQLVESGGGEVQPGGSLRLSCGPSEIITSDKSVGWFRQAPGKQ RNLVAGISNVGSTNYAQSVKGRFTISRDNAKNTLYLQMSSLRA EDTAVYYCYARDFENEYWGQGTLVTVKP | hz8E7v11 |
| 274 | EVQLVESGGGEVQPGGSLRLSCGPSEIITSDKSVGWWRQAPGK GRELVAGISNVGSTNYAQSVKGRFTISRDNAKNTLYLQMSSLR AEDTAVYYCYARDFENEYWGQGTLVTVKP | hz8E7v12 |
| 275 | QVQLVQSGGGLVQAGGSLRLSCAASGSIFSINAMGWYREAPG KQRELVAGFTGDGMTKYAESVKGRFTFSRDNAKNTVYLQMN SLKPEDTGVYYCAADVFTDRDHVDWYWGQGTQVTVKP | L3G3 |
| 276 | EVQLVESGGGEVQPGGSLRLSCAASGSIFSINAMGWYRQAPGK QRELVAGFTGDGMTKYAESVKGRFTISRDNAKNTVYLQMSSL RAEDTAVYYCAADVFTDRDHVDWYWGQGTLVTVKPGG | hz3G3v1 |
| 277 | EVQLVESGGGEVQPGGSLRLSCAASGSIFSINAMGWYREAPGK QRELVAGFTGDGMTKYAESVKGRFTISRDNAKNTVYLQMSSL RAEDTAVYYCAADVFTDRDHVDWYWGQGTLVTVKP | hz3G3v2 |
| 278 | EVQLVESGGGEVQPGGSLRLSCAASGSIFSINAMGWYRQAPGK QRELVAGFTGDGMTKYAESVKGRFTFSRDNAKNTVYLQMSSL RAEDTAVYYCAADVFTDRDHVDWYWGQGTLVTVKP | hz3G3v3 |
| 279 | EVQLVESGGGEVQPGGSLRLSCAASGSIFSINAMGWYRQAPGK QRELVAGFTGDGMTKYAESVKGRFTISRDNAKNTVYLQMSSL RAEDTGVYYCAADVFTDRDHVDWYWGQGTLVTVKP | hz3G3v4 |
| 280 | EVQLVQSGGGLVQPGGSLRLSCAASGSDFSINAIGWYRQAPGK QRDMVAGFTGDGVTTYADSVKGRFTISRDNAKNTVYLQMNSL KPEDTAVYYCAADVKIGGDYEWFWGQGTQVTVKP | L5A7 |
| 281 | EVQLVESGGGEVQPGGSLRLSCAASGSDFSINAIGWYRQAPGK QRDMVAGFTGDGVTTYAESVKGRFTISRDNAKNTVYLQMSSL RAEDTAVYYCAADVKIGGDYEWFWGQGTLVTVKP | hz5A7v1 |
| 282 | EVQLVESGGGEVQPGGSLRLSCAASGSDFSINAIGWYRQAPGK QRDMVAGFTGDTVTTYAESVKGRFTISRDNAKNTVYLQMSSL RAEDTAVYYCAADVKIGGDYEWFWGQGTLVTVKP | hz5A7v2 |
| 283 | EVQLVESGGGEVQPGGSLRLSCAASGSDFSINAIGWYRQAPGK QRDMVAGFTGEGVTTYAESVKGRFTISRDNAKNTVYLQMSSL RAEDTAVYYCAADVKIGGDYEWFWGQGTLVTVKP | hz5A7v3 |
| 284 | EVQLVESGGGEVQPGGSLRLSCAASGSDFSINAIGWYRQAPGK QRDLVAGFTGDGVTTYAESVKGRFTISRDNAKNTVYLQMSSL RAEDTAVYYCAADVKIGGDYEWFWGQGTLVTVKP | hz5A7v4 |
| 285 | EVQLVESGGGEVQPGGSLRLSCAASGSDFSINAIGWYRQAPGK QRDWVAGFTGDGVTTYAESVKGRFTISRDNAKNTVYLQMSSL RAEDTAVYYCAADVKIGGDYEWFWGQGTLVTVKP | hz5A7v5 |
| 286 | EVQLVESGGGEVQPGGSLRLSCAASGSDFSINAIGWYRQPPGK QRDMVAGFTGDGVTTYAESVKGRFTISRDNAKNTVYLQMSSL RAEDTAVYYCAADVKIGGDYEWFWGQGTLVTVKP | hz5A7v6 |
| 287 | QVQLVQSGGGLVQAGESLRLSCAASGSIFSINAMGWYRQVLG KQRELVAVVSSDGRTTVAPSVKGRFTISRDNAKNTVSLQMNSL KPEDTGVYYCGVREWYSDSDWRDYEGQGTQVTVKP | L5A8 |
| 288 | EVQLVESGGGEVQPGGSLRLSCAASGSIFSINAMGWYRQAPGK QRELVAVVSSDGRTTVAESVKGRFTISRDNAKNTVYLQMSSLR AEDTAVYYCGVREWYSDSDWRDYEGQGTLVTVKP | hz5A8v1 |
| 289 | EVQLVESGGGEVQPGGSLRLSCAASGSIFSINAMGWYRQAPGK QRELVAVVSSDGRTTVAPSVKGRFTISRDNAKNTVYLQMSSLR AEDTAVYYCGVREWYSDSDWRDYEGQGTLVTVKP | hz5A8v2 |

| # | SEQUENCE | ANNOTATION |
|---|---|---|
| 290 | EVQLVESGGGEVQPGGSLRLSCAASGSIFSINAMGWYRQVLGK<br>QRELVAVVSSDGRTTVAPSVKGRFTISRDNAKNTVYLQMSSLR<br>AEDTAVYYCGVREWYSDSDWRDYEGQGTLVTVKP | hz5A8v3 |
| 291 | EVQLVESGGGEVQPGGSLRLSCAASGSIFSINAMGWYRQAPGK<br>QRELVAVVSSDGRTTVAPSVKGRFTISRDNAKNTVYLQMSSLR<br>AEDTGVYYCGVREWYSDSDWRDYEGQGTLVTVKP | hz5A8v5 |
| 292 | EVQLVESGGGEVQPGGSLRLSCAASGSIFSINAMGWYRQAPGK<br>QRELVAVVSSEGRTTVAPSVKGRFTISRDNAKNTVYLQMSSLR<br>AEDTAVYYCGVREWYSDSDWRDYEGQGTLVTVKP | hz5A8v6 |
| 293 | EVQLVESGGGEVQPGGSLRLSCAASGSIFSINAMGWYRQAPGK<br>QRELVAVVSSDARTTVAPSVKGRFTISRDNAKNTVYLQMSSLR<br>AEDTAVYYCGVREWYSDSDWRDYEGQGTLVTVKP | hz5A8v7 |
| 294 | EVQLVESGGGEVQPGGSLRLSCAASGSIFSINAMGWYRQAPGK<br>QRELVAVVSSDGRTTVAPSVKGRFTISRDNAKNTVYLQMSSLR<br>AEDTAVYYCGVREWYSDADWRDYEGQGTLVTVKP | hz5A8v8 |
| 295 | EVQLVESGGGEVQPGGSLRLSCAASGSIFSINAMGWYRQAPGK<br>QRELVAVVSSDGRTTVAPSVKGRFTISRDNAKNTVYLQMSSLR<br>AEDTAVYYCGVREWYSESDWRDYEGQGTLVTVKP | hz5A8v9 |
| 296 | EVQLVESGGGEVQPGGSLRLSCAASGSIFSINAMGWYRQAPGK<br>QRELVAVVSSDARTTVAPSVKGRFTISRDNAKNTVYLQMSSLR<br>AEDTAVYYCGVREWYSDADWRDYEGQGTLVTVKP | hz5A8v10 |
| 297 | EVQLVESGGGEVQPGGSLRLSCAASGSIFSINAMGWYRQAPGK<br>QREWVAVVSSDGRTTVAPSVKGRFTISRDNAKNTVYLQMSSL<br>RAEDTAVYYCGVREWYSDSDWRDYEGQGTLVTVKP | hz5A8v11 |
| 298 | EVQLVESGGGEVQAGGSLRLSCAASGSIFSINAMGWYRQAPGK<br>QRELVAVVSSDGRTTVAPSVKGRFTISRDNAKNTVYLQMSSLR<br>AEDTAVYYCGVREWYSDSDWRDYEGQGTLVTVKP | hz5A8v12 |
| 299 | QVQLQESGGGLVQTGGSLTLSCGASEITFSDKTVGWYRQAPGK<br>QRVLVAVISNVDSTNYAHSVKGRFTISRDNAKNTVYLQMNSL<br>KPEDTAVYYCHARDFENEYWGRGTQVTVKP | L6C5 |
| 300 | EVQLVESGGGEVQPGGSLRLSCAASEITFSDKTVGWYRQAPGK<br>QRVLVAVISNVDSTNYAESVKGRFTISRDNAKNTLYLQMSSLR<br>AEDTAVYYCHARDFENEYWGQGTLVTVKP | hz6C5v1 |
| 301 | EVQLVESGGGEVQPGGSLRLSCAASEITFSDKTVGWYRQAPGK<br>QRVLVAVISNVDSTNYAESVKGRFTISRDNAKNTVYLQMSSLR<br>AEDTAVYYCHARDFENEYWGQGTLVTVKPG | hz6C5v2 |
| 302 | EVQLVESGGGEVQPGGSLRLSCAASEITFSDKTVGWYRQAPGK<br>QRVLVAVISNVDSTNYAHSVKGRFTISRDNAKNTVYLQMSSLR<br>AEDTAVYYCHARDFENEYWGQGTLVTVKP | hz6C5v3 |
| 303 | EVQLVESGGGEVQPGGSLRLSCGASEITFSDKTVGWYRQAPGK<br>QRVLVAVISNVDSTNYAESVKGRFTISRDNAKNTVYLQMSSLR<br>AEDTAVYYCHARDFENEYWGQGTLVTVKP | hz6C5v4 |
| 304 | EVQLVESGGGEVQPGGSLRLSCAASEITFSDKTVGWYRQAPGK<br>QRVLVAVISNVESTNYAESVKGRFTISRDNAKNTVYLQMSSLR<br>AEDTAVYYCHARDFENEYWGQGTLVTVKP | hz6C5v5 |
| 305 | EVQLVESGGGEVQPGGSLRLSCAASEITFSDKTVGWYRQAPGK<br>QRVLVAVISNVDATNYAESVKGRFTISRDNAKNTVYLQMSSLR<br>AEDTAVYYCHARDFENEYWGQGTLVTVKP | hz6C5v6 |
| 306 | QVQLVQSGGGLVQAGGSLRLSCGASEIIFSDKTVGWYRQAPGK<br>QRVLVAVISNVDSTNYAQSVKGRFTISRDNAKNTVYLQMNSL<br>KPEDTAVYYCYARDFESEYWGRGTQVTVK | L6F1 |
| 307 | EVQLVESGGGEVQPGGSLRLSCAASEIIFSDKTVGWYRQAPGK<br>QRVLVAVISNVDSTNYAESVKGRFTISRDNAKNTLYLQMSSLR<br>AEDTAVYYCYARDFESEYWGQGTLVTVK | hz6F1v1 |

| # | SEQUENCE | ANNOTATION |
|---|---|---|
| 308 | EVQLVESGGGEVQPGGSLRLSCAASEIIFSDKTVGWYRQAPGK<br>QRVLVAVISNVDSTNYAESVKGRFTISRDNAKNTVYLQMSSLR<br>AEDTAVYYCYARDFESEYWGQGTLVTVK | hz6F1v2 |
| 309 | EVQLVESGGGEVQPGGSLRLSCAASEIIFSDKTVGWYRQAPGK<br>QRVLVAVISNVDSTNYAQSVKGRFTISRDNAKNTVYLQMSSLR<br>AEDTAVYYCYARDFESEYWGQGTLVTVK | hz6F1v3 |
| 310 | EVQLVESGGGEVQPGGSLRLSCGASEIIFSDKTVGWYRQAPGK<br>QRVLVAVISNVDSTNYAESVKGRFTISRDNAKNTVYLQMSSLR<br>AEDTAVYYCYARDFESEYWGQGTLVTVK | hz6F1v4 |
| 311 | EVQLVESGGGEVQPGGSLRLSCAASEIIFSDKTVGWYRQAPGK<br>QRVLVAVISNVDSTNYAESVKGRFTISRDNAKNTVYLQMSSLR<br>AEDTAVYYCYARDFESEYWGRGTQVTVK | hz6F1v5 |
| 312 | EVQLVESGGGEVQPGGSLRLSCAASEIIFSDKTVGWYRQAPGK<br>QRVLVAVISNVESTNYAESVKGRFTISRDNAKNTVYLQMSSLR<br>AEDTAVYYCYARDFESEYWGQGTLVTVK | hz6F1v6 |
| 313 | EVQLVESGGGEVQPGGSLRLSCAASEIIFSDKTVGWYRQAPGK<br>QRVLVAVISNVDATNYAESVKGRFTISRDNAKNTVYLQMSSLR<br>AEDTAVYYCYARDFESEYWGQGTLVTVK | hz6F1v7 |
| 314 | QVQLQQSGGGLVQAGGSLRLSCAASGSDFSINAMGWYRQGEL<br>VAGFTGDGNPIYADSVKGRFTISRGNAENTVSLQMNSLKPEDT<br>AVYYCAADVKIGGDYEWYWGQGTQVTVKP | 3B4 |
| 315 | QVQLVQSGGGLVQAGGSLRLSCAASGFSLDDYTIGWFRQAPG<br>KEREGVSCISSSGGSTVHADSVKGRFTISRDNAKNTVWLQMNS<br>LKPEDTAVYYCATWCGVATMTEDLPFDYWGQGTLVTVK | 6A1 |
| 316 | QVQLQESGGGLVQAGGSLTLSCAASGSIFSINAMGWYRQGDL<br>VAGFTSEGSAKYADSVKGRFTISRDDAKNMVTLQMNSLKPED<br>TAVYYCAADIFSDRDHVDWYWGQGTLVTVK | 5H8 |
| 317 | QVQLQESGGGLVQSGGSLRLSCAASGFSLDDYTIGWFRQAPGK<br>EREGVSCISSSGGSTYYADSVKGRFTISRDNAENTVYLQMNSL<br>KPEDTAVYYCATYCPVTIADELGFDYWGQGTLVTVK | 3B12 |
| 318 | QVTLRESGGGLVQAGGSLRLSCGASEITLSDKTVGWYRQAPG<br>KQRVLVAVISNVDSTNYAHSVKGRFTISRDNAKNTVYLQMNS<br>LKPEDTAVYYCYARDFEAEYWGQGTLVTVK | 6B4 |
| 319 | GSILSINAMG | CDR-H1 (L10D9, hz10D9v1, 2, 3, 4, 5, 6) |
| 320 | GSIFSINAMG | CDR-H1 (hz10D9v7, L3G3, hz3G3v1, 2, 3, 4, L5A8, hz5A8v1, 2, 3, 4, 5, 6, 7, 8, 9, 10, 11, 12, DLL3-5H8-3245.seq, DLL3-3G12-3245.seq, DLL3-3C9-3245.seq, DLL3-3C5-3245.seq, DLL3-3F6-3245.seq, DLL3-3H12-3245.seq, 3C5, hz3C5v1, 2, 3, 4, 5, 6, 7, 8) |
| 321 | GFTFSINAMG | CDR-H1 (hz10D9v8) |
| 322 | GFTFSSYAMG | CDR-H1 (hz10D9v9) |

-continued

| # | SEQUENCE | ANNOTATION |
|---|---|---|
| 323 | GSIFSSNAMG | CDR-H1 (hz10D9v10) |
| 324 | GFIFSSYAMG | CDR-H1 (hz10D9v11) |
| 325 | GSIFSIYAMG | CDR-H1 (hz10D9v12) |
| 326 | GFIFSINAMG | CDR-H1 (hz10D9v13) |
| 327 | GFTLDDYTIG | CDR-H1 (L10E5, hz10E5v1, 2, 3, 4, 5) |
| 328 | EIITSDKSVG | CDR-H1 (L8E7, hz8E7v1, 2, 3, 4, 5, 8, 9, 10, 11, 12, 14) |
| 329 | EIIFSDKSVG | CDR-H1 (hz8E7v6) |
| 330 | GSDFSINAIG | CDR-H1 (L5A7, hz5A7v1, 2, 3, 4, 5, 6) |
| 331 | EITFSDKTVG | CDR-H1 (L6C5, hz6C5v1, 2, 3, 4, 5, 6) |
| 332 | EIIFSDKTVG | CDR-H1 (L6F1, hz6F1v1, 2, 3, 4, 5, 6, 7) |
| 333 | GSDFSINAMG | CDR-H1 (3B4) |
| 334 | GFSLDDYTIG | CDR-H1 (DLL3-6A1-3245.seq, DLL3-3B12-3245.seq) |
| 335 | EITLSDKTVG | CDR-H1 (DLL3-6B4-3245.seq) |
| 336 | GFTGDGNTI | CDR-H2 (L10D9, hz10D9v1,2) |
| 337 | GFTGEGNTI | CDR-H2 (hz10D9v3) |
| 338 | GFTGDTNTI | CDR-H2 (hz10D9v4, 5, 6, 7, 8, 9, 10, 11, 12, 13) |
| 339 | CISSSGGSTY | CDR-H2 (L10E5, hz10E5v1, 2, 3, 4, 5, DLL3-3B12-3245.seq) |
| 340 | GISNVGSTN | CDR-H2 (L8E7, hz8E7v1, 2, 3, 4, 5, 6, 8, 9, 10, 11, 12, 13, 14, 15, 16) |
| 341 | GFTGDGMTK | CDR-H2 (L3G3, hz3G3v1, 2, 3, 4, DLL3-3G12-3245.seq, DLL3-3H12-3245.seq) |
| 342 | GFTGDGVTT | CDR-H2 (L5A7, hz5A7v1, 4, 5, 6) |
| 343 | GFTGDTVTT | CDR-H2 (hz5A7v2) |

-continued

| # | SEQUENCE | ANNOTATION |
|---|---|---|
| 344 | GFTGEGVTT | CDR-H2 (hz5A7v3) |
| 345 | VVSSDGRTT | CDR-H2 (L5A8, hz5A8v1, 2, 3, 4, 5, 8, 9, 11, 12, DLL3-3E7-3245.seq) |
| 346 | VVSSEGRTT | CDR-H2 (hz5A8v6) |
| 347 | VVSSDARTT | CDR-H2 (hz5A8v7, 10) |
| 348 | VISNVDSTN | CDR-H2 (L6C5, hz6C5v1, 2, 3, 4, L6F1, hz6F1v1, 2, 3, 4, 5, DLL3-6B4-3245.seq) |
| 349 | VISNVESTN | CDR-H2 (hz6C5v5, hz6F1v6) |
| 350 | VISNVDATN | CDR-H2 (hz6C5v6, hz6F1v7) |
| 351 | GFTGDGNPI | CDR-H2 (3B4) |
| 352 | CISSSGGSTV | CDR-H2 (DLL3-6A1-3245.seq) |
| 353 | GFTSEGSAK | CDR-H2 (DLL3-5H8-3245.seq) |
| 354 | DVQLFSRDYEFY | CDR-H3 (L10D9, hz10D9v1, 2, 3, 4, 5, 6, 7, 8, 9, 10, 11, 12, 13) |
| 355 | YCPVVVGPELGYDY | CDR-H3 (L10E5, hz10E5v1, 2, 3, 4, 5) |
| 356 | RDFENEY | CDR-H3 (L8E7, hz8E7v1, 2, 3, 4, 5, 6, 7, 8, 9, 10, 11, 12, 13, 14, 15, 16; L6C5, hz6C5v1, 2, 3, 4, 5, 6) |
| 357 | DVFTDRDHVDWY | CDR-H3 (L3G3, hz3G3v1, 2, 3, 4, DLL3-3G12-3245.seq) |
| 358 | DVKIGGDYEWF | CDR-H3 (L5A7, hz5A7v1, 2, 3, 4, 5, 6) |
| 359 | REWYSDSDWRDY | CDR-H3 (L5A8, hz5A8v1, 2, 3, 4, 5, 6, 7, 11, 12, DLL3-3E7-3245.seq) |
| 360 | REWYSDADWRDY | CDR-H3 (hz5A8v8, 10) |
| 361 | REWYSESDWRDY | CDR-H3 (hz5A8v9) |
| 362 | RDFESEY | CDR-H3 (L6F1, hz6F1v1, 2, 3, 4, 5, 6, 7) |

-continued

| # | SEQUENCE | ANNOTATION |
|---|---|---|
| 363 | DVKIGGDYEWY | CDR-H3 (3B4) |
| 364 | WCGVATMTEDLPFDY | CDR-H3 (DLL3-6A1-3245.seq) |
| 365 | DIFSDRDHVDWY | CDR-H3 (DLL3-5H8-3245.seq) |
| 366 | YCPVTIADELGFDY | CDR-H3 (DLL3-3B12-3245.seq) |
| 367 | RDFEAEY | CDR-H3 (DLL3-6B4-3245.seq) |
| 368 | QAVVTQEPSLTVSPGGTVTLTCGSSTGAVTTSNYANWVQQKPGQAFRGLIGGTNKRAPGVPARFSGSLLGGKAALTISGAQPEDEADYYCALWYSNHWVFGCGTKLTVL | anti-CD3 VL (CON) |
| 369 | GGSGGS | (GGS)2 linker |
| 370 | GGSGGSGGS | (GGS)3 linker |
| 371 | GGSGGSGGSGGS | (GGS)4 linker |
| 372 | GGSGGSGGSGGSGGS | (GGS)5 linker |
| 373 | GGGG | glycine linker |
| 374 | GGGGG | glycine linker |
| 375 | GGGGGG | glycine linker |
| 376 | GGSGGS | (GGS)2 linker |
| 377 | GGSGGSGGS | (GGS)3 linker |
| 378 | GGSGGSGGSGGS | (GGS)4 linker |
| 379 | GGSGGSGGSGGSGGS | (GGS)5 linker |
| 380 | GGGG | glycine linker |
| 381 | GGGGG | glycine linker |
| 382 | GGGGGG | glycine linker |
| 383 | GGGGGG | glycine linker |
| 384 | GFTGDGSTK | CDR-H2 (3C5, hz3C5v1, 2, 5, 6, 7, 8) |
| 385 | GGSGGS | (GGS)2 linker |
| 386 | GGSGGSGGS | (GGS)3 linker |
| 387 | GGSGGSGGSGGS | (GGS)4 linker |
| 388 | GGSGGSGGSGGSGGS | (GGS)5 linker |
| 389 | GGGG | glycine linker |
| 390 | GGGGG | glycine linker |
| 391 | GGGGGG | glycine linker |
| 392 | GGSGGSGGSGGS | (GGS)4 linker |
| 393 | GGSGGSGGSGGSGGS | (GGS)5 linker |
| 394 | GGGG | glycine linker |
| 395 | DVQLLNSDYEFY | CDR-H3 (3C5, hz3C5v1, 2, 3, 4) |

-continued

| # | SEQUENCE | ANNOTATION |
|---|---|---|
| 396 | GGSGGS | (GGS)2 linker |
| 397 | GGSGGSGGS | (GGS)3 linker |
| 398 | GGSGGSGGSGGS | (GGS)4 linker |
| 399 | GGSGGSGGSGGSGGS | (GGS)5 linker |
| 400 | GGGG | glycine linker |
| 401 | QVQLVQSGGGLVQAGGSLRLSCAASGSIFSINAMGWYRQPPG KQRELVAGFTGDGSTKYADSVKGRFTISRDNAKNTVYLQMNS LKPEDTAVYYCAADVQLLNSDYEFYWGQGTQVTVKP | 3C5 |
| 402 | EVQLVESGGGEVQPGGSLRLSCAASGSIFSINAMGWYRQAPGK QRELVAGFTGDGSTKYAESVKGRFTISRDNAKNTVYLQMSSLR AEDTAVYYCAADVQLLNSDYEFYWGQGTLVTVKPGG | hz3C5v1 |
| 403 | EVQLVESGGGEVQPGGSLRLSCAASGSIFSINAMGWYRQPPGK QRELVAGFTGDGSTKYAESVKGRFTISRDNAKNTVYLQMSSLR AEDTAVYYCAADVQLLNSDYEFYWGQGTLVTVKPGG | hz3C5v2 |
| 404 | EVQLVESGGGEVQPGGSLRLSCAASGSIFSINAMGWYRQAPGK QRELVAGFTGDTSTKYAESVKGRFTISRDNAKNTVYLQMSSLR AEDTAVYYCAADVQLLNSDYEFYWGQGTLVTVKPGG | hz3C5v3 |
| 405 | EVQLVESGGGEVQPGGSLRLSCAASGSIFSINAMGWYRQAPGK QRELVAGFTGEGSTKYAESVKGRFTISRDNAKNTVYLQMSSLR AEDTAVYYCAADVQLLNSDYEFYWGQGTLVTVKPGG | hz3C5v4 |
| 406 | EVQLVESGGGEVQPGGSLRLSCAASGSIFSINAMGWYRQAPGK QRELVAGFTGDGSTKYAESVKGRFTISRDNAKNTVYLQMSSLR AEDTAVYYCAADVQLLSSDYEFYWGQGTLVTVKPGG | hz3C5v5 |
| 407 | EVQLVESGGGEVQPGGSLRLSCAASGSIFSINAMGWYRQAPGK QRELVAGFTGDGSTKYAESVKGRFTISRDNAKNTVYLQMSSLR AEDTAVYYCAADVQLLTSDYEFYWGQGTLVTVKPGG | hz3C5v6 |
| 408 | EVQLVESGGGEVQPGGSLRLSCAASGSIFSINAMGWYRQAPGK QRELVAGFTGDGSTKYAESVKGRFTISRDNAKNTVYLQMSSLR AEDTAVYYCAADVQLLQSDYEFYWGQGTLVTVKPGG | hz3C5v7 |
| 409 | EVQLVESGGGEVQPGGSLRLSCAASGSIFSINAMGWYRQAPGK QRELVAGFTGDGSTKYAESVKGRFTISRDNAKNTVYLQMSSLR AEDTAVYYCAADVQLLNTDYEFYWGQGTLVTVKPGG | hz3C5v8 |
| 410 | GFTGDTSTK | CDR-H2 (hz3C5v3) |
| 411 | GFTGEGSTK | CDR-H2 (hz3C5v4) |
| 412 | DVQLLSSDYEFY | CDR-H3 (hz3C5v5) |
| 413 | DVQLLTSDYEFY | CDR-H3 (hz3C5v6) |
| 414 | DVQLLQSDYEFY | CDR-H3 (hz3C5v7) |
| 415 | DVQLLNTDYEFY | CDR-H3 (hz3C5v8) |
| 416 | EVQLVESGGGEVQPGGSLRLSCGPSEIITSDKSVGWWRQAPGK QRNLVAGISNVGSTNYAQSVKGRFTISRDNAKNTVYLQMSSLR AEDTAVYYCYARDFENEYWGQGTLVTVKP | hz8E7v5 |
| 417 | EVQLVESGGGEVQPGGSLRLSCAASGSMTGANTMGWYRQAP GKGRDLVSLIGNYVTHYAESVKGRFTISRDNAKNTLYLQMSSL RAEDTAVYYCYLYTDNLGTSWGQGTLVTVKPGG | hz18H10v1 |

| # | SEQUENCE | ANNOTATION |
|---|---|---|
| 418 | EVQLVESGGGEVQPGGSLRLSCAASGSMTGANTMGWYRQAP GKQRDLVSLIGNYVTHYAESVKGRFTISRDNAKNTLYLQMSSL RAEDTAVYYCYLYTDNLGTSWGQGTLVTVKPGG | hz18H10v2 |
| 419 | EVQLVESGGGEVQPGGSLRLSCAASGSMTGANTMGWYRQAP GKQRDLVSLIGNYVTHYAESVKGRFTISRDNAKNTVYLQMSSL RAEDTAVYYCYLYTDNLGTSWGQGTLVTVKPGG | hz18H10v3 |
| 420 | EVQLVESGGGEVQPGGSLRLSCAASGSMTGANTMGWYRQAP GKQRDLVALIGNYVTHYAESVKGRFTISRDNAKNTVYLQMSS LRAEDTAVYYCYLYTDNLGTSWGQGTLVTVKPGG | hz18H10v4 |
| 421 | EVQLVESGGGEVQPGGSLRLSCAASGSMTGANTMGWYRQAP GKQRDLVALIGNYVTHYAESVKGRFTISRENAKNTVYLQMSSL RAEDTAVYYCYLYTDNLGTSWGQGTLVTVKPGG | hz18H10v5 |
| 422 | EVQLVESGGGEVQPGGSLRLSCAASGSVTGANTMGWYRQAPG KQRDLVALIGNYVTHYAESVKGRFTISRDNAKNTVYLQMSSLR AEDTAVYYCYLYTDNLGTSWGQGTLVTVKPGG | hz18H10v6 |
| 423 | EVQLVESGGGEVQPGGSLRLSCAASGSITGANTMGWYRQAPG KQRDLVALIGNYVTHYAESVKGRFTISRDNAKNTVYLQMSSLR AEDTAVYYCYLYTDNLGTSWGQGTLVTVKPGG | hz18H10v7 |
| 424 | EVQLVESGGGEVQPGGSLRLSCAASGSVTGANTMGWYRQAPG KQRDLVSLIGNYVTHYAESVKGRFTISRDNAKNTLYLQMSSLR AEDTAVYYCYLYTDNLGTSWGQGTLVTVKPGG | hz18H10v8 |
| 425 | EVQLVESGGGEVQPGGSLRLSCAASGSVTGANTMGWYRQAPG KQRDLVSLIGNYVTHYAESVKGRFTISRDNAKNTVYLQMSSLR AEDTAVYYCYLYTDNLGTSWGQGTLVTVKPGG | hz18H10v9 |
| 426 | EVQLVESGGGEVQPGGSLRLSCAASGSMTGANTMGWYRQAP GKQRDLVSLIGNYVTHYAESVKGRFTISRENAKNTVYLQMSSL RAEDTAVYYCYLYTDNLGTSWGQGTLVTVKPGG | hz18H10v10 |
| 427 | EVQLVESGGGEVQPGGSLRLSCAASGSVTGANTMGWYRQAPG KQRDLVSLIGNYVTHYAESVKGRFTISRENAKNTVYLQMSSLR AEDTAVYYCYLYTDNLGTSWGQGTLVTVKPGG | hz18H10v11 |
| 428 | EVQLVESGGGEVQPGGSLRLSCAASGSVTGANTMGWYRQAPG KQRDLVALIGNYVTHYAESVKGRFTISRENAKNTVYLQMSSLR AEDTAVYYCYLYTDNLGTSWGQGTLVTVKPGG | hz18H10v12 |
| 429 | EVQLVESGGGEVQPGGSLRLSCAASGSMTGANTMGWYRQAP GKQRELVALIGNYVTHYAESVKGRFTISRENAKNTVYLQMSSL RAEDTAVYYCYLYTDNLGTSWGQGTLVTVKPGG | hz18H10v13 |
| 430 | EVQLVESGGGEVQPGGSLRLSCAASGSVTGANTMGWYRQAPG KQRDLVALIGNYVTHYAESVKGRFTISRDNAKNTLYLQMSSLR AEDTAVYYCYLYTDNLGTSWGQGTLVTVKPGG | hz18H10v14 |
| 431 | EVQLVESGGGEVQPGGSLRLSCAASGSITGANTMGWYRQAPG KQRDLVALIGNYVTHYAESVKGRFTISRDNAKNTLYLQMSSLR AEDTAVYYCYLYTDNLGTSWGQGTLVTVKPGG | hz18H10v15 |
| 432 | EVQLVESGGGEVQPGGSLRLSCAASGSITGANTMGWYRQAPG KQRDLVALIGNYVTHYAESVKGRFTISRENAKNTVYLQMSSLR AEDTAVYYCYLYTDNLGTSWGQGTLVTVKPGG | hz18H10v16 |
| 433 | EVQLVESGGGEVQPGGSLRLSCAASGSITGANTMGWYRQAPG KQRDLVALIGNYVTHYAESVKGRFTISRDNAKNTVYLQMNSL RAEDTAVYYCYLYTDNLGTSWGQGTLVTVKPGG | hz18H10v17 |
| 434 | GSMTGANTMG | CDR1 |
| 435 | GSVTGANTMG | CDR1 |
| 436 | GSITGANTMG | CDR1 |
| 437 | LIGNYVTH | CDR2 |
| 438 | YTDNLGTS | CDR3 |

| # | SEQUENCE | ANNOTATION |
|---|---|---|
| 439 | QVQLVQSGGGLVQPGGSLRLSCVASGSMTGANTMGWYRQAP GKQRDLVALIGNYHYADSVKGRFTISRENAKNTVILQMNSLNP EDTAVYYCYLYTDNLGTSWGQGTLVTVKPGG | 18H10 |
| 440 | DKTHTCPPCPAPELLGGPSVFLFPPKPKDTLMISRTPEVTCVVV DVSHEDPEVKFNWYVDGVEVHNAKTKPREEQYNSTYRVVSV LTVLHQDWLNGKEYKCKVSNKALPAPIEKTISKAKGQPREPQV YTLPPCRDELTKNQVSLWCLVKGFYPSDIAVEWESNGQPENNY KTTPPVLDSDGSFFLYSKLTVDKSRWQQGNVFSCSVMHEALH NHYTQKSLSLSP | Knob Fc |
| 441 | DKTHTCPPCPAPELLGGPSVFLFPPKPKDTLMRSRTPEVTCVVV DVSHEDPEVKFNWYVDGVEVHNAKTKPREEQYNSTYRVVSV LTVLHQDWLNGKEYKCKVSNKALPAPIEKTISKAKGQPREPQV CTLPPSRDELTKNQVSLSCAVKGFYPSDIAVEWESNGQPENNY KTTPPVLDSDGSFFLVSKLTVDKSRWQQGNVFSCSVMHEALH NHYTQKSLSLSP | Hole Fc |
| 442 | DKTHTCPPCPAPGGPSVFLFPPKPKDTLMISRTPEVTCVVVDVS HEDPEVKFNWYVDGVEVHNAKTKPREEQYNSTYRVVSVLTVL HQDWLNGKEYKCKVSNKALPAPIEKTISKAKGQPREPQVYTLP PCRDELTKNQVSLWCLVKGFYPSDIAVEWESNGQPENNYKTTP PVLDSDGSFFLYSKLTVDKSRWQQGNVFSCSVMHEALHNHYT QKSLSLSP | Knob Fc |
| 443 | DKTHTCPPCPAPGGPSVFLFPPKPKDTLMRSRTPEVTCVVVDVS HEDPEVKFNWYVDGVEVHNAKTKPREEQYNSTYRVVSVLTVL HQDWLNGKEYKCKVSNKALPAPIEKTISKAKGQPREPQVCTLP PSRDELTKNQVSLSCAVKGFYPSDIAVEWESNGQPENNYKTTP PVLDSDGSFFLVSKLTVDKSRWQQGNVFSCSVMHEALHNHYT QKSLSLSP | Hole Fc |
| 444 | DKTHTCPPCPAPELLGGPSVFLFPPKPKDTLMISRTPEVTCVVV DVSHEDPEVKFNWYVDGVEVHNAKTKPREEQYNSTYRVVSV LTVLHQDWLNGKEYKCKVSNKALPAPIEKTISKAKGQPREPQV CTLPPSRDELTKNQVSLSCAVKGFYPSDIAVEWESNGQPENNY KTTPPVLDSDGSFFLVSKLTVDKSRWQQGNVFSCSVMHEALH NRYTQKSLSLSP | Hole Fc |
| 445 | DKTHTCPPCPAPGGPSVFLFPPKPKDTLMISRTPEVTCVVVDVS HEDPEVKFNWYVDGVEVHNAKTKPREEQYNSTYRVVSVLTVL HQDWLNGKEYKCKVSNKALPAPIEKTISKAKGQPREPQVCTLP PSRDELTKNQVSLSCAVKGFYPSDIAVEWESNGQPENNYKTTP PVLDSDGSFFLVSKLTVDKSRWQQGNVFSCSVMHEALHNRYT QKSLSLSP | Hole Fc |
| 446 | DKTHTCPPCPAPELLGGPSVFLFPPKPKDTLYISRTPEVTCVVVD VSHEDPEVKFNWYVDGVEVHNAKTKPREEQYNSTYRVVSVLT VLHQDWLNGKEYKCKVSNKALPAPIEKTISKAKGQPREPQVYT LPPCRDELTKNQVSLWCLVKGFYPSDIAVEWESNGQPENNYKT TPPVLDSDGSFFLYSKLTVDKSRWQQGNVFSCSVVHEALHNH YTQKSLSLSP | Knob Fc |
| 447 | DKTHTCPPCPAPGGPSVFLFPPKPKDTLYISRTPEVTCVVVDVS HEDPEVKFNWYVDGVEVHNAKTKPREEQYNSTYRVVSVLTVL HQDWLNGKEYKCKVSNKALPAPIEKTISKAKGQPREPQVYTLP PCRDELTKNQVSLWCLVKGFYPSDIAVEWESNGQPENNYKTTP PVLDSDGSFFLYSKLTVDKSRWQQGNVFSCSVVHEALHNHYT QKSLSLSP | Knob Fc |
| 448 | DKTHTCPPCPAPELLGGPSVFLFPPKPKDTLYISRTPEVTCVVVD VSHEDPEVKFNWYVDGVEVHNAKTKPREEQYNSTYRVVSVLT VLHQDWLNGKEYKCKVSNKALPAPIEKTISKAKGQPREPQVCT LPPSRDELTKNQVSLSCAVKGFYPSDIAVEWESNGQPENNYKT TPPVLDSDGSFFLVSKLTVDKSRWQQGNVFSCSVVHEALHNRY TQKSLSLSP | Hole Fc |
| 449 | DKTHTCPPCPAPGGPSVFLFPPKPKDTLYISRTPEVTCVVVDVS HEDPEVKFNWYVDGVEVHNAKTKPREEQYNSTYRVVSVLTVL HQDWLNGKEYKCKVSNKALPAPIEKTISKAKGQPREPQVCTLP PSRDELTKNQVSLSCAVKGFYPSDIAVEWESNGQPENNYKTTP PVLDSDGSFFLVSKLTVDKSRWQQGNVFSCSVVHEALHNRYT QKSLSLSP | Hole Fc |

-continued

| # | SEQUENCE | ANNOTATION |
|---|---|---|
| 450 | PGGGG | linker |
| 451 | QAVVTQEPSLTVSPGGTVTLTCGSSTGAVTTSNYANWVQQKP GKSPRGLIGGTNKRAPGVPARFSGSLLGGKAALTISGAQPEDEA DYYCALWYSNHWVFGGGTKLTVL | CD3-VL20 |
| 452 | QAVVTQEPSLTVSPGGTVTLTCGSSTGAVTTSNYANWVQQKP GKSPRGLIGGTNKRAPGVPARFSGSLLGGKAALTISGAQPEDEA DYYCALWYSNHWVFGCGTKLTVL | CD3-VL21 |
| 453 | EVQLVESGGGLVQPGGSLRLSCAASGFTFSTYAMNWVRQAPG KGLEWVGRIRSKYNNYATYYADSVKGRFTISRDDSKNTLYLQ MNSLRAEDTAVYYCVRHGNFGDSYVSWFAYWGQGTLVTVSS | CD3-VH32 |
| 454 | EVQLVESGGGLVQPGGSLRLSCAASGFTFSTYAMNWVRQAPG KCLEWVARIRSKYNNYATYYADTVKGRFTISRDDAKNTLYLQ MSSLRAEDTAVYYCVRHGNFGDSYVSWFAYWGQGTLVTV | CD3-VH34 |
| 455 | EVQLVESGGGEVQPGGSLRLSCGPSEIITSDKSMGWVRQAPGK QRNLVAGISNVGSTNYAQSVKGRFTISRDNAKNTVYLQMSSLR AEDTAVYYCYARDFENEYWGQGTLVTVKP | hz8E7v16 |
| 456 | EIITSDKSMG | CDR-H1 (L8E7, hz8E7v13, 15, 16) |
| 457 | GFSFSINAMG | 41BB CDR1 |
| 458 | AIESGRNTV | 41BB CDR2 |
| 459 | LKGNRVVSPSVAY | 41BB CDR3 |
| 460 | EVQLVESGGGLVQPGGSLRLSCAASGFTFSTYAMNWVRQAPG KCLEWVGRIRSKYNNYATYYADSVKGRFTISRDDSKNTLYLQ MNSLRAEDTAVYYCVRHGNFGDSYVSWFAYWGQGTLVTVSS | CD3-VH33 |
| 461 | GFTFNTYAMN | anti-CD3 VH CDR1 |
| 462 | RIRSKYNNYATY | anti-CD3 VH CDR2 |
| 463 | HGNFGDSYVSWFAY | CD3-VH7, VH33 CDR3 |
| 464 | ALWYSNHWV | CD3-VL2, VL21 CDR3 |
| 465 | VLWYSNRWV | CD3-VL8 CDR3 |
| 466 | GFTFSTYAMN | CD3 VH33 CDR1 |
| 467 | RIRSKYNNYATY | CD3 VH33 CDR2 |
| 468 | GSSTGAVTTSNYAN | CD3 VL21 CDR1 |
| 469 | GTNKRAP | CD3 VL21 CDR2 |
| 470 | EVQLVESGGGEVQPGGSLRLSCAASGFSFSINAMGWYRQAPG KRREFVAAIESGRNTVYAESVKGRFTISRDNAKNTVYLQMSSL RAEDTAVYYCGLLKGNRVVSPSVAYWGQGTLVTVKP | 41BB sdAb |
| 471 | IEPDP | Linker |
| 472 | DKTHTCPPCPAPPVAGPSVFLFPPKPKDTLMISRTPEVTCVVVD VKHEDPEVKFNWYVDGVEVHNAKTKPREEEYNSTYRVVSVLT VLHQDWLNGKEYKCKVSNKALPAPIEKTISKAKGQPREPQVYT LPPSREEMTKNQVSLTCDVSGFYPSDIAVEWESDGQPENNYKT TPPVLDSDGSFFLYSKLTVDKSRWEQGDVFSCSVMHEALHNH YTQKSLSLSPGK | Fc-Het-1 |
| 473 | DKTHTCPPCPAPPVAGPSVFLFPPKPKDTLMISRTPEVTCVVVD VKHEDPEVKFNWYVDGVEVHNAKTKPREEQYNSTYRVVSVL TVLHQDWLNGKEYKCKVSNKALPAPIEKTISKAKGQPREPQVY TLPPSREQMTKNQVKLTCLVKGFYPSDIAVEWESNGQPENNYK | Fc-Het-2 |

-continued

| # | SEQUENCE | ANNOTATION |
|---|---|---|
| | TTPPVLDSDGSFFLYSKLTVDKSRWQQGNVFSCSVMHEALHN<br>HYTQKSLSLSPGK | |
| 474 | GGS(GGS)n, where n = to 10 | linker |
| 475 | AGVFELQIHSFGPGPGPAPRSPCSARLPCRLFFRVCLKPGLSEE<br>AAESPCALGAALSARGPVYTEQPGAPAPDLPLPDGLLQVPFRD<br>AWPGTFSFIIETWREELGDQIGGPAWSLLARVAGRRRLAAGGP<br>WARDIQRAGAWELRFSYRARCEPPAVGTACTRLCRPRSAPSRC<br>GPGLRPCAPLEDECEAPLVCRAGCSPEHGFCEQPGECRCLEGW<br>TGPLCTVPVSTSSCLSPRGPSSATTGCLVPGPGPCDGNPCANGG<br>SCSETPRSFECTCPRGFYGLRCEVSGVTCADGPCFNGGLCVGG<br>ADPDSAYICHCPPGFQGSNCEKRVDRCSLQPCRNGGLCLDLGH<br>ALRCRCRAGFAGPRCEHDLDDCAGRACANGGTCVEGGGAHR<br>CSCALGFGGRDCRERADPCAARPCAHGGRCYAHFSGLVCACA<br>PGYMGARCEFPVHPDGASALPAAPPGLRPGDPQRYL | DLL3 ECD; amino<br>acids 27-492 of<br>human DLL3,<br>UniProt No.<br>Q9NYJ7 |
| 476 | EVQLVESGGGEVQPGGSLRLSCGPSEIITSDKSMGWWRQAPGK<br>QRNLVAGISNVGSTNYAQSVKGRFTISRDNAKNTVYLQMSSLR<br>AEDTAVYYCYARDFENEYWGQGTLVTVKP | hz8E7v13 |
| 477 | EVQLVESGGGEVQPGGSLRLSCGPSEIITSDKSVGWVRQAPGK<br>QRNLVAGISNVGSTNYAQSVKGRFTISRDNAKNTVYLQMSSLR<br>AEDTAVYYCYARDFENEYWGQGTLVTVKP | hz8E7v14 |
| 478 | EVQLVESGGGEVQPGGSLRLSCGPSEIITSDKSMGWVRQAPGK<br>QRNLVAGISNVGSTNYAQSVKGRFTISRDNAKNTLYLQMSSLR<br>AEDTAVYYCYARDFENEYWGQGTLVTVKP | hz8E7v15 |
| 479 | EVQLVESGGGEVQPGGSLRLSCAASGSIFSINAMGWYRQAPGK<br>QRELVAGFTGDGMTKYAESVKGRFTISRDNAKNTVYLQMSSL<br>RAEDTAVYYCAADVFTDRDHVDWYWGQGTLVTVKP | hz3G3v1 |
| 480 | EVQLVESGGGEVQPGGSLRLSCAASEITFSDKTVGWYRQAPGK<br>QRVLVAVISNVDSTNYAESVKGRFTISRDNAKNTVYLQMSSLR<br>AEDTAVYYCHARDFENEYWGQGTLVTVKP | hz6C5v2 |
| 481 | EVQLVESGGGEVQPGGSLRLSCAASGSIFSINAMGWYRQAPGK<br>QRELVAGFTGDGSTKYAESVKGRFTISRDNAKNTVYLQMSSLR<br>AEDTAVYYCAADVQLLNSDYEFYWGQGTLVTVKP | hz3C5v1 |
| 482 | EVQLVESGGGEVQPGGSLRLSCAASGSIFSINAMGWYRQPPGK<br>QRELVAGFTGDGSTKYAESVKGRFTISRDNAKNTVYLQMSSLR<br>AEDTAVYYCAADVQLLNSDYEFYWGQGTLVTVKP | hz3C5v2 |
| 483 | EVQLVESGGGEVQPGGSLRLSCAASGSIFSINAMGWYRQAPGK<br>QRELVAGFTGDTSTKYAESVKGRFTISRDNAKNTVYLQMSSLR<br>AEDTAVYYCAADVQLLNSDYEFYWGQGTLVTVKP | hz3C5v3 |
| 484 | EVQLVESGGGEVQPGGSLRLSCAASGSIFSINAMGWYRQAPGK<br>QRELVAGFTGEGSTKYAESVKGRFTISRDNAKNTVYLQMSSLR<br>AEDTAVYYCAADVQLLNSDYEFYWGQGTLVTVKP | hz3C5v4 |
| 485 | EVQLVESGGGEVQPGGSLRLSCAASGSIFSINAMGWYRQAPGK<br>QRELVAGFTGDGSTKYAESVKGRFTISRDNAKNTVYLQMSSLR<br>AEDTAVYYCAADVQLLSSDYEFYWGQGTLVTVKP | hz3C5v5 |
| 486 | EVQLVESGGGEVQPGGSLRLSCAASGSIFSINAMGWYRQAPGK<br>QRELVAGFTGDGSTKYAESVKGRFTISRDNAKNTVYLQMSSLR<br>AEDTAVYYCAADVQLLTSDYEFYWGQGTLVTVKP | hz3C5v6 |
| 487 | EVQLVESGGGEVQPGGSLRLSCAASGSIFSINAMGWYRQAPGK<br>QRELVAGFTGDGSTKYAESVKGRFTISRDNAKNTVYLQMSSLR<br>AEDTAVYYCAADVQLLQSDYEFYWGQGTLVTVKP | hz3C5v7 |
| 488 | EVQLVESGGGEVQPGGSLRLSCAASGSIFSINAMGWYRQAPGK<br>QRELVAGFTGDGSTKYAESVKGRFTISRDNAKNTVYLQMSSLR<br>AEDTAVYYCAADVQLLNTDYEFYWGQGTLVTVKP | hz3C5v8 |
| 489 | QVQLVQSGGGLVQPGGSLRLSCVASGSMTGANTMGWYRQAP<br>GKQRDLVALIGNYHYADSVKGRFTISRENAKNTVILQMNSLNP<br>EDTAVYYCYLYTDNLGTSWGQGTLVTVKP | 18H10 |

-continued

| # | SEQUENCE | ANNOTATION |
|---|---|---|
| 490 | EVQLVESGGGEVQPGGSLRLSCAASGSMTGANTMGWYRQAP GKGRDLVSLIGNYVTHYAESVKGRFTISRDNAKNTLYLQMSSL RAEDTAVYYCYLYTDNLGTSWGQGTLVTVKP | hz18H10v1 |
| 491 | EVQLVESGGGEVQPGGSLRLSCAASGSMTGANTMGWYRQAP GKQRDLVSLIGNYVTHYAESVKGRFTISRDNAKNTLYLQMSSL RAEDTAVYYCYLYTDNLGTSWGQGTLVTVKP | hz18H10v2 |
| 492 | EVQLVESGGGEVQPGGSLRLSCAASGSMTGANTMGWYRQAP GKQRDLVSLIGNYVTHYAESVKGRFTISRDNAKNTVYLQMSSL RAEDTAVYYCYLYTDNLGTSWGQGTLVTVKP | hz18H10v3 |
| 493 | EVQLVESGGGEVQPGGSLRLSCAASGSMTGANTMGWYRQAP GKQRDLVALIGNYVTHYAESVKGRFTISRDNAKNTVYLQMSS LRAEDTAVYYCYLYTDNLGTSWGQGTLVTVKP | hz18H10v4 |
| 494 | EVQLVESGGGEVQPGGSLRLSCAASGSMTGANTMGWYRQAP GKQRDLVALIGNYVTHYAESVKGRFTISRENAKNTVYLQMSSL RAEDTAVYYCYLYTDNLGTSWGQGTLVTVKP | hz18H10v5 |
| 495 | EVQLVESGGGEVQPGGSLRLSCAASGSVTGANTMGWYRQAPG KQRDLVALIGNYVTHYAESVKGRFTISRDNAKNTVYLQMSSLR AEDTAVYYCYLYTDNLGTSWGQGTLVTVKP | hz18H10v6 |
| 496 | EVQLVESGGGEVQPGGSLRLSCAASGSITGANTMGWYRQAPG KQRDLVALIGNYVTHYAESVKGRFTISRDNAKNTVYLQMSSLR AEDTAVYYCYLYTDNLGTSWGQGTLVTVKP | hz18H10v7 |
| 497 | EVQLVESGGGEVQPGGSLRLSCAASGSVTGANTMGWYRQAPG KQRDLVSLIGNYVTHYAESVKGRFTISRDNAKNTLYLQMSSLR AEDTAVYYCYLYTDNLGTSWGQGTLVTVKP | hz18H10v8 |
| 498 | EVQLVESGGGEVQPGGSLRLSCAASGSVTGANTMGWYRQAPG KQRDLVSLIGNYVTHYAESVKGRFTISRDNAKNTVYLQMSSLR AEDTAVYYCYLYTDNLGTSWGQGTLVTVKP | hz18H10v9 |
| 499 | EVQLVESGGGEVQPGGSLRLSCAASGSMTGANTMGWYRQAP GKQRDLVSLIGNYVTHYAESVKGRFTISRENAKNTVYLQMSSL RAEDTAVYYCYLYTDNLGTSWGQGTLVTVKP | hz18H10v10 |
| 500 | EVQLVESGGGEVQPGGSLRLSCAASGSVTGANTMGWYRQAPG KQRDLVSLIGNYVTHYAESVKGRFTISRENAKNTVYLQMSSLR AEDTAVYYCYLYTDNLGTSWGQGTLVTVKP | hz18H10v11 |
| 501 | EVQLVESGGGEVQPGGSLRLSCAASGSVTGANTMGWYRQAPG KQRDLVALIGNYVTHYAESVKGRFTISRENAKNTVYLQMSSLR AEDTAVYYCYLYTDNLGTSWGQGTLVTVKP | hz18H10v12 |
| 502 | EVQLVESGGGEVQPGGSLRLSCAASGSMTGANTMGWYRQAP GKQRELVALIGNYVTHYAESVKGRFTISRENAKNTVYLQMSSL RAEDTAVYYCYLYTDNLGTSWGQGTLVTVKP | hz18H10v13 |
| 503 | EVQLVESGGGEVQPGGSLRLSCAASGSVTGANTMGWYRQAPG KQRDLVALIGNYVTHYAESVKGRFTISRDNAKNTLYLQMSSLR AEDTAVYYCYLYTDNLGTSWGQGTLVTVKP | hz18H10v14 |
| 504 | EVQLVESGGGEVQPGGSLRLSCAASGSITGANTMGWYRQAPG KQRDLVALIGNYVTHYAESVKGRFTISRDNAKNTLYLQMSSLR AEDTAVYYCYLYTDNLGTSWGQGTLVTVKP | hz18H10v15 |
| 505 | EVQLVESGGGEVQPGGSLRLSCAASGSITGANTMGWYRQAPG KQRDLVALIGNYVTHYAESVKGRFTISRENAKNTVYLQMSSLR AEDTAVYYCYLYTDNLGTSWGQGTLVTVKP | hz18H10v16 |
| 506 | EVQLVESGGGEVQPGGSLRLSCAASGSITGANTMGWYRQAPG KQRDLVALIGNYVTHYAESVKGRFTISRDNAKNTVYLQMNSL RAEDTAVYYCYLYTDNLGTSWGQGTLVTVKP | hz18H10v17 |
| 507 | QVQLVQSGGGLVQAGGSLRLSCGASEIIFSDKTVGWYRQAPGK QRVLVAVISNVDSTNYAQSVKGRFTISRDNAKNTVYLQMNSL KPEDTAVYYCYARDFESEYWGRGTQVTVKP | L6F1 |

-continued

| # | SEQUENCE | ANNOTATION |
|---|---|---|
| 508 | EVQLVESGGGEVQPGGSLRLSCAASEIIFSDKTVGWYRQAPGK QRVLVAVISNVDSTNYAESVKGRFTISRDNAKNTLYLQMSSLR AEDTAVYYCYARDFESEYWGQGTLVTVKP | hz6F1v1 |
| 509 | EVQLVESGGGEVQPGGSLRLSCAASEIIFSDKTVGWYRQAPGK QRVLVAVISNVDSTNYAESVKGRFTISRDNAKNTVYLQMSSLR AEDTAVYYCYARDFESEYWGQGTLVTVKP | hz6F1v2 |
| 510 | EVQLVESGGGEVQPGGSLRLSCAASEIIFSDKTVGWYRQAPGK QRVLVAVISNVDSTNYAQSVKGRFTISRDNAKNTVYLQMSSLR AEDTAVYYCYARDFESEYWGQGTLVTVKP | hz6F1v3 |
| 511 | EVQLVESGGGEVQPGGSLRLSCGASEIIFSDKTVGWYRQAPGK QRVLVAVISNVDSTNYAESVKGRFTISRDNAKNTVYLQMSSLR AEDTAVYYCYARDFESEYWGQGTLVTVKP | hz6F1v4 |
| 512 | EVQLVESGGGEVQPGGSLRLSCAASEIIFSDKTVGWYRQAPGK QRVLVAVISNVDSTNYAESVKGRFTISRDNAKNTVYLQMSSLR AEDTAVYYCYARDFESEYWGRGTQVTVKP | hz6F1v5 |
| 513 | EVQLVESGGGEVQPGGSLRLSCAASEIIFSDKTVGWYRQAPGK QRVLVAVISNVESTNYAESVKGRFTISRDNAKNTVYLQMSSLR AEDTAVYYCYARDFESEYWGQGTLVTVKP | hz6F1v6 |
| 514 | EVQLVESGGGEVQPGGSLRLSCAASEIIFSDKTVGWYRQAPGK QRVLVAVISNVDATNYAESVKGRFTISRDNAKNTVYLQMSSLR AEDTAVYYCYARDFESEYWGQGTLVTVKP | hz6F1v7 |
| 515 | QVQLQESGGGLVQAGGSLTLSCAASGSIFSINAMGWYRQGDL VAGFTSEGSAKYADSVKGRFTISRDDAKNMVTLQMNSLKPED TAVYYCAADIFSDRDHVDWYWGQGTLVTVKP | 5H8 |
| 516 | QVQLQESGGGLVQSGGSLRLSCAASGFSLDDYTIGWFRQAPGK EREGVSCISSSGGSTYYADSVKGRFTISRDNAENTVYLQMNSL KPEDTAVYYCATYCPVTIADELGFDYWGQGTLVTVKP | 3B12 |
| 517 | QVTLRESGGGLVQAGGSLRLSCGASEITLSDKTVGWYRQAPG KQRVLVAVISNVDSTNYAHSVKGRFTISRDNAKNTVYLQMNS LKPEDTAVYYCYARDFEAEYWGQGTLVTVKP | 6B4 |
| 518 | QVQLVQSGGGLVQAGGSLRLSCAASGFSLDDYTIGWFRQAPG KEREGVSCISSSGGSTVHADSVKGRFTISRDNAKNTVWLQMNS LKPEDTAVYYCATWCGVATMTEDLPFDYWGQGTLVTVKP | 6A1 |
| 519 | EVQLVESGGGLVQPGRSLRLSCAASGFTFDDYAMHWVRQAPG KGLEWVSGISWNSGSIGYADSVKGFTISRDNAKNSLYLQMNSL RAEDTALYYCAKDSRGYGDYRLGGAYWGQGTLVTVSS | Anti-CD3 VH 312557 |
| 520 | EVQLVESGGGLVQPGRSLRLSCAASGFTFDDYAMHWVRQAPG KCLEWVSGISWNSGSIGYADSVKGFTISRDNAKNSLYLQMNSL RAEDTALYYCAKDSRGYGDYRLGGAYWGQGTLVTVSS | Anti-CD3 VH 312557 G44C |
| 521 | EIVMTQSPATLSVSPGERATLSCRASQSVSSNLAWYQQKPGQA PRLLIYGASTRATGIPARFSGSGSGTEFTLTISSLQSEDFAVYYC QQYNNWPWTFGQGTKVEIK | Anti-CD3 VL 312557 |
| 522 | EIVMTQSPATLSVSPGERATLSCRASQSVSSNLAWYQQKPGQA PRLLIYGASTRATGIPARFSGSGSGTEFTLTISSLQSEDFAVYYC QQYNNWPWTFGCGTKVEIK | Anti-CD3 VL 312557Q100C |
| 523 | EVQLVESGGGLVQPGRSLRLSCVASGFTFDDYSMHWVRQAPG KGLEWVSGISWNSGSKDYADSVKGRFTISRDNAKNSLYLQMN SLRAEDTALYYCAKYGSGYGKFYHYGLDVWGQGTTVTVSS | CD3-VH-G |
| 524 | EVQLVESGGGLVQPGRSLRLSCVASGFTFDDYSMHWVRQAPG KCLEWVSGISWNSGSKDYADSVKGRFTISRDNAKNSLYLQMN SLRAEDTALYYCAKYGSGYGKFYHYGLDVWGQGTTVTVSS | CD3-VH-G |
| 525 | DIQMTQSPSSLSASVGDRVTITCRASQSISSYLNWYQQKPGKAP KLLIYAASSLQSGVPSRFSGSGSGTDFTLTISSLQPEDFATYYCQ QSYSTPPITFGQGTRLEIK | $V_{K1}$-39R5 |

| # | SEQUENCE | ANNOTATION |
|---|---|---|
| 526 | DIQMTQSPSSLSASVGDRVTITCRASQSISSYLNWYQQKPGKAP KLLIYAASSLQSGVPSRFSGSGSGTDFTLTISSLQPEDFATYYCQ QSYSTPPITFGCGTRLEIK | $V_{K1}$-39J$\kappa$5Q100C |
| 527 | (ADAAP)n<br>n = 2-20 | linker |
| 528 | (ADAAP)n-G<br>n = 2-20 | linker |
| 529 | (GEPQG)n<br>n = 2-20 | linker |
| 530 | (GEPQG)n-G<br>n = 2-20 | linker |
| 531 | (AGGEP)n<br>n = 2-20 | linker |
| 532 | (AGGEP)n-G<br>n = 2-20 | linker |
| 533 | (AGSEP)n<br>n = 2-20 | linker |
| 534 | (AGSEP)n-G<br>n = 2-20 | linker |
| 535 | (GGGEQ)n<br>n = 2-20 | linker |
| 536 | (GGGEQ)n-G<br>n = 2-20 | linker |
| 537 | ADAAPADAAPG | linker |
| 538 | GEPQGGEPQGG | linker |
| 539 | AGGEPAGGEPG | linker |
| 540 | AGSEPAGSEPG | linker |
| 541 | GGGEQGGGEQG | linker |

The invention claimed is:

1. A DLL3-binding polypeptide construct, comprising at least one heavy chain only variable domain (DLL3 VHH domain) wherein the at least one DLL3 VHH domain comprises a CDR1, CDR2 and CDR3 set forth in SEQ ID NOS: 319, 336 and 354, respectively; SEQ ID NOS: 319, 337 and 354, respectively; SEQ ID NOS: 319, 338 and 354, respectively; SEQ ID NOS: 320, 338 and 354, respectively; SEQ ID NOS: 321, 338 and 354, respectively; SEQ ID NOS: 322, 338 and 354, respectively; SEQ ID NOS: 323, 338 and 354, respectively; SEQ ID NOS: 324, 338 and 354, respectively; SEQ ID NOS: 325, 338 and 354, respectively; SEQ ID NOS: 326, 338 and 354, respectively; SEQ ID NO: 327, 339 and 355, respectively; SEQ ID NOS: 328, 340 and 356, respectively; SEQ ID NOS: 329, 340 and 356, respectively, SEQ ID NOS: 456, 340 and 356, respectively; SEQ ID NOS: 320, 341, and 357, respectively; SEQ ID NOS: 330, 342, and 358, SEQ ID NOS: 330, 343 and 358, respectively; SEQ ID NOS: 330, 344 and 358, respectively; respectively; SEQ ID NOS: 320, 345 and 359, respectively; SEQ ID NOS: 320, 346, and 359, respectively; SEQ ID NOS: 320, 347, and 359, respectively; SEQ ID NOS: 320, 345 and 360, respectively; SEQ ID NOS: 320, 345 and 361, respectively; SEQ ID NOS: 320, 347 and 360, respectively; SEQ ID NOS: 331, 348 and 356, respectively; SEQ ID NOS: 331, 349 and 356, respectively; SEQ ID NOS: 331, 350 and 356, respectively; SEQ ID NOS: 332, 348 and 362, respectively; SEQ ID NOS: 332, 349 and 362, respectively; SEQ ID NOS: 332, 350 and 362, respectively; SEQ ID NOS: 320, 384 and 395, respectively; SEQ ID NOS: 320, 410 and 395, respectively; SEQ ID NOS: 320, 411 and 395, respectively; SEQ ID NOS: 320, 384 and 412, respectively; SEQ ID NOS: 320, 384 and 413, respectively; SEQ ID NOS: 320, 384 and 414, respectively; SEQ ID NOS: 320, 384 and 415, respectively; SEQ ID NOS: 333, 351, and 363, respectively; 334, 352 and 364, respectively; 320, 353 and 365, respectively; 334, 339 and 366, respectively; or 335, 348 and 367, respectively, and binds DLL3.

2. The DLL3-binding polypeptide construct of claim 1, comprising one or more additional binding domain that binds to a target other than DLL3.

3. The DLL3-binding polypeptide construct of claim 1, wherein the at least one DLL3 VHH domain is humanized.

4. The DLL3-binding polypeptide construct of claim 1, wherein the one or more additional binding domains binds to an activating receptor on an immune cell.

5. The DLL3-binding polypeptide construct of claim 4, wherein the activating receptor is CD3.

6. The DLL3-binding polypeptide construct of claim 1, wherein the polypeptide comprises an immunoglobulin Fc region.

7. The DLL3-binding polypeptide construct of claim 1 that is a dimer.

8. The DLL3-binding polypeptide construct of claim 6, wherein the Fc region is a heterodimeric Fc region.

9. The DLL3-binding polypeptide construct of claim 1, wherein the at least one DLL3 VHH domain comprises:

(a) the sequence set forth in (i) SEQ ID NO: 244, (ii) a humanized variant of SEQ ID NO: 244, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 244, and binds DLL3;

(b) the sequence set forth in (i) SEQ ID NO:258, (ii) a humanized variant of SEQ ID NO: 258, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 258, and binds DLL3;

(c) the sequence set forth in (i) SEQ ID NO: 264, (ii) a humanized variant of SEQ ID NO: 264, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 264, and binds DLL3;

(d) the sequence set forth in (i) SEQ ID NO: 275 (ii) a humanized variant of SEQ ID NO: 275, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 275, and binds DLL3;

(e) the sequence set forth in (i) SEQ ID NO: 280 (ii) a humanized variant of SEQ ID NO: 280, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 280, and binds DLL3;

(f) the sequence set forth in (i) SEQ ID NO: 287, (ii) a humanized variant of SEQ ID NO: 287, or (iii) a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 287, and binds DLL3;

(g) the sequence set forth in (i) SEQ ID NO: 299, (ii) a humanized variant of SEQ ID NO: 299, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 299, and binds DLL3;
(h) the sequence set forth in (i) SEQ ID NO: 507, (ii) a humanized variant of SEQ ID NO: 507, or (iii) a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 507, and binds DLL3;
(i) the sequence set forth in (i) SEQ ID NO: 401, (ii) a humanized variant of SEQ ID NO: 401, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 401, and binds DLL3;
(j) the sequence set forth in (i) SEQ ID NO: 314, (ii) a humanized variant of SEQ ID NO: 314, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 314, and binds DLL3;
(k) the sequence set forth in (i) SEQ ID NO: 515, (ii) a humanized variant of SEQ ID NO: 515, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 515, and binds DLL3;
(l) the sequence set forth in (i) SEQ ID NO: 516, (ii) a humanized variant of SEQ ID NO: 516, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 516, and binds DLL3;
(m) the sequence set forth in (i) SEQ ID NO: 517, (ii) a humanized variant of SEQ ID NO: 517, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 517, and binds DLL3; or
(n) the sequence set forth in (i) SEQ ID NO: 518, (ii) a humanized variant of SEQ ID NO: 518, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 518, and binds DLL3.

10. The DLL3-binding polypeptide construct of claim 1, wherein:
(a) the at least one DLL3 VHH domain comprises the sequence of amino acids set forth in any one of SEQ ID NOs: 245-257 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 245-257, and binds DLL3;
(b) the at least one DLL3 VHH domain comprises the sequence of amino acids set forth in any one of SEQ ID NOs: 259-263 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOs: 259-263, and binds DLL3;
(c) the at least one DLL3 VHH domain comprises the sequence of amino acids set forth in any one of SEQ ID NOs: 265-274, 416, 455, or 476-478, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOs: 265-274, 416, 455, or 476-478, and binds DLL3;
(d) the at least one DLL3 VHH domain comprises the sequence of amino acids set forth in any one of SEQ ID NOs: 277-279 and 479 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOs: 277-279 and 479, and binds DLL3;
(e) the at least one DLL3 VHH domain comprises the sequence of amino acids set forth in any one of SEQ ID NOs: 281-286 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 281-286, and binds DLL3;
(f) the at least one DLL3 VHH domain comprises the sequence of amino acids set forth in any one of SEQ ID NOs: 288-298 and 102 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOs: 288-298 and 102, and binds DLL3;
(g) the at least one DLL3 VHH domain comprises the sequence of amino acids set forth in any one of SEQ ID NOs: 300, 302-305, and 480 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO: 300, 302-305, and 480, and binds DLL3;
(h) the at least one DLL3 VHH domain comprises the sequence of amino acids set forth in any one of SEQ ID NOs: 307-313, and 508-514 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOs: 508-514, and binds DLL3;
(i) the at least one DLL3 VHH domain comprises the sequence of amino acids set forth in any one of SEQ ID NOs: 402-409, and 481-488 or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOs: 481-488, and binds DLL3; or
(j) the at least one DLL3 VHH domain comprises the sequence set forth in (i) SEQ ID NO: 314, 518, 515, 516 or 517 (ii) a humanized variant of SEQ ID NO: 314, 518, 515, 516 or 517, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 314, 518, 515, 516 or 517, and binds DLL3.

11. The DLL3-binding polypeptide construct of claim 1 that is a multispecific polypeptide construct, the multispecific polypeptide construct comprising: (a) a first component comprising a heterodimeric Fc region comprising a first Fc polypeptide and a second Fc polypeptide and (b) a second component comprising an anti-CD3 antibody or antigen-binding fragment comprising a variable heavy chain region (VH) and a variable light chain region (VL), wherein:
the VH and VL that comprise the anti-CD3 antibody or antigen binding fragment are linked to opposite polypeptides of the heterodimeric Fc;
the first and second components are coupled by a linker, wherein the heterodimeric Fc region is positioned N-terminal to the anti-CD3 antibody; and
one or both of the first and second components comprises the at least one DLL3 VHH domain.

12. The DLL3-binding polypeptide construct of claim 11, wherein each of the first and second Fc polypeptides of the heterodimeric Fc region comprise a knob-into-hole modification or comprise a charge mutation to increase electrostatic complementarity of the polypeptides.

13. The DLL3-binding polypeptide construct of claim 11, wherein the anti-CD3 antibody or antigen binding fragment is an Fv antibody fragment.

14. The DLL3-binding polypeptide construct of claim 13, wherein the Fv antibody fragment comprises a disulfide stabilized anti-CD3 binding Fv fragment (dsFv).

15. The DLL3-binding polypeptide construct of claim 11, wherein the anti-CD3 antibody or antigen-binding fragment comprises:
- a VH CDR1 comprising the amino acid sequence TYAMN (SEQ ID NO: 29); a VH CDR2 comprising the amino acid sequence RIRSKYNNYATYYADSVKD (SEQ ID NO: 30); a VH CDR3 comprising the amino acid sequence HGNFGNSYVSWFAY (SEQ ID NO: 31), a VL CDR1 comprising the amino acid sequence RSSTGAVTTSNYAN (SEQ ID NO: 32); a VL CDR2 comprising the amino acid sequence GTNKRAP (SEQ ID NO: 33); and a VL CDR3 comprising the amino acid sequence ALWYSNLWV (SEQ ID NO: 34);
- a VH CDR1 comprising the amino acid sequence GFTFNTYAMN (SEQ ID NO: 461); a VH CDR2 comprising the amino acid sequence RIRSKYNNYATY (SEQ ID NO: 462); a VH CDR3 comprising the amino acid sequence HGNFGNSYVSWFAY (SEQ ID NO: 31), a VL CDR1 comprising the amino acid sequence RSSTGAVTTSNYAN (SEQ ID NO: 32); a VL CDR2 comprising the amino acid sequence GTNKRAP (SEQ ID NO: 33); and a VL CDR3 comprising the amino acid sequence ALWYSNLWV (SEQ ID NO: 34);
- a VH CDR1 comprising the amino acid sequence GFTFNTYAMN (SEQ ID NO: 461); a VH CDR2 comprising the amino acid sequence RIRSKYNNYATY (SEQ ID NO: 462); a VH CDR3 comprising the amino acid sequence HGNFGNSYVSWFAY (SEQ ID NO: 31), a VL CDR1 comprising the amino acid sequence GSSTGAVTTSNYAN (SEQ ID NO: 468); a VL CDR2 comprising the amino acid sequence GTNKRAP (SEQ ID NO: 469); and a VL CDR3 comprising the amino acid sequence ALWYSNHWV (SEQ ID NO: 464); or
- a VH CDR1 comprising the amino acid sequence GFTFSTYAMN (SEQ ID NO: 466); a VH CDR2 comprising the amino acid sequence RIRSKYNNYATY (SEQ ID NO: 467); a VH CDR3 comprising the amino acid sequence HGNFGDSYVSWFAY (SEQ ID NO: 463), a VL CDR1 comprising the amino acid sequence GSSTGAVTTSNYAN (SEQ ID NO: 468); a VL CDR2 comprising the amino acid sequence GTNKRAP (SEQ ID NO: 469); and a VL CDR3 comprising the amino acid sequence ALWYSNHWV (SEQ ID NO: 464).

16. The DLL3-binding polypeptide construct of claim 11, wherein the anti-CD3 antibody or antigen-binding fragment comprises:
- a VH having the amino acid sequence of any of SEQ ID NOS: 35-65, 453, 460 and 454 or a sequence that exhibits at least 90%, 91%, 92%, 93%, 94%, 95%, 96%, 97%, 98% or 99% sequence identity to any of SEQ ID NOS: 35-65; and
- a VL having the amino acid sequence of any of SEQ ID NOS: 66-84, 368, 451 and 452 or a sequence that exhibits at least 90%, 91%, 92%, 93%, 94%, 95%, 96%, 97%, 98% or 99% sequence identity to any of SEQ ID NOS: 66-84 and 368.

17. The DLL3-binding polypeptide construct of claim 11, wherein the at least one DLL3 VHH domain is positioned amino-terminally relative to the Fc region and/or carboxy-terminally relative to the CD3 binding region of the multispecific polypeptide construct.

18. The DLL3-binding polypeptide construct of claim 11, wherein the multispecific polypeptide construct comprises a first DLL3 VHH domain that specifically binds DLL3 and a second DLL3 VHH domain that specifically binds DLL3.

19. The DLL3-binding polypeptide construct of claim 18, wherein:
(a) each of the first and second DLL3 VHH domains, independently comprises the VHH domain sequence set forth in any of SEQ ID NOS: 102, 244-275, 277-300, 302-305, 307-314, 401, 416, 455, 476-488, or 507-518, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOS: 102, 244-275, 277-300, 302-305, 314, 401-409, 416, 455, 476-488, or 507-518, and binds DLL3; or
(b) the first VHH domain comprises the amino acid sequence set forth in any one of 251, 264, 267, 268, 287, 299, 507, 314, 517, or 455, a humanized variant thereof, or a sequence of amino acids that exhibits at least 85%, 86%, 87%, 88%, 89%, 90%, 91%, 92%, 93%, 94%, 95%, 96%, 97%, 98%, or 99% sequence identity to any of 251, 264, 267, 268, 287, 299, 507, 314, 517, or 455, and binds DLL3; and
the second VHH domain comprises the amino acid sequence set forth in any one of 244, 251, 258, 267, 275, 280, 314, 518, 515, 516, 517, 455, or a humanized variant thereof, or a sequence of amino acids that exhibits at least 85%, 86%, 87%, 88%, 89%, 90%, 91%, 92%, 93%, 94%, 95%, 96%, 97%, 98%, or 99% sequence identity to any of 244, 251, 258, 267, 275, 280, 314, 518, 515, 516, 517, 455, and binds DLL3.

20. The DLL3-binding polypeptide construct of claim 11, wherein one or both of the first and second component comprises at least one co-stimulatory receptor binding region (CRBR) that binds a co-stimulatory receptor.

21. The DLL3-binding polypeptide construct of claim 11, wherein one or both of the first and second components comprises at least one inhibitory receptor binding region (IRBR) that binds an inhibitory receptor.

22. The DLL3-binding polypeptide construct of claim 11, wherein the linker is a non-cleavable linker.

23. A polynucleotide(s) encoding the DLL3-binding polypeptide construct of claim 1.

24. A polynucleotide(s) encoding the DLL3-binding polypeptide construct of claim 11.

25. A vector comprising the polynucleotide of claim 23.

26. A cell comprising a polynucleotide or polynucleotides of claim 23.

27. A method of producing a DLL3-binding polypeptide construct, the method comprising introducing into a cell a polynucleotide or polynucleotides of claim 23 and culturing the cell under conditions to produce the multispecific polypeptide construct.

28. A pharmaceutical composition comprising the DLL3-binding polypeptide construct of claim 1.

29. A pharmaceutical composition comprising the DLL3-binding polypeptide construct of claim 11.

30. A method of stimulating or inducing an immune response in a subject, the method comprising administering, to a subject in need thereof, the pharmaceutical composition of claim 29.

31. A method of treating a disease or condition in a subject, the method comprising administering, to a subject in need thereof, the pharmaceutical composition of claim 28.

32. A method of treating a disease or condition in a subject, the method comprising administering, to a subject in need thereof, the pharmaceutical composition of claim 29.

* * * * *

SEQUENCE LISTING

<160> NUMBER OF SEQ ID NOS: 541

<210> SEQ ID NO 1
<211> LENGTH: 6
<212> TYPE: PRT
<213> ORGANISM: Artificial Sequence
<220> FEATURE:
<223> OTHER INFORMATION: (GGS)2 linker

<400> SEQUENCE: 1

Gly Gly Ser Gly Gly Ser
1               5

<210> SEQ ID NO 2
<211> LENGTH: 9
<212> TYPE: PRT
<213> ORGANISM: Artificial Sequence
<220> FEATURE:
<223> OTHER INFORMATION: GGS)3  linker

<400> SEQUENCE: 2

Gly Gly Ser Gly Gly Ser Gly Gly Ser
1               5

<210> SEQ ID NO 3
<211> LENGTH: 12
<212> TYPE: PRT
<213> ORGANISM: Artificial Sequence
<220> FEATURE:
<223> OTHER INFORMATION: (GGS)4 linker

<400> SEQUENCE: 3

Gly Gly Ser Gly Gly Ser Gly Gly Ser Gly Gly Ser
1               5                  10

<210> SEQ ID NO 4
<211> LENGTH: 15
<212> TYPE: PRT
<213> ORGANISM: Artificial Sequence
<220> FEATURE:
<223> OTHER INFORMATION: (GGS)5 linker

<400> SEQUENCE: 4

Gly Gly Ser Gly Gly Ser Gly Gly Ser Gly Gly Ser Gly Gly Ser
1               5                  10                  15

<210> SEQ ID NO 5
<211> LENGTH: 4
<212> TYPE: PRT
<213> ORGANISM: Artificial Sequence
<220> FEATURE:
<223> OTHER INFORMATION: glycine linker

<400> SEQUENCE: 5

Gly Gly Gly Gly
1

<210> SEQ ID NO 6
<211> LENGTH: 5
<212> TYPE: PRT
<213> ORGANISM: Artificial Sequence
<220> FEATURE:
<223> OTHER INFORMATION: glycine linker

<400> SEQUENCE: 6

Gly Gly Gly Gly Gly
1               5

<210> SEQ ID NO 7
<211> LENGTH: 6
<212> TYPE: PRT
<213> ORGANISM: Artificial Sequence
<220> FEATURE:
<223> OTHER INFORMATION: glycine linker

<400> SEQUENCE: 7

Gly Gly Gly Gly Gly Gly
1               5

<210> SEQ ID NO 8
<211> LENGTH: 218
<212> TYPE: PRT
<213> ORGANISM: Homo sapiens
<220> FEATURE:
<223> OTHER INFORMATION: human IgG1 Fc

<400> SEQUENCE: 8

Pro Ala Pro Glu Leu Leu Gly Gly Pro Ser Val Phe Leu Phe Pro Pro

```
1               5                   10                  15
Lys Pro Lys Asp Thr Leu Met Ile Ser Arg Thr Pro Glu Val Thr Cys
            20                  25                  30

Val Val Asp Val Ser His Glu Asp Pro Glu Val Lys Phe Asn Trp
        35                  40                  45

Tyr Val Asp Gly Val Glu Val His Asn Ala Lys Thr Lys Pro Arg Glu
    50                  55                  60

Glu Gln Tyr Asn Ser Thr Tyr Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95

Lys Ala Leu Pro Ala Pro Ile Glu Lys Thr Ile Ser Lys Ala Lys Gly
            100                 105                 110

Gln Pro Arg Glu Pro Gln Val Tyr Thr Leu Pro Pro Ser Arg Asp Glu
        115                 120                 125

Leu Thr Lys Asn Gln Val Ser Leu Thr Cys Leu Val Lys Gly Phe Tyr
    130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Val Phe Ser Cys Ser Val Met His Glu Ala Leu His Asn His Tyr Thr
        195                 200                 205

Gln Lys Ser Leu Ser Leu Ser Pro Gly Lys
    210                 215

<210> SEQ ID NO 9
<211> LENGTH: 215
<212> TYPE: PRT
<213> ORGANISM: Artificial Sequence
<220> FEATURE:
<223> OTHER INFORMATION: Fc xELL

<400> SEQUENCE: 9

Pro Ala Pro Gly Gly Pro Ser Val Phe Leu Phe Pro Pro Lys Pro Lys
1               5                   10                  15

Asp Thr Leu Met Ile Ser Arg Thr Pro Glu Val Thr Cys Val Val
            20                  25                  30

Asp Val Ser His Glu Asp Pro Glu Val Lys Phe Asn Trp Tyr Val Asp
        35                  40                  45

Gly Val Glu Val His Asn Ala Lys Thr Lys Pro Arg Glu Glu Gln Tyr
    50                  55                  60

Asn Ser Thr Tyr Arg Val Val Ser Val Leu Thr Val Leu His Gln Asp
65                  70                  75                  80

Trp Leu Asn Gly Lys Glu Tyr Lys Cys Lys Val Ser Asn Lys Ala Leu
                85                  90                  95

Pro Ala Pro Ile Glu Lys Thr Ile Ser Lys Ala Lys Gly Gln Pro Arg
            100                 105                 110

Glu Pro Gln Val Tyr Thr Leu Pro Pro Ser Arg Asp Glu Leu Thr Lys
        115                 120                 125

Asn Gln Val Ser Leu Thr Cys Leu Val Lys Gly Phe Tyr Pro Ser Asp
    130                 135                 140

Ile Ala Val Glu Trp Glu Ser Asn Gly Gln Pro Glu Asn Asn Tyr Lys
```

```
145                 150                 155                 160
Thr Thr Pro Pro Val Leu Asp Ser Asp Gly Ser Phe Leu Tyr Ser
                165                 170                 175

Lys Leu Thr Val Asp Lys Ser Arg Trp Gln Gln Gly Asn Val Phe Ser
            180                 185                 190

Cys Ser Val Met His Glu Ala Leu His Asn His Tyr Thr Gln Lys Ser
        195                 200                 205

Leu Ser Leu Ser Pro Gly Lys
    210                 215

<210> SEQ ID NO 10
<211> LENGTH: 217
<212> TYPE: PRT
<213> ORGANISM: Homo sapiens
<220> FEATURE:
<223> OTHER INFORMATION: human IgG2 Fc

<400> SEQUENCE: 10

Pro Ala Pro Pro Val Ala Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Phe Arg Val Val Ser Val Leu Thr Val Val His
65                  70                  75                  80

Gln Asp Trp Leu Asn Gly Lys Glu Tyr Lys Cys Lys Val Ser Asn Lys
                85                  90                  95

Gly Leu Pro Ala Pro Ile Glu Lys Thr Ile Ser Lys Thr Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ser Val Glu Trp Glu Ser Asn Gly Gln Pro Glu Asn Asn
145                 150                 155                 160

Tyr Lys Thr Thr Pro Pro Met Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 11
<211> LENGTH: 218
<212> TYPE: PRT
<213> ORGANISM: Homo sapiens
<220> FEATURE:
<223> OTHER INFORMATION: human IgG3 Fc

<400> SEQUENCE: 11

Pro Ala Pro Glu Leu Leu Gly Gly Pro Ser Val Phe Leu Phe Pro Pro
1               5                   10                  15
```

```
Lys Pro Lys Asp Thr Leu Met Ile Ser Arg Thr Pro Glu Val Thr Cys
            20                  25                  30

Val Val Val Asp Val Ser His Glu Asp Pro Glu Val Gln Phe Lys Trp
            35                  40                  45

Tyr Val Asp Gly Val Glu Val His Asn Ala Lys Thr Lys Pro Arg Glu
        50                  55                  60

Glu Gln Tyr Asn Ser Thr Phe Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95

Lys Ala Leu Pro Ala Pro Ile Glu Lys Thr Ile Ser Lys Thr Lys Gly
            100                 105                 110

Gln Pro Arg Glu Pro Gln Val Tyr Thr Leu Pro Pro Ser Arg Glu Glu
        115                 120                 125

Met Thr Lys Asn Gln Val Ser Leu Thr Cys Leu Val Lys Gly Phe Tyr
    130                 135                 140

Pro Ser Asp Ile Ala Val Glu Trp Glu Ser Ser Gly Gln Pro Glu Asn
145                 150                 155                 160

Asn Tyr Asn Thr Thr Pro Pro Met Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Ile Phe Ser Cys Ser Val Met His Glu Ala Leu His Asn Arg Phe Thr
        195                 200                 205

Gln Lys Ser Leu Ser Leu Ser Pro Gly Lys
    210                 215

<210> SEQ ID NO 12
<211> LENGTH: 218
<212> TYPE: PRT
<213> ORGANISM: Homo sapiens
<220> FEATURE:
<223> OTHER INFORMATION: human IgG4 Fc

<400> SEQUENCE: 12

Pro Ala Pro Glu Phe Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser Gln Glu Asp Pro Glu Val Gln Phe Asn Trp
            35                  40                  45

Tyr Val Asp Gly Val Glu Val His Asn Ala Lys Thr Lys Pro Arg Glu
        50                  55                  60

Glu Gln Phe Asn Ser Thr Tyr Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95

Lys Gly Leu Pro Ser Ser Ile Glu Lys Thr Ile Ser Lys Ala Lys Gly
            100                 105                 110

Gln Pro Arg Glu Pro Gln Val Tyr Thr Leu Pro Pro Ser Gln Glu Glu
        115                 120                 125

Met Thr Lys Asn Gln Val Ser Leu Thr Cys Leu Val Lys Gly Phe Tyr
    130                 135                 140

Pro Ser Asp Ile Ala Val Glu Trp Glu Ser Asn Gly Gln Pro Glu Asn
145                 150                 155                 160
```

```
Asn Tyr Lys Thr Thr Pro Pro Val Leu Asp Ser Asp Gly Ser Phe Phe
                165                 170                 175

Leu Tyr Ser Arg Leu Thr Val Asp Lys Ser Arg Trp Gln Glu Gly Asn
            180                 185                 190

Val Phe Ser Cys Ser Val Met His Glu Ala Leu His Asn His Tyr Thr
        195                 200                 205

Gln Lys Ser Leu Ser Leu Ser Leu Gly Lys
    210                 215

<210> SEQ ID NO 13
<211> LENGTH: 218
<212> TYPE: PRT
<213> ORGANISM: Homo sapiens
<220> FEATURE:
<223> OTHER INFORMATION: human IgG4 Fc

<400> SEQUENCE: 13

Pro Ala Pro Glu Leu Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser Gln Glu Asp Pro Glu Val Gln Phe Asn Trp
        35                  40                  45

Tyr Val Asp Gly Val Glu Val His Asn Ala Lys Thr Lys Pro Arg Glu
    50                  55                  60

Glu Gln Phe Asn Ser Thr Tyr Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95

Lys Gly Leu Pro Ser Ser Ile Glu Lys Thr Ile Ser Lys Ala Lys Gly
            100                 105                 110

Gln Pro Arg Glu Pro Gln Val Tyr Thr Leu Pro Pro Ser Gln Glu Glu
        115                 120                 125

Met Thr Lys Asn Gln Val Ser Leu Thr Cys Leu Val Lys Gly Phe Tyr
    130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Arg Leu Thr Val Asp Lys Ser Arg Trp Gln Glu Gly Asn
            180                 185                 190

Val Phe Ser Cys Ser Val Met His Glu Ala Leu His Asn His Tyr Thr
        195                 200                 205

Gln Lys Ser Leu Ser Leu Ser Leu Gly Lys
    210                 215

<210> SEQ ID NO 14
<211> LENGTH: 14
<212> TYPE: PRT
<213> ORGANISM: Artificial Sequence
<220> FEATURE:
<223> OTHER INFORMATION: modified IgG1 hinge

<400> SEQUENCE: 14

Glu Pro Lys Ser Ser Asp Lys Thr His Thr Cys Pro Pro Cys
1               5                   10

<210> SEQ ID NO 15
```

```
<211> LENGTH: 9
<212> TYPE: PRT
<213> ORGANISM: Artificial Sequence
<220> FEATURE:
<223> OTHER INFORMATION: truncated IgG1 hinge

<400> SEQUENCE: 15

Asp Lys Thr His Thr Cys Pro Pro Cys
1               5

<210> SEQ ID NO 16
<211> LENGTH: 11
<212> TYPE: PRT
<213> ORGANISM: Artificial Sequence
<220> FEATURE:
<223> OTHER INFORMATION: modified IgG4 hinge

<400> SEQUENCE: 16

Glu Ser Lys Tyr Gly Pro Pro Cys Pro Pro Cys
1               5                   10

<210> SEQ ID NO 17
<211> LENGTH: 12
<212> TYPE: PRT
<213> ORGANISM: Artificial Sequence
<220> FEATURE:
<223> OTHER INFORMATION: carboxy-terminal sequence

<400> SEQUENCE: 17

Gly Gln Gly Thr Leu Val Thr Val Lys Pro Gly Gly
1               5                   10

<210> SEQ ID NO 18
<211> LENGTH: 12
<212> TYPE: PRT
<213> ORGANISM: Artificial Sequence
<220> FEATURE:
<223> OTHER INFORMATION: carboxy-terminal sequence

<400> SEQUENCE: 18

Gly Gln Gly Thr Leu Val Thr Val Glu Pro Gly Gly
1               5                   10

<210> SEQ ID NO 19
<211> LENGTH: 119
<212> TYPE: PRT
<213> ORGANISM: Artificial Sequence
<220> FEATURE:
<223> OTHER INFORMATION: OKT3 VH

<400> SEQUENCE: 19

Gln Val Gln Leu Val Gln Ser Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Val
    50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Cys Leu Asp Tyr Trp Gly Gln Gly
```

Thr Pro Val Thr Val Ser Ser
            115

<210> SEQ ID NO 20
<211> LENGTH: 106
<212> TYPE: PRT
<213> ORGANISM: Artificial Sequence
<220> FEATURE:
<223> OTHER INFORMATION: OKT3 VL

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Asn Trp Tyr Gln Gln Thr Pro Gly Lys Ala Pro Lys Arg Trp Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gln Gly Thr Lys Leu Gln Ile Thr
            100                 105

<210> SEQ ID NO 21
<211> LENGTH: 119
<212> TYPE: PRT
<213> ORGANISM: Artificial Sequence
<220> FEATURE:
<223> OTHER INFORMATION: OKT3 humanized VH

<400> SEQUENCE: 21

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Val
    50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Ser Leu Asp Tyr Trp Gly Gln Gly
            100                 105                 110

Thr Pro Val Thr Val Ser Ser
            115

<210> SEQ ID NO 22
<211> LENGTH: 119
<212> TYPE: PRT
<213> ORGANISM: Artificial Sequence
<220> FEATURE:
<223> OTHER INFORMATION: OKT3 humanized VH

<400> SEQUENCE: 22

```
Asp Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Gly Leu Glu Trp Ile
        35                  40                  45

Gly Tyr Ile Asn Pro Ser Arg Gly Tyr Thr Asn Tyr Ala Asp Ser Val
    50                  55                  60

Lys Gly Arg Phe Thr Ile Thr Thr Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Tyr Tyr Asp Asp His Tyr Cys Leu Asp Tyr Trp Gly Gln Gly
            100                 105                 110

Thr Thr Val Thr Val Ser Ser
            115
```

<210> SEQ ID NO 23
<211> LENGTH: 119
<212> TYPE: PRT
<213> ORGANISM: Artificial Sequence
<220> FEATURE:
<223> OTHER INFORMATION: OKT3 humanized VH

<400> SEQUENCE: 23

```
Gln Val Gln Leu Val Gln Ser Gly Ala Glu Leu Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Cys Leu Glu Trp Met
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Ala Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Leu Val Thr Val Ser Ser
            115
```

<210> SEQ ID NO 24
<211> LENGTH: 106
<212> TYPE: PRT
<213> ORGANISM: Artificial Sequence
<220> FEATURE:
<223> OTHER INFORMATION: OKT3 humanized VL

<400> SEQUENCE: 24

```
Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
```

```
                50             55             60
Gly Ser Gly Thr Ser Tyr Ser Leu Thr Ile Ser Gly Met Glu Ala Glu
 65                 70                  75                  80

Asp Ala Ala Thr Tyr Tyr Cys Gln Gln Trp Ser Ser Asn Pro Phe Thr
                 85                  90                  95

Phe Gly Ser Gly Thr Lys Leu Glu Ile Asn
                100                 105

<210> SEQ ID NO 25
<211> LENGTH: 106
<212> TYPE: PRT
<213> ORGANISM: Artificial Sequence
<220> FEATURE:
<223> OTHER INFORMATION: OKT3 humanized VL

<400> SEQUENCE: 25

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Val Ser Tyr Met
                20                  25                  30

Asn Trp Tyr Gln Gln Lys Pro Gly Lys Ala Pro Lys Arg Trp Ile Tyr
             35                  40                  45

Asp Thr Ser Lys Val Ala Ser Gly Val Pro Ala Arg Phe Ser Gly Ser
         50                  55                  60

Gly Ser Gly Thr Asp Tyr Ser Leu Thr Ile Asn Ser Leu Glu Ala Glu
 65                 70                  75                  80

Asp Ala Ala Thr Tyr Tyr Cys Gln Gln Trp Ser Ser Asn Pro Leu Thr
                 85                  90                  95

Phe Gly Gly Gly Thr Lys Val Glu Ile Lys
                100                 105

<210> SEQ ID NO 26
<211> LENGTH: 108
<212> TYPE: PRT
<213> ORGANISM: Artificial Sequence
<220> FEATURE:
<223> OTHER INFORMATION: OKT3 humanized VL

<400> SEQUENCE: 26

Asp Ile Gln Leu Thr Gln Ser Pro Ser Ile Leu Ser Ala Ser Val Gly
 1               5                  10                  15

Asp Arg Val Thr Ile Thr Cys Arg Ala Ser Ser Ser Val Ser Tyr Met
                20                  25                  30

Asn Trp Tyr Gln Gln Lys Pro Gly Lys Ala Pro Lys Arg Trp Ile Tyr
             35                  40                  45

Asp Thr Ser Lys Val Ala Ser Gly Val Pro Tyr Arg Phe Ser Gly Ser
         50                  55                  60

Gly Ser Gly Thr Glu Tyr Thr Leu Thr Ile Ser Ser Met Gln Pro Glu
 65                 70                  75                  80

Asp Phe Ala Thr Tyr Tyr Cys Gln Gln Trp Ser Ser Asn Pro Leu Thr
                 85                  90                  95

Phe Gly Cys Gly Thr Lys Val Glu Ile Lys Arg Thr
                100                 105

<210> SEQ ID NO 27
<211> LENGTH: 125
<212> TYPE: PRT
<213> ORGANISM: Artificial Sequence
<220> FEATURE:
```

-continued

<223> OTHER INFORMATION: anti-CD3 Hv

<400> SEQUENCE: 27

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ala
        115                 120                 125

<210> SEQ ID NO 28
<211> LENGTH: 109
<212> TYPE: PRT
<213> ORGANISM: Artificial Sequence
<220> FEATURE:
<223> OTHER INFORMATION: anti-CD3 Lv

<400> SEQUENCE: 28

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

Leu Trp Val Phe Gly Gly Gly Thr Lys Leu Thr Val Leu
            100                 105

<210> SEQ ID NO 29
<211> LENGTH: 5
<212> TYPE: PRT
<213> ORGANISM: Artificial Sequence
<220> FEATURE:
<223> OTHER INFORMATION: anti-CD3 VH CDR1

<400> SEQUENCE: 29

Thr Tyr Ala Met Asn
1               5

<210> SEQ ID NO 30
<211> LENGTH: 19
<212> TYPE: PRT
<213> ORGANISM: Artificial Sequence
<220> FEATURE:
<223> OTHER INFORMATION: anti-CD3 VH CDR2

-continued

<400> SEQUENCE: 30

Arg Ile Arg Ser Lys Tyr Asn Asn Tyr Ala Thr Tyr Tyr Ala Asp Ser
1               5                   10                  15

Val Lys Asp

<210> SEQ ID NO 31
<211> LENGTH: 14
<212> TYPE: PRT
<213> ORGANISM: Artificial Sequence
<220> FEATURE:
<223> OTHER INFORMATION: anti-CD3 VH CDR3

<400> SEQUENCE: 31

His Gly Asn Phe Gly Asn Ser Tyr Val Ser Trp Phe Ala Tyr
1               5                   10

<210> SEQ ID NO 32
<211> LENGTH: 14
<212> TYPE: PRT
<213> ORGANISM: Artificial Sequence
<220> FEATURE:
<223> OTHER INFORMATION: anti-CD3 VL CDR1

<400> SEQUENCE: 32

Arg Ser Ser Thr Gly Ala Val Thr Thr Ser Asn Tyr Ala Asn
1               5                   10

<210> SEQ ID NO 33
<211> LENGTH: 7
<212> TYPE: PRT
<213> ORGANISM: Artificial Sequence
<220> FEATURE:
<223> OTHER INFORMATION: anti-CD3 VL CDR2

<400> SEQUENCE: 33

Gly Thr Asn Lys Arg Ala Pro
1               5

<210> SEQ ID NO 34
<211> LENGTH: 9
<212> TYPE: PRT
<213> ORGANISM: Artificial Sequence
<220> FEATURE:
<223> OTHER INFORMATION: anti-CD3 VL CDR3

<400> SEQUENCE: 34

Ala Leu Trp Tyr Ser Asn Leu Trp Val
1               5

<210> SEQ ID NO 35
<211> LENGTH: 125
<212> TYPE: PRT
<213> ORGANISM: Artificial Sequence
<220> FEATURE:
<223> OTHER INFORMATION: anti-CD3 VH1

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
                20                  25                  30

Ala Met Asn Trp Val Arg Gln Ala Pro Gly Lys Gly Leu Glu Trp Val
            35                  40                  45

```
Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                 85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser
                115                 120                 125

<210> SEQ ID NO 36
<211> LENGTH: 125
<212> TYPE: PRT
<213> ORGANISM: Artificial Sequence
<220> FEATURE:
<223> OTHER INFORMATION: anti-CD3 VH2

<400> SEQUENCE: 36

Glu Val Lys Leu Val Glu Ser Gly Gly Gly Leu Val Gln Pro Gly Gly
  1               5                  10                  15

Ser Leu Arg Leu Ser Cys Ala Ala Ser Gly Phe Thr Phe Asn Thr Tyr
                 20                  25                  30

Ala Met Asn Trp Val Arg Gln Ala Pro Gly Lys Gly Leu Glu Trp Val
                 35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
 65                  70                  75                  80

Leu Tyr Leu Gln Met Asn Asn Leu Lys Thr Glu Asp Thr Ala Met Tyr
                 85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser
                115                 120                 125

<210> SEQ ID NO 37
<211> LENGTH: 125
<212> TYPE: PRT
<213> ORGANISM: Artificial Sequence
<220> FEATURE:
<223> OTHER INFORMATION: anti-CD3 VH3

<400> SEQUENCE: 37

Glu Val Lys Leu Val Glu Ser Gly Gly Gly Leu Val Lys Pro Gly Arg
  1               5                  10                  15

Ser Leu Arg Leu Ser Cys Ala Ala Ser Gly Phe Thr Phe Asn Thr Tyr
                 20                  25                  30

Ala Met Asn Trp Val Arg Gln Ala Pro Gly Lys Gly Leu Glu Trp Val
                 35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ile
 65                  70                  75                  80

Leu Tyr Leu Gln Met Asn Asn Leu Lys Thr Glu Asp Thr Ala Met Tyr
                 85                  90                  95

Tyr Cys Val Arg His Gly Asn Phe Gly Asn Ser Tyr Val Ser Trp Phe
                100                 105                 110
```

```
Ala Tyr Trp Gly Gln Gly Thr Leu Val Thr Val Ser Ser
        115                 120                 125

<210> SEQ ID NO 38
<211> LENGTH: 125
<212> TYPE: PRT
<213> ORGANISM: Artificial Sequence
<220> FEATURE:
<223> OTHER INFORMATION: anti-CD3 VH4

<400> SEQUENCE: 38

Glu Val Lys Leu Val Glu Ser Gly Gly Gly Leu Val Lys Pro Gly Arg
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ile
65                  70                  75                  80

Leu Tyr Leu Gln Met Asn Ser Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 39
<211> LENGTH: 125
<212> TYPE: PRT
<213> ORGANISM: Artificial Sequence
<220> FEATURE:
<223> OTHER INFORMATION: anti-CD3 VH5

<400> SEQUENCE: 39

Glu Val Lys Leu Val Glu Ser Gly Gly Gly Leu Val Lys Pro Gly Arg
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ile
65                  70                  75                  80

Leu Tyr Leu Gln Met Asn Ser Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 40
<211> LENGTH: 125
<212> TYPE: PRT
<213> ORGANISM: Artificial Sequence
<220> FEATURE:
<223> OTHER INFORMATION: anti-CD3 VH6
```

<400> SEQUENCE: 40

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
            115                 120                 125

<210> SEQ ID NO 41
<211> LENGTH: 125
<212> TYPE: PRT
<213> ORGANISM: Artificial Sequence
<220> FEATURE:
<223> OTHER INFORMATION: anti-CD3 VH7

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
            100                 105                 110

Ala Tyr Trp Gly Gln Gly Thr Leu Val Thr Val Ser Ser
            115                 120                 125

<210> SEQ ID NO 42
<211> LENGTH: 124
<212> TYPE: PRT
<213> ORGANISM: Artificial Sequence
<220> FEATURE:
<223> OTHER INFORMATION: anti-CD3 VH8

<400> SEQUENCE: 42

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

```
Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                    85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser
        115                 120

<210> SEQ ID NO 43
<211> LENGTH: 125
<212> TYPE: PRT
<213> ORGANISM: Artificial Sequence
<220> FEATURE:
<223> OTHER INFORMATION: anti-CD3 VH9

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
        50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                    85                  90                  95

Tyr Cys Val Arg His Gly Asn Phe Gly Asn Ser Tyr Val Ser Trp Phe
            100                 105                 110

Ala Tyr Trp Gly Gln Gly Thr Thr Val Thr Val Ser Ser
        115                 120                 125

<210> SEQ ID NO 44
<211> LENGTH: 125
<212> TYPE: PRT
<213> ORGANISM: Artificial Sequence
<220> FEATURE:
<223> OTHER INFORMATION: anti-CD3 VH10

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
        50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                    85                  90                  95

Tyr Cys Val Arg His Gly Asn Phe Gly Asn Ser Tyr Val Ser Tyr Phe
```

```
                  100                 105                 110
Ala Tyr Trp Gly Gln Gly Thr Thr Val Thr Val Ser Ser
        115                 120                 125

<210> SEQ ID NO 45
<211> LENGTH: 125
<212> TYPE: PRT
<213> ORGANISM: Artificial Sequence
<220> FEATURE:
<223> OTHER INFORMATION: anti-CD3 VH11

<400> SEQUENCE: 45

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 46
<211> LENGTH: 125
<212> TYPE: PRT
<213> ORGANISM: Artificial Sequence
<220> FEATURE:
<223> OTHER INFORMATION: VH12

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ala Lys Asn Thr
65                  70                  75                  80

Leu Tyr Leu Gln Met Ser Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Lys Pro
        115                 120                 125

<210> SEQ ID NO 47
<211> LENGTH: 125
<212> TYPE: PRT
<213> ORGANISM: Artificial Sequence
<220> FEATURE:
```

<223> OTHER INFORMATION: anti-CD3 VH13

<400> SEQUENCE: 47

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ala Lys Asn Thr
65                  70                  75                  80

Leu Tyr Leu Gln Met Ser Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Lys Pro
        115                 120                 125

<210> SEQ ID NO 48
<211> LENGTH: 125
<212> TYPE: PRT
<213> ORGANISM: Artificial Sequence
<220> FEATURE:
<223> OTHER INFORMATION: anti-CD3 VH14

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ala Lys Asn Thr
65                  70                  75                  80

Leu Tyr Leu Gln Met Ser Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Cys Gly Thr Leu Val Thr Val Lys Pro
        115                 120                 125

<210> SEQ ID NO 49
<211> LENGTH: 125
<212> TYPE: PRT
<213> ORGANISM: Artificial Sequence
<220> FEATURE:
<223> OTHER INFORMATION: anti-CD3 VH15

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val

```
                35                  40                  45

Ala Arg Ile Arg Ser Lys Tyr Asn Asn Tyr Ala Thr Tyr Tyr Ala Asp
            50                  55                  60

Ser Val Lys Gly Arg Phe Thr Ile Ser Arg Asp Asp Ala Lys Asn Thr
 65                  70                  75                  80

Leu Tyr Leu Gln Met Ser Ser Leu Arg Ala Glu Asp Thr Ala Val Tyr
                85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser
            115                 120                 125

<210> SEQ ID NO 50
<211> LENGTH: 125
<212> TYPE: PRT
<213> ORGANISM: Artificial Sequence
<220> FEATURE:
<223> OTHER INFORMATION: anti-CD3 VH16

<400> SEQUENCE: 50

Glu Val Gln Leu Val Glu Ser Gly Gly Gly Leu Val Gln Pro Gly Gly
 1                5                  10                  15

Ser Leu Arg Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
                35                  40                  45

Ser Arg Ile Arg Ser Lys Tyr Asn Asn Tyr Ala Thr Tyr Tyr Ala Asp
            50                  55                  60

Ser Val Lys Gly Arg Phe Thr Ile Ser Arg Asp Asp Ala Lys Asn Thr
 65                  70                  75                  80

Leu Tyr Leu Gln Met Ser Ser Leu Arg Ala Glu Asp Thr Ala Val Tyr
                85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser
            115                 120                 125

<210> SEQ ID NO 51
<211> LENGTH: 125
<212> TYPE: PRT
<213> ORGANISM: Artificial Sequence
<220> FEATURE:
<223> OTHER INFORMATION: anti-CD3 VH17

<400> SEQUENCE: 51

Glu Val Gln Leu Val Glu Ser Gly Gly Gly Leu Val Gln Pro Gly Gly
 1                5                  10                  15

Ser Leu Arg Leu Ser Cys Ala Ala Ser Gly Phe Thr Phe Ser Thr Tyr
                20                  25                  30

Ala Met Asn Trp Val Arg Gln Ala Pro Gly Lys Gly Leu Glu Trp Val
                35                  40                  45

Ser Arg Ile Arg Ser Lys Tyr Asn Asn Tyr Ala Thr Tyr Tyr Ala Asp
            50                  55                  60

Ser Val Lys Gly Arg Phe Thr Ile Ser Arg Asp Asp Ala Lys Asn Thr
 65                  70                  75                  80

Leu Tyr Leu Gln Met Ser Ser Leu Arg Ala Glu Asp Thr Ala Val Tyr
                85                  90                  95
```

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 52
<211> LENGTH: 125
<212> TYPE: PRT
<213> ORGANISM: Artificial Sequence
<220> FEATURE:
<223> OTHER INFORMATION: anti-CD3 VH18

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ala Lys Asn Thr
65                  70                  75                  80

Leu Tyr Leu Gln Met Ser Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 53
<211> LENGTH: 125
<212> TYPE: PRT
<213> ORGANISM: Artificial Sequence
<220> FEATURE:
<223> OTHER INFORMATION: anti-CD3 VH19

<400> SEQUENCE: 53

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Cys Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ala Lys Asn Thr
65                  70                  75                  80

Leu Tyr Leu Gln Met Ser Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 54
<211> LENGTH: 125
<212> TYPE: PRT
<213> ORGANISM: Artificial Sequence
<220> FEATURE:
<223> OTHER INFORMATION: anti-CD3 VH20

<400> SEQUENCE: 54

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Cys Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ala Lys Asn Thr
65                  70                  75                  80

Leu Tyr Leu Gln Met Ser Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 55
<211> LENGTH: 125
<212> TYPE: PRT
<213> ORGANISM: Artificial Sequence
<220> FEATURE:
<223> OTHER INFORMATION: anti-CD3 VH21

<400> SEQUENCE: 55

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Cys Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 56
<211> LENGTH: 125
<212> TYPE: PRT
<213> ORGANISM: Artificial Sequence
<220> FEATURE:
<223> OTHER INFORMATION: anti-CD3 VH22

<400> SEQUENCE: 56

```
Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30
```

```
Ala Met Asn Trp Val Arg Gln Ala Pro Gly Lys Cys Leu Glu Trp Val
            35                  40                  45

Ala Arg Ile Arg Ser Lys Tyr Asn Asn Tyr Ala Thr Tyr Tyr Ala Asp
 50                  55                  60

Ser Val Lys Asp Arg Phe Thr Ile Ser Arg Asp Asp Ser Lys Ser Ser
 65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser
            115                 120                 125

<210> SEQ ID NO 57
<211> LENGTH: 125
<212> TYPE: PRT
<213> ORGANISM: Artificial Sequence
<220> FEATURE:
<223> OTHER INFORMATION: anti-CD3 VH23

<400> SEQUENCE: 57

Glu Val Lys Leu Val Glu Ser Gly Gly Gly Leu Val Lys Pro Gly Arg
  1               5                  10                  15

Ser Leu Arg Leu Ser Cys Ala Ala Ser Gly Phe Thr Phe Asn Thr Tyr
                20                  25                  30

Ala Met Asn Trp Val Arg Gln Ala Pro Gly Lys Cys Leu Glu Trp Val
            35                  40                  45

Ala Arg Ile Arg Ser Lys Tyr Asn Asn Tyr Ala Thr Tyr Tyr Ala Asp
 50                  55                  60

Ser Val Lys Asp Arg Phe Thr Ile Ser Arg Asp Asp Ser Lys Ser Ile
 65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser
            115                 120                 125

<210> SEQ ID NO 58
<211> LENGTH: 125
<212> TYPE: PRT
<213> ORGANISM: Artificial Sequence
<220> FEATURE:
<223> OTHER INFORMATION: anti-CD3 VH24

<400> SEQUENCE: 58

Glu Val Lys Leu Val Glu Ser Gly Gly Gly Leu Val Lys Pro Gly Arg
  1               5                  10                  15

Ser Leu Arg Leu Ser Cys Ala Ser Gly Phe Thr Phe Asn Thr Tyr
                20                  25                  30

Ala Met Asn Trp Val Arg Gln Ala Pro Gly Lys Cys Leu Glu Trp Val
            35                  40                  45

Ala Arg Ile Arg Ser Lys Tyr Asn Asn Tyr Ala Thr Tyr Tyr Ala Asp
 50                  55                  60

Ser Val Lys Asp Arg Phe Thr Ile Ser Arg Asp Asp Ser Lys Ser Ile
 65                  70                  75                  80

Leu Tyr Leu Gln Met Asn Ser Leu Lys Thr Glu Asp Thr Ala Met Tyr
                85                  90                  95
```

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
            115                 120                 125

<210> SEQ ID NO 59
<211> LENGTH: 125
<212> TYPE: PRT
<213> ORGANISM: Artificial Sequence
<220> FEATURE:
<223> OTHER INFORMATION: anti-CD3 VH25

<400> SEQUENCE: 59

Glu Val Lys Leu Val Glu Ser Gly Gly Gly Leu Val Lys Pro Gly Arg
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ile
65                  70                  75                  80

Leu Tyr Leu Gln Met Asn Ser Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
            115                 120                 125

<210> SEQ ID NO 60
<211> LENGTH: 125
<212> TYPE: PRT
<213> ORGANISM: Artificial Sequence
<220> FEATURE:
<223> OTHER INFORMATION: anti-CD3 VH26

<400> SEQUENCE: 60

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Cys Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
            115                 120                 125

<210> SEQ ID NO 61
<211> LENGTH: 125
<212> TYPE: PRT

<213> ORGANISM: Artificial Sequence
<220> FEATURE:
<223> OTHER INFORMATION: anti-CD3 VH27

<400> SEQUENCE: 61

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Cys Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
            100                 105                 110

Ala Tyr Trp Gly Gln Gly Thr Leu Val Thr Val Ser Ser
        115                 120                 125

<210> SEQ ID NO 62
<211> LENGTH: 124
<212> TYPE: PRT
<213> ORGANISM: Artificial Sequence
<220> FEATURE:
<223> OTHER INFORMATION: anti-CD3 VH28

<400> SEQUENCE: 62

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser
        115                 120

<210> SEQ ID NO 63
<211> LENGTH: 125
<212> TYPE: PRT
<213> ORGANISM: Artificial Sequence
<220> FEATURE:
<223> OTHER INFORMATION: anti-CD3 VH29

<400> SEQUENCE: 63

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Thr Val Thr Val Ser Ser
            115                 120                 125

<210> SEQ ID NO 64
<211> LENGTH: 125
<212> TYPE: PRT
<213> ORGANISM: Artificial Sequence
<220> FEATURE:
<223> OTHER INFORMATION: anti-CD3 VH30

<400> SEQUENCE: 64

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Tyr Phe
            100                 105                 110

Ala Tyr Trp Gly Gln Gly Thr Thr Val Thr Val Ser Ser
            115                 120                 125

<210> SEQ ID NO 65
<211> LENGTH: 125
<212> TYPE: PRT
<213> ORGANISM: Artificial Sequence
<220> FEATURE:
<223> OTHER INFORMATION: anti-CD3 VH31

<400> SEQUENCE: 65

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr

```
                        85                  90                  95

Tyr Cys Val Arg His Gly Asn Phe Gly Asn Ser Tyr Val Ser Trp Phe
               100                 105                 110

Ala Tyr Trp Gly Gln Gly Thr Leu Val Thr Val Ser Ser
        115                 120                 125

<210> SEQ ID NO 66
<211> LENGTH: 125
<212> TYPE: PRT
<213> ORGANISM: Artificial Sequence
<220> FEATURE:
<223> OTHER INFORMATION: anti-CD3 VH31

<400> SEQUENCE: 66

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
               100                 105                 110

Ala Tyr Trp Gly Gln Gly Thr Leu Val Thr Val Ser Ser
        115                 120                 125

<210> SEQ ID NO 67
<211> LENGTH: 109
<212> TYPE: PRT
<213> ORGANISM: Artificial Sequence
<220> FEATURE:
<223> OTHER INFORMATION: anti-CD3 VL2

<400> SEQUENCE: 67

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Lys Ser Pro Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Cys Gly Thr Lys Leu Glu Ile Lys
               100                 105

<210> SEQ ID NO 68
<211> LENGTH: 109
<212> TYPE: PRT
<213> ORGANISM: Artificial Sequence
<220> FEATURE:
```

<223> OTHER INFORMATION: anti-CD3 VL3

<400> SEQUENCE: 68

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 69
<211> LENGTH: 109
<212> TYPE: PRT
<213> ORGANISM: Artificial Sequence
<220> FEATURE:
<223> OTHER INFORMATION: anti-CD3 VL4

<400> SEQUENCE: 69

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Thr Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Leu Trp Val Phe Gly Gly Gly Thr Lys Leu Thr Val Leu
            100                 105

<210> SEQ ID NO 70
<211> LENGTH: 109
<212> TYPE: PRT
<213> ORGANISM: Artificial Sequence
<220> FEATURE:
<223> OTHER INFORMATION: anti-CD3 VL5

<400> SEQUENCE: 70

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Thr Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Ile Leu Gly Asn Lys Ala Ala Leu Thr Ile Thr Gly Ala

```
                   65                  70                  75                  80
Gln Ala Asp Asp Glu Ser Ile Tyr Phe Cys Ala Leu Trp Tyr Ser Asn
                85                  90                  95

Leu Trp Val Phe Gly Gly Gly Thr Lys Leu Thr Val Leu
               100                 105

<210> SEQ ID NO 71
<211> LENGTH: 109
<212> TYPE: PRT
<213> ORGANISM: Artificial Sequence
<220> FEATURE:
<223> OTHER INFORMATION: anti-CD3 VL6

<400> SEQUENCE: 71

Gln Ala Val Val Thr Gln Glu Pro Ser Phe Ser Val Ser Pro Gly Gly
1               5                  10                  15

Thr Val Thr Leu Thr Cys Arg Ser Ser Thr Gly Ala Val Thr Thr Ser
                20                  25                  30

Asn Tyr Ala Asn Trp Val Gln Gln Thr Pro Gly Gln Ala Phe Arg Gly
            35                  40                  45

Leu Ile Gly Gly Thr Asn Lys Arg Ala Pro Gly Val Pro Ala Arg Phe
        50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Ala Leu Trp Tyr Ser Asn
                85                  90                  95

Leu Trp Val Phe Gly Gly Gly Thr Lys Leu Thr Val Leu
               100                 105

<210> SEQ ID NO 72
<211> LENGTH: 109
<212> TYPE: PRT
<213> ORGANISM: Artificial Sequence
<220> FEATURE:
<223> OTHER INFORMATION: anti-CD3 VL7

<400> SEQUENCE: 72

Gln Ala Val Val Thr Gln Glu Pro Ser Leu Thr Val Ser Pro Gly Gly
1               5                  10                  15

Thr Val Thr Leu Thr Cys Gly Ser Ser Thr Gly Ala Val Thr Thr Ser
                20                  25                  30

Asn Tyr Ala Asn Trp Val Gln Glu Lys Pro Gly Gln Ala Phe Arg Gly
            35                  40                  45

Leu Ile Gly Gly Thr Asn Lys Arg Ala Pro Gly Thr Pro Ala Arg Phe
        50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
               100                 105

<210> SEQ ID NO 73
<211> LENGTH: 109
<212> TYPE: PRT
<213> ORGANISM: Artificial Sequence
<220> FEATURE:
<223> OTHER INFORMATION: anti-CD3 VL8

<400> SEQUENCE: 73
```

```
Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Asn Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Val Leu Trp Tyr Ser Asn
                85                  90                  95

Arg Trp Val Phe Gly Gly Gly Thr Lys Leu Thr Val Leu
                100                 105
```

<210> SEQ ID NO 74
<211> LENGTH: 109
<212> TYPE: PRT
<213> ORGANISM: Artificial Sequence
<220> FEATURE:
<223> OTHER INFORMATION: anti-CD3 VL9

<400> SEQUENCE: 74

```
Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Gly Gly Thr Lys Leu Glu Ile Lys
                100                 105
```

<210> SEQ ID NO 75
<211> LENGTH: 109
<212> TYPE: PRT
<213> ORGANISM: Artificial Sequence
<220> FEATURE:
<223> OTHER INFORMATION: anti-CD3 VL10

<400> SEQUENCE: 75

```
Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
```

```
                     85                  90                  95
His Trp Val Phe Gly Cys Gly Thr Lys Leu Glu Ile Lys
                100                 105

<210> SEQ ID NO 76
<211> LENGTH: 109
<212> TYPE: PRT
<213> ORGANISM: Artificial Sequence
<220> FEATURE:
<223> OTHER INFORMATION: anti-CD3 VL11

<400> SEQUENCE: 76

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Gln Cys Phe Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Glu Gly Thr Lys Leu Glu Ile Lys
                100                 105

<210> SEQ ID NO 77
<211> LENGTH: 109
<212> TYPE: PRT
<213> ORGANISM: Artificial Sequence
<220> FEATURE:
<223> OTHER INFORMATION: anti-CD3 VL12

<400> SEQUENCE: 77

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

Leu Trp Val Phe Gly Cys Gly Thr Lys Leu Thr Val Leu
                100                 105

<210> SEQ ID NO 78
<211> LENGTH: 109
<212> TYPE: PRT
<213> ORGANISM: Artificial Sequence
<220> FEATURE:
<223> OTHER INFORMATION: anti-CD3 VL13

<400> SEQUENCE: 78

Gln Ala Val Val Thr Gln Glu Pro Ser Leu Thr Val Ser Pro Gly Gly
1               5                   10                  15
```

```
Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Lys Ser Pro Arg Gly
            35                  40                  45

Leu Ile Gly Gly Thr Asn Lys Arg Ala Pro Gly Val Pro Ala Arg Phe
        50                  55                  60

Ser Gly Ser Leu Leu Gly Gly Lys Ala Ala Leu Thr Ile Ser Gly Ala
65              70                  75                  80

Gln Pro Glu Asp Glu Ala Asp Tyr Tyr Cys Ala Leu Trp Tyr Ser Asn
                85                  90                  95

His Trp Val Phe Gly Gly Gly Thr Lys Leu Glu Ile Lys
            100                 105
```

<210> SEQ ID NO 79
<211> LENGTH: 109
<212> TYPE: PRT
<213> ORGANISM: Artificial Sequence
<220> FEATURE:
<223> OTHER INFORMATION: anti-CD3 VL14

<400> SEQUENCE: 79

```
Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
            35                  40                  45

Leu Ile Gly Gly Thr Asn Lys Arg Ala Pro Trp Thr Pro Ala Arg Phe
        50                  55                  60

Ser Gly Ser Leu Leu Gly Gly Lys Ala Ala Leu Thr Ile Thr Gly Ala
65              70                  75                  80

Gln Ala Glu Asp Glu Ala Asp Tyr Tyr Cys Ala Leu Trp Tyr Ser Asn
                85                  90                  95

Leu Trp Val Phe Gly Cys Gly Thr Lys Leu Thr Val Leu
            100                 105
```

<210> SEQ ID NO 80
<211> LENGTH: 109
<212> TYPE: PRT
<213> ORGANISM: Artificial Sequence
<220> FEATURE:
<223> OTHER INFORMATION: anti-CD3 VL15

<400> SEQUENCE: 80

```
Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Thr Pro Gly Gln Ala Phe Arg Gly
            35                  40                  45

Leu Ile Gly Gly Thr Asn Lys Arg Ala Pro Gly Val Pro Ala Arg Phe
        50                  55                  60

Ser Gly Ser Leu Ile Gly Asp Lys Ala Ala Leu Thr Ile Thr Gly Ala
65              70                  75                  80

Gln Ala Asp Asp Glu Ser Ile Tyr Phe Cys Ala Leu Trp Tyr Ser Asn
                85                  90                  95

Leu Trp Val Phe Gly Gly Gly Thr Lys Leu Thr Val Leu
```

<210> SEQ ID NO 81
<211> LENGTH: 109
<212> TYPE: PRT
<213> ORGANISM: Artificial Sequence
<220> FEATURE:
<223> OTHER INFORMATION: anti-CD3 VL16

<400> SEQUENCE: 81

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Thr Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Leu Trp Val Phe Gly Cys Gly Thr Lys Leu Thr Val Leu
            100                 105

<210> SEQ ID NO 82
<211> LENGTH: 109
<212> TYPE: PRT
<213> ORGANISM: Artificial Sequence
<220> FEATURE:
<223> OTHER INFORMATION: anti-CD3 VL17

<400> SEQUENCE: 82

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Thr Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Ala Leu Trp Tyr Ser Asn
                85                  90                  95

Leu Trp Val Phe Gly Cys Gly Thr Lys Leu Thr Val Leu
            100                 105

<210> SEQ ID NO 83
<211> LENGTH: 109
<212> TYPE: PRT
<213> ORGANISM: Artificial Sequence
<220> FEATURE:
<223> OTHER INFORMATION: anti-CD3 VL18

<400> SEQUENCE: 83

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

```
Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
 50                  55                  60

Ser Gly Ser Leu Leu Gly Gly Lys Ala Ala Leu Thr Leu Ser Gly Ala
 65                  70                  75                  80

Gln Pro Glu Asp Glu Ala Glu Tyr Tyr Cys Ala Leu Trp Tyr Ser Asn
                 85                  90                  95

Leu Trp Val Phe Gly Cys Gly Thr Lys Leu Thr Val Leu
            100                 105

<210> SEQ ID NO 84
<211> LENGTH: 109
<212> TYPE: PRT
<213> ORGANISM: Artificial Sequence
<220> FEATURE:
<223> OTHER INFORMATION: anti-CD3 VL19

<400> SEQUENCE: 84

Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
                20                  25                  30

Asn Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
 50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Val Leu Trp Tyr Ser Asn
                 85                  90                  95

Arg Trp Val Phe Gly Cys Gly Thr Lys Leu Thr Val Leu
            100                 105

<210> SEQ ID NO 85
<211> LENGTH: 129
<212> TYPE: PRT
<213> ORGANISM: Artificial Sequence
<220> FEATURE:
<223> OTHER INFORMATION: anti-CD3 VHH

<400> SEQUENCE: 85

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Asn Tyr
                20                  25                  30

His Met Gly Trp Phe Arg Gln Ala Pro Gly Lys Glu Arg Glu Leu Val
        35                  40                  45

Ala Ala Ile Ser Gly Ser Gly Gly Ser Thr Tyr Tyr Thr Asp Ser Val
    50                  55                  60

Lys Gly Arg Phe Thr Ile Ser Arg Asn Asn Ala Lys Asn Thr Met Ser
65                  70                  75                  80

Leu Gln Met Ser Asn Leu Lys Pro Glu Asp Thr Gly Val Tyr Tyr Cys
                 85                  90                  95

Thr Thr Pro Thr Glu Lys Gly Ser Ser Ile Asp Tyr Trp Gly Gln Gly
            100                 105                 110

Thr Gln Val Thr Val Ser Ser Gly Arg Tyr Pro Tyr Asp Val Pro Asp
```

115                 120                 125
Tyr

<210> SEQ ID NO 86
<211> LENGTH: 618
<212> TYPE: PRT
<213> ORGANISM: Homo sapiens
<220> FEATURE:
<223> OTHER INFORMATION: Canonical DLL3 sequence

<400> SEQUENCE: 86

Met Val Ser Pro Arg Met Ser Gly Leu Leu Ser Gln Thr Val Ile Leu
1               5                   10                  15

Ala Leu Ile Phe Leu Pro Gln Thr Arg Pro Ala Gly Val Phe Glu Leu
            20                  25                  30

Gln Ile His Ser Phe Gly Pro Gly Pro Gly Pro Gly Ala Pro Arg Ser
        35                  40                  45

Pro Cys Ser Ala Arg Leu Pro Cys Arg Leu Phe Phe Arg Val Cys Leu
    50                  55                  60

Lys Pro Gly Leu Ser Glu Glu Ala Ala Glu Ser Pro Cys Ala Leu Gly
65                  70                  75                  80

Ala Ala Leu Ser Ala Arg Gly Pro Val Tyr Thr Glu Gln Pro Gly Ala
                85                  90                  95

Pro Ala Pro Asp Leu Pro Leu Pro Asp Gly Leu Leu Gln Val Pro Phe
            100                 105                 110

Arg Asp Ala Trp Pro Gly Thr Phe Ser Phe Ile Ile Glu Thr Trp Arg
        115                 120                 125

Glu Glu Leu Gly Asp Gln Ile Gly Gly Pro Ala Trp Ser Leu Leu Ala
    130                 135                 140

Arg Val Ala Gly Arg Arg Leu Ala Ala Gly Gly Pro Trp Ala Arg
145                 150                 155                 160

Asp Ile Gln Arg Ala Gly Ala Trp Glu Leu Arg Phe Ser Tyr Arg Ala
                165                 170                 175

Arg Cys Glu Pro Pro Ala Val Gly Thr Ala Cys Thr Arg Leu Cys Arg
            180                 185                 190

Pro Arg Ser Ala Pro Ser Arg Cys Gly Pro Gly Leu Arg Pro Cys Ala
        195                 200                 205

Pro Leu Glu Asp Glu Cys Glu Ala Pro Leu Val Cys Arg Ala Gly Cys
    210                 215                 220

Ser Pro Glu His Gly Phe Cys Glu Gln Pro Gly Glu Cys Arg Cys Leu
225                 230                 235                 240

Glu Gly Trp Thr Gly Pro Leu Cys Thr Val Pro Val Ser Thr Ser Ser
                245                 250                 255

Cys Leu Ser Pro Arg Gly Pro Ser Ser Ala Thr Thr Gly Cys Leu Val
            260                 265                 270

Pro Gly Pro Gly Pro Cys Asp Gly Asn Pro Cys Ala Asn Gly Gly Ser
        275                 280                 285

Cys Ser Glu Thr Pro Arg Ser Phe Glu Cys Thr Cys Pro Arg Gly Phe
    290                 295                 300

Tyr Gly Leu Arg Cys Glu Val Ser Gly Val Thr Cys Ala Asp Gly Pro
305                 310                 315                 320

Cys Phe Asn Gly Gly Leu Cys Val Gly Ala Asp Pro Asp Ser Ala
                325                 330                 335

Tyr Ile Cys His Cys Pro Pro Gly Phe Gln Gly Ser Asn Cys Glu Lys
            340                 345                 350

-continued

Arg Val Asp Arg Cys Ser Leu Gln Pro Cys Arg Asn Gly Gly Leu Cys
         355                 360                 365

Leu Asp Leu Gly His Ala Leu Arg Cys Arg Cys Arg Ala Gly Phe Ala
     370                 375                 380

Gly Pro Arg Cys Glu His Asp Leu Asp Asp Cys Ala Gly Arg Ala Cys
385                 390                 395                 400

Ala Asn Gly Gly Thr Cys Val Glu Gly Gly Ala His Arg Cys Ser
                 405                 410                 415

Cys Ala Leu Gly Phe Gly Gly Arg Asp Cys Arg Glu Arg Ala Asp Pro
                 420                 425                 430

Cys Ala Ala Arg Pro Cys Ala His Gly Gly Arg Cys Tyr Ala His Phe
                 435                 440                 445

Ser Gly Leu Val Cys Ala Cys Ala Pro Gly Tyr Met Gly Ala Arg Cys
     450                 455                 460

Glu Phe Pro Val His Pro Asp Gly Ala Ser Ala Leu Pro Ala Ala Pro
465                 470                 475                 480

Pro Gly Leu Arg Pro Gly Asp Pro Gln Arg Tyr Leu Pro Pro Ala
                 485                 490                 495

Leu Gly Leu Leu Val Ala Ala Gly Val Ala Gly Ala Ala Leu Leu Leu
                 500                 505                 510

Val His Val Arg Arg Arg Gly His Ser Gln Asp Ala Gly Ser Arg Leu
     515                 520                 525

Leu Ala Gly Thr Pro Glu Pro Ser Val His Ala Leu Pro Asp Ala Leu
     530                 535                 540

Asn Asn Leu Arg Thr Gln Glu Gly Ser Gly Asp Gly Pro Ser Ser Ser
545                 550                 555                 560

Val Asp Trp Asn Arg Pro Glu Asp Val Asp Pro Gln Gly Ile Tyr Val
                 565                 570                 575

Ile Ser Ala Pro Ser Ile Tyr Ala Arg Glu Val Ala Thr Pro Leu Phe
                 580                 585                 590

Pro Pro Leu His Thr Gly Arg Ala Gly Gln Arg Gln His Leu Leu Phe
                 595                 600                 605

Pro Tyr Pro Ser Ser Ile Leu Ser Val Lys
                 610                 615

<210> SEQ ID NO 87
<211> LENGTH: 587
<212> TYPE: PRT
<213> ORGANISM: Homo sapiens
<220> FEATURE:
<223> OTHER INFORMATION: Non-Canonical DLL3 sequence

<400> SEQUENCE: 87

Met Val Ser Pro Arg Met Ser Gly Leu Leu Ser Gln Thr Val Ile Leu
1               5                   10                  15

Ala Leu Ile Phe Leu Pro Gln Thr Arg Pro Ala Gly Val Phe Glu Leu
                 20                  25                  30

Gln Ile His Ser Phe Gly Pro Gly Pro Gly Pro Gly Ala Pro Arg Ser
                 35                  40                  45

Pro Cys Ser Ala Arg Leu Pro Cys Arg Leu Phe Phe Arg Val Cys Leu
         50                  55                  60

Lys Pro Gly Leu Ser Glu Glu Ala Ala Glu Ser Pro Cys Ala Leu Gly
65                  70                  75                  80

Ala Ala Leu Ser Ala Arg Gly Pro Val Tyr Thr Glu Gln Pro Gly Ala
                 85                  90                  95

```
Pro Ala Pro Asp Leu Pro Leu Pro Asp Gly Leu Leu Gln Val Pro Phe
            100                 105                 110

Arg Asp Ala Trp Pro Gly Thr Phe Ser Phe Ile Ile Glu Thr Trp Arg
            115                 120                 125

Glu Glu Leu Gly Asp Gln Ile Gly Gly Pro Ala Trp Ser Leu Leu Ala
130                 135                 140

Arg Val Ala Gly Arg Arg Leu Ala Ala Gly Gly Pro Trp Ala Arg
145                 150                 155                 160

Asp Ile Gln Arg Ala Gly Ala Trp Glu Leu Arg Phe Ser Tyr Arg Ala
                165                 170                 175

Arg Cys Glu Pro Pro Ala Val Gly Thr Ala Cys Thr Arg Leu Cys Arg
            180                 185                 190

Pro Arg Ser Ala Pro Ser Arg Cys Gly Pro Gly Leu Arg Pro Cys Ala
            195                 200                 205

Pro Leu Glu Asp Glu Cys Glu Ala Pro Leu Val Cys Arg Ala Gly Cys
            210                 215                 220

Ser Pro Glu His Gly Phe Cys Glu Gln Pro Gly Glu Cys Arg Cys Leu
225                 230                 235                 240

Glu Gly Trp Thr Gly Pro Leu Cys Thr Val Pro Val Ser Thr Ser Ser
                245                 250                 255

Cys Leu Ser Pro Arg Gly Pro Ser Ser Ala Thr Thr Gly Cys Leu Val
            260                 265                 270

Pro Gly Pro Gly Pro Cys Asp Gly Asn Pro Cys Ala Asn Gly Gly Ser
            275                 280                 285

Cys Ser Glu Thr Pro Arg Ser Phe Glu Cys Thr Cys Pro Arg Gly Phe
290                 295                 300

Tyr Gly Leu Arg Cys Glu Val Ser Gly Val Thr Cys Ala Asp Gly Pro
305                 310                 315                 320

Cys Phe Asn Gly Gly Leu Cys Val Gly Gly Ala Asp Pro Asp Ser Ala
                325                 330                 335

Tyr Ile Cys His Cys Pro Pro Gly Phe Gln Gly Ser Asn Cys Glu Lys
            340                 345                 350

Arg Val Asp Arg Cys Ser Leu Gln Pro Cys Arg Asn Gly Gly Leu Cys
            355                 360                 365

Leu Asp Leu Gly His Ala Leu Arg Cys Arg Cys Arg Ala Gly Phe Ala
370                 375                 380

Gly Pro Arg Cys Glu His Asp Leu Asp Asp Cys Ala Gly Arg Ala Cys
385                 390                 395                 400

Ala Asn Gly Gly Thr Cys Val Glu Gly Gly Ala His Arg Cys Ser
                405                 410                 415

Cys Ala Leu Gly Phe Gly Gly Arg Asp Cys Arg Glu Arg Ala Asp Pro
            420                 425                 430

Cys Ala Ala Arg Pro Cys Ala His Gly Gly Arg Cys Tyr Ala His Phe
            435                 440                 445

Ser Gly Leu Val Cys Ala Cys Ala Pro Gly Tyr Met Gly Ala Arg Cys
            450                 455                 460

Glu Phe Pro Val His Pro Asp Gly Ala Ser Ala Leu Pro Ala Ala Pro
465                 470                 475                 480

Pro Gly Leu Arg Pro Gly Asp Pro Gln Arg Tyr Leu Pro Pro Ala
                485                 490                 495

Leu Gly Leu Leu Val Ala Ala Gly Val Ala Gly Ala Ala Leu Leu Leu
            500                 505                 510
```

-continued

```
Val His Val Arg Arg Gly His Ser Gln Asp Ala Gly Ser Arg Leu
            515                 520                 525

Leu Ala Gly Thr Pro Glu Pro Ser Val His Ala Leu Pro Asp Ala Leu
        530                 535                 540

Asn Asn Leu Arg Thr Gln Glu Gly Ser Gly Asp Gly Pro Ser Ser Ser
545                 550                 555                 560

Val Asp Trp Asn Arg Pro Glu Asp Val Asp Pro Gln Gly Ile Tyr Val
                565                 570                 575

Ile Ser Ala Pro Ser Ile Tyr Ala Arg Glu Ala
            580                 585

<210> SEQ ID NO 88
<211> LENGTH: 6
<212> TYPE: PRT
<213> ORGANISM: Artificial Sequence
<220> FEATURE:
<223> OTHER INFORMATION: (GGS)2 linker

<400> SEQUENCE: 88

Gly Gly Ser Gly Gly Ser
1               5

<210> SEQ ID NO 89
<211> LENGTH: 9
<212> TYPE: PRT
<213> ORGANISM: Artificial Sequence
<220> FEATURE:
<223> OTHER INFORMATION: (GGS)3 linker

<400> SEQUENCE: 89

Gly Gly Ser Gly Gly Ser Gly Gly Ser
1               5

<210> SEQ ID NO 90
<211> LENGTH: 12
<212> TYPE: PRT
<213> ORGANISM: Artificial Sequence
<220> FEATURE:
<223> OTHER INFORMATION: (GGS)4 linker

<400> SEQUENCE: 90

Gly Gly Ser Gly Gly Ser Gly Gly Ser Gly Gly Ser
1               5                   10

<210> SEQ ID NO 91
<211> LENGTH: 15
<212> TYPE: PRT
<213> ORGANISM: Artificial Sequence
<220> FEATURE:
<223> OTHER INFORMATION: (GGS)5 linker

<400> SEQUENCE: 91

Gly Gly Ser Gly Gly Ser Gly Gly Ser Gly Gly Ser Gly Gly Ser
1               5                   10                  15

<210> SEQ ID NO 92
<211> LENGTH: 4
<212> TYPE: PRT
<213> ORGANISM: Artificial Sequence
<220> FEATURE:
<223> OTHER INFORMATION: glycine linker

<400> SEQUENCE: 92

Gly Gly Gly Gly
1
```

```
<210> SEQ ID NO 93
<211> LENGTH: 5
<212> TYPE: PRT
<213> ORGANISM: Artificial Sequence
<220> FEATURE:
<223> OTHER INFORMATION: glycine linker

<400> SEQUENCE: 93

Gly Gly Gly Gly Gly
1               5

<210> SEQ ID NO 94
<211> LENGTH: 6
<212> TYPE: PRT
<213> ORGANISM: Artificial Sequence
<220> FEATURE:
<223> OTHER INFORMATION: glycine linker

<400> SEQUENCE: 94

Gly Gly Gly Gly Gly Gly
1               5

<210> SEQ ID NO 95
<211> LENGTH: 6
<212> TYPE: PRT
<213> ORGANISM: Artificial Sequence
<220> FEATURE:
<223> OTHER INFORMATION: (GGS)2 linker

<400> SEQUENCE: 95

Gly Gly Ser Gly Gly Ser
1               5

<210> SEQ ID NO 96
<211> LENGTH: 9
<212> TYPE: PRT
<213> ORGANISM: Artificial Sequence
<220> FEATURE:
<223> OTHER INFORMATION: (GGS)3  linker

<400> SEQUENCE: 96

Gly Gly Ser Gly Gly Ser Gly Gly Ser
1               5

<210> SEQ ID NO 97
<211> LENGTH: 12
<212> TYPE: PRT
<213> ORGANISM: Artificial Sequence
<220> FEATURE:
<223> OTHER INFORMATION: (GGS)4 linker

<400> SEQUENCE: 97

Gly Gly Ser Gly Gly Ser Gly Gly Ser Gly Gly Ser
1               5                   10

<210> SEQ ID NO 98
<211> LENGTH: 15
<212> TYPE: PRT
<213> ORGANISM: Artificial Sequence
<220> FEATURE:
<223> OTHER INFORMATION: (GGS)5 linker

<400> SEQUENCE: 98

Gly Gly Ser Gly Gly Ser Gly Gly Ser Gly Gly Ser Gly Gly Ser
1               5                   10                  15
```

<210> SEQ ID NO 99
<211> LENGTH: 4
<212> TYPE: PRT
<213> ORGANISM: Artificial Sequence
<220> FEATURE:
<223> OTHER INFORMATION: glycine linker

<400> SEQUENCE: 99

Gly Gly Gly Gly
1

<210> SEQ ID NO 100
<211> LENGTH: 5
<212> TYPE: PRT
<213> ORGANISM: Artificial Sequence
<220> FEATURE:
<223> OTHER INFORMATION: Glycine linker

<400> SEQUENCE: 100

Gly Gly Gly Gly Gly
1               5

<210> SEQ ID NO 101
<211> LENGTH: 6
<212> TYPE: PRT
<213> ORGANISM: Artificial Sequence
<220> FEATURE:
<223> OTHER INFORMATION: glycine linker

<400> SEQUENCE: 101

Gly Gly Gly Gly Gly Gly
1               5

<210> SEQ ID NO 102
<211> LENGTH: 120
<212> TYPE: PRT
<213> ORGANISM: Artificial Sequence
<220> FEATURE:
<223> OTHER INFORMATION: hz5A8v4

<400> SEQUENCE: 102

Glu Val Gln Leu Val Glu Ser Gly Gly Gly Val Gln Pro Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Gln Arg Glu Leu Val
        35                  40                  45

Ala Val Val Ser Ser Asp Gly Arg Thr Thr Val Ala Pro Ser Val Lys
    50                  55                  60

Gly Arg Phe Thr Ile Ser Arg Asp Asn Ala Lys Asn Thr Val Ser Leu
65                  70                  75                  80

Gln Met Ser Ser Leu Arg Ala Glu Asp Thr Ala Val Tyr Tyr Cys Gly
                85                  90                  95

Val Arg Glu Trp Tyr Ser Asp Ser Asp Trp Arg Asp Tyr Glu Gly Gln
            100                 105                 110

Gly Thr Leu Val Thr Val Lys Pro
        115                 120

<210> SEQ ID NO 103
<211> LENGTH: 226
<212> TYPE: PRT
<213> ORGANISM: Artificial Sequence
<220> FEATURE:

<223> OTHER INFORMATION: Knob Fc

<400> SEQUENCE: 103

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Thr
225
```

<210> SEQ ID NO 104
<211> LENGTH: 226
<212> TYPE: PRT
<213> ORGANISM: Artificial Sequence
<220> FEATURE:
<223> OTHER INFORMATION: Hole Fc

<400> SEQUENCE: 104

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Arg Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110
```

```
Glu Lys Thr Ile Ser Lys Ala Lys Gly Gln Pro Arg Glu Pro Gln Val
            115                 120                 125

Cys Thr Leu Pro Pro Ser Arg Asp Glu Leu Thr Lys Asn Gln Val Ser
        130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
                180                 185                 190

Asp Lys Ser Arg Trp Gln Gln Gly Asn Val Phe Ser Cys Ser Val Met
                195                 200                 205

His Glu Ala Leu His Asn His Tyr Thr Gln Lys Ser Leu Ser Leu Ser
            210                 215                 220

Pro Thr
225

<210> SEQ ID NO 105
<211> LENGTH: 223
<212> TYPE: PRT
<213> ORGANISM: Artificial Sequence
<220> FEATURE:
<223> OTHER INFORMATION: Knob Fc

<400> SEQUENCE: 105

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Met Ile Ser Arg
                20                  25                  30

Thr Pro Glu Val Thr Cys Val Val Val Asp Val Ser His Glu Asp Pro
            35                  40                  45

Glu Val Lys Phe Asn Trp Tyr Val Asp Gly Val Glu Val His Asn Ala
        50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Tyr Thr Leu
        115                 120                 125

Pro Pro Cys Arg Asp Glu Leu Thr Lys Asn Gln Val Ser Leu Trp Cys
    130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
                180                 185                 190

Arg Trp Gln Gln Gly Asn Val Phe Ser Cys Ser Val Met His Glu Ala
                195                 200                 205

Leu His Asn His Tyr Thr Gln Lys Ser Leu Ser Leu Ser Pro Thr
            210                 215                 220

<210> SEQ ID NO 106
```

```
<211> LENGTH: 223
<212> TYPE: PRT
<213> ORGANISM: Artificial Sequence
<220> FEATURE:
<223> OTHER INFORMATION: Hole Fc

<400> SEQUENCE: 106

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Met Arg Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Cys Thr Leu
        115                 120                 125

Pro Pro Ser Arg Asp Glu Leu Thr Lys Asn Gln Val Ser Leu Ser Cys
    130                 135                 140

Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Val Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro Thr
    210                 215                 220

<210> SEQ ID NO 107
<211> LENGTH: 226
<212> TYPE: PRT
<213> ORGANISM: Artificial Sequence
<220> FEATURE:
<223> OTHER INFORMATION: Knob Fc

<400> SEQUENCE: 107

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
```

```
            100                 105                 110
Glu Lys Thr Ile Ser Lys Ala Lys Gly Gln Pro Arg Glu Pro Gln Val
            115                 120                 125

Tyr Thr Leu Pro Pro Cys Arg Asp Glu Leu Thr Lys Asn Gln Val Ser
            130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                    165                 170                 175

Val Leu Asp Ser Asp Gly Ser Phe Phe Leu Tyr Ser Lys Leu Thr Val
                    180                 185                 190

Asp Lys Ser Arg Trp Gln Gln Gly Asn Val Phe Ser Cys Ser Val Met
                    195                 200                 205

His Glu Ala Leu His Asn His Tyr Thr Gln Lys Ser Leu Ser Leu Ser
            210                 215                 220

Pro Gly
225

<210> SEQ ID NO 108
<211> LENGTH: 226
<212> TYPE: PRT
<213> ORGANISM: Artificial Sequence
<220> FEATURE:
<223> OTHER INFORMATION: Hole Fc

<400> SEQUENCE: 108

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Arg Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Cys Thr Leu Pro Pro Ser Arg Asp Glu Leu Thr Lys Asn Gln Val Ser
            130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                    165                 170                 175

Val Leu Asp Ser Asp Gly Ser Phe Phe Leu Val Ser Lys Leu Thr Val
                    180                 185                 190

Asp Lys Ser Arg Trp Gln Gln Gly Asn Val Phe Ser Cys Ser Val Met
                    195                 200                 205

His Glu Ala Leu His Asn His Tyr Thr Gln Lys Ser Leu Ser Leu Ser
            210                 215                 220

Pro Gly
```

<210> SEQ ID NO 109
<211> LENGTH: 223
<212> TYPE: PRT
<213> ORGANISM: Artificial Sequence
<220> FEATURE:
<223> OTHER INFORMATION: Knob Fc

<400> SEQUENCE: 109

```
Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Tyr Thr Leu
        115                 120                 125

Pro Pro Cys Arg Asp Glu Leu Thr Lys Asn Gln Val Ser Leu Trp Cys
    130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro Gly
    210                 215                 220
```

<210> SEQ ID NO 110
<211> LENGTH: 223
<212> TYPE: PRT
<213> ORGANISM: Artificial Sequence
<220> FEATURE:
<223> OTHER INFORMATION: Hole Fc

<400> SEQUENCE: 110

```
Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Met Arg Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80
```

```
Ser Val Leu Thr Val Leu His Gln Asp Trp Leu Asn Gly Lys Glu Tyr
            85                  90                  95

Lys Cys Lys Val Ser Asn Lys Ala Leu Pro Ala Pro Ile Glu Lys Thr
        100                 105                 110

Ile Ser Lys Ala Lys Gly Gln Pro Arg Glu Pro Gln Val Cys Thr Leu
        115                 120                 125

Pro Pro Ser Arg Asp Glu Leu Thr Lys Asn Gln Val Ser Leu Ser Cys
        130                 135                 140

Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Val Leu Asp
                165                 170                 175

Ser Asp Gly Ser Phe Phe Leu Val Ser Lys Leu Thr Val Asp Lys Ser
            180                 185                 190

Arg Trp Gln Gln Gly Asn Val Phe Ser Cys Ser Val Met His Glu Ala
                195                 200                 205

Leu His Asn His Tyr Thr Gln Lys Ser Leu Ser Leu Ser Pro Gly
            210                 215                 220

<210> SEQ ID NO 111
<211> LENGTH: 226
<212> TYPE: PRT
<213> ORGANISM: Artificial Sequence
<220> FEATURE:
<223> OTHER INFORMATION: Hole Fc

<400> SEQUENCE: 111

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
        130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn Arg Tyr Thr Gln Lys Ser Leu Ser Leu Ser
        210                 215                 220
```

```
Pro Thr
225

<210> SEQ ID NO 112
<211> LENGTH: 223
<212> TYPE: PRT
<213> ORGANISM: Artificial Sequence
<220> FEATURE:
<223> OTHER INFORMATION: Hole Fc

<400> SEQUENCE: 112

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Cys Thr Leu
        115                 120                 125

Pro Pro Ser Arg Asp Glu Leu Thr Lys Asn Gln Val Ser Leu Ser Cys
    130                 135                 140

Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Val Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn Arg Tyr Thr Gln Lys Ser Leu Ser Leu Ser Pro Thr
    210                 215                 220

<210> SEQ ID NO 113
<211> LENGTH: 226
<212> TYPE: PRT
<213> ORGANISM: Artificial Sequence
<220> FEATURE:
<223> OTHER INFORMATION: Hole Fc

<400> SEQUENCE: 113

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80
```

```
Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn Arg Tyr Thr Gln Lys Ser Leu Ser Leu Ser
    210                 215                 220

Pro Gly
225

<210> SEQ ID NO 114
<211> LENGTH: 223
<212> TYPE: PRT
<213> ORGANISM: Artificial Sequence
<220> FEATURE:
<223> OTHER INFORMATION: Hole Fc

<400> SEQUENCE: 114

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Cys Thr Leu
        115                 120                 125

Pro Pro Ser Arg Asp Glu Leu Thr Lys Asn Gln Val Ser Leu Ser Cys
130                 135                 140

Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Val Ser Lys Leu Thr Val Asp Lys Ser
            180                 185                 190

Arg Trp Gln Gln Gly Asn Val Phe Ser Cys Ser Val Met His Glu Ala
        195                 200                 205
```

Leu His Asn Arg Tyr Thr Gln Lys Ser Leu Ser Leu Ser Pro Gly
            210                 215                 220

<210> SEQ ID NO 115
<211> LENGTH: 226
<212> TYPE: PRT
<213> ORGANISM: Artificial Sequence
<220> FEATURE:
<223> OTHER INFORMATION: Knob Fc

<400> SEQUENCE: 115

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Val
        195                 200                 205

His Glu Ala Leu His Asn His Tyr Thr Gln Lys Ser Leu Ser Leu Ser
    210                 215                 220

Pro Thr
225

<210> SEQ ID NO 116
<211> LENGTH: 223
<212> TYPE: PRT
<213> ORGANISM: Artificial Sequence
<220> FEATURE:
<223> OTHER INFORMATION: Knob Fc

<400> SEQUENCE: 116

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Tyr Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala

```
                 50                  55                  60
Lys Thr Lys Pro Arg Glu Glu Gln Tyr Asn Ser Thr Tyr Arg Val Val
 65                  70                  75                  80

Ser Val Leu Thr Val Leu His Gln Asp Trp Leu Asn Gly Lys Glu Tyr
                     85                  90                  95

Lys Cys Lys Val Ser Asn Lys Ala Leu Pro Ala Pro Ile Glu Lys Thr
                    100                 105                 110

Ile Ser Lys Ala Lys Gly Gln Pro Arg Glu Pro Gln Val Tyr Thr Leu
                115                 120                 125

Pro Pro Cys Arg Asp Glu Leu Thr Lys Asn Gln Val Ser Leu Trp Cys
130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
                180                 185                 190

Arg Trp Gln Gln Gly Asn Val Phe Ser Cys Ser Val Val His Glu Ala
                195                 200                 205

Leu His Asn His Tyr Thr Gln Lys Ser Leu Ser Leu Ser Pro Thr
                210                 215                 220
```

```
<210> SEQ ID NO 117
<211> LENGTH: 226
<212> TYPE: PRT
<213> ORGANISM: Artificial Sequence
<220> FEATURE:
<223> OTHER INFORMATION: Knob Fc

<400> SEQUENCE: 117

Asp Lys Thr His Thr Cys Pro Pro Cys Pro Ala Pro Glu Leu Leu Gly
  1               5                  10                  15

Gly Pro Ser Val Phe Leu Phe Pro Pro Lys Pro Lys Asp Thr Leu Tyr
                 20                  25                  30

Ile Ser Arg Thr Pro Glu Val Thr Cys Val Val Val Asp Val Ser His
             35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Cys Arg Asp Glu Leu Thr Lys Asn Gln Val Ser
130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Val
```

195                 200                 205
His Glu Ala Leu His Asn His Tyr Thr Gln Lys Ser Leu Ser Leu Ser
    210                 215                 220

Pro Gly
225

<210> SEQ ID NO 118
<211> LENGTH: 223
<212> TYPE: PRT
<213> ORGANISM: Artificial Sequence
<220> FEATURE:
<223> OTHER INFORMATION: Knob Fc

<400> SEQUENCE: 118

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Tyr Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Tyr Thr Leu
        115                 120                 125

Pro Pro Cys Arg Asp Glu Leu Thr Lys Asn Gln Val Ser Leu Trp Cys
130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Val His Glu Ala
        195                 200                 205

Leu His Asn His Tyr Thr Gln Lys Ser Leu Ser Leu Ser Pro Gly
    210                 215                 220

<210> SEQ ID NO 119
<211> LENGTH: 226
<212> TYPE: PRT
<213> ORGANISM: Artificial Sequence
<220> FEATURE:
<223> OTHER INFORMATION: Hole Fc

<400> SEQUENCE: 119

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
 50                  55                  60

His Asn Ala Lys Thr Lys Pro Arg Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Val
        195                 200                 205

His Glu Ala Leu His Asn Arg Tyr Thr Gln Lys Ser Leu Ser Leu Ser
210                 215                 220

Pro Thr
225

<210> SEQ ID NO 120
<211> LENGTH: 223
<212> TYPE: PRT
<213> ORGANISM: Artificial Sequence
<220> FEATURE:
<223> OTHER INFORMATION: Hole Fc

<400> SEQUENCE: 120

Asp Lys Thr His Thr Cys Pro Pro Cys Pro Ala Pro Gly Gly Pro Ser
 1                5                  10                  15

Val Phe Leu Phe Pro Pro Lys Pro Lys Asp Thr Leu Tyr Ile Ser Arg
                 20                  25                  30

Thr Pro Glu Val Thr Cys Val Val Val Asp Val Ser His Glu Asp Pro
             35                  40                  45

Glu Val Lys Phe Asn Trp Tyr Val Asp Gly Val Glu Val His Asn Ala
 50                  55                  60

Lys Thr Lys Pro Arg Glu Glu Gln Tyr Asn Ser Thr Tyr Arg Val Val
 65                  70                  75                  80

Ser Val Leu Thr Val Leu His Gln Asp Trp Leu Asn Gly Lys Glu Tyr
                 85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Cys Thr Leu
        115                 120                 125

Pro Pro Ser Arg Asp Glu Leu Thr Lys Asn Gln Val Ser Leu Ser Cys
130                 135                 140

Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Val Ser Lys Leu Thr Val Asp Lys Ser
            180                 185                 190

Arg Trp Gln Gln Gly Asn Val Phe Ser Cys Ser Val Val His Glu Ala
        195                 200                 205

Leu His Asn Arg Tyr Thr Gln Lys Ser Leu Ser Leu Ser Pro Thr
    210                 215                 220

<210> SEQ ID NO 121
<211> LENGTH: 226
<212> TYPE: PRT
<213> ORGANISM: Artificial Sequence
<220> FEATURE:
<223> OTHER INFORMATION: Hole Fc

<400> SEQUENCE: 121

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Val
        195                 200                 205

His Glu Ala Leu His Asn Arg Tyr Thr Gln Lys Ser Leu Ser Leu Ser
    210                 215                 220

Pro Gly
225

<210> SEQ ID NO 122
<211> LENGTH: 223
<212> TYPE: PRT
<213> ORGANISM: Artificial Sequence
<220> FEATURE:
<223> OTHER INFORMATION: Hole Fc

<400> SEQUENCE: 122

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Tyr Ile Ser Arg
            20                  25                  30

```
Thr Pro Glu Val Thr Cys Val Val Asp Val Ser His Glu Asp Pro
        35                  40                  45

Glu Val Lys Phe Asn Trp Tyr Val Asp Gly Val Glu Val His Asn Ala
 50                  55                  60

Lys Thr Lys Pro Arg Glu Glu Gln Tyr Asn Ser Thr Tyr Arg Val Val
 65                  70                  75                  80

Ser Val Leu Thr Val Leu His Gln Asp Trp Leu Asn Gly Lys Glu Tyr
                 85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Cys Thr Leu
            115                 120                 125

Pro Pro Ser Arg Asp Glu Leu Thr Lys Asn Gln Val Ser Leu Ser Cys
        130                 135                 140

Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Val Ser Lys Leu Thr Val Asp Lys Ser
            180                 185                 190

Arg Trp Gln Gln Gly Asn Val Phe Ser Cys Ser Val Val His Glu Ala
            195                 200                 205

Leu His Asn Arg Tyr Thr Gln Lys Ser Leu Ser Leu Ser Pro Gly
        210                 215                 220

<210> SEQ ID NO 123
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (10)...(5)
<223> OTHER INFORMATION: Repeated 1 to 5 times

<400> SEQUENCE: 123

Gly Gly Gly Gly Ser
1               5

<210> SEQ ID NO 124
<211> LENGTH: 6
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)...(6)
<223> OTHER INFORMATION: Repeated 1 to 4 times

<400> SEQUENCE: 124

Gly Gly Gly Gly Gly Ser
1               5

<210> SEQ ID NO 125
<211> LENGTH: 5
<212> TYPE: PRT
<213> ORGANISM: Artificial Sequence
<220> FEATURE:
<223> OTHER INFORMATION: Linker
```

```
<400> SEQUENCE: 125

Gly Gly Gly Gly Ser
1               5

<210> SEQ ID NO 126
<211> LENGTH: 6
<212> TYPE: PRT
<213> ORGANISM: Artificial Sequence
<220> FEATURE:
<223> OTHER INFORMATION: Linker

<400> SEQUENCE: 126

Gly Gly Gly Gly Gly Ser
1               5

<210> SEQ ID NO 127
<211> LENGTH: 18
<212> TYPE: PRT
<213> ORGANISM: Artificial Sequence
<220> FEATURE:
<223> OTHER INFORMATION: Linker

<400> SEQUENCE: 127

Gly Gly Gly Gly Gly Ser Gly Gly Gly Gly Ser Gly Gly Gly Gly
1               5                   10                  15

Gly Ser

<210> SEQ ID NO 128
<211> LENGTH: 15
<212> TYPE: PRT
<213> ORGANISM: Artificial Sequence
<220> FEATURE:
<223> OTHER INFORMATION: Linker

<400> SEQUENCE: 128

Gly Gly Gly Gly Ser Gly Gly Gly Gly Ser Gly Gly Gly Gly Ser
1               5                   10                  15

<210> SEQ ID NO 129
<211> LENGTH: 18
<212> TYPE: PRT
<213> ORGANISM: Artificial Sequence
<220> FEATURE:
<223> OTHER INFORMATION: Linker

<400> SEQUENCE: 129

Gly Gly Ser Gly Gly Gly Gly Ser Gly Gly Gly Gly Ser Gly Gly
1               5                   10                  15

Gly Ser

<210> SEQ ID NO 130
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: VARIANT
<222> LOCATION: 2
<223> OTHER INFORMATION: Xaa is independently selected from A, V, L, I,
      M,F, W, P, G, S, T, C, Y, N,Q, K, R, H, D, or E
<220> FEATURE:
<221> NAME/KEY: VARIANT
<222> LOCATION: 4
<223> OTHER INFORMATION: Xaa is independently selected from A, V, L, I,
      M,F, W, P, G, S, T, C, Y, N,Q, K, R, H, D, or E
<220> FEATURE:
```

```
<221> NAME/KEY: REPEAT
<222> LOCATION: 1
<223> OTHER INFORMATION: Repeated 1 to 5 times
<220> FEATURE:
<221> NAME/KEY: REPEAT
<222> LOCATION: 3
<223> OTHER INFORMATION: Repeated 1 to 5 times
<220> FEATURE:
<221> NAME/KEY: REPEAT
<222> LOCATION: 5
<223> OTHER INFORMATION: Repeated 1 to 5 times

<400> SEQUENCE: 130

Gly Xaa Gly Xaa Gly
1               5

<210> SEQ ID NO 131
<211> LENGTH: 11
<212> TYPE: PRT
<213> ORGANISM: Artificial Sequence
<220> FEATURE:
<223> OTHER INFORMATION: Linker
<220> FEATURE:
<221> NAME/KEY: VARIANT
<222> LOCATION: 4
<223> OTHER INFORMATION: Xaa is independently selected from A, V, L, I,
      M,F, W, P, G, S, T, C, Y, N,Q, K, R, H, D, or E
<220> FEATURE:
<221> NAME/KEY: VARIANT
<222> LOCATION: 8
<223> OTHER INFORMATION: Xaa is independently selected from A, V, L, I,
      M,F, W, P, G, S, T, C, Y, N,Q, K, R, H, D, or E

<400> SEQUENCE: 131

Gly Gly Gly Xaa Gly Gly Gly Xaa Gly Gly Gly
1               5                   10

<210> SEQ ID NO 132
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)...(5)
<223> OTHER INFORMATION: Repeated 1 to 9 times

<400> SEQUENCE: 132

Ser Ser Ser Ser Gly
1               5

<210> SEQ ID NO 133
<211> LENGTH: 11
<212> TYPE: PRT
<213> ORGANISM: Artificial Sequence
<220> FEATURE:
<223> OTHER INFORMATION: Linker

<400> SEQUENCE: 133

Gly Gly Gly Gly Gly Cys Gly Gly Gly Gly Gly
1               5                   10

<210> SEQ ID NO 134
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: REPEAT
```

-continued

```
<222> LOCATION: (1)...(5)
<223> OTHER INFORMATION: Repeated 1 to 9 times

<400> SEQUENCE: 134

Glu Ala Ala Ala Lys
1               5

<210> SEQ ID NO 135
<211> LENGTH: 6
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (3)...(4)
<223> OTHER INFORMATION: Repeated 2 to 20 times

<400> SEQUENCE: 135

Ala Ser Ala Pro Gly Thr
1               5

<210> SEQ ID NO 136
<211> LENGTH: 9
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (3)...(7)
<223> OTHER INFORMATION: Rpeated 2 to 20 times

<400> SEQUENCE: 136

Ala Ser Glu Ala Ala Ala Lys Gly Thr
1               5

<210> SEQ ID NO 137
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)...(5)
<223> OTHER INFORMATION: Repeat 2 to 20 times

<400> SEQUENCE: 137

Gly Gly Gly Gly Ala
1               5

<210> SEQ ID NO 138
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)...(5)
<223> OTHER INFORMATION: Repeat 2 to 20 times

<400> SEQUENCE: 138

Pro Gly Gly Gly Ser
1               5

<210> SEQ ID NO 139
<211> LENGTH: 5
```

```
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)...(5)
<223> OTHER INFORMATION: Repeat 2 to 20 times

<400> SEQUENCE: 139

Ala Gly Gly Gly Ser
1               5

<210> SEQ ID NO 140
<211> LENGTH: 20
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (4)...(17)
<223> OTHER INFORMATION: Repeat 2 to 20 times

<400> SEQUENCE: 140

Gly Gly Ser Glu Gly Lys Ser Ser Gly Ser Gly Ser Glu Ser Lys Ser
1               5                   10                  15

Thr Gly Gly Ser
            20

<210> SEQ ID NO 141
<211> LENGTH: 9
<212> TYPE: PRT
<213> ORGANISM: Artificial Sequence
<220> FEATURE:
<223> OTHER INFORMATION: Linker

<400> SEQUENCE: 141

Ser Ser Ser Ala Ser Ala Ser Ser Ala
1               5

<210> SEQ ID NO 142
<211> LENGTH: 7
<212> TYPE: PRT
<213> ORGANISM: Artificial Sequence
<220> FEATURE:
<223> OTHER INFORMATION: Linker

<400> SEQUENCE: 142

Gly Ser Pro Gly Ser Pro Gly
1               5

<210> SEQ ID NO 143
<211> LENGTH: 11
<212> TYPE: PRT
<213> ORGANISM: Artificial Sequence
<220> FEATURE:
<223> OTHER INFORMATION: Linker

<400> SEQUENCE: 143

Ala Thr Thr Thr Gly Ser Ser Pro Gly Pro Thr
1               5                   10

<210> SEQ ID NO 144
<211> LENGTH: 5
<212> TYPE: PRT
<213> ORGANISM: Artificial Sequence
<220> FEATURE:
```

```
<223> OTHER INFORMATION: Linker
<220> FEATURE:
<221> NAME/KEY: VARIANT
<222> LOCATION: 1
<223> OTHER INFORMATION: Xaa is  I, L, Y, M, F, V, or A
<220> FEATURE:
<221> NAME/KEY: VARIANT
<222> LOCATION: 2
<223> OTHER INFORMATION: Xaa is A, G, S, V, E, D, Q, N, or Y
<220> FEATURE:
<221> NAME/KEY: VARIANT
<222> LOCATION: 3
<223> OTHER INFORMATION: Xaa is H, P, A, V, G, S, or T
<220> FEATURE:
<221> NAME/KEY: VARIANT
<222> LOCATION: 4
<223> OTHER INFORMATION: Xaa is D or E
<220> FEATURE:
<221> NAME/KEY: VARIANT
<222> LOCATION: 5
<223> OTHER INFORMATION: Xaa is I, L, Y, M, F, V, T, S, G or A

<400> SEQUENCE: 144

Xaa Xaa Xaa Xaa Xaa
1               5

<210> SEQ ID NO 145
<211> LENGTH: 5
<212> TYPE: PRT
<213> ORGANISM: Artificial Sequence
<220> FEATURE:
<223> OTHER INFORMATION: Linker consensus
<220> FEATURE:
<221> NAME/KEY: VARIANT
<222> LOCATION: 1
<223> OTHER INFORMATION: Xaa is I or L
<220> FEATURE:
<221> NAME/KEY: VARIANT
<222> LOCATION: 3
<223> OTHER INFORMATION: Xaa is P or A
<220> FEATURE:
<221> NAME/KEY: VARIANT
<222> LOCATION: 5
<223> OTHER INFORMATION: Xaa is I, V, T, S, or G

<400> SEQUENCE: 145

Xaa Glu Xaa Asp Xaa
1               5

<210> SEQ ID NO 146
<211> LENGTH: 4
<212> TYPE: PRT
<213> ORGANISM: Artificial Sequence
<220> FEATURE:
<223> OTHER INFORMATION: Granzyme B substrte

<400> SEQUENCE: 146

Leu Glu Ala Asp
1

<210> SEQ ID NO 147
<211> LENGTH: 4
<212> TYPE: PRT
<213> ORGANISM: Artificial Sequence
<220> FEATURE:
<223> OTHER INFORMATION: Linker

<400> SEQUENCE: 147

Leu Glu Pro Asp
1
```

```
<210> SEQ ID NO 148
<211> LENGTH: 4
<212> TYPE: PRT
<213> ORGANISM: Artificial Sequence
<220> FEATURE:
<223> OTHER INFORMATION: Linker

<400> SEQUENCE: 148

Leu Glu Ala Glu
1

<210> SEQ ID NO 149
<211> LENGTH: 5
<212> TYPE: PRT
<213> ORGANISM: Artificial Sequence
<220> FEATURE:
<223> OTHER INFORMATION: Linker

<400> SEQUENCE: 149

Ile Glu Pro Asp Ile
1               5

<210> SEQ ID NO 150
<211> LENGTH: 5
<212> TYPE: PRT
<213> ORGANISM: Artificial Sequence
<220> FEATURE:
<223> OTHER INFORMATION: Linker

<400> SEQUENCE: 150

Leu Glu Pro Asp Gly
1               5

<210> SEQ ID NO 151
<211> LENGTH: 5
<212> TYPE: PRT
<213> ORGANISM: Artificial Sequence
<220> FEATURE:
<223> OTHER INFORMATION: Linker

<400> SEQUENCE: 151

Leu Glu Ala Asp Thr
1               5

<210> SEQ ID NO 152
<211> LENGTH: 5
<212> TYPE: PRT
<213> ORGANISM: Artificial Sequence
<220> FEATURE:
<223> OTHER INFORMATION: Linker

<400> SEQUENCE: 152

Ile Glu Pro Asp Gly
1               5

<210> SEQ ID NO 153
<211> LENGTH: 5
<212> TYPE: PRT
<213> ORGANISM: Artificial Sequence
<220> FEATURE:
<223> OTHER INFORMATION: Linker

<400> SEQUENCE: 153

Ile Glu Pro Asp Val
1               5

<210> SEQ ID NO 154
```

```
<211> LENGTH: 5
<212> TYPE: PRT
<213> ORGANISM: Artificial Sequence
<220> FEATURE:
<223> OTHER INFORMATION: Linker

<400> SEQUENCE: 154

Ile Glu Pro Asp Ser
1               5

<210> SEQ ID NO 155
<211> LENGTH: 5
<212> TYPE: PRT
<213> ORGANISM: Artificial Sequence
<220> FEATURE:
<223> OTHER INFORMATION: Linker

<400> SEQUENCE: 155

Ile Glu Pro Asp Thr
1               5

<210> SEQ ID NO 156
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: VARIANT
<222> LOCATION: 1
<223> OTHER INFORMATION: Xaa is any amnio acid
<220> FEATURE:
<221> NAME/KEY: VARIANT
<222> LOCATION: 5
<223> OTHER INFORMATION: Xaa is A or V

<400> SEQUENCE: 156

Xaa Gln Ala Arg Xaa
1               5

<210> SEQ ID NO 157
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: VARIANT
<222> LOCATION: 5
<223> OTHER INFORMATION: Xaa is A or V

<400> SEQUENCE: 157

Arg Gln Ala Arg Xaa
1               5

<210> SEQ ID NO 158
<211> LENGTH: 4
<212> TYPE: PRT
<213> ORGANISM: Artificial Sequence
<220> FEATURE:
<223> OTHER INFORMATION: matriptase substrate

<400> SEQUENCE: 158

Arg Gln Ala Arg
1

<210> SEQ ID NO 159
<211> LENGTH: 5
<212> TYPE: PRT
```

```
<213> ORGANISM: Artificial Sequence
<220> FEATURE:
<223> OTHER INFORMATION: Linker

<400> SEQUENCE: 159

Arg Gln Ala Arg Val
1               5

<210> SEQ ID NO 160
<211> LENGTH: 4
<212> TYPE: PRT
<213> ORGANISM: Artificial Sequence
<220> FEATURE:
<223> OTHER INFORMATION: Linker consensus
<220> FEATURE:
<221> NAME/KEY: VARIANT
<222> LOCATION: 1
<223> OTHER INFORMATION: Xaa is P, V or A
<220> FEATURE:
<221> NAME/KEY: VARIANT
<222> LOCATION: 2
<223> OTHER INFORMATION: Xaa is Q or D
<220> FEATURE:
<221> NAME/KEY: VARIANT
<222> LOCATION: 3
<223> OTHER INFORMATION: Xaa is A or N
<220> FEATURE:
<221> NAME/KEY: VARIANT
<222> LOCATION: 4
<223> OTHER INFORMATION: Xaa is L, I, or M

<400> SEQUENCE: 160

Xaa Xaa Xaa Xaa
1

<210> SEQ ID NO 161
<211> LENGTH: 4
<212> TYPE: PRT
<213> ORGANISM: Artificial Sequence
<220> FEATURE:
<223> OTHER INFORMATION: Linker consensus
<220> FEATURE:
<221> NAME/KEY: VARIANT
<222> LOCATION: 2
<223> OTHER INFORMATION: Xaa is Q or D
<220> FEATURE:
<221> NAME/KEY: VARIANT
<222> LOCATION: 3
<223> OTHER INFORMATION: Xaa is A or N
<220> FEATURE:
<221> NAME/KEY: VARIANT
<222> LOCATION: 4
<223> OTHER INFORMATION: Xaa is L or I

<400> SEQUENCE: 161

Pro Xaa Xaa Xaa
1

<210> SEQ ID NO 162
<211> LENGTH: 4
<212> TYPE: PRT
<213> ORGANISM: Artificial Sequence
<220> FEATURE:
<223> OTHER INFORMATION: MMP substrate

<400> SEQUENCE: 162

Pro Ala Gly Leu
1

<210> SEQ ID NO 163
<211> LENGTH: 19
```

```
<212> TYPE: PRT
<213> ORGANISM: Artificial Sequence
<220> FEATURE:
<223> OTHER INFORMATION: Linker

<400> SEQUENCE: 163

Thr Gly Leu Glu Ala Asp Gly Ser Pro Ala Gly Leu Gly Arg Gln Ala
1               5                   10                  15

Arg Val Gly

<210> SEQ ID NO 164
<211> LENGTH: 19
<212> TYPE: PRT
<213> ORGANISM: Artificial Sequence
<220> FEATURE:
<223> OTHER INFORMATION: Linker

<400> SEQUENCE: 164

Thr Gly Leu Glu Ala Asp Gly Ser Arg Gln Ala Arg Val Gly Pro Ala
1               5                   10                  15

Gly Leu Gly

<210> SEQ ID NO 165
<211> LENGTH: 19
<212> TYPE: PRT
<213> ORGANISM: Artificial Sequence
<220> FEATURE:
<223> OTHER INFORMATION: Linker

<400> SEQUENCE: 165

Thr Gly Ser Pro Ala Gly Leu Glu Ala Asp Gly Ser Arg Gln Ala Arg
1               5                   10                  15

Val Gly Ser

<210> SEQ ID NO 166
<211> LENGTH: 19
<212> TYPE: PRT
<213> ORGANISM: Artificial Sequence
<220> FEATURE:
<223> OTHER INFORMATION: Linker

<400> SEQUENCE: 166

Thr Gly Pro Ala Gly Leu Gly Leu Glu Ala Asp Gly Ser Arg Gln Ala
1               5                   10                  15

Arg Val Gly

<210> SEQ ID NO 167
<211> LENGTH: 19
<212> TYPE: PRT
<213> ORGANISM: Artificial Sequence
<220> FEATURE:
<223> OTHER INFORMATION: Linker

<400> SEQUENCE: 167

Thr Gly Arg Gln Ala Arg Val Gly Leu Glu Ala Asp Gly Ser Pro Ala
1               5                   10                  15

Gly Leu Gly

<210> SEQ ID NO 168
<211> LENGTH: 18
<212> TYPE: PRT
<213> ORGANISM: Artificial Sequence
<220> FEATURE:
<223> OTHER INFORMATION: Linker
```

-continued

<400> SEQUENCE: 168

Thr Gly Ser Arg Gln Ala Arg Val Gly Pro Ala Gly Leu Glu Ala Asp
1               5                   10                  15

Gly Ser

<210> SEQ ID NO 169
<211> LENGTH: 20
<212> TYPE: PRT
<213> ORGANISM: Artificial Sequence
<220> FEATURE:
<223> OTHER INFORMATION: Linker

<400> SEQUENCE: 169

Thr Gly Pro Ala Gly Leu Gly Ser Arg Gln Ala Arg Val Gly Leu Glu
1               5                   10                  15

Ala Asp Gly Ser
            20

<210> SEQ ID NO 170
<211> LENGTH: 18
<212> TYPE: PRT
<213> ORGANISM: Artificial Sequence
<220> FEATURE:
<223> OTHER INFORMATION: Linker

<400> SEQUENCE: 170

Gly Pro Ala Gly Leu Gly Leu Glu Pro Asp Gly Ser Arg Gln Ala Arg
1               5                   10                  15

Val Gly

<210> SEQ ID NO 171
<211> LENGTH: 18
<212> TYPE: PRT
<213> ORGANISM: Artificial Sequence
<220> FEATURE:
<223> OTHER INFORMATION: Linker

<400> SEQUENCE: 171

Gly Gly Ser Gly Gly Gly Gly Ile Glu Pro Asp Ile Gly Gly Ser Gly
1               5                   10                  15

Gly Ser

<210> SEQ ID NO 172
<211> LENGTH: 18
<212> TYPE: PRT
<213> ORGANISM: Artificial Sequence
<220> FEATURE:
<223> OTHER INFORMATION: Linker

<400> SEQUENCE: 172

Gly Gly Ser Gly Gly Gly Gly Leu Glu Ala Asp Thr Gly Gly Ser Gly
1               5                   10                  15

Gly Ser

<210> SEQ ID NO 173
<211> LENGTH: 9
<212> TYPE: PRT
<213> ORGANISM: Artificial Sequence
<220> FEATURE:
<223> OTHER INFORMATION: Linker

<400> SEQUENCE: 173

```
Gly Ser Ile Glu Pro Asp Ile Gly Ser
1               5
```

<210> SEQ ID NO 174
<211> LENGTH: 9
<212> TYPE: PRT
<213> ORGANISM: Artificial Sequence
<220> FEATURE:
<223> OTHER INFORMATION: Linker

<400> SEQUENCE: 174

```
Gly Ser Leu Glu Ala Asp Thr Gly Ser
1               5
```

<210> SEQ ID NO 175
<211> LENGTH: 18
<212> TYPE: PRT
<213> ORGANISM: Artificial Sequence
<220> FEATURE:
<223> OTHER INFORMATION: Linker

<400> SEQUENCE: 175

```
Gly Gly Ser Gly Gly Gly Gly Ile Glu Pro Asp Gly Gly Ser Gly
1               5                   10                  15

Gly Ser
```

<210> SEQ ID NO 176
<211> LENGTH: 18
<212> TYPE: PRT
<213> ORGANISM: Artificial Sequence
<220> FEATURE:
<223> OTHER INFORMATION: Linker

<400> SEQUENCE: 176

```
Gly Gly Ser Gly Gly Gly Gly Ile Glu Pro Asp Val Gly Gly Ser Gly
1               5                   10                  15

Gly Ser
```

<210> SEQ ID NO 177
<211> LENGTH: 18
<212> TYPE: PRT
<213> ORGANISM: Artificial Sequence
<220> FEATURE:
<223> OTHER INFORMATION: Linker

<400> SEQUENCE: 177

```
Gly Gly Ser Gly Gly Gly Gly Ile Glu Pro Asp Ser Gly Gly Ser Gly
1               5                   10                  15

Gly Ser
```

<210> SEQ ID NO 178
<211> LENGTH: 18
<212> TYPE: PRT
<213> ORGANISM: Artificial Sequence
<220> FEATURE:
<223> OTHER INFORMATION: Linker

<400> SEQUENCE: 178

```
Gly Gly Ser Gly Gly Gly Gly Ile Glu Pro Asp Thr Gly Gly Ser Gly
1               5                   10                  15

Gly Ser
```

<210> SEQ ID NO 179
<211> LENGTH: 12

```
<212> TYPE: PRT
<213> ORGANISM: Artificial Sequence
<220> FEATURE:
<223> OTHER INFORMATION: Linker

<400> SEQUENCE: 179

Gly Gly Gly Ser Leu Glu Pro Asp Gly Ser Gly Ser
1               5                   10

<210> SEQ ID NO 180
<211> LENGTH: 18
<212> TYPE: PRT
<213> ORGANISM: Artificial Sequence
<220> FEATURE:
<223> OTHER INFORMATION: Linker

<400> SEQUENCE: 180

Gly Pro Ala Gly Leu Gly Leu Glu Ala Asp Gly Ser Arg Gln Ala Arg
1               5                   10                  15

Val Gly

<210> SEQ ID NO 181
<211> LENGTH: 15
<212> TYPE: PRT
<213> ORGANISM: Artificial Sequence
<220> FEATURE:
<223> OTHER INFORMATION: Linker

<400> SEQUENCE: 181

Gly Gly Glu Gly Gly Gly Gly Ser Gly Gly Ser Gly Gly Gly Ser
1               5                   10                  15

<210> SEQ ID NO 182
<211> LENGTH: 18
<212> TYPE: PRT
<213> ORGANISM: Artificial Sequence
<220> FEATURE:
<223> OTHER INFORMATION: Linker

<400> SEQUENCE: 182

Gly Ser Ser Ala Gly Ser Glu Ala Gly Gly Ser Gly Gln Ala Gly Val
1               5                   10                  15

Gly Ser

<210> SEQ ID NO 183
<211> LENGTH: 18
<212> TYPE: PRT
<213> ORGANISM: Artificial Sequence
<220> FEATURE:
<223> OTHER INFORMATION: Linker

<400> SEQUENCE: 183

Gly Gly Ser Gly Gly Gly Gly Leu Glu Ala Glu Gly Ser Gly Gly Gly
1               5                   10                  15

Gly Ser

<210> SEQ ID NO 184
<211> LENGTH: 18
<212> TYPE: PRT
<213> ORGANISM: Artificial Sequence
<220> FEATURE:
<223> OTHER INFORMATION: Linker

<400> SEQUENCE: 184

Gly Gly Ser Gly Gly Gly Gly Ile Glu Pro Asp Pro Gly Gly Ser Gly
```

```
1               5                   10                  15

Gly Ser

<210> SEQ ID NO 185
<211> LENGTH: 19
<212> TYPE: PRT
<213> ORGANISM: Artificial Sequence
<220> FEATURE:
<223> OTHER INFORMATION: Linker

<400> SEQUENCE: 185

Thr Gly Gly Ser Gly Gly Gly Ile Glu Pro Asp Ile Gly Ser
1               5                   10                  15

Gly Gly Ser

<210> SEQ ID NO 186
<211> LENGTH: 204
<212> TYPE: PRT
<213> ORGANISM: Artificial Sequence
<220> FEATURE:
<223> OTHER INFORMATION: 41BBL

<400> SEQUENCE: 186

Ala Cys Pro Trp Ala Val Ser Gly Ala Arg Ala Ser Pro Gly Ser Ala
1               5                   10                  15

Ala Ser Pro Arg Leu Arg Glu Gly Pro Glu Leu Ser Pro Asp Asp Pro
                20                  25                  30

Ala Gly Leu Leu Asp Leu Arg Gln Gly Met Phe Ala Gln Leu Val Ala
        35                  40                  45

Gln Asn Val Leu Leu Ile Asp Gly Pro Leu Ser Trp Tyr Ser Asp Pro
    50                  55                  60

Gly Leu Ala Gly Val Ser Leu Thr Gly Gly Leu Ser Tyr Lys Glu Asp
65                  70                  75                  80

Thr Lys Glu Leu Val Val Ala Lys Ala Gly Val Tyr Tyr Val Phe Phe
                85                  90                  95

Gln Leu Glu Leu Arg Arg Val Val Ala Gly Glu Gly Ser Gly Ser Val
                100                 105                 110

Ser Leu Ala Leu His Leu Gln Pro Leu Arg Ser Ala Ala Gly Ala Ala
        115                 120                 125

Ala Leu Ala Leu Thr Val Asp Leu Pro Pro Ala Ser Ser Glu Ala Asn
    130                 135                 140

Ser Ala Phe Gly Phe Gln Gly Arg Leu Leu His Leu Ser Ala Gly Gln
145                 150                 155                 160

Arg Leu Gly Val His Leu His Thr Glu Ala Arg Ala Arg His Ala Trp
                165                 170                 175

Gln Leu Thr Gln Gly Ala Thr Val Leu Gly Leu Phe Arg Val Thr Pro
                180                 185                 190

Glu Ile Pro Ala Gly Leu Pro Ser Pro Arg Ser Glu
        195                 200

<210> SEQ ID NO 187
<211> LENGTH: 116
<212> TYPE: PRT
<213> ORGANISM: Artificial Sequence
<220> FEATURE:
<223> OTHER INFORMATION: 41BB VH

<400> SEQUENCE: 187

Glu Val Gln Leu Val Gln Ser Gly Ala Glu Val Lys Lys Pro Gly Glu
```

```
                1               5                  10                  15
         Ser Leu Arg Ile Ser Cys Lys Gly Ser Gly Tyr Ser Phe Ser Thr Tyr
                         20                  25                  30

Trp Ile Ser Trp Val Arg Gln Met Pro Gly Lys Gly Leu Glu Trp Met
                         35                  40                  45

Gly Lys Ile Tyr Pro Gly Asp Ser Tyr Thr Asn Tyr Ser Pro Ser Phe
                         50                  55                  60

Gln Gly Gln Val Thr Ile Ser Ala Asp Lys Ser Ile Ser Thr Ala Tyr
         65                  70                  75                  80

Leu Gln Trp Ser Ser Leu Lys Ala Ser Asp Thr Ala Met Tyr Tyr Cys
                         85                  90                  95

Ala Arg Gly Tyr Gly Ile Phe Asp Tyr Trp Gly Gln Gly Thr Leu Val
                         100                 105                 110

Thr Val Ser Ser
                         115

<210> SEQ ID NO 188
<211> LENGTH: 108
<212> TYPE: PRT
<213> ORGANISM: Artificial Sequence
<220> FEATURE:
<223> OTHER INFORMATION: 41BB VL

<400> SEQUENCE: 188

Ser Tyr Glu Leu Thr Gln Pro Pro Ser Val Ser Val Ser Pro Gly Gln
         1               5                   10                  15

Thr Ala Ser Ile Thr Cys Ser Gly Asp Asn Ile Gly Asp Gln Tyr Ala
                         20                  25                  30

His Trp Tyr Gln Gln Lys Pro Gly Gln Ser Pro Val Leu Val Ile Tyr
                         35                  40                  45

Gln Asp Lys Asn Arg Pro Ser Gly Ile Pro Glu Arg Phe Ser Gly Ser
                         50                  55                  60

Asn Ser Gly Asn Thr Ala Thr Leu Thr Ile Ser Gly Thr Gln Ala Met
         65                  70                  75                  80

Asp Glu Ala Asp Tyr Tyr Cys Ala Thr Tyr Thr Gly Phe Gly Ser Leu
                         85                  90                  95

Ala Val Phe Gly Gly Gly Thr Lys Leu Thr Val Leu
                         100                 105

<210> SEQ ID NO 189
<211> LENGTH: 121
<212> TYPE: PRT
<213> ORGANISM: Artificial Sequence
<220> FEATURE:
<223> OTHER INFORMATION: 41BB VH

<400> SEQUENCE: 189

Gln Val Gln Leu Gln Gln Trp Gly Ala Gly Leu Leu Lys Pro Ser Glu
         1               5                   10                  15

Thr Leu Ser Leu Thr Cys Ala Val Tyr Gly Gly Ser Phe Ser Gly Tyr
                         20                  25                  30

Tyr Trp Ser Trp Ile Arg Gln Ser Pro Glu Lys Gly Leu Glu Trp Ile
                         35                  40                  45

Gly Glu Ile Asn His Gly Gly Tyr Val Thr Tyr Asn Pro Ser Leu Glu
                         50                  55                  60

Ser Arg Val Thr Ile Ser Val Asp Thr Ser Lys Asn Gln Phe Ser Leu
         65                  70                  75                  80
```

```
              Lys Leu Ser Ser Val Thr Ala Ala Asp Thr Ala Val Tyr Tyr Cys Ala
                          85                  90                  95

Arg Asp Tyr Gly Pro Gly Asn Tyr Asp Trp Tyr Phe Asp Leu Trp Gly
                      100                 105                 110

Arg Gly Thr Leu Val Thr Val Ser Ser
                      115                 120

<210> SEQ ID NO 190
<211> LENGTH: 109
<212> TYPE: PRT
<213> ORGANISM: Artificial Sequence
<220> FEATURE:
<223> OTHER INFORMATION: 41BB VL

<400> SEQUENCE: 190

Glu Ile Val Leu Thr Gln Ser Pro Ala Thr Leu Ser Leu Ser Pro Gly
              1               5                   10                  15

Glu Arg Ala Thr Leu Ser Cys Arg Ala Ser Gln Ser Val Ser Ser Tyr
                          20                  25                  30

Leu Ala Trp Tyr Gln Gln Lys Pro Gly Gln Ala Pro Arg Leu Leu Ile
                      35                  40                  45

Tyr Asp Ala Ser Asn Arg Ala Thr Gly Ile Pro Ala Arg Phe Ser Gly
              50                  55                  60

Ser Gly Ser Gly Thr Asp Phe Thr Leu Thr Ile Ser Ser Leu Glu Pro
              65                  70                  75                  80

Glu Asp Phe Ala Val Tyr Tyr Cys Gln Gln Arg Ser Asn Trp Pro Pro
                          85                  90                  95

Ala Leu Thr Phe Gly Gly Gly Thr Lys Val Glu Ile Lys
                      100                 105

<210> SEQ ID NO 191
<211> LENGTH: 120
<212> TYPE: PRT
<213> ORGANISM: Artificial Sequence
<220> FEATURE:
<223> OTHER INFORMATION: 41BB VH

<400> SEQUENCE: 191

Gln Met Gln Leu Val Gln Ser Gly Ala Glu Val Lys Lys Pro Gly Ala
              1               5                   10                  15

Ser Val Lys Val Ser Cys Lys Ala Ser Gly Tyr Ser Phe Ser Gly Tyr
                          20                  25                  30

Tyr Met His Trp Val Arg Gln Ala Pro Gly Gln Gly Leu Glu Trp Met
                      35                  40                  45

Gly Trp Val Asn Pro Met Ser Gly Gly Thr Asn Tyr Ala Gln Lys Phe
              50                  55                  60

Gln Gly Arg Val Thr Ile Thr Arg Asp Thr Ser Ala Ser Thr Ala Tyr
              65                  70                  75                  80

Met Glu Leu Ser Ser Leu Arg Ser Glu Asp Thr Ala Val Tyr Tyr Cys
                          85                  90                  95

Ala Arg Glu Gly Met Ala Met Arg Leu Glu Leu Asp Lys Trp Gly Gln
                      100                 105                 110

Gly Thr Leu Val Thr Val Ser Ser
                      115                 120

<210> SEQ ID NO 192
<211> LENGTH: 106
<212> TYPE: PRT
<213> ORGANISM: Artificial Sequence
```

<220> FEATURE:
<223> OTHER INFORMATION: 41BB VL

<400> SEQUENCE: 192

Ser Tyr Glu Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Val Val
                85                  90                  95

Phe Gly Gly Gly Thr Gln Leu Thr Val Leu
            100                 105

<210> SEQ ID NO 193
<211> LENGTH: 178
<212> TYPE: PRT
<213> ORGANISM: Artificial Sequence
<220> FEATURE:
<223> OTHER INFORMATION: 41BB Anticalin

<400> SEQUENCE: 193

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Gln Ala Gly Asn Ile Lys Leu Arg Glu Asp Lys Asp Pro
        35                  40                  45

Asn Lys Met Met Ala Thr Ile Tyr Glu Leu Lys Glu Asp Lys Ser Tyr
    50                  55                  60

Asn Val Thr Gly Val Thr Phe Asp Asp Lys Lys Cys Thr Tyr Ala Ile
65                  70                  75                  80

Ser Thr Phe Val Pro Gly Ser Gln Pro Gly Glu Phe Thr Leu Gly Lys
                85                  90                  95

Ile Lys Ser Phe Pro Gly His Thr Ser Ser Leu Val Arg Val Val Ser
            100                 105                 110

Thr Asn Tyr Asn Gln His Ala Met Val Phe Phe Lys Phe Val Phe Gln
        115                 120                 125

Asn Arg Glu Glu Phe Tyr Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 194
<211> LENGTH: 178
<212> TYPE: PRT
<213> ORGANISM: Artificial Sequence
<220> FEATURE:
<223> OTHER INFORMATION: 41BB Anticalin

<400> SEQUENCE: 194

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Gln Ala Gly Asn Ile Arg Leu Arg Glu Asp Lys Asp Pro
        35                  40                  45

Ile Lys Met Met Ala Thr Ile Tyr Glu Leu Lys Glu Asp Lys Ser Tyr
50                  55                  60

Asp Val Thr Met Val Lys Phe Asp Asp Lys Lys Cys Met Tyr Asp Ile
65                  70                  75                  80

Trp Thr Phe Val Pro Gly Ser Gln Pro Gly Glu Phe Thr Leu Gly Lys
                85                  90                  95

Ile Lys Ser Phe Pro Gly His Thr Ser Ser Leu Val Arg Val Val Ser
            100                 105                 110

Thr Asn Tyr Asn Gln His Ala Met Val Phe Phe Lys Phe Val Phe Gln
            115                 120                 125

Asn Arg Glu Glu Phe Tyr Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 195
<211> LENGTH: 178
<212> TYPE: PRT
<213> ORGANISM: Artificial Sequence
<220> FEATURE:
<223> OTHER INFORMATION: 41BB Anticalin

<400> SEQUENCE: 195

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Gln Ala Gly Asn Ile Arg Leu Arg Glu Asp Lys Asp Pro
        35                  40                  45

Asn Lys Met Met Ala Thr Ile Tyr Glu Leu Lys Glu Asp Lys Ser Tyr
50                  55                  60

Asp Val Thr Ala Val Ala Phe Asp Asp Lys Lys Cys Thr Tyr Asp Ile
65                  70                  75                  80

Trp Thr Phe Val Pro Gly Ser Gln Pro Gly Glu Phe Thr Leu Gly Lys
                85                  90                  95

Ile Lys Ser Phe Pro Gly His Thr Ser Ser Leu Val Arg Val Val Ser
            100                 105                 110

Thr Asn Tyr Asn Gln His Ala Met Val Phe Phe Lys Phe Val Phe Gln
            115                 120                 125

Asn Arg Glu Glu Phe Tyr Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 196
<211> LENGTH: 178
<212> TYPE: PRT
<213> ORGANISM: Artificial Sequence
<220> FEATURE:
<223> OTHER INFORMATION: 41BB Anticalin

<400> SEQUENCE: 196

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Gln Ala Gly Asn Ile Lys Leu Arg Glu Asp Lys Asp Pro
        35                  40                  45

Asn Lys Met Met Ala Thr Ile Tyr Glu Leu Lys Glu Asp Lys Ser Tyr
50                  55                  60

Asp Val Thr Ala Val Ala Phe Asp Asp Lys Lys Cys Thr Tyr Asp Ile
65                  70                  75                  80

Trp Thr Phe Val Pro Gly Ser Gln Pro Gly Glu Phe Thr Leu Gly Lys
                85                  90                  95

Ile Lys Ser Phe Pro Gly His Thr Ser Ser Leu Val Arg Val Val Ser
            100                 105                 110

Thr Asn Tyr Asn Gln His Ala Met Val Phe Phe Lys Phe Val Phe Gln
        115                 120                 125

Asn Arg Glu Glu Phe Tyr Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 197
<211> LENGTH: 175
<212> TYPE: PRT
<213> ORGANISM: Artificial Sequence
<220> FEATURE:
<223> OTHER INFORMATION: 41BB Anticalin

<400> SEQUENCE: 197

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Gln Ala Gly Asn Ile Lys Leu Arg Glu Asp Ser Lys Met
        35                  40                  45

Met Ala Thr Ile Tyr Glu Leu Lys Glu Asp Lys Ser Tyr Asp Val Thr
50                  55                  60

Gly Val Ser Phe Asp Asp Lys Lys Cys Thr Tyr Ala Ile Met Thr Phe
65                  70                  75                  80

Val Pro Gly Ser Gln Pro Gly Glu Phe Thr Leu Gly Lys Ile Lys Ser
                85                  90                  95

Phe Pro Gly His Thr Ser Ser Leu Val Arg Val Val Ser Thr Asn Tyr
            100                 105                 110

```
Asn Gln His Ala Met Val Phe Phe Lys Phe Val Phe Gln Asn Arg Glu
            115                 120                 125
Glu Phe Tyr Ile Thr Leu Tyr Gly Arg Thr Lys Glu Leu Thr Ser Glu
        130                 135                 140
Leu Lys Glu Asn Phe Ile Arg Phe Ser Lys Ser Leu Gly Leu Pro Glu
145                 150                 155                 160
Asn His Ile Val Phe Pro Val Pro Ile Asp Gln Cys Ile Asp Gly
                165                 170                 175
```

<210> SEQ ID NO 198
<211> LENGTH: 178
<212> TYPE: PRT
<213> ORGANISM: Artificial Sequence
<220> FEATURE:
<223> OTHER INFORMATION: 41BB Anticalin

<400> SEQUENCE: 198

```
Gln Asp Ser Thr Ser Asp Leu Ile Pro Ala Pro Pro Leu Ser Lys Val
1               5                   10                  15
Pro Leu Gln Gln Asn Phe Gln Asp Asn Gln Phe His Gly Lys Trp Tyr
            20                  25                  30
Val Val Gly Gln Ala Gly Asn Ile Lys Leu Arg Glu Asp Lys Asp Pro
        35                  40                  45
Val Lys Met Met Ala Thr Ile Tyr Glu Leu Lys Glu Asp Lys Ser Tyr
50                  55                  60
Asp Val Thr Gly Val Thr Phe Asp Lys Lys Cys Arg Tyr Asp Ile
65                  70                  75                  80
Ser Thr Phe Val Pro Gly Ser Gln Pro Gly Phe Thr Phe Gly Lys
                85                  90                  95
Ile Lys Ser Phe Pro Gly His Thr Ser Ser Leu Val Arg Val Val Ser
            100                 105                 110
Thr Asn Tyr Asn Gln His Ala Met Val Phe Phe Lys Phe Val Phe Gln
        115                 120                 125
Asn Arg Glu Glu Phe Tyr Ile Thr Leu Tyr Gly Arg Thr Lys Glu Leu
    130                 135                 140
Thr Ser Glu Leu Lys Glu Asn Phe Ile Arg Phe Ser Lys Ser Leu Gly
145                 150                 155                 160
Leu Pro Glu Asn His Ile Val Phe Pro Val Pro Ile Asp Gln Cys Ile
                165                 170                 175
Asp Gly
```

<210> SEQ ID NO 199
<211> LENGTH: 178
<212> TYPE: PRT
<213> ORGANISM: Artificial Sequence
<220> FEATURE:
<223> OTHER INFORMATION: 41BB Anticalin

<400> SEQUENCE: 199

```
Gln Asp Ser Thr Ser Asp Leu Ile Pro Ala Pro Pro Leu Ser Lys Val
1               5                   10                  15
Pro Leu Gln Gln Asn Phe Gln Asp Asn Gln Phe His Gly Lys Trp Tyr
            20                  25                  30
Val Val Gly Gln Ala Gly Asn Ile Arg Leu Arg Glu Asp Lys Asp Pro
        35                  40                  45
His Lys Met Met Ala Thr Ile Tyr Glu Leu Lys Glu Asp Lys Ser Tyr
50                  55                  60
```

Asp Val Thr Gly Val Thr Phe Asp Asp Lys Lys Cys Thr Tyr Ala Ile
65                  70                  75                  80

Ser Thr Phe Val Pro Gly Ser Gln Pro Gly Glu Phe Thr Leu Gly Lys
                85                  90                  95

Ile Lys Ser Phe Pro Gly His Thr Ser Ser Leu Val Arg Val Val Ser
            100                 105                 110

Thr Asn Tyr Asn Gln His Ala Met Val Phe Phe Lys Phe Val Phe Gln
        115                 120                 125

Asn Arg Glu Glu Phe Tyr Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 200
<211> LENGTH: 178
<212> TYPE: PRT
<213> ORGANISM: Artificial Sequence
<220> FEATURE:
<223> OTHER INFORMATION: 41BB Anticalin

<400> SEQUENCE: 200

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Gln Ala Gly Asn Ile Lys Leu Arg Glu Asp Lys Asp Pro
            35                  40                  45

Asn Lys Met Met Ala Thr Ile Tyr Glu Leu Lys Glu Asp Lys Ser Tyr
        50                  55                  60

Asp Val Thr Gly Val Thr Phe Asp Lys Lys Cys Thr Tyr Ala Ile
65                  70                  75                  80

Ser Thr Leu Val Pro Gly Ser Gln Pro Gly Glu Phe Thr Phe Gly Lys
                85                  90                  95

Ile Lys Ser Phe Pro Gly His Thr Ser Ser Leu Val Arg Val Val Ser
            100                 105                 110

Thr Asn Tyr Asn Gln His Ala Met Val Phe Phe Lys Phe Val Phe Gln
        115                 120                 125

Asn Arg Glu Glu Phe Tyr Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 201
<211> LENGTH: 178
<212> TYPE: PRT
<213> ORGANISM: Artificial Sequence
<220> FEATURE:
<223> OTHER INFORMATION: 41BB Anticalin

<400> SEQUENCE: 201

Gln Asp Ser Thr Ser Asp Leu Ile Pro Ala Pro Pro Leu Ser Lys Val

```
            1               5                  10                 15
Pro Leu Gln Gln Asn Phe Gln Asp Asn Gln Phe His Gly Lys Trp Tyr
                20                  25                 30
Val Val Gly Gln Ala Gly Asn Ile Arg Leu Arg Glu Asp Lys Asp Pro
                35                  40                 45
Ser Lys Met Met Ala Thr Ile Tyr Glu Leu Lys Glu Asp Lys Ser Tyr
        50                  55                 60
Asp Val Thr Ala Val Thr Phe Asp Asp Lys Lys Cys Asn Tyr Ala Ile
65                  70                  75                 80
Ser Thr Phe Val Pro Gly Ser Gln Pro Gly Glu Phe Thr Leu Gly Lys
                85                  90                 95
Ile Lys Ser Phe Pro Gly His Thr Ser Ser Leu Val Arg Val Val Ser
                100                 105                110
Thr Asn Tyr Asn Gln His Ala Met Val Phe Phe Lys Phe Val Phe Gln
                115                 120                125
Asn Arg Glu Glu Phe Tyr Ile Thr Leu Tyr Gly Arg Thr Lys Glu Leu
                130                 135                140
Thr Ser Glu Leu Lys Glu Asn Phe Ile Arg Phe Ser Lys Ser Leu Gly
145                 150                 155                160
Leu Pro Glu Asn His Ile Val Phe Pro Val Pro Ile Asp Gln Cys Ile
                165                 170                175
Asp Gly

<210> SEQ ID NO 202
<211> LENGTH: 184
<212> TYPE: PRT
<213> ORGANISM: Homo sapiens

<400> SEQUENCE: 202

Arg Glu Gly Pro Glu Leu Ser Pro Asp Asp Pro Ala Gly Leu Leu Asp
1               5                   10                 15
Leu Arg Gln Gly Met Phe Ala Gln Leu Val Ala Gln Asn Val Leu Leu
                20                  25                 30
Ile Asp Gly Pro Leu Ser Trp Tyr Ser Asp Pro Gly Leu Ala Gly Val
            35                  40                 45
Ser Leu Thr Gly Gly Leu Ser Tyr Lys Glu Asp Thr Lys Glu Leu Val
    50                  55                 60
Val Ala Lys Ala Gly Val Tyr Tyr Val Phe Phe Gln Leu Glu Leu Arg
65              70                  75                 80
Arg Val Val Ala Gly Glu Gly Ser Gly Ser Val Ser Leu Ala Leu His
                85                  90                 95
Leu Gln Pro Leu Arg Ser Ala Gly Ala Ala Leu Ala Leu Thr
                100                 105                110
Val Asp Leu Pro Pro Ala Ser Ser Glu Ala Arg Asn Ser Ala Phe Gly
            115                 120                125
Phe Gln Gly Arg Leu Leu His Leu Ser Ala Gly Gln Arg Leu Gly Val
            130                 135                140
His Leu His Thr Glu Ala Arg Ala Arg His Ala Trp Gln Leu Thr Gln
145                 150                 155                160
Gly Ala Thr Val Leu Gly Leu Phe Arg Val Thr Pro Glu Ile Pro Ala
                165                 170                175
Gly Leu Pro Ser Pro Arg Ser Glu
                180
```

```
<210> SEQ ID NO 203
<211> LENGTH: 170
<212> TYPE: PRT
<213> ORGANISM: Homo sapiens
<220> FEATURE:
<223> OTHER INFORMATION: 85-254 of human 41BBL

<400> SEQUENCE: 203

Leu Asp Leu Arg Gln Gly Met Phe Ala Gln Leu Val Ala Gln Asn Val
1               5                   10                  15

Leu Leu Ile Asp Gly Pro Leu Ser Trp Tyr Ser Asp Pro Gly Leu Ala
            20                  25                  30

Gly Val Ser Leu Thr Gly Gly Leu Ser Tyr Lys Glu Asp Thr Lys Glu
        35                  40                  45

Leu Val Val Ala Lys Ala Gly Val Tyr Tyr Val Phe Phe Gln Leu Glu
50                  55                  60

Leu Arg Arg Val Val Ala Gly Glu Gly Ser Gly Ser Val Ser Leu Ala
65                  70                  75                  80

Leu His Leu Gln Pro Leu Arg Ser Ala Ala Gly Ala Ala Ala Leu Ala
                85                  90                  95

Leu Thr Val Asp Leu Pro Pro Ala Ser Ser Glu Ala Arg Asn Ser Ala
            100                 105                 110

Phe Gly Phe Gln Gly Arg Leu Leu His Leu Ser Ala Gly Gln Arg Leu
        115                 120                 125

Gly Val His Leu His Thr Glu Ala Arg Ala Arg His Ala Trp Gln Leu
    130                 135                 140

Thr Gln Gly Ala Thr Val Leu Gly Leu Phe Arg Val Thr Pro Glu Ile
145                 150                 155                 160

Pro Ala Gly Leu Pro Ser Pro Arg Ser Glu
                165                 170

<210> SEQ ID NO 204
<211> LENGTH: 175
<212> TYPE: PRT
<213> ORGANISM: Homo sapiens
<220> FEATURE:
<223> OTHER INFORMATION: 80-254 of human 41BBL

<400> SEQUENCE: 204

Asp Pro Ala Gly Leu Leu Asp Leu Arg Gln Gly Met Phe Ala Gln Leu
1               5                   10                  15

Val Ala Gln Asn Val Leu Leu Ile Asp Gly Pro Leu Ser Trp Tyr Ser
            20                  25                  30

Asp Pro Gly Leu Ala Gly Val Ser Leu Thr Gly Gly Leu Ser Tyr Lys
        35                  40                  45

Glu Asp Thr Lys Glu Leu Val Val Ala Lys Ala Gly Val Tyr Tyr Val
50                  55                  60

Phe Phe Gln Leu Glu Leu Arg Arg Val Val Ala Gly Glu Gly Ser Gly
65                  70                  75                  80

Ser Val Ser Leu Ala Leu His Leu Gln Pro Leu Arg Ser Ala Ala Gly
                85                  90                  95

Ala Ala Ala Leu Ala Leu Thr Val Asp Leu Pro Pro Ala Ser Ser Glu
            100                 105                 110

Ala Arg Asn Ser Ala Phe Gly Phe Gln Gly Arg Leu Leu His Leu Ser
        115                 120                 125

Ala Gly Gln Arg Leu Gly Val His Leu His Thr Glu Ala Arg Ala Arg
    130                 135                 140
```

```
His Ala Trp Gln Leu Thr Gln Gly Ala Thr Val Leu Gly Leu Phe Arg
145                 150                 155                 160

Val Thr Pro Glu Ile Pro Ala Gly Leu Pro Ser Pro Arg Ser Glu
                165                 170                 175

<210> SEQ ID NO 205
<211> LENGTH: 203
<212> TYPE: PRT
<213> ORGANISM: Homo sapiens
<220> FEATURE:
<223> OTHER INFORMATION: 52-254 of human 4-1BBL

<400> SEQUENCE: 205

Pro Trp Ala Val Ser Gly Ala Arg Ala Ser Pro Gly Ser Ala Ala Ser
1               5                   10                  15

Pro Arg Leu Arg Glu Gly Pro Glu Leu Ser Pro Asp Asp Pro Ala Gly
            20                  25                  30

Leu Leu Asp Leu Arg Gln Gly Met Phe Ala Gln Leu Val Ala Gln Asn
        35                  40                  45

Val Leu Leu Ile Asp Gly Pro Leu Ser Trp Tyr Ser Asp Pro Gly Leu
    50                  55                  60

Ala Gly Val Ser Leu Thr Gly Gly Leu Ser Tyr Lys Glu Asp Thr Lys
65                  70                  75                  80

Glu Leu Val Val Ala Lys Ala Gly Val Tyr Tyr Val Phe Phe Gln Leu
                85                  90                  95

Glu Leu Arg Arg Val Val Ala Gly Glu Gly Ser Gly Ser Val Ser Leu
            100                 105                 110

Ala Leu His Leu Gln Pro Leu Arg Ser Ala Ala Gly Ala Ala Ala Leu
        115                 120                 125

Ala Leu Thr Val Asp Leu Pro Pro Ala Ser Ser Glu Ala Arg Asn Ser
    130                 135                 140

Ala Phe Gly Phe Gln Gly Arg Leu Leu His Leu Ser Ala Gly Gln Arg
145                 150                 155                 160

Leu Gly Val His Leu His Thr Glu Ala Arg Ala Arg His Ala Trp Gln
                165                 170                 175

Leu Thr Gln Gly Ala Thr Val Leu Gly Leu Phe Arg Val Thr Pro Glu
            180                 185                 190

Ile Pro Ala Gly Leu Pro Ser Pro Arg Ser Glu
        195                 200

<210> SEQ ID NO 206
<211> LENGTH: 178
<212> TYPE: PRT
<213> ORGANISM: Homo sapiens
<220> FEATURE:
<223> OTHER INFORMATION: 71-248 of human 41BBL

<400> SEQUENCE: 206

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
    50                  55                  60

Val Ala Lys Ala Gly Val Tyr Tyr Val Phe Phe Gln Leu Glu Leu Arg
65                  70                  75                  80
```

-continued

```
Arg Val Val Ala Gly Glu Gly Ser Gly Ser Val Ser Leu Ala Leu His
                85                  90                  95

Leu Gln Pro Leu Arg Ser Ala Ala Gly Ala Ala Ala Leu Ala Leu Thr
            100                 105                 110

Val Asp Leu Pro Pro Ala Ser Ser Glu Ala Arg Asn Ser Ala Phe Gly
        115                 120                 125

Phe Gln Gly Arg Leu Leu His Leu Ser Ala Gly Gln Arg Leu Gly Val
    130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu

<210> SEQ ID NO 207
<211> LENGTH: 164
<212> TYPE: PRT
<213> ORGANISM: Homo sapiens
<220> FEATURE:
<223> OTHER INFORMATION: 85-248 of human 41BBL

<400> SEQUENCE: 207

Leu Asp Leu Arg Gln Gly Met Phe Ala Gln Leu Val Ala Gln Asn Val
1               5                   10                  15

Leu Leu Ile Asp Gly Pro Leu Ser Trp Tyr Ser Asp Pro Gly Leu Ala
            20                  25                  30

Gly Val Ser Leu Thr Gly Gly Leu Ser Tyr Lys Glu Asp Thr Lys Glu
        35                  40                  45

Leu Val Val Ala Lys Ala Gly Val Tyr Tyr Val Phe Phe Gln Leu Glu
    50                  55                  60

Leu Arg Arg Val Val Ala Gly Glu Gly Ser Gly Ser Val Ser Leu Ala
65                  70                  75                  80

Leu His Leu Gln Pro Leu Arg Ser Ala Ala Gly Ala Ala Ala Leu Ala
                85                  90                  95

Leu Thr Val Asp Leu Pro Pro Ala Ser Ser Glu Ala Arg Asn Ser Ala
            100                 105                 110

Phe Gly Phe Gln Gly Arg Leu Leu His Leu Ser Ala Gly Gln Arg Leu
        115                 120                 125

Gly Val His Leu His Thr Glu Ala Arg Ala Arg His Ala Trp Gln Leu
    130                 135                 140

Thr Gln Gly Ala Thr Val Leu Gly Leu Phe Arg Val Thr Pro Glu Ile
145                 150                 155                 160

Pro Ala Gly Leu

<210> SEQ ID NO 208
<211> LENGTH: 169
<212> TYPE: PRT
<213> ORGANISM: Homo sapiens
<220> FEATURE:
<223> OTHER INFORMATION: 80-248 of human 41BBL

<400> SEQUENCE: 208

Asp Pro Ala Gly Leu Leu Asp Leu Arg Gln Gly Met Phe Ala Gln Leu
1               5                   10                  15

Val Ala Gln Asn Val Leu Leu Ile Asp Gly Pro Leu Ser Trp Tyr Ser
            20                  25                  30
```

Asp Pro Gly Leu Ala Gly Val Ser Leu Thr Gly Gly Leu Ser Tyr Lys
        35                  40                  45

Glu Asp Thr Lys Glu Leu Val Val Ala Lys Ala Gly Val Tyr Tyr Val
 50                  55                  60

Phe Gln Leu Glu Leu Arg Arg Val Val Ala Gly Glu Gly Ser Gly
65                   70                  75                  80

Ser Val Ser Leu Ala Leu His Leu Gln Pro Leu Arg Ser Ala Ala Gly
                 85                  90                  95

Ala Ala Ala Leu Ala Leu Thr Val Asp Leu Pro Pro Ala Ser Ser Glu
             100                 105                 110

Ala Arg Asn Ser Ala Phe Gly Phe Gln Gly Arg Leu Leu His Leu Ser
         115                 120                 125

Ala Gly Gln Arg Leu Gly Val His Leu His Thr Glu Ala Arg Ala Arg
     130                 135                 140

His Ala Trp Gln Leu Thr Gln Gly Ala Thr Val Leu Gly Leu Phe Arg
145                 150                 155                 160

Val Thr Pro Glu Ile Pro Ala Gly Leu
                165

<210> SEQ ID NO 209
<211> LENGTH: 197
<212> TYPE: PRT
<213> ORGANISM: Homo sapiens
<220> FEATURE:
<223> OTHER INFORMATION: 52-248 of human 41BBL

<400> SEQUENCE: 209

Pro Trp Ala Val Ser Gly Ala Arg Ala Ser Pro Gly Ser Ala Ala Ser
1               5                   10                  15

Pro Arg Leu Arg Glu Gly Pro Glu Leu Ser Pro Asp Asp Pro Ala Gly
                20                  25                  30

Leu Leu Asp Leu Arg Gln Gly Met Phe Ala Gln Leu Val Ala Gln Asn
             35                  40                  45

Val Leu Leu Ile Asp Gly Pro Leu Ser Trp Tyr Ser Asp Pro Gly Leu
 50                  55                  60

Ala Gly Val Ser Leu Thr Gly Gly Leu Ser Tyr Lys Glu Asp Thr Lys
65                  70                  75                  80

Glu Leu Val Val Ala Lys Ala Gly Val Tyr Tyr Val Phe Gln Leu
                85                  90                  95

Glu Leu Arg Arg Val Val Ala Gly Glu Gly Ser Gly Ser Val Ser Leu
            100                 105                 110

Ala Leu His Leu Gln Pro Leu Arg Ser Ala Ala Gly Ala Ala Ala Leu
        115                 120                 125

Ala Leu Thr Val Asp Leu Pro Pro Ala Ser Ser Glu Ala Arg Asn Ser
    130                 135                 140

Ala Phe Gly Phe Gln Gly Arg Leu Leu His Leu Ser Ala Gly Gln Arg
145                 150                 155                 160

Leu Gly Val His Leu His Thr Glu Ala Arg Ala Arg His Ala Trp Gln
                165                 170                 175

Leu Thr Gln Gly Ala Thr Val Leu Gly Leu Phe Arg Val Thr Pro Glu
            180                 185                 190

Ile Pro Ala Gly Leu
        195

<210> SEQ ID NO 210
<211> LENGTH: 121

```
<212> TYPE: PRT
<213> ORGANISM: Artificial Sequence
<220> FEATURE:
<223> OTHER INFORMATION: 41BB sdAb

<400> SEQUENCE: 210
```

Glu Val Gln Leu Leu Glu Ser Gly Gly Gly Val Gln Pro Gly Gly
1               5                   10                  15

Ser Leu Arg Leu Ser Cys Ala Ala Ser Gly Phe Ser Phe Ser Ile Asn
            20                  25                  30

Ala Met Gly Trp Tyr Arg Gln Ala Pro Gly Lys Arg Arg Glu Phe Val
        35                  40                  45

Ala Ala Ile Glu Ser Gly Arg Asn Thr Val Tyr Ala Glu Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Gly
                85                  90                  95

Leu Leu Lys Gly Asn Arg Val Val Ser Pro Ser Val Ala Tyr Trp Gly
            100                 105                 110

Gln Gly Thr Leu Val Thr Val Lys Pro
        115                 120

```
<210> SEQ ID NO 211
<211> LENGTH: 133
<212> TYPE: PRT
<213> ORGANISM: Artificial Sequence
<220> FEATURE:
<223> OTHER INFORMATION: OX40 ligand

<400> SEQUENCE: 211
```

Gln Val Ser His Arg Tyr Pro Arg Ile Gln Ser Ile Lys Val Gln Phe
1               5                   10                  15

Thr Glu Tyr Lys Lys Glu Lys Gly Phe Ile Leu Thr Ser Gln Lys Glu
            20                  25                  30

Asp Glu Ile Met Lys Val Gln Asn Asn Ser Val Ile Ile Asn Cys Asp
        35                  40                  45

Gly Phe Tyr Leu Ile Ser Leu Lys Gly Tyr Phe Ser Gln Glu Val Asn
    50                  55                  60

Ile Ser Leu His Tyr Gln Lys Asp Glu Glu Pro Leu Phe Gln Leu Lys
65                  70                  75                  80

Lys Val Arg Ser Val Asn Ser Leu Met Val Ala Ser Leu Thr Tyr Lys
                85                  90                  95

Asp Lys Val Tyr Leu Asn Val Thr Thr Asp Asn Thr Ser Leu Asp Asp
            100                 105                 110

Phe His Val Asn Gly Gly Glu Leu Ile Leu Ile His Gln Asn Pro Gly
        115                 120                 125

Glu Phe Cys Val Leu
    130

```
<210> SEQ ID NO 212
<211> LENGTH: 133
<212> TYPE: PRT
<213> ORGANISM: Artificial Sequence
<220> FEATURE:
<223> OTHER INFORMATION: OX40 ligand

<400> SEQUENCE: 212
```

Gln Val Ser His Arg Tyr Pro Arg Phe Gln Ser Ile Lys Val Gln Phe

```
                1               5                  10                 15
            Thr Glu Tyr Lys Lys Glu Lys Gly Phe Ile Leu Thr Ser Gln Lys Glu
                            20                  25                  30

Asp Glu Ile Met Lys Val Gln Asn Asn Ser Val Ile Ile Asn Cys Asp
                            35                  40                  45

Gly Phe Tyr Leu Ile Ser Leu Lys Gly Tyr Phe Ser Gln Glu Val Asn
                            50                  55                  60

Ile Ser Leu His Tyr Gln Lys Asp Glu Glu Pro Leu Phe Gln Leu Lys
             65                 70                  75                  80

Lys Val Arg Ser Val Asn Ser Leu Met Val Ala Ser Leu Thr Tyr Lys
                            85                  90                  95

Asp Lys Val Tyr Leu Asn Val Thr Thr Asp Asn Thr Ser Leu Asp Asp
                           100                 105                 110

Phe His Val Asn Gly Gly Glu Leu Ile Leu Ile His Gln Asn Pro Gly
                           115                 120                 125

Glu Phe Cys Val Leu
                           130

<210> SEQ ID NO 213
<211> LENGTH: 133
<212> TYPE: PRT
<213> ORGANISM: Artificial Sequence
<220> FEATURE:
<223> OTHER INFORMATION: OX40 ligand

<400> SEQUENCE: 213

Gln Val Ser His Arg Tyr Pro Arg Ile Gln Ser Ile Lys Val Gln Phe
             1               5                  10                  15

Thr Glu Tyr Lys Lys Glu Lys Gly Phe Ile Leu Thr Ser Gln Lys Glu
                            20                  25                  30

Asp Glu Ile Met Lys Val Gln Asn Asn Ser Val Ile Ile Asn Cys Asp
                            35                  40                  45

Gly Phe Tyr Leu Ile Ser Leu Lys Gly Tyr Phe Ser Gln Glu Val Asn
                            50                  55                  60

Ile Ser Leu His Tyr Gln Lys Asp Glu Glu Pro Leu Phe Gln Leu Lys
             65                 70                  75                  80

Lys Val Arg Ser Val Asn Ser Leu Met Val Ala Ser Leu Thr Tyr Lys
                            85                  90                  95

Asp Lys Val Tyr Leu Asn Val Thr Thr Asp Asn Thr Ser Leu Asp Asp
                           100                 105                 110

Phe His Val Asn Gly Gly Glu Leu Ile Leu Ile His Gln Asn Pro Gly
                           115                 120                 125

Glu Phe Cys Val Leu
                           130

<210> SEQ ID NO 214
<211> LENGTH: 133
<212> TYPE: PRT
<213> ORGANISM: Artificial Sequence
<220> FEATURE:
<223> OTHER INFORMATION: OX40 ligand

<400> SEQUENCE: 214

Gln Val Ser His Arg Tyr Pro Arg Ile Gln Ser Ile Lys Val Gln Phe
             1               5                  10                  15

Thr Glu Tyr Lys Lys Glu Lys Gly Phe Ile Leu Thr Ser Gln Lys Glu
                            20                  25                  30
```

```
Asp Glu Ile Met Lys Val Gln Asn Asn Ser Val Ile Ile Asn Cys Asp
         35                  40                  45

Gly Phe Tyr Leu Ile Ser Leu Lys Gly Tyr Phe Ser Gln Glu Val Asn
 50                  55                  60

Ile Ser Leu His Tyr Gln Lys Asp Glu Glu Pro Leu Phe Gln Leu Lys
 65                  70                  75                  80

Lys Val Arg Ser Val Asn Ser Leu Met Val Ala Ser Leu Thr Tyr Lys
                 85                  90                  95

Asp Lys Val Tyr Leu Asn Val Thr Thr Asp Asn Thr Ser Leu Asp Asp
                100                 105                 110

Phe His Val Asn Gly Gly Glu Leu Ile Leu Ile His Gln Asn Pro Gly
            115                 120                 125

Glu Phe Cys Val Leu
        130

<210> SEQ ID NO 215
<211> LENGTH: 132
<212> TYPE: PRT
<213> ORGANISM: Artificial Sequence
<220> FEATURE:
<223> OTHER INFORMATION: OX40 ligand

<400> SEQUENCE: 215

Val Ser His Arg Tyr Pro Arg Ile Gln Ser Ile Lys Val Gln Phe Thr
 1               5                  10                  15

Glu Tyr Lys Lys Glu Lys Gly Phe Ile Leu Thr Ser Gln Lys Glu Asp
                 20                  25                  30

Glu Ile Met Lys Val Gln Asn Asn Ser Val Ile Ile Asn Cys Asp Gly
             35                  40                  45

Phe Tyr Leu Ile Ser Leu Lys Gly Tyr Phe Ser Gln Glu Val Asn Ile
 50                  55                  60

Ser Leu His Tyr Gln Lys Asp Glu Glu Pro Leu Phe Gln Leu Lys Lys
 65                  70                  75                  80

Val Arg Ser Val Asn Ser Leu Met Val Ala Ser Leu Thr Tyr Lys Asp
                 85                  90                  95

Lys Val Tyr Leu Asn Val Thr Thr Asp Asn Thr Ser Leu Asp Asp Phe
                100                 105                 110

His Val Asn Gly Gly Glu Leu Ile Leu Ile His Gln Asn Pro Gly Glu
            115                 120                 125

Phe Cys Val Leu
        130

<210> SEQ ID NO 216
<211> LENGTH: 117
<212> TYPE: PRT
<213> ORGANISM: Artificial Sequence
<220> FEATURE:
<223> OTHER INFORMATION: OX40 VH

<400> SEQUENCE: 216

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Ser
                 20                  25                  30

Tyr Met Ser Trp Val Arg Gln Ala Pro Gly Gln Gly Leu Glu Trp Ile
             35                  40                  45

Gly Asp Met Tyr Pro Asp Asn Gly Asp Ser Ser Tyr Asn Gln Lys Phe
 50                  55                  60
```

```
Arg Glu Arg Val Thr Ile Thr Arg Asp Thr Ser Thr Ser Thr Ala Tyr
 65                  70                  75                  80

Leu Glu Leu Ser Ser Leu Arg Ser Glu Asp Thr Ala Val Tyr Tyr Cys
             85                  90                  95

Val Leu Ala Pro Arg Trp Tyr Phe Ser Val Trp Gly Gln Gly Thr Leu
            100                 105                 110

Val Thr Val Ser Ser
        115

<210> SEQ ID NO 217
<211> LENGTH: 109
<212> TYPE: PRT
<213> ORGANISM: Artificial Sequence
<220> FEATURE:
<223> OTHER INFORMATION: OX40 VL

<400> SEQUENCE: 217

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Asn Tyr
             20                  25                  30

Leu Asn Trp Tyr Gln Gln Lys Pro Gly Lys Ala Pro Lys Leu Leu Ile
         35                  40                  45

Tyr Tyr Thr Ser Arg Leu Arg Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly His Thr Leu Pro Pro
             85                  90                  95

Thr Phe Gly Gln Gly Thr Lys Val Glu Ile Lys Arg Thr
            100                 105

<210> SEQ ID NO 218
<211> LENGTH: 121
<212> TYPE: PRT
<213> ORGANISM: Artificial Sequence
<220> FEATURE:
<223> OTHER INFORMATION: OX40 VH

<400> SEQUENCE: 218

Glu Val Gln Leu Val Glu Ser Gly Gly Gly Leu Val Gln Pro Gly Gly
 1               5                  10                  15

Ser Leu Lys Leu Ser Cys Ala Ala Ser Gly Phe Thr Phe Ser Gly Ser
             20                  25                  30

Ala Met His Trp Val Arg Gln Ala Ser Gly Lys Gly Leu Glu Trp Val
         35                  40                  45

Gly Arg Ile Arg Ser Lys Ala Asn Ser Tyr Ala Thr Ala Tyr Ala Ala
 50                  55                  60

Ser Val Lys Gly Arg Phe Thr Ile Ser Arg Asp Asp Ser Lys Asn Thr
 65                  70                  75                  80

Ala Tyr Leu Gln Met Asn Ser Leu Lys Thr Glu Asp Thr Ala Val Tyr
             85                  90                  95

Tyr Cys Thr Ser Gly Ile Tyr Asp Ser Ser Gly Tyr Asp Tyr Trp Gly
            100                 105                 110

Gln Gly Thr Leu Val Thr Val Ser Ser
            115                 120
```

-continued

```
<210> SEQ ID NO 219
<211> LENGTH: 112
<212> TYPE: PRT
<213> ORGANISM: Artificial Sequence
<220> FEATURE:
<223> OTHER INFORMATION: OX40 VL

<400> SEQUENCE: 219

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 220
<211> LENGTH: 115
<212> TYPE: PRT
<213> ORGANISM: Artificial Sequence
<220> FEATURE:
<223> OTHER INFORMATION: OX40 sdAb

<400> SEQUENCE: 220

Glu Val Gln Leu Leu Glu Ser Gly Gly Gly Glu Val Gln Pro Gly Gly
1               5                   10                  15

Ser Leu Arg Leu Ser Cys Ala Ala Ser Gly Phe Thr Phe Ser Asp Ala
            20                  25                  30

Phe Met Tyr Trp Val Arg Gln Ala Pro Gly Lys Gly Leu Glu Trp Val
        35                  40                  45

Ser Ser Ile Ser Asn Arg Gly Leu Lys Thr Ala Tyr Ala Glu Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Ser Arg Asp Val Asp Gly Asp Phe Arg Gly Gln Gly Thr Leu Val Thr
            100                 105                 110

Val Lys Pro
        115

<210> SEQ ID NO 221
<211> LENGTH: 128
<212> TYPE: PRT
<213> ORGANISM: Artificial Sequence
<220> FEATURE:
<223> OTHER INFORMATION: GITR ligand

<400> SEQUENCE: 221

Gln Leu Glu Thr Ala Lys Glu Pro Cys Met Ala Lys Phe Gly Pro Leu
1               5                   10                  15

Pro Ser Lys Trp Gln Met Ala Ser Ser Glu Pro Pro Cys Val Asn Lys
            20                  25                  30
```

```
Val Ser Asp Trp Lys Leu Glu Ile Leu Gln Asn Gly Leu Tyr Leu Ile
        35                  40                  45

Tyr Gly Gln Val Ala Pro Asn Ala Asn Tyr Asn Asp Val Ala Pro Phe
    50                  55                  60

Glu Val Arg Leu Tyr Lys Asn Lys Asp Met Ile Gln Thr Leu Thr Asn
65                  70                  75                  80

Lys Ser Lys Ile Gln Asn Val Gly Gly Thr Tyr Glu Leu His Val Gly
                85                  90                  95

Asp Thr Ile Asp Leu Ile Phe Asn Ser Glu His Gln Val Leu Lys Asn
            100                 105                 110

Asn Thr Tyr Trp Gly Ile Ile Leu Leu Ala Asn Pro Gln Phe Ile Ser
        115                 120                 125

<210> SEQ ID NO 222
<211> LENGTH: 118
<212> TYPE: PRT
<213> ORGANISM: Artificial Sequence
<220> FEATURE:
<223> OTHER INFORMATION: GITR VH

<400> SEQUENCE: 222

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Ser Ile Ser Ser Gly Gly Thr Thr Tyr Tyr Pro Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Val Gly Gly Tyr Tyr Asp Ser Met Asp Tyr Trp Gly Gln Gly Thr
            100                 105                 110

Leu Val Thr Val Ser Ser
        115

<210> SEQ ID NO 223
<211> LENGTH: 111
<212> TYPE: PRT
<213> ORGANISM: Artificial Sequence
<220> FEATURE:
<223> OTHER INFORMATION: GITR VL

<400> SEQUENCE: 223

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Val Ser Phe Met Asn Trp Tyr Gln Gln Lys Pro Gly Gln Ala Pro
        35                  40                  45

Arg Leu Leu Ile Tyr Ala Ala Ser Asn Gln Gly Ser Gly Ile Pro Asp
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Thr Lys
```

```
                    85                  90                  95

Glu Val Thr Trp Thr Phe Gly Gln Gly Thr Lys Val Glu Ile Lys
                100                 105                 110

<210> SEQ ID NO 224
<211> LENGTH: 119
<212> TYPE: PRT
<213> ORGANISM: Artificial Sequence
<220> FEATURE:
<223> OTHER INFORMATION: GITR VH

<400> SEQUENCE: 224

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Met Gly Val Gly Trp Ile Arg Gln Pro Pro Gly Lys Ala Leu Glu
            35                  40                  45

Trp Leu Ala His Ile Trp Trp Asp Asp Lys Tyr Tyr Gln Pro Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Thr Arg Arg Tyr Phe Pro Phe Ala Tyr Trp Gly Gln Gly
                100                 105                 110

Thr Leu Val Thr Val Ser Ser
            115

<210> SEQ ID NO 225
<211> LENGTH: 107
<212> TYPE: PRT
<213> ORGANISM: Artificial Sequence
<220> FEATURE:
<223> OTHER INFORMATION: GITR VL

<400> SEQUENCE: 225

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Asn Val Gly Thr Asn
                20                  25                  30

Val Ala Trp Tyr Gln Gln Lys Pro Gly Gln Ala Pro Arg Leu Leu Ile
            35                  40                  45

Tyr Ser Ala Ser Tyr Arg Tyr Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Thr Asp Pro Leu
                85                  90                  95

Thr Phe Gly Gly Gly Thr Lys Val Glu Ile Lys
                100                 105

<210> SEQ ID NO 226
<211> LENGTH: 125
<212> TYPE: PRT
<213> ORGANISM: Artificial Sequence
<220> FEATURE:
<223> OTHER INFORMATION: GITR VH

<400> SEQUENCE: 226
```

-continued

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Gly Tyr Phe Trp Ser Trp Ile Arg Gln Pro Pro Gly Lys Gly Leu Glu
        35                  40                  45

Trp Ile Gly Tyr Ile Tyr Tyr Ser Gly Thr Thr Tyr Tyr Asn Pro Ser
50                  55                  60

Leu Lys Ser Arg Val Thr Ile Ser Ile Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Asp Leu Phe Tyr Tyr Asp Thr Ser Gly Pro Arg Gly Phe
        100                 105                 110

Asp Pro Trp Gly Gln Gly Thr Leu Val Thr Val Ser Ser
        115                 120                 125

<210> SEQ ID NO 227
<211> LENGTH: 108
<212> TYPE: PRT
<213> ORGANISM: Artificial Sequence
<220> FEATURE:
<223> OTHER INFORMATION: GITR VL

<400> SEQUENCE: 227

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Thr Val Ser Ser Asn
            20                  25                  30

Tyr Leu Ala Trp Tyr Gln Gln Lys Pro Gly Gln Ala Pro Arg Leu Leu
        35                  40                  45

Ile Tyr Gly Ser Ser Thr Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asp Ser Ser Pro
            85                  90                  95

Trp Thr Phe Gly Gln Gly Thr Lys Val Glu Ile Lys
        100                 105

<210> SEQ ID NO 228
<211> LENGTH: 123
<212> TYPE: PRT
<213> ORGANISM: Artificial Sequence
<220> FEATURE:
<223> OTHER INFORMATION: GITR VH

<400> SEQUENCE: 228

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Pro Gly Ser Asn Lys Tyr Tyr Ala Glu Ser Val
50                  55                  60

Lys Gly Arg Phe Thr Ile Ser Arg Asp Asn Ser Lys Asn Thr Leu Tyr
```

```
              65                  70                  75                  80
Leu Gln Met Asn Ser Leu Arg Ala Glu Asp Thr Ala Val Tyr Tyr Cys
                    85                  90                  95

Ala Arg Gly Gly Glu Leu Gly Arg Tyr Tyr Tyr Gly Met Asp Val
                100                 105                 110

Trp Gly Gln Gly Thr Thr Val Thr Val Ser Ser
        115                 120

<210> SEQ ID NO 229
<211> LENGTH: 107
<212> TYPE: PRT
<213> ORGANISM: Artificial Sequence
<220> FEATURE:
<223> OTHER INFORMATION: GITR VL

<400> SEQUENCE: 229

Asp Ile Gln Met Thr Gln Ser Pro Ser Ser Leu Ser Ala Ser Val Gly
1               5                   10                  15

Asp Arg Val Thr Val Thr Cys Arg Ala Ser Gln Gly Ile Arg Asn Asp
                20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Asn Tyr Pro Trp
                85                  90                  95

Thr Phe Gly Gln Gly Thr Lys Val Asp Ile Lys
            100                 105

<210> SEQ ID NO 230
<211> LENGTH: 119
<212> TYPE: PRT
<213> ORGANISM: Artificial Sequence
<220> FEATURE:
<223> OTHER INFORMATION: GITR sdAb

<400> SEQUENCE: 230

Glu Val Gln Leu Leu Glu Ser Gly Gly Glu Val Gln Pro Gly Gly
1               5                   10                  15

Ser Leu Arg Leu Ser Cys Ala Ala Ser Gly Ser Val Phe Ser Ile Asp
                20                  25                  30

Ala Met Gly Trp Tyr Arg Gln Ala Pro Gly Lys Gln Arg Glu Leu Val
            35                  40                  45

Ala Val Leu Ser Gly Ile Ser Ser Ala Lys Tyr Ala Ala Ser Ala Pro
        50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Tyr
                85                  90                  95

Ala Asp Val Ser Thr Gly Trp Gly Arg Asp Ala His Gly Tyr Trp Gly
            100                 105                 110

Gln Gly Thr Leu Val Thr Val
        115

<210> SEQ ID NO 231
<211> LENGTH: 193
```

```
<212> TYPE: PRT
<213> ORGANISM: Homo sapiens
<220> FEATURE:
<223> OTHER INFORMATION: UniProt no. P32970; CD70-ECD

<400> SEQUENCE: 231

Met Pro Glu Glu Gly Ser Gly Cys Ser Val Arg Arg Arg Pro Tyr Gly
1               5                   10                  15

Cys Val Leu Arg Ala Ala Leu Val Pro Leu Val Ala Gly Leu Val Ile
            20                  25                  30

Cys Leu Val Val Cys Ile Gln Arg Phe Ala Gln Ala Gln Gln Gln Leu
        35                  40                  45

Pro Leu Glu Ser Leu Gly Trp Asp Val Ala Glu Leu Gln Leu Asn His
    50                  55                  60

Thr Gly Pro Gln Gln Asp Pro Arg Leu Tyr Trp Gln Gly Gly Pro Ala
65                  70                  75                  80

Leu Gly Arg Ser Phe Leu His Gly Pro Glu Leu Asp Lys Gly Gln Leu
                85                  90                  95

Arg Ile His Arg Asp Gly Ile Tyr Met Val His Ile Gln Val Thr Leu
            100                 105                 110

Ala Ile Cys Ser Ser Thr Thr Ala Ser Arg His His Pro Thr Thr Leu
        115                 120                 125

Ala Val Gly Ile Cys Ser Pro Ala Ser Arg Ser Ile Ser Leu Leu Arg
    130                 135                 140

Leu Ser Phe His Gln Gly Cys Thr Ile Ala Ser Gln Arg Leu Thr Pro
145                 150                 155                 160

Leu Ala Arg Gly Asp Thr Leu Cys Thr Asn Leu Thr Gly Thr Leu Leu
                165                 170                 175

Pro Ser Arg Asn Thr Asp Glu Thr Phe Phe Gly Val Gln Trp Val Arg
            180                 185                 190

Pro

<210> SEQ ID NO 232
<211> LENGTH: 119
<212> TYPE: PRT
<213> ORGANISM: Artificial Sequence
<220> FEATURE:
<223> OTHER INFORMATION: CD70 VH

<400> SEQUENCE: 232

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Gly Asn Trp Gly Phe Phe Asp Tyr Trp Gly Gln Gly
            100                 105                 110

Thr Leu Val Thr Val Ser Ser
        115
```

<210> SEQ ID NO 233
<211> LENGTH: 107
<212> TYPE: PRT
<213> ORGANISM: Artificial Sequence
<220> FEATURE:
<223> OTHER INFORMATION: CD70 VL

<400> SEQUENCE: 233

Asp Ile Gln Met Thr Gln Ser Pro Ser Leu Ser Ala Ser Val Gly
1               5                   10                  15

Asp Arg Val Thr Ile Thr Cys Arg Ala Ser Gln Gly Ile Ser Arg Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Thr Tyr Pro Arg
                85                  90                  95

Thr Phe Gly Gln Gly Thr Lys Val Glu Ile Lys
            100                 105

<210> SEQ ID NO 234
<211> LENGTH: 124
<212> TYPE: PRT
<213> ORGANISM: Artificial Sequence
<220> FEATURE:
<223> OTHER INFORMATION: ICOS sdAb

<400> SEQUENCE: 234

Gln Val Gln Leu Gln Gln Ser Gly Gly Gly Leu Val Gln Pro Gly Gly
1               5                   10                  15

Ser Leu Arg Leu Ser Cys Ala Ala Ser Gly Ser Ile Phe Ser Ile Asn
            20                  25                  30

Gly Met Gly Trp Tyr Arg Gln Ala Pro Gly Lys Glu Arg Glu Leu Val
        35                  40                  45

Ala Gly Leu Thr Ser Gly Gly Ser Val Thr Asn Tyr Ala Asp Ser Val
50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Arg Ala Glu Ile Phe Thr Arg Thr Gly Glu Asn Tyr Tyr Gly Met Asp
            100                 105                 110

Tyr Trp Gly Lys Gly Thr Gln Val Thr Val Lys Pro
        115                 120

<210> SEQ ID NO 235
<211> LENGTH: 124
<212> TYPE: PRT
<213> ORGANISM: Artificial Sequence
<220> FEATURE:
<223> OTHER INFORMATION: CD28 sdAb

<400> SEQUENCE: 235

Glu Val Gln Leu Val Glu Ser Gly Gly Gly Glu Val Gln Pro Gly Gly
1               5                   10                  15

Ser Leu Arg Leu Ser Cys Ala Ala Ser Gly Arg Met Phe Ser Asn Tyr

```
                    20                  25                  30

Ala Met Gly Trp Phe Arg Gln Ala Pro Gly Lys Glu Arg Glu Phe Val
                35                  40                  45

Ala Ala Ile Asn Tyr Arg Arg Asp Ala Ala Asp Tyr Ala Glu Ser Val
 50                  55                  60

Lys Gly Arg Phe Thr Ile Ser Arg Asp Asn Ala Lys Asn Thr Val Tyr
 65                  70                  75                  80

Leu Gln Met Asn Ser Leu Arg Ala Glu Asp Thr Ala Val Tyr Tyr Cys
                85                  90                  95

Gly Phe Thr Tyr Ala Gly Trp Ala Ser Ser Arg Arg Asp Asp Tyr Asn
                100                 105                 110

Tyr Trp Gly Gln Gly Thr Leu Val Thr Val Lys Pro
                115                 120

<210> SEQ ID NO 236
<211> LENGTH: 112
<212> TYPE: PRT
<213> ORGANISM: Artificial Sequence
<220> FEATURE:
<223> OTHER INFORMATION: CD3zeta signaling domain

<400> SEQUENCE: 236

Arg Val Lys Phe Ser Arg Ser Ala Asp Ala Pro Ala Tyr Gln Gln Gly
 1               5                  10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
                35                  40                  45

Pro Arg Arg Lys Asn Pro Gln Glu Gly Leu Tyr Asn Glu Leu Gln Lys
 50                  55                  60

Asp Lys Met Ala Glu Ala Tyr Ser Glu Ile Gly Met Lys Gly Glu Arg
 65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
                100                 105                 110

<210> SEQ ID NO 237
<211> LENGTH: 42
<212> TYPE: PRT
<213> ORGANISM: Artificial Sequence
<220> FEATURE:
<223> OTHER INFORMATION: 4-1BB-derived costimulatory domain

<400> SEQUENCE: 237

Lys Arg Gly Arg Lys Lys Leu Leu Tyr Ile Phe Lys Gln Pro Phe Met
 1               5                  10                  15

Arg Pro Val Gln Thr Thr Gln Glu Glu Asp Gly Cys Ser Cys Arg Phe
                20                  25                  30

Pro Glu Glu Glu Glu Gly Gly Cys Glu Leu
                35                  40

<210> SEQ ID NO 238
<211> LENGTH: 40
<212> TYPE: PRT
<213> ORGANISM: Artificial Sequence
<220> FEATURE:
<223> OTHER INFORMATION: CD28-derived costimulatory domain

<400> SEQUENCE: 238
```

-continued

```
Ser Lys Arg Ser Arg Leu Leu His Ser Asp Tyr Met Asn Met Thr Pro
1               5                   10                  15

Arg Arg Pro Gly Pro Thr Arg Lys His Tyr Gln Pro Tyr Ala Pro Pro
            20                  25                  30

Arg Asp Phe Ala Ala Tyr Arg Ser
        35                  40

<210> SEQ ID NO 239
<211> LENGTH: 41
<212> TYPE: PRT
<213> ORGANISM: Artificial Sequence
<220> FEATURE:
<223> OTHER INFORMATION: CD28-derived costimulatory domain 2

<400> SEQUENCE: 239

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 240
<211> LENGTH: 44
<212> TYPE: PRT
<213> ORGANISM: Artificial Sequence
<220> FEATURE:
<223> OTHER INFORMATION: CD28-derived costimulatory domain 3

<400> SEQUENCE: 240

Phe Trp Val Arg Ser Lys Arg Ser Arg Leu Leu His Ser Asp Tyr Met
1               5                   10                  15

Asn Met Thr Pro Arg Arg Pro Gly Pro Thr Arg Lys His Tyr Gln Pro
            20                  25                  30

Tyr Ala Pro Pro Arg Asp Phe Ala Ala Tyr Arg Ser
        35                  40

<210> SEQ ID NO 241
<211> LENGTH: 71
<212> TYPE: PRT
<213> ORGANISM: Artificial Sequence
<220> FEATURE:
<223> OTHER INFORMATION: CD8-derived hinge and transmembrane domain

<400> SEQUENCE: 241

Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Ser Arg Pro Ala
            20                  25                  30

Ala Gly Gly Ala Val His Thr Arg Gly Leu Asp Phe Ala Ser Asp Ile
        35                  40                  45

Tyr Ile Trp Ala Pro Leu Ala Gly Thr Cys Gly Val Leu Leu Leu Ser
    50                  55                  60

Leu Val Ile Thr Leu Tyr Cys
65                  70

<210> SEQ ID NO 242
<211> LENGTH: 69
<212> TYPE: PRT
<213> ORGANISM: Artificial Sequence
<220> FEATURE:
```

<223> OTHER INFORMATION: CD8-derived hinge and transmembrane domain

<400> SEQUENCE: 242

Ala Lys Pro Thr Thr Thr Pro Ala Pro Arg Pro Pro Thr Pro Ala Pro
1               5                   10                  15

Thr Ile Ala Ser Gln Pro Leu Ser Leu Arg Pro Glu Ala Cys Arg Pro
            20                  25                  30

Ala Ala Gly Gly Ala Val His Thr Arg Gly Leu Asp Phe Ala Cys Asp
        35                  40                  45

Ile Tyr Ile Trp Ala Pro Leu Ala Gly Thr Cys Gly Val Leu Leu Leu
50                  55                  60

Ser Leu Val Ile Thr
65

<210> SEQ ID NO 243
<211> LENGTH: 68
<212> TYPE: PRT
<213> ORGANISM: Artificial Sequence
<220> FEATURE:
<223> OTHER INFORMATION: CD8 hinge and transmembrane domain

<400> SEQUENCE: 243

Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Cys Arg Pro Ala
            20                  25                  30

Ala Gly Gly Ala Val His Thr Arg Gly Leu Asp Phe Ala Cys Asp Ile
        35                  40                  45

Tyr Ile Trp Ala Pro Leu Ala Gly Thr Cys Gly Val Leu Leu Leu Ser
50                  55                  60

Leu Val Ile Thr
65

<210> SEQ ID NO 244
<211> LENGTH: 120
<212> TYPE: PRT
<213> ORGANISM: Artificial Sequence
<220> FEATURE:
<223> OTHER INFORMATION: L10D9

<400> SEQUENCE: 244

Glu Val Gln Leu Val Gln Ser Gly Gly Gly Leu Val Gln Ala Gly Gly
1               5                   10                  15

Ser Leu Arg Leu Ser Cys Ala Ala Ser Gly Ser Ile Leu Ser Ile Asn
            20                  25                  30

Ala Met Gly Trp Tyr Arg Gln Pro Pro Gly Lys Gln Arg Glu Met Val
        35                  40                  45

Ala Gly Phe Thr Gly Asp Gly Asn Thr Ile Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Asp Val Gln Leu Phe Ser Arg Asp Tyr Glu Phe Tyr Trp Gly Gln
                100                 105                 110

Gly Thr Gln Val Thr Val Lys Pro
            115                 120

```
<210> SEQ ID NO 245
<211> LENGTH: 120
<212> TYPE: PRT
<213> ORGANISM: Artificial Sequence
<220> FEATURE:
<223> OTHER INFORMATION: hz10D9v1

<400> SEQUENCE: 245

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Ile Leu Ser Ile Asn
            20                  25                  30

Ala Met Gly Trp Tyr Arg Gln Ala Pro Gly Lys Gln Arg Glu Met Val
        35                  40                  45

Ala Gly Phe Thr Gly Asp Gly Asn Thr Ile Tyr Ala Glu Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Ala
                85                  90                  95

Ala Asp Val Gln Leu Phe Ser Arg Asp Tyr Glu Phe Tyr Trp Gly Gln
            100                 105                 110

Gly Thr Leu Val Thr Val Lys Pro
        115                 120

<210> SEQ ID NO 246
<211> LENGTH: 120
<212> TYPE: PRT
<213> ORGANISM: Artificial Sequence
<220> FEATURE:
<223> OTHER INFORMATION: hz10D9v2

<400> SEQUENCE: 246

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Ile Leu Ser Ile Asn
            20                  25                  30

Ala Met Gly Trp Tyr Arg Gln Ala Pro Gly Lys Gln Arg Glu Leu Val
        35                  40                  45

Ala Gly Phe Thr Gly Asp Gly Asn Thr Ile Tyr Ala Glu Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Ala
                85                  90                  95

Ala Asp Val Gln Leu Phe Ser Arg Asp Tyr Glu Phe Tyr Trp Gly Gln
            100                 105                 110

Gly Thr Leu Val Thr Val Lys Pro
        115                 120

<210> SEQ ID NO 247
<211> LENGTH: 120
<212> TYPE: PRT
<213> ORGANISM: Artificial Sequence
<220> FEATURE:
<223> OTHER INFORMATION: hz10D9v3

<400> SEQUENCE: 247

Glu Val Gln Leu Val Glu Ser Gly Gly Gly Glu Val Gln Pro Gly Gly
1               5                   10                  15
```

```
Ser Leu Arg Leu Ser Cys Ala Ala Ser Gly Ser Ile Leu Ser Ile Asn
            20                  25                  30

Ala Met Gly Trp Tyr Arg Gln Ala Pro Gly Lys Gln Arg Glu Met Val
        35                  40                  45

Ala Gly Phe Thr Gly Glu Gly Asn Thr Ile Tyr Ala Glu Ser Val Lys
50                      55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Ala
                85                  90                  95

Ala Asp Val Gln Leu Phe Ser Arg Asp Tyr Glu Phe Tyr Trp Gly Gln
            100                 105                 110

Gly Thr Leu Val Thr Val Lys Pro
        115                 120

<210> SEQ ID NO 248
<211> LENGTH: 120
<212> TYPE: PRT
<213> ORGANISM: Artificial Sequence
<220> FEATURE:
<223> OTHER INFORMATION: hz10D9v4

<400> SEQUENCE: 248

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Ile Leu Ser Ile Asn
            20                  25                  30

Ala Met Gly Trp Tyr Arg Gln Ala Pro Gly Lys Gln Arg Glu Met Val
        35                  40                  45

Ala Gly Phe Thr Gly Asp Thr Asn Thr Ile Tyr Ala Glu Ser Val Lys
50                      55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Ala
                85                  90                  95

Ala Asp Val Gln Leu Phe Ser Arg Asp Tyr Glu Phe Tyr Trp Gly Gln
            100                 105                 110

Gly Thr Leu Val Thr Val Lys Pro
        115                 120

<210> SEQ ID NO 249
<211> LENGTH: 120
<212> TYPE: PRT
<213> ORGANISM: Artificial Sequence
<220> FEATURE:
<223> OTHER INFORMATION: hz10D9v5

<400> SEQUENCE: 249

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Ile Leu Ser Ile Asn
            20                  25                  30

Ala Met Gly Trp Tyr Arg Gln Ala Pro Gly Lys Gln Arg Glu Leu Val
        35                  40                  45

Ala Gly Phe Thr Gly Asp Thr Asn Thr Ile Tyr Ala Glu Ser Val Lys
50                      55                  60

Gly Arg Phe Thr Ile Ser Arg Asp Asn Ala Lys Asn Thr Val Tyr Leu
```

```
                 65                  70                  75                  80
Gln Met Ser Ser Leu Arg Ala Glu Asp Thr Ala Val Tyr Tyr Cys Ala
                85                  90                  95

Ala Asp Val Gln Leu Phe Ser Arg Asp Tyr Glu Phe Tyr Trp Gly Gln
                100                 105                 110

Gly Thr Leu Val Thr Val Lys Pro
                115                 120

<210> SEQ ID NO 250
<211> LENGTH: 120
<212> TYPE: PRT
<213> ORGANISM: Artificial Sequence
<220> FEATURE:
<223> OTHER INFORMATION: hz10D9v6

<400> SEQUENCE: 250

Glu Val Gln Leu Val Glu Ser Gly Gly Gly Val Gln Pro Gly Gly
1               5                   10                  15

Ser Leu Arg Leu Ser Cys Ala Ala Ser Gly Ser Ile Leu Ser Ile Asn
                20                  25                  30

Ala Met Gly Trp Tyr Arg Gln Pro Pro Gly Lys Gln Arg Glu Leu Val
                35                  40                  45

Ala Gly Phe Thr Gly Asp Thr Asn Thr Ile Tyr Ala Glu Ser Val Lys
                50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Ala
                85                  90                  95

Ala Asp Val Gln Leu Phe Ser Arg Asp Tyr Glu Phe Tyr Trp Gly Gln
                100                 105                 110

Gly Thr Leu Val Thr Val Lys Pro
                115                 120

<210> SEQ ID NO 251
<211> LENGTH: 120
<212> TYPE: PRT
<213> ORGANISM: Artificial Sequence
<220> FEATURE:
<223> OTHER INFORMATION: hz10D9v7

<400> SEQUENCE: 251

Glu Val Gln Leu Val Glu Ser Gly Gly Gly Val Gln Pro Gly Gly
1               5                   10                  15

Ser Leu Arg Leu Ser Cys Ala Ala Ser Gly Ser Ile Phe Ser Ile Asn
                20                  25                  30

Ala Met Gly Trp Tyr Arg Gln Ala Pro Gly Lys Gln Arg Glu Leu Val
                35                  40                  45

Ala Gly Phe Thr Gly Asp Thr Asn Thr Ile Tyr Ala Glu Ser Val Lys
                50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Ala
                85                  90                  95

Ala Asp Val Gln Leu Phe Ser Arg Asp Tyr Glu Phe Tyr Trp Gly Gln
                100                 105                 110

Gly Thr Leu Val Thr Val Lys Pro
                115                 120
```

```
<210> SEQ ID NO 252
<211> LENGTH: 120
<212> TYPE: PRT
<213> ORGANISM: Artificial Sequence
<220> FEATURE:
<223> OTHER INFORMATION: hz10D9v8

<400> SEQUENCE: 252

Glu Val Gln Leu Val Glu Ser Gly Gly Gly Glu Val Gln Pro Gly Gly
1               5                   10                  15

Ser Leu Arg Leu Ser Cys Ala Ala Ser Gly Phe Thr Phe Ser Ile Asn
            20                  25                  30

Ala Met Gly Trp Tyr Arg Gln Ala Pro Gly Lys Gln Arg Glu Leu Val
        35                  40                  45

Ala Gly Phe Thr Gly Asp Thr Asn Thr Ile Tyr Ala Glu Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Ala
                85                  90                  95

Ala Asp Val Gln Leu Phe Ser Arg Asp Tyr Glu Phe Tyr Trp Gly Gln
            100                 105                 110

Gly Thr Leu Val Thr Val Lys Pro
        115                 120

<210> SEQ ID NO 253
<211> LENGTH: 120
<212> TYPE: PRT
<213> ORGANISM: Artificial Sequence
<220> FEATURE:
<223> OTHER INFORMATION: hz10D9v9

<400> SEQUENCE: 253

Glu Val Gln Leu Val Glu Ser Gly Gly Gly Glu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Tyr Arg Gln Ala Pro Gly Lys Gln Arg Glu Leu Val
        35                  40                  45

Ala Gly Phe Thr Gly Asp Thr Asn Thr Ile Tyr Ala Glu Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Ala
                85                  90                  95

Ala Asp Val Gln Leu Phe Ser Arg Asp Tyr Glu Phe Tyr Trp Gly Gln
            100                 105                 110

Gly Thr Leu Val Thr Val Lys Pro
        115                 120

<210> SEQ ID NO 254
<211> LENGTH: 120
<212> TYPE: PRT
<213> ORGANISM: Artificial Sequence
<220> FEATURE:
<223> OTHER INFORMATION: hz10D9v10

<400> SEQUENCE: 254

Glu Val Gln Leu Val Glu Ser Gly Gly Gly Glu Val Gln Pro Gly Gly
```

```
                1               5                  10                 15
            Ser Leu Arg Leu Ser Cys Ala Ala Ser Gly Ser Ile Phe Ser Ser Asn
                            20                  25                  30

Ala Met Gly Trp Tyr Arg Gln Ala Pro Gly Lys Gln Arg Glu Leu Val
                            35                  40                  45

Ala Gly Phe Thr Gly Asp Thr Asn Thr Ile Tyr Ala Glu Ser Val Lys
                            50                  55                  60

Gly Arg Phe Thr Ile Ser Arg Asp Asn Ala Lys Asn Thr Val Tyr Leu
            65                  70                  75                  80

Gln Met Ser Ser Leu Arg Ala Glu Asp Thr Ala Val Tyr Tyr Cys Ala
                            85                  90                  95

Ala Asp Val Gln Leu Phe Ser Arg Asp Tyr Glu Phe Tyr Trp Gly Gln
                            100                 105                 110

Gly Thr Leu Val Thr Val Lys Pro
                            115                 120

<210> SEQ ID NO 255
<211> LENGTH: 120
<212> TYPE: PRT
<213> ORGANISM: Artificial Sequence
<220> FEATURE:
<223> OTHER INFORMATION: hz10D9v11

<400> SEQUENCE: 255

Glu Val Gln Leu Val Glu Ser Gly Gly Gly Val Gln Pro Gly Gly
            1               5                   10                  15

Ser Leu Arg Leu Ser Cys Ala Ala Ser Gly Phe Ile Phe Ser Ser Tyr
                            20                  25                  30

Ala Met Gly Trp Tyr Arg Gln Ala Pro Gly Lys Gln Arg Glu Leu Val
                            35                  40                  45

Ala Gly Phe Thr Gly Asp Thr Asn Thr Ile Tyr Ala Glu Ser Val Lys
                            50                  55                  60

Gly Arg Phe Thr Ile Ser Arg Asp Asn Ala Lys Asn Thr Val Tyr Leu
            65                  70                  75                  80

Gln Met Ser Ser Leu Arg Ala Glu Asp Thr Ala Val Tyr Tyr Cys Ala
                            85                  90                  95

Ala Asp Val Gln Leu Phe Ser Arg Asp Tyr Glu Phe Tyr Trp Gly Gln
                            100                 105                 110

Gly Thr Leu Val Thr Val Lys Pro
                            115                 120

<210> SEQ ID NO 256
<211> LENGTH: 120
<212> TYPE: PRT
<213> ORGANISM: Artificial Sequence
<220> FEATURE:
<223> OTHER INFORMATION: hz10D9v12

<400> SEQUENCE: 256

Glu Val Gln Leu Val Glu Ser Gly Gly Gly Val Gln Pro Gly Gly
            1               5                   10                  15

Ser Leu Arg Leu Ser Cys Ala Ala Ser Gly Ser Ile Phe Ser Ile Tyr
                            20                  25                  30

Ala Met Gly Trp Tyr Arg Gln Ala Pro Gly Lys Gln Arg Glu Leu Val
                            35                  40                  45

Ala Gly Phe Thr Gly Asp Thr Asn Thr Ile Tyr Ala Glu Ser Val Lys
                            50                  55                  60
```

```
Gly Arg Phe Thr Ile Ser Arg Asp Asn Ala Lys Asn Thr Val Tyr Leu
 65                  70                  75                  80

Gln Met Ser Ser Leu Arg Ala Glu Asp Thr Ala Val Tyr Tyr Cys Ala
                 85                  90                  95

Ala Asp Val Gln Leu Phe Ser Arg Asp Tyr Glu Phe Tyr Trp Gly Gln
                100                 105                 110

Gly Thr Leu Val Thr Val Lys Pro
            115                 120

<210> SEQ ID NO 257
<211> LENGTH: 120
<212> TYPE: PRT
<213> ORGANISM: Artificial Sequence
<220> FEATURE:
<223> OTHER INFORMATION: hz10D9v13

<400> SEQUENCE: 257

Glu Val Gln Leu Val Glu Ser Gly Gly Gly Val Gln Pro Gly Gly
 1               5                   10                  15

Ser Leu Arg Leu Ser Cys Ala Ala Ser Gly Phe Ile Phe Ser Ile Asn
                 20                  25                  30

Ala Met Gly Trp Tyr Arg Gln Ala Pro Gly Lys Gln Arg Glu Leu Val
                 35                  40                  45

Ala Gly Phe Thr Gly Asp Thr Asn Thr Ile Tyr Ala Glu Ser Val Lys
             50                  55                  60

Gly Arg Phe Thr Ile Ser Arg Asp Asn Ala Lys Asn Thr Val Tyr Leu
 65                  70                  75                  80

Gln Met Ser Ser Leu Arg Ala Glu Asp Thr Ala Val Tyr Tyr Cys Ala
                 85                  90                  95

Ala Asp Val Gln Leu Phe Ser Arg Asp Tyr Glu Phe Tyr Trp Gly Gln
                100                 105                 110

Gly Thr Leu Val Thr Val Lys Pro
            115                 120

<210> SEQ ID NO 258
<211> LENGTH: 123
<212> TYPE: PRT
<213> ORGANISM: Artificial Sequence
<220> FEATURE:
<223> OTHER INFORMATION: L10E5

<400> SEQUENCE: 258

Glu Val Gln Leu Val Gln Ser Gly Gly Gly Leu Val Gln Pro Gly Gly
 1               5                   10                  15

Ser Leu Arg Leu Ser Cys Ala Ala Ser Gly Phe Thr Leu Asp Asp Tyr
                 20                  25                  30

Thr Ile Gly Trp Phe Arg Gln Phe Pro Gly Lys Glu Arg Glu Gly Val
                 35                  40                  45

Ser Cys Ile Ser Ser Ser Gly Gly Ser Thr Tyr Tyr Ala Asp Ser Val
             50                  55                  60

Lys Gly Arg Phe Thr Ile Ser Arg Asp Asn Ala Lys Asn Thr Val Trp
 65                  70                  75                  80

Leu Gln Met Asn Asp Leu Lys Ser Glu Asp Thr Ala Ile Tyr Tyr Cys
                 85                  90                  95

Ala Thr Tyr Cys Pro Val Val Val Gly Pro Glu Leu Gly Tyr Asp Tyr
                100                 105                 110

Trp Gly Gln Gly Thr Gln Val Thr Val Lys Pro
            115                 120
```

-continued

<210> SEQ ID NO 259
<211> LENGTH: 123
<212> TYPE: PRT
<213> ORGANISM: Artificial Sequence
<220> FEATURE:
<223> OTHER INFORMATION: hz10E5v1

<400> SEQUENCE: 259

```
Glu Val Gln Leu Val Glu Ser Gly Gly Gly Val Gln Pro Gly Gly
1               5                   10                  15

Ser Leu Arg Leu Ser Cys Ala Ala Ser Gly Phe Thr Leu Asp Asp Tyr
            20                  25                  30

Thr Ile Gly Trp Phe Arg Gln Ala Pro Gly Lys Glu Arg Glu Gly Val
        35                  40                  45

Ser Cys Ile Ser Ser Ser Gly Gly Ser Thr Tyr Tyr Ala Glu Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Thr Tyr Cys Pro Val Val Val Gly Pro Glu Leu Gly Tyr Asp Tyr
            100                 105                 110

Trp Gly Gln Gly Thr Leu Val Thr Val Lys Pro
        115                 120
```

<210> SEQ ID NO 260
<211> LENGTH: 123
<212> TYPE: PRT
<213> ORGANISM: Artificial Sequence
<220> FEATURE:
<223> OTHER INFORMATION: hz10E5v2

<400> SEQUENCE: 260

```
Glu Val Gln Leu Val Glu Ser Gly Gly Gly Val Gln Pro Gly Gly
1               5                   10                  15

Ser Leu Arg Leu Ser Cys Ala Ala Ser Gly Phe Thr Leu Asp Asp Tyr
            20                  25                  30

Thr Ile Gly Trp Phe Arg Gln Ala Pro Gly Lys Glu Arg Glu Gly Val
        35                  40                  45

Ser Cys Ile Ser Ser Ser Gly Gly Ser Thr Tyr Tyr Ala Glu Ser Val
    50                  55                  60

Lys Gly Arg Phe Thr Ile Ser Arg Asp Asn Ala Lys Asn Thr Val Trp
65                  70                  75                  80

Leu Gln Met Ser Ser Leu Arg Ala Glu Asp Thr Ala Val Tyr Tyr Cys
                85                  90                  95

Ala Thr Tyr Cys Pro Val Val Val Gly Pro Glu Leu Gly Tyr Asp Tyr
            100                 105                 110

Trp Gly Gln Gly Thr Leu Val Thr Val Lys Pro
        115                 120
```

<210> SEQ ID NO 261
<211> LENGTH: 123
<212> TYPE: PRT
<213> ORGANISM: Artificial Sequence
<220> FEATURE:
<223> OTHER INFORMATION: hz10E5v3

<400> SEQUENCE: 261

Glu Val Gln Leu Val Glu Ser Gly Gly Gly Val Gln Pro Gly Gly
1               5                   10                  15

Ser Leu Arg Leu Ser Cys Ala Ala Ser Gly Phe Thr Leu Asp Asp Tyr
            20                  25                  30

Thr Ile Gly Trp Phe Arg Gln Ala Pro Gly Lys Glu Arg Glu Gly Val
        35                  40                  45

Ser Cys Ile Ser Ser Ser Gly Gly Ser Thr Tyr Tyr Ala Glu Ser Val
50                  55                  60

Lys Gly Arg Phe Thr Ile Ser Arg Asp Asn Ala Lys Asn Thr Leu Tyr
65                  70                  75                  80

Leu Gln Met Asn Asp Leu Arg Ala Glu Asp Thr Ala Val Tyr Tyr Cys
                85                  90                  95

Ala Thr Tyr Cys Pro Val Val Val Gly Pro Glu Leu Gly Tyr Asp Tyr
            100                 105                 110

Trp Gly Gln Gly Thr Leu Val Thr Val Lys Pro
            115                 120

<210> SEQ ID NO 262
<211> LENGTH: 123
<212> TYPE: PRT
<213> ORGANISM: Artificial Sequence
<220> FEATURE:
<223> OTHER INFORMATION: hz10E5v4

<400> SEQUENCE: 262

Glu Val Gln Leu Val Glu Ser Gly Gly Gly Val Gln Pro Gly Gly
1               5                   10                  15

Ser Leu Arg Leu Ser Cys Ala Ala Ser Gly Phe Thr Leu Asp Asp Tyr
            20                  25                  30

Thr Ile Gly Trp Phe Arg Gln Ala Pro Gly Lys Glu Arg Glu Gly Val
        35                  40                  45

Ser Cys Ile Ser Ser Ser Gly Gly Ser Thr Tyr Tyr Ala Glu Ser Val
50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Ile Tyr Tyr Cys
                85                  90                  95

Ala Thr Tyr Cys Pro Val Val Val Gly Pro Glu Leu Gly Tyr Asp Tyr
            100                 105                 110

Trp Gly Gln Gly Thr Leu Val Thr Val Lys Pro
            115                 120

<210> SEQ ID NO 263
<211> LENGTH: 123
<212> TYPE: PRT
<213> ORGANISM: Artificial Sequence
<220> FEATURE:
<223> OTHER INFORMATION: hz10E5v5

<400> SEQUENCE: 263

Glu Val Gln Leu Val Glu Ser Gly Gly Gly Val Gln Pro Gly Gly
1               5                   10                  15

Ser Leu Arg Leu Ser Cys Ala Ala Ser Gly Phe Thr Leu Asp Asp Tyr
            20                  25                  30

Thr Ile Gly Trp Phe Arg Gln Phe Pro Gly Lys Glu Arg Glu Gly Val
        35                  40                  45

Ser Cys Ile Ser Ser Ser Gly Gly Ser Thr Tyr Tyr Ala Glu Ser Val
50                  55                  60

```
Lys Gly Arg Phe Thr Ile Ser Arg Asp Asn Ala Lys Asn Thr Leu Tyr
 65                  70                  75                  80

Leu Gln Met Ser Ser Leu Arg Ala Glu Asp Thr Ala Val Tyr Tyr Cys
                 85                  90                  95

Ala Thr Tyr Cys Pro Val Val Val Gly Pro Glu Leu Gly Tyr Asp Tyr
            100                 105                 110

Trp Gly Gln Gly Thr Leu Val Thr Val Lys Pro
            115                 120

<210> SEQ ID NO 264
<211> LENGTH: 115
<212> TYPE: PRT
<213> ORGANISM: Artificial Sequence
<220> FEATURE:
<223> OTHER INFORMATION: L8E7

<400> SEQUENCE: 264

Glu Val Gln Leu Gln Glu Ser Gly Gly Gly Leu Val Gln Ala Gly Gly
 1               5                  10                  15

Ser Leu Arg Leu Ser Cys Gly Pro Ser Glu Ile Ile Thr Ser Asp Lys
                20                  25                  30

Ser Val Gly Trp Trp Arg Gln Ala Pro Gly Lys Gln Arg Asn Leu Val
            35                  40                  45

Ala Gly Ile Ser Asn Val Gly Ser Thr Asn Tyr Ala Gln Ser Val Lys
        50                  55                  60

Gly Arg Phe Thr Ile Ser Arg Asp Asn Ala Lys Asn Thr Leu Phe Leu
 65                  70                  75                  80

Gln Met Asn Ser Leu Lys Pro Glu Asp Thr Ala Val Tyr Tyr Cys Tyr
                 85                  90                  95

Ala Arg Asp Phe Glu Asn Glu Tyr Trp Gly Arg Gly Thr Gln Val Thr
            100                 105                 110

Val Lys Pro
        115

<210> SEQ ID NO 265
<211> LENGTH: 115
<212> TYPE: PRT
<213> ORGANISM: Artificial Sequence
<220> FEATURE:
<223> OTHER INFORMATION: hz8E7v1

<400> SEQUENCE: 265

Glu Val Gln Leu Val Glu Ser Gly Gly Gly Glu Val Gln Pro Gly Gly
 1               5                  10                  15

Ser Leu Arg Leu Ser Cys Ala Ala Ser Glu Ile Ile Thr Ser Asp Lys
                20                  25                  30

Ser Val Gly Trp Trp Arg Gln Ala Pro Gly Lys Gln Arg Asn Leu Val
            35                  40                  45

Ala Gly Ile Ser Asn Val Gly Ser Thr Asn Tyr Ala Glu Ser Val Lys
        50                  55                  60

Gly Arg Phe Thr Ile Ser Arg Asp Asn Ala Lys Asn Thr Leu Tyr Leu
 65                  70                  75                  80

Gln Met Ser Ser Leu Arg Ala Glu Asp Thr Ala Val Tyr Tyr Cys Tyr
                 85                  90                  95

Ala Arg Asp Phe Glu Asn Glu Tyr Trp Gly Gln Gly Thr Leu Val Thr
            100                 105                 110

Val Lys Pro
```

115

<210> SEQ ID NO 266
<211> LENGTH: 115
<212> TYPE: PRT
<213> ORGANISM: Artificial Sequence
<220> FEATURE:
<223> OTHER INFORMATION: hz8E7v2

<400> SEQUENCE: 266

Glu Val Gln Leu Val Glu Ser Gly Gly Gly Glu Val Gln Pro Gly Gly
1               5                   10                  15

Ser Leu Arg Leu Ser Cys Ala Ala Ser Glu Ile Ile Thr Ser Asp Lys
            20                  25                  30

Ser Val Gly Trp Trp Arg Gln Ala Pro Gly Lys Gln Arg Asn Leu Val
        35                  40                  45

Ala Gly Ile Ser Asn Val Gly Ser Thr Asn Tyr Ala Gln Ser Val Lys
    50                  55                  60

Gly Arg Phe Thr Ile Ser Arg Asp Asn Ala Lys Asn Thr Leu Tyr Leu
65                  70                  75                  80

Gln Met Ser Ser Leu Arg Ala Glu Asp Thr Ala Val Tyr Tyr Cys Tyr
                85                  90                  95

Ala Arg Asp Phe Glu Asn Glu Tyr Trp Gly Gln Gly Thr Leu Val Thr
            100                 105                 110

Val Lys Pro
        115

<210> SEQ ID NO 267
<211> LENGTH: 115
<212> TYPE: PRT
<213> ORGANISM: Artificial Sequence
<220> FEATURE:
<223> OTHER INFORMATION: hz8E7v3

<400> SEQUENCE: 267

Glu Val Gln Leu Val Glu Ser Gly Gly Gly Glu Val Gln Pro Gly Gly
1               5                   10                  15

Ser Leu Arg Leu Ser Cys Gly Pro Ser Glu Ile Ile Thr Ser Asp Lys
            20                  25                  30

Ser Val Gly Trp Trp Arg Gln Ala Pro Gly Lys Gln Arg Asn Leu Val
        35                  40                  45

Ala Gly Ile Ser Asn Val Gly Ser Thr Asn Tyr Ala Gln Ser Val Lys
    50                  55                  60

Gly Arg Phe Thr Ile Ser Arg Asp Asn Ala Lys Asn Thr Leu Tyr Leu
65                  70                  75                  80

Gln Met Ser Ser Leu Arg Ala Glu Asp Thr Ala Val Tyr Tyr Cys Tyr
                85                  90                  95

Ala Arg Asp Phe Glu Asn Glu Tyr Trp Gly Gln Gly Thr Leu Val Thr
            100                 105                 110

Val Lys Pro
        115

<210> SEQ ID NO 268
<211> LENGTH: 115
<212> TYPE: PRT
<213> ORGANISM: Artificial Sequence
<220> FEATURE:
<223> OTHER INFORMATION: hz8E7v4

<400> SEQUENCE: 268

Glu Val Gln Leu Val Glu Ser Gly Gly Gly Glu Val Gln Pro Gly Gly
1               5                   10                  15

Ser Leu Arg Leu Ser Cys Ala Ala Ser Glu Ile Ile Thr Ser Asp Lys
            20                  25                  30

Ser Val Gly Trp Trp Arg Gln Ala Pro Gly Lys Gln Arg Asn Leu Val
            35                  40                  45

Ala Gly Ile Ser Asn Val Gly Ser Thr Asn Tyr Ala Gln Ser Val Lys
        50                  55                  60

Gly Arg Phe Thr Ile Ser Arg Asp Asn Ala Lys Asn Thr Leu Phe Leu
65                  70                  75                  80

Gln Met Ser Ser Leu Arg Ala Glu Asp Thr Ala Val Tyr Tyr Cys Tyr
                85                  90                  95

Ala Arg Asp Phe Glu Asn Glu Tyr Trp Gly Gln Gly Thr Leu Val Thr
            100                 105                 110

Val Lys Pro
        115

<210> SEQ ID NO 269
<211> LENGTH: 115
<212> TYPE: PRT
<213> ORGANISM: Artificial Sequence
<220> FEATURE:
<223> OTHER INFORMATION: hz8E7v6

<400> SEQUENCE: 269

Glu Val Gln Leu Val Glu Ser Gly Gly Gly Glu Val Gln Pro Gly Gly
1               5                   10                  15

Ser Leu Arg Leu Ser Cys Gly Pro Ser Glu Ile Ile Phe Ser Asp Lys
            20                  25                  30

Ser Val Gly Trp Trp Arg Gln Ala Pro Gly Lys Gln Arg Asn Leu Val
            35                  40                  45

Ala Gly Ile Ser Asn Val Gly Ser Thr Asn Tyr Ala Gln Ser Val Lys
        50                  55                  60

Gly Arg Phe Thr Ile Ser Arg Asp Asn Ala Lys Asn Thr Leu Tyr Leu
65                  70                  75                  80

Gln Met Ser Ser Leu Arg Ala Glu Asp Thr Ala Val Tyr Tyr Cys Tyr
                85                  90                  95

Ala Arg Asp Phe Glu Asn Glu Tyr Trp Gly Gln Gly Thr Leu Val Thr
            100                 105                 110

Val Lys Pro
        115

<210> SEQ ID NO 270
<211> LENGTH: 115
<212> TYPE: PRT
<213> ORGANISM: Artificial Sequence
<220> FEATURE:
<223> OTHER INFORMATION: hz8E7v8

<400> SEQUENCE: 270

Glu Val Gln Leu Val Glu Ser Gly Gly Gly Glu Val Gln Pro Gly Gly
1               5                   10                  15

Ser Leu Arg Leu Ser Cys Gly Pro Ser Glu Ile Ile Thr Ser Asp Lys
            20                  25                  30

Ser Val Gly Trp Tyr Arg Gln Ala Pro Gly Lys Gln Arg Asn Leu Val
            35                  40                  45

Ala Gly Ile Ser Asn Val Gly Ser Thr Asn Tyr Ala Gln Ser Val Lys

```
                 50                  55                  60
Gly Arg Phe Thr Ile Ser Arg Asp Asn Ala Lys Asn Thr Leu Tyr Leu
 65                  70                  75                  80

Gln Met Ser Ser Leu Arg Ala Glu Asp Thr Ala Val Tyr Tyr Cys Tyr
                     85                  90                  95

Ala Arg Asp Phe Glu Asn Glu Tyr Trp Gly Gln Gly Thr Leu Val Thr
                100                 105                 110

Val Lys Pro
        115

<210> SEQ ID NO 271
<211> LENGTH: 115
<212> TYPE: PRT
<213> ORGANISM: Artificial Sequence
<220> FEATURE:
<223> OTHER INFORMATION: hz8E7v9

<400> SEQUENCE: 271

Glu Val Gln Leu Val Glu Ser Gly Gly Gly Val Gln Pro Gly Gly
 1               5                  10                  15

Ser Leu Arg Leu Ser Cys Gly Pro Ser Glu Ile Ile Thr Ser Asp Lys
                 20                  25                  30

Ser Val Gly Trp Val Arg Gln Ala Pro Gly Lys Gln Arg Asn Leu Val
                 35                  40                  45

Ala Gly Ile Ser Asn Val Gly Ser Thr Asn Tyr Ala Gln Ser Val Lys
             50                  55                  60

Gly Arg Phe Thr Ile Ser Arg Asp Asn Ala Lys Asn Thr Leu Tyr Leu
 65                  70                  75                  80

Gln Met Ser Ser Leu Arg Ala Glu Asp Thr Ala Val Tyr Tyr Cys Tyr
                     85                  90                  95

Ala Arg Asp Phe Glu Asn Glu Tyr Trp Gly Gln Gly Thr Leu Val Thr
                100                 105                 110

Val Lys Pro
        115

<210> SEQ ID NO 272
<211> LENGTH: 115
<212> TYPE: PRT
<213> ORGANISM: Artificial Sequence
<220> FEATURE:
<223> OTHER INFORMATION: hz8E7v10

<400> SEQUENCE: 272

Glu Val Gln Leu Val Glu Ser Gly Gly Gly Val Gln Pro Gly Gly
 1               5                  10                  15

Ser Leu Arg Leu Ser Cys Gly Pro Ser Glu Ile Ile Thr Ser Asp Lys
                 20                  25                  30

Ser Val Gly Trp Trp Arg Gln Ala Pro Gly Lys Gln Arg Glu Leu Val
                 35                  40                  45

Ala Gly Ile Ser Asn Val Gly Ser Thr Asn Tyr Ala Gln Ser Val Lys
             50                  55                  60

Gly Arg Phe Thr Ile Ser Arg Asp Asn Ala Lys Asn Thr Leu Tyr Leu
 65                  70                  75                  80

Gln Met Ser Ser Leu Arg Ala Glu Asp Thr Ala Val Tyr Tyr Cys Tyr
                     85                  90                  95

Ala Arg Asp Phe Glu Asn Glu Tyr Trp Gly Gln Gly Thr Leu Val Thr
                100                 105                 110
```

Val Lys Pro
        115

<210> SEQ ID NO 273
<211> LENGTH: 115
<212> TYPE: PRT
<213> ORGANISM: Artificial Sequence
<220> FEATURE:
<223> OTHER INFORMATION: hz8E7v11

<400> SEQUENCE: 273

Glu Val Gln Leu Val Glu Ser Gly Gly Gly Val Gln Pro Gly Gly
1               5                   10                  15

Ser Leu Arg Leu Ser Cys Gly Pro Ser Glu Ile Ile Thr Ser Asp Lys
        20                  25                  30

Ser Val Gly Trp Phe Arg Gln Ala Pro Gly Lys Gln Arg Asn Leu Val
        35                  40                  45

Ala Gly Ile Ser Asn Val Gly Ser Thr Asn Tyr Ala Gln Ser Val Lys
    50                  55                  60

Gly Arg Phe Thr Ile Ser Arg Asp Asn Ala Lys Asn Thr Leu Tyr Leu
65              70                  75                  80

Gln Met Ser Ser Leu Arg Ala Glu Asp Thr Ala Val Tyr Tyr Cys Tyr
                85                  90                  95

Ala Arg Asp Phe Glu Asn Glu Tyr Trp Gly Gln Gly Thr Leu Val Thr
            100                 105                 110

Val Lys Pro
        115

<210> SEQ ID NO 274
<211> LENGTH: 115
<212> TYPE: PRT
<213> ORGANISM: Artificial Sequence
<220> FEATURE:
<223> OTHER INFORMATION: hz8E7v12

<400> SEQUENCE: 274

Glu Val Gln Leu Val Glu Ser Gly Gly Gly Val Gln Pro Gly Gly
1               5                   10                  15

Ser Leu Arg Leu Ser Cys Gly Pro Ser Glu Ile Ile Thr Ser Asp Lys
        20                  25                  30

Ser Val Gly Trp Trp Arg Gln Ala Pro Gly Lys Gly Arg Glu Leu Val
        35                  40                  45

Ala Gly Ile Ser Asn Val Gly Ser Thr Asn Tyr Ala Gln Ser Val Lys
    50                  55                  60

Gly Arg Phe Thr Ile Ser Arg Asp Asn Ala Lys Asn Thr Leu Tyr Leu
65              70                  75                  80

Gln Met Ser Ser Leu Arg Ala Glu Asp Thr Ala Val Tyr Tyr Cys Tyr
                85                  90                  95

Ala Arg Asp Phe Glu Asn Glu Tyr Trp Gly Gln Gly Thr Leu Val Thr
            100                 105                 110

Val Lys Pro
        115

<210> SEQ ID NO 275
<211> LENGTH: 120
<212> TYPE: PRT
<213> ORGANISM: Artificial Sequence
<220> FEATURE:
<223> OTHER INFORMATION: L3G3

-continued

<400> SEQUENCE: 275

```
Gln Val Gln Leu Val Gln Ser Gly Gly Gly Leu Val Gln Ala Gly Gly
1               5                   10                  15
Ser Leu Arg Leu Ser Cys Ala Ala Ser Gly Ser Ile Phe Ser Ile Asn
            20                  25                  30
Ala Met Gly Trp Tyr Arg Glu Ala Pro Gly Lys Gln Arg Glu Leu Val
        35                  40                  45
Ala Gly Phe Thr Gly Asp Gly Met Thr Lys Tyr Ala Glu Ser Val Lys
    50                  55                  60
Gly Arg Phe Thr Phe Ser Arg Asp Asn Ala Lys Asn Thr Val Tyr Leu
65                  70                  75                  80
Gln Met Asn Ser Leu Lys Pro Glu Asp Thr Gly Val Tyr Tyr Cys Ala
                85                  90                  95
Ala Asp Val Phe Thr Asp Arg Asp His Val Asp Trp Tyr Trp Gly Gln
            100                 105                 110
Gly Thr Gln Val Thr Val Lys Pro
        115                 120
```

<210> SEQ ID NO 276
<211> LENGTH: 122
<212> TYPE: PRT
<213> ORGANISM: Artificial Sequence
<220> FEATURE:
<223> OTHER INFORMATION: hz3G3v1

<400> SEQUENCE: 276

```
Glu Val Gln Leu Val Glu Ser Gly Gly Gly Glu Val Gln Pro Gly Gly
1               5                   10                  15
Ser Leu Arg Leu Ser Cys Ala Ala Ser Gly Ser Ile Phe Ser Ile Asn
            20                  25                  30
Ala Met Gly Trp Tyr Arg Gln Ala Pro Gly Lys Gln Arg Glu Leu Val
        35                  40                  45
Ala Gly Phe Thr Gly Asp Gly Met Thr Lys Tyr Ala Glu Ser Val Lys
    50                  55                  60
Gly Arg Phe Thr Ile Ser Arg Asp Asn Ala Lys Asn Thr Val Tyr Leu
65                  70                  75                  80
Gln Met Ser Ser Leu Arg Ala Glu Asp Thr Ala Val Tyr Tyr Cys Ala
                85                  90                  95
Ala Asp Val Phe Thr Asp Arg Asp His Val Asp Trp Tyr Trp Gly Gln
            100                 105                 110
Gly Thr Leu Val Thr Val Lys Pro Gly Gly
        115                 120
```

<210> SEQ ID NO 277
<211> LENGTH: 120
<212> TYPE: PRT
<213> ORGANISM: Artificial Sequence
<220> FEATURE:
<223> OTHER INFORMATION: hz3G3v2

<400> SEQUENCE: 277

```
Glu Val Gln Leu Val Glu Ser Gly Gly Gly Glu Val Gln Pro Gly Gly
1               5                   10                  15
Ser Leu Arg Leu Ser Cys Ala Ala Ser Gly Ser Ile Phe Ser Ile Asn
            20                  25                  30
Ala Met Gly Trp Tyr Arg Glu Ala Pro Gly Lys Gln Arg Glu Leu Val
        35                  40                  45
```

```
Ala Gly Phe Thr Gly Asp Gly Met Thr Lys Tyr Ala Glu Ser Val Lys
    50                  55                  60

Gly Arg Phe Thr Ile Ser Arg Asp Asn Ala Lys Asn Thr Val Tyr Leu
 65                  70                  75                  80

Gln Met Ser Ser Leu Arg Ala Glu Asp Thr Ala Val Tyr Tyr Cys Ala
                 85                  90                  95

Ala Asp Val Phe Thr Asp Arg Asp His Val Asp Trp Tyr Trp Gly Gln
            100                 105                 110

Gly Thr Leu Val Thr Val Lys Pro
            115                 120

<210> SEQ ID NO 278
<211> LENGTH: 120
<212> TYPE: PRT
<213> ORGANISM: Artificial Sequence
<220> FEATURE:
<223> OTHER INFORMATION: hz3G3v3

<400> SEQUENCE: 278

Glu Val Gln Leu Val Glu Ser Gly Gly Gly Val Gln Pro Gly Gly
  1               5                  10                  15

Ser Leu Arg Leu Ser Cys Ala Ala Ser Gly Ser Ile Phe Ser Ile Asn
                 20                  25                  30

Ala Met Gly Trp Tyr Arg Gln Ala Pro Gly Lys Gln Arg Glu Leu Val
             35                  40                  45

Ala Gly Phe Thr Gly Asp Gly Met Thr Lys Tyr Ala Glu Ser Val Lys
    50                  55                  60

Gly Arg Phe Thr Phe Ser Arg Asp Asn Ala Lys Asn Thr Val Tyr Leu
 65                  70                  75                  80

Gln Met Ser Ser Leu Arg Ala Glu Asp Thr Ala Val Tyr Tyr Cys Ala
                 85                  90                  95

Ala Asp Val Phe Thr Asp Arg Asp His Val Asp Trp Tyr Trp Gly Gln
            100                 105                 110

Gly Thr Leu Val Thr Val Lys Pro
            115                 120

<210> SEQ ID NO 279
<211> LENGTH: 120
<212> TYPE: PRT
<213> ORGANISM: Artificial Sequence
<220> FEATURE:
<223> OTHER INFORMATION: hz3G3v4

<400> SEQUENCE: 279

Glu Val Gln Leu Val Glu Ser Gly Gly Gly Val Gln Pro Gly Gly
  1               5                  10                  15

Ser Leu Arg Leu Ser Cys Ala Ala Ser Gly Ser Ile Phe Ser Ile Asn
                 20                  25                  30

Ala Met Gly Trp Tyr Arg Gln Ala Pro Gly Lys Gln Arg Glu Leu Val
             35                  40                  45

Ala Gly Phe Thr Gly Asp Gly Met Thr Lys Tyr Ala Glu Ser Val Lys
    50                  55                  60

Gly Arg Phe Thr Ile Ser Arg Asp Asn Ala Lys Asn Thr Val Tyr Leu
 65                  70                  75                  80

Gln Met Ser Ser Leu Arg Ala Glu Asp Thr Gly Val Tyr Tyr Cys Ala
                 85                  90                  95

Ala Asp Val Phe Thr Asp Arg Asp His Val Asp Trp Tyr Trp Gly Gln
            100                 105                 110
```

```
Gly Thr Leu Val Thr Val Lys Pro
        115                 120

<210> SEQ ID NO 280
<211> LENGTH: 119
<212> TYPE: PRT
<213> ORGANISM: Artificial Sequence
<220> FEATURE:
<223> OTHER INFORMATION: L5A7

<400> SEQUENCE: 280

Glu Val Gln Leu Val Gln Ser Gly Gly Leu Val Gln Pro Gly Gly
1               5                   10                  15

Ser Leu Arg Leu Ser Cys Ala Ala Ser Gly Ser Asp Phe Ser Ile Asn
            20                  25                  30

Ala Ile Gly Trp Tyr Arg Gln Ala Pro Gly Lys Gln Arg Asp Met Val
        35                  40                  45

Ala Gly Phe Thr Gly Asp Gly Val Thr Thr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Asp Val Lys Ile Gly Gly Asp Tyr Glu Trp Phe Trp Gly Gln Gly
            100                 105                 110

Thr Gln Val Thr Val Lys Pro
        115

<210> SEQ ID NO 281
<211> LENGTH: 119
<212> TYPE: PRT
<213> ORGANISM: Artificial Sequence
<220> FEATURE:
<223> OTHER INFORMATION: hz5A7v1

<400> SEQUENCE: 281

Glu Val Gln Leu Val Glu Ser Gly Gly Gly Val Gln Pro Gly Gly
1               5                   10                  15

Ser Leu Arg Leu Ser Cys Ala Ala Ser Gly Ser Asp Phe Ser Ile Asn
            20                  25                  30

Ala Ile Gly Trp Tyr Arg Gln Ala Pro Gly Lys Gln Arg Asp Met Val
        35                  40                  45

Ala Gly Phe Thr Gly Asp Gly Val Thr Thr Tyr Ala Glu Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Ala
                85                  90                  95

Ala Asp Val Lys Ile Gly Gly Asp Tyr Glu Trp Phe Trp Gly Gln Gly
            100                 105                 110

Thr Leu Val Thr Val Lys Pro
        115

<210> SEQ ID NO 282
<211> LENGTH: 119
<212> TYPE: PRT
<213> ORGANISM: Artificial Sequence
<220> FEATURE:
<223> OTHER INFORMATION: hz5A7v2
```

<400> SEQUENCE: 282

Glu Val Gln Leu Val Glu Ser Gly Gly Gly Val Gln Pro Gly Gly
1               5                   10                  15

Ser Leu Arg Leu Ser Cys Ala Ala Ser Gly Ser Asp Phe Ser Ile Asn
            20                  25                  30

Ala Ile Gly Trp Tyr Arg Gln Ala Pro Gly Lys Gln Arg Asp Met Val
        35                  40                  45

Ala Gly Phe Thr Gly Asp Thr Val Thr Thr Tyr Ala Glu Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Ala
                85                  90                  95

Ala Asp Val Lys Ile Gly Gly Asp Tyr Glu Trp Phe Trp Gly Gln Gly
            100                 105                 110

Thr Leu Val Thr Val Lys Pro
        115

<210> SEQ ID NO 283
<211> LENGTH: 119
<212> TYPE: PRT
<213> ORGANISM: Artificial Sequence
<220> FEATURE:
<223> OTHER INFORMATION: hz5A7v3

<400> SEQUENCE: 283

Glu Val Gln Leu Val Glu Ser Gly Gly Gly Val Gln Pro Gly Gly
1               5                   10                  15

Ser Leu Arg Leu Ser Cys Ala Ala Ser Gly Ser Asp Phe Ser Ile Asn
            20                  25                  30

Ala Ile Gly Trp Tyr Arg Gln Ala Pro Gly Lys Gln Arg Asp Met Val
        35                  40                  45

Ala Gly Phe Thr Gly Glu Gly Val Thr Thr Tyr Ala Glu Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Ala
                85                  90                  95

Ala Asp Val Lys Ile Gly Gly Asp Tyr Glu Trp Phe Trp Gly Gln Gly
            100                 105                 110

Thr Leu Val Thr Val Lys Pro
        115

<210> SEQ ID NO 284
<211> LENGTH: 119
<212> TYPE: PRT
<213> ORGANISM: Artificial Sequence
<220> FEATURE:
<223> OTHER INFORMATION: hz5A7v4

<400> SEQUENCE: 284

Glu Val Gln Leu Val Glu Ser Gly Gly Gly Val Gln Pro Gly Gly
1               5                   10                  15

Ser Leu Arg Leu Ser Cys Ala Ala Ser Gly Ser Asp Phe Ser Ile Asn
            20                  25                  30

Ala Ile Gly Trp Tyr Arg Gln Ala Pro Gly Lys Gln Arg Asp Leu Val
        35                  40                  45

```
Ala Gly Phe Thr Gly Asp Gly Val Thr Thr Tyr Ala Glu Ser Val Lys
        50                  55                  60

Gly Arg Phe Thr Ile Ser Arg Asp Asn Ala Lys Asn Thr Val Tyr Leu
 65                  70                  75                  80

Gln Met Ser Ser Leu Arg Ala Glu Asp Thr Ala Val Tyr Tyr Cys Ala
                85                  90                  95

Ala Asp Val Lys Ile Gly Gly Asp Tyr Glu Trp Phe Trp Gly Gln Gly
            100                 105                 110

Thr Leu Val Thr Val Lys Pro
            115

<210> SEQ ID NO 285
<211> LENGTH: 119
<212> TYPE: PRT
<213> ORGANISM: Artificial Sequence
<220> FEATURE:
<223> OTHER INFORMATION: hz5A7v5

<400> SEQUENCE: 285

Glu Val Gln Leu Val Glu Ser Gly Gly Gly Val Gln Pro Gly Gly
 1               5                  10                  15

Ser Leu Arg Leu Ser Cys Ala Ala Ser Gly Ser Asp Phe Ser Ile Asn
                20                  25                  30

Ala Ile Gly Trp Tyr Arg Gln Ala Pro Gly Lys Gln Arg Asp Trp Val
            35                  40                  45

Ala Gly Phe Thr Gly Asp Gly Val Thr Thr Tyr Ala Glu Ser Val Lys
        50                  55                  60

Gly Arg Phe Thr Ile Ser Arg Asp Asn Ala Lys Asn Thr Val Tyr Leu
 65                  70                  75                  80

Gln Met Ser Ser Leu Arg Ala Glu Asp Thr Ala Val Tyr Tyr Cys Ala
                85                  90                  95

Ala Asp Val Lys Ile Gly Gly Asp Tyr Glu Trp Phe Trp Gly Gln Gly
            100                 105                 110

Thr Leu Val Thr Val Lys Pro
            115

<210> SEQ ID NO 286
<211> LENGTH: 119
<212> TYPE: PRT
<213> ORGANISM: Artificial Sequence
<220> FEATURE:
<223> OTHER INFORMATION: hz5A7v6

<400> SEQUENCE: 286

Glu Val Gln Leu Val Glu Ser Gly Gly Gly Val Gln Pro Gly Gly
 1               5                  10                  15

Ser Leu Arg Leu Ser Cys Ala Ala Ser Gly Ser Asp Phe Ser Ile Asn
                20                  25                  30

Ala Ile Gly Trp Tyr Arg Gln Pro Pro Gly Lys Gln Arg Asp Met Val
            35                  40                  45

Ala Gly Phe Thr Gly Asp Gly Val Thr Thr Tyr Ala Glu Ser Val Lys
        50                  55                  60

Gly Arg Phe Thr Ile Ser Arg Asp Asn Ala Lys Asn Thr Val Tyr Leu
 65                  70                  75                  80

Gln Met Ser Ser Leu Arg Ala Glu Asp Thr Ala Val Tyr Tyr Cys Ala
                85                  90                  95

Ala Asp Val Lys Ile Gly Gly Asp Tyr Glu Trp Phe Trp Gly Gln Gly
```

-continued

```
                100                 105                 110
Thr Leu Val Thr Val Lys Pro
            115

<210> SEQ ID NO 287
<211> LENGTH: 120
<212> TYPE: PRT
<213> ORGANISM: Artificial Sequence
<220> FEATURE:
<223> OTHER INFORMATION: L5A8

<400> SEQUENCE: 287

Gln Val Gln Leu Val Gln Ser Gly Gly Gly Leu Val Gln Ala Gly Glu
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Val Leu Gly Lys Gln Arg Glu Leu Val
        35                  40                  45

Ala Val Val Ser Ser Asp Gly Arg Thr Thr Val Ala Pro Ser Val Lys
    50                  55                  60

Gly Arg Phe Thr Ile Ser Arg Asp Asn Ala Lys Asn Thr Val Ser Leu
65                  70                  75                  80

Gln Met Asn Ser Leu Lys Pro Glu Asp Thr Gly Val Tyr Tyr Cys Gly
                85                  90                  95

Val Arg Glu Trp Tyr Ser Asp Ser Asp Trp Arg Asp Tyr Glu Gly Gln
            100                 105                 110

Gly Thr Gln Val Thr Val Lys Pro
        115                 120

<210> SEQ ID NO 288
<211> LENGTH: 120
<212> TYPE: PRT
<213> ORGANISM: Artificial Sequence
<220> FEATURE:
<223> OTHER INFORMATION: hz5A8v1

<400> SEQUENCE: 288

Glu Val Gln Leu Val Glu Ser Gly Gly Gly Val Gln Pro Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Gln Arg Glu Leu Val
        35                  40                  45

Ala Val Val Ser Ser Asp Gly Arg Thr Thr Val Ala Glu Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Gly
                85                  90                  95

Val Arg Glu Trp Tyr Ser Asp Ser Asp Trp Arg Asp Tyr Glu Gly Gln
            100                 105                 110

Gly Thr Leu Val Thr Val Lys Pro
        115                 120

<210> SEQ ID NO 289
<211> LENGTH: 120
<212> TYPE: PRT
<213> ORGANISM: Artificial Sequence
<220> FEATURE:
```

<223> OTHER INFORMATION: hz5A8v2

<400> SEQUENCE: 289

Glu Val Gln Leu Val Glu Ser Gly Gly Gly Val Gln Pro Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Gln Arg Glu Leu Val
        35                  40                  45

Ala Val Val Ser Ser Asp Gly Arg Thr Thr Val Ala Pro Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Gly
                85                  90                  95

Val Arg Glu Trp Tyr Ser Asp Ser Asp Trp Arg Asp Tyr Glu Gly Gln
            100                 105                 110

Gly Thr Leu Val Thr Val Lys Pro
        115                 120

<210> SEQ ID NO 290
<211> LENGTH: 120
<212> TYPE: PRT
<213> ORGANISM: Artificial Sequence
<220> FEATURE:
<223> OTHER INFORMATION: hz5A8v3

<400> SEQUENCE: 290

Glu Val Gln Leu Val Glu Ser Gly Gly Gly Val Gln Pro Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Val Leu Gly Lys Gln Arg Glu Leu Val
        35                  40                  45

Ala Val Val Ser Ser Asp Gly Arg Thr Thr Val Ala Pro Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Gly
                85                  90                  95

Val Arg Glu Trp Tyr Ser Asp Ser Asp Trp Arg Asp Tyr Glu Gly Gln
            100                 105                 110

Gly Thr Leu Val Thr Val Lys Pro
        115                 120

<210> SEQ ID NO 291
<211> LENGTH: 120
<212> TYPE: PRT
<213> ORGANISM: Artificial Sequence
<220> FEATURE:
<223> OTHER INFORMATION: hz5A8v5

<400> SEQUENCE: 291

Glu Val Gln Leu Val Glu Ser Gly Gly Gly Val Gln Pro Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Gln Arg Glu Leu Val

```
                35                  40                  45
Ala Val Val Ser Ser Asp Gly Arg Thr Thr Val Ala Pro Ser Val Lys
 50                  55                  60

Gly Arg Phe Thr Ile Ser Arg Asp Asn Ala Lys Asn Thr Val Tyr Leu
 65                  70                  75                  80

Gln Met Ser Ser Leu Arg Ala Glu Asp Thr Gly Val Tyr Tyr Cys Gly
                 85                  90                  95

Val Arg Glu Trp Tyr Ser Asp Ser Asp Trp Arg Asp Tyr Glu Gly Gln
                100                 105                 110

Gly Thr Leu Val Thr Val Lys Pro
        115                 120

<210> SEQ ID NO 292
<211> LENGTH: 120
<212> TYPE: PRT
<213> ORGANISM: Artificial Sequence
<220> FEATURE:
<223> OTHER INFORMATION: hz5A8v6

<400> SEQUENCE: 292

Glu Val Gln Leu Val Glu Ser Gly Gly Glu Val Gln Pro Gly Gly
 1               5                  10                  15

Ser Leu Arg Leu Ser Cys Ala Ala Ser Gly Ser Ile Phe Ser Ile Asn
                 20                  25                  30

Ala Met Gly Trp Tyr Arg Gln Ala Pro Gly Lys Gln Arg Glu Leu Val
                 35                  40                  45

Ala Val Val Ser Ser Glu Gly Arg Thr Thr Val Ala Pro Ser Val Lys
 50                  55                  60

Gly Arg Phe Thr Ile Ser Arg Asp Asn Ala Lys Asn Thr Val Tyr Leu
 65                  70                  75                  80

Gln Met Ser Ser Leu Arg Ala Glu Asp Thr Ala Val Tyr Tyr Cys Gly
                 85                  90                  95

Val Arg Glu Trp Tyr Ser Asp Ser Asp Trp Arg Asp Tyr Glu Gly Gln
                100                 105                 110

Gly Thr Leu Val Thr Val Lys Pro
        115                 120

<210> SEQ ID NO 293
<211> LENGTH: 120
<212> TYPE: PRT
<213> ORGANISM: Artificial Sequence
<220> FEATURE:
<223> OTHER INFORMATION: hz5A8v7

<400> SEQUENCE: 293

Glu Val Gln Leu Val Glu Ser Gly Gly Glu Val Gln Pro Gly Gly
 1               5                  10                  15

Ser Leu Arg Leu Ser Cys Ala Ala Ser Gly Ser Ile Phe Ser Ile Asn
                 20                  25                  30

Ala Met Gly Trp Tyr Arg Gln Ala Pro Gly Lys Gln Arg Glu Leu Val
                 35                  40                  45

Ala Val Val Ser Ser Asp Ala Arg Thr Thr Val Ala Pro Ser Val Lys
 50                  55                  60

Gly Arg Phe Thr Ile Ser Arg Asp Asn Ala Lys Asn Thr Val Tyr Leu
 65                  70                  75                  80

Gln Met Ser Ser Leu Arg Ala Glu Asp Thr Ala Val Tyr Tyr Cys Gly
                 85                  90                  95
```

```
Val Arg Glu Trp Tyr Ser Asp Ser Trp Arg Asp Tyr Glu Gly Gln
            100                 105                 110

Gly Thr Leu Val Thr Val Lys Pro
        115                 120

<210> SEQ ID NO 294
<211> LENGTH: 120
<212> TYPE: PRT
<213> ORGANISM: Artificial Sequence
<220> FEATURE:
<223> OTHER INFORMATION: hz5A8v8

<400> SEQUENCE: 294

Glu Val Gln Leu Val Glu Ser Gly Gly Gly Val Gln Pro Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Gln Arg Glu Leu Val
            35                  40                  45

Ala Val Val Ser Ser Asp Gly Arg Thr Thr Val Ala Pro Ser Val Lys
        50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Gly
                85                  90                  95

Val Arg Glu Trp Tyr Ser Asp Ala Asp Trp Arg Asp Tyr Glu Gly Gln
            100                 105                 110

Gly Thr Leu Val Thr Val Lys Pro
        115                 120

<210> SEQ ID NO 295
<211> LENGTH: 120
<212> TYPE: PRT
<213> ORGANISM: Artificial Sequence
<220> FEATURE:
<223> OTHER INFORMATION: hz5A8v9

<400> SEQUENCE: 295

Glu Val Gln Leu Val Glu Ser Gly Gly Gly Val Gln Pro Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Gln Arg Glu Leu Val
            35                  40                  45

Ala Val Val Ser Ser Asp Gly Arg Thr Thr Val Ala Pro Ser Val Lys
        50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Gly
                85                  90                  95

Val Arg Glu Trp Tyr Ser Glu Ser Asp Trp Arg Asp Tyr Glu Gly Gln
            100                 105                 110

Gly Thr Leu Val Thr Val Lys Pro
        115                 120

<210> SEQ ID NO 296
<211> LENGTH: 120
<212> TYPE: PRT
<213> ORGANISM: Artificial Sequence
```

```
<220> FEATURE:
<223> OTHER INFORMATION: hz5A8v10

<400> SEQUENCE: 296

Glu Val Gln Leu Val Glu Ser Gly Gly Gly Val Gln Pro Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Gln Arg Glu Leu Val
        35                  40                  45

Ala Val Val Ser Ser Asp Ala Arg Thr Thr Val Ala Pro Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Gly
                85                  90                  95

Val Arg Glu Trp Tyr Ser Asp Ala Asp Trp Arg Asp Tyr Glu Gly Gln
            100                 105                 110

Gly Thr Leu Val Thr Val Lys Pro
        115                 120

<210> SEQ ID NO 297
<211> LENGTH: 120
<212> TYPE: PRT
<213> ORGANISM: Artificial Sequence
<220> FEATURE:
<223> OTHER INFORMATION: hz5A8v11

<400> SEQUENCE: 297

Glu Val Gln Leu Val Glu Ser Gly Gly Gly Val Gln Pro Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Gln Arg Glu Trp Val
        35                  40                  45

Ala Val Val Ser Ser Asp Gly Arg Thr Thr Val Ala Pro Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Gly
                85                  90                  95

Val Arg Glu Trp Tyr Ser Asp Ser Asp Trp Arg Asp Tyr Glu Gly Gln
            100                 105                 110

Gly Thr Leu Val Thr Val Lys Pro
        115                 120

<210> SEQ ID NO 298
<211> LENGTH: 120
<212> TYPE: PRT
<213> ORGANISM: Artificial Sequence
<220> FEATURE:
<223> OTHER INFORMATION: hz5A8v12

<400> SEQUENCE: 298

Glu Val Gln Leu Val Glu Ser Gly Gly Gly Val Gln Ala Gly Gly
1               5                   10                  15

Ser Leu Arg Leu Ser Cys Ala Ala Ser Gly Ser Ile Phe Ser Ile Asn
            20                  25                  30
```

```
Ala Met Gly Trp Tyr Arg Gln Ala Pro Gly Lys Gln Arg Glu Leu Val
            35                  40                  45

Ala Val Val Ser Ser Asp Gly Arg Thr Thr Val Ala Pro Ser Val Lys
 50                  55                  60

Gly Arg Phe Thr Ile Ser Arg Asp Asn Ala Lys Asn Thr Val Tyr Leu
 65                  70                  75                  80

Gln Met Ser Ser Leu Arg Ala Glu Asp Thr Ala Val Tyr Tyr Cys Gly
                 85                  90                  95

Val Arg Glu Trp Tyr Ser Asp Ser Asp Trp Arg Asp Tyr Glu Gly Gln
            100                 105                 110

Gly Thr Leu Val Thr Val Lys Pro
        115                 120
```

<210> SEQ ID NO 299
<211> LENGTH: 115
<212> TYPE: PRT
<213> ORGANISM: Artificial Sequence
<220> FEATURE:
<223> OTHER INFORMATION: L6C5

<400> SEQUENCE: 299

```
Gln Val Gln Leu Gln Glu Ser Gly Gly Gly Leu Val Gln Thr Gly Gly
 1               5                   10                  15

Ser Leu Thr Leu Ser Cys Gly Ala Ser Glu Ile Thr Phe Ser Asp Lys
            20                  25                  30

Thr Val Gly Trp Tyr Arg Gln Ala Pro Gly Lys Gln Arg Val Leu Val
            35                  40                  45

Ala Val Ile Ser Asn Val Asp Ser Thr Asn Tyr Ala His Ser Val Lys
 50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys His
                 85                  90                  95

Ala Arg Asp Phe Glu Asn Glu Tyr Trp Gly Arg Gly Thr Gln Val Thr
            100                 105                 110

Val Lys Pro
        115
```

<210> SEQ ID NO 300
<211> LENGTH: 115
<212> TYPE: PRT
<213> ORGANISM: Artificial Sequence
<220> FEATURE:
<223> OTHER INFORMATION: hz6C5v1

<400> SEQUENCE: 300

```
Glu Val Gln Leu Val Glu Ser Gly Gly Gly Val Gln Pro Gly Gly
 1               5                   10                  15

Ser Leu Arg Leu Ser Cys Ala Ala Ser Glu Ile Thr Phe Ser Asp Lys
            20                  25                  30

Thr Val Gly Trp Tyr Arg Gln Ala Pro Gly Lys Gln Arg Val Leu Val
            35                  40                  45

Ala Val Ile Ser Asn Val Asp Ser Thr Asn Tyr Ala Glu Ser Val Lys
 50                  55                  60

Gly Arg Phe Thr Ile Ser Arg Asp Asn Ala Lys Asn Thr Leu Tyr Leu
 65                  70                  75                  80

Gln Met Ser Ser Leu Arg Ala Glu Asp Thr Ala Val Tyr Tyr Cys His
                 85                  90                  95
```

Ala Arg Asp Phe Glu Asn Glu Tyr Trp Gly Gln Gly Thr Leu Val Thr
            100                 105                 110

Val Lys Pro
        115

<210> SEQ ID NO 301
<211> LENGTH: 116
<212> TYPE: PRT
<213> ORGANISM: Artificial Sequence
<220> FEATURE:
<223> OTHER INFORMATION: hz6C5v2

<400> SEQUENCE: 301

Glu Val Gln Leu Val Glu Ser Gly Gly Gly Glu Val Gln Pro Gly Gly
1               5                   10                  15

Ser Leu Arg Leu Ser Cys Ala Ala Ser Glu Ile Thr Phe Ser Asp Lys
            20                  25                  30

Thr Val Gly Trp Tyr Arg Gln Ala Pro Gly Lys Gln Arg Val Leu Val
        35                  40                  45

Ala Val Ile Ser Asn Val Asp Ser Thr Asn Tyr Ala Glu Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys His
                85                  90                  95

Ala Arg Asp Phe Glu Asn Glu Tyr Trp Gly Gln Gly Thr Leu Val Thr
            100                 105                 110

Val Lys Pro Gly
        115

<210> SEQ ID NO 302
<211> LENGTH: 115
<212> TYPE: PRT
<213> ORGANISM: Artificial Sequence
<220> FEATURE:
<223> OTHER INFORMATION: hz6C5v3

<400> SEQUENCE: 302

Glu Val Gln Leu Val Glu Ser Gly Gly Gly Glu Val Gln Pro Gly Gly
1               5                   10                  15

Ser Leu Arg Leu Ser Cys Ala Ala Ser Glu Ile Thr Phe Ser Asp Lys
            20                  25                  30

Thr Val Gly Trp Tyr Arg Gln Ala Pro Gly Lys Gln Arg Val Leu Val
        35                  40                  45

Ala Val Ile Ser Asn Val Asp Ser Thr Asn Tyr Ala His Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys His
                85                  90                  95

Ala Arg Asp Phe Glu Asn Glu Tyr Trp Gly Gln Gly Thr Leu Val Thr
            100                 105                 110

Val Lys Pro
        115

<210> SEQ ID NO 303
<211> LENGTH: 115
<212> TYPE: PRT

```
<213> ORGANISM: Artificial Sequence
<220> FEATURE:
<223> OTHER INFORMATION: hz6C5v4

<400> SEQUENCE: 303

Glu Val Gln Leu Val Glu Ser Gly Gly Gly Glu Val Gln Pro Gly Gly
1               5                   10                  15

Ser Leu Arg Leu Ser Cys Gly Ala Ser Glu Ile Thr Phe Ser Asp Lys
            20                  25                  30

Thr Val Gly Trp Tyr Arg Gln Ala Pro Gly Lys Gln Arg Val Leu Val
        35                  40                  45

Ala Val Ile Ser Asn Val Asp Ser Thr Asn Tyr Ala Glu Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys His
                85                  90                  95

Ala Arg Asp Phe Glu Asn Glu Tyr Trp Gly Gln Gly Thr Leu Val Thr
            100                 105                 110

Val Lys Pro
        115

<210> SEQ ID NO 304
<211> LENGTH: 115
<212> TYPE: PRT
<213> ORGANISM: Artificial Sequence
<220> FEATURE:
<223> OTHER INFORMATION: hz6C5v5

<400> SEQUENCE: 304

Glu Val Gln Leu Val Glu Ser Gly Gly Gly Glu Val Gln Pro Gly Gly
1               5                   10                  15

Ser Leu Arg Leu Ser Cys Ala Ala Ser Glu Ile Thr Phe Ser Asp Lys
            20                  25                  30

Thr Val Gly Trp Tyr Arg Gln Ala Pro Gly Lys Gln Arg Val Leu Val
        35                  40                  45

Ala Val Ile Ser Asn Val Glu Ser Thr Asn Tyr Ala Glu Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys His
                85                  90                  95

Ala Arg Asp Phe Glu Asn Glu Tyr Trp Gly Gln Gly Thr Leu Val Thr
            100                 105                 110

Val Lys Pro
        115

<210> SEQ ID NO 305
<211> LENGTH: 115
<212> TYPE: PRT
<213> ORGANISM: Artificial Sequence
<220> FEATURE:
<223> OTHER INFORMATION: hz6C5v6

<400> SEQUENCE: 305

Glu Val Gln Leu Val Glu Ser Gly Gly Gly Glu Val Gln Pro Gly Gly
1               5                   10                  15

Ser Leu Arg Leu Ser Cys Ala Ala Ser Glu Ile Thr Phe Ser Asp Lys
            20                  25                  30
```

```
Thr Val Gly Trp Tyr Arg Gln Ala Pro Gly Lys Gln Arg Val Leu Val
            35                  40                  45

Ala Val Ile Ser Asn Val Asp Ala Thr Asn Tyr Ala Glu Ser Val Lys
 50                  55                  60

Gly Arg Phe Thr Ile Ser Arg Asp Asn Ala Lys Asn Thr Val Tyr Leu
 65                  70                  75                  80

Gln Met Ser Ser Leu Arg Ala Glu Asp Thr Ala Val Tyr Tyr Cys His
                 85                  90                  95

Ala Arg Asp Phe Glu Asn Glu Tyr Trp Gly Gln Gly Thr Leu Val Thr
            100                 105                 110

Val Lys Pro
        115

<210> SEQ ID NO 306
<211> LENGTH: 114
<212> TYPE: PRT
<213> ORGANISM: Artificial Sequence
<220> FEATURE:
<223> OTHER INFORMATION: L6F1

<400> SEQUENCE: 306

Gln Val Gln Leu Val Gln Ser Gly Gly Gly Leu Val Gln Ala Gly Gly
 1               5                  10                  15

Ser Leu Arg Leu Ser Cys Gly Ala Ser Glu Ile Ile Phe Ser Asp Lys
            20                  25                  30

Thr Val Gly Trp Tyr Arg Gln Ala Pro Gly Lys Gln Arg Val Leu Val
            35                  40                  45

Ala Val Ile Ser Asn Val Asp Ser Thr Asn Tyr Ala Gln Ser Val Lys
 50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Tyr
                 85                  90                  95

Ala Arg Asp Phe Glu Ser Glu Tyr Trp Gly Arg Gly Thr Gln Val Thr
            100                 105                 110

Val Lys

<210> SEQ ID NO 307
<211> LENGTH: 114
<212> TYPE: PRT
<213> ORGANISM: Artificial Sequence
<220> FEATURE:
<223> OTHER INFORMATION: hz6F1v1

<400> SEQUENCE: 307

Glu Val Gln Leu Val Glu Ser Gly Gly Gly Glu Val Gln Pro Gly Gly
 1               5                  10                  15

Ser Leu Arg Leu Ser Cys Ala Ala Ser Glu Ile Ile Phe Ser Asp Lys
            20                  25                  30

Thr Val Gly Trp Tyr Arg Gln Ala Pro Gly Lys Gln Arg Val Leu Val
            35                  40                  45

Ala Val Ile Ser Asn Val Asp Ser Thr Asn Tyr Ala Glu Ser Val Lys
 50                  55                  60

Gly Arg Phe Thr Ile Ser Arg Asp Asn Ala Lys Asn Thr Leu Tyr Leu
 65                  70                  75                  80

Gln Met Ser Ser Leu Arg Ala Glu Asp Thr Ala Val Tyr Tyr Cys Tyr
                 85                  90                  95
```

Ala Arg Asp Phe Glu Ser Glu Tyr Trp Gly Gln Gly Thr Leu Val Thr
            100                 105                 110

Val Lys

<210> SEQ ID NO 308
<211> LENGTH: 114
<212> TYPE: PRT
<213> ORGANISM: Artificial Sequence
<220> FEATURE:
<223> OTHER INFORMATION: hz6F1v2

<400> SEQUENCE: 308

Glu Val Gln Leu Val Glu Ser Gly Gly Gly Val Gln Pro Gly Gly
1               5                   10                  15

Ser Leu Arg Leu Ser Cys Ala Ala Ser Glu Ile Ile Phe Ser Asp Lys
            20                  25                  30

Thr Val Gly Trp Tyr Arg Gln Ala Pro Gly Lys Gln Arg Val Leu Val
            35                  40                  45

Ala Val Ile Ser Asn Val Asp Ser Thr Asn Tyr Ala Glu Ser Val Lys
        50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Tyr
                85                  90                  95

Ala Arg Asp Phe Glu Ser Glu Tyr Trp Gly Gln Gly Thr Leu Val Thr
            100                 105                 110

Val Lys

<210> SEQ ID NO 309
<211> LENGTH: 114
<212> TYPE: PRT
<213> ORGANISM: Artificial Sequence
<220> FEATURE:
<223> OTHER INFORMATION: hz6F1v3

<400> SEQUENCE: 309

Glu Val Gln Leu Val Glu Ser Gly Gly Gly Val Gln Pro Gly Gly
1               5                   10                  15

Ser Leu Arg Leu Ser Cys Ala Ala Ser Glu Ile Ile Phe Ser Asp Lys
            20                  25                  30

Thr Val Gly Trp Tyr Arg Gln Ala Pro Gly Lys Gln Arg Val Leu Val
            35                  40                  45

Ala Val Ile Ser Asn Val Asp Ser Thr Asn Tyr Ala Gln Ser Val Lys
        50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Tyr
                85                  90                  95

Ala Arg Asp Phe Glu Ser Glu Tyr Trp Gly Gln Gly Thr Leu Val Thr
            100                 105                 110

Val Lys

<210> SEQ ID NO 310
<211> LENGTH: 114
<212> TYPE: PRT
<213> ORGANISM: Artificial Sequence
<220> FEATURE:
<223> OTHER INFORMATION: hz6F1v4

<400> SEQUENCE: 310

Glu Val Gln Leu Val Glu Ser Gly Gly Gly Glu Val Gln Pro Gly Gly
1               5                   10                  15

Ser Leu Arg Leu Ser Cys Gly Ala Ser Glu Ile Ile Phe Ser Asp Lys
            20                  25                  30

Thr Val Gly Trp Tyr Arg Gln Ala Pro Gly Lys Gln Arg Val Leu Val
        35                  40                  45

Ala Val Ile Ser Asn Val Asp Ser Thr Asn Tyr Ala Glu Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Tyr
                85                  90                  95

Ala Arg Asp Phe Glu Ser Glu Tyr Trp Gly Gln Gly Thr Leu Val Thr
            100                 105                 110

Val Lys

<210> SEQ ID NO 311
<211> LENGTH: 114
<212> TYPE: PRT
<213> ORGANISM: Artificial Sequence
<220> FEATURE:
<223> OTHER INFORMATION: hz6F1v4

<400> SEQUENCE: 311

Glu Val Gln Leu Val Glu Ser Gly Gly Gly Glu Val Gln Pro Gly Gly
1               5                   10                  15

Ser Leu Arg Leu Ser Cys Gly Ala Ser Glu Ile Ile Phe Ser Asp Lys
            20                  25                  30

Thr Val Gly Trp Tyr Arg Gln Ala Pro Gly Lys Gln Arg Val Leu Val
        35                  40                  45

Ala Val Ile Ser Asn Val Asp Ser Thr Asn Tyr Ala Glu Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Tyr
                85                  90                  95

Ala Arg Asp Phe Glu Ser Glu Tyr Trp Gly Gln Gly Thr Leu Val Thr
            100                 105                 110

Val Lys

<210> SEQ ID NO 312
<211> LENGTH: 114
<212> TYPE: PRT
<213> ORGANISM: Artificial Sequence
<220> FEATURE:
<223> OTHER INFORMATION: hz6F1v6

<400> SEQUENCE: 312

Glu Val Gln Leu Val Glu Ser Gly Gly Gly Glu Val Gln Pro Gly Gly
1               5                   10                  15

Ser Leu Arg Leu Ser Cys Ala Ala Ser Glu Ile Ile Phe Ser Asp Lys
            20                  25                  30

Thr Val Gly Trp Tyr Arg Gln Ala Pro Gly Lys Gln Arg Val Leu Val
        35                  40                  45

Ala Val Ile Ser Asn Val Glu Ser Thr Asn Tyr Ala Glu Ser Val Lys

```
            50                  55                  60
Gly Arg Phe Thr Ile Ser Arg Asp Asn Ala Lys Asn Thr Val Tyr Leu
 65                  70                  75                  80

Gln Met Ser Ser Leu Arg Ala Glu Asp Thr Ala Val Tyr Tyr Cys Tyr
                 85                  90                  95

Ala Arg Asp Phe Glu Ser Glu Tyr Trp Gly Gln Gly Thr Leu Val Thr
                100                 105                 110

Val Lys

<210> SEQ ID NO 313
<211> LENGTH: 114
<212> TYPE: PRT
<213> ORGANISM: Artificial Sequence
<220> FEATURE:
<223> OTHER INFORMATION: hz6F1v7

<400> SEQUENCE: 313

Glu Val Gln Leu Val Glu Ser Gly Gly Gly Val Gln Pro Gly Gly
 1               5                  10                  15

Ser Leu Arg Leu Ser Cys Ala Ala Ser Glu Ile Ile Phe Ser Asp Lys
                 20                  25                  30

Thr Val Gly Trp Tyr Arg Gln Ala Pro Gly Lys Gln Arg Val Leu Val
                 35                  40                  45

Ala Val Ile Ser Asn Val Asp Ala Thr Asn Tyr Ala Glu Ser Val Lys
 50                  55                  60

Gly Arg Phe Thr Ile Ser Arg Asp Asn Ala Lys Asn Thr Val Tyr Leu
 65                  70                  75                  80

Gln Met Ser Ser Leu Arg Ala Glu Asp Thr Ala Val Tyr Tyr Cys Tyr
                 85                  90                  95

Ala Arg Asp Phe Glu Ser Glu Tyr Trp Gly Gln Gly Thr Leu Val Thr
                100                 105                 110

Val Lys

<210> SEQ ID NO 314
<211> LENGTH: 114
<212> TYPE: PRT
<213> ORGANISM: Artificial Sequence
<220> FEATURE:
<223> OTHER INFORMATION: 3B4

<400> SEQUENCE: 314

Gln Val Gln Leu Gln Gln Ser Gly Gly Gly Leu Val Gln Ala Gly Gly
 1               5                  10                  15

Ser Leu Arg Leu Ser Cys Ala Ala Ser Gly Ser Asp Phe Ser Ile Asn
                 20                  25                  30

Ala Met Gly Trp Tyr Arg Gln Gly Glu Leu Val Ala Gly Phe Thr Gly
                 35                  40                  45

Asp Gly Asn Pro Ile Tyr Ala Asp Ser Val Lys Gly Arg Phe Thr Ile
 50                  55                  60

Ser Arg Gly Asn Ala Glu Asn Thr Val Ser Leu Gln Met Asn Ser Leu
 65                  70                  75                  80

Lys Pro Glu Asp Thr Ala Val Tyr Tyr Cys Ala Ala Val Lys Ile
                 85                  90                  95

Gly Gly Asp Tyr Glu Trp Tyr Trp Gly Gln Gly Thr Gln Val Thr Val
                100                 105                 110

Lys Pro
```

-continued

```
<210> SEQ ID NO 315
<211> LENGTH: 123
<212> TYPE: PRT
<213> ORGANISM: Artificial Sequence
<220> FEATURE:
<223> OTHER INFORMATION: 6A1

<400> SEQUENCE: 315

Gln Val Gln Leu Val Gln Ser Gly Gly Gly Leu Val Gln Ala Gly Gly
1               5                   10                  15

Ser Leu Arg Leu Ser Cys Ala Ala Ser Gly Phe Ser Leu Asp Asp Tyr
            20                  25                  30

Thr Ile Gly Trp Phe Arg Gln Ala Pro Gly Lys Glu Arg Glu Gly Val
        35                  40                  45

Ser Cys Ile Ser Ser Ser Gly Gly Ser Thr Val His Ala Asp Ser Val
    50                  55                  60

Lys Gly Arg Phe Thr Ile Ser Arg Asp Asn Ala Lys Asn Thr Val Trp
65                  70                  75                  80

Leu Gln Met Asn Ser Leu Lys Pro Glu Asp Thr Ala Val Tyr Tyr Cys
                85                  90                  95

Ala Thr Trp Cys Gly Val Ala Thr Met Thr Glu Asp Leu Pro Phe Asp
            100                 105                 110

Tyr Trp Gly Gln Gly Thr Leu Val Thr Val Lys
        115                 120

<210> SEQ ID NO 316
<211> LENGTH: 114
<212> TYPE: PRT
<213> ORGANISM: Artificial Sequence
<220> FEATURE:
<223> OTHER INFORMATION: 5H8

<400> SEQUENCE: 316

Gln Val Gln Leu Gln Glu Ser Gly Gly Gly Leu Val Gln Ala Gly Gly
1               5                   10                  15

Ser Leu Thr Leu Ser Cys Ala Ala Ser Gly Ser Ile Phe Ser Ile Asn
            20                  25                  30

Ala Met Gly Trp Tyr Arg Gln Gly Asp Leu Val Ala Gly Phe Thr Ser
        35                  40                  45

Glu Gly Ser Ala Lys Tyr Ala Asp Ser Val Lys Gly Arg Phe Thr Ile
    50                  55                  60

Ser Arg Asp Asp Ala Lys Asn Met Val Thr Leu Gln Met Asn Ser Leu
65                  70                  75                  80

Lys Pro Glu Asp Thr Ala Val Tyr Tyr Cys Ala Ala Asp Ile Phe Ser
                85                  90                  95

Asp Arg Asp His Val Asp Trp Tyr Trp Gly Gln Gly Thr Leu Val Thr
            100                 105                 110

Val Lys

<210> SEQ ID NO 317
<211> LENGTH: 122
<212> TYPE: PRT
<213> ORGANISM: Artificial Sequence
<220> FEATURE:
<223> OTHER INFORMATION: 6B4

<400> SEQUENCE: 317

Gln Val Gln Leu Gln Glu Ser Gly Gly Gly Leu Val Gln Ser Gly Gly
1               5                   10                  15
```

-continued

```
Ser Leu Arg Leu Ser Cys Ala Ala Ser Gly Phe Ser Leu Asp Asp Tyr
            20                  25                  30

Thr Ile Gly Trp Phe Arg Gln Ala Pro Gly Lys Glu Arg Glu Gly Val
        35                  40                  45

Ser Cys Ile Ser Ser Ser Gly Gly Ser Thr Tyr Tyr Ala Asp Ser Val
50                  55                  60

Lys Gly Arg Phe Thr Ile Ser Arg Asp Asn Ala Glu Asn Thr Val Tyr
65                  70                  75                  80

Leu Gln Met Asn Ser Leu Lys Pro Glu Asp Thr Ala Val Tyr Tyr Cys
                85                  90                  95

Ala Thr Tyr Cys Pro Val Thr Ile Ala Asp Glu Leu Gly Phe Asp Tyr
            100                 105                 110

Trp Gly Gln Gly Thr Leu Val Thr Val Lys
        115                 120
```

<210> SEQ ID NO 318
<211> LENGTH: 114
<212> TYPE: PRT
<213> ORGANISM: Artificial Sequence
<220> FEATURE:
<223> OTHER INFORMATION: 6B4

<400> SEQUENCE: 318

```
Gln Val Thr Leu Arg Glu Ser Gly Gly Gly Leu Val Gln Ala Gly Gly
1               5                   10                  15

Ser Leu Arg Leu Ser Cys Gly Ala Ser Glu Ile Thr Leu Ser Asp Lys
            20                  25                  30

Thr Val Gly Trp Tyr Arg Gln Ala Pro Gly Lys Gln Arg Val Leu Val
        35                  40                  45

Ala Val Ile Ser Asn Val Asp Ser Thr Asn Tyr Ala His Ser Val Lys
50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Tyr
                85                  90                  95

Ala Arg Asp Phe Glu Ala Glu Tyr Trp Gly Gln Gly Thr Leu Val Thr
            100                 105                 110

Val Lys
```

<210> SEQ ID NO 319
<211> LENGTH: 10
<212> TYPE: PRT
<213> ORGANISM: Artificial Sequence
<220> FEATURE:
<223> OTHER INFORMATION: CDR-H1 (L10D9, hz10D9v1,2,3,4,5,6)

<400> SEQUENCE: 319

```
Gly Ser Ile Leu Ser Ile Asn Ala Met Gly
1               5                   10
```

<210> SEQ ID NO 320
<211> LENGTH: 10
<212> TYPE: PRT
<213> ORGANISM: Artificial Sequence
<220> FEATURE:
<223> OTHER INFORMATION: CDR-H1 (hz10D9v7, L3G3, hz3G3v1,2,3,4, L5A8,
      hz5A8v1,2,3,4,5,6,7,8,9,10,11,12)

<400> SEQUENCE: 320

```
Gly Ser Ile Phe Ser Ile Asn Ala Met Gly
1               5                   10

<210> SEQ ID NO 321
<211> LENGTH: 10
<212> TYPE: PRT
<213> ORGANISM: Artificial Sequence
<220> FEATURE:
<223> OTHER INFORMATION: CDR-H1 (hz10D9v8)

<400> SEQUENCE: 321

Gly Phe Thr Phe Ser Ile Asn Ala Met Gly
1               5                   10

<210> SEQ ID NO 322
<211> LENGTH: 10
<212> TYPE: PRT
<213> ORGANISM: Artificial Sequence
<220> FEATURE:
<223> OTHER INFORMATION: CDR-H1 (hz10D9v9)

<400> SEQUENCE: 322

Gly Phe Thr Phe Ser Ser Tyr Ala Met Gly
1               5                   10

<210> SEQ ID NO 323
<211> LENGTH: 10
<212> TYPE: PRT
<213> ORGANISM: Artificial Sequence
<220> FEATURE:
<223> OTHER INFORMATION: CDR-H1 (hz10D9v10)

<400> SEQUENCE: 323

Gly Ser Ile Phe Ser Ser Asn Ala Met Gly
1               5                   10

<210> SEQ ID NO 324
<211> LENGTH: 10
<212> TYPE: PRT
<213> ORGANISM: Artificial Sequence
<220> FEATURE:
<223> OTHER INFORMATION: CDR-H1 (hz10D9v11)

<400> SEQUENCE: 324

Gly Phe Ile Phe Ser Ser Tyr Ala Met Gly
1               5                   10

<210> SEQ ID NO 325
<211> LENGTH: 10
<212> TYPE: PRT
<213> ORGANISM: Artificial Sequence
<220> FEATURE:
<223> OTHER INFORMATION: CDR-H1 (hz10D9v12)

<400> SEQUENCE: 325

Gly Ser Ile Phe Ser Ile Tyr Ala Met Gly
1               5                   10

<210> SEQ ID NO 326
<211> LENGTH: 10
<212> TYPE: PRT
<213> ORGANISM: Artificial Sequence
<220> FEATURE:
<223> OTHER INFORMATION: CDR-H1 (hz10D9v13)

<400> SEQUENCE: 326

Gly Phe Ile Phe Ser Ile Asn Ala Met Gly
```

```
1               5                  10

<210> SEQ ID NO 327
<211> LENGTH: 10
<212> TYPE: PRT
<213> ORGANISM: Artificial Sequence
<220> FEATURE:
<223> OTHER INFORMATION: CDR-H1 (L10E5, hz10E5v1,2,3,4,5)

<400> SEQUENCE: 327

Gly Phe Thr Leu Asp Asp Tyr Thr Ile Gly
1               5                  10

<210> SEQ ID NO 328
<211> LENGTH: 10
<212> TYPE: PRT
<213> ORGANISM: Artificial Sequence
<220> FEATURE:
<223> OTHER INFORMATION: CDR-H1 (L8E7, hz8E7v1,2,3,4,5,8,9,10,11,12,14)

<400> SEQUENCE: 328

Glu Ile Ile Thr Ser Asp Lys Ser Val Gly
1               5                  10

<210> SEQ ID NO 329
<211> LENGTH: 10
<212> TYPE: PRT
<213> ORGANISM: Artificial Sequence
<220> FEATURE:
<223> OTHER INFORMATION: CDR-H1 (hz8E7v6)

<400> SEQUENCE: 329

Glu Ile Ile Phe Ser Asp Lys Ser Val Gly
1               5                  10

<210> SEQ ID NO 330
<211> LENGTH: 10
<212> TYPE: PRT
<213> ORGANISM: Artificial Sequence
<220> FEATURE:
<223> OTHER INFORMATION: CDR-H1 (L5A7, hz5A7v1,2,3,4,5,6)

<400> SEQUENCE: 330

Gly Ser Asp Phe Ser Ile Asn Ala Ile Gly
1               5                  10

<210> SEQ ID NO 331
<211> LENGTH: 10
<212> TYPE: PRT
<213> ORGANISM: Artificial Sequence
<220> FEATURE:
<223> OTHER INFORMATION: CDR-H1 (L6C5, hz6C5v1,2,3,4,5,6)

<400> SEQUENCE: 331

Glu Ile Thr Phe Ser Asp Lys Thr Val Gly
1               5                  10

<210> SEQ ID NO 332
<211> LENGTH: 10
<212> TYPE: PRT
<213> ORGANISM: Artificial Sequence
<220> FEATURE:
<223> OTHER INFORMATION: CDR-H1 (L6F1, hz6F1v1,2,3,4,5,6,7)

<400> SEQUENCE: 332

Glu Ile Ile Phe Ser Asp Lys Thr Val Gly
1               5                  10
```

<210> SEQ ID NO 333
<211> LENGTH: 10
<212> TYPE: PRT
<213> ORGANISM: Artificial Sequence
<220> FEATURE:
<223> OTHER INFORMATION: CDR-H1 (DLL3-6A1-3245.seq, DLL3-3B12-3245.seq)

<400> SEQUENCE: 333

Gly Ser Asp Phe Ser Ile Asn Ala Met Gly
1               5                   10

<210> SEQ ID NO 334
<211> LENGTH: 10
<212> TYPE: PRT
<213> ORGANISM: Artificial Sequence
<220> FEATURE:
<223> OTHER INFORMATION: CDR-H1 (DLL3-6A1-3245.seq, DLL3-3B12-3245.seq)

<400> SEQUENCE: 334

Gly Phe Ser Leu Asp Asp Tyr Thr Ile Gly
1               5                   10

<210> SEQ ID NO 335
<211> LENGTH: 10
<212> TYPE: PRT
<213> ORGANISM: Artificial Sequence
<220> FEATURE:
<223> OTHER INFORMATION: CDR-H1 (DLL3-6B4-3245.seq)

<400> SEQUENCE: 335

Glu Ile Thr Leu Ser Asp Lys Thr Val Gly
1               5                   10

<210> SEQ ID NO 336
<211> LENGTH: 9
<212> TYPE: PRT
<213> ORGANISM: Artificial Sequence
<220> FEATURE:
<223> OTHER INFORMATION: CDR-H2 (L10D9, hz10D9v1,2)

<400> SEQUENCE: 336

Gly Phe Thr Gly Asp Gly Asn Thr Ile
1               5

<210> SEQ ID NO 337
<211> LENGTH: 9
<212> TYPE: PRT
<213> ORGANISM: Artificial Sequence
<220> FEATURE:
<223> OTHER INFORMATION: CDR-H2 (hz10D9v3)

<400> SEQUENCE: 337

Gly Phe Thr Gly Glu Gly Asn Thr Ile
1               5

<210> SEQ ID NO 338
<211> LENGTH: 9
<212> TYPE: PRT
<213> ORGANISM: Artificial Sequence
<220> FEATURE:
<223> OTHER INFORMATION: CDR-H2 (hz10D9v4,5,6,7,8,9,10,11,12,13)

<400> SEQUENCE: 338

Gly Phe Thr Gly Asp Thr Asn Thr Ile
1               5

```
<210> SEQ ID NO 339
<211> LENGTH: 10
<212> TYPE: PRT
<213> ORGANISM: Artificial Sequence
<220> FEATURE:
<223> OTHER INFORMATION: CDR-H2 (L10E5, hz10E5v1,2,3,4,5,
      DLL3-3B12-3245.seq)

<400> SEQUENCE: 339

Cys Ile Ser Ser Ser Gly Gly Ser Thr Tyr
1               5                   10

<210> SEQ ID NO 340
<211> LENGTH: 9
<212> TYPE: PRT
<213> ORGANISM: Artificial Sequence
<220> FEATURE:
<223> OTHER INFORMATION: CDR-H2 (L8E7, hz8E7v1,2,3,4,5,6,8,9,10,11,12,
      13, 14, 15, 16)

<400> SEQUENCE: 340

Gly Ile Ser Asn Val Gly Ser Thr Asn
1               5

<210> SEQ ID NO 341
<211> LENGTH: 9
<212> TYPE: PRT
<213> ORGANISM: Artificial Sequence
<220> FEATURE:
<223> OTHER INFORMATION: CDR-H2 (L3G3, hz3G3v1,2,3,4, DLL3-3G12-
      3245.seq, DLL3-3H12-3245.seq)

<400> SEQUENCE: 341

Gly Phe Thr Gly Asp Gly Met Thr Lys
1               5

<210> SEQ ID NO 342
<211> LENGTH: 9
<212> TYPE: PRT
<213> ORGANISM: Artificial Sequence
<220> FEATURE:
<223> OTHER INFORMATION: CDR-H2 (L5A7, hz5A7v1,4,5,6)

<400> SEQUENCE: 342

Gly Phe Thr Gly Asp Gly Val Thr Thr
1               5

<210> SEQ ID NO 343
<211> LENGTH: 9
<212> TYPE: PRT
<213> ORGANISM: Artificial Sequence
<220> FEATURE:
<223> OTHER INFORMATION: CDR-H2 (hz5A7v2)

<400> SEQUENCE: 343

Gly Phe Thr Gly Asp Thr Val Thr Thr
1               5

<210> SEQ ID NO 344
<211> LENGTH: 9
<212> TYPE: PRT
<213> ORGANISM: Artificial Sequence
<220> FEATURE:
<223> OTHER INFORMATION: CDR-H2 (hz5A7v3)

<400> SEQUENCE: 344

Gly Phe Thr Gly Glu Gly Val Thr Thr
```

```
1               5

<210> SEQ ID NO 345
<211> LENGTH: 9
<212> TYPE: PRT
<213> ORGANISM: Artificial Sequence
<220> FEATURE:
<223> OTHER INFORMATION: CDR-H2 (L5A8, hz5A8v1,2,3,4,5,8,9,11,12,
      DLL3-3E7-3245.seq)

<400> SEQUENCE: 345

Val Val Ser Ser Asp Gly Arg Thr Thr
1               5

<210> SEQ ID NO 346
<211> LENGTH: 9
<212> TYPE: PRT
<213> ORGANISM: Artificial Sequence
<220> FEATURE:
<223> OTHER INFORMATION: CDR-H2 (hz5A8v6)

<400> SEQUENCE: 346

Val Val Ser Ser Glu Gly Arg Thr Thr
1               5

<210> SEQ ID NO 347
<211> LENGTH: 9
<212> TYPE: PRT
<213> ORGANISM: Artificial Sequence
<220> FEATURE:
<223> OTHER INFORMATION: CDR-H2 (hz5A8v7,10)

<400> SEQUENCE: 347

Val Val Ser Ser Asp Ala Arg Thr Thr
1               5

<210> SEQ ID NO 348
<211> LENGTH: 9
<212> TYPE: PRT
<213> ORGANISM: Artificial Sequence
<220> FEATURE:
<223> OTHER INFORMATION: CDR-H2 (L6C5, hz6C5v1,2,3,4, L6F1,
      hz6F1v1,2,3,4,5, DLL3-6B4-3245.seq

<400> SEQUENCE: 348

Val Ile Ser Asn Val Asp Ser Thr Asn
1               5

<210> SEQ ID NO 349
<211> LENGTH: 9
<212> TYPE: PRT
<213> ORGANISM: Artificial Sequence
<220> FEATURE:
<223> OTHER INFORMATION: CDR-H2 (hz6C5v5, hz6F1v6)

<400> SEQUENCE: 349

Val Ile Ser Asn Val Glu Ser Thr Asn
1               5

<210> SEQ ID NO 350
<211> LENGTH: 9
<212> TYPE: PRT
<213> ORGANISM: Artificial Sequence
<220> FEATURE:
<223> OTHER INFORMATION: CDR-H2 (hz6C5v6,hz6F1v7 )

<400> SEQUENCE: 350
```

Val Ile Ser Asn Val Asp Ala Thr Asn
1               5

<210> SEQ ID NO 351
<211> LENGTH: 9
<212> TYPE: PRT
<213> ORGANISM: Artificial Sequence
<220> FEATURE:
<223> OTHER INFORMATION: CDR-H2 (3B4)

<400> SEQUENCE: 351

Gly Phe Thr Gly Asp Gly Asn Pro Ile
1               5

<210> SEQ ID NO 352
<211> LENGTH: 10
<212> TYPE: PRT
<213> ORGANISM: Artificial Sequence
<220> FEATURE:
<223> OTHER INFORMATION: CDR-H2 (DLL3-6A1-3245.seq)

<400> SEQUENCE: 352

Cys Ile Ser Ser Ser Gly Gly Ser Thr Val
1               5                   10

<210> SEQ ID NO 353
<211> LENGTH: 9
<212> TYPE: PRT
<213> ORGANISM: Artificial Sequence
<220> FEATURE:
<223> OTHER INFORMATION: CDR-H2 (DLL3-5H8-3245.seq)

<400> SEQUENCE: 353

Gly Phe Thr Ser Glu Gly Ser Ala Lys
1               5

<210> SEQ ID NO 354
<211> LENGTH: 12
<212> TYPE: PRT
<213> ORGANISM: Artificial Sequence
<220> FEATURE:
<223> OTHER INFORMATION: CDR-H3 (L10D9,
     hz10D9v1,2,3,4,5,6,7,8,9,10,11,12,13)

<400> SEQUENCE: 354

Asp Val Gln Leu Phe Ser Arg Asp Tyr Glu Phe Tyr
1               5                   10

<210> SEQ ID NO 355
<211> LENGTH: 14
<212> TYPE: PRT
<213> ORGANISM: Artificial Sequence
<220> FEATURE:
<223> OTHER INFORMATION: CDR-H3 (L10E5,

<400> SEQUENCE: 355

Tyr Cys Pro Val Val Val Gly Pro Glu Leu Gly Tyr Asp Tyr
1               5                   10

<210> SEQ ID NO 356
<211> LENGTH: 7
<212> TYPE: PRT
<213> ORGANISM: Artificial Sequence
<220> FEATURE:
<223> OTHER INFORMATION: CDR-H3 (L8E7, hz8E7v1,2,3,4,5,6,7,8,9,10,11,12,
     13, 14, 15, 16; L6C5, hz6C5v1,2,3,4,5,6)

<400> SEQUENCE: 356

Arg Asp Phe Glu Asn Glu Tyr
1               5

<210> SEQ ID NO 357
<211> LENGTH: 12
<212> TYPE: PRT
<213> ORGANISM: Artificial Sequence
<220> FEATURE:
<223> OTHER INFORMATION: CDR-H3 (L3G3, hz3G3v1,2,3,4, DLL3-3G12-
      3245.seq)

<400> SEQUENCE: 357

Asp Val Phe Thr Asp Arg Asp His Val Asp Trp Tyr
1               5                   10

<210> SEQ ID NO 358
<211> LENGTH: 11
<212> TYPE: PRT
<213> ORGANISM: Artificial Sequence
<220> FEATURE:
<223> OTHER INFORMATION: CDR-H3 (L5A7, hz5A7v1,2,3,4,5,6)

<400> SEQUENCE: 358

Asp Val Lys Ile Gly Gly Asp Tyr Glu Trp Phe
1               5                   10

<210> SEQ ID NO 359
<211> LENGTH: 12
<212> TYPE: PRT
<213> ORGANISM: Artificial Sequence
<220> FEATURE:
<223> OTHER INFORMATION: CDR-H3 (L5A8, hz5A8v1,2,3,4,5,6,7,11,12,
      DLL3-3E7-3245.seq)

<400> SEQUENCE: 359

Arg Glu Trp Tyr Ser Asp Ser Asp Trp Arg Asp Tyr
1               5                   10

<210> SEQ ID NO 360
<211> LENGTH: 12
<212> TYPE: PRT
<213> ORGANISM: Artificial Sequence
<220> FEATURE:
<223> OTHER INFORMATION: CDR-H3 (hz5A8v8,10)

<400> SEQUENCE: 360

Arg Glu Trp Tyr Ser Asp Ala Asp Trp Arg Asp Tyr
1               5                   10

<210> SEQ ID NO 361
<211> LENGTH: 12
<212> TYPE: PRT
<213> ORGANISM: Artificial Sequence
<220> FEATURE:
<223> OTHER INFORMATION: CDR-H3 (hz5A8v9)

<400> SEQUENCE: 361

Arg Glu Trp Tyr Ser Glu Ser Asp Trp Arg Asp Tyr
1               5                   10

<210> SEQ ID NO 362
<211> LENGTH: 7
<212> TYPE: PRT
<213> ORGANISM: Artificial Sequence
<220> FEATURE:
<223> OTHER INFORMATION: CDR-H3 (L6F1, hz6F1v1,2,3,4,5,6,7)

```
<400> SEQUENCE: 362

Arg Asp Phe Glu Ser Glu Tyr
1               5

<210> SEQ ID NO 363
<211> LENGTH: 11
<212> TYPE: PRT
<213> ORGANISM: Artificial Sequence
<220> FEATURE:
<223> OTHER INFORMATION: CDR-H3 (3B4)

<400> SEQUENCE: 363

Asp Val Lys Ile Gly Gly Asp Tyr Glu Trp Tyr
1               5                   10

<210> SEQ ID NO 364
<211> LENGTH: 15
<212> TYPE: PRT
<213> ORGANISM: Artificial Sequence
<220> FEATURE:
<223> OTHER INFORMATION: CDR-H3 (DLL3-6A1-3245.seq)

<400> SEQUENCE: 364

Trp Cys Gly Val Ala Thr Met Thr Glu Asp Leu Pro Phe Asp Tyr
1               5                   10                  15

<210> SEQ ID NO 365
<211> LENGTH: 12
<212> TYPE: PRT
<213> ORGANISM: Artificial Sequence
<220> FEATURE:
<223> OTHER INFORMATION: CDR-H3 (DLL3-5H8-3245.seq)

<400> SEQUENCE: 365

Asp Ile Phe Ser Asp Arg Asp His Val Asp Trp Tyr
1               5                   10

<210> SEQ ID NO 366
<211> LENGTH: 14
<212> TYPE: PRT
<213> ORGANISM: Artificial Sequence
<220> FEATURE:
<223> OTHER INFORMATION: CDR-H3 (DLL3-3B12-3245.seq)

<400> SEQUENCE: 366

Tyr Cys Pro Val Thr Ile Ala Asp Glu Leu Gly Phe Asp Tyr
1               5                   10

<210> SEQ ID NO 367
<211> LENGTH: 7
<212> TYPE: PRT
<213> ORGANISM: Artificial Sequence
<220> FEATURE:
<223> OTHER INFORMATION: CDR-H3 (DLL3-6B4-3245.seq)

<400> SEQUENCE: 367

Arg Asp Phe Glu Ala Glu Tyr
1               5

<210> SEQ ID NO 368
<211> LENGTH: 109
<212> TYPE: PRT
<213> ORGANISM: Artificial Sequence
<220> FEATURE:
<223> OTHER INFORMATION: anti-CD3 VL (CON)

<400> SEQUENCE: 368
```

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
                20                  25                  30

Asn Tyr Ala Asn Trp Val Gln Gln Lys Pro Gly Gln Ala Phe Arg Gly
            35                  40                  45

Leu Ile Gly Gly Thr Asn Lys Arg Ala Pro Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Cys Gly Thr Lys Leu Thr Val Leu
                100                 105

<210> SEQ ID NO 369
<211> LENGTH: 6
<212> TYPE: PRT
<213> ORGANISM: Artificial Sequence
<220> FEATURE:
<223> OTHER INFORMATION: (GGS)2 linker

<400> SEQUENCE: 369

Gly Gly Ser Gly Gly Ser
1               5

<210> SEQ ID NO 370
<211> LENGTH: 9
<212> TYPE: PRT
<213> ORGANISM: Artificial Sequence
<220> FEATURE:
<223> OTHER INFORMATION: (GGS)3 linker

<400> SEQUENCE: 370

Gly Gly Ser Gly Gly Ser Gly Gly Ser
1               5

<210> SEQ ID NO 371
<211> LENGTH: 12
<212> TYPE: PRT
<213> ORGANISM: Artificial Sequence
<220> FEATURE:
<223> OTHER INFORMATION: (GGS)4 linker

<400> SEQUENCE: 371

Gly Gly Ser Gly Gly Ser Gly Gly Ser Gly Gly Ser
1               5                   10

<210> SEQ ID NO 372
<211> LENGTH: 15
<212> TYPE: PRT
<213> ORGANISM: Artificial Sequence
<220> FEATURE:
<223> OTHER INFORMATION: (GGS)5 linker

<400> SEQUENCE: 372

Gly Gly Ser Gly Gly Ser Gly Gly Ser Gly Gly Ser Gly Gly Ser
1               5                   10                  15

<210> SEQ ID NO 373
<211> LENGTH: 4
<212> TYPE: PRT
<213> ORGANISM: Artificial Sequence

```
<220> FEATURE:
<223> OTHER INFORMATION: glycine lnker

<400> SEQUENCE: 373

Gly Gly Gly Gly
1

<210> SEQ ID NO 374
<211> LENGTH: 5
<212> TYPE: PRT
<213> ORGANISM: Artificial Sequence
<220> FEATURE:
<223> OTHER INFORMATION: glycine linker

<400> SEQUENCE: 374

Gly Gly Gly Gly Gly
1               5

<210> SEQ ID NO 375
<211> LENGTH: 6
<212> TYPE: PRT
<213> ORGANISM: Artificial Sequence
<220> FEATURE:
<223> OTHER INFORMATION: glycine linker

<400> SEQUENCE: 375

Gly Gly Gly Gly Gly Gly
1               5

<210> SEQ ID NO 376
<211> LENGTH: 6
<212> TYPE: PRT
<213> ORGANISM: Artificial Sequence
<220> FEATURE:
<223> OTHER INFORMATION: (GGS)2 linker

<400> SEQUENCE: 376

Gly Gly Ser Gly Gly Ser
1               5

<210> SEQ ID NO 377
<211> LENGTH: 9
<212> TYPE: PRT
<213> ORGANISM: Artificial Sequence
<220> FEATURE:
<223> OTHER INFORMATION: (GGS)3  linker

<400> SEQUENCE: 377

Gly Gly Ser Gly Gly Ser Gly Gly Ser
1               5

<210> SEQ ID NO 378
<211> LENGTH: 12
<212> TYPE: PRT
<213> ORGANISM: Artificial Sequence
<220> FEATURE:
<223> OTHER INFORMATION: (GGS)4 linker

<400> SEQUENCE: 378

Gly Gly Ser Gly Gly Ser Gly Gly Ser Gly Gly Ser
1               5                   10

<210> SEQ ID NO 379
<211> LENGTH: 15
<212> TYPE: PRT
<213> ORGANISM: Artificial Sequence
<220> FEATURE:
```

```
<223> OTHER INFORMATION: (GGS)5 linker

<400> SEQUENCE: 379

Gly Gly Ser Gly Gly Ser Gly Gly Ser Gly Gly Ser Gly Gly Ser
1               5                   10                  15

<210> SEQ ID NO 380
<211> LENGTH: 4
<212> TYPE: PRT
<213> ORGANISM: Artificial Sequence
<220> FEATURE:
<223> OTHER INFORMATION: glycine linker

<400> SEQUENCE: 380

Gly Gly Gly Gly
1

<210> SEQ ID NO 381
<211> LENGTH: 5
<212> TYPE: PRT
<213> ORGANISM: Artificial Sequence
<220> FEATURE:
<223> OTHER INFORMATION: glycine linker

<400> SEQUENCE: 381

Gly Gly Gly Gly Gly
1               5

<210> SEQ ID NO 382
<211> LENGTH: 6
<212> TYPE: PRT
<213> ORGANISM: Artificial Sequence
<220> FEATURE:
<223> OTHER INFORMATION: glycine linker

<400> SEQUENCE: 382

Gly Gly Gly Gly Gly Gly
1               5

<210> SEQ ID NO 383
<211> LENGTH: 6
<212> TYPE: PRT
<213> ORGANISM: Artificial Sequence
<220> FEATURE:
<223> OTHER INFORMATION: glycine linker

<400> SEQUENCE: 383

Gly Gly Gly Gly Gly Gly
1               5

<210> SEQ ID NO 384
<211> LENGTH: 9
<212> TYPE: PRT
<213> ORGANISM: Artificial Sequence
<220> FEATURE:
<223> OTHER INFORMATION: CDR-H2 (3C5, hz3C5v1,2,5,6,7,8)

<400> SEQUENCE: 384

Gly Phe Thr Gly Asp Gly Ser Thr Lys
1               5

<210> SEQ ID NO 385
<211> LENGTH: 6
<212> TYPE: PRT
<213> ORGANISM: Artificial Sequence
<220> FEATURE:
<223> OTHER INFORMATION: (GGS)2 linker
```

```
<400> SEQUENCE: 385

Gly Gly Ser Gly Gly Ser
1               5

<210> SEQ ID NO 386
<211> LENGTH: 9
<212> TYPE: PRT
<213> ORGANISM: Artificial Sequence
<220> FEATURE:
<223> OTHER INFORMATION: (GGS)3 linker

<400> SEQUENCE: 386

Gly Gly Ser Gly Gly Ser Gly Gly Ser
1               5

<210> SEQ ID NO 387
<211> LENGTH: 12
<212> TYPE: PRT
<213> ORGANISM: Artificial Sequence
<220> FEATURE:
<223> OTHER INFORMATION: (GGS)4 linker

<400> SEQUENCE: 387

Gly Gly Ser Gly Gly Ser Gly Gly Ser Gly Gly Ser
1               5                   10

<210> SEQ ID NO 388
<211> LENGTH: 15
<212> TYPE: PRT
<213> ORGANISM: Artificial Sequence
<220> FEATURE:
<223> OTHER INFORMATION: (GGS)5 linker

<400> SEQUENCE: 388

Gly Gly Ser Gly Gly Ser Gly Gly Ser Gly Gly Ser Gly Gly Ser
1               5                   10                  15

<210> SEQ ID NO 389
<211> LENGTH: 4
<212> TYPE: PRT
<213> ORGANISM: Artificial Sequence
<220> FEATURE:
<223> OTHER INFORMATION: glycine linker

<400> SEQUENCE: 389

Gly Gly Gly Gly
1

<210> SEQ ID NO 390
<211> LENGTH: 5
<212> TYPE: PRT
<213> ORGANISM: Artificial Sequence
<220> FEATURE:
<223> OTHER INFORMATION: Glycine linker

<400> SEQUENCE: 390

Gly Gly Gly Gly Gly
1               5

<210> SEQ ID NO 391
<211> LENGTH: 6
<212> TYPE: PRT
<213> ORGANISM: Artificial Sequence
<220> FEATURE:
<223> OTHER INFORMATION: glycine linker
```

<400> SEQUENCE: 391

Gly Gly Gly Gly Gly Gly
1               5

<210> SEQ ID NO 392
<211> LENGTH: 12
<212> TYPE: PRT
<213> ORGANISM: Artificial Sequence
<220> FEATURE:
<223> OTHER INFORMATION: (GGS)4 linker

<400> SEQUENCE: 392

Gly Gly Ser Gly Gly Ser Gly Gly Ser Gly Gly Ser
1               5                   10

<210> SEQ ID NO 393
<211> LENGTH: 15
<212> TYPE: PRT
<213> ORGANISM: Artificial Sequence
<220> FEATURE:
<223> OTHER INFORMATION: (GGS)5 linker

<400> SEQUENCE: 393

Gly Gly Ser Gly Gly Ser Gly Gly Ser Gly Gly Ser Gly Gly Ser
1               5                   10                  15

<210> SEQ ID NO 394
<211> LENGTH: 4
<212> TYPE: PRT
<213> ORGANISM: Artificial Sequence
<220> FEATURE:
<223> OTHER INFORMATION: glycine linker

<400> SEQUENCE: 394

Gly Gly Gly Gly
1

<210> SEQ ID NO 395
<211> LENGTH: 12
<212> TYPE: PRT
<213> ORGANISM: Artificial Sequence
<220> FEATURE:
<223> OTHER INFORMATION: CDR-H3 (3C5, hz3C5v1,2,3,4)

<400> SEQUENCE: 395

Asp Val Gln Leu Leu Asn Ser Asp Tyr Glu Phe Tyr
1               5                   10

<210> SEQ ID NO 396
<211> LENGTH: 6
<212> TYPE: PRT
<213> ORGANISM: Artificial Sequence
<220> FEATURE:
<223> OTHER INFORMATION: (GGS)2 linker

<400> SEQUENCE: 396

Gly Gly Ser Gly Gly Ser
1               5

<210> SEQ ID NO 397
<211> LENGTH: 9
<212> TYPE: PRT
<213> ORGANISM: Artificial Sequence
<220> FEATURE:
<223> OTHER INFORMATION: (GGS)3  linker

<400> SEQUENCE: 397

Gly Gly Ser Gly Gly Ser Gly Gly Ser
1               5

<210> SEQ ID NO 398
<211> LENGTH: 12
<212> TYPE: PRT
<213> ORGANISM: Artificial Sequence
<220> FEATURE:
<223> OTHER INFORMATION: (GGS)4 linker

<400> SEQUENCE: 398

Gly Gly Ser Gly Gly Ser Gly Gly Ser Gly Gly Ser
1               5                   10

<210> SEQ ID NO 399
<211> LENGTH: 15
<212> TYPE: PRT
<213> ORGANISM: Artificial Sequence
<220> FEATURE:
<223> OTHER INFORMATION: (GGS)5 linker

<400> SEQUENCE: 399

Gly Gly Ser Gly Gly Ser Gly Gly Ser Gly Gly Ser Gly Gly Ser
1               5                   10                  15

<210> SEQ ID NO 400
<211> LENGTH: 4
<212> TYPE: PRT
<213> ORGANISM: Artificial Sequence
<220> FEATURE:
<223> OTHER INFORMATION: glycine linker

<400> SEQUENCE: 400

Gly Gly Gly Gly
1

<210> SEQ ID NO 401
<211> LENGTH: 120
<212> TYPE: PRT
<213> ORGANISM: Artificial Sequence
<220> FEATURE:
<223> OTHER INFORMATION: 3C5

<400> SEQUENCE: 401

Gln Val Gln Leu Val Gln Ser Gly Gly Gly Leu Val Gln Ala Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Pro Pro Gly Lys Gln Arg Glu Leu Val
        35                  40                  45

Ala Gly Phe Thr Gly Asp Gly Ser Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Asp Val Gln Leu Leu Asn Ser Asp Tyr Glu Phe Tyr Trp Gly Gln
            100                 105                 110

Gly Thr Gln Val Thr Val Lys Pro
        115                 120

<210> SEQ ID NO 402

<211> LENGTH: 122
<212> TYPE: PRT
<213> ORGANISM: Artificial Sequence
<220> FEATURE:
<223> OTHER INFORMATION: hz3C5v1

<400> SEQUENCE: 402

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Gln Arg Glu Leu Val
        35                  40                  45

Ala Gly Phe Thr Gly Asp Gly Ser Thr Lys Tyr Ala Glu Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Ala
                85                  90                  95

Ala Asp Val Gln Leu Leu Asn Ser Asp Tyr Glu Phe Tyr Trp Gly Gln
            100                 105                 110

Gly Thr Leu Val Thr Val Lys Pro Gly Gly
        115                 120

<210> SEQ ID NO 403
<211> LENGTH: 122
<212> TYPE: PRT
<213> ORGANISM: Artificial Sequence
<220> FEATURE:
<223> OTHER INFORMATION: hz3C5v2

<400> SEQUENCE: 403

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Pro Pro Gly Lys Gln Arg Glu Leu Val
        35                  40                  45

Ala Gly Phe Thr Gly Asp Gly Ser Thr Lys Tyr Ala Glu Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Ala
                85                  90                  95

Ala Asp Val Gln Leu Leu Asn Ser Asp Tyr Glu Phe Tyr Trp Gly Gln
            100                 105                 110

Gly Thr Leu Val Thr Val Lys Pro Gly Gly
        115                 120

<210> SEQ ID NO 404
<211> LENGTH: 122
<212> TYPE: PRT
<213> ORGANISM: Artificial Sequence
<220> FEATURE:
<223> OTHER INFORMATION: hz3C5v3

<400> SEQUENCE: 404

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Gln Arg Glu Leu Val
        35                  40                  45

Ala Gly Phe Thr Gly Asp Thr Ser Thr Lys Tyr Ala Glu Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Ala
                85                  90                  95

Ala Asp Val Gln Leu Leu Asn Ser Asp Tyr Glu Phe Tyr Trp Gly Gln
            100                 105                 110

Gly Thr Leu Val Thr Val Lys Pro Gly Gly
            115                 120

<210> SEQ ID NO 405
<211> LENGTH: 122
<212> TYPE: PRT
<213> ORGANISM: Artificial Sequence
<220> FEATURE:
<223> OTHER INFORMATION: hz3C5v4

<400> SEQUENCE: 405

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Gln Arg Glu Leu Val
        35                  40                  45

Ala Gly Phe Thr Gly Glu Gly Ser Thr Lys Tyr Ala Glu Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Ala
                85                  90                  95

Ala Asp Val Gln Leu Leu Asn Ser Asp Tyr Glu Phe Tyr Trp Gly Gln
            100                 105                 110

Gly Thr Leu Val Thr Val Lys Pro Gly Gly
            115                 120

<210> SEQ ID NO 406
<211> LENGTH: 122
<212> TYPE: PRT
<213> ORGANISM: Artificial Sequence
<220> FEATURE:
<223> OTHER INFORMATION: hz3C5v5

<400> SEQUENCE: 406

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Gln Arg Glu Leu Val
        35                  40                  45

Ala Gly Phe Thr Gly Asp Gly Ser Thr Lys Tyr Ala Glu Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Ala
            85                  90                  95

Ala Asp Val Gln Leu Leu Ser Ser Asp Tyr Glu Phe Tyr Trp Gly Gln
            100                 105                 110

Gly Thr Leu Val Thr Val Lys Pro Gly Gly
        115                 120

<210> SEQ ID NO 407
<211> LENGTH: 122
<212> TYPE: PRT
<213> ORGANISM: Artificial Sequence
<220> FEATURE:
<223> OTHER INFORMATION: hz3C5v6

<400> SEQUENCE: 407

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Gln Arg Glu Leu Val
        35                  40                  45

Ala Gly Phe Thr Gly Asp Gly Ser Thr Lys Tyr Ala Glu Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Ala
            85                  90                  95

Ala Asp Val Gln Leu Leu Thr Ser Asp Tyr Glu Phe Tyr Trp Gly Gln
            100                 105                 110

Gly Thr Leu Val Thr Val Lys Pro Gly Gly
        115                 120

<210> SEQ ID NO 408
<211> LENGTH: 122
<212> TYPE: PRT
<213> ORGANISM: Artificial Sequence
<220> FEATURE:
<223> OTHER INFORMATION: hz3C5v7

<400> SEQUENCE: 408

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Gln Arg Glu Leu Val
        35                  40                  45

Ala Gly Phe Thr Gly Asp Gly Ser Thr Lys Tyr Ala Glu Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Ala
            85                  90                  95

Ala Asp Val Gln Leu Leu Gln Ser Asp Tyr Glu Phe Tyr Trp Gly Gln
            100                 105                 110

Gly Thr Leu Val Thr Val Lys Pro Gly Gly
        115                 120

```
<210> SEQ ID NO 409
<211> LENGTH: 122
<212> TYPE: PRT
<213> ORGANISM: Artificial Sequence
<220> FEATURE:
<223> OTHER INFORMATION: hz3C5v8

<400> SEQUENCE: 409

Glu Val Gln Leu Val Glu Ser Gly Gly Glu Val Gln Pro Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Gln Arg Glu Leu Val
        35                  40                  45

Ala Gly Phe Thr Gly Asp Gly Ser Thr Lys Tyr Ala Glu Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Ala
                85                  90                  95

Ala Asp Val Gln Leu Leu Asn Thr Asp Tyr Glu Phe Tyr Trp Gly Gln
            100                 105                 110

Gly Thr Leu Val Thr Val Lys Pro Gly Gly
        115                 120

<210> SEQ ID NO 410
<211> LENGTH: 9
<212> TYPE: PRT
<213> ORGANISM: Artificial Sequence
<220> FEATURE:
<223> OTHER INFORMATION: CDR-H2 (hz3C5v3)

<400> SEQUENCE: 410

Gly Phe Thr Gly Asp Thr Ser Thr Lys
1               5

<210> SEQ ID NO 411
<211> LENGTH: 9
<212> TYPE: PRT
<213> ORGANISM: Artificial Sequence
<220> FEATURE:
<223> OTHER INFORMATION: CDR-H2 (hz3C5v4)

<400> SEQUENCE: 411

Gly Phe Thr Gly Glu Gly Ser Thr Lys
1               5

<210> SEQ ID NO 412
<211> LENGTH: 12
<212> TYPE: PRT
<213> ORGANISM: Artificial Sequence
<220> FEATURE:
<223> OTHER INFORMATION: CDR-H3 (hz3C5v5)

<400> SEQUENCE: 412

Asp Val Gln Leu Leu Ser Ser Asp Tyr Glu Phe Tyr
1               5                   10

<210> SEQ ID NO 413
<211> LENGTH: 12
<212> TYPE: PRT
<213> ORGANISM: Artificial Sequence
<220> FEATURE:
<223> OTHER INFORMATION: CDR-H3 (hz3C5v6)
```

<400> SEQUENCE: 413

Asp Val Gln Leu Leu Thr Ser Asp Tyr Glu Phe Tyr
1               5                   10

<210> SEQ ID NO 414
<211> LENGTH: 12
<212> TYPE: PRT
<213> ORGANISM: Artificial Sequence
<220> FEATURE:
<223> OTHER INFORMATION: CDR-H3 (hz3C5v7)

<400> SEQUENCE: 414

Asp Val Gln Leu Leu Gln Ser Asp Tyr Glu Phe Tyr
1               5                   10

<210> SEQ ID NO 415
<211> LENGTH: 12
<212> TYPE: PRT
<213> ORGANISM: Artificial Sequence
<220> FEATURE:
<223> OTHER INFORMATION: CDR-H3 (hz3C5v8)

<400> SEQUENCE: 415

Asp Val Gln Leu Leu Asn Thr Asp Tyr Glu Phe Tyr
1               5                   10

<210> SEQ ID NO 416
<211> LENGTH: 115
<212> TYPE: PRT
<213> ORGANISM: Artificial Sequence
<220> FEATURE:
<223> OTHER INFORMATION: hz8E7v5

<400> SEQUENCE: 416

Glu Val Gln Leu Val Glu Ser Gly Gly Gly Glu Val Gln Pro Gly Gly
1               5                   10                  15

Ser Leu Arg Leu Ser Cys Gly Pro Ser Glu Ile Ile Thr Ser Asp Lys
            20                  25                  30

Ser Val Gly Trp Trp Arg Gln Ala Pro Gly Lys Gln Arg Asn Leu Val
        35                  40                  45

Ala Gly Ile Ser Asn Val Gly Ser Thr Asn Tyr Ala Gln Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Tyr
                85                  90                  95

Ala Arg Asp Phe Glu Asn Glu Tyr Trp Gly Gln Gly Thr Leu Val Thr
            100                 105                 110

Val Lys Pro
        115

<210> SEQ ID NO 417
<211> LENGTH: 117
<212> TYPE: PRT
<213> ORGANISM: Artificial Sequence
<220> FEATURE:
<223> OTHER INFORMATION: hz18H10v1

<400> SEQUENCE: 417

Glu Val Gln Leu Val Glu Ser Gly Gly Gly Glu Val Gln Pro Gly Gly
1               5                   10                  15

```
Ser Leu Arg Leu Ser Cys Ala Ala Ser Gly Ser Met Thr Gly Ala Asn
            20                  25                  30

Thr Met Gly Trp Tyr Arg Gln Ala Pro Gly Lys Gly Arg Asp Leu Val
            35                  40                  45

Ser Leu Ile Gly Asn Tyr Val Thr His Tyr Ala Glu Ser Val Lys Gly
            50                  55                  60

Arg Phe Thr Ile Ser Arg Asp Asn Ala Lys Asn Thr Leu Tyr Leu Gln
 65                  70                  75                  80

Met Ser Ser Leu Arg Ala Glu Asp Thr Ala Val Tyr Tyr Cys Tyr Leu
                 85                  90                  95

Tyr Thr Asp Asn Leu Gly Thr Ser Trp Gly Gln Gly Thr Leu Val Thr
            100                 105                 110

Val Lys Pro Gly Gly
            115

<210> SEQ ID NO 418
<211> LENGTH: 117
<212> TYPE: PRT
<213> ORGANISM: Artificial Sequence
<220> FEATURE:
<223> OTHER INFORMATION: hz18H10v2

<400> SEQUENCE: 418

Glu Val Gln Leu Val Glu Ser Gly Gly Gly Glu Val Gln Pro Gly Gly
 1               5                  10                  15

Ser Leu Arg Leu Ser Cys Ala Ala Ser Gly Ser Met Thr Gly Ala Asn
            20                  25                  30

Thr Met Gly Trp Tyr Arg Gln Ala Pro Gly Lys Gln Arg Asp Leu Val
            35                  40                  45

Ser Leu Ile Gly Asn Tyr Val Thr His Tyr Ala Glu Ser Val Lys Gly
            50                  55                  60

Arg Phe Thr Ile Ser Arg Asp Asn Ala Lys Asn Thr Leu Tyr Leu Gln
 65                  70                  75                  80

Met Ser Ser Leu Arg Ala Glu Asp Thr Ala Val Tyr Tyr Cys Tyr Leu
                 85                  90                  95

Tyr Thr Asp Asn Leu Gly Thr Ser Trp Gly Gln Gly Thr Leu Val Thr
            100                 105                 110

Val Lys Pro Gly Gly
            115

<210> SEQ ID NO 419
<211> LENGTH: 117
<212> TYPE: PRT
<213> ORGANISM: Artificial Sequence
<220> FEATURE:
<223> OTHER INFORMATION: hz18H10v3

<400> SEQUENCE: 419

Glu Val Gln Leu Val Glu Ser Gly Gly Gly Glu Val Gln Pro Gly Gly
 1               5                  10                  15

Ser Leu Arg Leu Ser Cys Ala Ala Ser Gly Ser Met Thr Gly Ala Asn
            20                  25                  30

Thr Met Gly Trp Tyr Arg Gln Ala Pro Gly Lys Gln Arg Asp Leu Val
            35                  40                  45

Ser Leu Ile Gly Asn Tyr Val Thr His Tyr Ala Glu Ser Val Lys Gly
            50                  55                  60

Arg Phe Thr Ile Ser Arg Asp Asn Ala Lys Asn Thr Val Tyr Leu Gln
 65                  70                  75                  80
```

```
Met Ser Ser Leu Arg Ala Glu Asp Thr Ala Val Tyr Cys Tyr Leu
                85                  90                  95

Tyr Thr Asp Asn Leu Gly Thr Ser Trp Gly Gln Gly Thr Leu Val Thr
            100                 105                 110

Val Lys Pro Gly Gly
        115

<210> SEQ ID NO 420
<211> LENGTH: 117
<212> TYPE: PRT
<213> ORGANISM: Artificial Sequence
<220> FEATURE:
<223> OTHER INFORMATION: hz18H10v4

<400> SEQUENCE: 420

Glu Val Gln Leu Val Glu Ser Gly Gly Gly Val Gln Pro Gly Gly
1               5                   10                  15

Ser Leu Arg Leu Ser Cys Ala Ala Ser Gly Ser Met Thr Gly Ala Asn
            20                  25                  30

Thr Met Gly Trp Tyr Arg Gln Ala Pro Gly Lys Gln Arg Asp Leu Val
            35                  40                  45

Ala Leu Ile Gly Asn Tyr Val Thr His Tyr Ala Glu Ser Val Lys Gly
        50                  55                  60

Arg Phe Thr Ile Ser Arg Asp Asn Ala Lys Asn Thr Val Tyr Leu Gln
65                  70                  75                  80

Met Ser Ser Leu Arg Ala Glu Asp Thr Ala Val Tyr Cys Tyr Leu
                85                  90                  95

Tyr Thr Asp Asn Leu Gly Thr Ser Trp Gly Gln Gly Thr Leu Val Thr
            100                 105                 110

Val Lys Pro Gly Gly
        115

<210> SEQ ID NO 421
<211> LENGTH: 117
<212> TYPE: PRT
<213> ORGANISM: Artificial Sequence
<220> FEATURE:
<223> OTHER INFORMATION: hz18H10v5

<400> SEQUENCE: 421

Glu Val Gln Leu Val Glu Ser Gly Gly Gly Val Gln Pro Gly Gly
1               5                   10                  15

Ser Leu Arg Leu Ser Cys Ala Ala Ser Gly Ser Met Thr Gly Ala Asn
            20                  25                  30

Thr Met Gly Trp Tyr Arg Gln Ala Pro Gly Lys Gln Arg Asp Leu Val
            35                  40                  45

Ala Leu Ile Gly Asn Tyr Val Thr His Tyr Ala Glu Ser Val Lys Gly
        50                  55                  60

Arg Phe Thr Ile Ser Arg Glu Asn Ala Lys Asn Thr Val Tyr Leu Gln
65                  70                  75                  80

Met Ser Ser Leu Arg Ala Glu Asp Thr Ala Val Tyr Cys Tyr Leu
                85                  90                  95

Tyr Thr Asp Asn Leu Gly Thr Ser Trp Gly Gln Gly Thr Leu Val Thr
            100                 105                 110

Val Lys Pro Gly Gly
        115
```

-continued

```
<210> SEQ ID NO 422
<211> LENGTH: 117
<212> TYPE: PRT
<213> ORGANISM: Artificial Sequence
<220> FEATURE:
<223> OTHER INFORMATION: hz18H10v6

<400> SEQUENCE: 422

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Val Thr Gly Ala Asn
            20                  25                  30

Thr Met Gly Trp Tyr Arg Gln Ala Pro Gly Lys Gln Arg Asp Leu Val
        35                  40                  45

Ala Leu Ile Gly Asn Tyr Val Thr His Tyr Ala Glu Ser Val Lys Gly
    50                  55                  60

Arg Phe Thr Ile Ser Arg Asp Asn Ala Lys Asn Thr Val Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
            100                 105                 110

Val Lys Pro Gly Gly
        115

<210> SEQ ID NO 423
<211> LENGTH: 117
<212> TYPE: PRT
<213> ORGANISM: Artificial Sequence
<220> FEATURE:
<223> OTHER INFORMATION: hz18H10v7

<400> SEQUENCE: 423

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Ile Thr Gly Ala Asn
            20                  25                  30

Thr Met Gly Trp Tyr Arg Gln Ala Pro Gly Lys Gln Arg Asp Leu Val
        35                  40                  45

Ala Leu Ile Gly Asn Tyr Val Thr His Tyr Ala Glu Ser Val Lys Gly
    50                  55                  60

Arg Phe Thr Ile Ser Arg Asp Asn Ala Lys Asn Thr Val Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
            100                 105                 110

Val Lys Pro Gly Gly
        115

<210> SEQ ID NO 424
<211> LENGTH: 117
<212> TYPE: PRT
<213> ORGANISM: Artificial Sequence
<220> FEATURE:
<223> OTHER INFORMATION: hz18H10v8

<400> SEQUENCE: 424

Glu Val Gln Leu Val Glu Ser Gly Gly Gly Glu Val Gln Pro Gly Gly
1               5                   10                  15
```

```
Ser Leu Arg Leu Ser Cys Ala Ala Ser Gly Ser Val Thr Gly Ala Asn
            20                  25                  30

Thr Met Gly Trp Tyr Arg Gln Ala Pro Gly Lys Gln Arg Asp Leu Val
            35                  40                  45

Ser Leu Ile Gly Asn Tyr Val Thr His Tyr Ala Glu Ser Val Lys Gly
        50                  55                  60

Arg Phe Thr Ile Ser Arg Asp Asn Ala Lys Asn Thr Leu Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
            100                 105                 110

Val Lys Pro Gly Gly
            115

<210> SEQ ID NO 425
<211> LENGTH: 117
<212> TYPE: PRT
<213> ORGANISM: Artificial Sequence
<220> FEATURE:
<223> OTHER INFORMATION: hz18H10v9

<400> SEQUENCE: 425

Glu Val Gln Leu Val Glu Ser Gly Gly Gly Val Gln Pro Gly Gly
1               5                   10                  15

Ser Leu Arg Leu Ser Cys Ala Ala Ser Gly Ser Val Thr Gly Ala Asn
            20                  25                  30

Thr Met Gly Trp Tyr Arg Gln Ala Pro Gly Lys Gln Arg Asp Leu Val
            35                  40                  45

Ser Leu Ile Gly Asn Tyr Val Thr His Tyr Ala Glu Ser Val Lys Gly
        50                  55                  60

Arg Phe Thr Ile Ser Arg Asp Asn Ala Lys Asn Thr Val Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
            100                 105                 110

Val Lys Pro Gly Gly
            115

<210> SEQ ID NO 426
<211> LENGTH: 117
<212> TYPE: PRT
<213> ORGANISM: Artificial Sequence
<220> FEATURE:
<223> OTHER INFORMATION: hz18H10v10

<400> SEQUENCE: 426

Glu Val Gln Leu Val Glu Ser Gly Gly Gly Val Gln Pro Gly Gly
1               5                   10                  15

Ser Leu Arg Leu Ser Cys Ala Ala Ser Gly Ser Met Thr Gly Ala Asn
            20                  25                  30

Thr Met Gly Trp Tyr Arg Gln Ala Pro Gly Lys Gln Arg Asp Leu Val
            35                  40                  45

Ser Leu Ile Gly Asn Tyr Val Thr His Tyr Ala Glu Ser Val Lys Gly
        50                  55                  60

Arg Phe Thr Ile Ser Arg Glu Asn Ala Lys Asn Thr Val Tyr Leu Gln
```

```
                65                  70                  75                  80
Met Ser Ser Leu Arg Ala Glu Asp Thr Ala Val Tyr Tyr Cys Tyr Leu
                    85                  90                  95

Tyr Thr Asp Asn Leu Gly Thr Ser Trp Gly Gln Gly Thr Leu Val Thr
                100                 105                 110

Val Lys Pro Gly Gly
        115

<210> SEQ ID NO 427
<211> LENGTH: 117
<212> TYPE: PRT
<213> ORGANISM: Artificial Sequence
<220> FEATURE:
<223> OTHER INFORMATION: hz18H10v11

<400> SEQUENCE: 427

Glu Val Gln Leu Val Glu Ser Gly Gly Gly Val Gln Pro Gly Gly
1               5                   10                  15

Ser Leu Arg Leu Ser Cys Ala Ala Ser Gly Ser Val Thr Gly Ala Asn
                20                  25                  30

Thr Met Gly Trp Tyr Arg Gln Ala Pro Gly Lys Gln Arg Asp Leu Val
            35                  40                  45

Ser Leu Ile Gly Asn Tyr Val Thr His Tyr Ala Glu Ser Val Lys Gly
        50                  55                  60

Arg Phe Thr Ile Ser Arg Glu Asn Ala Lys Asn Thr Val Tyr Leu Gln
65                  70                  75                  80

Met Ser Ser Leu Arg Ala Glu Asp Thr Ala Val Tyr Tyr Cys Tyr Leu
                    85                  90                  95

Tyr Thr Asp Asn Leu Gly Thr Ser Trp Gly Gln Gly Thr Leu Val Thr
                100                 105                 110

Val Lys Pro Gly Gly
        115

<210> SEQ ID NO 428
<211> LENGTH: 117
<212> TYPE: PRT
<213> ORGANISM: Artificial Sequence
<220> FEATURE:
<223> OTHER INFORMATION: hz18H10v12

<400> SEQUENCE: 428

Glu Val Gln Leu Val Glu Ser Gly Gly Gly Val Gln Pro Gly Gly
1               5                   10                  15

Ser Leu Arg Leu Ser Cys Ala Ala Ser Gly Ser Val Thr Gly Ala Asn
                20                  25                  30

Thr Met Gly Trp Tyr Arg Gln Ala Pro Gly Lys Gln Arg Asp Leu Val
            35                  40                  45

Ala Leu Ile Gly Asn Tyr Val Thr His Tyr Ala Glu Ser Val Lys Gly
        50                  55                  60

Arg Phe Thr Ile Ser Arg Glu Asn Ala Lys Asn Thr Val Tyr Leu Gln
65                  70                  75                  80

Met Ser Ser Leu Arg Ala Glu Asp Thr Ala Val Tyr Tyr Cys Tyr Leu
                    85                  90                  95

Tyr Thr Asp Asn Leu Gly Thr Ser Trp Gly Gln Gly Thr Leu Val Thr
                100                 105                 110

Val Lys Pro Gly Gly
        115
```

<210> SEQ ID NO 429
<211> LENGTH: 117
<212> TYPE: PRT
<213> ORGANISM: Artificial Sequence
<220> FEATURE:
<223> OTHER INFORMATION: hz18H10v13

<400> SEQUENCE: 429

```
Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Met Thr Gly Ala Asn
            20                  25                  30

Thr Met Gly Trp Tyr Arg Gln Ala Pro Gly Lys Gln Arg Glu Leu Val
        35                  40                  45

Ala Leu Ile Gly Asn Tyr Val Thr His Tyr Ala Glu Ser Val Lys Gly
    50                  55                  60

Arg Phe Thr Ile Ser Arg Glu Asn Ala Lys Asn Thr Val Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
            100                 105                 110

Val Lys Pro Gly Gly
        115
```

<210> SEQ ID NO 430
<211> LENGTH: 117
<212> TYPE: PRT
<213> ORGANISM: Artificial Sequence
<220> FEATURE:
<223> OTHER INFORMATION: hz18H10v14

<400> SEQUENCE: 430

```
Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Val Thr Gly Ala Asn
            20                  25                  30

Thr Met Gly Trp Tyr Arg Gln Ala Pro Gly Lys Gln Arg Asp Leu Val
        35                  40                  45

Ala Leu Ile Gly Asn Tyr Val Thr His Tyr Ala Glu Ser Val Lys Gly
    50                  55                  60

Arg Phe Thr Ile Ser Arg Asp Asn Ala Lys Asn Thr Leu Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
            100                 105                 110

Val Lys Pro Gly Gly
        115
```

<210> SEQ ID NO 431
<211> LENGTH: 117
<212> TYPE: PRT
<213> ORGANISM: Artificial Sequence
<220> FEATURE:
<223> OTHER INFORMATION: hz18H10v15

<400> SEQUENCE: 431

```
Glu Val Gln Leu Val Glu Ser Gly Gly Gly Glu Val Gln Pro Gly Gly
```

```
1               5                   10                  15
Ser Leu Arg Leu Ser Cys Ala Ala Ser Gly Ser Ile Thr Gly Ala Asn
            20                  25                  30

Thr Met Gly Trp Tyr Arg Gln Ala Pro Gly Lys Gln Arg Asp Leu Val
            35                  40                  45

Ala Leu Ile Gly Asn Tyr Val Thr His Tyr Ala Glu Ser Val Lys Gly
            50                  55                  60

Arg Phe Thr Ile Ser Arg Asp Asn Ala Lys Asn Thr Leu Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
                100                 105                 110

Val Lys Pro Gly Gly
            115

<210> SEQ ID NO 432
<211> LENGTH: 117
<212> TYPE: PRT
<213> ORGANISM: Artificial Sequence
<220> FEATURE:
<223> OTHER INFORMATION: hz18H10v16

<400> SEQUENCE: 432

Glu Val Gln Leu Val Glu Ser Gly Gly Gly Val Gln Pro Gly Gly
1               5                   10                  15

Ser Leu Arg Leu Ser Cys Ala Ala Ser Gly Ser Ile Thr Gly Ala Asn
            20                  25                  30

Thr Met Gly Trp Tyr Arg Gln Ala Pro Gly Lys Gln Arg Asp Leu Val
            35                  40                  45

Ala Leu Ile Gly Asn Tyr Val Thr His Tyr Ala Glu Ser Val Lys Gly
            50                  55                  60

Arg Phe Thr Ile Ser Arg Glu Asn Ala Lys Asn Thr Val Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
                100                 105                 110

Val Lys Pro Gly Gly
            115

<210> SEQ ID NO 433
<211> LENGTH: 117
<212> TYPE: PRT
<213> ORGANISM: Artificial Sequence
<220> FEATURE:
<223> OTHER INFORMATION: hz18H10v17

<400> SEQUENCE: 433

Glu Val Gln Leu Val Glu Ser Gly Gly Gly Val Gln Pro Gly Gly
1               5                   10                  15

Ser Leu Arg Leu Ser Cys Ala Ala Ser Gly Ser Ile Thr Gly Ala Asn
            20                  25                  30

Thr Met Gly Trp Tyr Arg Gln Ala Pro Gly Lys Gln Arg Asp Leu Val
            35                  40                  45

Ala Leu Ile Gly Asn Tyr Val Thr His Tyr Ala Glu Ser Val Lys Gly
            50                  55                  60
```

```
Arg Phe Thr Ile Ser Arg Asp Asn Ala Lys Asn Thr Val Tyr Leu Gln
 65                  70                  75                  80

Met Asn Ser Leu Arg Ala Glu Asp Thr Ala Val Tyr Tyr Cys Tyr Leu
                 85                  90                  95

Tyr Thr Asp Asn Leu Gly Thr Ser Trp Gly Gln Gly Thr Leu Val Thr
            100                 105                 110

Val Lys Pro Gly Gly
        115

<210> SEQ ID NO 434
<211> LENGTH: 10
<212> TYPE: PRT
<213> ORGANISM: Artificial Sequence
<220> FEATURE:
<223> OTHER INFORMATION: CDR1

<400> SEQUENCE: 434

Gly Ser Met Thr Gly Ala Asn Thr Met Gly
1               5                   10

<210> SEQ ID NO 435
<211> LENGTH: 10
<212> TYPE: PRT
<213> ORGANISM: Artificial Sequence
<220> FEATURE:
<223> OTHER INFORMATION: CDR1

<400> SEQUENCE: 435

Gly Ser Val Thr Gly Ala Asn Thr Met Gly
1               5                   10

<210> SEQ ID NO 436
<211> LENGTH: 10
<212> TYPE: PRT
<213> ORGANISM: Artificial Sequence
<220> FEATURE:
<223> OTHER INFORMATION: CDR1

<400> SEQUENCE: 436

Gly Ser Ile Thr Gly Ala Asn Thr Met Gly
1               5                   10

<210> SEQ ID NO 437
<211> LENGTH: 8
<212> TYPE: PRT
<213> ORGANISM: Artificial Sequence
<220> FEATURE:
<223> OTHER INFORMATION: CDR2

<400> SEQUENCE: 437

Leu Ile Gly Asn Tyr Val Thr His
1               5

<210> SEQ ID NO 438
<211> LENGTH: 8
<212> TYPE: PRT
<213> ORGANISM: Artificial Sequence
<220> FEATURE:
<223> OTHER INFORMATION: CDR3

<400> SEQUENCE: 438

Tyr Thr Asp Asn Leu Gly Thr Ser
1               5

<210> SEQ ID NO 439
```

```
<211> LENGTH: 115
<212> TYPE: PRT
<213> ORGANISM: Artificial Sequence
<220> FEATURE:
<223> OTHER INFORMATION: 18H10

<400> SEQUENCE: 439

Gln Val Gln Leu Val Gln Ser Gly Gly Gly Leu Val Gln Pro Gly Gly
1               5                   10                  15

Ser Leu Arg Leu Ser Cys Val Ala Ser Gly Ser Met Thr Gly Ala Asn
            20                  25                  30

Thr Met Gly Trp Tyr Arg Gln Ala Pro Gly Lys Gln Arg Asp Leu Val
        35                  40                  45

Ala Leu Ile Gly Asn Tyr His Tyr Ala Asp Ser Val Lys Gly Arg Phe
    50                  55                  60

Thr Ile Ser Arg Glu Asn Ala Lys Asn Thr Val Ile Leu Gln Met Asn
65                  70                  75                  80

Ser Leu Asn Pro Glu Asp Thr Ala Val Tyr Tyr Cys Tyr Leu Tyr Thr
                85                  90                  95

Asp Asn Leu Gly Thr Ser Trp Gly Gln Gly Thr Leu Val Thr Val Lys
            100                 105                 110

Pro Gly Gly
        115

<210> SEQ ID NO 440
<211> LENGTH: 225
<212> TYPE: PRT
<213> ORGANISM: Artificial Sequence
<220> FEATURE:
<223> OTHER INFORMATION: Knob Fc

<400> SEQUENCE: 440

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
```

His Glu Ala Leu His Asn His Tyr Thr Gln Lys Ser Leu Ser Leu Ser
            210                 215                 220

Pro
225

<210> SEQ ID NO 441
<211> LENGTH: 225
<212> TYPE: PRT
<213> ORGANISM: Artificial Sequence
<220> FEATURE:
<223> OTHER INFORMATION: Hole Fc

<400> SEQUENCE: 441

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Arg Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro
225

<210> SEQ ID NO 442
<211> LENGTH: 222
<212> TYPE: PRT
<213> ORGANISM: Artificial Sequence
<220> FEATURE:
<223> OTHER INFORMATION: Knob Fc

<400> SEQUENCE: 442

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Met Ile Ser Arg
            20                  25                  30

-continued

Thr Pro Glu Val Thr Cys Val Val Asp Val Ser His Glu Asp Pro
            35                  40                  45

Glu Val Lys Phe Asn Trp Tyr Val Asp Gly Val Glu Val His Asn Ala
 50                  55                  60

Lys Thr Lys Pro Arg Glu Gln Tyr Asn Ser Thr Tyr Arg Val Val
 65                  70                  75                  80

Ser Val Leu Thr Val Leu His Gln Asp Trp Leu Asn Gly Lys Glu Tyr
                 85                  90                  95

Lys Cys Lys Val Ser Asn Lys Ala Leu Pro Ala Pro Ile Glu Lys Thr
                100                 105                 110

Ile Ser Lys Ala Lys Gly Gln Pro Arg Glu Pro Gln Val Tyr Thr Leu
            115                 120                 125

Pro Pro Cys Arg Asp Glu Leu Thr Lys Asn Gln Val Ser Leu Trp Cys
130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro
210                 215                 220

<210> SEQ ID NO 443
<211> LENGTH: 222
<212> TYPE: PRT
<213> ORGANISM: Artificial Sequence
<220> FEATURE:
<223> OTHER INFORMATION: Hole Fc

<400> SEQUENCE: 443

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Met Arg Ser Arg
            20                  25                  30

Thr Pro Glu Val Thr Cys Val Val Val Asp Val Ser His Glu Asp Pro
            35                  40                  45

Glu Val Lys Phe Asn Trp Tyr Val Asp Gly Val Glu Val His Asn Ala
 50                  55                  60

Lys Thr Lys Pro Arg Glu Gln Tyr Asn Ser Thr Tyr Arg Val Val
 65                  70                  75                  80

Ser Val Leu Thr Val Leu His Gln Asp Trp Leu Asn Gly Lys Glu Tyr
                 85                  90                  95

Lys Cys Lys Val Ser Asn Lys Ala Leu Pro Ala Pro Ile Glu Lys Thr
                100                 105                 110

Ile Ser Lys Ala Lys Gly Gln Pro Arg Glu Pro Gln Val Cys Thr Leu
            115                 120                 125

Pro Pro Ser Arg Asp Glu Leu Thr Lys Asn Gln Val Ser Leu Ser Cys
130                 135                 140

Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

```
Ser Asp Gly Ser Phe Phe Leu Val Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro
        210                 215                 220

<210> SEQ ID NO 444
<211> LENGTH: 225
<212> TYPE: PRT
<213> ORGANISM: Artificial Sequence
<220> FEATURE:
<223> OTHER INFORMATION: Hole Fc

<400> SEQUENCE: 444

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn Arg Tyr Thr Gln Lys Ser Leu Ser Leu Ser
    210                 215                 220

Pro
225

<210> SEQ ID NO 445
<211> LENGTH: 222
<212> TYPE: PRT
<213> ORGANISM: Artificial Sequence
<220> FEATURE:
<223> OTHER INFORMATION: Hole Fc

<400> SEQUENCE: 445

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Met Ile Ser Arg
            20                  25                  30
```

Thr Pro Glu Val Thr Cys Val Val Asp Val Ser His Glu Asp Pro
                35                  40                  45

Glu Val Lys Phe Asn Trp Tyr Val Asp Gly Val Glu Val His Asn Ala
 50                  55                  60

Lys Thr Lys Pro Arg Glu Gln Tyr Asn Ser Thr Tyr Arg Val Val
 65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
                100                 105                 110

Ile Ser Lys Ala Lys Gly Gln Pro Arg Glu Pro Gln Val Cys Thr Leu
                115                 120                 125

Pro Pro Ser Arg Asp Glu Leu Thr Lys Asn Gln Val Ser Leu Ser Cys
 130                 135                 140

Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Val Leu Asp
                165                 170                 175

Ser Asp Gly Ser Phe Phe Leu Val Ser Lys Leu Thr Val Asp Lys Ser
                180                 185                 190

Arg Trp Gln Gln Gly Asn Val Phe Ser Cys Ser Val Met His Glu Ala
                195                 200                 205

Leu His Asn Arg Tyr Thr Gln Lys Ser Leu Ser Leu Ser Pro
                210                 215                 220

<210> SEQ ID NO 446
<211> LENGTH: 225
<212> TYPE: PRT
<213> ORGANISM: Artificial Sequence
<220> FEATURE:
<223> OTHER INFORMATION: Knob Fc

<400> SEQUENCE: 446

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
                20                  25                  30

Ile Ser Arg Thr Pro Glu Val Thr Cys Val Val Val Asp Val Ser His
                35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
                115                 120                 125

Tyr Thr Leu Pro Pro Cys Arg Asp Glu Leu Thr Lys Asn Gln Val Ser
 130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

```
Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Val
        195                 200                 205

His Glu Ala Leu His Asn His Tyr Thr Gln Lys Ser Leu Ser Leu Ser
    210                 215                 220

Pro
225

<210> SEQ ID NO 447
<211> LENGTH: 222
<212> TYPE: PRT
<213> ORGANISM: Artificial Sequence
<220> FEATURE:
<223> OTHER INFORMATION: Knob Fc

<400> SEQUENCE: 447

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Tyr Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Tyr Thr Leu
        115                 120                 125

Pro Pro Cys Arg Asp Glu Leu Thr Lys Asn Gln Val Ser Leu Trp Cys
    130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Val His Glu Ala
        195                 200                 205

Leu His Asn His Tyr Thr Gln Lys Ser Leu Ser Leu Ser Pro
    210                 215                 220

<210> SEQ ID NO 448
<211> LENGTH: 225
<212> TYPE: PRT
<213> ORGANISM: Artificial Sequence
<220> FEATURE:
<223> OTHER INFORMATION: Hole Fc

<400> SEQUENCE: 448

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
```

```
            20                  25                  30
Ile Ser Arg Thr Pro Glu Val Thr Cys Val Val Val Asp Val Ser His
         35                  40                  45
Glu Asp Pro Glu Val Lys Phe Asn Trp Tyr Val Asp Gly Val Glu Val
     50                  55                  60
His Asn Ala Lys Thr Lys Pro Arg Glu Glu Gln Tyr Asn Ser Thr Tyr
 65                  70                  75                  80
Arg Val Val Ser Val Leu Thr Val Leu His Gln Asp Trp Leu Asn Gly
                 85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Cys Thr Leu Pro Pro Ser Arg Asp Glu Leu Thr Lys Asn Gln Val Ser
    130                 135                 140
Leu Ser Cys Ala Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Val Ser Lys Leu Thr Val
            180                 185                 190
Asp Lys Ser Arg Trp Gln Gln Gly Asn Val Phe Ser Cys Ser Val Val
        195                 200                 205
His Glu Ala Leu His Asn Arg Tyr Thr Gln Lys Ser Leu Ser Leu Ser
    210                 215                 220
Pro
225

<210> SEQ ID NO 449
<211> LENGTH: 222
<212> TYPE: PRT
<213> ORGANISM: Artificial Sequence
<220> FEATURE:
<223> OTHER INFORMATION: Hole Fc

<400> SEQUENCE: 449

Asp Lys Thr His Thr Cys Pro Pro Cys Pro Ala Pro Gly Gly Pro Ser
1               5                  10                  15
Val Phe Leu Phe Pro Pro Lys Pro Lys Asp Thr Leu Tyr Ile Ser Arg
            20                  25                  30
Thr Pro Glu Val Thr Cys Val Val Val Asp Val Ser His Glu Asp Pro
        35                  40                  45
Glu Val Lys Phe Asn Trp Tyr Val Asp Gly Val Glu Val His Asn Ala
    50                  55                  60
Lys Thr Lys Pro Arg Glu Glu Gln Tyr Asn Ser Thr Tyr Arg Val Val
65                  70                  75                  80
Ser Val Leu Thr Val Leu His Gln Asp Trp Leu Asn Gly Lys Glu Tyr
                85                  90                  95
Lys Cys Lys Val Ser Asn Lys Ala Leu Pro Ala Pro Ile Glu Lys Thr
            100                 105                 110
Ile Ser Lys Ala Lys Gly Gln Pro Arg Glu Pro Gln Val Cys Thr Leu
        115                 120                 125
Pro Pro Ser Arg Asp Glu Leu Thr Lys Asn Gln Val Ser Leu Ser Cys
    130                 135                 140
Ala Val Lys Gly Phe Tyr Pro Ser Asp Ile Ala Val Glu Trp Glu Ser
```

```
145                 150                 155                 160
Asn Gly Gln Pro Glu Asn Asn Tyr Lys Thr Thr Pro Val Leu Asp
                165                 170                 175

Ser Asp Gly Ser Phe Phe Leu Val Ser Lys Leu Thr Val Asp Lys Ser
            180                 185                 190

Arg Trp Gln Gln Gly Asn Val Phe Ser Cys Ser Val Val His Glu Ala
        195                 200                 205

Leu His Asn Arg Tyr Thr Gln Lys Ser Leu Ser Leu Ser Pro
    210                 215                 220

<210> SEQ ID NO 450
<211> LENGTH: 5
<212> TYPE: PRT
<213> ORGANISM: Artificial Sequence
<220> FEATURE:
<223> OTHER INFORMATION: Linker

<400> SEQUENCE: 450

Pro Gly Gly Gly Gly
1               5

<210> SEQ ID NO 451
<211> LENGTH: 109
<212> TYPE: PRT
<213> ORGANISM: Artificial Sequence
<220> FEATURE:
<223> OTHER INFORMATION: CD3-VL20

<400> SEQUENCE: 451

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Lys Ser Pro Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Gly Gly Thr Lys Leu Thr Val Leu
            100                 105

<210> SEQ ID NO 452
<211> LENGTH: 109
<212> TYPE: PRT
<213> ORGANISM: Artificial Sequence
<220> FEATURE:
<223> OTHER INFORMATION: CD3-VL21

<400> SEQUENCE: 452

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Lys Ser Pro Arg Gly
        35                  40                  45

Leu Ile Gly Gly Thr Asn Lys Arg Ala Pro Gly Val Pro Ala Arg Phe
    50                  55                  60
```

```
Ser Gly Ser Leu Leu Gly Gly Lys Ala Ala Leu Thr Ile Ser Gly Ala
 65                  70                  75                  80

Gln Pro Glu Asp Glu Ala Asp Tyr Tyr Cys Ala Leu Trp Tyr Ser Asn
                 85                  90                  95

His Trp Val Phe Gly Cys Gly Thr Lys Leu Thr Val Leu
            100                 105
```

<210> SEQ ID NO 453
<211> LENGTH: 125
<212> TYPE: PRT
<213> ORGANISM: Artificial Sequence
<220> FEATURE:
<223> OTHER INFORMATION: CD3-VH32

<400> SEQUENCE: 453

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 454
<211> LENGTH: 123
<212> TYPE: PRT
<213> ORGANISM: Artificial Sequence
<220> FEATURE:
<223> OTHER INFORMATION: CD3-VH34

<400> SEQUENCE: 454

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
    50                  55                  60

Thr Val Lys Gly Arg Phe Thr Ile Ser Arg Asp Asp Ala Lys Asn Thr
65                  70                  75                  80

Leu Tyr Leu Gln Met Ser Ser Leu Arg Ala Glu Asp Thr Ala Val Tyr
                85                  90                  95

Tyr Cys Val Arg His Gly Asn Phe Gly Asp Ser Tyr Val Ser Trp Phe
            100                 105                 110

Ala Tyr Trp Gly Gln Gly Thr Leu Val Thr Val
        115                 120
```

```
<210> SEQ ID NO 455
<211> LENGTH: 115
<212> TYPE: PRT
<213> ORGANISM: Artificial Sequence
<220> FEATURE:
<223> OTHER INFORMATION: hz8E7v16

<400> SEQUENCE: 455

Glu Val Gln Leu Val Glu Ser Gly Gly Gly Val Gln Pro Gly Gly
1               5                   10                  15

Ser Leu Arg Leu Ser Cys Gly Pro Ser Glu Ile Ile Thr Ser Asp Lys
            20                  25                  30

Ser Met Gly Trp Val Arg Gln Ala Pro Gly Lys Gln Arg Asn Leu Val
        35                  40                  45

Ala Gly Ile Ser Asn Val Gly Ser Thr Asn Tyr Ala Gln Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Tyr
                85                  90                  95

Ala Arg Asp Phe Glu Asn Glu Tyr Trp Gly Gln Gly Thr Leu Val Thr
            100                 105                 110

Val Lys Pro
    115

<210> SEQ ID NO 456
<211> LENGTH: 10
<212> TYPE: PRT
<213> ORGANISM: Artificial Sequence
<220> FEATURE:
<223> OTHER INFORMATION: CDR-H1 (L8E7, hz8E7v13, 15, 16)

<400> SEQUENCE: 456

Glu Ile Ile Thr Ser Asp Lys Ser Met Gly
1               5                   10

<210> SEQ ID NO 457
<211> LENGTH: 10
<212> TYPE: PRT
<213> ORGANISM: Artificial Sequence
<220> FEATURE:
<223> OTHER INFORMATION: 41BB CDR1

<400> SEQUENCE: 457

Gly Phe Ser Phe Ser Ile Asn Ala Met Gly
1               5                   10

<210> SEQ ID NO 458
<211> LENGTH: 9
<212> TYPE: PRT
<213> ORGANISM: Artificial Sequence
<220> FEATURE:
<223> OTHER INFORMATION: 41BB CDR2

<400> SEQUENCE: 458

Ala Ile Glu Ser Gly Arg Asn Thr Val
1               5

<210> SEQ ID NO 459
<211> LENGTH: 13
<212> TYPE: PRT
<213> ORGANISM: Artificial Sequence
<220> FEATURE:
<223> OTHER INFORMATION: 41BB CDR3
```

<400> SEQUENCE: 459

Leu Lys Gly Asn Arg Val Val Ser Pro Ser Val Ala Tyr
1               5                   10

<210> SEQ ID NO 460
<211> LENGTH: 125
<212> TYPE: PRT
<213> ORGANISM: Artificial Sequence
<220> FEATURE:
<223> OTHER INFORMATION: CD3-VH33

<400> SEQUENCE: 460

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Cys Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
            100                 105                 110

Ala Tyr Trp Gly Gln Gly Thr Leu Val Thr Val Ser Ser
        115                 120                 125

<210> SEQ ID NO 461
<211> LENGTH: 10
<212> TYPE: PRT
<213> ORGANISM: Artificial Sequence
<220> FEATURE:
<223> OTHER INFORMATION: anti-CD3 VH CDR1

<400> SEQUENCE: 461

Gly Phe Thr Phe Asn Thr Tyr Ala Met Asn
1               5                   10

<210> SEQ ID NO 462
<211> LENGTH: 12
<212> TYPE: PRT
<213> ORGANISM: Artificial Sequence
<220> FEATURE:
<223> OTHER INFORMATION: anti-CD3 VH CDR2

<400> SEQUENCE: 462

Arg Ile Arg Ser Lys Tyr Asn Asn Tyr Ala Thr Tyr
1               5                   10

<210> SEQ ID NO 463
<211> LENGTH: 14
<212> TYPE: PRT
<213> ORGANISM: Artificial Sequence
<220> FEATURE:
<223> OTHER INFORMATION: CD3-VH7, VH33 CDR3

<400> SEQUENCE: 463

His Gly Asn Phe Gly Asp Ser Tyr Val Ser Trp Phe Ala Tyr
1               5                   10

```
<210> SEQ ID NO 464
<211> LENGTH: 9
<212> TYPE: PRT
<213> ORGANISM: Artificial Sequence
<220> FEATURE:
<223> OTHER INFORMATION: CD3-VL2, VL21 CDR3

<400> SEQUENCE: 464

Ala Leu Trp Tyr Ser Asn His Trp Val
1               5

<210> SEQ ID NO 465
<211> LENGTH: 9
<212> TYPE: PRT
<213> ORGANISM: Artificial Sequence
<220> FEATURE:
<223> OTHER INFORMATION: CD3-VL8 CDR3

<400> SEQUENCE: 465

Val Leu Trp Tyr Ser Asn Arg Trp Val
1               5

<210> SEQ ID NO 466
<211> LENGTH: 10
<212> TYPE: PRT
<213> ORGANISM: Artificial Sequence
<220> FEATURE:
<223> OTHER INFORMATION: CD3 VH33 CDR1

<400> SEQUENCE: 466

Gly Phe Thr Phe Ser Thr Tyr Ala Met Asn
1               5                   10

<210> SEQ ID NO 467
<211> LENGTH: 12
<212> TYPE: PRT
<213> ORGANISM: Artificial Sequence
<220> FEATURE:
<223> OTHER INFORMATION: CD3 VH33 CDR21

<400> SEQUENCE: 467

Arg Ile Arg Ser Lys Tyr Asn Asn Tyr Ala Thr Tyr
1               5                   10

<210> SEQ ID NO 468
<211> LENGTH: 14
<212> TYPE: PRT
<213> ORGANISM: Artificial Sequence
<220> FEATURE:
<223> OTHER INFORMATION: CD3 VL21 CDR1

<400> SEQUENCE: 468

Gly Ser Ser Thr Gly Ala Val Thr Thr Ser Asn Tyr Ala Asn
1               5                   10

<210> SEQ ID NO 469
<211> LENGTH: 7
<212> TYPE: PRT
<213> ORGANISM: Artificial Sequence
<220> FEATURE:
<223> OTHER INFORMATION: CD3 VL21 CDR2

<400> SEQUENCE: 469

Gly Thr Asn Lys Arg Ala Pro
1               5
```

```
<210> SEQ ID NO 470
<211> LENGTH: 121
<212> TYPE: PRT
<213> ORGANISM: Artificial Sequence
<220> FEATURE:
<223> OTHER INFORMATION: 41BB sdAb

<400> SEQUENCE: 470
```

Glu Val Gln Leu Val Glu Ser Gly Gly Gly Val Gln Pro Gly Gly
1               5                   10                  15

Ser Leu Arg Leu Ser Cys Ala Ala Ser Gly Phe Ser Phe Ser Ile Asn
            20                  25                  30

Ala Met Gly Trp Tyr Arg Gln Ala Pro Gly Lys Arg Arg Glu Phe Val
        35                  40                  45

Ala Ala Ile Glu Ser Gly Arg Asn Thr Val Tyr Ala Glu Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Gly
                85                  90                  95

Leu Leu Lys Gly Asn Arg Val Val Ser Pro Ser Val Ala Tyr Trp Gly
            100                 105                 110

Gln Gly Thr Leu Val Thr Val Lys Pro
        115                 120

```
<210> SEQ ID NO 471
<211> LENGTH: 5
<212> TYPE: PRT
<213> ORGANISM: Artificial Sequence
<220> FEATURE:
<223> OTHER INFORMATION: Linker

<400> SEQUENCE: 471
```

Ile Glu Pro Asp Pro
1               5

```
<210> SEQ ID NO 472
<211> LENGTH: 226
<212> TYPE: PRT
<213> ORGANISM: Artificial Sequence
<220> FEATURE:
<223> OTHER INFORMATION: Fc-Het-1

<400> SEQUENCE: 472
```

Asp Lys Thr His Thr Cys Pro Pro Cys Pro Ala Pro Pro Val Ala Gly
1               5                   10                  15

Pro Ser Val Phe Leu Phe Pro Pro Lys Pro Lys Asp Thr Leu Met Ile
            20                  25                  30

Ser Arg Thr Pro Glu Val Thr Cys Val Val Val Asp Val Lys His Glu
        35                  40                  45

Asp Pro Glu Val Lys Phe Asn Trp Tyr Val Asp Gly Val Glu Val His
    50                  55                  60

Asn Ala Lys Thr Lys Pro Arg Glu Glu Glu Tyr Asn Ser Thr Tyr Arg
65                  70                  75                  80

Val Val Ser Val Leu Thr Val Leu His Gln Asp Trp Leu Asn Gly Lys
                85                  90                  95

Glu Tyr Lys Cys Lys Val Ser Asn Lys Ala Leu Pro Ala Pro Ile Glu
            100                 105                 110

Lys Thr Ile Ser Lys Ala Lys Gly Gln Pro Arg Glu Pro Gln Val Tyr
        115                 120                 125

```
Thr Leu Pro Pro Ser Arg Glu Glu Met Thr Lys Asn Gln Val Ser Leu
        130                 135                 140

Thr Cys Asp Val Ser Gly Phe Tyr Pro Ser Asp Ile Ala Val Glu Trp
145                     150                 155                 160

Glu Ser Asp Gly Gln Pro Glu Asn Asn Tyr Lys Thr Thr Pro Pro Val
                    165                 170                 175

Leu Asp Ser Asp Gly Ser Phe Phe Leu Tyr Ser Lys Leu Thr Val Asp
                180                 185                 190

Lys Ser Arg Trp Gln Gln Gly Asp Val Phe Ser Cys Ser Val Met His
            195                 200                 205

Glu Ala Leu His Asn His Tyr Thr Gln Lys Ser Leu Ser Leu Ser Pro
        210                 215                 220

Gly Lys
225

<210> SEQ ID NO 473
<211> LENGTH: 226
<212> TYPE: PRT
<213> ORGANISM: Artificial Sequence
<220> FEATURE:
<223> OTHER INFORMATION: Fc-Het-2

<400> SEQUENCE: 473

Asp Lys Thr His Thr Cys Pro Pro Cys Pro Ala Pro Pro Val Ala Gly
1               5                   10                  15

Pro Ser Val Phe Leu Phe Pro Pro Lys Pro Lys Asp Thr Leu Met Ile
                20                  25                  30

Ser Arg Thr Pro Glu Val Thr Cys Val Val Val Asp Val Lys His Glu
            35                  40                  45

Asp Pro Glu Val Lys Phe Asn Trp Tyr Val Asp Gly Val Glu Val His
        50                  55                  60

Asn Ala Lys Thr Lys Pro Arg Glu Glu Gln Tyr Asn Ser Thr Tyr Arg
65                  70                  75                  80

Val Val Ser Val Leu Thr Val Leu His Gln Asp Trp Leu Asn Gly Lys
                85                  90                  95

Glu Tyr Lys Cys Lys Val Ser Asn Lys Ala Leu Pro Ala Pro Ile Glu
            100                 105                 110

Lys Thr Ile Ser Lys Ala Lys Gly Gln Pro Arg Glu Pro Gln Val Tyr
        115                 120                 125

Thr Leu Pro Pro Ser Arg Glu Gln Met Thr Lys Asn Gln Val Lys Leu
    130                 135                 140

Thr Cys Leu Val Lys Gly Phe Tyr Pro Ser Asp Ile Ala Val Glu Trp
145                 150                 155                 160

Glu Ser Asn Gly Gln Pro Glu Asn Asn Tyr Lys Thr Thr Pro Pro Val
                165                 170                 175

Leu Asp Ser Asp Gly Ser Phe Phe Leu Tyr Ser Lys Leu Thr Val Asp
            180                 185                 190

Lys Ser Arg Trp Gln Gln Gly Asn Val Phe Ser Cys Ser Val Met His
        195                 200                 205

Glu Ala Leu His Asn His Tyr Thr Gln Lys Ser Leu Ser Leu Ser Pro
    210                 215                 220

Gly Lys
225

<210> SEQ ID NO 474
```

```
<211> LENGTH: 6
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (4)...(6)
<223> OTHER INFORMATION: Repeat 0 to 10 times

<400> SEQUENCE: 474

Gly Gly Ser Gly Gly Ser
1               5

<210> SEQ ID NO 475
<211> LENGTH: 466
<212> TYPE: PRT
<213> ORGANISM: Homo sapiens
<220> FEATURE:
<223> OTHER INFORMATION: DLL3 ECD; amino acids 27-492 of human DLL3,
      UniProt No. Q9NYJ7

<400> SEQUENCE: 475

Ala Gly Val Phe Glu Leu Gln Ile His Ser Phe Gly Pro Gly Pro Gly
1               5                   10                  15

Pro Gly Ala Pro Arg Ser Pro Cys Ser Ala Arg Leu Pro Cys Arg Leu
            20                  25                  30

Phe Phe Arg Val Cys Leu Lys Pro Gly Leu Ser Glu Glu Ala Ala Glu
        35                  40                  45

Ser Pro Cys Ala Leu Gly Ala Ala Leu Ser Ala Arg Gly Pro Val Tyr
    50                  55                  60

Thr Glu Gln Pro Gly Ala Pro Ala Pro Asp Leu Pro Leu Pro Asp Gly
65                  70                  75                  80

Leu Leu Gln Val Pro Phe Arg Asp Ala Trp Pro Gly Thr Phe Ser Phe
                85                  90                  95

Ile Ile Glu Thr Trp Arg Glu Glu Leu Gly Asp Gln Ile Gly Gly Pro
            100                 105                 110

Ala Trp Ser Leu Leu Ala Arg Val Ala Gly Arg Arg Arg Leu Ala Ala
        115                 120                 125

Gly Gly Pro Trp Ala Arg Asp Ile Gln Arg Ala Gly Ala Trp Glu Leu
    130                 135                 140

Arg Phe Ser Tyr Arg Ala Arg Cys Glu Pro Pro Ala Val Gly Thr Ala
145                 150                 155                 160

Cys Thr Arg Leu Cys Arg Pro Arg Ser Ala Pro Ser Arg Cys Gly Pro
                165                 170                 175

Gly Leu Arg Pro Cys Ala Pro Leu Glu Asp Glu Cys Glu Ala Pro Leu
            180                 185                 190

Val Cys Arg Ala Gly Cys Ser Pro Glu His Gly Phe Cys Glu Gln Pro
        195                 200                 205

Gly Glu Cys Arg Cys Leu Glu Gly Trp Thr Gly Pro Leu Cys Thr Val
    210                 215                 220

Pro Val Ser Thr Ser Ser Cys Leu Ser Pro Arg Gly Pro Ser Ser Ala
225                 230                 235                 240

Thr Thr Gly Cys Leu Val Pro Gly Pro Gly Pro Cys Asp Gly Asn Pro
                245                 250                 255

Cys Ala Asn Gly Gly Ser Cys Ser Glu Thr Pro Arg Ser Phe Glu Cys
            260                 265                 270

Thr Cys Pro Arg Gly Phe Tyr Gly Leu Arg Cys Glu Val Ser Gly Val
        275                 280                 285
```

```
Thr Cys Ala Asp Gly Pro Cys Phe Asn Gly Gly Leu Cys Val Gly Gly
    290                 295                 300
Ala Asp Pro Asp Ser Ala Tyr Ile Cys His Cys Pro Pro Gly Phe Gln
305                 310                 315                 320
Gly Ser Asn Cys Glu Lys Arg Val Asp Arg Cys Ser Leu Gln Pro Cys
                325                 330                 335
Arg Asn Gly Gly Leu Cys Leu Asp Leu Gly His Ala Leu Arg Cys Arg
            340                 345                 350
Cys Arg Ala Gly Phe Ala Gly Pro Arg Cys Glu His Asp Leu Asp Asp
        355                 360                 365
Cys Ala Gly Arg Ala Cys Ala Asn Gly Gly Thr Cys Val Glu Gly Gly
    370                 375                 380
Gly Ala His Arg Cys Ser Cys Ala Leu Gly Phe Gly Gly Arg Asp Cys
385                 390                 395                 400
Arg Glu Arg Ala Asp Pro Cys Ala Ala Arg Pro Cys Ala His Gly Gly
                405                 410                 415
Arg Cys Tyr Ala His Phe Ser Gly Leu Val Cys Ala Cys Ala Pro Gly
            420                 425                 430
Tyr Met Gly Ala Arg Cys Glu Phe Pro Val His Pro Asp Gly Ala Ser
        435                 440                 445
Ala Leu Pro Ala Ala Pro Pro Gly Leu Arg Pro Gly Asp Pro Gln Arg
    450                 455                 460
Tyr Leu
465

<210> SEQ ID NO 476
<211> LENGTH: 115
<212> TYPE: PRT
<213> ORGANISM: Artificial Sequence
<220> FEATURE:
<223> OTHER INFORMATION: hz8E7v13

<400> SEQUENCE: 476

Glu Val Gln Leu Val Glu Ser Gly Gly Gly Val Gln Pro Gly Gly
1               5                   10                  15
Ser Leu Arg Leu Ser Cys Gly Pro Ser Glu Ile Ile Thr Ser Asp Lys
                20                  25                  30
Ser Met Gly Trp Trp Arg Gln Ala Pro Gly Lys Gln Arg Asn Leu Val
            35                  40                  45
Ala Gly Ile Ser Asn Val Gly Ser Thr Asn Tyr Ala Gln Ser Val Lys
        50                  55                  60
Gly Arg Phe Thr Ile Ser Arg Asp Asn Ala Lys Asn Thr Val Tyr Leu
65                  70                  75                  80
Gln Met Ser Ser Leu Arg Ala Glu Asp Thr Ala Val Tyr Tyr Cys Tyr
                85                  90                  95
Ala Arg Asp Phe Glu Asn Glu Tyr Trp Gly Gln Gly Thr Leu Val Thr
            100                 105                 110
Val Lys Pro
        115

<210> SEQ ID NO 477
<211> LENGTH: 115
<212> TYPE: PRT
<213> ORGANISM: Artificial Sequence
<220> FEATURE:
<223> OTHER INFORMATION: hz8E7v14
```

-continued

<400> SEQUENCE: 477

Glu Val Gln Leu Val Glu Ser Gly Gly Gly Glu Val Gln Pro Gly Gly
1               5                   10                  15

Ser Leu Arg Leu Ser Cys Gly Pro Ser Glu Ile Ile Thr Ser Asp Lys
            20                  25                  30

Ser Val Gly Trp Val Arg Gln Ala Pro Gly Lys Gln Arg Asn Leu Val
        35                  40                  45

Ala Gly Ile Ser Asn Val Gly Ser Thr Asn Tyr Ala Gln Ser Val Lys
    50                  55                  60

Gly Arg Phe Thr Ile Ser Arg Asp Asn Ala Lys Asn Thr Val Tyr Leu
65              70                  75                  80

Gln Met Ser Ser Leu Arg Ala Glu Asp Thr Ala Val Tyr Tyr Cys Tyr
                85                  90                  95

Ala Arg Asp Phe Glu Asn Glu Tyr Trp Gly Gln Gly Thr Leu Val Thr
            100                 105                 110

Val Lys Pro
        115

<210> SEQ ID NO 478
<211> LENGTH: 115
<212> TYPE: PRT
<213> ORGANISM: Artificial Sequence
<220> FEATURE:
<223> OTHER INFORMATION: hz8E7v15

<400> SEQUENCE: 478

Glu Val Gln Leu Val Glu Ser Gly Gly Gly Glu Val Gln Pro Gly Gly
1               5                   10                  15

Ser Leu Arg Leu Ser Cys Gly Pro Ser Glu Ile Ile Thr Ser Asp Lys
            20                  25                  30

Ser Met Gly Trp Val Arg Gln Ala Pro Gly Lys Gln Arg Asn Leu Val
        35                  40                  45

Ala Gly Ile Ser Asn Val Gly Ser Thr Asn Tyr Ala Gln Ser Val Lys
    50                  55                  60

Gly Arg Phe Thr Ile Ser Arg Asp Asn Ala Lys Asn Thr Leu Tyr Leu
65              70                  75                  80

Gln Met Ser Ser Leu Arg Ala Glu Asp Thr Ala Val Tyr Tyr Cys Tyr
                85                  90                  95

Ala Arg Asp Phe Glu Asn Glu Tyr Trp Gly Gln Gly Thr Leu Val Thr
            100                 105                 110

Val Lys Pro
        115

<210> SEQ ID NO 479
<211> LENGTH: 120
<212> TYPE: PRT
<213> ORGANISM: Artificial Sequence
<220> FEATURE:
<223> OTHER INFORMATION: hz3G3v1

<400> SEQUENCE: 479

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Gln Arg Glu Leu Val
        35                  40                  45

```
Ala Gly Phe Thr Gly Asp Gly Met Thr Lys Tyr Ala Glu Ser Val Lys
    50                  55                  60

Gly Arg Phe Thr Ile Ser Arg Asp Asn Ala Lys Asn Thr Val Tyr Leu
 65                  70                  75                  80

Gln Met Ser Ser Leu Arg Ala Glu Asp Thr Ala Val Tyr Tyr Cys Ala
                 85                  90                  95

Ala Asp Val Phe Thr Asp Arg Asp His Val Asp Trp Tyr Trp Gly Gln
            100                 105                 110

Gly Thr Leu Val Thr Val Lys Pro
        115                 120

<210> SEQ ID NO 480
<211> LENGTH: 115
<212> TYPE: PRT
<213> ORGANISM: Artificial Sequence
<220> FEATURE:
<223> OTHER INFORMATION: hz6C5v2

<400> SEQUENCE: 480

Glu Val Gln Leu Val Glu Ser Gly Gly Gly Val Gln Pro Gly Gly
 1               5                  10                  15

Ser Leu Arg Leu Ser Cys Ala Ala Ser Glu Ile Thr Phe Ser Asp Lys
            20                  25                  30

Thr Val Gly Trp Tyr Arg Gln Ala Pro Gly Lys Gln Arg Val Leu Val
        35                  40                  45

Ala Val Ile Ser Asn Val Asp Ser Thr Asn Tyr Ala Glu Ser Val Lys
    50                  55                  60

Gly Arg Phe Thr Ile Ser Arg Asp Asn Ala Lys Asn Thr Val Tyr Leu
 65                  70                  75                  80

Gln Met Ser Ser Leu Arg Ala Glu Asp Thr Ala Val Tyr Tyr Cys His
                 85                  90                  95

Ala Arg Asp Phe Glu Asn Glu Tyr Trp Gly Gln Gly Thr Leu Val Thr
            100                 105                 110

Val Lys Pro
        115

<210> SEQ ID NO 481
<211> LENGTH: 120
<212> TYPE: PRT
<213> ORGANISM: Artificial Sequence
<220> FEATURE:
<223> OTHER INFORMATION: hz3C5v1

<400> SEQUENCE: 481

Glu Val Gln Leu Val Glu Ser Gly Gly Gly Glu Val Gln Pro Gly Gly
 1               5                  10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Gln Arg Glu Leu Val
        35                  40                  45

Ala Gly Phe Thr Gly Asp Gly Ser Thr Lys Tyr Ala Glu Ser Val Lys
    50                  55                  60

Gly Arg Phe Thr Ile Ser Arg Asp Asn Ala Lys Asn Thr Val Tyr Leu
 65                  70                  75                  80

Gln Met Ser Ser Leu Arg Ala Glu Asp Thr Ala Val Tyr Tyr Cys Ala
                 85                  90                  95

Ala Asp Val Gln Leu Leu Asn Ser Asp Tyr Glu Phe Tyr Trp Gly Gln
            100                 105                 110
```

```
Gly Thr Leu Val Thr Val Lys Pro
        115                 120

<210> SEQ ID NO 482
<211> LENGTH: 120
<212> TYPE: PRT
<213> ORGANISM: Artificial Sequence
<220> FEATURE:
<223> OTHER INFORMATION: hz3C5v2

<400> SEQUENCE: 482

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Pro Pro Gly Lys Gln Arg Glu Leu Val
        35                  40                  45

Ala Gly Phe Thr Gly Asp Gly Ser Thr Lys Tyr Ala Glu Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Ala
                85                  90                  95

Ala Asp Val Gln Leu Leu Asn Ser Asp Tyr Glu Phe Tyr Trp Gly Gln
            100                 105                 110

Gly Thr Leu Val Thr Val Lys Pro
        115                 120

<210> SEQ ID NO 483
<211> LENGTH: 120
<212> TYPE: PRT
<213> ORGANISM: Artificial Sequence
<220> FEATURE:
<223> OTHER INFORMATION: hz3C5v3

<400> SEQUENCE: 483

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Gln Arg Glu Leu Val
        35                  40                  45

Ala Gly Phe Thr Gly Asp Thr Ser Thr Lys Tyr Ala Glu Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Ala
                85                  90                  95

Ala Asp Val Gln Leu Leu Asn Ser Asp Tyr Glu Phe Tyr Trp Gly Gln
            100                 105                 110

Gly Thr Leu Val Thr Val Lys Pro
        115                 120

<210> SEQ ID NO 484
<211> LENGTH: 120
<212> TYPE: PRT
<213> ORGANISM: Artificial Sequence
<220> FEATURE:
<223> OTHER INFORMATION: hz3C5v4
```

<400> SEQUENCE: 484

Glu Val Gln Leu Val Glu Ser Gly Gly Gly Val Gln Pro Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Gln Arg Glu Leu Val
        35                  40                  45

Ala Gly Phe Thr Gly Glu Gly Ser Thr Lys Tyr Ala Glu Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Ala
                85                  90                  95

Ala Asp Val Gln Leu Leu Asn Ser Asp Tyr Glu Phe Tyr Trp Gly Gln
            100                 105                 110

Gly Thr Leu Val Thr Val Lys Pro
        115                 120

<210> SEQ ID NO 485
<211> LENGTH: 120
<212> TYPE: PRT
<213> ORGANISM: Artificial Sequence
<220> FEATURE:
<223> OTHER INFORMATION: hz3C5v5

<400> SEQUENCE: 485

Glu Val Gln Leu Val Glu Ser Gly Gly Gly Val Gln Pro Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Gln Arg Glu Leu Val
        35                  40                  45

Ala Gly Phe Thr Gly Asp Gly Ser Thr Lys Tyr Ala Glu Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Ala
                85                  90                  95

Ala Asp Val Gln Leu Leu Ser Ser Asp Tyr Glu Phe Tyr Trp Gly Gln
            100                 105                 110

Gly Thr Leu Val Thr Val Lys Pro
        115                 120

<210> SEQ ID NO 486
<211> LENGTH: 120
<212> TYPE: PRT
<213> ORGANISM: Artificial Sequence
<220> FEATURE:
<223> OTHER INFORMATION: hz3C5v6

<400> SEQUENCE: 486

Glu Val Gln Leu Val Glu Ser Gly Gly Gly Val Gln Pro Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Gln Arg Glu Leu Val
        35                  40                  45

```
Ala Gly Phe Thr Gly Asp Gly Ser Thr Lys Tyr Ala Glu Ser Val Lys
        50                  55                  60

Gly Arg Phe Thr Ile Ser Arg Asp Asn Ala Lys Asn Thr Val Tyr Leu
 65                  70                  75                  80

Gln Met Ser Ser Leu Arg Ala Glu Asp Thr Ala Val Tyr Tyr Cys Ala
                 85                  90                  95

Ala Asp Val Gln Leu Leu Thr Ser Asp Tyr Glu Phe Tyr Trp Gly Gln
                100                 105                 110

Gly Thr Leu Val Thr Val Lys Pro
        115                 120

<210> SEQ ID NO 487
<211> LENGTH: 120
<212> TYPE: PRT
<213> ORGANISM: Artificial Sequence
<220> FEATURE:
<223> OTHER INFORMATION: hz3C5v7

<400> SEQUENCE: 487

Glu Val Gln Leu Val Glu Ser Gly Gly Gly Val Gln Pro Gly Gly
 1               5                  10                  15

Ser Leu Arg Leu Ser Cys Ala Ala Ser Gly Ser Ile Phe Ser Ile Asn
                 20                  25                  30

Ala Met Gly Trp Tyr Arg Gln Ala Pro Gly Lys Gln Arg Glu Leu Val
            35                  40                  45

Ala Gly Phe Thr Gly Asp Gly Ser Thr Lys Tyr Ala Glu Ser Val Lys
        50                  55                  60

Gly Arg Phe Thr Ile Ser Arg Asp Asn Ala Lys Asn Thr Val Tyr Leu
 65                  70                  75                  80

Gln Met Ser Ser Leu Arg Ala Glu Asp Thr Ala Val Tyr Tyr Cys Ala
                 85                  90                  95

Ala Asp Val Gln Leu Leu Gln Ser Asp Tyr Glu Phe Tyr Trp Gly Gln
                100                 105                 110

Gly Thr Leu Val Thr Val Lys Pro
        115                 120

<210> SEQ ID NO 488
<211> LENGTH: 120
<212> TYPE: PRT
<213> ORGANISM: Artificial Sequence
<220> FEATURE:
<223> OTHER INFORMATION: hz3C5v8

<400> SEQUENCE: 488

Glu Val Gln Leu Val Glu Ser Gly Gly Gly Val Gln Pro Gly Gly
 1               5                  10                  15

Ser Leu Arg Leu Ser Cys Ala Ala Ser Gly Ser Ile Phe Ser Ile Asn
                 20                  25                  30

Ala Met Gly Trp Tyr Arg Gln Ala Pro Gly Lys Gln Arg Glu Leu Val
            35                  40                  45

Ala Gly Phe Thr Gly Asp Gly Ser Thr Lys Tyr Ala Glu Ser Val Lys
        50                  55                  60

Gly Arg Phe Thr Ile Ser Arg Asp Asn Ala Lys Asn Thr Val Tyr Leu
 65                  70                  75                  80

Gln Met Ser Ser Leu Arg Ala Glu Asp Thr Ala Val Tyr Tyr Cys Ala
                 85                  90                  95

Ala Asp Val Gln Leu Leu Asn Thr Asp Tyr Glu Phe Tyr Trp Gly Gln
```

```
                      100                 105                 110
Gly Thr Leu Val Thr Val Lys Pro
            115                 120
```

<210> SEQ ID NO 489
<211> LENGTH: 113
<212> TYPE: PRT
<213> ORGANISM: Artificial Sequence
<220> FEATURE:
<223> OTHER INFORMATION: 18H10

<400> SEQUENCE: 489

```
Gln Val Gln Leu Val Gln Ser Gly Gly Gly Leu Val Gln Pro Gly Gly
1               5                   10                  15

Ser Leu Arg Leu Ser Cys Val Ala Ser Gly Ser Met Thr Gly Ala Asn
            20                  25                  30

Thr Met Gly Trp Tyr Arg Gln Ala Pro Gly Lys Gln Arg Asp Leu Val
        35                  40                  45

Ala Leu Ile Gly Asn Tyr His Tyr Ala Asp Ser Val Lys Gly Arg Phe
50                  55                  60

Thr Ile Ser Arg Glu Asn Ala Lys Asn Thr Val Ile Leu Gln Met Asn
65                  70                  75                  80

Ser Leu Asn Pro Glu Asp Thr Ala Val Tyr Tyr Cys Tyr Leu Tyr Thr
                85                  90                  95

Asp Asn Leu Gly Thr Ser Trp Gly Gln Gly Thr Leu Val Thr Val Lys
            100                 105                 110

Pro
```

<210> SEQ ID NO 490
<211> LENGTH: 115
<212> TYPE: PRT
<213> ORGANISM: Artificial Sequence
<220> FEATURE:
<223> OTHER INFORMATION: hz18H10v1

<400> SEQUENCE: 490

```
Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Met Thr Gly Ala Asn
            20                  25                  30

Thr Met Gly Trp Tyr Arg Gln Ala Pro Gly Lys Gly Arg Asp Leu Val
        35                  40                  45

Ser Leu Ile Gly Asn Tyr Val Thr His Tyr Ala Glu Ser Val Lys Gly
50                  55                  60

Arg Phe Thr Ile Ser Arg Asp Asn Ala Lys Asn Thr Leu Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
            100                 105                 110

Val Lys Pro
        115
```

<210> SEQ ID NO 491
<211> LENGTH: 115
<212> TYPE: PRT
<213> ORGANISM: Artificial Sequence
<220> FEATURE:
<223> OTHER INFORMATION: hz18H10v2

-continued

```
<400> SEQUENCE: 491

Glu Val Gln Leu Val Glu Ser Gly Gly Gly Val Gln Pro Gly Gly
1               5                   10                  15

Ser Leu Arg Leu Ser Cys Ala Ala Ser Gly Ser Met Thr Gly Ala Asn
            20                  25                  30

Thr Met Gly Trp Tyr Arg Gln Ala Pro Gly Lys Gln Arg Asp Leu Val
        35                  40                  45

Ser Leu Ile Gly Asn Tyr Val Thr His Tyr Ala Glu Ser Val Lys Gly
    50                  55                  60

Arg Phe Thr Ile Ser Arg Asp Asn Ala Lys Asn Thr Leu Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
            100                 105                 110

Val Lys Pro
        115

<210> SEQ ID NO 492
<211> LENGTH: 115
<212> TYPE: PRT
<213> ORGANISM: Artificial Sequence
<220> FEATURE:
<223> OTHER INFORMATION: hz18H10v3

<400> SEQUENCE: 492

Glu Val Gln Leu Val Glu Ser Gly Gly Gly Val Gln Pro Gly Gly
1               5                   10                  15

Ser Leu Arg Leu Ser Cys Ala Ala Ser Gly Ser Met Thr Gly Ala Asn
            20                  25                  30

Thr Met Gly Trp Tyr Arg Gln Ala Pro Gly Lys Gln Arg Asp Leu Val
        35                  40                  45

Ser Leu Ile Gly Asn Tyr Val Thr His Tyr Ala Glu Ser Val Lys Gly
    50                  55                  60

Arg Phe Thr Ile Ser Arg Asp Asn Ala Lys Asn Thr Val Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
            100                 105                 110

Val Lys Pro
        115

<210> SEQ ID NO 493
<211> LENGTH: 115
<212> TYPE: PRT
<213> ORGANISM: Artificial Sequence
<220> FEATURE:
<223> OTHER INFORMATION: hz18H10v4

<400> SEQUENCE: 493

Glu Val Gln Leu Val Glu Ser Gly Gly Gly Val Gln Pro Gly Gly
1               5                   10                  15

Ser Leu Arg Leu Ser Cys Ala Ala Ser Gly Ser Met Thr Gly Ala Asn
            20                  25                  30

Thr Met Gly Trp Tyr Arg Gln Ala Pro Gly Lys Gln Arg Asp Leu Val
        35                  40                  45
```

```
Ala Leu Ile Gly Asn Tyr Val Thr His Tyr Ala Glu Ser Val Lys Gly
        50                  55                  60

Arg Phe Thr Ile Ser Arg Asp Asn Ala Lys Asn Thr Val Tyr Leu Gln
 65                  70                  75                  80

Met Ser Ser Leu Arg Ala Glu Asp Thr Ala Val Tyr Tyr Cys Tyr Leu
                 85                  90                  95

Tyr Thr Asp Asn Leu Gly Thr Ser Trp Gly Gln Gly Thr Leu Val Thr
            100                 105                 110

Val Lys Pro
        115

<210> SEQ ID NO 494
<211> LENGTH: 115
<212> TYPE: PRT
<213> ORGANISM: Artificial Sequence
<220> FEATURE:
<223> OTHER INFORMATION: hz18H10v5

<400> SEQUENCE: 494

Glu Val Gln Leu Val Glu Ser Gly Gly Gly Val Gln Pro Gly Gly
 1               5                   10                  15

Ser Leu Arg Leu Ser Cys Ala Ala Ser Gly Ser Met Thr Gly Ala Asn
             20                  25                  30

Thr Met Gly Trp Tyr Arg Gln Ala Pro Gly Lys Gln Arg Asp Leu Val
         35                  40                  45

Ala Leu Ile Gly Asn Tyr Val Thr His Tyr Ala Glu Ser Val Lys Gly
        50                  55                  60

Arg Phe Thr Ile Ser Arg Glu Asn Ala Lys Asn Thr Val Tyr Leu Gln
 65                  70                  75                  80

Met Ser Ser Leu Arg Ala Glu Asp Thr Ala Val Tyr Tyr Cys Tyr Leu
                 85                  90                  95

Tyr Thr Asp Asn Leu Gly Thr Ser Trp Gly Gln Gly Thr Leu Val Thr
            100                 105                 110

Val Lys Pro
        115

<210> SEQ ID NO 495
<211> LENGTH: 115
<212> TYPE: PRT
<213> ORGANISM: Artificial Sequence
<220> FEATURE:
<223> OTHER INFORMATION: hz18H10v6

<400> SEQUENCE: 495

Glu Val Gln Leu Val Glu Ser Gly Gly Gly Val Gln Pro Gly Gly
 1               5                   10                  15

Ser Leu Arg Leu Ser Cys Ala Ala Ser Gly Ser Val Thr Gly Ala Asn
             20                  25                  30

Thr Met Gly Trp Tyr Arg Gln Ala Pro Gly Lys Gln Arg Asp Leu Val
         35                  40                  45

Ala Leu Ile Gly Asn Tyr Val Thr His Tyr Ala Glu Ser Val Lys Gly
        50                  55                  60

Arg Phe Thr Ile Ser Arg Asp Asn Ala Lys Asn Thr Val Tyr Leu Gln
 65                  70                  75                  80

Met Ser Ser Leu Arg Ala Glu Asp Thr Ala Val Tyr Tyr Cys Tyr Leu
                 85                  90                  95

Tyr Thr Asp Asn Leu Gly Thr Ser Trp Gly Gln Gly Thr Leu Val Thr
```

-continued

```
                100                 105                 110

Val Lys Pro
        115

<210> SEQ ID NO 496
<211> LENGTH: 115
<212> TYPE: PRT
<213> ORGANISM: Artificial Sequence
<220> FEATURE:
<223> OTHER INFORMATION: hz18H10v7

<400> SEQUENCE: 496

Glu Val Gln Leu Val Glu Ser Gly Gly Gly Val Gln Pro Gly Gly
1               5                   10                  15

Ser Leu Arg Leu Ser Cys Ala Ala Ser Gly Ser Ile Thr Gly Ala Asn
            20                  25                  30

Thr Met Gly Trp Tyr Arg Gln Ala Pro Gly Lys Gln Arg Asp Leu Val
        35                  40                  45

Ala Leu Ile Gly Asn Tyr Val Thr His Tyr Ala Glu Ser Val Lys Gly
    50                  55                  60

Arg Phe Thr Ile Ser Arg Asp Asn Ala Lys Asn Thr Val Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
            100                 105                 110

Val Lys Pro
        115

<210> SEQ ID NO 497
<211> LENGTH: 115
<212> TYPE: PRT
<213> ORGANISM: Artificial Sequence
<220> FEATURE:
<223> OTHER INFORMATION: hz18H10v8

<400> SEQUENCE: 497

Glu Val Gln Leu Val Glu Ser Gly Gly Gly Val Gln Pro Gly Gly
1               5                   10                  15

Ser Leu Arg Leu Ser Cys Ala Ala Ser Gly Ser Val Thr Gly Ala Asn
            20                  25                  30

Thr Met Gly Trp Tyr Arg Gln Ala Pro Gly Lys Gln Arg Asp Leu Val
        35                  40                  45

Ser Leu Ile Gly Asn Tyr Val Thr His Tyr Ala Glu Ser Val Lys Gly
    50                  55                  60

Arg Phe Thr Ile Ser Arg Asp Asn Ala Lys Asn Thr Leu Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
            100                 105                 110

Val Lys Pro
        115

<210> SEQ ID NO 498
<211> LENGTH: 115
<212> TYPE: PRT
<213> ORGANISM: Artificial Sequence
<220> FEATURE:
```

<223> OTHER INFORMATION: hz18H10v9

<400> SEQUENCE: 498

Glu Val Gln Leu Val Glu Ser Gly Gly Gly Val Gln Pro Gly Gly
1               5                   10                  15

Ser Leu Arg Leu Ser Cys Ala Ala Ser Gly Ser Val Thr Gly Ala Asn
            20                  25                  30

Thr Met Gly Trp Tyr Arg Gln Ala Pro Gly Lys Gln Arg Asp Leu Val
        35                  40                  45

Ser Leu Ile Gly Asn Tyr Val Thr His Tyr Ala Glu Ser Val Lys Gly
    50                  55                  60

Arg Phe Thr Ile Ser Arg Asp Asn Ala Lys Asn Thr Val Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
                100                 105                 110

Val Lys Pro
        115

<210> SEQ ID NO 499
<211> LENGTH: 115
<212> TYPE: PRT
<213> ORGANISM: Artificial Sequence
<220> FEATURE:
<223> OTHER INFORMATION: hz18H10v10

<400> SEQUENCE: 499

Glu Val Gln Leu Val Glu Ser Gly Gly Gly Val Gln Pro Gly Gly
1               5                   10                  15

Ser Leu Arg Leu Ser Cys Ala Ala Ser Gly Ser Met Thr Gly Ala Asn
            20                  25                  30

Thr Met Gly Trp Tyr Arg Gln Ala Pro Gly Lys Gln Arg Asp Leu Val
        35                  40                  45

Ser Leu Ile Gly Asn Tyr Val Thr His Tyr Ala Glu Ser Val Lys Gly
    50                  55                  60

Arg Phe Thr Ile Ser Arg Glu Asn Ala Lys Asn Thr Val Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
                100                 105                 110

Val Lys Pro
        115

<210> SEQ ID NO 500
<211> LENGTH: 115
<212> TYPE: PRT
<213> ORGANISM: Artificial Sequence
<220> FEATURE:
<223> OTHER INFORMATION: hz18H10v11

<400> SEQUENCE: 500

Glu Val Gln Leu Val Glu Ser Gly Gly Gly Val Gln Pro Gly Gly
1               5                   10                  15

Ser Leu Arg Leu Ser Cys Ala Ala Ser Gly Ser Val Thr Gly Ala Asn
            20                  25                  30

Thr Met Gly Trp Tyr Arg Gln Ala Pro Gly Lys Gln Arg Asp Leu Val

```
                35                  40                  45
Ser Leu Ile Gly Asn Tyr Val Thr His Tyr Ala Glu Ser Val Lys Gly
 50                  55                  60

Arg Phe Thr Ile Ser Arg Glu Asn Ala Lys Asn Thr Val Tyr Leu Gln
 65                  70                  75                  80

Met Ser Ser Leu Arg Ala Glu Asp Thr Ala Val Tyr Tyr Cys Tyr Leu
                 85                  90                  95

Tyr Thr Asp Asn Leu Gly Thr Ser Trp Gly Gln Gly Thr Leu Val Thr
                100                 105                 110

Val Lys Pro
        115

<210> SEQ ID NO 501
<211> LENGTH: 115
<212> TYPE: PRT
<213> ORGANISM: Artificial Sequence
<220> FEATURE:
<223> OTHER INFORMATION: hz18H10v12

<400> SEQUENCE: 501

Glu Val Gln Leu Val Glu Ser Gly Gly Gly Glu Val Gln Pro Gly Gly
 1                   5                  10                  15

Ser Leu Arg Leu Ser Cys Ala Ala Ser Gly Ser Val Thr Gly Ala Asn
                 20                  25                  30

Thr Met Gly Trp Tyr Arg Gln Ala Pro Gly Lys Gln Arg Asp Leu Val
                35                  40                  45

Ala Leu Ile Gly Asn Tyr Val Thr His Tyr Ala Glu Ser Val Lys Gly
 50                  55                  60

Arg Phe Thr Ile Ser Arg Glu Asn Ala Lys Asn Thr Val Tyr Leu Gln
 65                  70                  75                  80

Met Ser Ser Leu Arg Ala Glu Asp Thr Ala Val Tyr Tyr Cys Tyr Leu
                 85                  90                  95

Tyr Thr Asp Asn Leu Gly Thr Ser Trp Gly Gln Gly Thr Leu Val Thr
                100                 105                 110

Val Lys Pro
        115

<210> SEQ ID NO 502
<211> LENGTH: 115
<212> TYPE: PRT
<213> ORGANISM: Artificial Sequence
<220> FEATURE:
<223> OTHER INFORMATION: hz18H10v13

<400> SEQUENCE: 502

Glu Val Gln Leu Val Glu Ser Gly Gly Gly Glu Val Gln Pro Gly Gly
 1                   5                  10                  15

Ser Leu Arg Leu Ser Cys Ala Ala Ser Gly Ser Met Thr Gly Ala Asn
                 20                  25                  30

Thr Met Gly Trp Tyr Arg Gln Ala Pro Gly Lys Gln Arg Glu Leu Val
                35                  40                  45

Ala Leu Ile Gly Asn Tyr Val Thr His Tyr Ala Glu Ser Val Lys Gly
 50                  55                  60

Arg Phe Thr Ile Ser Arg Glu Asn Ala Lys Asn Thr Val Tyr Leu Gln
 65                  70                  75                  80

Met Ser Ser Leu Arg Ala Glu Asp Thr Ala Val Tyr Tyr Cys Tyr Leu
                 85                  90                  95
```

Tyr Thr Asp Asn Leu Gly Thr Ser Trp Gly Gln Gly Thr Leu Val Thr
                100                 105                 110

Val Lys Pro
        115

<210> SEQ ID NO 503
<211> LENGTH: 115
<212> TYPE: PRT
<213> ORGANISM: Artificial Sequence
<220> FEATURE:
<223> OTHER INFORMATION: hz18H10v14

<400> SEQUENCE: 503

Glu Val Gln Leu Val Glu Ser Gly Gly Gly Val Gln Pro Gly Gly
1               5                   10                  15

Ser Leu Arg Leu Ser Cys Ala Ala Ser Gly Ser Val Thr Gly Ala Asn
                20                  25                  30

Thr Met Gly Trp Tyr Arg Gln Ala Pro Gly Lys Gln Arg Asp Leu Val
                35                  40                  45

Ala Leu Ile Gly Asn Tyr Val Thr His Tyr Ala Glu Ser Val Lys Gly
            50                  55                  60

Arg Phe Thr Ile Ser Arg Asp Asn Ala Lys Asn Thr Leu Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
                100                 105                 110

Val Lys Pro
        115

<210> SEQ ID NO 504
<211> LENGTH: 115
<212> TYPE: PRT
<213> ORGANISM: Artificial Sequence
<220> FEATURE:
<223> OTHER INFORMATION: hz18H10v15

<400> SEQUENCE: 504

Glu Val Gln Leu Val Glu Ser Gly Gly Gly Val Gln Pro Gly Gly
1               5                   10                  15

Ser Leu Arg Leu Ser Cys Ala Ala Ser Gly Ser Ile Thr Gly Ala Asn
                20                  25                  30

Thr Met Gly Trp Tyr Arg Gln Ala Pro Gly Lys Gln Arg Asp Leu Val
                35                  40                  45

Ala Leu Ile Gly Asn Tyr Val Thr His Tyr Ala Glu Ser Val Lys Gly
            50                  55                  60

Arg Phe Thr Ile Ser Arg Asp Asn Ala Lys Asn Thr Leu Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
                100                 105                 110

Val Lys Pro
        115

<210> SEQ ID NO 505
<211> LENGTH: 115
<212> TYPE: PRT
<213> ORGANISM: Artificial Sequence

```
<220> FEATURE:
<223> OTHER INFORMATION: hz18H10v16

<400> SEQUENCE: 505

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Ile Thr Gly Ala Asn
            20                  25                  30

Thr Met Gly Trp Tyr Arg Gln Ala Pro Gly Lys Gln Arg Asp Leu Val
        35                  40                  45

Ala Leu Ile Gly Asn Tyr Val Thr His Tyr Ala Glu Ser Val Lys Gly
    50                  55                  60

Arg Phe Thr Ile Ser Arg Glu Asn Ala Lys Asn Thr Val Tyr Leu Gln
65                  70                  75                  80

Met Ser Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
            100                 105                 110

Val Lys Pro
        115

<210> SEQ ID NO 506
<211> LENGTH: 115
<212> TYPE: PRT
<213> ORGANISM: Artificial Sequence
<220> FEATURE:
<223> OTHER INFORMATION: hz18H10v17

<400> SEQUENCE: 506

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Ile Thr Gly Ala Asn
            20                  25                  30

Thr Met Gly Trp Tyr Arg Gln Ala Pro Gly Lys Gln Arg Asp Leu Val
        35                  40                  45

Ala Leu Ile Gly Asn Tyr Val Thr His Tyr Ala Glu Ser Val Lys Gly
    50                  55                  60

Arg Phe Thr Ile Ser Arg Asp Asn Ala Lys Asn Thr Val Tyr Leu Gln
65                  70                  75                  80

Met Asn Ser Leu Arg Ala Glu Asp Thr Ala Val Tyr Tyr Cys Tyr Leu
                85                  90                  95

Tyr Thr Asp Asn Leu Gly Thr Ser Trp Gly Gln Gly Thr Leu Val Thr
            100                 105                 110

Val Lys Pro
        115

<210> SEQ ID NO 507
<211> LENGTH: 115
<212> TYPE: PRT
<213> ORGANISM: Artificial Sequence
<220> FEATURE:
<223> OTHER INFORMATION: L6F1

<400> SEQUENCE: 507

Gln Val Gln Leu Val Gln Ser Gly Gly Gly Leu Val Gln Ala Gly Gly
1               5                   10                  15

Ser Leu Arg Leu Ser Cys Gly Ala Ser Glu Ile Ile Phe Ser Asp Lys
            20                  25                  30
```

```
Thr Val Gly Trp Tyr Arg Gln Ala Pro Gly Lys Gln Arg Val Leu Val
        35                  40                  45

Ala Val Ile Ser Asn Val Asp Ser Thr Asn Tyr Ala Gln Ser Val Lys
 50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Tyr
                 85                  90                  95

Ala Arg Asp Phe Glu Ser Glu Tyr Trp Gly Arg Gly Thr Gln Val Thr
                100                 105                 110

Val Lys Pro
        115
```

<210> SEQ ID NO 508
<211> LENGTH: 115
<212> TYPE: PRT
<213> ORGANISM: Artificial Sequence
<220> FEATURE:
<223> OTHER INFORMATION: hz6F1v1

<400> SEQUENCE: 508

```
Glu Val Gln Leu Val Glu Ser Gly Gly Gly Glu Val Gln Pro Gly Gly
 1               5                  10                  15

Ser Leu Arg Leu Ser Cys Ala Ala Ser Glu Ile Ile Phe Ser Asp Lys
                 20                  25                  30

Thr Val Gly Trp Tyr Arg Gln Ala Pro Gly Lys Gln Arg Val Leu Val
        35                  40                  45

Ala Val Ile Ser Asn Val Asp Ser Thr Asn Tyr Ala Glu Ser Val Lys
 50                  55                  60

Gly Arg Phe Thr Ile Ser Arg Asp Asn Ala Lys Asn Thr Leu Tyr Leu
 65                  70                  75                  80

Gln Met Ser Ser Leu Arg Ala Glu Asp Thr Ala Val Tyr Tyr Cys Tyr
                 85                  90                  95

Ala Arg Asp Phe Glu Ser Glu Tyr Trp Gly Gln Gly Thr Leu Val Thr
                100                 105                 110

Val Lys Pro
        115
```

<210> SEQ ID NO 509
<211> LENGTH: 115
<212> TYPE: PRT
<213> ORGANISM: Artificial Sequence
<220> FEATURE:
<223> OTHER INFORMATION: hz6F1v2

<400> SEQUENCE: 509

```
Glu Val Gln Leu Val Glu Ser Gly Gly Gly Glu Val Gln Pro Gly Gly
 1               5                  10                  15

Ser Leu Arg Leu Ser Cys Ala Ala Ser Glu Ile Ile Phe Ser Asp Lys
                 20                  25                  30

Thr Val Gly Trp Tyr Arg Gln Ala Pro Gly Lys Gln Arg Val Leu Val
        35                  40                  45

Ala Val Ile Ser Asn Val Asp Ser Thr Asn Tyr Ala Glu Ser Val Lys
 50                  55                  60

Gly Arg Phe Thr Ile Ser Arg Asp Asn Ala Lys Asn Thr Val Tyr Leu
 65                  70                  75                  80

Gln Met Ser Ser Leu Arg Ala Glu Asp Thr Ala Val Tyr Tyr Cys Tyr
                 85                  90                  95
```

```
Ala Arg Asp Phe Glu Ser Glu Tyr Trp Gly Gln Gly Thr Leu Val Thr
            100                 105                 110

Val Lys Pro
        115

<210> SEQ ID NO 510
<211> LENGTH: 115
<212> TYPE: PRT
<213> ORGANISM: Artificial Sequence
<220> FEATURE:
<223> OTHER INFORMATION: hz6F1v3

<400> SEQUENCE: 510

Glu Val Gln Leu Val Glu Ser Gly Gly Gly Glu Val Gln Pro Gly Gly
1               5                   10                  15

Ser Leu Arg Leu Ser Cys Ala Ala Ser Glu Ile Ile Phe Ser Asp Lys
            20                  25                  30

Thr Val Gly Trp Tyr Arg Gln Ala Pro Gly Lys Gln Arg Val Leu Val
        35                  40                  45

Ala Val Ile Ser Asn Val Asp Ser Thr Asn Tyr Ala Gln Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Tyr
                85                  90                  95

Ala Arg Asp Phe Glu Ser Glu Tyr Trp Gly Gln Gly Thr Leu Val Thr
            100                 105                 110

Val Lys Pro
        115

<210> SEQ ID NO 511
<211> LENGTH: 115
<212> TYPE: PRT
<213> ORGANISM: Artificial Sequence
<220> FEATURE:
<223> OTHER INFORMATION: hz6F1v4

<400> SEQUENCE: 511

Glu Val Gln Leu Val Glu Ser Gly Gly Gly Glu Val Gln Pro Gly Gly
1               5                   10                  15

Ser Leu Arg Leu Ser Cys Gly Ala Ser Glu Ile Ile Phe Ser Asp Lys
            20                  25                  30

Thr Val Gly Trp Tyr Arg Gln Ala Pro Gly Lys Gln Arg Val Leu Val
        35                  40                  45

Ala Val Ile Ser Asn Val Asp Ser Thr Asn Tyr Ala Glu Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Tyr
                85                  90                  95

Ala Arg Asp Phe Glu Ser Glu Tyr Trp Gly Gln Gly Thr Leu Val Thr
            100                 105                 110

Val Lys Pro
        115

<210> SEQ ID NO 512
<211> LENGTH: 115
<212> TYPE: PRT
```

```
<213> ORGANISM: Artificial Sequence
<220> FEATURE:
<223> OTHER INFORMATION: hz6F1v5

<400> SEQUENCE: 512

Glu Val Gln Leu Val Glu Ser Gly Gly Gly Glu Val Gln Pro Gly Gly
1               5                   10                  15

Ser Leu Arg Leu Ser Cys Ala Ala Ser Glu Ile Ile Phe Ser Asp Lys
            20                  25                  30

Thr Val Gly Trp Tyr Arg Gln Ala Pro Gly Lys Gln Arg Val Leu Val
        35                  40                  45

Ala Val Ile Ser Asn Val Asp Ser Thr Asn Tyr Ala Glu Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Tyr
                85                  90                  95

Ala Arg Asp Phe Glu Ser Glu Tyr Trp Gly Arg Gly Thr Gln Val Thr
            100                 105                 110

Val Lys Pro
        115

<210> SEQ ID NO 513
<211> LENGTH: 115
<212> TYPE: PRT
<213> ORGANISM: Artificial Sequence
<220> FEATURE:
<223> OTHER INFORMATION: hz6F1v6

<400> SEQUENCE: 513

Glu Val Gln Leu Val Glu Ser Gly Gly Gly Glu Val Gln Pro Gly Gly
1               5                   10                  15

Ser Leu Arg Leu Ser Cys Ala Ala Ser Glu Ile Ile Phe Ser Asp Lys
            20                  25                  30

Thr Val Gly Trp Tyr Arg Gln Ala Pro Gly Lys Gln Arg Val Leu Val
        35                  40                  45

Ala Val Ile Ser Asn Val Glu Ser Thr Asn Tyr Ala Glu Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Tyr
                85                  90                  95

Ala Arg Asp Phe Glu Ser Glu Tyr Trp Gly Gln Gly Thr Leu Val Thr
            100                 105                 110

Val Lys Pro
        115

<210> SEQ ID NO 514
<211> LENGTH: 115
<212> TYPE: PRT
<213> ORGANISM: Artificial Sequence
<220> FEATURE:
<223> OTHER INFORMATION: hz6F1v7

<400> SEQUENCE: 514

Glu Val Gln Leu Val Glu Ser Gly Gly Gly Glu Val Gln Pro Gly Gly
1               5                   10                  15

Ser Leu Arg Leu Ser Cys Ala Ala Ser Glu Ile Ile Phe Ser Asp Lys
            20                  25                  30
```

```
Thr Val Gly Trp Tyr Arg Gln Ala Pro Gly Lys Gln Arg Val Leu Val
        35                  40                  45

Ala Val Ile Ser Asn Val Asp Ala Thr Asn Tyr Ala Glu Ser Val Lys
 50                  55                  60

Gly Arg Phe Thr Ile Ser Arg Asp Asn Ala Lys Asn Thr Val Tyr Leu
 65                  70                  75                  80

Gln Met Ser Ser Leu Arg Ala Glu Asp Thr Ala Val Tyr Tyr Cys Tyr
                 85                  90                  95

Ala Arg Asp Phe Glu Ser Glu Tyr Trp Gly Gln Gly Thr Leu Val Thr
            100                 105                 110

Val Lys Pro
    115

<210> SEQ ID NO 515
<211> LENGTH: 115
<212> TYPE: PRT
<213> ORGANISM: Artificial Sequence
<220> FEATURE:
<223> OTHER INFORMATION: 5H8

<400> SEQUENCE: 515

Gln Val Gln Leu Gln Glu Ser Gly Gly Gly Leu Val Gln Ala Gly Gly
 1               5                  10                  15

Ser Leu Thr Leu Ser Cys Ala Ala Ser Gly Ser Ile Phe Ser Ile Asn
                 20                  25                  30

Ala Met Gly Trp Tyr Arg Gln Gly Asp Leu Val Ala Gly Phe Thr Ser
            35                  40                  45

Glu Gly Ser Ala Lys Tyr Ala Asp Ser Val Lys Gly Arg Phe Thr Ile
 50                  55                  60

Ser Arg Asp Asp Ala Lys Asn Met Val Thr Leu Gln Met Asn Ser Leu
 65                  70                  75                  80

Lys Pro Glu Asp Thr Ala Val Tyr Tyr Cys Ala Ala Asp Ile Phe Ser
                 85                  90                  95

Asp Arg Asp His Val Asp Trp Tyr Trp Gly Gln Gly Thr Leu Val Thr
            100                 105                 110

Val Lys Pro
    115

<210> SEQ ID NO 516
<211> LENGTH: 123
<212> TYPE: PRT
<213> ORGANISM: Artificial Sequence
<220> FEATURE:
<223> OTHER INFORMATION: 3B12

<400> SEQUENCE: 516

Gln Val Gln Leu Gln Glu Ser Gly Gly Gly Leu Val Gln Ser Gly Gly
 1               5                  10                  15

Ser Leu Arg Leu Ser Cys Ala Ala Ser Gly Phe Ser Leu Asp Asp Tyr
                 20                  25                  30

Thr Ile Gly Trp Phe Arg Gln Ala Pro Gly Lys Glu Arg Glu Gly Val
            35                  40                  45

Ser Cys Ile Ser Ser Ser Gly Ser Thr Tyr Tyr Ala Asp Ser Val
 50                  55                  60

Lys Gly Arg Phe Thr Ile Ser Arg Asp Asn Ala Glu Asn Thr Val Tyr
 65                  70                  75                  80

Leu Gln Met Asn Ser Leu Lys Pro Glu Asp Thr Ala Val Tyr Tyr Cys
```

```
                85                  90                  95
Ala Thr Tyr Cys Pro Val Thr Ile Ala Asp Glu Leu Gly Phe Asp Tyr
            100                 105                 110

Trp Gly Gln Gly Thr Leu Val Thr Val Lys Pro
            115                 120

<210> SEQ ID NO 517
<211> LENGTH: 115
<212> TYPE: PRT
<213> ORGANISM: Artificial Sequence
<220> FEATURE:
<223> OTHER INFORMATION: 6B4

<400> SEQUENCE: 517

Gln Val Thr Leu Arg Glu Ser Gly Gly Gly Leu Val Gln Ala Gly Gly
1               5                   10                  15

Ser Leu Arg Leu Ser Cys Gly Ala Ser Glu Ile Thr Leu Ser Asp Lys
            20                  25                  30

Thr Val Gly Trp Tyr Arg Gln Ala Pro Gly Lys Gln Arg Val Leu Val
        35                  40                  45

Ala Val Ile Ser Asn Val Asp Ser Thr Asn Tyr Ala His Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Tyr
                85                  90                  95

Ala Arg Asp Phe Glu Ala Glu Tyr Trp Gly Gln Gly Thr Leu Val Thr
            100                 105                 110

Val Lys Pro
        115

<210> SEQ ID NO 518
<211> LENGTH: 124
<212> TYPE: PRT
<213> ORGANISM: Artificial Sequence
<220> FEATURE:
<223> OTHER INFORMATION: 6A1

<400> SEQUENCE: 518

Gln Val Gln Leu Val Gln Ser Gly Gly Gly Leu Val Gln Ala Gly Gly
1               5                   10                  15

Ser Leu Arg Leu Ser Cys Ala Ala Ser Gly Phe Ser Leu Asp Asp Tyr
            20                  25                  30

Thr Ile Gly Trp Phe Arg Gln Ala Pro Gly Lys Glu Arg Glu Gly Val
        35                  40                  45

Ser Cys Ile Ser Ser Ser Gly Gly Ser Thr Val His Ala Asp Ser Val
    50                  55                  60

Lys Gly Arg Phe Thr Ile Ser Arg Asp Asn Ala Lys Asn Thr Val Trp
65                  70                  75                  80

Leu Gln Met Asn Ser Leu Lys Pro Glu Asp Thr Ala Val Tyr Tyr Cys
                85                  90                  95

Ala Thr Trp Cys Gly Val Ala Thr Met Thr Glu Asp Leu Pro Phe Asp
            100                 105                 110

Tyr Trp Gly Gln Gly Thr Leu Val Thr Val Lys Pro
        115                 120

<210> SEQ ID NO 519
<211> LENGTH: 122
```

```
<212> TYPE: PRT
<213> ORGANISM: Artificial Sequence
<220> FEATURE:
<223> OTHER INFORMATION: Anti-CD3 VH 312557

<400> SEQUENCE: 519

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Phe Thr Ile Ser Arg Asp Asn Ala Lys Asn Ser Leu Tyr Leu
65                  70                  75                  80

Gln Met Asn Ser Leu Arg Ala Glu Asp Thr Ala Leu Tyr Tyr Cys Ala
                85                  90                  95

Lys Asp Ser Arg Gly Tyr Gly Asp Tyr Arg Leu Gly Gly Ala Tyr Trp
            100                 105                 110

Gly Gln Gly Thr Leu Val Thr Val Ser Ser
        115                 120

<210> SEQ ID NO 520
<211> LENGTH: 122
<212> TYPE: PRT
<213> ORGANISM: Artificial Sequence
<220> FEATURE:
<223> OTHER INFORMATION: Anti-CD3 VH 312557 G44C

<400> SEQUENCE: 520

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Cys Leu Glu Trp Val
        35                  40                  45

Ser Gly Ile Ser Trp Asn Ser Gly Ser Ile Gly Tyr Ala Asp Ser Val
    50                  55                  60

Lys Gly Phe Thr Ile Ser Arg Asp Asn Ala Lys Asn Ser Leu Tyr Leu
65                  70                  75                  80

Gln Met Asn Ser Leu Arg Ala Glu Asp Thr Ala Leu Tyr Tyr Cys Ala
                85                  90                  95

Lys Asp Ser Arg Gly Tyr Gly Asp Tyr Arg Leu Gly Gly Ala Tyr Trp
            100                 105                 110

Gly Gln Gly Thr Leu Val Thr Val Ser Ser
        115                 120

<210> SEQ ID NO 521
<211> LENGTH: 107
<212> TYPE: PRT
<213> ORGANISM: Artificial Sequence
<220> FEATURE:
<223> OTHER INFORMATION: Anti-CD3 VL  312557

<400> SEQUENCE: 521

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
```

```
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Trp
                85                  90                  95

Thr Phe Gly Gln Gly Thr Lys Val Glu Ile Lys
            100                 105

<210> SEQ ID NO 522
<211> LENGTH: 107
<212> TYPE: PRT
<213> ORGANISM: Artificial Sequence
<220> FEATURE:
<223> OTHER INFORMATION: Anti-CD3 VL 312557 Q100C

<400> SEQUENCE: 522

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Trp
                85                  90                  95

Thr Phe Gly Cys Gly Thr Lys Val Glu Ile Lys
            100                 105

<210> SEQ ID NO 523
<211> LENGTH: 124
<212> TYPE: PRT
<213> ORGANISM: Artificial Sequence
<220> FEATURE:
<223> OTHER INFORMATION: CD3-VH-G

<400> SEQUENCE: 523

Glu Val Gln Leu Val Glu Ser Gly Gly Gly Leu Val Gln Pro Gly Arg
1               5                   10                  15

Ser Leu Arg Leu Ser Cys Val Ala Ser Gly Phe Thr Phe Asp Asp Tyr
                20                  25                  30

Ser Met His Trp Val Arg Gln Ala Pro Gly Lys Gly Leu Glu Trp Val
            35                  40                  45

Ser Gly Ile Ser Trp Asn Ser Gly Ser Lys Asp Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Tyr Gly Ser Gly Tyr Gly Lys Phe Tyr His Tyr Gly Leu Asp
            100                 105                 110
```

```
Val Trp Gly Gln Gly Thr Thr Val Thr Val Ser Ser
        115                 120
```

<210> SEQ ID NO 524
<211> LENGTH: 124
<212> TYPE: PRT
<213> ORGANISM: Artificial Sequence
<220> FEATURE:
<223> OTHER INFORMATION: CD3-VH-G

<400> SEQUENCE: 524

```
Glu Val Gln Leu Val Glu Ser Gly Gly Gly Leu Val Gln Pro Gly Arg
1               5                   10                  15

Ser Leu Arg Leu Ser Cys Val Ala Ser Gly Phe Thr Phe Asp Asp Tyr
            20                  25                  30

Ser Met His Trp Val Arg Gln Ala Pro Gly Lys Cys Leu Glu Trp Val
        35                  40                  45

Ser Gly Ile Ser Trp Asn Ser Gly Ser Lys Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
            85                  90                  95

Ala Lys Tyr Gly Ser Gly Tyr Gly Lys Phe Tyr His Tyr Gly Leu Asp
            100                 105                 110

Val Trp Gly Gln Gly Thr Thr Val Thr Val Ser Ser
        115                 120
```

<210> SEQ ID NO 525
<211> LENGTH: 108
<212> TYPE: PRT
<213> ORGANISM: Artificial Sequence
<220> FEATURE:
<223> OTHER INFORMATION: VK1-39J?5

<400> SEQUENCE: 525

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
            85                  90                  95

Ile Thr Phe Gly Gln Gly Thr Arg Leu Glu Ile Lys
            100                 105
```

<210> SEQ ID NO 526
<211> LENGTH: 108
<212> TYPE: PRT
<213> ORGANISM: Artificial Sequence
<220> FEATURE:
<223> OTHER INFORMATION: VK1-39J?5 Q100C

<400> SEQUENCE: 526

```
Asp Ile Gln Met Thr Gln Ser Pro Ser Ser Leu Ser Ala Ser Val Gly
```

```
                1               5                  10                 15
            Asp Arg Val Thr Ile Thr Cys Arg Ala Ser Gln Ser Ile Ser Ser Tyr
                               20                  25                 30

Leu Asn Trp Tyr Gln Gln Lys Pro Gly Lys Ala Pro Lys Leu Leu Ile
                           35                  40                 45

Tyr Ala Ala Ser Ser Leu Gln Ser Gly Val Pro Ser Arg Phe Ser Gly
                       50                  55                  60

Ser Gly Ser Gly Thr Asp Phe Thr Leu Thr Ile Ser Ser Leu Gln Pro
             65                 70                  75                  80

Glu Asp Phe Ala Thr Tyr Tyr Cys Gln Gln Ser Tyr Ser Thr Pro Pro
                               85                  90                  95

Ile Thr Phe Gly Cys Gly Thr Arg Leu Glu Ile Lys
                           100                 105
```

<210> SEQ ID NO 527
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)...(5)
<223> OTHER INFORMATION: Repeated 2 to 20 times

<400> SEQUENCE: 527

```
Ala Asp Ala Ala Pro
 1               5
```

<210> SEQ ID NO 528
<211> LENGTH: 6
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)...(5)
<223> OTHER INFORMATION: Repeated 2 to 20 times

<400> SEQUENCE: 528

```
Ala Asp Ala Ala Pro Gly
 1               5
```

<210> SEQ ID NO 529
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)...(5)
<223> OTHER INFORMATION: Repeated 2 to 20 times

<400> SEQUENCE: 529

```
Gly Glu Pro Gln Gly
 1               5
```

<210> SEQ ID NO 530
<211> LENGTH: 6
<212> TYPE: PRT
<213> ORGANISM: Artificial Sequence
<220> FEATURE:
<223> OTHER INFORMATION: Linker
<220> FEATURE:

```
<221> NAME/KEY: REPEAT
<222> LOCATION: (1)...(5)
<223> OTHER INFORMATION: Repeated 2 to 20 times

<400> SEQUENCE: 530

Gly Glu Pro Gln Gly Gly
1               5

<210> SEQ ID NO 531
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)...(5)
<223> OTHER INFORMATION: Repeated 2 to 20 times

<400> SEQUENCE: 531

Ala Gly Gly Glu Pro
1               5

<210> SEQ ID NO 532
<211> LENGTH: 6
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)...(5)
<223> OTHER INFORMATION: Repeated 2 to 20 times

<400> SEQUENCE: 532

Ala Gly Gly Glu Pro Gly
1               5

<210> SEQ ID NO 533
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)...(5)
<223> OTHER INFORMATION: Repeated 2 to 20 times

<400> SEQUENCE: 533

Ala Gly Ser Glu Pro
1               5

<210> SEQ ID NO 534
<211> LENGTH: 6
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)...(5)
<223> OTHER INFORMATION: Repeated 2 to 20 times

<400> SEQUENCE: 534

Ala Gly Ser Glu Pro Gly
1               5

<210> SEQ ID NO 535
```

```
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)...(5)
<223> OTHER INFORMATION: Repeated 2 to 20 times

<400> SEQUENCE: 535

Gly Gly Gly Glu Gln
1               5

<210> SEQ ID NO 536
<211> LENGTH: 6
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (1)...(5)
<223> OTHER INFORMATION: Repeated 2 to 20 times

<400> SEQUENCE: 536

Gly Gly Gly Glu Gln Gly
1               5

<210> SEQ ID NO 537
<211> LENGTH: 11
<212> TYPE: PRT
<213> ORGANISM: Artificial Sequence
<220> FEATURE:
<223> OTHER INFORMATION: Linker

<400> SEQUENCE: 537

Ala Asp Ala Ala Pro Ala Asp Ala Ala Pro Gly
1               5                   10

<210> SEQ ID NO 538
<211> LENGTH: 11
<212> TYPE: PRT
<213> ORGANISM: Artificial Sequence
<220> FEATURE:
<223> OTHER INFORMATION: Linker

<400> SEQUENCE: 538

Gly Glu Pro Gln Gly Gly Glu Pro Gln Gly Gly
1               5                   10

<210> SEQ ID NO 539
<211> LENGTH: 11
<212> TYPE: PRT
<213> ORGANISM: Artificial Sequence
<220> FEATURE:
<223> OTHER INFORMATION: Linker

<400> SEQUENCE: 539

Ala Gly Gly Glu Pro Ala Gly Gly Glu Pro Gly
1               5                   10

<210> SEQ ID NO 540
<211> LENGTH: 11
<212> TYPE: PRT
<213> ORGANISM: Artificial Sequence
<220> FEATURE:
<223> OTHER INFORMATION: Linker
```

```
<400> SEQUENCE: 540

Ala Gly Ser Glu Pro Ala Gly Ser Glu Pro Gly
1               5                   10

<210> SEQ ID NO 541
<211> LENGTH: 11
<212> TYPE: PRT
<213> ORGANISM: Artificial Sequence
<220> FEATURE:
<223> OTHER INFORMATION: Linker

<400> SEQUENCE: 541

Gly Gly Gly Glu Gln Gly Gly Gly Glu Gln Gly
1               5                   10
```